(12) United States Patent
Scott et al.

(10) Patent No.: US 8,309,794 B2
(45) Date of Patent: Nov. 13, 2012

(54) POLYOLEOSINS

(75) Inventors: Richard William Scott, Palmerston North (NZ); Vickery Laurence Arcus, Hamilton (NZ); Nicholas John Roberts, Feilding (NZ)

(73) Assignees: Agriculture Victoria Services Pty Ltd, Attwood, Victoria (AU); AgResearch Limited, Hamilton (NZ)

( * ) Notice: Subject to any disclaimer, the term of this patent is extended or adjusted under 35 U.S.C. 154(b) by 1214 days.

(21) Appl. No.: 12/090,758

(22) PCT Filed: Oct. 16, 2006

(86) PCT No.: PCT/AU2006/001528
§ 371 (c)(1),
(2), (4) Date: Apr. 18, 2008

(87) PCT Pub. No.: WO2007/045019
PCT Pub. Date: Apr. 26, 2007

(65) Prior Publication Data
US 2009/0133160 A1    May 21, 2009

(30) Foreign Application Priority Data

Oct. 19, 2005  (AU) .............................. 2005905787
Nov. 16, 2005  (AU) .............................. 2005906364

(51) Int. Cl.
A01H 1/00 (2006.01)
A01H 5/10 (2006.01)
C12N 15/82 (2006.01)
C12N 5/04 (2006.01)
C07H 21/04 (2006.01)
A61K 38/00 (2006.01)
A61K 35/00 (2006.01)

(52) U.S. Cl. ..... 800/278; 800/298; 435/419; 435/320.1; 536/23.4; 536/23.6; 536/24.1; 530/370; 530/377; 514/1; 514/1.1

(58) Field of Classification Search ........................ None
See application file for complete search history.

(56) References Cited

U.S. PATENT DOCUMENTS 5,856,452 A * 1/1999 Moloney et al. .............. 530/412
2002/0088025 A1 7/2002 Moloney et al.
2003/0167524 A1 9/2003 Rooijen et al.

FOREIGN PATENT DOCUMENTS
WO    93/21320 A1    10/1993
WO    2004/113376 A1    12/2004

OTHER PUBLICATIONS

Scott et al, Plant Biotechnology Journal, Oct. 2010, vol. 8, No. 8, p. 912, abstract.*
Lee et al., "Sesame oleosin and prepro-2S albumin expressed as a fusion polypeptide in transgenic rice were split, processed and separately assembled into oil bodies and protein bodies", Journal of Cereal Science, 2006, pp. 333-341, vol. 44.
Robert, Laurian et al. "Molecular characterization of two *Brassica napus* genes related to oleosins which are highly expressed in the tapetum" The Plant Journal, 1994, pp. 927-933, vol. 6, No. 6.
Ross, Joanne et al."Characterization of anther-expressed genes encoding a major class of extracellular oleosin-like proteins in the pollen coat of Brassicaceae" The Plant Journal, 1996, pp. 625-637, vol. 9, No. 5.
Roberts, Michael et al. "*Brassica napus* pollen oleosins possess a characteristic C-terminal domain" 1995 pp. 469-470, vol. 195, No. 3.

* cited by examiner

*Primary Examiner* — Eileen B O Hara
(74) *Attorney, Agent, or Firm* — Larson & Anderson, LLC

(57) ABSTRACT

The present invention relates to constructs including one or more nucleic acids encoding two or more oleosin repeat units, and methods of use thereof. The present invention also relates to recombinant polypeptides including two or more oleosin repeat units, and methods of use thereof.

35 Claims, 163 Drawing Sheets

Figure 1:
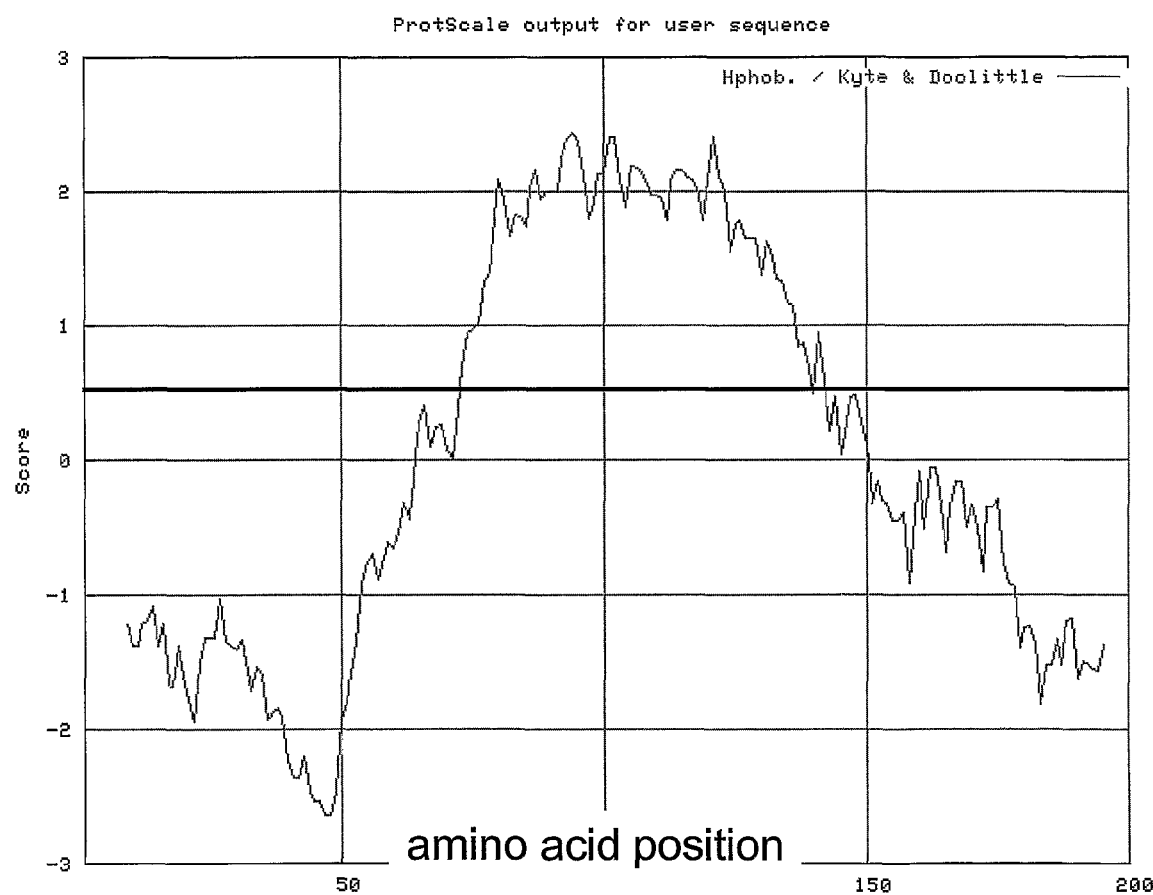

| SacI | • | • | • | • | • | • | XbaI | SpeI | | BamHI | SmaI |
|------|---|---|---|---|---|---|------|------|---|-------|------|
| GAG | CTC | CAC | CGC | GGT | GGC | GGC | CGC | TCT | AGA | ACT | AGT | ☐G | ATCC | CCC | GGG |
| E | L | H | R | G | G | G | R | S | R | T | S | G | S | P | G |

| PstI | EcoRI | EcoRV | HindIII | Bsp106I | • | SalI | XhoI |
|------|-------|-------|---------|---------|---|------|------|
| CTG | CAG | GAA | TTC | GAT | ATC | AAG | CTT | ATC | GAT | ACC | GTC | GAC | CTC | GAG |
| L | Q | E | F | D | I | K | L | I | D | T | V | D | L | E |

Figure 8

|  | restriction sites | additional amino acids | ~18bp of oleosin sequence as initiator of |
|---|---|---|---|
| Primer | RSRSRS | AAAAAA | OLESOSIN SEQUENCE |

PCR Product     *Enz*I/aacids/OLEOSIN/aacids/*Enz*II

TOPO Cloned     generates pOLE01,02,03,04,05-MC

Figure 9

| | |
|---|---|
| pOLEO1-MC | CACCATGGCACAACCTC |
| NEWOLEOSIN | CACCATGGCACAACCTC |
| pOLEO1-MC | AAGTTCAAGTCCACTCAACAACAACACACCGTCAAGAAACTGCTACCTAC |
| NEWOLEOSIN | AAGTTCAAGTCCACTCAACAACAACACACCGTCAAGAAACTGCTACCTAC |
| pOLEO1-MC | CCATCAACCCAAAAACATTCGTAAAGATGTTTACGAAAATGTTAACTATCC |
| NEWOLEOSIN | CCATCAACCCAAAAACATTCGTAAAGATGTTTACGAAAATGTTAACTATCC |
| pOLEO1-MC | CGGCCAACGCGGTCGTTATAACGACCGCTATAATGATAGTGGTCGTTATG |
| NEWOLEOSIN | CGGCCAACGCGGTCGTTATAACGACCGCTATAATGATAGTGGTCGTTATG |
| pOLEO1-MC | ATGGTGGTATTGCCTCCTTTTTGTCAGAGAGAAGTCCTCCAGCCTCTCAA |
| NEWOLEOSIN | ATGGTGGTATTGCCTCCTTTTTGTCAGAGAGAAGTCCTCCAGCCTCTCAA |
| pOLEO1-MC | ATCCTCGCTACCGTTGGAGGATTTTTCATAGGTGGTACTCTATTTTTATT |
| NEWOLEOSIN | ATCCTCGCTACCGTTGGAGGATTTTTCATAGGTGGTACTCTATTTTTATT |
| pOLEO1-MC | AGCTAGCATTTCATTTATCGCCAGTCTTATTGGATTGGCGATAATGACAC |
| NEWOLEOSIN | AGCTAGCATTTCATTTATCGCCAGTCTTATTGGATTGGCGATAATGACAC |
| pOLEO1-MC | CACTTTTTATCCTTTTTAGCCCGGTTTTAGTCCCTGCTGCCCTCACTATA |
| NEWOLEOSIN | CACTTTTTATCCTTTTTAGCCCGGTTTTAGTCCCTGCTGCCCTCACTATA |
| pOLEO1-MC | GGGCTAGCAGTGGCTGGAATATTGACAGCAGATGCTTGCGGGTTGACGGG |
| NEWOLEOSIN | GGGCTAGCAGTGGCTGGAATATTGACAGCAGATGCTTGCGGGTTGACGGG |
| pOLEO1-MC | GCTTATGTCGTTGTCGTGGACCGTGAAATATGTTAGGGATTTACAAGCAG |
| NEWOLEOSIN | GCTTATGTCGTTGTCGTGGACCGTGAAATATGTTAGGGATTTACAAGCAG |
| pOLEO1-MC | TAGTGCCCGAACAAATGGATTCGATGAAGGGACGTGTCGCGGATGTCGCG |
| NEWOLEOSIN | TAGTGCCCGAACAAATGGATTCGATGAAGGGACGTGTCGCGGATGTCGCG |
| pOLEO1-MC | AGTTATGTTGGACAAAAGACTAAGGATGTTGGACAAAAAACTAAAGAGGT |
| NEWOLEOSIN | AGTTATGTTGGACAAAAGACTAAGGATGTTGGACAAAAAACTAAAGAGGT |
| pOLEO1-MC | TGGACAAGACATACAAACAAAAGCACATGAAGCTAAGAGATCAACA |
| NEWOLEOSIN | TGGACAAGACATACAAACAAAAGCACATGAAGCTAAGAGATCAACA |
| pOLEO1-MC | TGA |
| NEWOLEOSIN | TGA |

Figure 13

3

| | |
|---|---|
| clone 2 | TCTAGAGGTACTATGGCACAACCTCAAGTTCAAGTCCACTCAACAACAAC |
| pOLEO2-MC | TCTAGAGGTACTATGGCACAACCTCAAGTTCAAGTCCACTCAACAACAAC |
| clone 2.5@1 | ACACCGTCAAGAAACTGCTACCTACCCATCAACCCAAAACATTCGTAAAG |
| pOLEO2-MC | ACACCGTCAAGAAACTGCTACCTACCCATCAACCCAAAACATTCGTAAAG |
| pOLEO2-MC | ATGTTTACGAAAATGTTAACTATCCCGGCCAACGCGGTCGTTATAACGAC |
| Orginal oleosin | ATGTTTACGAAAATGTTAACTATCCCGGCCAACGCGGTCGTTATAACGAC |
| clone 2.5@1 | CGCTATAATGATAGTGGTCGTTATGATGGTGGTATTGCCTCCTTTTTGTC |
| pOLEO2-MC | CGCTATAATGATAGTGGTCGTTATGATGGTGGTATTGCCTCCTTTTTGTC |
| clone 2.5@1 | AGAGAGAAGTCCTCCAGCCTCTCAAATCCTCGCTACCGTTGGAGGATTTT |
| pOLEO2-MC | AGAGAGAAGTCCTCCAGCCTCTCAAATCCTCGCTACCGTTGGAGGATTTT |
| clone 2.5@1 | TCATAGGTGGTACTCTATTTTTATTAGCTAGCATTTCATTTATCGCCAGT |
| pOLEO2-MC | TCATAGGTGGTACTCTATTTTTATTAGCTAGCATTTCATTTATCGCCAGT |
| clone 2.5@1 | CTTATTGGATTGGCGATAATGACACCACTTTTTATCCTTTTTAGCCCGGT |
| pOLEO2-MC | CTTATTGGATTGGCGATAATGACACCACTTTTTATCCTTTTTAGCCCGGT |
| clone 2.5@1 | TTTAGTCCCTGCTGCCCTCACTATAGGGCTAGCAGTGGCTGGAATATTGA |
| pOLEO2-MC | TTTAGTCCCTGCTGCCCTCACTATAGGGCTAGCAGTGGCTGGAATATTGA |
| clone 2.5@1 | CAGCAGATGCTTGCGGGTTGACGGGGCTTATGTCGTTGTCGTGGACCGTG |
| pOLEO2-MC | CAGCAGATGCTTGCGGGTTGACGGGGCTTATGTCGTTGTCGTGGACCGTG |
| clone 2.5@1 | AAATATGTTAGGGATTTACAAGCAGTAGTGCCCGAACAAATGGATTCGAT |
| pOLEO2-MC | AAATATGTTAGGGATTTACAAGCAGTAGTGCCCGAACAAATGGATTCGAT |
| clone 2.5@1 | GAAGGGACGTGTCGCGGATGTCGCGAGTTATGTTGGACAAAAGACTAAGG |
| pOLEO2-MC | GAAGGGACGTGTCGCGGATGTCGCGAGTTATGTTGGACAAAAGACTAAGG |
| clone 2.5@1 | ATGTTGGACAAAAAACTAAAGAGGTTGGACAAGACATACAAACAAAAGCA |
| pOLEO2-MC | ATGTTGGACAAAAAACTAAAGAGGTTGGACAAGACATACAAACAAAAGCA |
| clone 2.5@1 | CATGAAGCTAAGAGATCAACAGGTACT |
| pOLEO2-MC | CATGAAGCTAAGAGATCAACAGGTACT |

Figure 15

```
clone3      CCCGGGGTACTATGGCACAACCTCAAGTTCAAGTCCACTCAACAACAACA
pOLEO3-MC   CCCGGGGTACTATGGCACAACCTCAAGTTCAAGTCCACTCAACAACAACA clone3      CACCGTCAAGAAACTGCTACCTACCCATCAACCCAAAACATTCGTAAAGA
pOLEO3-MC   CACCGTCAAGAAACTGCTACCTACCCATCAACCCAAAACATTCGTAAAGA clone3      TGTTTACGAAAATGTTAACTATCCCGGCCAACGCGGTCGTTATAACGACC
pOLEO3-MC   TGTTTACGAAAATGTTAACTATCCCGGCCAACGCGGTCGTTATAACGACC clone3      GCTATAATGATAGTGGTCGTTATGATGGTGGTATTGCCTCCTTTTTGTCA
pOLEO3-MC   GCTATAATGATAGTGGTCGTTATGATGGTGGTATTGCCTCCTTTTTGTCA clone3      GAGAGAAGTCCTCCAGCCTCTCAAATCCTCGCTACCGTTGGAGGATTTTT
pOLEO3-MC   GAGAGAAGTCCTCCAGCCTCTCAAATCCTCGCTACCGTTGGAGGATTTTT clone3      CATAGGTGGTACTCTATTTTTATTAGCTAGCATTTCATTTATCGCCAGTC
pOLEO3-MC   CATAGGTGGTACTCTATTTTTATTAGCTAGCATTTCATTTATCGCCAGTC clone3      TTATTGGATTGGCGATAATGACACCACTTTTTATCCTTTTTAGCCCGGTT
pOLEO3-MC   TTATTGGATTGGCGATAATGACACCACTTTTTATCCTTTTTAGCCCGGTT clone3      TTAGTCCCTGCTGCCCTCACTATAGGGCTAGCAGTGGCTGGAATATTGAC
pOLEO3-MC   TTAGTCCCTGCTGCCCTCACTATAGGGCTAGCAGTGGCTGGAATATTGAC clone3      AGCAGATGCTTGCGGGTTGACGGGGCTTATGTCGTTGTCGTGGACCGTGA
pOLEO3-MC   AGCAGATGCTTGCGGGTTGACGGGGCTTATGTCGTTGTCGTGGACCGTGA clone3      AATATGTTAGGGATTTACAAGCAGTAGTGCCCGAACAAATGGATTCGATG
pOLEO3-MC   AATATGTTAGGGATTTACAAGCAGTAGTGCCCGAACAAATGGATTCGATG clone3      AAGGGACGTGTCGCGGATGTCGCGAGTTATGTTGGACAAAAGACTAAGGA
pOLEO3-MC   AAGGGACGTGTCGCGGATGTCGCGAGTTATGTTGGACAAAAGACTAAGGA clone3      TGTTGGACAAAAAACTAAAGAGGTTGGACAAGACATACAAACAAAAGCAC
pOLEO3-MC   TGTTGGACAAAAAACTAAAGAGGTTGGACAAGACATACAAACAAAAGCAC clone3      AGGTACT
pOLEO3-MC   AGCTACT
```

Figure 17

| | |
|---|---|
| clone 4 | AAGCTTGGTACTATGGCACAACCTCAAGTTCAAGTCCACTCAACAACA |
| pOLEO4-MC | AAGCTTGGTACTATGGCACAACCTCAAGTTCAAGTCCACTCAACAACA |
| clone 4 | ACACACCGTCAAGAAACTGCTACCTACCCATCAACCCAAAACATTCGTAA |
| pOLEO4-MC | ACACACCGTCAAGAAACTGCTACCTACCCATCAACCCAAAACATTCGTAA |
| clone 4 | AGATGTTTACGAAAATGTTAACTATCCCGGCCAACGCGGTCGTTATAACG |
| pOLEO4-MC | AGATGTTTACGAAAATGTTAACTATCCCGGCCAACGCGGTCGTTATAACG |
| clone 4 | ACCGCTATAATGATAGTGGTCGTTATGATGGTGGTATTGCCTCCTTTTTG |
| pOLEO4-MC | ACCGCTATAATGATAGTGGTCGTTATGATGGTGGTATTGCCTCCTTTTTG |
| clone 4 | TCAGAGAGAAGTCCTCCAGCCTCTCAAATCCTCGCTACCGTTGGAGGATT |
| pOLEO4-MC | TCAGAGAGAAGTCCTCCAGCCTCTCAAATCCTCGCTACCGTTGGAGGATT |
| clone 4 | TTTCATAGGTGGTACTCTATTTTTATTAGCTAGCATTTCATTTATCGCCA |
| pOLEO4-MC | TTTCATAGGTGGTACTCTATTTTTATTAGCTAGCATTTCATTTATCGCCA |
| clone 4 | GTCTTATTGGATTGGCGATAATGACACCACTTTTTATCCTTTTTAGCCCG |
| pOLEO4-MC | GTCTTATTGGATTGGCGATAATGACACCACTTTTTATCCTTTTTAGCCCG |
| clone 4 | GTTTTAGTCCCTGCTGCCCTCACTATAGGGCTAGCAGTGGCTGGAATATT |
| pOLEO4-MC | GTTTTAGTCCCTGCTGCCCTCACTATAGGGCTAGCAGTGGCTGGAATATT |
| clone 4 | GACAGCAGATGCTTGCGGGTTGACGGGGCTTATGTCGTTGTCGTGGACCG |
| pOLEO4-MC | GACAGCAGATGCTTGCGGGTTGACGGGGCTTATGTCGTTGTCGTGGACCG |
| clone 4 | TGAAATATGTTAGGGATTTACAAGCAGTAGTGCCCGAACAAATGGATTCG |
| pOLEO4-MC | TGAAATATGTTAGGGATTTACAAGCAGTAGTGCCCGAACAAATGGATTCG |
| clone 4 | ATGAAGGGACGTGTCGCGGATGTCGCGAGTTATGTTGGACAAAAGACTAA |
| pOLEO4-MC | ATGAAGGGACGTGTCGCGGATGTCGCGAGTTATGTTGGACAAAAGACTAA |
| clone 4 | GGATGTTGGACAAAAAACTAAAGAGGTTGGACAAGACATACAAACAAAAG |
| pOLEO4-MC | GGATGTTGGACAAAAAACTAAAGAGGTTGGACAAGACATACAAACAAAAG |
| clone 4 | CACATGAAGCTAAGAGATCAACAGGTACT |
| pOLEO4-MC | CACATGAAGCTAAGAGATCAACAGGTACT |

Figure 19

| | |
|---|---|
| clone 5.7<br>pOLEO5-MC | GTCGACGGTACTTCTATGGCACAACCTCAAGTTCAAGTCCACTCAACAAC<br>GTCGACGGTACTTCTATGGCACAACCTCAAGTTCAAGTCCACTCAACAAC |
| clone 5.7<br>pOLEO5-MC | AACACACCGTCAAGAAACTGCTACCTACCCATCAACCCAAAACATTCGTA<br>AACACACCGTCAAGAAACTGCTACCTACCCATCAACCCAAAACATTCGTA |
| clone 5.7<br>pOLEO5-MC | AAGATGTTTACGAAAATGTTAACTATCCCGGCCAACGCGGTCGTTATAAC<br>AAGATGTTTACGAAAATGTTAACTATCCCGGCCAACGCGGTCGTTATAAC |
| clone 5.7<br>pOLEO5-MC | GACCGCTATAATGATAGTGGTCGTTATGATGGTGGTATTGCCTCCTTTTT<br>GACCGCTATAATGATAGTGGTCGTTATGATGGTGGTATTGCCTCCTTTTT |
| clone 5.7<br>pOLEO5-M | GTCAGAGAGAAGTCCTCCAGCCTCTCAAATCCTCGCTACCGTTGGAGGAT<br>GTCAGAGAGAAGTCCTCCAGCCTCTCAAATCCTCGCTACCGTTGGAGGAT |
| clone 5.7<br>pOLEO5-MC | TTTTCATAGGTGGTACTCTATTTTTATTAGCTAGCATTTCATTTATCGCC<br>TTTTCATAGGTGGTACTCTATTTTTATTAGCTAGCATTTCATTTATCGCC |
| clone 5.7<br>pOLEO5-MC | AGTCTTATTGGATTGGCGATAATGACACCACTTTTTATCCTTTTTAGCCC<br>AGTCTTATTGGATTGGCGATAATGACACCACTTTTTATCCTTTTTAGCCC |
| clone 5.7<br>pOLEO5-MC | GGTTTTAGTCCCTGCTGCCCTCACTATAGGGCTAGCAGTGGCTGGAATA<br>GGTTTTAGTCCCTGCTGCCCTCACTATAGGGCTAGCAGTGGCTGGAATA |
| clone 5.7<br>pOLEO5-MC | TTGACAGCAGATGCTTGCGGGTTGACGGGGCTTATGTCGTTGTCGTGGAC<br>TTGACAGCAGATGCTTGCGGGTTGACGGGGCTTATGTCGTTGTCGTGGAC |
| clone 5.7<br>pOLEO5-MC | CGTGAAATATGTTAGGGATTTACAAGCAGTAGTGCCCGAACAAATGGATT<br>CGTGAAATATGTTAGGGATTTACAAGCAGTAGTGCCCGAACAAATGGATT |
| clone 5.7mod<br>pOLEO5-MC | CGATGAAGGGACGTGTCGCGGATGTCGCGAGTTATGTTGGACAAAAGACT<br>CGATGAAGGGACGTGTCGCGGATGTCGCGAGTTATGTTGGACAAAAGACT |
| clone 5.7<br>pOLEO5-MC | AAGGATGTTGGACAAAAAACTAAAGAGGTTGGACAAGACATACAAACAAA<br>AAGGATGTTGGACAAAAAACTAAAGAGGTTGGACAAGACATACAAACAAA |
| clone 5.7<br>pOLEO5-MC | AGCACATGAAGCTAAGAGATCAACACTCGAG<br>AGCACATGAAGCTAAGAGATCAACACTCGAG |

Figure 21

| | |
|---|---|
| pOLEO6-MC | CACCATGGCACAACC |
| clone 6 fwd | CACCATGGCACAACC |
| pOLEO6-MC | TCAAGTTCAAGTCCACTCAACAACAACACACCGTCAAGAAACTGCTACCT |
| clone 6 fwd | TCAAGTTCAAGTCCACTCAACAACAACACACCGTCAAGAAACTGCTACCT |
| pOLEO6-MC | ACCCATCAACCCAAAACATTCGTAAAGATGTTTACGAAAATGTTAACTAT |
| clone 6 fwd | ACCCATCAACCCAAAACATTCGTAAAGATGTTTACGAAAATGTTAACTAT |
| pOLEO6-MC | CCCGGCCAACGCGGTCGTTATAACGACCGCTATAATGATAGTGGTCGTTA |
| clone 6 fwd | CCCGGCCAACGCGGTCGTTATAACGACCGCTATAATGATAGTGGTCGTTA |
| pOLEO6-MC | TGATGGTGGTATTGCCTCCTTTTTGTCAGAGAGAAGTCCTCCAGCCTCTC |
| clone 6 fwd | TGATGGTGGTATTGCCTCCTTTTTGTCAGAGAGAAGTCCTCCAGCCTCTC |
| pOLEO6-MC | AAATCCTCGCTACCGTTGGAGGATTTTTCATAGGTGGTACTCTATTTTTA |
| clone 6 fwd | AAATCCTCGCTACCGTTGGAGGATTTTTCATAGGTGGTACTCTATTTTTA |
| pOLEO6-MC | TTAGCTAGCATTTCATTTATCGCCAGTCTTATTGGATTGGCGATAATGAC |
| clone 6 fwd | TTAGCTAGCATTTCATTTATCGCCAGTCTTATTGGATTGGCGATAATGAC |
| pOLEO6-MC | ACCACTTTTTATCCTTTTTAGCCCGGTTTTAGTCCCTGCTGCCCTCACTA |
| clone 6 rvs | ACCACTTTTTATCCTTTTTAGCCCGGTTTTAGTCCCTGCTGCCCTCACTA |
| pOLEO6-MC | TAGGGCTAGCAGTGGCTGGAATATTGACAGCAGATGCTTGCGGGTTGACG |
| clone 6 rvs | TAGGGCTAGCAGTGGCTGGAATATTGACAGCAGATGCTTGCGGGTTGACG |
| pOLEO6-MC | GGGCTTATGTCGTTGTCGTGGACCGTGAAATATGTTAGGGATTTACAAGC |
| clone 6 rvs | GGGCTTATGTCGTTGTCGTGGACCGTGAAATATGTTAGGGATTTACAAGC |
| pOLEO6-MC | AGTAGTGCCCGAACAAATGGATTCGATGAAGGGACGTGTCGCGGATGTCG |
| clone 6 rvs | AGTAGTGCCCGAACAAATGGATTCGATGAAGGGACGTGTCGCGGATGTCG |
| pOLEO6-MC | CGAGTTATGTTGGACAAAAGACTAAGGATGTTGGACAAAAAACTAAAGAG |
| clone 6 rvs | CGAGTTATGTTGGACAAAAGACTAAGGATGTTGGACAAAAAACTAAAGAG |
| pOLEO6-MC | GTTGGACAAGACATACAAACAAAAGCACATGAAGCTAAGAGATCAACA*GA* |
| clone 6 rvs | GTTGGACAAGACATACAAACAAAAGCACATGAAGCTAAGAGATCAACA*GA* |
| pOLEO6-MC | *GCTCCACCGCGGTGGCGGCCGCTCTAGAACTAGTGGATCCCCCGGGCTGC* |
| clone 6 rvs | *GCTCCACCGCGGTGGCGGCCGCTCTAGAACTAGTGGATCCCCCGGGCTGC* |
| pOLEO6-MC | <u>AGGAATTCGATATCAAGCTTATCGATACCGTCGACCTCGAG</u>TGA |
| clone 6 rvs | <u>AGGAATTCGATATCAAGCTTATCGATACCGTCGACCTCGAG</u>TGA |

Figure 23

```
pOLEO7-MC      CACCATGGCACAACCTCAAGTTCAAGTCCACTCAACAACAACACACCGTCAA
  clone 7.3fwd CACCATGGCACAACCTCAAGTTCAAGTCCACTCAACAACAACACACCGTCAA pOLEO7-MC      GAAACTGCTACCTACCCATCAACCCAAAACATTCGTAAAGATGTTTACGA
  clone 7.3fwd GAAACTGCTACCTACCCATCAACCCAAAACATTCGTAAAGATGTTTACGA pOLEO7-MC      AAATGTTAACTATCCCGGCCAACGCGGTCGTTATAACGACCGCTATAATG
  clone 7.3fwd AAATGTTAACTATCCCGGCCAACGCGGTCGTTATAACGACCGCTATAATG pOLEO7-MC      ATAGTGGTCGTTATGATGGTGGTATTGCCTCCTTTTTGTCAGAGAGAAGT
  clone 7.3fwd ATAGTGGTCGTTATGATGGTGGTATTGCCTCCTTTTTGTCAGAGAGAAGT pOLEO7-MC      CCTCCAGCCTCTCAAATCCTCGCTACCGTTGGAGGATTTTTCATAGGTGG
  clone 7.3fwd CCTCCAGCCTCTCAAATCCTCGCTACCGTTGGAGGATTTTTCATAGGTGG pOLEO7-MC      TACTCTATTTTTATTAGCTAGCATTTCATTTATCGCCAGTCTTATTGGAT
  clone 7.3fwd TACTCTATTTTTATTAGCTAGCATTTCATTTATCGCCAGTCTTATTGGAT pOLEO7-MC      TGGCGATAATGACACCACTTTTTATCCTTTTTAGCCCCGGTTTTAGTCCCT
  clone 7.3fwd TGGCGATAATGACACCACTTTTTATCCTTTTTAGCCCCGGTTTTAGTCCCT pOLEO7-MC      GCTGCCCTCACTATAGGGCTAGCAGTGGCTGGAATATTGACAGCAGATGC
  clone 7.3fwd GCTGCCCTCACTATAGGGCTAGCAGTGGCTGGAATATTGACAGCAGATGC pOLEO7-MC      TTGCGGGTTGACGGGGCTTATGTCGTTGTCGTGGACCGTGAAATATGTT
  clone 7.3fwd TTCCGGGTTGACGGGGCTTATGTCGTTGTCGTGGACCGTGAAATATGTT pOLEO7-MC      AGGGATTTACAAGCAGTAGTGCCCGAACAAATGGATTCGATGAAGGGACG
  clone 7.3fwd AGGGATTTACAAGCAGTAGTGCCCGAACAAATGGATTCGATGAAGGGACG pOLEO7-MC      TGTCGCGGATGTCGCGAGTTATGTTGGACAAAAGACTAAGGATGTTGGAC
  clone 7.3fwd TGTCGCGGATGTCGCGAGTTATGTTGGACAAAAGACTAAGGATGTTGGAC pOLEO7-MC      AAAAAACTAAAGAGGTTGGACAAGACATACAAACAAAAGCACATGAAGCT
  clone 7.3fwd AAAAAACTAAAGAGGTTGGACAAGACATACAAACAAAAGCACATGAAGCT pOLEO7-MC      AAGAGATCAACAGAGCTCCACCGCGGTGGCGGCCGCTCTAGAGGTACTAT
  clone 7.3fwd AAGAGATCAACAGAGCTCCACCGCGGTGGCGGCCGCTCTAGAGGTACTAT pOLEO7-MC      GGCACAACCTCAAGTTCAAGTCCACTCAACAACAACACACCGTCAAGAAA
  clone 7.3fwd GGCACAACCTCAAGTTCAAGTCCACTCAACAACAACACACCGTCAAGAAA pOLEO7-MC      CTGCTACCTACCCATCAACCCAAAACATTCGTAAAGATGTTTACGAAAA
  clone 7.3fwd CTGCTACCTACCCATCAACCCAAAACATTCGTAAAGATGTTTACGAAAA pOLEO7-MC      TGTTAACTATCCCGGCCAACGCGGTCGTTATAACGACCGCTATAATGAT
   7.3revs     TGTTAACTATCCCGGCCAACGCGGTCGTTATAACGACCGCTATAATGAT pOLEO7-MC      AGTGGTCGTTATGATGGTGGTATTGCCTCCTTTTTGTCAGAGAGAAGTCC
   7.3revs     AGTGGTCGTTATGATGGTGGTATTGCCTCCTTTTTGTCAGAGAGAAGTCC pOLEO7-MC      TCCAGCCTCTCAAATCCTCGCTACCGTTGGAGGATTTTTCATAGGTGGTA
   7.3revs     TCCAGCCTCTCAAATCCTCGCTACCGTTGGAGGATTTTTCATAGGTGGTA pOLEO7-MC      CTCTATTTTTATTAGCTAGCATTTCATTTATCGCCAGTCTTATTGGATTG
   7.3revs     CTCTATTTTTATTAGCTAGCATTTCATTTATCGCCAGTCTTATTGGATTG pOLEO7-MC      GCGATAATGACACCACTTTTTATCCTTTTTAGCCCGGTTTTAGTCCCTGC
   7.3revs     GCGATAATGACACCACTTTTTATCCTTTTTAGCCCGGTTTTAGTCCCTGC pOLEO7-MC      TGCCCTCACTATAGGGCTAGCAGTGGCTGGAATATTGACAGCAGATGCTT
   7.3revs     TGCCCTCACTATAGGGCTAGCAGTGGCTGGAATATTGACAGCAGATGCTT
```

Figure 25

```
pOLEO7-MC    GCGGGTTGACGGGGCTTATGTCGTTCTCGTGGACCGTCAAATATGTTAGG
    7.3revs  GCGGGTTGACGGGGCTTATGTCGTTGTCGTGGACCGTCAAATATGTTAGG pOLEO7-MC    GATTTACAAGCAGTAGTGCCCGAACAAATGGATTCGATGAAGGGACGTGT
    7.3revs  GATTTACAAGCAGTAGTGCCCGAACAAATGGATTCGATGAAGGGACGTGT pOLEO7-MC    CGCGGATGTCGCGAGTTATGTTGGACAAAAGACTAAGGATGTTGGACAAA
    7.3revs  CGCGCATGTCGCGAGTTATGTTGGACAAAAGACTAAGGATGTTGGACAAA pOLEO7-MC    AAACTAAAGAGGTTGGACAAGACATACAAACAAAAGCACATGAAGCTAAG
    7.3revs  AAACTAAAGAGGTTGGACAAGACATACAAACAAAAGCACATGAAGCTAAG pOLEO7-MC    AGATCAACA*GGTACTACTAG*AACTAGTGGATCCCCCGGGCTGCAGGAATT
    7.3revs  AGATCAACA*GGTACTACTAG*AACTAGTGGATCCCCCGGGCTGCAGGAATT pOLEO7-MC    CGATATCAAGCTTATCGATACCGTCGACCTCGAGTGA
    7.3revs  CGATATCAAGCTTATCGATACCGTCGACCTCGAGTGA
```

Figure 25 continued

| | |
|---|---|
| pOLE08-MC | CACCATGGCACAACCTCAAGTTCAAGTCCACTCAACAACAACACACCGTCAA |
| Clone8fwd | CACCATGGCACAACCTCAAGTTCAAGTCCACTCAACAACAACACACCGTCAA |
| pOLE08-MC | GAAACTGCTACCTACCCATCAACCCAAAACATTCGTAAAGATGTTTACGGA |
| Clone8fwd | GAAACTGCTACCTACCCATCAACCCAAAACATTCGTAAAGATGTTTACGGA |
| pOLE08-MC | AAATGTTAACTATCCCGGCCAACGCGGTCGTTATAACGACCGCTATAATG |
| Clone8fwd | AAATGTTAACTATCCCGGCCAACGCGGTCGTTATAACGACCGCTATAATG |
| pOLE08-MC | ATAGTGGTCGTTATGATGGTGGTATTGCCTCCTTTTTGTCAGAGAGAAGT |
| Clone8fwd | ATAGTGGTCGTTATGATGGTGGTATTGCCTCCTTTTTGTCAGAGAGAAGT |
| pOLE08-MC | CCTCCAGCCTCTCAAATCCTCGCTACCGTTGGAGGATTTTTCATAGGTGG |
| Clone8fwd | CCTCCAGCCTCTCAAATCCTCGCTACCGTTGGAGGATTTTTCATAGGTGG |
| pOLE08-MC | TACTCTATTTTTATTAGCTAGCATTTCATTTATCGCCAGTCTTATTGGAT |
| Clone8fwd | TACTCTATTTTTATTAGCTAGCATTTCATTTATCGCCAGTCTTATTGGAT |
| pOLE08-MC | TGGCGATAATGACACCACTTTTTATCCTTTTTAGCCCGGTTTTAGTCCCT |
| Clone8fwd | TGGCGATAATGACACCACTTTTTATCCTTTTTAGCCCGGTTTTAGTCCCT |
| pOLE08-MC | GCTGCCCTCACTATAGGGCTAGCAGTGGCTGGAATATTGACAGCAGATGC |
| Clone8fwd | GCTGCCCTCACTATAGGGCTAGCAGTGGCTGGAATATTGACAGCAGATGC |
| pOLE08-MC | TTGCGGGTTGACGGGGCTTATGTCGTTGTCGTGGACCGTGAAATATGTTA |
| Clone8fwd | TTGCGGGTTGACGGGGCTTATGTCGTTGTCGTGGACCGTGAAATATGTTA |
| pOLE08-MC | GGGATTTACAAGCAGTAGTGCCCGAACAAATGGATTCGATGAAGGGACGT |
| Clone8rev | GGGATTTACAAGCAGTAGTGCCCGAACAAATGGATTCGATGAAGGGACGT |
| pOLE08-MC | GTCGCGGATGTCGCGAGTTATGTTGGACAAAAGACTAAGGATGTTGGACA |
| Clone8rev | GTCGCGGATGTCGCGAGTTATGTTGGACAAAAGACTAAGGATGTTGGACA |
| pOLE08-MC | AAAACTAAAGAGGTTGGACAAGACATACAAACAAAAGCACATGAAGCTA |
| Clone8rev | AAAACTAAAGAGGTTGGACAAGACATACAAACAAAAGCACATGAAGCTA |
| pOLE08-MC | AGAGATCAACA*GAGCTC*CACCGCGGTGGCGGCCGC*TCTAGA*GGTACTAT |
| Clone8rev | AGAGATCAACA*GAGCTC*CACCGCGGTGGCGGCCGC*TCTAGA*GGTACTAT |
| pOLE08-MC | GGCACAACCTCAAGTTCAAGTCCACTCAACAACAACACACCGTCAAGAAA |
| Clone8rev | GGCACAACCTCAAGTTCAAGTCCACTCAACAACAACACACCGTCAAGAAA |
| pOLE08-MC | CTGCTACCTACCCATCAACCCAAAACATTCGTAAAGATGTTTACGAAAAT |
| Clone8rev | CTGCTACCTACCCATCAACCCAAAACATTCGTAAAGATGTTTACGAAAAT |
| pOLE08-MC | GTTAACTATCCCGGCCAACGCGGTCGTTATAACGACCGCTATAATGATAG |
| Clone8rev | GTTAACTATCCCGGCCAACGCGGTCGTTATAACGACCGCTATAATGATAG |
| pOLE08-MC | TGGTCGTTATGATGGTGGTATTGCCTCCTTTTTGTCAGAGAGAAGTCCTC |
| Clone8rev | TGGTCGTTATGATGGTGGTATTGCCTCCTTTTTGTCAGAGAGAAGTCCTC |

Figure 27

```
pOLEO8-MC   CAGCCTCTCAAATCCTCGCTACCGTTGGAGGATTTTTCATAGGTGGTACT
Clone8rev   CAGCCTCTCAAATCCTCGCTACCGTTGGAGGATTTTTCATAGGTGGTACT pOLEO8-MC   CTATTTTTATTAGCTAGCATTTCATTTATCGCCAGTCTTATTGGATTGGC
Clone8rev   CTATTTTTATTAGCTAGCATTTCATTTATCGCCAGTCTTATTGGATTGGC pOLEO8-MC   GATAATGACACCACTTTTTATCCTTTTTAGCCCGGTTTTAGTCCCTGCTG
Clone8rev   GATAATGACACCACTTTTTATCCTTTTTAGCCCGGTTTTAGTCCCTGCTG pOLEO8-MC   CCCTCACTATAGGGCTAGCAGTGGCTGGAATATTGACAGCAGATGCTTGC
Clone8rev   CCCTCACTATAGGGCTAGCAGTGGCTGGAATATTGACAGCAGATGCTTGC pOLEO8-MC   GGGTTGACGGGGCTTATGTCGTTGTCGTGGACCGTGAAATATGTTAGGGA
Clone8rev   GGGTTGACGGGGCTTATGTCGTTGTCGTGGACCGTGAAATATGTTAGGGA pOLEO8-MC   TTTACAAGCAGTAGTGCCCGAACAAATGGATTCGATGAAGGGACGTGTCG
Clone8rev   TTTACAAGCAGTAGTGCCCGAACAAATGGATTCGATGAAGGGACGTGTCG pOLEO8-MC   CGGATGTCGCGAGTTATGTTGGACAAAAGACTAAGGATGTTGGACAAAAA
Clone8rev   CGGATGTCGCGAGTTATGTTGGACAAAAGACTAAGGATGTTGGACAAAAA pOLEO8-MC   ACTAAAGAGGTTGGACAAGACATACAAACAAAAGCACATGAAGCTAAGAG
Clone8rev   ACTAAAGAGGTTGGACAAGACATACAAACAAAAGCACATGAAGCTAAGAG pOLEO8-MC   ATCAACA*GGTACTACTAGAACTAGTGGATCCCCCGGGGGTACT*
Clone8rev   ATCAACA*GGTACTACTAGAACTAGTGGATCCCCCGGGGGTACT* pOLEO8-MC            ATGGCACAACCTCAAGTTCAAGTCCACTCAACAACAACACACCGTCA
Clone8rev            ATGGCACAACCTCAAGTTCAAGTCCACTCAACAACAACACACCGTCA pOLEO8-MC   AGAAACTGCTACCTACCCATCAACCCAAAACATTCGTAAAGATGTTTACG
Clone8rev   AGAAACTGCTACCTACCCATCAACCCAAAACATTCGTAAAGATGTTTACG pOLEO8-MC   AAAATGTTAACTATCCCGGCCAACGCGGTCGTTATAACGACCGCTATAAT
Clone8rev   AAAATGTTAACTATCCCGGCCAACGCGGTCGTTATAACGACCGCTATAAT pOLEO8-MC   GATAGTGGTCGTTATGATGGTGGTATTGCCTCCTTTTTGTCAGAGAGAAG
Clone8rev   GATAGTGGTCGTTATGATGGTGGTATTGCCTCCTTTTTGTCAGAGAGAAG pOLEO8-MC   TCCTCCAGCCTCTCAAATCCTCGCTACCGTTGGAGGATTTTTCATAGGTG
Clone8rev   TCCTCCAGCCTCTCAAATCCTCGCTACCGTTGGAGGATTTTTCATAGGTG pOLEO8-MC   GTACTCTATTTTTATTAGCTAGCATTTCATTTATCGCCAGTCTTATTGGA
Clone8rev   GTACTCTATTTTTATTAGCTAGCATTTCATTTATCGCCAGTCTTATTGGA pOLEO8-MC   TTGGCGATAATGACACCACTTTTTATCCTTTTTAGCCCGGTTTTAGTCCC
Clone8rev   TTGGCGATAATGACACCACTTTTTATCCTTTTTAGCCCGGTTTTAGTCCC pOLEO8-MC   TGCTGCCCTCACTATAGGGCTAGCAGTGGCTGGAATATTGACAGCAGATG
Clone8rev   TGCTGCCCTCACTATAGGGCTAGCAGTGGCTGGAATATTGACAGCAGATG
```

Figure 27 Continued

| | |
|---|---|
| pOLE08-MC | CTTGCGGGTTGACGGGGCTTATGTCGTTGTCGTGGACCGTGAAATATGTT |
| Clone8rev | CTTGCGGGTTGACGGGGCTTATGTCGTTGTCGTGGACCGTGAAATATGTT |
| pOLE08-MC | AGGGATTTACAAGCAGTAGTGCCCGAACAAATGGATTCGATGAAGGGACG |
| Clone8rev | AGGGATTTACAAGCAGTAGTGCCCGAACAAATGGATTCGATGAAGGGACG |
| pOLE08-MC | TGTCGCGGATGTCGCGAGTTATGTTGGACAAAAGACTAAGGATGTTGGAC |
| Clone8rev | TGTCGCGGATGTCGCGAGTTATGTTGGACAAAAGACTAAGGATGTTGGAC |
| pOLE08-MC | AAAAAACTAAAGAGGTTGGACAAGACATACAAACAAAAGCACATGAAGCT |
| Clone8rev | AAAAAACTAAAGAGGTTGGACAAGACATACAAACAAAAGCACATGAAGCT |
| pOLE08-MC | AAGAGATCAACA*GGTACTCTGCAG*GAATTCGATATCAAGCTTATCGATAC |
| Clone8rev | AAGAGATCAACA*GGTACTCTGCAG*GAATTCGATATCAAGCTTATCGATAC |
| pOLE08-MC | CGTCGACCTCGAGTGA |
| Clone8rev | CGTCGACCTCGAGTGA |

```
            MAEHYGQQQQTRAPHLQLQPRAQRVVKAATAVTAGGSLLVLSGLTLAGTVIALTIATPLLVIFSPVLVPAVITIF
Translation     of      High       GC       oleosins       spliced                          (1)
            MAEHYGQQQQTRAPHLQLQPRAQRVVKAATAVTAGGSLLVLSGLTLAGTVIALTIATPLLVIFSPVLVPAVITIF
                                    Consensus                                                (1)
            MAEHYGQQQQTRAPHLQLQPRAQRVVKAATAVTAGGSLLVLSGLTLAGTVIALTIATPLLVIFSPVLVPAVITIF
                                                                 76
150
            6x      OLEOSIN       AF091840          ORF           only                      (76)
LLGAGFLASGGFGVAALSVLSWIYRYLTGKHPPGADQLESAKTKLASKAREMKDRAEQFSQQPVAGSQTS-----
Translation     of      High       GC       oleosins       spliced                         (76)
LLGAGFLASGGFGVAALSVLSWIYRYLTGKHPPGADQLESAKTKLASKAREMKDRAEQFSQQPVAGSQTSIDPSS
                                    Consensus                                              (76)
            LLGAGFLASGGFGVAALSVLSWIYRYLTGKHPPGADQLESAKTKLASKAREMKDRAEQFSQQPVAGSQTS
                                                                 151
225
            6x OLEOSIN AF091840 ORF only  (145)
---MAEHYGQQQQTRAPHLQLQPRAQRVVKAATAVTAGGSLLVLSGLTLAGTVIALTIATPLLVIFSPVLVPAVI
Translation     of      High       GC       oleosins       spliced                         (151)
WLEMAEHYGQQQQTRAPHLQLQPRAQRVVKAATAVTAGGSLLVLSGLTLAGTVIALTIATPLLVIFSPVLVPAVI
                                    Consensus                                              (151)
            MAEHYGQQQQTRAPHLQLQPRAQRVVKAATAVTAGGSLLVLSGLTLAGTVIALTIATPLLVIFSPVLVPAVI
                                                                 226
300
            6x      OLEOSIN       AF091840          ORF           only                     (218)
TIFLLGAGFLASGGFGVAALSVLSWIYRYLTGKHPPGADQLESAKTKLASKAREMKDRAEQFSQQPVAGSQTS--
Translation     of      High       GC       oleosins       spliced                         (226)
TIFLLGAGFLASGGFGVAALSVLSWIYRYLTGKHPPGADQLESAKTKLASKAREMKDRAEQFSQQPVAGSQTSHM
                                    Consensus                                              (226)
            TIFLLGAGFLASGGFGVAALSVLSWIYRYLTGKHPPGADQLESAKTKLASKAREMKDRAEQFSQQPVAGSQTS
                                                                 301
375
            6x OLEOSIN AF091840 ORF only  (291)
------MAEHYGQQQQTRAPHLQLQPRAQRVVKAATAVTAGGSLLVLSGLTLAGTVIALTIATPLLVIFSPVLVP
Translation     of      High       GC       oleosins       spliced                         (301)
FKWPSAMAEHYGQQQQTRAPHLQLQPRAQRVVKAATAVTAGGSLLVLSGLTLAGTVIALTIATPLLVIFSPVLVP
                                    Consensus                                              (301)
            MAEHYGQQQQTRAPHLQLQPRAQRVVKAATAVTAGGSLLVLSGLTLAGTVIALTIATPLLVIFSPVLVP
                                                                 376
450
            6x      OLEOSIN       AF091840          ORF           only                     (360)
AVITIFLLGAGFLASGGFGVAALSVLSWIYRYLTGKHPPGADQLESAKTKLASKAREMKDRAEQFSQQPVAGSQT
Translation     of      High       GC       oleosins       spliced                         (376)
AVITIFLLGAGFLASGGFGVAALSVLSWIYRYLTGKHPPGADQLESAKTKLASKAREMKDRAEQFSQQPVAGSQT
                                    Consensus                                              (376)
AVITIFLLGAGFLASGGFGVAALSVLSWIYRYLTGKHPPGADQLESAKTKLASKAREMKDRAEQFSQQPVAGSQT
                                                                 451
525
            6x OLEOSIN AF091840 ORF only  (435)
S-------MAEHYGQQQQTRAPHLQLQPRAQRVVKAATAVTAGGSLLVLSGLTLAGTVIALTIATPLLVIFSPV
Translation     of      High       GC       oleosins       spliced                         (451)
SSSELPWVDMAEHYGQQQQTRAPHLQLQPRAQRVVKAATAVTAGGSLLVLSGLTLAGTVIALTIATPLLVIFSPV
                                    Consensus  (451)
S           MAEHYGQQQQTRAPHLQLQPRAQRVVKAATAVTAGGSLLVLSGLTLAGTVIALTIATPLLVIFSPV
                                                                 526
600
            6x      OLEOSIN       AF091840          ORF           only                     (502)
LVPAVITIFLLGAGFLASGGFGVAALSVLSWIYRYLTGKHPPGADQLESAKTKLASKAREMKDRAEQFSQQPVAG
Translation     of      High       GC       oleosins       spliced                         (526)
LVPAVITIFLLGAGFLASGGFGVAALSVLSWIYRYLTGKHPPGADQLESAKTKLASKAREMKDRAEQFSQQPVAG
                                    Consensus                                              (526)
LVPAVITIFLLGAGFLASGGFGVAALSVLSWIYRYLTGKHPPGADQLESAKTKLASKAREMKDRAEQFSQQPVAG
                                                                 601
675
            6x OLEOSIN AF091840 ORF only  (577)
SQTS--------MAEHYGQQQQTRAPHLQLQPRAQRVVKAATAVTAGGSLLVLSGLTLAGTVIALTIATPLLVIF
Translation     of      High       GC       oleosins       spliced                         (601)
SQTSHMEFKLSTMAEHYGQQQQTRAPHLQLQPRAQRVVKAATAVTAGGSLLVLSGLTLAGTVIALTIATPLLVIF
                                    Consensus                                         (601)    SQTS
            MAEHYGQQQQTRAPHLQLQPRAQRVVKAATAVTAGGSLLVLSGLTLAGTVIALTIATPLLVIF
                                                                 676
```

Figure 69

```
750
             6x      OLEOSIN       AF091840        ORF     only              (644)
SPVLVPAVITIFLLGAGFLASGGFGVAALSVLSWIYRYLTGKHPPGADQLESAKTKLASKAREMKDRAEQFSQQP
Translation      of       High       GC       oleosins     spliced           (676)
SPVLVPAVITIFLLGAGFLASGGFGVAALSVLSWIYRYLTGKHPPGADQLESAKTKLASKAREMKDRAEQFSQQP
                              Consensus                                      (676)
         SPVLVPAVITIFLLGAGFLASGGFGVAALSVLSWIYRYLTGKHPPGADQLESAKTKLASKAREMKDRAEQFSQQP 825
          6x OLEOSIN AF091840 ORF only    (719)
VAGSQT--------SMAEHYGQQQQTRAPHLQLQPRAQRVVKAATAVTAGGSLLVLSGLTLAGTVIALTIATPLL
Translation     of      High      GC     oleosins     spliced                (751)
VAGSQTSIDQQVNVHMAEHYGQQQQTRAPHLQLQPRAQRVVKAATAVTAGGSLLVLSGLTLAGTVIALTIATPLL
                       Consensus   (751)
VAGSQT         MAEHYGQQQQTRAPHLQLQPRAQRVVKAATAVTAGGSLLVLSGLTLAGTVIALTIATPLL
                                                 826
900
             6x      OLEOSIN      AF091840       ORF     only                (786)
VIFSPVLVPAVITIFLLGAGFLASGGFGVAALSVLSWIYRYLTGKHPPGADQLESAKTKLASKAREMKDRAEQFS
Translation      of       High      GC      oleosins     spliced             (826)
VIFSPVLVPAVITIFLLGAGFLASGGFGVAALSVLSWIYRYLTGKHPPGADQLESAKTKLASKAREMKDRAEQFS
                              Consensus                                      (826)
VIFSPVLVPAVITIFLLGAGFLASGGFGVAALSVLSWIYRYLTGKHPPGADQLESAKTKLASKAREMKDRAEQFS
                                                   901           916
              6x OLEOSIN AF091840 ORF only   (861) QQPVAGSQTS------
       Translation of High GC oleosins spliced  (901) QQPVAGSQTSPWLE--
                              Consensus      (901) QQPVAGSQTS
```

Figure 69 continued

Figure 70

```
CAAATAATGATTTTATTTTGACTGATAGTGACCTGTTCGTTGCAACAAATTGATGAGCAATGCTTTTTTATAATGCCAACTTTGTACAAAAAAG
CAGGCTCCGCGGCCGCTTGCTCCGTTAAAAAAAACCATGGCAGAGCACTACGGGCAGCAGCAACAAACACGTGCCCCCACTTGCAACTGCAAC
CGCGTGCTCAGCGTGTTGTAAAGGCAGCGACCGCGGTTACTGCCGGAGGTAGCCTGTTGGTGTTATCCGGGTTGACCCTGGCTGGAACGGTCAT
TGCGCTGACAATCGCCACACCTCTCCTGGTGATCTTCTCGCCTGTACTGGTCCCTGCAGGTAAATTTCTGTGTTCCTTATTCTCTCAAAATCTT
CGATTTTGTTTTCGTTCGATCCCAATTTCGTATATGTTCTTTGGTTTAGATTCTGTTAATCTTAGATCGAAGACGATTTTCTGGGTTTGATCGT
TAGATATCATCTTAATTCTCGATTAGGGTTTCATAGATATCATCCGATTTGTTCAAATAATTTGAGTTTTGTCGAATAATTACTCTTCGATTTG
TGATTTCTATCTAGATCTGGTGTTAGTTTCTAGTTTGTGCGATCGAATTTGTCGATTAATCTGAGTTTTTCTGATCTGCAGTCATCACCATCTT
CCTGTTGGGAGCGGGTTTTCTGGCAAGCGGGGATTTGGTGTTGCCGCTCTGTCTGTGCTGTCCTGGATCTACCGTTACCTGACGGGGAAACAT
CCACCCGGAGCGGATCAGTTGGAGTCGGCCAAGACAAAGTTGGCGAGCAAGGCCCGTGAAATGAAGGACCGTGCCGAGCAGTTCAGTCAGCAAC
CGGTAGCAGGGTCTCAGACCAGCATCGATCCATCCTCCTGGCTCGAGATGGCGGAACACTACGGGCAACAACAGCAGACTCGTGCTCCCCACCT
GCAATTACAACCCCGTGCCCAACGTGTTGTGAAAGCGGCAACAGCAGTAACGGCAGGGGGAAGTTTGCTGGTCTTATCGGGGTTGACCTTAGCG
GGAACCGTGATTGCCCTGACAATTGCGACTCCGCTGCTGGTTATCTTCAGCCCCGTATTGGTTCCGGCCGTGATCACGATTTTTTTGCTGGGGG
CAGGATTTTTAGCCAGCGGAGGATTTGGGGTCGCAGCGTTGTCTGTGCTGAGTTGGATCTATCGTTATTTGACCGGGAAGCACCCACCTGGAGC
AGACCAGCTGGAGAGCGCGAAAACGAAGCTGGCATCGAAGGCGCGTGAAATGAAGGATCGTGCTGAACAATTCTCCCAGCAGCCTGTTGCCGGT
TCTCAGACCAGCCATATGTTTAAATGGCCAAGCGCTATGGCCGAGCATTATGGGCAGCAACAGCAAACCCGTGCCCCGCATCTGCAATTGCAAC
CTCGTGCCCAGCGTGTCGTTAAGGCGGCTACTGCGGTAACAGCGGGAGGGAGCTTACTGGTATTAAGCGGGCTGACATTGGCCGGAACGGTGAT
CGCCTTAACAATCGCGACACCCTTGCTGGTCATCTTCAGTCCGGTTCTGGTGCCCGCGGTGATTACGATTTTCCTGCTGGGAGCCGGTTTCTTA
GCATCGGGGGTTTTGGGGTAGCAGCCTTGAGTGTCCTGTCGTGGATCTATCGTTACTTAACTGGAAAACACCCGCCAGGAGCTGACCAGTTGG
AGTCTGCAAAAACTAAGCTGGCGTCCAAAGCCCGTGAAATGAAGGATCGTGCTGAGCAGTTTAGCCAGCAGCCAGTTGCGGGAAGTCAGACCTC
TTCATCTGAGCTCCCATGGGTCGACATGGCGGAGCATTACGGTCAACAGCAACAGACCCGTGCTCCGCACTTACAATTGCAACCACGTGCTCAA
CGTGTCGTAAAAGCCGCCACGGCAGTTACTGCGGGGGATCATTGCTGGTGTTAAGTGGGTTGACACTGGCGGGGACAGTTATTGCACTGACGA
TCGCGACCCCCTTGTTAGTGATCTTCTCCCCCGTTCTGGTTCCGGCGGTCATTACAATCTTTCTGTTGGGTGCCGGATTTTTAGCCTCTGGGGG
ATTTGGAGTAGCTGCCCTGTCAGTGTTGAGCTGGATCTACCGTTACTTAACAGGGAAGCACCCTCCCGGGGCAGATCAGTTGGAAAGCGCCAAG
ACCAAGCTGGCAAGTAAAGCGCGTGAAATGAAGGACCGTGCCGAACAATTTTCGCAGCAACCGGTTGCGGGATCACAGACCTCTAGTACTCCAT
CCTCCTGGCATATGATGGCCGAGCACTATGGACAACAGCAGCAGACGCGTGCCCCTCATCTGCAACTGCAACCCCGTGCTCAACGTGTCGTTAA
GGCTGCGACAGCAGTAACCGCTGGGGGTTCTCTGTTAGTGTTGTCAGGGCTGACTTTGGCGGGACGGTAATTGCGTTGACCATTGCCACCCCG
CTGTTAGTGATTTTCAGCCCGGTACTGGTGCCAGCAGTTATCACGATCTTCTTGCTGGGTGCCGGATTCTTGGCAAGTGGAGGTTTTGGAGTTG
CGGCGCTGTCAGTTTTATCCTGGATCTATCGTTATCTGACAGGAAAACATCCCCAGGTGCCGATCAGCTGGAGAGTGCCAAGACAAAACTGGC
GTCTAAGGCACGTGAAATGAAGGATCGTGCCGAACAGTTTTCTCAACAGCCCGTAGCGGGGTCACAGACCTCGATCGATCAGCAGGTTAACGTG
CACATGGCCGAACATTACGGACAGCAACAACAGACGCGTGCTCCACACCTGCAATTGCAACCGCGTGCTCAACGTGTTGTCAAAGCGGCGACCG
CCGTAACAGCAGGAGGATCACTGTTAGTGCTGTCGGGTTTAACCTTGGCCGGGACCGTCATTGCATTGACTATTGCGACGCCCTTACTGGTGAT
CTTTTCTCCGGTGCTGGTTCCCGCCGTTATTACCATCTTCTTGTTAGGGGCAGGATTCCTGGCATCAGGGGGATTCGGAGTTGCGGCGTTGAGT
GTCTTAAGTTGGATCTACCGTTATCTGACTGGAAAGCACCCGCCTGGGGCCGATCAACTGGAGTCAGCCAAAACGAAATTGGCGTCAAAAGCGC
GTGAAATGAAGGACCGTGCTGAGCAGTTTTCTCAGCAGCCTGTGGCAGGATCCCAGACATCACCATGGCTCGAGTAATGAAGCGGCCGCACCCA
GCTTTCTTGTACAAAGTTGGCATTATAAGAAAGCATTGCTTATCAATTTGTTGCAACGAACAGGTCACTATCAGTCAAAATAAAATCATTATTT
G
```

Figure 72

```
                                                      ATG
                        -20 to -10 from original oleosin
                                                                                                    sesame oleosin1
                                    modified Joshi context seq NcoI                                                                                                    PstI
                                                                                                                                            PstI
101  TTGC TCCGTTAAAA AAAACCATGG CTGAGCATTA TGGTCAACAA CAGCAGACCA GGGCGCCTCA CCTGCAGCTG CAGCCCGCCG
                                           sesame oleosin1
201  CCCAGCGGGT AGTGAAGGCG GCCACCGCCG TGACAGCCGG CGGCTCGCTT CTCGTCCTCT CTGGCCTCAC TTTAGCCGGA ACTGTTATTG CGCTCACCAT
                                                           sesame oleosin1
301  CGCCACTCCG CTGCTTGTGA TCTTTAGCCC CGTTCTGGTG CCGGCGGTCA TAACCATTTT CTTGCTGGGT GCGGGTTTTC TGGCATCCGG AGGCTTCGGC
                                                           sesame oleosin1
401  GTGGCGGCGC TGAGTGTGCT GTCGTGGATT TACAGATATC TGACAGGGAA ACACCCCGCCG GGGGCGGATC AGCTGGAATC GGCAAAGACG AAGCTGGCGA
                                           sesame oleosin1                                                                                    sesame oleosin2
                                                                                                    BamHI
501  GCAAGGGCGCG AGAGATGAAG GATAGGGCAG AGCAGTTCTC GCAGCAGCCT GTTGGAGGCG GTGGATCCGG AGGCGGTGGT AGTATGGCTG AGCATTATGG
                                                           sesame oleosin2
                                                PstI
                                                PstI
601  TCAACAACAG CAGACCAGGG CGCCTCACCT GCAGCTGCAG CCGGCGCCCC AGCGGGTAGT GAAGGCGGCC ACCGCCGTGA CAGCCGGCGG CTCGCTTCTC
                                                           sesame oleosin2
701  GTCCTCTCTG GCCTCACTTT AGCCGGAACT GTTATTGCGC TCACCATCGC CACTCCGCTG CTTGTGATCT TTAGCCCCGT TCTGGTGCCG GCGGTCATAA
                                                           sesame oleosin2
801  CCATTTTCTT GCTGGGTGCG GGTTTTCTGG CATCCGGAGG CTTCGGCGTG GCGGCGCTGA GTGTGCTGTC GCGGATTTAC AGATATCTGA CAGGGAAACA
                                                           sesame oleosin2
```

Figure 73

```
 901  CCCGCCGGGG GCGGATCCAGC TGGAATCGGC AAAGACGAAG CTGGCGAGCA AGGCGCGAGA GATGAAGGAT AGGGCAGAGC AGTTCTCGCA GCAGCCTGTT
                                                              sesame oleosin3                                PstI
              NcoI                                                                                          --------
              --------
           BamHI                                                                                              PstI
           --------                                                                                         --------
1001  GGGGGCGGTG GATCCGGTGG AGGGGGATCC ATGGCTGAGC ATTATGTCA ACAACAGCAG ACCAGGGCGC CTCACCTGCA GCTGCAGCCG CGCGCCCAGC
                                                  sesame oleosin3
1101  GGGTAGTGAA GGCGGCCACC GCCGTGACAG CCGGCGGCTC GCTTCTCGTC CTCTCTGGCC TCACTTTAGC CGGAACTGTT ATTGCGCTCA CCATCGCCAC
                                                              sesame oleosin3
1201  TCCGCTGCTT GTGATCTTTA GCCCCGTTCT GGTGCCGGCG GTCATAACCA TTTTCTTGCT GGGTGCGGGT TTTCTGGCAT CCGGAGGCTT CGGCGTGGCG
                                                              sesame oleosin3
1301  GCGCTGAGTG TGCTGTCGTG GATTTACAGA TATCTGACAG GGAAACACCC GCCGGGGGCG GATCAGCTGG AATCGGCAAA GACGAAGCTG GCGAGCAAGG
                 sesame oleosin3                                                      4xSTOP
                                                                            NcoI      -----
                                                                            --------
                                                                                   AvaI
                                                                                   --------
1401  CGCGAGAGAT GAAGGATAGG GCAGAGCAGT TCTCGGAGCA GCCTGTTCCA TGGCTCGAGT AATGAA
```

Figure 73 continued

```
                                                    RBS              ATG        S-Tag
                                             GAAGGAG ATATACATAT GAAAGAAACC
                                                          thrombin
                                                                        Sesame Oleosin
  1
101   GCTGCTGCTA AATTCGAACG CCAGCACATG GACAGCCCAG ATCTGGGTAC CCTGGTGCCA CGCGGTTCCA TGGCTGAGCA TTATGGTCAA CAACAGCAGA
                                                                  Sesame Oleosin
201   CCAGGGCGCC TCACCTGCAG CTGCAGCCGC GCGCCCAGCG GGTAGTGAAG GCGGCCACCG CCGTGACAGC CGGCGGCTCG CTTCTCGTCC TCTCTGGCCT
                                                                  Sesame Oleosin
301   CACTTTAGCC GGAACTGTTA TTGCCTCTCAC CATCGCCACT CCGCTGCTTG TGATCTTTAG CCCCGTTCTG GTGCCGGCGG TCATAACCAT TTTCTTGCTG
                                                                  Sesame Oleosin
401   GGTGCGGGGTT TTCTGGCATC CGGAGGCTTC GGCGTGGCGG CGCTGAGTGT GCTGTCGTGG CTGCTGCTGG ATTTACAGAT ATCTGACAGG GAAACACCCG CCGGGGGCGG
                                                                  Sesame Oleosin
501   ATCAGCTGGA ATCGGCAAAG ACGAAGCTGG CGAGAGATG GCGAGCAAGG CAGAGCAGTT CTCGCAGCAG CCTGTTCCAT GGCTGATATC
                                                                  Sesa2
601   GGATCCGAAT TCGAGCTCCG TCGACAAGCT TGCGGCCGCA CTCGAGATGG CGGAACACTA CGGGCAACAA CAGCAGACTC GTGCTCCCCA CCTGCAATTA
                                                                  Sesa2
701   CAACCCCGTG CCCAACGTGT TGTGAAAGCG GCAACAGCAG TAACGGCAGG GGGAAGTTTG CTGGTCTTAT CGGGGTTGAC CTTTAGCGGGA ACCGTGATTG
                                                                  Sesa2
801   CCCTGACAAT TGCGACTCCG CTGCTGGTTA TCTTTCAGCCC CGTATTGGTT CCGGCCGTGA TCACGATTTT TTTGCTGGGG GCAGGATTTT TAGCCAGCGG
                                                                  Sesa2
901   AGGATTTGGG GTCGCAGCGT TGTCTGTGCT GAGTTGGATC TATCGTTATT TGACCGGGAA GCACCCACCT GGAGCAGACC AGCTGGAGAG CGCGAAAACG
                                                                  Sesa2
1001  AAGCTGGCAT CGAAGGCGCG TGAAATGAAG GATCGTGCTG AACAATTCTC CCAGCAGCCT GTTGCCGGGT CTCAGACCAG CCATATGTTT AAATGGCCAA
                                                                  Sesa3
```

Figure 74

```
1101  GCGCTATGGC CGAGCATTAT GGGCAGCAAC AGCAAACCCG TGCCCCGCAT CTGCAATTGC AACCTCGTGC CCAGCGTGTC GTTAAGGCGG CTACTGCGGT
1201  AACAGCGGGA GGGAGCTTAC TGGTATTAAG CGGGCTGACA TTGGCCGAA CGGTGATCGC CTTAACAATC GCGACACCCT TGCTGGTCAT CTTCAGTCCG
                                                    Sesa3
1301  GTTCTGGTGC CCGCGGTGAT TACGATTTTC CTGCTGGGAG CCGGTTTCTT AGCATCGGGG GGTTTTGGGG TAGCAGCCTT GAGTGTCCTG TCGTGGATCT
                                                                              Sesa3
1401  ATCGTTACTT AACTGGAAAA CACCCGCCAG GAGCTGACCA GTTGGAGTCT GCAAAAACTA AGCTGGCGTC CAAAGCCCGT GAAATGAAGG ATCGTGCTGA
              Sesa3                                                                                        Sesa4
1501  GCAGTTTAGC CAGCAGCCAG TTGCGGGAAG TCAGACCTCT TCATCTGAGC TCCCATGGGT CGACATGGCG GAGCATTACG GTCAACAGCA ACAGACCCGT
1601  GCTCCCGCACT TACAATTGCA ACCACGTGCT CAACGTGTCG TAAAAGCCGC CACGGCAGTT ACTGCGGGGG GATCATTGCT GGTGTTAAGT GGGTTGACAC
                                        Sesa4
1701  TGGCGGGGAC AGTTATTGCA CTGACGATCG CCACCCCCTT GTTAGTGATC TTCTCCCCG TTCTGGTTCC GGCCGGTCAT ACAATCTTTC TGTTGGGTGC
                                                                  Sesa4
1801  CGGATTTTTA GCCTCTGGGG GATTTGGAGT AGCTGCCCTG TCAGTGTTGA GCTGGATCTA CCGTTACTTA ACAGGGAAGC ACCCTCCCGG GGCAGATCAG
                                                                                            Sesa5
1901  TTGGAAAGCG CCAAGACCAA GCTGGCAAGT AAAGCGCGTG AAATGAAGGA CCGTGCCGAA CAATTTTCGC AGCAACCGGT TGCGGGATCA CAGACCTCTA
                                                                           Sesa5
2001  GTACTCCATC CTCCTGGCAT ATGATGGCCG AGCACTATGG ACAACAGCAG CAGACGCGTG CCCCTCATCT GCAACTGCAA CCCCGTGCTC AACGTGTCGT
                                                                   Sesa5
2101  TAAGGCTGCG ACAGACTGGA CCGCTGGGGG TTCTCTGTTA GTGTTGTCAG GGCTGACTTT GGCGGGGACG GTAATTGCGT TGACCATTGC CACCCCGCTG
                                                         Sesa5
2201  TTAGTGATTT TCAGCCCCGGT ACTGGTGCCA GCAGTTATCA CGATCTTCTT GCTGGGTGCC GGATTCTTGG CAAGTGGAGG TTTTGGAGTT GCGGCGCTGT
                Sesa5
2301  CAGTTTTATC CTGGATCTAT CGTTATCTGA CAGGAAAACA TCCCCCAGGT GCCGATCAGC TGGAGAGTGC CAAGACAAAA CTGGCGTCTA AGGCACGTGA
                        Sesa5                                                                            Sesa6
2401  AATGAAGGAT CGTGCCGAAC AGTTTTCTCA ACAGCCCGTA GCGGGGTCAC AGACCTTCGAT CGATCAGCAG GTTAACGTGC ACATGGCCGA ACATTACGGA
                                                        Sesa6
```

Figure 74 continued

```
2501  CAGCAACAAC AGACGCGTGC TCCACACCTG CAATTGCAAC CGCGTGCTCA ACGTGTTGTC AAAGCGGCGA CCGCCGTAAC AGCAGGAGGA TCACTGTTAG
                                                                    Sesa6

2601  TGCTGTCGGG TTTAACCTTG GCCGGGACCG TCATTGCATT GACTATTGCG ACGCCCTTAC TGGTGATCTT TTCTCCGGTG CTGGTTCCCG CCGTTATTAC
                                                                    Sesa6

2701  CATCTTCTTG TTAGGGGCAG GATTCCTGGC ATCAGGGGGA TTCGGAGTTG CGGCGTTGAG TGTCTTAAGT TGGATCTACC GTTATCTGAC TGGAAAGCAC
                                                                    Sesa6

2801  CCGCCTGGGG CCGATCAACT GGAGTCAGCC AAAACGAAAT TGGCGTCAAA AGCGCGTGAA ATGAAGGACC GTGCTGAGCA GTTTTCTCAG CAGCCTGTGG
                                                                           stop
             Sesa6                                                6x His Tag

2901  CAGGATCCCA GACATCACCA TGGCTCGAGC ACCACCACCA CCACCACTGA G
```

Figure 74 continued.

```
                                                                                                        S-Tag
                                                                    rbs
                                                            GAAGGAG ATATACATAT GAAAGAAACC
  1
                                                                    Ole3.1
              S-Tag                          thrombin
101  GCTGCTGCTA AATTCGAACG CCAGCACATG GACAGCCCAG ATCTGGGTAC CCTGGTGCCA CGCGGTTCCA TTATGGTCAA CAACAGCAGA
                                                            Ole3.1
201  CCAGGGCGCC TCACCTGCAG CTGCAGCCGC GCGCCCAGCG GCGGCCACCG CCGTGACAGC CGGCGGCTCG CTTCTCGTCC TCTCTGGCCT
                                                            Ole3.1
301  CACTTTAGCC GGAACTGTTA TTGCGCTCAC CATCGCCACT CCGCTCGCTT CCCCGTTCTG TGATCTTTAG GTGCCGGCGG TCATAACCAT TTTCTTGCTG
                                                            Ole3.1
401  GGTGCGGGGTT TTCTGGCATC CGGAGGCTTC GGCCTGGCGG CGCTGAGTGT GCTGTCGTGG ATTTACAGAT ATCTGACAGG GAAACACCCG CCGGGGGCGG
                                                                                                  Hinge-1_to_2
501  ATCAGCTGGA ATCGGCAAAG ACGAAGCTGG CGAGCAAGGC CGAGAGATGG AAGGATAGGG CAGAGCAGTT CTCGCAGCAG CCTGTTGGAG GCGGTGGATC
      Hinge-1_to_2                                              Ole3.2
601  CGGAGGGCGGT GGTAGTATGG CTGAGCATTA TGGTCAACAA CAGCAGACCA GGGGCGCCTCA CCTGCAGCTG ACTGTTATTG CGCTCACCAT CGCCACTCCG AGTGAAGGCG
                                                            Ole3.2
701  GCCACCGCCG TGACAGCCGG CGGCTCGCTT CTCGTCCTCT CTGGCCTCAC TTTAGCCGGA ACTGTTATTG CGCTCACCAT CGCCACTCCG CTGCTTGTGA
                                                            Ole3.2
801  TCTTTAGCCC CGTTCTGGTG CCGGCGGTCA TAACCATTTT CTTGCTGGGT GCGGGTTTTC TGGCATCCGG AGGCTTCGGC GTGGCGGCGC TGAGTGTGCT
                                                            Ole3.2
901  GTCGTGGATT TACAGATATC TGACAGGGAA ACACCCCGCCG GGGGCGGATC AGCTGGAATC GGCAAAGACG AAGCTGGCGA GCAAGGCGCG AGAGATGAAG
                                                                       Hinge-2_to_3         stop
1001 GATAGGGCAG AGCAGTTCTC GCAGCAGCCT GTTGGGGGCG GTGGATCCGG TGGAGGGGGA TCCATGGCGA TATCGGATCC GAATTCGAGC TCCGTCGACA
                Ole3.2                                         His-Tag
1101 AGCTTGCGGC CGCACTCGAG CACCACCACC ACCACCACTG A
```

Figure 75

```
                                                               rbs              S-Tag
                                                          GAAGGAG ATATACATAT GAAAGAAACC
                                                                  Sesame oleosin S-Tag                              thrombin
  1  GCTGCTGCTA AATTCGAACG CCAGCACATG GACAGCCCAG ATCTGGGTAC CCTGGTGCCA CGCGGTTCCA TGGCTGAGCA TTATGGTCAA CAACAGCAGA
                                                                                    Sesame oleosin 101  CCAGGGGCGCC TCACCTGCAG CTGCAGCCGC GCGCCCAGCG GGTAGTGAAG GCGGCCACCG CCGTGACACAGC CGGCGGCTCG CTTCTCGTCC TCTCTTGGCCT
                                                                                           Sesame oleosin 201  CACTTTAGCC GGAACTGTTA TTGCGCTCAC CATCGCCACT CCGCTGCTTG TGATCTTTTAG CCCCGTTCTG GTGCCGGCGG TCATAACCAT TTTCTTGCTG
                                                                                           Sesame oleosin 301  GGTGCGGGTT TTCTGGCATC CGGAGGCTTC GGCGTGGCGG CGCTGAGTGT GCTGTCGTGG ATTTACAGAT ATCTGACAGG GAAACACCCG CCGGGGGCGG
                                                                                                    Sesame oleosin 401  ATCAGCTGGA ATCGGCAAAG ACGAAGCTGG CGAGCAAGGC GCGAGAGATG AAGGATAGGG CAGAGCAGTT CTCGCAGCAG CCTGTTCCAT GGCGATATCG
                                                                                                                   Ole3.1

501  GATCCGAATT CGAGCTCCGT CGACAAGCTT GCGGCCCGCTT GCTCCGTTAA AAAAAACCAT GGCTGAGCAT TATGGTCAAC AACAGCAGAC CAGGGCGCCT
                                                                           Ole3.1

601  CACCTGCAGC TGCAGCCGCG CGCCCAGCGG GTAGTGAAGG CGGCCACCGC CGTGACACCGC GGCGGCTCGC TTCTCGTCCT CTCTGGCCTC ACTTTAGCCG
                                                              Ole3.1

701  GAACTGTTAT TGCGCTCACC ATCGCCACTC CGCTGCTTGT GATCTTTTAG CCCGTTCTGG TGCCGGCGGT CATAACCATT TTCTTGCTGG GTGCGGGTTT
                                                                Ole3.1

801  TCTGGCATCC GGAGGCTTCG GCGTGGCGGC GCTGAGTGTG CTGTCGTGGA TTTACAGAGG AACACCCGC CGGGGGCGGA TCAGCTGGAA
                                             Ole3.1                                         Hinge-1_to_2
```

Figure 76

```
1001  TCGGCAAAGA CGAAGCTGGC GAGCAAGGCG GAGAGATGA AGGATAGGGC AGAGCAGTTC TCGCAGCAGC CTGTTGGAGG CGGTGGATCC GGAAGGCGGTG
                                                              Ole3.2
      Hinge-1_to_2
1101  GTAGTATGGC TGAGCATTAT GGTCAACAAC AGCAGACCAG GGCGGCCTCAC CTGCAGCTGC AGCCGCGCGC CCAGCGGGTA GTGAAGGCGG CCACCGCCGT
                                                              Ole3.2
1201  GACAGCCGGC GGCTCGCTTC TCGTCCTCTC TGGCCCTCACT TTAGCCGGAA CTGTTATTGC GCTCACCATC GCCACTCCGC TGCTTGTGAT CTTTAGCCCC
                                                              Ole3.2
1301  GTTCTGGTGC CGGCGGTCAT AACCATTTTC TTGCTGGGTG CGGGTTTTCT GGCATCCGGA GGCTTCGGCG TGGCGGCGCT GAGTGTGCTG TCGTGGATTT
                                                              Ole3.2
1401  ACAGATATCT GACAGGGAAA CACCCGCCGG GGGCGGATCA GCTGGAATCG GCAAAGACGA AGCTGGCGAG CAAGGCGCGA GAGATGAAGG ATAGGGCAGA
              Ole3.2                       Hinge-2_to_3
1501  GCAGTTCTCG CAGCAGCCTG TTGGGGGCGG TGGATCCGGT GGAGGGGGAT CCATGGCTGA GCATTATGGT CAACAACAGC AGACCAGGGC GCCTCACCTG
                                                              Ole3.3
1601  CAGCTGCAGC CGCGCGCCCA GCGGGTAGTG AAGGCGGCCA CCGCCGTGAC AGCCGGCGGC TCGCTTCTCG TCCTCTCTGG CCTCACTTTA GCCGGAACTG
                                                              Ole3.3
1701  TTATTGCGCT CACCATCGCC ACTCCGCTGC TTGTGATCTT TAGCCCCGTT CTGGTGCCGG CGGTCATAAC CATTTTCTTG CTGGGTGCGG GTTTTCTGGC
                                                              Ole3.3
1801  ATCCGGAGGC TTCGGCGTGG CGGCGCTGAG TGTGCTGTCG TGGATTTACA GATATCTGAC AGGGAAACAC CCGCCGGGGG CGGATCAGCT GGAATCGGCA
                                                              Ole3.3                                                    Stop
                                                                                                                    His-Tag
1901  AAGACGAAGC TGGCGAGCAA GGCGCGAGAG ATGAAGGATA GGGCAGAGCA GTTCTCGCAG CAGCCTGTTC CATGGCTCGA GCACCACCAC CACCACCACT
      Stop
2001  GA
```

Figure 76 continued

```
                                                                                  GAAGGAG ATATACATAT GAAAGAAACC
                                                                                          Ole3.1
                                        rbs              S-Tag
                                                thrombin
  1                                                                               |---------------------------
      |-----------------------------------------------------------------|
                            S-Tag
101   GCTGCTGCTA AATTCGAACG CCAGCACATG GACAGCCCAG ATCTGGGTAC CCTGGTGCCA CGCGGTTCCA TGGCTGAGCA TTATGGTCAA CAACAGCAGA
                                                         Ole3.1
201   CCAGGGCGCC TCACCTGCAG CTGCAGCCGC GCGCCCAGCG GGTAGTGAAG GCGGCCACCG CCGTGACAGC CGGCGGCTCG CTTCTCGTCC TCTCTGGCCT
                                                             Ole3.1
301   CACTTTAGCC GGAACTGTTA TTGCGCTCAC CATCGCCACT CCGCTGCTCT CGCCGTTCTG TGATCTTTAG CCCCGTTCTG GTGCCGGGCGG TCATAACCAT TTTCTTGCTG
                                                                 Ole3.1
401   GGTGCGGGTT TTCTGGCATC CGGAGGCTTC GGCGTGGCGG CGCTGAGTGT GCTGTCGTGG ATTTACAGAT ATCTGACAGG GAAACACCCG CCGGGGCGG
                                                                                                       Hinge-1_to_2
                     Ole3.1
501   ATCAGCTGGA ATCGCAAAG ACGAAGCTGG CGAGCAAGGC GCGAGAGATG AAGGATAGGG CAGAGCAGTT CTCGCAGCAG CCTGTTGGAG GCGGTGGATC
       |--------------|
       Hinge-1_to_2                                                  Ole3.2
601   CGGAGGCGGT GGTAGTATGG CTGAGCATTA TGGTCAACAA CAGCAGACCA GGGCGGCCTCA CCTGCAGCTG CAGCCCGCCG CCCAGCGGGT AGTGAAGGCG
                                                      Ole3.2
701   GCCACCGCCG TGACAGCCGG CGGCTCGCTT CTCGTCCTCT CTGGCCTCAC TTTAGCCGGA ACTGTTATTG CGCTCACCAT CGCCACTCCG CTGCTTGTGA
                                              Ole3.2
801   TCTTTAGCCC CGTTCTGGTG CCGGCGGTCA TAACCATTTT CTTGCTGGGT GCGGGTTTTC TGGCATCCGG AGGCTTCGGC GTGGCGGCGC TGAGTGTGCT
                                              Ole3.2
```

Figure 77

```
 901  GTCGTGGATT TACAGATATC TGACAGGGAA ACACCCGCCG GGGGCGGATC AGCTGAATC GGCAAAGACG AAGCTGGCGA GCAAGGCGCG AGAGATGAAG
                                          Ole3.2                                    Hinge-2_to_3

1001  GATAGGGCAG AGCAGTTCTC GCAGCAGCCT GTTGGGGGCG TGGAGGGGGA TCCATGGGAT ATCGGATCCG AATTCGAGCT CCGTCGACAA
                                                                         Ole3.1

1101  GCTTGCGGCC GCTTGCTCCG TTAAAAAAAA CCATGGCTGA GCATTATGGT CAACAACAGC AGACCAGGGC GCCTCACCTG CAGCTGCAGC CGCGCGCCA
                                                                                     Ole3.1

1201  GCGGGTAGTG AAGGCGGCCA CCGGCCGTGAC AGCCGGCGGC TCGCTTCCTG CCTCTCTCGG CCCGGAACTG TTATTGCGCT CACCATCGCC
                                                                     Ole3.1

1301  ACTCCGCTGC TTGTGATCTT TAGCCCCCGTT CTGGTGCCGG CGGTCATAAC CATTTTCTTG CTGGGTGCGG GTTTTCTCGG ATCCGGAGGC TTCGGCGTGG
                                                       Ole3.1

1401  CGGCGCTGAG TGTGCTGCTG GGATTTACA GATATCTGAC AGGGAAACAC CCGCCGGGGG CGGATCAGCT GGAATCGGCA AAGACGAAGC TGGCGAGCAA
                                                                                    Hinge-1_to_2                              Ole3.2

1501  GGCGCCGAGAG ATGAAGGATA GGGCAGAGCA GTTCTCGCAG CAGCCTGTTG GAGGCGGTGG ATCCGGAGGC GGTGGTAGTA TGGCTGAGCA TTATGGTCAA
                                                        Ole3.2

1601  CAACAGCAGA CCAGGGCGCC TCACCTGCAG CTGCAGCCGC GCGCCCAGCG GGTAGTGAAG GCGGCCACCG CCGTGACAGC CGGCGGCTCG CTTCTCGTCC
                                                        Ole3.2

1701  TCTCTCGGCCT CACTTTAGCC GGAACTGTTA TTGCGCTCAC CATCGCCACT CCGCTGCTTG TGATCTTTAG CCCCGTTCTG GTGCCGGCGG TCATAACCAT
                                                        Ole3.2

1801  TTTCTTGCTG GGTGCGGGTT TTCTCGGCAT CCGGAGGCTTC GGCGTGGCGG CGCTGAGTGT GCTGCTGGTGG ATTTACAGAG GAAACACCCG
                                                                                                           Hinge-
   2_to_3                                                                                                   Ole3.2

1901  CCGGGGGCGG ATCAGCTGGA ATCGGCAAAG ACGAAGCTGG CGAGCAAGGC CGAGAGATG AAGGATAGGG CAGAGCAGTT CTCGCAGCAG CCTGTTGGGG
               Hinge_2_to_3                                                    Ole3.3

2001  GCGGTGGATC CGGTGGAGGG GGATCCATGG CTGAGCATTA TGGTCAACAA CAGCAGACCA GGGCGCCTCA CCTGCAGCTG CAGCCGCGCG CCCAGCGGGT
                                                                   Ole3.3

2101  AGTGAAGGCG GCCACCGCCG TGACAGCCGG CGGCTCGCTT CTCGTCCTCT CTGGCCTCAC TTTAGCCGGA ACTGTTATTG CGCTCACCAT CGCCACTCCG
```

Figure 77 continued

```
                                            Ole3.3
2201  CTGCTTGTGA TCTTTAGCCCC CGTTCTGGTG CCGGCGGTCA TAACCATTTT CTTGCTGGGT GCGGGTTTTC TGGCATCCGG AGGCTTCGGC GTGGCGGCGC
                                                              Ole3.3
2301  TGAGTGTGCT GTCGTGGATT TACAGATATC TGACAGGGAA ACACCCGCCG GGGGCGGATC AGCTGGAATC GGCAAAGACG AAGCTGGCGA GCAAGGCGCG
              Ole3.3                                                       His-Tag
2401  AGAGATGAAG GATAGGGCAG AGCAGTTCTC GCAGCAGCCT GTTCCATGGC TCGAGCACCA CCACCACCAC CACTGA
```

Figure 77 continued

```
  1  MKETAAAKFE    RQHMDSPDLG    TLVPRGSMAE    HYGQQQQTRA
     PHLQLQPRAQ
 51  RVVKAATAVT    AGGSLLVLSG    LTLAGTVIAL    TIATPLLVIF
     SPVLVPAVIT
101  IFLLGAGFLA    SGGFGVAALS    VLSWIYRYLT    GKHPPGADQL
     ESAKTKLASK
151  AREMKDRAEQ    FSQQPVPWLI    SDPNSSSVDK    LAAALEMAEH
     YGQQQQTRAP
201  HLQLQPRAQR    VVKAATAVTA    GGSLLVLSGL    TLAGTVIALT
     IATPLLVIFS
251  PVLVPAVITI    FLLGAGFLAS    GGFGVAALSV    LSWIYRYLTG
     KHPPGADQLE
301  SAKTKLASKA    REMKDRAEQF    SQQPVAGSQT    SHMFKWPSAM
     AEHYGQQQQT
351  RAPHLQLQPR    AQRVVKAATA    VTAGGSLLVL    SGLTLAGTVI
     ALTIATPLLV
401  IFSPVLVPAV    ITIFLLGAGF    LASGGFGVAA    LSVLSWIYRY
     LTGKHPPGAD
451  QLESAKTKLA    SKAREMKDRA    EQFSQQPVAG    SQTSSSELPW
     VDMAEHYGQQ
501  QQTRAPHLQL    QPRAQRVVKA    ATAVTAGGSL    LVLSGLTLAG
     TVIALTIATP
551  LLVIFSPVLV    PAVITIFLLG    AGFLASGGFG    VAALSVLSWI
     YRYLTGKHPP
601  GADQLESAKT    KLASKAREMK    DRAEQFSQQP    VAGSQTSSTP
     SSWHMMAEHY
651  GQQQQTRAPH    LQLQPRAQRV    VKAATAVTAG    GSLLVLSGLT
     LAGTVIALTI
701  ATPLLVIFSP    VLVPAVITIF    LLGAGFLASG    GFGVAALSVL
     SWIYRYLTGK
```

Figure 78

```
751  HPPGADQLES   AKTKLASKAR   EMKDRAEQFS   QQPVAGSQTS
     IDQQVNVHMA
801  EHYGQQQQTR   APHLQLQPRA   QRVVKAATAV   TAGGSLLVLS
     GLTLAGTVIA
851  LTIATPLLVI   FSPVLVPAVI   TIFLLGAGFL   ASGGFGVAAL
     SVLSWIYRYL
901  TGKHPPGADQ   LESAKTKLAS   KAREMKDRAE   QFSQQPVAGS
     QTSPWLEHHH
951  HHH*
```

Figure 78 continued

```
  1  MKETAAAKFE    RQHMDSPDLG    TLVPRGSMAE    HYGQQQQTRA
     PHLQLQPRAQ
 51  RVVKAATAVT    AGGSLLVLSG    LTLAGTVIAL    TIATPLLVIF
     SPVLVPAVIT
101  IFLLGAGFLA    SGGFGVAALS    VLSWIYRYLT    GKHPPGADQL
     ESAKTKLASK
151  AREMKDRAEQ    FSQQPVGGGG    SGGGGSMAEH    YGQQQQTRAP
     HLQLQPRAQR
201  VVKAATAVTA    GGSLLVLSGL    TLAGTVIALT    IATPLLVIFS
     PVLVPAVITI
251  FLLGAGFLAS    GGFGVAALSV    LSWIYRYLTG    KHPPGADQLE
     SAKTKLASKA
301  REMKDRAEQF    SQQPVGGGGS    GGGGSMAISD    PNSSSVDKLA
     AALEHHHHHH
351  *
```

Figure 79

```
  1  MKETAAAKFE   RQHMDSPDLG   TLVPRGSMAE   HYGQQQQTRA
     PHLQLQPRAQ
 51  RVVKAATAVT   AGGSLLVLSG   LTLAGTVIAL   TIATPLLVIF
     SPVLVPAVIT
101  IFLLGAGFLA   SGGFGVAALS   VLSWIYRYLT   GKHPPGADQL
     ESAKTKLASK
151  AREMKDRAEQ   FSQQPVPWRY   RIRIRAPSTS   LRPLAPLKKT
     MAEHYGQQQQ
201  TRAPHLQLQP   RAQRVVKAAT   AVTAGGSLLV   LSGLTLAGTV
     IALTIATPLL
251  VIFSPVLVPA   VITIFLLGAG   FLASGGFGVA   ALSVLSWIYR
     YLTGKHPPGA
301  DQLESAKTKL   ASKAREMKDR   AEQFSQQPVG   GGGSGGGGSM
     AEHYGQQQQT
351  RAPHLQLQPR   AQRVVKAATA   VTAGGSLLVL   SGLTLAGTVI
     ALTIATPLLV
401  IFSPVLVPAV   ITIFLLGAGF   LASGGFGVAA   LSVLSWIYRY
     LTGKHPPGAD
451  QLESAKTKLA   SKAREMKDRA   EQFSQQPVGG   GGSGGGGSMA
     EHYGQQQQTR
501  APHLQLQPRA   QRVVKAATAV   TAGGSLLVLS   GLTLAGTVIA
     LTIATPLLVI
551  FSPVLVPAVI   TIFLLGAGFL   ASGGFGVAAL   SVLSWIYRYL
     TGKHPPGADQ
601  LESAKTKLAS   KAREMKDRAE   QFSQQPVPWL   EHHHHHH*
```

Figure 80

```
  1  MKETAAAKFE    RQHMDSPDLG    TLVPRGSMAE    HYGQQQQTRA
     PHLQLQPRAQ
 51  RVVKAATAVT    AGGSLLVLSG    LTLAGTVIAL    TIATPLLVIF
     SPVLVPAVIT
101  IFLLGAGFLA    SGGFGVAALS    VLSWIYRYLT    GKHPPGADQL
     ESAKTKLASK
151  AREMKDRAEQ    FSQQPVGGGG    SGGGGSMAEH    YGQQQQTRAP
     HLQLQPRAQR
201  VVKAATAVTA    GGSLLVLSGL    TLAGTVIALT    IATPLLVIFS
     PVLVPAVITI
251  FLLGAGFLAS    GGFGVAALSV    LSWIYRYLTG    KHPPGADQLE
     SAKTKLASKA
301  REMKDRAEQF    SQQPVGGGGS    GGGGSMGYRI    RIRAPSTSLR
     PLAPLKKTMA
351  EHYGQQQQTR    APHLQLQPRA    QRVVKAATAV    TAGGSLLVLS
     GLTLAGTVIA
401  LTIATPLLVI    FSPVLVPAVI    TIFLLGAGFL    ASGGFGVAAL
     SVLSWIYRYL
451  TGKHPPGADQ    LESAKTKLAS    KAREMKDRAE    QFSQQPVGGG
     GSGGGGSMAE
501  HYGQQQQTRA    PHLQLQPRAQ    RVVKAATAVT    AGGSLLVLSG
     LTLAGTVIAL
551  TIATPLLVIF    SPVLVPAVIT    IFLLGAGFLA    SGGFGVAALS
     VLSWIYRYLT
601  GKHPPGADQL    ESAKTKLASK    AREMKDRAEQ    FSQQPVGGGG
     SGGGGSMAEH
651  YGQQQQTRAP    HLQLQPRAQR    VVKAATAVTA    GGSLLVLSGL
     TLAGTVIALT
```

Figure 81

701 IATPLLVIFS    PVLVPAVITI    FLLGAGFLAS    GGFGVAALSV
    LSWIYRYLTG
751 KHPPGADQLE SAKTKLASKA REMKDRAEQF SQQPVPWLEH HHHHH*

Figure 81 continued

```
  1  MAEHYGQQQQ    TRAPHLQLQP    RAQRVVKAAT    AVTAGGSLLV
     LSGLTLAGTV
 51  IALTIATPLL    VIFSPVLVPA    VITIFLLGAG    FLASGGFGVA
     ALSVLSWIYR
101  YLTGKHPPGA    DQLESAKTKL    ASKAREMKDR    AEQFSQQPVG
     GGGSGGGGSM
151  AEHYGQQQQT    RAPHLQLQPR    AQRVVKAATA    VTAGGSLLVL
     SGLTLAGTVI
201  ALTIATPLLV    IFSPVLVPAV    ITIFLLGAGF    LASGGFGVAA
     LSVLSWIYRY
251  LTGKHPPGAD    QLESAKTKLA    SKAREMKDRA    EQFSQQPVGG
     GGSGGGGSMA
301  EHYGQQQQTR    APHLQLQPRA    QRVVKAATAV    TAGGSLLVLS
     GLTLAGTVIA
351  LTIATPLLVI    FSPVLVPAVI    TIFLLGAGFL    ASGGFGVAAL
     SVLSWIYRYL
401  TGKHPPGADQ LESAKTKLAS KAREMKDRAE QFSQQPVPWL E*
```

Figure 82

```
301    MAEHY GQQQQTRAPH LQLQPRAQRV
351    VKAATAVTAG    GSLLVLSGLT    LAGTVIALTI    ATPLLVIFSP
       VLVPAVITIF
401    LLGAGFLASG    GFGVAALSVL    SWIYRYLTGK    HPPGADQLES
       AKTKLASKAR
451    EMKDRAEQFS QQPVPWLEHH HHHH*
```

Figure 83

```
         CaMV 35S                                                                          TCGACGAATT AATTCCAATC
12501                                                        CaMV 35S
12601    CCACAAAAAT CTGAGCTTAA CAGCACACAGTT GCTCCTCTCA GAGCAGAATC GGGTATTCAA CACCCTCATA TCAACTACTA CGTTGTGTAT AACGGTCCAC
                                                             CaMV 35S
12701    ATGCCGGTAT ATACGATGAC TGGGGTTGTA CAAAGGCGGC AACAAACGGC GTTCCCGGAG TTGCACACAA GAAATTTGCC ACTATTACAG AGGCAAGAGC
                                                             CaMV 35S
12801    AGCAGCTGAC GCGTACACAA CAAGTCAGCA AACAGACAGG TTGAACTTCA TCCCCAAAGG AGAAGCTCAA CTCAAGCCCA AGAGCTTTGC TAAGGCCCTA
                                                             CaMV 35S
12901    ACAAGCCCAC CAAAGCAAAA AGCCCACTGG CTCACGCTAG GAACCAAAAG GCCCAGCAGT GATCCAGCCC CAAAAGAGAT CTCCTTTGCC CCGGAGATTA
                                                             CaMV 35S
13001    CAATGGACGA TTTCCTCTAT CTTTACGATC TAGGAAGGAA GTTCGAAGGT GAAGGTGACG ACACTATGTT CACCACTGAT AATGAGAAGG TTAGCCTCTT
                                                             CaMV 35S
13101    CAATTTCAGA AAGAATGCTG ACCCACAGAG GGTTAGAGAG GCCTACGCAG CAGGTCTCCAT CAAGACGATC TACCCGAGTA ACAATCTCCA GGAGATCAAA
                                                             CaMV 35S
13201    TACCTTCCCA AGAAGGTTCA AGATGCAGTC AAAAGATTCA GGACTAATTG CATCAAGAAC ACAGAGAAAG ACATATTTCT CAAGATCAGA AGTACTATTC
                                                             CaMV 35S
13301    CAGTATGGAC GATTCAAGGC TTGCTTCCATA AACCAAGGCA AGTAATAGAG ATTGGAGTCT CTAAAAAGGT AGTTCCTACT GAATCTAAGG CCATGCATGG
                                                             CaMV 35S
13401    AGTCTAAGAT TCAAATCGAG GATCTAACAG AACTCGCCGT GAAGACTGGC GAACAGTTCA TACAGAGTCT TTTACGACTC AATGACACGA AGAAAATCTT
                                                             CaMV 35S
13501    CGTCAACATG GTGGAGCACG ACACCCTGGT CTACTCCAAA AATGTCAAAG ATACAGTCTC AGAAGACCAA AGGGCTATTG AGACTTTTCA ACAAAGGATA
                                                             CaMV 35S
13601    ATTTCGGGAA ACCTCCTCGG ATTCCATTGC CCAGCTATCT GTCACTTCAT CGAAAGGACA GTAGAAAAGG AAGTGGCTC CTACAAATGC CATCATTGCG
```

Figure 97

```
13701  ATAAAGGAAA GGCTATCATT CAAGATTCTT CTGCCGACAG TGGTCCCAAA GATGGACCCC CACCCACGAG GAGCATCGTG GAAAAAGAAG ACGTTCCAAC
                                                              CaMV 35S
13801  CACGTCTTCA AAGCAAGTGG ATTGATGTGA CATCTCCACT GACGTAAGGG ATGACGCACA ATCCCACTAT CCTTCGCAAG ACCCTTCCTC TATATAAGGA
                             Primer - 35S(3'end)Fwd
       CaMV 35S
                                                                                                             -20 to -10 from
                                                                                                                          modified
                                             XhoI
                                                  EcoRI
13901  AGTTCATTTC ATTTGGAGAG GACACGCTCG AGGAATTCGG TACCCCATC
       original oleosin
       Joshi context seq
                                                                                        attB1a
                                                                                               attB1b
13901                                                         A CAAGTTTGTA CAAAAAAGCA GGCTCCGCGG CCGTTGCTC CGTTAAAAA
       modified Joshi context seq NcoI                                              sesala
14001  AACCATGGCA GAGCACTACG GGCAGCAGCA ACAAACACGT GCCCCCCACT TGCAACTGCA ACCGGCGTGCT CAGGCGTGTTG TAAAGGCAGC GACCGCGGTT
                                                                                    sesala
14101  ACTGCCGGAG GTAGCCTGTT GGTGTTATCC GGGTTGACCC TGGCTGGAAC GGTCATTGCG CTGACAATCG CCACACCTCT CCTGGTGATC TTCTCGCCTG
                                                                                              UBQ10-Intron
       sesala
14201  TACTGGTCCC TGCAGGTAAA TTTCTGTGTT CCTTATTCTC TCAAAATCTT CGATTTTGTT TTCGTTCGAT CCCAATTTCG TATATGTTCT TTGGTTTAGA
                                                         UBQ10-Intron
14301  TTTCTGTTAAT CTTAGATCGA AGACGATTTT CTGGGTTTGA TCGTTAGATA TCATCTTAAT TCTCGATTAG GGTTTCATAG ATATCATCCG ATTTGTTCAA
                                                         UBQ10-Intron
```

Figure 97 continued

```
14401  ATAATTTGAG TTTTGTCGAA TAATTACTCT TCGATTTGTG ATTTCTATCT AGATCTGGTG TTAGTTTCTA GTTTGTGCGA TCGAATTTGT CGATTAATCT
       UBQ10-Intron                                                    sesa1b 14501  GAGTTTTTCT GATCTGCAGT CATCACCATC TTCCTCGTTGG GAGCGGGTTT TCTGGCAAGC GGGGGATTTG GTGTTGCCGC TCTGTCTGTG CTGTCCTGGA
                                                                          sesa1b 14601  TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
       sesa1b                                                                                         4xSTOP attB2a
14701  CGAGCAGTTC AGTCAGCAAC CGGTAGCAGG GTCTCAGACC AGCATCGATC CATCCTCCTG GCTCGAGTAA TGAAGCGGCC GCACCCAGCT TT
       attB2b

1  CTTGTACAAA GTGGT
```

Figure 97 continued

```
CaMV 35S                                                                                    TCGACGAATT AATTCCAATC
12501                                                                                            CaMV 35S
12601   CCACAAAAAT CTGAGCTTAA CAGCACAGTT GCTCCTCTCA GAGCAGAATC GGGTATTCAA CACCCTCATA TCAACTACTA CGTTGTGTAT AACGGTCCAC
                                                                CaMV 35S
12701   ATGCCGGTAT ATACGATGAC TGGGGTTGTA CAAAGGCGGC AACAAACGGC GTTCCCGGAG TTGCACACAA GAAATTTGCC ACTATTACAG AGGCAAGAGC
                                                                CaMV 35S
12801   AGCAGCTGAC GCGTACACAA CAAGTCAGCA AACAGACAGG TTGAACTTCA TCCCCAAAGG AGAAGCTCAA CTCAAGCCCA AGAGCTTTGC TAAGGCCCTA
                                                                CaMV 35S
12901   ACAAGCCCAC CAAAGCAAAA AGCCCACTGG CTCACGCTAG GAACCAAAAG GCCCAGCAGT GATCCAGCCC CAAAAGAGAT CTCCCTTGCC CCGGAGATTA
                                                                CaMV 35S
13001   CAATGGACGA TTTCCTCTAT CTTTACGATC TAGGAAGGAA GTTCGAAGGT GAAGGTGACG ACACTATGTT CACCACTGAT AATGAGAAGG TTAGCCTCTT
                                                                CaMV 35S
13101   CAATTTCAGA AAGAATGCTG ACCCACAGAT GGTTAGAGAG GCCTACGCAG CAGGTCTCAT CAAGACGATC TACCCGAGTA ACAATCTCCA GGAGATCAAA
                                                                CaMV 35S
13201   TACCTTCCCA AGAAGGTTAA AGATGCAGTC GGACTAATTG CATCAAGAAC ACAGAGAAAG ACATATATTCT CAAGATCAGA AGTACTATTC
                                                                CaMV 35S
13301   CAGTATGGAC GATTCAAGGC TTGCTTCATA AACCAAGGCA AGTAATAGAG ATTGGAGTCT CTAAAAAGGT AGTTCCTACT GAATCTAAGG CCATGCATGG
                                                                CaMV 35S
13401   AGTCTAAGAT TCAAATCGAG GATCTAACAG AACTCGCCGT GAAGACTGGC GAACAGTTCA TACAGAGTCT TTTTACGACTC AATGACAAGA AGAAAATCTT
                                                                CaMV 35S
13501   CGTCAACATG GTGGAGCACG ACACTCTGGT CTACTCCAAA AATGTCAAAG ATACAGTCTC AGAAGACCAA AGGGCTATTG AGACTTTTCA ACAAAGGATA
                                                                CaMV 35S
13601   ATTTCGGGAA ACCTCCTCGG ATTCCATTGC CCAGCTATCT GTCACTTCAT CGAAAGGACA GTAGAAAAGG AAGGTGGCTC CTACAAATGC CATCATTGCG
                                                                CaMV 35S
13701   ATAAAGGAAA GGCTATCATT CAAGATCTCT CTGCCGACAG TGGTCCCAAA GATGGACCCC CACCCACGAG GAGCATCGTG GAAAAAGAAG ACGTTCCAAC
                                                                CaMV 35S
```

Figure 98

```
13801  CACGTCTTCA AAGCAAGTGG ATTGATGTGA CATCTCCACT GACGTAAGGG ATGACGCACA ATCCCACTAT CCTTCGCAAG ACCCTTCCTC TATATAAGGA
                                                    Primer - 35S(3'end)Fwd
       ---------- CaMV 35S -------------------------------------------------------------------------------------

13901  AGTTCATTTC ATTTGGAGAG GACACGCTCG AGGAATTCGG TACCCCATC
                                    XhoI
                                         EcoRI
       ------ original oleosin -----------
       --- Joshi context seq --------------                                                       -20 to -10 from
                                                                                                      modified
       ------------------------------ modified Joshi context seq ----------                       ----------- attB1a
                                                                                   -----------------
13901                                       A CAAGTTTGTA CAAAAAAGCA GGCTCCGCGG CCGCTTGCTC CGTTAAAAAA
                                                                                              attB1b
                                                                                    -----------
       ------- sesa1a ---------------------

14001  AACCATGGCA GAGCACTACG GGCAGCAGCA ACAAACACGT GCCCCCCACT TGCAACTGCA ACCGCGTGCT CAGCGTGTTG TAAAGGCAGC GACCGCGGTT
                                                                                                       sesa1a 14101  ACTGCCGGAG GTAGCCTGTT GGTGTTATCC GGGTTGACCC TGGCTGGAAC GGTCATTGCG CTGACAATCG CCACACCTCT CCTGTGATC TTCTCGCCTG
       ----- sesa1a -----------------                                                                              --
                                                                                                          UBQ10-Intron 14201  TACTGGTCCC TGCAGGTAAA TTTCTGTGTT CCTTATTCTC TCAAAATCTT CGATTTTGTT TTCGTTCGAT CCCAATTTCG TATATGTTCT TTGGTTTAGA
       ------------------------------------------------- UBQ10-Intron --------------------------------------------

14301  TTCTGTTAAT CTTAGATCGA AGACGATTTT CTGGGTTTGA TCGTTAGATA TCATCTTAAT TCTCGATTAG GGTTTCATAG ATATCATCCG ATTTGTTCAA
       ------------------------------------------------- UBQ10-Intron --------------------------------------------

14401  ATAATTTGAG TTTTGTCGAA TAATTACTCT TCGATTTGTG ATTTCTATCT AGATCTGGTG TTAGTTTCTA GTTTGTGCGA TCGAATTTGT CGATTAATCT
       -------------------------------- UBQ10-Intron ------------                                  -----------------
                                                                                                          sesa1b
```

Figure 98 continued

```
14501  GAGTTTTTCT GATCTGCAGT CATCACCATC TTCCTGTTGG GAGCGGGTTT TCTGGCAAGC GGGGGATTTG GTGTTGCCGC TCTGTCTGTG CTGTCCTGGA
                                                                    sesa1b
14601  TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
             sesa1b                                                                                      sesa5
14701  CGAGCAGTTC AGTCAGCAAC CGGTAGCAGG GTCTCAGACC AGCATCGATC CATCCTCCTG GCATATGATG GCCGAGCACT ATGGACAACA GCAGCAGACG
                                                      sesa5
14801  CGTGCCCCTC ATCTGCAACT GCAACCCCGT GCTCAAACGTG TCGTTAAGGC TGCGACAGCA GTAACCGCTG GGGGTTCTCT GTTAGTGTTG TCAGGGCTGA
                                                      sesa5
14901  CTTTGGCGGG GACGTTAATT GCGTTGACCA TTGCCACCCC GCTGTTAGTG ATTTTCAGCC CGGTACTGGT GCCAGCAGTT ATCACGATCT TCTTGCTGGG
                                                               sesa5
15001  TGCCGGATTC TTGGCAAGTG GAGGTTTTGG AGTTGCGGCG CTGTCAGTTT TATCGTTAT CTGACAGGAA AACATCCCCC AGGTGCCGAT
                                                sesa5
15101  CAGCTGGAGA GTGCCAAGAC AAAACTGGGC TCTAAGGCAC GTGAAATGAA GGATCGTGCC GAACAGTTTT CTCAACAGCC CGTAGCGGGG TCACAGACCT
                                                                         sesa6
15201  CGATCGATCA GCAGGTTAAC GTGCACATGG CCGAACATTA CGGACAGCAA CAACAGACGC GTGCTCCACA CCTGCAATTG CAACCGCGTG CTCAACGTGT
                                                                       sesa6
15301  TGTCAAAGCG GCGACCGCCG TAACAGCAGG AGGATCACTG TTAGTGCTGT CGGGTTTAAC CTTGGCCGGG ACCGTCATTG CATTGACTAT TGCGACGCCC
                                                                       sesa6
15401  TTACTGGTGA TCTTTTCTCC GGTGCTGGTT CCCGCCGTTA TTACCATCTT CTTGTTAGGG GCAGGATTCC TGGCATCAGG GGGATTCGGA GTTGCGGCGT
                                                                       sesa6
15501  TGAGTGTCTT AAGTTGGATC TACCGTTATC TGACTGGAAA GCACCCGCCT GGGGCCGATC AACTGGAGTC AGCCAAAACG AAATTGGCGT CAAAAGCGCG
             sesa6                                                                      4xSTOP
                                                                                                              attB2a
15601  TGAAATGAAG GACCGTGCTG AGCAGTTTTC TCAGCAGCCT GTGGCAGGAT CCCAGACATC ACCATGGCTC GAGTAATGAA GCGGCCGCAC CCAGCTTT
             attB2b
   1   CTTGTACAAA GTGGT
```

Figure 98 continued

```
        CaMV 35S                                                                TCGACGAATT AATTCCAATC
12501                                                               CaMV 35S
12601   CCACAAAAAT CTGAGCTTAA CAGCAGCAGTT GCTCCTCTCA GAGCAGAATC GGGTATTCAA CACCCTCATA TCAACTACTA CGTTGTGTAT AACGGTCCAC
                                                                          CaMV 35S
12701   ATGCCGGTAT ATACGATGAC TGGGGTTGTA CAAAGGCGGC AACAAACGGC GTTCCCGGAG TTGCACACAA GAAATTTGCC ACTATTACAG AGGCAAGAGC
                                                                          CaMV 35S
12801   AGCAGCTGAC GCGTACACAA CAAGTCAGCA AACAGACAGG TTGAACTTCA TCCCCAAAGG AGAAGCTCAA CTCAAGCCCA AGAGCTTTGC TAAGGCCCTA
                                                                          CaMV 35S
12901   ACAAGCCCAC CAAAGCAAAA AGCCCACTGG CTCACGCTAG GAACCAAAAG GCCCAGCAGT GATCCAGCGC CAAAAGAGAT CTCCTTTGCC CCGGAGATTA
                                                                          CaMV 35S
13001   CAATGGACGA TTTCCTCTAT CTTTACGATC TAGGAAGGAA GTTCGAAGGT GAAGGTGACG ACACTATGTT CACCACTGAT AATGAGAAGG TTAGCCTCTT
                                                                          CaMV 35S
13101   CAATTTCAGA AAGAATGCTG ACCCACAGAT GGTTAGAGAG GCCTACGCAG CAGGTCTCAT CAAGACGATC TACCCGAGTA ACAATCTCCA GGAGATCAAA
                                                                          CaMV 35S
13201   TACCTTCCCA AGAAGGTTCA AGATGCAGTC AAAAGATTCA GGACTAATTG AACCAAGGCA AGTAATAGAG ATTGGAGTCT CTAAAAAGGT CTAAAAAGGT GAATCTAAGG CCATGCATGG
                                                                          CaMV 35S
13301   CAGTATGGAC GATTCAAGGC TTGCTTTCATA AACCAAGGCA AGTAATAGAG ATTGGAGTCT CTAAAAAGGT AGTTCCTACT GAATCTAAGG CCATGCATGG
                                                                          CaMV 35S
13401   AGTCTAAGAT TCAAATCGAG GATCTAACAG AACTCGCCGT GAAGACTGGC GAACAGTTCA TACAGAGTCT TTTACGACTC AATGACAAGA AGAAAATCTT
                                                                          CaMV 35S
13501   CGTCAACATG GTGGAGCACG ACACTCTGGT CTACTCCAAA AATGTCAAAG ATACAGTCTC AGAAGACCAA AGGGCTATTG AGACTTTTCA ACAAAGGATA
                                                                          CaMV 35S
13601   ATTTCGGGAA ACCTCCTCGG ATTCCATTGC CCAGCTATCT GTCACTTTCT CGAAAGGACA GTAGAAAAGG AAGGTGGCTC CTACAAATGC CATCATTGCG
                                                                          CaMV 35S
```

Figure 99

```
13701  ATAAAGGAAA GGCTATCATT CAAGATCTCT CTGCCGACAG TGGTCCCAAA GATGGACCCC CACCCAGAGA GAGCATCGTG GAAAAGAAG ACGTTCCAAC
                                                                  CaMV 35S
13801  CACGTCTTCA AAGCAAGTGG ATTGATGTGA CATCTCCACT GACGTAAGGG ATGACGCACA ATCCCACTAT CCTTCGCAAG ACCCTTCCTC TATATAAGGA
                                        Primer - 35S(3'end)Fwd
        CaMV 35S                                                                                              -20 to -10 from
                                                                                                                  modified
                        XhoI
                        EcoRI
13901  AGTTCATTTC ATTTGGAGAG GACACGCTCG AGGAATTCGG TACCCCATC
        original oleosin
        Joshi context seq
                                                                                                    attB1b
                                                                                     attB1a       NotI
                                                                 A CAAGTTTGTA CAAAAAAGCA GGCTCCGCGG CCGCTTGCTC CGTTAAAAAP
13901  modified Joshi context seq
                                                     sesala
                NcoI
14001  AACCATGGCA GAGCACTACG GGCAGCAGCA ACAAACACGT GCCCCCCACT TGCAACTGCA ACCGGGTGCT CAGCGGTGTTG TAAAGGCAGC GACCGCGGTT
                                                                         sesala
14101  ACTGCCGGAG GTAGCCTGTT GGTGTTATCC GGGTTGACCC TGGCTGGAAC GGTCATTGCG CTGACAATCG CCACACCTCT CCTGTGATC TTCTCGCCTG
                                                                         UBQ10-Intron
        sesala
        PstI
```

Figure 99 continued

```
14201  TACTGGTCCCC TGCAGGTAAA TTTCTGTGTT CCTTATTCTC TCAAAATCTT CGATTTGTT  TTCGTTCGAT CCCAATTTCG TATATGTTCT TTGGTTTAGA
                                                     UBQ10-Intron 14301  TTCTGTTAAT CTTAGATCGA AGACGATTTT CTGGGTTTGA TCGTTAGATA TCATCTTAAT TCTCGATTAG GGTTTCATAG ATATCATCCG ATTTGTTCAA
                                                     UBQ10-Intron                                                   XbaI 14401  ATAATTTGAG TTTTGTCGAA TAATTACTCT TCGATTGTG ATTTCTATCT AGATCTGGTG TTAGTTTCTA GTTTGTGCGA TCGAATTTGT CGATTAATCT
       UBQ10-Intron
                       PstI                                                   sesa1b 14501  GAGTTTTTCT GATCTGCAGT CATCACCATC TTCCTGTTGG GAGCGGGTTT TCTGCAAGC GGGGGATTTG GTGTTGCCGC TCTGTCTGTG CTGTCCTGGA
                                                              sesa1b 14601  TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
       sesa1b                                                                                                sesa2
                                                              BstXI
                                                                     ClaI            XhoI
14701  CGAGCAGTTC AGTCAGCAAC CGGTAGCAGG GTCTCAGACC AGCATCGATC CATCCTCCTG GCTCGAGATG GCGGAACACT ACGGGCAACA ACAGCAGACT
                                                     sesa2

14801  CGTGCTCCCC ACCTGCAATT ACAACCCCGT GCCCAACGTG TTGTGAAAGC GGCAACAGCA GTAACGGCAG GGGGAAGTTT GCTGGTCTTA TCGGGGTTGA
       sesa2

Primer- Polyses-2R
                                      Primer- Polyses-2F
```

Figure 99 continued

```
14901 CCTTAGCGGG AACCGTGATT GCCCTGACAA TTGCGACTCC GCTGCTGGTT ATCTTCAGCC CCGTATTGGT TCCGGCCGTG ATCACGATTT TTTTGCTGGG
                                         sesa2
15001 GGCAGGATTT TTAGCCAGCG GAGGATTTGG GGTCGCAGCG TTGTCTGTGC TGAGTTGGAT CTATCGTTAT TTGACCGGGA AGCACCCACC TGGAGCAGAC
                                         sesa2
15101 CAGCTGGAGA GCGCGAAAAC GAAGCTGGCA TCGAAGGCGC GTGAAATGAA GGATCGTGCT GAACAATTCT CCCAGCAGCC TGTTGCCGGT TCTCAGACCA
       NdeI                                                                 sesa5
15201 GCCATATGAT GGCCGAGCAC TATGGACAAC AGCAGCAGAC GCGTGCCCCT CATCTGCAAC TGCAACCCCG TGCTCAACGT GTCGTTAAGG CTGCCGACAGC
                                                 sesa5
15301 AGTAACCGCT GGGGGTTCTC TGTTAGTGTT GTCAGGGCTG ACTTTGGCGG GGACGGTAAT TGCCGTTGACC CGCTGTTAGT GATTTTCAGC
                                                 sesa5
15401 CCGGTACTGG TGCCAGCAGT TATCACGATC TTCTTGCTGG GTGCCGGATT CTTTGGCAAGT GGAGTTGCGGC GCTGTCAGTT TTATCCTGGA
                                                 sesa5
15501 TCTATCGTTA TCTGACAGGA AAACATCCCC CAGGTGCCGA AGTGCCAAGA CAAAACTGGC GTCTAAGGCA CGTGAAATGA AGGATCGTGC
       sesa5                                                                                  sesa6
                                                            ClaI
15601 CGAACAGTTT TCTCAACAGC CCGTAGCGGG GTCACAGACC TCGATCGATC AGCAGGTTAA CGTGCACATG GCCGAACATT ACGGACAGCA ACAACGACG
                                                             sesa6
15701 CGTGCTCCAC ACCTGCAATT GCAACCGCGT GCTCAACCGTG TTGTCAAAGC GGCGACCGCC GTAACAGCAG GAGGATCACT GTTAGTGCTG TCGGGTTTAA
                                                             sesa6
       ---------
       Primer- Polyses-6R
       ---------
       Primer- Polyses-6F
15801 CCTTGGCCGG GACCGTCATT GCATTGACTA TTGCCGACGCC CTTACTGGTG ATCTTTTCTC CGGTGCTGGT TCCCGCCGTT ATTACCATCT TCTTGTTAGG
                                                             sesa6
```

Figure 99 continued

```
15901  GGCAGGATTC CTGGCATCAG GGGGATTCGG AGTTGCGGCG TTGAGTGTCT TAAGTTGGAT CTACCGTTAT CTGACTGGAA AGCACCCGCC TGGGGCCGAT
                                         ------------------sesa6------------------                              --BamHI--

16001  CAACTGGAGT CAGCCAAAAC GAAATTGGCG TCAAAAGCGC GTGAAATGAA GGACCGTGCT GAGCAGTTTT CTCAGCAGCC TGTGGCAGGA TCCCAGACAT
                        4xSTOP
            --XhoI--      --NotI--
       --NcoI--                              --attB2a--

16101  CACCATGGCT CGAGTAATGA AGCGGCCGCA CCCAGCTTT                XbaI
                                         --HindIII--
            --attB2b--                              --ClaI--  --BamHI--

1  CTTGTACAAA GTGGTGATGG GTTCGAAATC GATAAGCTTG GATCCTCTAG A
```

Figure 99 continued

```
                                                            TCGACGAATT AATTCCAATC
             CaMV 35S
12501
       CCACAAAAAT CTGAGCTTAA CAGCACACAGTT GCTCCTCTCA GAGCAGAATC GGGTATTCAA CACCCTCATA TCAACTACTA CGTTGTGTAT AACGGTCCAC
                                                            CaMV 35S
12601
       ATGCCGGTAT ATACGATGAC TGGGGTTGTA CAAAGGCGGC AACAAACGGC GTTCCCGGAG TTGCACACAA GAAATTTGCC ACTATTACAG AGGCAAGAGC
                                                            CaMV 35S
12701
       AGCAGCTGAC GCGTACACAA CAAGTCAGCA AACAGACAGG TTGAACTTCA TCCCCAAAGG AGAAGCTCAA CTCAAGCCCA AGAGCTTTGC TAAGGCCCTA
                                                            CaMV 35S
12801
       ACAAGCCCAC CAAAGCAAAA AGCCCACTGG CTCACGCTAG GAACCAAAAG GCCCAGCAGT GATCCAGCCC CAAAAGAGAT CTCCCTTTGCC CCGGAGATTA
                                                            CaMV 35S
12901
       CAATGGACGA TTTCCTCTAT CTTTACGATC TAGGAAGGAA GTTCGAAGGT GCCTACGCAG GAAGGTGACG ACACTATGTT CACCACTGAT AATGAGAAGG TTAGCCTCTT
                                                            CaMV 35S
13001
       CAATTTCAGA AAGAATGCTG ACCCACACAG GGTTAGAGAG GCCTACGCAG CAGGTCTCAT CAAGACGATC TACCCGAGTA ACAATCTCCA GGAGATCAAA
                                                            CaMV 35S
13101
       TACCTTCCCA AGAAGGTTAA AGATGCAGTC AAAAGATTCA GGACTAATTG CATCAAGAAC ACAGAGAAAG ACATATATTCT CAAGATCAGA AGTACTATTC
                                                            CaMV 35S
13201
       CAGTATGGAC GATTCAAGGC TTGCTTCATA AACCAAGGCA AGTAATAGAG ATTGGAGTCT CTAAAAAGGT AGTTCCTACT GAATCTAAGG CCATGCATGG
                                                            CaMV 35S
13301
       AGTCTAAGAT TCAAATCGAG GATCTAACAG AACTCGCCGT GAAGACTGGC GAACAGTTCA TACAGAGTCT TTTACGACTC AATGACAAGA AGAAAATCTT
                                                            CaMV 35S
13401
       CGTCAACATG GTGGAGCACG ACACTCTGGT CTACTCCAAA AATGTCAAAG ATACAGTCTC AGAAGACCAA AGGGCTATTG AGACTTTTCA ACAAAGGATA
                                                            CaMV 35S
13501
       ATTTCGGGAA ACCTCCTCGG ATTCCATTGC CCAGCTATCT GTCACTTCAT CGAAAGGACA GTAGAAAAGG AAGGTGGCTC CTACAAATGC CATCATTGCG
                                                            CaMV 35S
13601
       ATAAAGGAAA GGCTATCATT CAAGATCTCT CTGCCGACAG TGGTCCCAAA GATGGACCCC CACCCACGAG GAGCATCGTG GAAAAAGAAG ACGTTCCAAC
                                                            CaMV 35S
13701
```

Figure 100

```
13801  CACGTCTTCA AAGCAAGTGG ATTGATGTGA CATCTCCACT GACGTAAGGG ATGACGCACA ATCCCACTAT CCTTCGCAAG ACCCTTCCTC TATATAAGGA
                                            Primer - 35S(3'end) Fwd
                  CaMV 35S
                                    XhoI
                                                    EcoRI 13901  AGTTCATTTC ATTTGGAGAG GACACGCTCG AGGAATTCGG TACCCCATC
       original oleosin
                                                                                                -20    to    -10    from
       Joshi context seq
                                                                                                              modified
13901                                                          A CAAGTTTGTA CAAAAAAGCA GGCTCCGCCG CCGCTTGCTC CGTTAAAAAA
       modified Joshi context seq
                                                              attB1a          NotI
                                                                    attB1b
                                                               sesa1a 14001  AACCATGGCA GAGCACTACG GGCAGCAGCA ACAAAACGT GCCCCCCACT TGCAACTGCA ACCGGCGTGCT CAGCGTGTTG TAAAGGCAGC GACCGCGGTT
                                                               sesa1a 14101  ACTGCCGGAG GTAGCCTGTT GGTGTTATCC GGGTTGACCC TGGCTGGAAC GGTCATTGCG CTGACAATCG CCACACCTCT CCTGGTGATC TTCTCGCCTG
       sesa1a
                                                                                                UBQ10-Intron 14201  TACTGGTCCC TGCAGGTAAA TTTCTGTGTT CCTTATTCTC TCAAAATCTT CGATTTTGTT TTCGTTCGAT CCCAATTTCG TATATGTTCT TTGGTTTAGA
                                                                                                UBQ10-Intron 14301  TTCTGTTAAT CTTAGATCGA AGACGATTTT CTGGGTTTGA TCGTTAGATA TCATCCTTAAT TCTCGATTAG GGTTTCATAG ATATCATCCG ATTTGTTCAA
                                                                                                UBQ10-Intron 14401  ATAATTTGAG TTTTGTCGAA TAATTACTCT TCGATTTGTG ATTTCTATCT AGATCTGGTG TTAGTTTCTA GTTTGTGCGA TCGAATTTGT CGATTAATCT
                                                                                                UBQ10-Intron
                                                               sesa1b
```

Figure 100 continued

```
14501  GAGTTTTTCT GATCTGCAGT CATCACCATC TTCCTGTTGG GAGCGGGTTT TCTGGCAAGC GGGGGATTTG GTGTTGCCGC TCTGTCTGTG CTCTCCTGGA
                                                                                                sesa1b 14601  TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
              sesa1b                                                                       sesa2

14701  CGAGCAGTTC AGTCAGCAAC CGGTAGCAGG GTCTCAGACC AGCATCGATC CATCCTCCTG GCTCGAGATG GCGGAACACT ACGGGCAACA ACAGCAGACT

14801  CGTGCCTCCCC ACCTGCAATT ACAACCCCGT GCCCAACGTG TTGTGAAAGC GGCAACAGCA GTAACGGCAG GGGGAAGTTT GCTGGTCTTA TCGGGGTTGA
                  sesa2                                       sesa2

14901  CCTTAGCGGG AACCGTGATT GCCCTGACAA TTGCGACTCC GCTGCTGGTT ATCTTCAGCC CCGTATTGGT TCCGGCCGTG ATCACGATTT TTTTGCTGGG
                                                                     sesa2

15001  GGCAGGATTT TTAGCCAGCG GAGGATTTGG GGTCGCAGCG TTGTCTGTGC TGAGTTGGAT CTATCGTTAT TTGACCGGGA AGCACCCACC TGGAGCAGT
                                                                     sesa2

15101  CAGCTGAGA GCGCGAAAAC GAAGCTGGCA TCGAAGGCGC GTGAAATGAA GGATCGTGCT GAACAATTCT CCCAGCAGCC TGTTGCCGGT TCTCAGAC(
                                                                                                   sesa3

15201  GCCATATGTT TAAATGCCA AGCGCTATGG CCGAGCATTA TGGGCAGCAA CAGCAAACCC GTGCCCCGCA TCTGCAATTG CAACCTCGTG CCCAGCGTGT
                                                                              sesa3

15301  CGTTAAGGCG GCTACTGCGG TAACAGCGGG AGGGAGCTTA CTGGTATTAA GCGGGCTGAC ATTGGCCGGA ACGGTGATCG CCTTAACAAT CGCGACACCC
                                                                              sesa3

15401  TTGCTGGTCA TCTTCAGTCC GGTTCTGTG CCCGCGGTGA TTACGATTTT CCTGCTGGGA GCCGGTTTCT TAGCATCGGG GGGTTTTGGG GTAGCAGCCT
                                                                              sesa3

15501  TGAGTGTCCT GTCGTGATC TATCGTTACT TAACTGGAAA ACACCCCGCA GGAGCTGACC AGTTGGAGTC TGCAAAAACT AAGCTGGCGT CCAAAGCCCG
           sesa3                                                                                          sesa4

15601  TGAAATGAAG GATCGTGCTG AGCAGTTTAG CCAGCAGCCA GTTGCGGGAA GTCAGACCTC TTCATCTGAG CTCCCATGGG TCGACATGGC GGAGCATTAC
                                                                                 sesa4

15701  GGTCAACAGC AACAGACCCG TGCTCCGCAC TTACAAATTGC AACCACGTGC TCAACGTGTC GTAAAAGCCG CCACGGCAGT TACTGCGGGG GGATCATTGC
                                                                              sesa4

15801  TGGGTTTAAG TGGGTTGACA CTGGCGGGGA CAGTTATTGC ACTGACGATC GCGACCCCCT TGTTAGTGAT CTTCTCCCCC GTTCTGGTTC CGGCGGTCAT
                                                                              sesa4
```

Figure 100 continued

```
15901  TACAATCTTT CTGTTGGGTG CCGGATTTTT AGCCTCTGGG GGATTTGGAG TAGCTGCCCT GTCAGTGTTG AGCTGGATCT ACCGTTACTT AACAGGGAAG
                                         sesa4
16001  CACCCTCCCG GGGCAGATCA GTTGGAAAGC GCCAAGACCA AGCTGGCAAG TAAAGCGCGT GAAATGAAGG ACCGTGCCGA ACAATTTTCG CAGCAACCGG
       sesa4                                                                                           sesa5
16101  TTGCGGGATC ACAGACCTCT AGTACTCCAT CCTCCTGGCA TATGATGGCC GAGCACTATG GACAACAGCA GCAGACGCGT GCCCCTCATC TGCAACTGCA
                                                                sesa5
16201  ACCCCGTGCT CAACGTGTCG TTAAGGCTGC GACAGCAGTA ACCGCTGGGG GTTCTCTGTT AGTGTGTGTCA GGGCTGACTT TGGCGGGGAC GGTAATTGCG
                                         sesa5
16301  TTGACCATTG CCACCCCGCT GTTAGTGATT TTCAGCCCGG TACTGGTGCC AGCAGTTATC ACGATCTTCT TGCTGGGTGC CGGATTCTTG GCAAGTGGAG
                                         sesa5
16401  GTTTTGGAGT TGCGGCGCTG TCAGTTTTAT CCTTGATCTA TCGTTATCTG ACAGGAAAAC ATCCCCCAGG TGCCGATCAG CTGGAGAGTG CCAAGACAAA
                                         sesa5
16501  ACTGGCGTCT AAGGCACGTG AAATGAAGGA CAGTTTTCTC AACAGCCCGT AGCGGGGTCA CAGACCTCGA TCGATCAGCA GGTTAACGTG
16601  CACATGGCCG AACATTACGG ACAGCAACAA CAGACGCGTG CTCCACACCT GCAATTGCAA CCGCGTGCTC AACGTGTTGT CAAAGCGGCG ACCGCCGTAA
                                         sesa6
16701  CAGCAGGAGG ATCACTGTTA GTGCTGTCGG GTTAACCTTT GGCCGGGACC GTCATTGCAT TGACTATTGC GACGCCCTTA CTGGTGATCT TTTCTCCGGT
                                         sesa6
16801  GCTGGTTCCC GCCGTTATTA CCATCTTCTT GTTAGGGGCA GGATTCCTGG CATCAGGGGG ATTCGGAGTT GCGGCGTTGA GTGTCTTAAG TTGGATCTAC
                                         sesa6
16901  CGTTATCTGA CTGGAAAGCA CCCGCCTGGG GCCGATCAAC TGGAGTCAGC CAAAACGAAA TTGGCGTCAA AAGCGCGTGA AATGAAGGAC CGTGCTGAGC
       sesa6                                                            4xSTOP
                                                                        ----------
                                                                             NotI
                                                                        ----------
17001  AGTTTTCTCA GCAGGCTGTG GCAGGATCCC AGACATCACC ATGGCTCGAG TAATGAAGCG GCCGCACCCA GCTTT
       attB2b                                                                    attB2a
       -----------                                                      ----------
    1  CTTGTACAAA GTGGT
```

Figure 100 continued

```
                                                      oleosin promoter
          ┌─────────────────────────────────────────────────────────────────────────────────────────┐
13401     GCAG GAACTCTCTG GTAAGCTAGC TCCACTCCCC AGAAACAACC GGGCGCCAAAT TGCGCGAATT GCTGACCTGA AGACGGAACA TCATCGTCGG
        ┌─┴┐                                              └─────────────────────────────────────────────────────
        NotI                                                               oleosin promoter 13501     GTCCTTGGGC GATTGCGGCG GAAGATGGGT CAGCTTGGGC TTGAGGACGA GACCCGAATC CGAGTCTGTT GAAAAGGTTG TTCATTGGGG ATTTGTATAC
        ──────────────────────────────────────────────────────────────────────────────────────────────────────────
                                                      oleosin promoter 13601     GGAGATTGGT CGTCGAGAGG TTTGAGGGAA AGGACAAATG GGTTTGGCTC TGGAGAAAGA GAGTGCGGCT TTAGAGAGAG AATTGAGAGG TTTAGAGAGA
        ──────────────────────────────────────────────────────────────────────────────────────────────────────────
                                                      oleosin promoter 13701     GATGCGGCGG CGATGAGCGG AGGAGAGACG ACGAGGACCT GCATTATCAA AGCAGTGACG TGGTGAAATT TGGAACTTTT AAGAGGCAGA TAGATTTATT
        ──────────────────────────────────────────────────────────────────────────────────────────────────────────
                                                      oleosin promoter
                           ┌──────┐
                            XbaI 13801     ATTTGTATCC ATTTTCTTCA TTGTTCTAGA ATGTCGCGGA ACAAATTTTA AAACTAAATC CTAAATTTTT CTAATTTTGT TGCCAATAGT GGATATGTGG
        ──────────────────────────────────────────────────────────────────────────────────────────────────────────

13901     GCCGTATAGA AGGAATCTAT TGAAGGCCCA AACCCATACT GACGAGCCCA AAGGTTCGTT TTGCGTTTTA TGTTTCGGTT CGATGCCAAC GCCACATTCT
        ──────────────────────────────────────────────────────────────────────────────────────────────────────────
                                                      oleosin promoter 14001     GAGCTAGGCA AAAAACAAAC GTGTCTTTGA ATAGACTCCT CTCGTTAACA CATGCAGCGG CTGCATGGTG ACGCCATTAA CACGTGGCCT ACAATTGCAT
        ──────────────────────────────────────────────────────────────────────────────────────────────────────────
          ┌─────────────────┐
          Primer - OlePro                              oleosin promoter 14101     GATGTCTCCA TTGACACGTG ACTTCTCGTC TCCTTTCTTA ATATATCTAA CAAACACTCC TACCTCTTCC AAAATATATA CACATCTTTT TGATCAATCT
        ──────────────────────────────────────────────────────────────────────────────────────────────────────────
                                                      oleosin promoter
```

Figure 101

```
14201  CTCATTCAAA ATCTCATTCT CTCTAGTAAA CAAGAACAAA AAAGGTACCC CATC                              -20 to -10 from
       original oleosin
       Joshi context seq                                                                              modified 13901                                                  A CAAGTTTGTA CAAAAAAGCA GGCTCCGCGCG CCGCTTGCTC CGTTAAAAAA
       modified Joshi context seq
            NcoI                                                        attB1a
                                                                             attB1b 14001  AACCATGGCA GAGCACTACG GGCAGCAGCA ACAAACACGT GCCCCCCACT TGCAACTGCA ACCGGCGTGCT CAGGCGTGTTG TAAAGGCAGC GACCGCGGTT
                                                            sesa1a 14101  ACTGCCGGAG GTAGCCCTGT GGTGTTATCC TGGCTGGAAC GGTCATTGCG CTGACAATCG CCACACCTCT CCTGGTGATC TTCTCGCCTG
       sesa1a                                                                     UBQ10-Intron 14201  TACTGGTCCC TGCAGGTAAA TTTCTGTGTT CCTTATTCTC TCAAAATCTT CGATTTTGTT TTCGTTCGAT CCCAATTTCG TATATGTTCT TTGGTTTAGA
                                                            UBQ10-Intron 14301  TTTCTTTAAT CTTAGATCGA AGACGATTTT CTGGGTTTGA TCGTTAGATA TCATCCTTAAT TCTCGATTAG GGTTTCATAG ATATCATCCG ATTTGTTCAA
                                                            UBQ10-Intron 14401  ATAATTTGAG TTTTGTCGAA TAATTACTCT TCGATTTGTG ATTTCTATCT AGATCTGGTG TTAGTTTCTA GTTTGTGCGA TCGAATTTGT CGATTAATCT
       UBQ10-Intron                                                                     sesa1b 14501  GAGTTTTTCT GATCTGCAGT CATCACCATC TTCCTGTTGG GAGCGGGTTT TCTGGCAAGC GGGGGATTTG GTGTTGCCGC TCTGTCTGTG CTGTCCTGGA
                                                            sesa1b
```

Figure 101 continued

```
14601 TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
            sesa1b                                                                  4xSTOP 14701 CGAGCAGTTC AGTCAGCAAC CGGTAGCAAC GTCTCAGACC AGCATCGATC CATCCTCCTG GCTCGAGTAA TGAAGCGGCC GCACCCAGCT TT
      attB2b                                                                                    attB2a

1 CTTGTACAAA GTGGT
```

Figure 101 continued

```
                                                                                                    oleosin promoter
         |----------------------------------------------------------------------------------------------------------------------------------|
         NotI
         ~~
13401    GCAG GAACTCTCTG GTAAGCTAGC TCCACTCCCC AGAAACAACC GGGCCCAAAT TGCGCGAATT GCTGACCTGA AGACGGAACA TCATCGTCGG
         |----------------------------------------------------------------------------------------------------------------------------------|
                                                                       oleosin promoter 13501    GTCCTTGGGC GATTGCGGCG GAAGATGGGT CAGCTTGGGC TTGAGGACGA GACCCGAATC CGAGTCTCTGTT GAAAAGGTTG TTCATTGGGG ATTTGTATAC
         |----------------------------------------------------------------------------------------------------------------------------------|
                                                                       oleosin promoter 13601    GGAGATTGGT CGTCGAGAGG TTTGAGGGAA AGGACAAATG GGTTTGGCTC TGGAGAAAGA GAGTGCGGCT TTAGAGAGAG AATTGAGAGG TTTAGAGAGA
         |----------------------------------------------------------------------------------------------------------------------------------|
                                                                       oleosin promoter 13701    GATGCGGCGG CGATGAGCGG AGGAGAGACG ACGAGGACCT GCATTATCAA AGCAGTGACG TGGTGAAATT TGGAACTTTT AAGAGGCCAGA TAGATTTATT
         |----------------------------------------------------------------------------------------------------------------------------------|
                                                                       oleosin promoter
                    XbaI
                    ------
13801    ATTTGTATCC ATTTTCTTCA TTGTTCTAGA ATGTCGCGGA ACAAATTTTA AAACTAAATC CTAAATTTTT CTAATTTTGT TGCCAATAGT GGATATGTGG
         |----------------------------------------------------------------------------------------------------------------------------------|
                                                                       oleosin promoter 13901    GCCGTATAGA AGGAATTCTAT TGAAGGCCCA AACCCATACT GACGAGCCCA AAGGTTCGTT TTGCGTTTGTT TGTTTCGGTT CGATGCCAAC GCCACATTCT
         |----------------------------------------------------------------------------------------------------------------------------------|
                                                                       oleosin promoter 14001    GAGCTAGGCA AAAACAAAC GTGTCTTTGA ATAGACTCCT CTCGTTAACA CATGCAGCGG CTGCATGGTG ACGCCATTAA CACGTGGCCT ACAATTGCAT
         |----------------------------------------------------------------------------------------------------------------------------------|
             Primer - OlePro
             ----------------------
                                                                  oleosin promoter 14101    GATGCTCTCCA TTGACACGTG ACTTCTCGTC TCCTTTCTTA ATAGACTCTAA CAAACACTCC TACCTCTTCC AAAATATATA CACATCTTTT TGATCAATCT
         |----------------------------------------------------------------------------------------------------------------------------------|
                                                                       oleosin promoter
```

Figure 102

```
14201  CTCATTCAAA ATCTCATTCT CTCTAGTAAA CAAGAACAAA AAAGGTACCC CATC
       original oleosin Joshi context seq                                       -20 to -10 from
                                                                      modified attB1a
                                                  ----------
                                        A CAAGTTTGTA CAAAAAAGCA GGCTCCGCGG CCGCTTGCTC CGTTAAAAAA
13901                                                                         attB1b
                                                                              ----------
       modified Joshi context seq
       -----

14001  AACCATGGCA GAGCACTACG GGCAGCAGCA ACAAACACGT GCCCCCCACT TGCAACTGCA ACCGGCGTGCT CAGCGTGTTG TAAAGGCAGC GACCGCGGTT
                                                              sesa1a 14101  ACTGCCGGAG GTAGCCTGTT GGTGTTATCC TGGCTGGAAC GGTCATTGCG CTGACAATCG CCACACCTCT CCTGGTGATC TTCTCGCCTG
                                                              UBQ10-Intron
       ------
       sesa1a 14201  TACTGGTCCC TGCAGGTAAA TTTCTGTGTT CCTTATTCTC TCAAAATCTT CGATTTTGTT TTCGTTCGAT CCCAATTTCG TATATGTTCT TTGGTTTAGA
                                                              UBQ10-Intron 14301  TTTCTGTTAAT CTTAGATCGA AGACGATTTT CTGGGTTTGA TCGTTAGATA TCATCTTAAT TCTCGATTAG GGTTTCATAG ATATCATCCG ATTTGTTCAA
                                                              UBQ10-Intron 14401  ATAATTTGAG TTTTGTTCGAA TAATTACTCT TCGATTTGTG ATTTCTATCT AGATCTGGTG TTAGTTTCTA GTTTGTGCGA TCGAATTTGT CGATTAATCT
                                                              UBQ10-Intron                            sesa1b 14501  GAGTTTTTCT GATCTGCAGT CATCACCATC TTCCCTGTTGG GAGCGGGTTT TCTGGCAAGC GGGGGATTTG GTGTTGCCGC TCTGTCCTGTG CTGTCCTGGA
                                                              sesa1b 14601  TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
                                                                                                   sesa5
       sesa1b
```

Figure 102 continued

```
14701  CGAGACAGTTC AGTCAGCAAC CGGTAGCAGG GTCTCAGACC AGCATCGATC CATCCTCCTG GCATATGATG GCCGAGCACT ATGGACAACA GCAGCAGACG
                                                                          sesa5
14801  CGTGCCCCTC ATCTGCAACT GCAACCCCGT GCTCAACGTG TCGTTAAGGC TGCGACAGCA GTAACCGCTG GGGGTTCTCT GTTAGTGTTG TCAGGGCTGA
                                                            sesa5
14901  CTTTGGCGGG GACGGTAATT GCGTTGACCA TTGCCACCCC GCTGTTAGTG ATTTTCAGCC CGGTACTGGT GCCAGCAGTT ATCACGATCT TCTTGCTGGG
                                                                  sesa5
15001  TGCCGGATTC TTGGCAAGTG GAGGTTTTGG AGTTGCGGCG CTGTCAGTTT TATCCTGGAT CTATCGTTAT CTGACAGGAA AACATCCCCC AGGTGCCGAT
                                                      sesa5
15101  CAGCTGGAGA GTGCCAAGAC AAAACTGGGCG TCTAAGGCAC GTGAAATGAA GGATCGTGCC GAACAGTTTT CTCAACAGCC CGTAGCGGGG TCACAGACCT
                                                                                            sesa6
15201  CGATCGATCA GCAGGTTAAC GTGCACATGG CCGAACATTA CGGACAGCAA CAACAGACGC GTGCTCCACA CCTGCAATTG CAACCGCCTG CTCAACGTGT
                                                                              sesa6
15301  TGTCAAAGCG GCGACCGCCG TAACAGCAGG AGGATCACTG TTAGTGCTGT CGGGTTTAAC CTTGGCCGGG ACCGTCATTG CATTGACTAT TGCGACGCCC
                                                                      sesa6
15401  TTACTGGTGA TCTTTTCTCC GGTGCTGGTT CCCGCCGTTA TTACCATCTT CTTGTTAGGG GCAGGATTCC TGGCATCAGG GGGATTCGGA GTTGCGGCGT
                                                              sesa6
15501  TGAGTGTCTT AAGTTGGATC TACCGTTATC TGACTGTTAT GGGGCCGATC AACTGGAGTC AGCCAAAACG AAATTGGCGT CAAAAGCGCG
                                                                                     4xSTOP
15601  TGAAATGAAG GACCGTGCTG AGCAGTTTTC TCAGCAGCCT GTGGCAGGAT CCCAGACATC ACCATGGCTC GAGTAATGAA GCGGCCGCAC CCAGCTTT
        attB2b                                                                                              attB2a
    1  CTTGTACAAA GTGGT
```

Figure 102 continued

```
                                                        oleosin promoter
         ----------------------------------------------------------------------------------------------
              NotI
         ~~
13401    GCAG GAACTCTCTG GTAAGCTAGC TCCACTCCCC AGAAACAACC GGCGCCAAAT TGCGCGGAATT GCTGACCTGA AGACGGAACA TCATCGTCGG
         ----------------------------------------------------------------------------------------------
                                                        oleosin promoter 13501    GTCCTTGGGC GATTGCGGCG GAAGATGGGT CAGCTTGGGC TTGAGGACGA GACCCGAATC CGAGTCTGTT GAAAAGGTTG TTCATTGGGG ATTTGTATAC
         ----------------------------------------------------------------------------------------------
                                                        oleosin promoter 13601    GGAGATTGGT CGTCGAGAGG TTTGAGGGAA AGGACAAATG GGTTTGGCTC TGGAGAAAGA GAGTGCGGCT TTAGAGAGAG AATTGAGAGG TTTAGAGAGA
         ----------------------------------------------------------------------------------------------
                                                        oleosin promoter 13701    GATGCGGGCG CGATGAGCGG AGGAGAGACG ACGAGGACCT GCATTATCAA AGCAGTGACG TGGTGAAATT TGGAACTTTT AAGAGGCAGA TAGATTTATT
         ----------------------------------------------------------------------------------------------
                                                        oleosin promoter
                XbaI
         ----------
13801    ATTTGTATCC ATTTTCTTCA TTGTTCTAGA ATGTCGCGGA ACAAATTTTA AAACTAAATC CTAAATTTTT TGCCAATAGT GGATATGTGG
         ----------------------------------------------------------------------------------------------
                                                        oleosin promoter 13901    GCCGTATAGA AGGAATCTAT TGAAGGCCCA AACCCATACT GACGAGCCCA AAGGTTCGTT TTGCGTTTTA TGTTTCGGTT CGATGCCAAC GCCACATTCT
         ----------------------------------------------------------------------------------------------
                                                        oleosin promoter 14001    GAGCTAGGCA AAAACAAAC GTGTCTTTGA ATAGACTCCT CTCGTTAACA CATGCAGCGG CTGCATGGTG ACGCCATTAA CACGTGGCCT ACAATTGCAT
         ----------------------------------------------------------------------------------------------
         Primer - OlePro
         ------------------------                                             oleosin promoter 14101    GATGTCTCTCCA TTGACACGTG ACTTCTCGTC TCCTTTCTTA ATATATCTAA CAAACACTCC TACCTCTTCC AAAATATATA CACATCTCTTTT TGATCAATCT
         ----------------------------------------------------------------------------------------------
              oleosin promoter
```

Figure 103

```
14201  CTCATTCAAA ATCTCATTCT CTCTAGTAAA CAAGAACAAA AAAGGTACCC CATC
       -------------------------------------------------------------
       original oleosin
                                                          -20      to      -10     from
       ------------------------------------------------------------  ----------------
       Joshi context seq                                                     modified
                                                                              -------
                                                    attB1a                NotI
                                                    -----                 ----
13901                                             A CAAGTTTGTA CAAAAAAGCA GGCTCCGCGG CCGCTTGCTC CGTTAAAAAA
       modified Joshi context seq
       --------------------------
                                                                  -------------------------------------
                                                                  sesala
         NcoI
         ----
14001  AACCATGGCA GAGCACTACG GGCAGCAGCA ACAAACACGT GCCCCCCACT TGCAACTGCA ACCGGCTGCT CAGCGTGTTG TAAAGGCAGC GACCGCGGTT
       --------------------------------------------------------------------------------------------------------
                                                                    sesala
14101  ACTGCCGGAG GTAGCCTGTT GGTGTTATCC GGGTTGACCC TGGCTGGAAC GGTCATTGCG CTGACAATCG CCACACCTCT CCTGGTGATC TTCTCGCCTG
                                                                                    --------------------------
                                                                                    UBQ10-Intron
         PstI
         ----
14201  TACTGGTCCC TGCAGGTAAA TTTCTGTGTT CCTTATTCTC TCAAAATCTT CGATTTTGTT TTCGTTCGAT CCCAATTTCG TATATGTTCT TTGGTTAGA
       --------------------------------------------------------------------------------------------------------
       UBQ10-Intron XbaI
                                                                                                   ----
14301  TTTCTGTTAAT CTTAGATCGA AGACGATTTT CTGGGTTTGA TCGTTAGATA TCATCTTAAT TCTCGATTAG GGTTTCATAG ATATCATCCG ATTTGTTCAA
       --------------------------------------------------------------------------------------------------------
       UBQ10-Intron
```

Figure 103 continued

```
14401  ATAATTGAG TTTGTCGAA TAATTACTCT TCGATTTGTG ATTTCTATCT AGATCTGGTG TTAGTTTCTA GTTTGTGCGA TCGAATTTGT CGATTAATCT
       UBQ10-Intron                                                              sesa1b 14501  GAGTTTTTCT GATCTGCAGT CATCACCATC TTCCTGTTGG GAGCGGGTTT TCTGGCAAGC GGGGGATTTG GTGTTGCCGC TCTGTCTGTG CTGTCCTGGA
                  PstI                              sesa1b 14601  TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
       sesa1b                                                                                            sesa2

14701  CGAGCAGTTC AGTCAGCAAC CGGTAGCAGG GTCTCAGACC AGCATGATC CATCCTCCTG GCTCGAGATG GCGGAACACT ACGGGCAACA ACAGCAGACT
                                                  ClaI        XhoI
                                                      BstXI
                                          sesa2

14801  CGTGCTCCCC ACCTGCAATT ACAACCCCGT GCCCAACGTG TTGTGAAAGC GGCAACAGCA GTAACGGCAG GGGGAAGTTT GCTGGTCTTA TCGGGGTTGA
                                                                                  sesa2

14901  CCTTAGCGGG AACCGTGATT GCCCTGACAA TTGCGACTCC GCTGCTGGTT ATCTTCAGCC CCGTATTGGT TCCGGCCGTG ATCACGATTT TTTTGCTGGG
                                                                  sesa2

15001  GGCAGGAGATTT TTAGCCAGCG GAGGATTTGG GGTCGCAGCG TTGTCTGTGC TGAGTTGGAT CTATCGTTAT TTGACCGGGA AGCACCCACC TGGAGCAGAC
                                                                                                    sesa2

15101  CAGCTGGAGA GCGCGAAAAC GAAGCTGGCA TCGAAGGCGC GTGAAATGAA GGATCGTGCT GAACAATTCT CCCAGCAGCC TGTTGCCGGT TCTCAGACCA
                                                                                                    sesa5

15201  GCCATATGAT GGCCGAGCAC TATGGACAAC AGCAGCAGAC GCGTGCCCCT CATCTGCAAC TGCAACCCCG TGCTCAACGT GTCGTTAAGG CTGCGACAGC
       NdeI                                                            sesa5

15301  AGTAACCGCT GGGGGTTCTC TGTTAGTGTT GTCAGGGCTG ACTTTGGCGG GGACGGTAAT TGCGTTGACC ATTGCCACCC CGCTGTTAGT GATTTTCAGC
                                                  sesa5
```

Figure 103 continued

```
15401  CCGGTACTGG TGCCAGCAGT TATCACGATC TTCTTGCTGG GTGCCGGATT CTTGGCAAGT GGAGGTTTTG GAGTTGCGGC GCTGTCAGTT TTATCCTGGA
                                              sesa5
15501  TCTATCGTTA TCTGACAGGA AAACATCCCC CAGGTGCCGA AGTGCCAAGA TCAGCTGGAG AGTGCCAAGA CAAAACTGGC GTCTAAGGCA CGTGAAATGA AGGATCGTGC
                 sesa5                                                          ClaI                                 sesa6
15601  CGAACAGTTT TCTCAACAGC CCGTAGCGGG GTCACAGACC TCGATCGATC AGCAGGTTAA CGTGCACATG GCCGAACATT ACGGACAGCA ACAACAGACG
                                                              sesa6
15701  CGTGCTCCAC ACCTGCAATT GCAACCGCGT GCTCAACGTG TTGTCAAAGC GGCGACCGCC GTAACAGCAG GAGGATCACT GTTAGTGCTG TCGGGTTTAA
                                                              sesa6
                                      Primer- Polyses-6R
                                      Primer- Polyses-6F
15801  CCTTGGCCGG GACCGTCATT GCATTGACTA TTGCGACGCC CTTACTGGTG ATCTTTTCTC CGGTGCTGGT TCCCGCCGTT ATTACCATCT TCTTGTTAGG
                                                              sesa6
15901  GGCAGGATTC CTGGCATCAG GGGGATTCGG AGTTGCGGCG TTGAGTGTCT TAAGTTGGAT CTACCGTTAT CTGACTGGAA AGCACCCGCC TGGGGCCGAT
                                                       sesa6                                                           BamHI
16001  CAACTGGAGT CAGCCAAAAC GAAATTGGCG TCAAAAGCGC GTGAAATGAA GGACCGTGCT GAGCAGTTTT CTCAGCAGCC TGTGGCAGGA TCCCAGACAT
                                      4xSTOP
               XhoI          NotI
                                       attB2a
                NcoI                                            HindIII               XbaI
16101  CACCATGGCT CGAGTAATGA AGCGGCCGCA CCCAGCTTT
                attB2b                                ClaI           BamHI
    1  CTTGTACAAA GTGGTGATGG GTTCGAAATC GATAAGCTTG GATCCTCTAG A
```

Figure 103 continued

```
                                                             oleosin promoter
       ----------------------------------------------------------------------------------------
13401  GCAG GAACTCTCTG GTAAGCTAGC TCCACTCCCC AGAAACAACC GGCGCCAAAT TGCGCGAATT GCTGACCTGA AGACGGAACA TCATCGTCGG
           ~~~~                                        oleosin promoter
           NotI
       ----------------------------------------------------------------------------------------
13501  GTCCTTGGGC GATTGCGGCG GAAGATGGGT CAGCTTGGGC TTGAGGACGA GACCCGAATC CGAGTCTGTT GAAAAGGTTG TTCATTGGGG ATTTGTATAC
                                                    oleosin promoter
       ----------------------------------------------------------------------------------------
13601  GGAGATTGGT CGTCGAGAGG TTTGAGGGAA AGGACAAATG GGTTTGGCTC TGGAGAAAGA GAGTGCGGCT TTAGAGAGAG AATTGAGAGG TTTAGAGAGA
                                                    oleosin promoter
       ----------------------------------------------------------------------------------------
13701  GATGCGGCGG CGATGAGCGG AGGAGAGACG ACGAGGACCT GCATTATCAA AGCAGTGACG TGGTGAAATT TGGAACTTTT AAGAGGCAGA TAGATTTATT
                                ~~~~~~                       oleosin promoter
                                XbaI
       ----------------------------------------------------------------------------------------
13801  ATTTGTATCC ATTTTCTTCA TTGTTCTAGA ATGTCGCGGA ACAAATTTTA AAACTAAATC CTAAATTTTT CTAAATTTGT TGCCAATAGT GGATATGTGG
                                                    oleosin promoter
       ----------------------------------------------------------------------------------------
13901  GCCGTATAGA AGGAATCTAT TGAAGGCCCA AACCCATACT GACGAGCCCA AAGGTTCGTT TTGCCTTTTA TGTTTCGGTT CGATGCCAAC GCCACATTCT
                                                    oleosin promoter
       ----------------------------------------------------------------------------------------
14001  GAGCTAGGCA AAAACAAAC GTGTCTTTGA ATAGACTTCCT CTCGTTAACA CATGCAGCGG CTGCATGGTG ACGCCATTAA CACGTGGCCT ACAATTGCAT
              ~~~~~~~~~~~~~~~~~~~~~~~~
              Primer - OlePro                       oleosin promoter
       ----------------------------------------------------------------------------------------
14101  GATGTCTCCA TTGACACGTG ACTTCTCGTC TCCTTTCTTA ATATATCTAA CAAACACTCC TACCTCTTCC AAAATATATA CACATCTTTT TGATCAATCT
                                                    oleosin promoter
       ----------------------------------------------------------------------------------------
```

Figure 104

```
14201 CTCATTCAAA ATCTCATTCT CTCTAGTAAA CAAGAACAAA AAGGTACCC CATC
       original oleosin
       Joshi context seq
                                                                              -20 to -10 from
                                                                                      modified
13901 modified Joshi context seq
                                                         attB1a          NotI
                          A CAAGTTTGTA CAAAAAAGCA GGCTCCGCGG CCGCTTGCTC CGTTAAAAAA
                                                    sesa1a
14001 AACCATGGCA GAGCACTACG GGCAGCAGCA ACAAACACGT GCCCCCCACT TGCAACTGCA ACCGCGTGCT CAGCGTGTTG TAAAGGCAGC GACCGCGGTT
                                                    sesa1a
14101 ACTGCCGGAG GTAGCCTGTT GGTGTTATCC GGGTTGACCC TGGCTGGAAC GGTCATTGCG CTGACAATCG CCACACCTCT CCTGGTGATC TTCTCGCCTG
                                                                              UBQ10-Intron
       sesa1a
14201 TACTGGTCCC TGCAGGTAAA TTTTCTGTGTT CCTTATTCTC TCAAAAATCTT CGATTTTGTT TTCGTTCGAT CCCAATTTCG TATATGTTCT TTGGTTTAGA
                                         UBQ10-Intron
14301 TTCTGTTAAT CTTAGATGA AGACGATTTT CTGGGTTTGA TCGTTAGATA TCATCTTAAT TCTCGATTAG GGTTTCATAG ATATCATCCG ATTTGTTCAA
                                         UBQ10-Intron
14401 ATAATTGAG TTTTGTCGAA TAATTACTCT TCGATTTGTG ATTTCTATCT AGATCTGGTG TTAGTTTCTA GTTTGTGCGA TCGAATTTGT CGATTAATCT
       UBQ10-Intron
                                                            sesa1b
14501 GAGTTTTTCT GATCTGCAGT CATCACCATC TTCCTGTTGG GAGCGGGTTT TCTGGCAAGC GGGGGATTTG GTGTTGCCGC TCTGTCTGTG CTGTCCTGGA
                                                            sesa1b
14601 TCTACCGTTA CCTGACGGGG AAACATCCAC CCGGAGCGGA TCAGTTGGAG TCGGCCAAGA CAAAGTTGGC GAGCAAGGCC CGTGAAATGA AGGACCGTGC
       sesa1b                                                                                    sesa2
14701 CGAGCAGTTC AGTCAGCAAC CGGTAGCAGG GTCTCAGACC AGCATCGATC CATCCTCCTG GCTCGAGATG GCGGAACACT ACGGGCAACA ACAGCAGACT
                                                                              sesa2
```

Figure 104 continued

```
14801  CGTGCTCCCC ACCTGCAATT ACAACCCCGT GCCCAACGTG TTGTGAAAGC GGCAACAGCA GTAACGGCAG GGGGAAGTTT GCTGGTCTTA TCGGGGTTGA
                                                            sesa2
14901  CCTTAGCGGG AACCGTGATT GCCCTGACAA TTGCGACTCC GCTGCTGGTT ATCTTCAGCC CCGTATTGGT TCCGGCCGTG ATCACGATTT TTTTGCTGGG
                                                            sesa2
15001  GGCAGGATTT TTAGCCAGCG GAGGATTTGG GGTCGCAGCG TTGTCTGTGC TGAGTTGGAT CTATCGTTAT TTGACCGGGA AGCACCCACC TGGAGCAGAC
                                                            sesa2
15101  CAGCTGGAGA GCCCGAAAAC GAAGCTGGCA TCGAAGGCGC GTGAAATGAA GGATCGTGCT GAACAATTCT CCCAGCAGCC TGTTGCCGGT TCTCAGACCA
                                                            sesa3
15201  GCCATATGTT TAAATGGCCA AGCGCTATGG CCGAGCATTA TGGGCAGCAA CAGCAAAACC GTGCCCCCGCA TCTGCAATTG CAACCTCGTG CCCAGCGTGT
                                                            sesa3
15301  CGTTAAGGCG GCTACTGCGG TAACAGCGGG AGGGAGCTTA CTGGTATTAA GCGGGCTGAC ATTGGCCGGA ACGGTGATCG CCTTAACAAT CGGCGACACCC
                                                            sesa3
15401  TTGCTGGTCA TCTTCAGTCC GGTTCTGGTG CCCGCGGTGA TTACGATTTT CCTGCTGGGA GCCGGTTTCT TAGCATCGGG GGGTTTTGGG GTAGCAGCCT
                                                            sesa3
15501  TGAGTGTCCT GTCGTGGATC TATCGTTACT TAACTGGAAA ACACCCCGCCA GGAGCTGACC AGTTGGAGTC TGCAAAAACT AAGCTGGCGT CCAAAGCCCG
                                                                                                                sesa4
15601  TGAAATGAAG GATCGTGCTG AGCAGTTTAG CCAGCAGCCA GTTGCGGGAA GTCAGACCTC TTCATCTGAG CTCCCATGGG TCGACATGGC GGAGCATTAC
                                                            sesa4
15701  GGTCAACAGC AACAGACCCG TGCTCCGCAC TTACAATTGC AACCACGTGC TCAACGTGTC CCACGGCAGT TACTGCGGGG GGATCATTGC
                                                            sesa4
15801  TGGTGTTAAG TGGGTTGACA CTGGCGGGGA CAGTTATTGC ACTGACGATC GCGACCCCCT TGTTAGTGAT CTTCTCCCCC GTTCTGGTTC CGGCGGTCAT
                                                            sesa4
15901  TACAATCTTT CTGTTGGGTG CCGGATTTTT AGCCTCTGGG GGATTTGGAC TAGCTGCCCT GTCAGTGTTG AGCTGGATCT ACCGTTACTT AACAGGGAAG
                                                            sesa4
16001  CACCCTCCCG GGGCAGATCA GTTGGAAAGC GCCAAGACCA AGCTGGCAAG TAAAGCGCGT GAAATGAAGG ACCGTGCCGA ACAATTTTCG CAGCAACCGG
                                                                                                  sesa5
16101  TTGCGGGATC ACAGACCTCT AGTACTCCAT CCTCCTGGCA TATGATGGCC GAGCACTATG GACAACAGCA GCAGACGCGT GCCCCCTCATC TGCAACTGCA
```

Figure 104 continued

```
                                                                                                          sesa5
16201   ACCCCCGTGCT CAACGTGTCG TTAAGGCTGC GACAGCAGTA ACCGCTGGGG GTTCTCTCTT AGTGTTGTCA GGGCTGACTT TGGCGGGGAC GGTAATTGCG
                                                              sesa5
16301   TTGACCATTG CCACCCCGCT GTTAGTGATT TTCAGCCCGG TACTGGTGCC AGCAGTTATC ACGATCTTCT TGCTGGGTGC CGGATTCTTG GCAAGTGGAG
                                                              sesa5
16401   GTTTTGGAGT TGCGGCGCTG TCAGTTTTAT CCTGGATCTA TCGTTATCTG ACAGGAAAAC ATCCCCCAGG TGCCGATCAG CTGGAGAGTG CCAAGACAAA
                                           sesa5
16501   ACTGGCGTCT AAGGCACGTG AAATGAAGGA TCGTGCCGAA CAGTTTTCTC AACAGCCCGT AGCGGGGTCA CAGACCTCGA TCGATCAGCA GGTTAACGTG
                                                              sesa6
16601   CACATGGCCG AACATTACGG ACACAACAA CAGACGCGTG CTCCACACCT GCAATTGCAA CCGGCGTGCTC AACGTGTTGT CAAAGCGGGCG ACCGCCGTAA
                                                              sesa6
16701   CAGCAGGAGG ATCACTGTTA GTGCTGTCGG GTTTAACCTT GGCCGGGACC GTCATTGCAT TGACTATTGC GACGCCCTTA CTGGTGATCT TTTCTCCGGT
                                                              sesa6
16801   GCTGGTTCCC GCCGTTATTA CCATCTTCTT GTTAGGGGCA GGATTCCTGG CATCAGGGGG ATTCGGAGTT GCGGCGTTGA GTGTCTTAAG TTGGATCTAC
                                                              sesa6
16901   CGTTATCTGA CTGGAAAGCA CCCGCCTGGG GCCGATCAAC TGGAGTCAGC CAAAACGAAA TTGGCGTCAA AAGCGCGTGA AATGAAGGAC CGTGCTGAGC
            sesa6                                                         4xSTOP
                                                                                        NotI
                                                                                         --------             attB2a
                                                                                                            ------------
17001   AGTTTTCTCA GCAGCCTGTG GCAGGATCCC AGACATCACC ATGGCTCGAG TAATGAAGCG GCCCACCCA GCTTT
                   attB2b
            -------------
    1   CTTGTACAAA GTGGT
```

```
                                                                    CaMV 35S
                                                         TCGACGAATT AATTCCAATC
                CaMV 35S
12501
        CCACAAAAAT CTGAGCTTAA CAGCACAGTT GCTCCTCTCA GAGCAGAATC GGGTATTCAA CACCCCTCATA TCAACTACTA CGTTGTGTAT AACGGTCCAC
12601                                                   CaMV 35S
        ATGCCGGTAT ATACGATGAC TGGGGTTGTA CAAAGGCGGC AACAAACGGC GTTCCCCGGAG TTGCACACAA GAAATTTGCC ACTATTACAG AGGCAAGAGC
12701                                                   CaMV 35S
        AGCAGCTGAC GCGTACACAA CAAGTCAGCA AACAGACAGG TTGAACTTCA TCCCCAAAGG AGAAGCTCAA CTCAAGCCCA AGAGCTTTGC TAAGGCCCTA
12801                                                   CaMV 35S
        ACAAGCCCAC CAAAGCAAAA AGCCCACTGG CTCACGCTAG GAACCAAAAG GCCCAGCAGT GATCCAGCCC CAAAAGAGAT CTCCTTTGCC CCGGAGATTA
12901                                                   CaMV 35S
        CAATGGACGA TTTCCTCTAT CTTTACGATC TAGGAAGGAA GTTCGAAGGT GAAGGTGACG ACACTATGTT CACCACTGAT AATGAGAAGG TTAGCCTCTT
13001                                                   CaMV 35S
        CAATTTCAGA AAGAATGCTG ACCCACAGAT GGTTAGAGAG GCCTACGCAG CAGGTCTCAT CAAGACGATC TACCCGAGTA ACAATCTCCA GGAGATCAAA
13101                                                   CaMV 35S
        TACCTTCCCA AGAAGGTTAA AGATGCAGTC AAAAGATTCA GGACTAATTG CATCAAGAAC ACAGAGAAAG ACATATTTCT CAAGATCAGA AGTACTATTC
13201                                                   CaMV 35S
        CAGTATGGAC GATTCAAGGC TTGCTTCATA AACCAAGGCA AGTAATAGAG ATTGGAGTCT CTAAAAAGGT AGTTCCTACT GAATCTAAGG CCATGCATGG
13301                                                                               Primer - 35S(PSP)Fwd
                CaMV 35S
13401
        AGTCTAAGAT TCAAATCGAG GATCTAACAG AACTCGCCGT GAAGACTGGC GAACAGTTCA TACAGAGTCT TTTACGACTC AATGACAAGA AGAAAATCTT
                                                        CaMV 35S
13501
        CGTCAACATG GTGGAGCACG ACACTCTGGT CTACTCCAAA AATGTCAAAG ATACAGTCTC AGAAGACCAA AGGGCTATTG AGACTTTTCA ACAAAGGATA
                                                        CaMV 35S
13601
        ATTTCGGGAA ACCTCCTCGG ATTCCATTGC CCAGCTATCT GTCACTTCAT CGAAAGGACA GTAGAAAAGG AAGGTGGCTC CTACAAATGC CATCATTGCG
                                                        CaMV 35S
```

Figure 105

```
13701 ATAAAGGAAA GGCTATCATT CAAGATCTCT CTGCCGACAG TGGTCCCAAA GATGGACCCC CACCCACGAG GAGCATCGTG GAAAAAGAAG ACGTTCCAAC
                                                                    CaMV 35S

13801 CACGTCTTCA AAGCAAGTGG ATTGATGTGA CATCTCCACT GACGTAAGGG ATGACGCACA ATCCCACTAT CCTTCGCAAG ACCCTTCCTC TATATAAGGA
                           Primer - 35S(3'end)Fwd
                                                                                                    attB1
      CaMV 35S
                  XhoI
                             EcoRI                                                attB1a                      NotI 13901 AGTTCATTTC ATTTGGAGAG GACACGCTCG AGGAATTCGG TACCCCATCA CAAGTTTGTA CAAAAAAGCA GGCTCCGCGG CCGCTTGCTC CGTTAAAAAA
                                                            Ole3.1
                                                                          PstI
         NcoI                                                             PstI 14001 AACCATGGCT GAGCATTATG GTCAACAACA GCAGACCAGG GCGCCTCACC TGCAGCTGCA GCCGCGCGCC CAGCGGGTAG TGAAGGCGGC CACCGCCGTG
                                                            Ole3.1

14101 ACAGCCGGCG GCTCGCTTCT CGTCCCTCTCT GGCCTCACTT TAGCCGGAAC TGTTATTGCG CTCACCATCG CCACTCCGCT GCTTGTGATC TTTAGCCCCG
                                                            Ole3.1

14201 TTCTGGTGCC GGCGGTCATA ACCATTTTCT TGCTGGGTGC GGGTTTTCTG GCATCCGGAG GCTTCGGCGT GGCGGCGCTG AGTGTGCTGT CGTGGATTTA
                                                            Ole3.1

14301 CAGATATCTG ACAGGGAAAC ACCCGCCGGG GGCGGATCAG CTGGAATCGG CAAAGACGAA GCTGGCGAGC AAGGCGCGAG AGATGAAGGA TAGGGCAGAG
                Ole3.1                       Hinge-1_to_2                                                     Ole3.2
                           BamHI                                                                                       PstI
```

Figure 105 continued

```
14401 CAGTTCTCGC AGCAGCCTGT TGGAGGCGGT GGATCCGGAG GCGGTGGTAG TATGGCTGAG CATTATGGTC AACAACAGCA GACCAGGGCG CCTCACCTGC
                                                           Primer - Hinge1-2Rev
                                                                Ole3.2
          PstI
          ----
          PstI 14501 AGCTGCAGCC GCGCGCCCAG CGGGTAGTGA AGGCGGCCAC CGCCGTGACA GCCGGCGGCT CGCTTCTCGT CCTCTCTGGC CTCACTTTAG CCGGAACTGT
                                                            Ole3.2

14601 TATTGGCGCTC ACCATCGCCA CTCCGCTGCT TGTGATCTTT AGCCCCGTTC TGGTGCCGGC GGTCATAACC ATTTTCTTGC TGGGTGCGGG TTTTCTGGCA
                                                            Ole3.2

14701 TCCGGAGGCT TCGGCGTGGC GGCGCTGTGGC GTGCTGTCGT GGATTTACAG ATATCTGACA GGGAAACACC CGCCGGGGGC GGATCAGCTG GAATCGGCAA
                                                            Ole3.2                                                    Ole3.3
                                                                                               Primer - Hinge2-3Fwd#1

Primer - Hinge2-
      3Fwd#2                                                                                                                    NcoI
                                                                                                    Hinge-2_to_3                ----
                                                                                                                                BamHI
                                                                                                          BamHI
14801 AGACGAAGCT GGCGAGCAAG GCGCGAGAGA TGAAGGATAG GGCAGAGCAG TTCTTCGCAGC AGCCTGTTGG GGGCGGTGGA TCCGGTGGAG GGGGATCCAT
      Primer - Hinge2-3Fwd#2
                                                            Ole3.3
          NcoI                                                PstI
          ----                                                ----
14901 GGCTGAGCAT TATGGTCAAC AACAGCAGAC CAGGGGCCCT CACCTGCAGC TGCAGCCGCG CGCCCAGCGG CGCCACCGC GTAGTGAAGG CGGCCACCGC CGTGACAGCC
                                                            Ole3.3
```

Figure 105 continued

```
15001  GGCGGCTCGC TTCTCTGTCCT CTCTGGCCTC ACTTTAGCCG GAACTGTTAT TGCGCTCACC ATCGCCACTC CGCTGCTTGT GATCTTTAGC CCCGTTCTGG
                                                            Ole3.3

15101  TGCCGGCGGGT CATAACCATT TTCTTGCTGG GTGCGGGTTT TCTGGCATCC GGAGGCTTCG GCGTGGCGGC GCTGAGTGTG CTGTCGTGGA TTTACAGATA
                                                            Ole3.3

15201  TCTGACAGGG AAACACCCGC CGGGGGCGGA TCAGCTGGAA TCGGCAAAGA CGAAGCTGGC GAGCAAGGCG CGAGAGATGA AGGATAGGGC AGAGCAGTTC
            Ole3.3
                                        XhoI            NotI
                                        -----           -----
                                        NcoI                                                         attB2a
                                        -----                                                        ------

15301  TCGCAGCAGC CTGTTCCATG GCTCGAGTAA TGAAGCGGCC GCACCCAGCT TT
                                                                    attB2
                                                                    -----
            attB2b
            ------

1  CTTGTACAAA GTGGT
       ---------------
            attB2
```

Figure 105 continued

```
                                                                                    oleosin promoter
                                                                          ┌─────────────────────────────────────────────────────────
13901                                                                     GCAG GAACTCTCTG GTAAGCTAGC TCCACTCCCC
                                                                               NotI
       ─────────────────────────────────────────────────────────────────────────────────────────────────────────
14001  AGAAACAACC GGCGCCAAAT TGCGCGAATT GCTGACCTGA AGACGGAACA TCATCGTCGG GTCCTTGGGC GATTGCGGCG GAAGATGGGT CAGCTTGGGC
                                                          oleosin promoter
       ─────────────────────────────────────────────────────────────────────────────────────────────────────────
14101  TTGAGGACGA GACCCGAAATC CGAGTCTGTT GAAAAGGTTG TTCATTGGGG ATTTGTATAC GGAGATTGGT CGTCGAGAGG TTTGAGGGAA AGGACAAATC
                                                          oleosin promoter
       ─────────────────────────────────────────────────────────────────────────────────────────────────────────
14201  GGTTTGGCTC TGGAGAAAGA GAGTGCGGCT TTAGAGAGAG AATTGAGAGG TTTAGAGAGA GATGCGGGCG CGATGAGCGG AGGAGAGACG ACGAGGACCT
                                                          oleosin promoter
       ─────────────────────────────────────────────────────────────────────────────────────────────────────────
                                                                                                        XbaI
                                                                                                      ─────────
14301  GCATTATCAA AGCAGTGACG TGGTGAAATT TGGAACTTTT AAGAGGCAGA TAGATTTATT ATTTGTATCC ATTTTCTTCA TTGTTCTAGA ATGTCGCGGA
                                                          oleosin promoter
       ─────────────────────────────────────────────────────────────────────────────────────────────────────────
14401  ACAAATTTTA AAACTAAATC CTAAATTTTT CTAATTTTGT TGCCAATAGT GGATATGTGG GCCGTATAGA AGGAATCTAT TGAAGGCCCA AACCCATACT
                                                          oleosin promoter
       ─────────────────────────────────────────────────────────────────────────────────────────────────────────
14501  GACGAGCCCA AAGGTTCGTT TTGCGTTTTA TGTTTCGGTT CGATGCCAAC GCCACATTCT GAGCTAGGCA AAAAACAAAC GTGTCTTTGA ATAGACTCCT
                                                                                                     Primer - OlePro
                                         oleosin promoter                                           ───────────────
       ─────────────────────────────────────────────────────────────────────────────────────────────
14601  CTCGTTAACA CATGCAGCGG CTGCATGGTG ACGCCATTAA CACGTGGCCT ACAATTGCAT GATGTCTCCA TTGACACGTG ACTTCTCGTC TCCTTTCTTA
       ──────────────────────────────────────────────
```

Figure 106

```
14701  ATATATCTAA CAAACACTCC TACCTCTTCC AAAATATATA CACATCTTTT TGATCAATCT CTCATTCAAA ATCTCATTCT CTCTAGTAAA CAAGAACAAA
              ------------
              oleosin promoter
                                                                                                              ------
                                                                                                              attB1b
                                                                                  ----------
                                                                                  attB1a
14801  AAAGGTACCCC CATCACAAGT TTGTACAAA
       -----
       attB1
       ----------
       attB1b    NotI                                                                                         NcoI
    1  AAAGCAGGCT CCGCGGCCGC TTGCTCCGTT AAAAAAAACC ATGGCTGAGC ATTATGGTCA ACAACAGCAG ACCAGGGCGC CTCACCTGCA GCTGCAGCCC
                                                            ----------
                                                            Ole3.1                                          --------
                                                                                                            PstI
  101  CGCGCCCAGC GGGTAGTGAA GGCGGCCACC CCGGCCGGCTC GCTTCTCGTC CTCTCTGGCC TCACTTTAGC CGGAACTGTT ATTGCGCTCA
       -----------------------------------------------------------------------------------------------
                                                        Ole3.1
  201  CCATCGCCAC TCCGCTGCTT GTGATCTTTA GCCCCGTTCT GGTGCCGGCG GTCATAACCA TTTTCTTGCT GGGTGCGGGT TTTCTGGCAT CCGGAGGCTT
       -----------------------------------------------------------------------------------------------------------
                                                        Ole3.1
  301  CGGCGTGGCG GCGCTGAGTG TGCTGTCGTG GATTTACAGA TATCTGACAG GGAAACACCC GCCGGGGGCG GATCAGCTGG AATCGGCAAA GACGAAGCTG
       -----------------------------------                                                                  --------
                    Ole3.1                                                                                  Ole3.2
                                                                                  ----------
                                                                                  BamHI
                                                                                  Hinge-1_to_2
  401  GCGAGCAAGG CGCGAGAGAT GAAGGATAGG GCAGAGCAGT TCTCGCAGCA GCCTGTTGGA GGCGGTGGAT CCGGAGGCGG TGGTAGTATG GCTGAGCATT
       -----------------------------------------------------                      -----------------------------------
                          Ole3.2                                                            Primer - Hinge1-2Rev
                                                          --------
                                                          PstI
                                                                                                            --------
                                                                                                            PstI
```

Figure 106 continued

```
501  ATGGTCAACA ACAGCAGACC AGGGCGCCTC ACCTGCAGCT GCAGCCGCGC GCCCAGCGGG TAGTGAAGGC GGCCACCGCC GTGACAGCCG GCGGGCTCGCT
                                                          Ole3.2
601  TCTCGTCCTC TCTGGCCTCA CTTTAGCCGG AACTGTTATT GCGCTCACCA TCGCCACTCC GCTGCTTGTG ATCTTTAGCC CCGTTCTGGT GCCGGCGGTC
                                                          Ole3.2
701  ATAACCATTT TCTTGCTGGG TGCGGGTTTT CTGGCATCCG GAGGCTTCGG CGTGGCGGCG CTGAGTGTGC TGTCGTGGAT TTACAGATAT CTGACAGGGA
                                                          Ole3.2
801  AACACCCGCC GGGGGCGGAT CAGCTGGAAT CGGCAAAGAC GAAGCTGGCG AGCAAGGCGC GAGAGATGAA GGATAGGGCA GAGCAGTTCT CGCAGCAGCC
     Ole3.2    Primer - Hinge2-3Fwd#1                                                          Ole3.3
                           Primer - Hinge2-3Fwd#2
         Hinge-2_to_3
                           NcoI
           BamHI  BamHI
901  TGTTTGGGGGC GGTGGATCCG GTGGAGGGGG ATCCATGGCT GAGCATTATG GTCAACAACA GCAGACCAGG GCGCCTCACC TGCAGCTGCA GCCGGCGCCC
                                                          Ole3.3
1001 CAGCGGGTAG TGAAGGCGGC CACCGCCGTG ACAGCCGGCG GCTCGCTTCT CGTCCTCTCT GGCCTCACTT TAGCCGGAAC TGTTATTGCG CTCACCATCG
                                                          Ole3.3
1101 CCACTCCGCT GCTTGTGATC TTTAGCCCCG TTCTGGTGCC GGCGGTCATA ACCATTTTCT TGCTGGGTGC GGGTTTTCTG GCATCCGGAG GCTTCGGCGT
                                                          Ole3.3
                                                                                                         PstI
                                                                                            PstI
```

Figure 106 continued

```
1201 GGCGGCGCTG AGTGTGCTGT CGTGGATTTA CAGATATCTG ACAGGGAAAC ACCCGCCGGG GGCGGATCAG CTGGAATCGG CAAAGACGAA GCTGGCGAGC
                                              Ole3.3                                    XhoI         NotI              attB2b
                                                                                 NcoI                      attB2a
1301 AAGGCGCGAG AGATGAAGGA TAGGGCAGAG CAGTTCTCGC AGCAGCCTGT TCCATGGCTC GAGTAATGAA GCGGCCGCAC CCAGCTTTCT TGTACAAAGT
     attB2b                                                                                                       attB2
1401 GGT
     :
```

Figure 106 continued

```
  1  MAEHYGQQQQ   TRAPHLQLQP   RAQRVVKAAT   AVTAGGSLLV
     LSGLTLAGTV
 51  IALTIATPLL   VIFSPVLVPA   VITIFLLGAG   FLASGGFGVA
     ALSVLSWIYR
101  YLTGKHPPGA   DQLESAKTKL   ASKAREMKDR   AEQFSQQPVA
     GSQTSIDPSS
151  WLE**
```

Figure 107

```
  1  MAEHYGQQQQ   TRAPHLQLQP   RAQRVVKAAT   AVTAGGSLLV
     LSGLTLAGTV
 51  IALTIATPLL   VIFSPVLVPA   VITIFLLGAG   FLASGGFGVA
     ALSVLSWIYR
101  YLTGKHPPGA   DQLESAKTKL   ASKAREMKDR   AEQFSQQPVA
     GSQTSIDPSS
151  WHMMAEHYGQ   QQQTRAPHLQ   LQPRAQRVVK   AATAVTAGGS
     LLVLSGLTLA
201  GTVIALTIAT   PLLVIFSPVL   VPAVITIFLL   GAGFLASGGF
     GVAALSVLSW
251  IYRYLTGKHP   PGADQLESAK   TKLASKAREM   KDRAEQFSQQ
     PVAGSQTSID
301  QQVNVHMAEH   YGQQQQTRAP   HLQLQPRAQR   VVKAATAVTA
     GGSLLVLSGL
351  TLAGTVIALT   IATPLLVIFS   PVLVPAVITI   FLLGAGFLAS
     GGFGVAALSV
401  LSWIYRYLTG   KHPPGADQLE   SAKTKLASKA   REMKDRAEQF
     SQQPVAGSQT
451  SPWLE**
```

Figure 108

```
  1 MAEHYGQQQQ    TRAPHLQLQP    RAQRVVKAAT    AVTAGGSLLV
    LSGLTLAGTV
 51 IALTIATPLL    VIFSPVLVPA    VITIFLLGAG    FLASGGFGVA
    ALSVLSWIYR
101 YLTGKHPPGA    DQLESAKTKL    ASKAREMKDR    AEQFSQQPVA
    GSQTSIDPSS
151 WLEMAEHYGQ    QQQTRAPHLQ    LQPRAQRVVK    AATAVTAGGS
    LLVLSGLTLA
201 GTVIALTIAT    PLLVIFSPVL    VPAVITIFLL    GAGFLASGGF
    GVAALSVLSW
251 IYRYLTGKHP    PGADQLESAK    TKLASKAREM    KDRAEQFSQQ
    PVAGSQTSHM
301 MAEHYGQQQQ    TRAPHLQLQP    RAQRVVKAAT    AVTAGGSLLV
    LSGLTLAGTV
351 IALTIATPLL    VIFSPVLVPA    VITIFLLGAG    FLASGGFGVA
    ALSVLSWIYR
401 YLTGKHPPGA    DQLESAKTKL    ASKAREMKDR    AEQFSQQPVA
    GSQTSIDQQV
451 NVHMAEHYGQ    QQQTRAPHLQ    LQPRAQRVVK    AATAVTAGGS
    LLVLSGLTLA
501 GTVIALTIAT    PLLVIFSPVL    VPAVITIFLL    GAGFLASGGF
    GVAALSVLSW
551 IYRYLTGKHP    PGADQLESAK    TKLASKAREM    KDRAEQFSQQ
    PVAGSQTSPW
601 LE**
```

Figure 109

| | | | |
|---|---|---|---|
| 1 MAEHYGQQQQ | TRAPHLQLQP | RAQRVVKAAT | AVTAGGSLLV |
| LSGLTLAGTV | | | |
| 51 IALTIATPLL | VIFSPVLVPA | VITIFLLGAG | FLASGGFGVA |
| ALSVLSWIYR | | | |
| 101 YLTGKHPPGA | DQLESAKTKL | ASKAREMKDR | AEQFSQQPVA |
| GSQTSIDPSS | | | |
| 151 WLEMAEHYGQ | QQQTRAPHLQ | LQPRAQRVVK | AATAVTAGGS |
| LLVLSGLTLA | | | |
| 201 GTVIALTIAT | PLLVIFSPVL | VPAVITIFLL | GAGFLASGGF |
| GVAALSVLSW | | | |
| 251 IYRYLTGKHP | PGADQLESAK | TKLASKAREM | KDRAEQFSQQ |
| PVAGSQTSHM | | | |
| 301 FKWPSAMAEH | YGQQQQTRAP | HLQLQPRAQR | VVKAATAVTA |
| GGSLLVLSGL | | | |
| 351 TLAGTVIALT | IATPLLVIFS | PVLVPAVITI | FLLGAGFLAS |
| GGFGVAALSV | | | |
| 401 LSWIYRYLTG | KHPPGADQLE | SAKTKLASKA | REMKDRAEQF |
| SQQPVAGSQT | | | |
| 451 SSSELPWVDM | AEHYGQQQQT | RAPHLQLQPR | AQRVVKAATA |
| VTAGGSLLVL | | | |
| 501 SGLTLAGTVI | ALTIATPLLV | IFSPVLVPAV | ITIFLLGAGF |
| LASGGFGVAA | | | |
| 551 LSVLSWIYRY | LTGKHPPGAD | QLESAKTKLA | SKAREMKDRA |
| EQFSQQPVAG | | | |
| 601 SQTSSTPSSW | HMMAEHYGQQ | QQTRAPHLQL | QPRAQRVVKA |
| ATAVTAGGSL | | | |
| 651 LVLSGLTLAG | TVIALTIATP | LLVIFSPVLV | PAVITIFLLG |
| AGFLASGGFG | | | |

Figure 110

```
701  VAALSVLSWI    YRYLTGKHPP    GADQLESAKT    KLASKAREMK
     DRAEQFSQQP
751  VAGSQTSIDQ    QVNVHMAEHY    GQQQQTRAPH    LQLQPRAQRV
     VKAATAVTAG
801  GSLLVLSGLT    LAGTVIALTI    ATPLLVIFSP    VLVPAVITIF
     LLGAGFLASG
851  GFGVAALSVL    SWIYRYLTGK    HPPGADQLES    AKTKLASKAR
     EMKDRAEQFS
901  QQPVAGSQTS  PWLE**
```

Figure 110 continued

```
  1  MAEHYGQQQQ    TRAPHLQLQP    RAQRVVKAAT    AVTAGGSLLV
     LSGLTLAGTV
 51  IALTIATPLL    VIFSPVLVPA    VITIFLLGAG    FLASGGFGVA
     ALSVLSWIYR
101  YLTGKHPPGA    DQLESAKTKL    ASKAREMKDR    AEQFSQQPVA
     GSQTSIDPSS
151  WLE**
```

Figure 111

```
  1  MAEHYGQQQQ    TRAPHLQLQP    RAQRVVKAAT    AVTAGGSLLV
     LSGLTLAGTV
 51  IALTIATPLL    VIFSPVLVPA    VITIFLLGAG    FLASGGFGVA
     ALSVLSWIYR
101  YLTGKHPPGA    DQLESAKTKL    ASKAREMKDR    AEQFSQQPVA
     GSQTSIDPSS
151  WHMMAEHYGQ    QQQTRAPHLQ    LQPRAQRVVK    AATAVTAGGS
     LLVLSGLTLA
201  GTVIALTIAT    PLLVIFSPVL    VPAVITIFLL    GAGFLASGGF
     GVAALSVLSW
251  IYRYLTGKHP    PGADQLESAK    TKLASKAREM    KDRAEQFSQQ
     PVAGSQTSID
301  QQVNVHMAEH    YGQQQQTRAP    HLQLQPRAQR    VVKAATAVTA
     GGSLLVLSGL
351  TLAGTVIALT    IATPLLVIFS    PVLVPAVITI    FLLGAGFLAS
     GGFGVAALSV
401  LSWIYRYLTG    KHPPGADQLE    SAKTKLASKA    REMKDRAEQF
     SQQPVAGSQT
451  SPWLE**
```

Figure 112

```
  1  MAEHYGQQQQ    TRAPHLQLQP    RAQRVVKAAT    AVTAGGSLLV
     LSGLTLAGTV
 51  IALTIATPLL    VIFSPVLVPA    VITIFLLGAG    FLASGGFGVA
     ALSVLSWIYR
101  YLTGKHPPGA    DQLESAKTKL    ASKAREMKDR    AEQFSQQPVA
     GSQTSIDPSS
151  WLEMAEHYGQ    QQQTRAPHLQ    LQPRAQRVVK    AATAVTAGGS
     LLVLSGLTLA
201  GTVIALTIAT    PLLVIFSPVL    VPAVITIFLL    GAGFLASGGF
     GVAALSVLSW
251  IYRYLTGKHP    PGADQLESAK    TKLASKAREM    KDRAEQFSQQ
     PVAGSQTSHM
301  MAEHYGQQQQ    TRAPHLQLQP    RAQRVVKAAT    AVTAGGSLLV
     LSGLTLAGTV
351  IALTIATPLL    VIFSPVLVPA    VITIFLLGAG    FLASGGFGVA
     ALSVLSWIYR
401  YLTGKHPPGA    DQLESAKTKL    ASKAREMKDR    AEQFSQQPVA
     GSQTSIDQQV
451  NVHMAEHYGQ    QQQTRAPHLQ    LQPRAQRVVK    AATAVTAGGS
     LLVLSGLTLA
501  GTVIALTIAT    PLLVIFSPVL    VPAVITIFLL    GAGFLASGGF
     GVAALSVLSW
551  IYRYLTGKHP    PGADQLESAK    TKLASKAREM    KDRAEQFSQQ
     PVAGSQTSPW
601  LE**
```

Figure 113

| | | | |
|---|---|---|---|
| 1 MAEHYGQQQQ | TRAPHLQLQP | RAQRVVKAAT | AVTAGGSLLV |
| LSGLTLAGTV | | | |
| 51 IALTIATPLL | VIFSPVLVPA | VITIFLLGAG | FLASGGFGVA |
| ALSVLSWIYR | | | |
| 101 YLTGKHPPGA | DQLESAKTKL | ASKAREMKDR | AEQFSQQPVA |
| GSQTSIDPSS | | | |
| 151 WLEMAEHYGQ | QQQTRAPHLQ | LQPRAQRVVK | AATAVTAGGS |
| LLVLSGLTLA | | | |
| 201 GTVIALTIAT | PLLVIFSPVL | VPAVITIFLL | GAGFLASGGF |
| GVAALSVLSW | | | |
| 251 IYRYLTGKHP | PGADQLESAK | TKLASKAREM | KDRAEQFSQQ |
| PVAGSQTSHM | | | |
| 301 FKWPSAMAEH | YGQQQQTRAP | HLQLQPRAQR | VVKAATAVTA |
| GGSLLVLSGL | | | |
| 351 TLAGTVIALT | IATPLLVIFS | PVLVPAVITI | FLLGAGFLAS |
| GGFGVAALSV | | | |
| 401 LSWIYRYLTG | KHPPGADQLE | SAKTKLASKA | REMKDRAEQF |
| SQQPVAGSQT | | | |
| 451 SSSELPWVDM | AEHYGQQQQT | RAPHLQLQPR | AQRVVKAATA |
| VTAGGSLLVL | | | |
| 501 SGLTLAGTVI | ALTIATPLLV | IFSPVLVPAV | ITIFLLGAGF |
| LASGGFGVAA | | | |
| 551 LSVLSWIYRY | LTGKHPPGAD | QLESAKTKLA | SKAREMKDRA |
| EQFSQQPVAG | | | |
| 601 SQTSSTPSSW | HMMAEHYGQQ | QQTRAPHLQL | QPRAQRVVKA |
| ATAVTAGGSL | | | |
| 651 LVLSGLTLAG | TVIALTIATP | LLVIFSPVLV | PAVITIFLLG |
| AGFLASGGFG | | | |
| 701 VAALSVLSWI | YRYLTGKHPP | GADQLESAKT | KLASKAREMK |
| DRAEQFSQQP | | | |

Figure 114

```
751  VAGSQTSIDQ    QVNVHMAEHY    GQQQQTRAPH    LQLQPRAQRV
     VKAATAVTAG
801  GSLLVLSGLT    LAGTVIALTI    ATPLLVIFSP    VLVPAVITIF
     LLGAGFLASG
851  GFGVAALSVL    SWIYRYLTGK    HPPGADQLES    AKTKLASKAR
     EMKDRAEQFS
901  QQPVAGSQTS    PWLE**
```

Figure 114 continued

```
  1  MAEHYGQQQQ   TRAPHLQLQP   RAQRVVKAAT   AVTAGGSLLV
     LSGLTLAGTV
 51  IALTIATPLL   VIFSPVLVPA   VITIFLLGAG   FLASGGFGVA
     ALSVLSWIYR
101  YLTGKHPPGA   DQLESAKTKL   ASKAREMKDR   AEQFSQQPVG
     GGGSGGGGSM
151  AEHYGQQQQT   RAPHLQLQPR   AQRVVKAATA   VTAGGSLLVL
     SGLTLAGTVI
201  ALTIATPLLV   IFSPVLVPAV   ITIFLLGAGF   LASGGFGVAA
     LSVLSWIYRY
251  LTGKHPPGAD   QLESAKTKLA   SKAREMKDRA   EQFSQQPVGG
     GGSGGGGSMA
301  EHYGQQQQTR   APHLQLQPRA   QRVVKAATAV   TAGGSLLVLS
     GLTLAGTVIA
351  LTIATPLLVI   FSPVLVPAVI   TIFLLGAGFL   ASGGFGVAAL
     SVLSWIYRYL
401   TGKHPPGADQ LESAKTKLAS KAREMKDRAE QFSQQPVPWL E**
```

Figure 115

```
  1 MAEHYGQQQQ   TRAPHLQLQP   RAQRVVKAAT   AVTAGGSLLV
    LSGLTLAGTV
 51 IALTIATPLL   VIFSPVLVPA   VITIFLLGAG   FLASGGFGVA
    ALSVLSWIYR
101 YLTGKHPPGA   DQLESAKTKL   ASKAREMKDR   AEQFSQQPVG
    GGGSGGGGSM
151 AEHYGQQQQT   RAPHLQLQPR   AQRVVKAATA   VTAGGSLLVL
    SGLTLAGTVI
201 ALTIATPLLV   IFSPVLVPAV   ITIFLLGAGF   LASGGFGVAA
    LSVLSWIYRY
251 LTGKHPPGAD   QLESAKTKLA   SKAREMKDRA   EQFSQQPVGG
    GGSGGGGSMA
301 EHYGQQQQTR   APHLQLQPRA   QRVVKAATAV   TAGGSLLVLS
    GLTLAGTVIA
351 LTIATPLLVI   FSPVLVPAVI   TIFLLGAGFL   ASGGFGVAAL
    SVLSWIYRYL
401 TGKHPPGADQ LESAKTKLAS KAREMKDRAE QFSQQPVPWL E**
```

Figure 116

SEQUENCE LISTING

```
<160> NUMBER OF SEQ ID NOS: 84

<210> SEQ ID NO 1
<211> LENGTH: 4
<212> TYPE: DNA
<213> ORGANISM: Artificial Sequence
<220> FEATURE:
<223> OTHER INFORMATION: Primer sequence

<400> SEQUENCE: 1 cacc                                                                     4

<210> SEQ ID NO 2
<211> LENGTH: 15
<212> TYPE: DNA
<213> ORGANISM: Artificial Sequence
<220> FEATURE:
<223> OTHER INFORMATION: Primer sequence

<400> SEQUENCE: 2
tcactcgagg agctc                                                        15

<210> SEQ ID NO 3
<211> LENGTH: 12
<212> TYPE: DNA
<213> ORGANISM: Artificial Sequence
<220> FEATURE:
<223> OTHER INFORMATION: Primer sequence

<400> SEQUENCE: 3
tctagaggta ct                                                           12

<210> SEQ ID NO 4
<211> LENGTH: 12
<212> TYPE: DNA
<213> ORGANISM: Artificial Sequence
<220> FEATURE:
<223> OTHER INFORMATION: Primer sequence

<400> SEQUENCE: 4
```

-continued

```
actagtagta cc                                                              12

<210> SEQ ID NO 5
<211> LENGTH: 12
<212> TYPE: DNA
<213> ORGANISM: Artificial Sequence
<220> FEATURE:
<223> OTHER INFORMATION: Primer sequence

<400> SEQUENCE: 5
cccgggggta ct                                                              12

<210> SEQ ID NO 6
<211> LENGTH: 12
<212> TYPE: DNA
<213> ORGANISM: Artificial Sequence
<220> FEATURE:
<223> OTHER INFORMATION: Primer sequence

<400> SEQUENCE: 6
ctgcagagta cc                                                              12

<210> SEQ ID NO 7
<211> LENGTH: 12
<212> TYPE: DNA
<213> ORGANISM: Artificial Sequence
<220> FEATURE:
<223> OTHER INFORMATION: Primer sequence

<400> SEQUENCE: 7
aagcttggta ct                                                              12

<210> SEQ ID NO 8
<211> LENGTH: 12
<212> TYPE: DNA
<213> ORGANISM: Artificial Sequence
<220> FEATURE:
<223> OTHER INFORMATION: Primer sequence

<400> SEQUENCE: 8
atcgatagta cc                                                              12

<210> SEQ ID NO 9
<211> LENGTH: 15
<212> TYPE: DNA
<213> ORGANISM: Artificial Sequence
<220> FEATURE:
<223> OTHER INFORMATION: Primer sequence

<400> SEQUENCE: 9
gtcgacggta cttct                                                           15

<210> SEQ ID NO 10
<211> LENGTH: 6
<212> TYPE: DNA
<213> ORGANISM: Artificial Sequence
<220> FEATURE:
<223> OTHER INFORMATION: Primer sequence

<400> SEQUENCE: 10 ctcgag                                                                      6

<210> SEQ ID NO 11
<211> LENGTH: 22
<212> TYPE: DNA
<213> ORGANISM: Artificial Sequence
<220> FEATURE:
```

-continued

<223> OTHER INFORMATION: Primer sequence

<400> SEQUENCE: 11
tcagatctcg gtgacgggca gg                                              22

<210> SEQ ID NO 12
<211> LENGTH: 22
<212> TYPE: DNA
<213> ORGANISM: Artificial Sequence
<220> FEATURE:
<223> OTHER INFORMATION: Primer sequence

<400> SEQUENCE: 12
atgagccaag aacgacgccc gg                                              22

<210> SEQ ID NO 13
<211> LENGTH: 22
<212> TYPE: DNA
<213> ORGANISM: Artificial Sequence
<220> FEATURE:
<223> OTHER INFORMATION: Primer sequence

<400> SEQUENCE: 13
caccatggca caacctcaag tt                                              22

<210> SEQ ID NO 14
<211> LENGTH: 11
<212> TYPE: DNA
<213> ORGANISM: Artificial Sequence
<220> FEATURE:
<223> OTHER INFORMATION: Primer sequence

<400> SEQUENCE: 14
gctccaccgc g                                                          11

<210> SEQ ID NO 15
<211> LENGTH: 14
<212> TYPE: DNA
<213> ORGANISM: Artificial Sequence
<220> FEATURE:
<223> OTHER INFORMATION: Primer sequence

<400> SEQUENCE: 15
tccactagtt ctag                                                       14

<210> SEQ ID NO 16
<211> LENGTH: 15
<212> TYPE: DNA
<213> ORGANISM: Artificial Sequence
<220> FEATURE:
<223> OTHER INFORMATION: Primer sequence

<400> SEQUENCE: 16
ctagaactag tggat                                                      15

<210> SEQ ID NO 17
<211> LENGTH: 13
<212> TYPE: DNA
<213> ORGANISM: Artificial Sequence
<220> FEATURE:
<223> OTHER INFORMATION: Primer sequence

<400> SEQUENCE: 17
tcctgcagag tac                                                        13

<210> SEQ ID NO 18

```
<211> LENGTH: 13
<212> TYPE: DNA
<213> ORGANISM: Artificial Sequence
<220> FEATURE:
<223> OTHER INFORMATION: Primer sequence

<400> SEQUENCE: 18
gtactctgca gga                                                          13

<210> SEQ ID NO 19
<211> LENGTH: 12
<212> TYPE: DNA
<213> ORGANISM: Artificial Sequence
<220> FEATURE:
<223> OTHER INFORMATION: Primer sequence

<400> SEQUENCE: 19
atacgatagt ac                                                           12

<210> SEQ ID NO 20
<211> LENGTH: 15
<212> TYPE: DNA
<213> ORGANISM: Artificial Sequence
<220> FEATURE:
<223> OTHER INFORMATION: Primer sequence

<400> SEQUENCE: 20
ctatcgatac cgtcg                                                        15

<210> SEQ ID NO 21
<211> LENGTH: 24
<212> TYPE: DNA
<213> ORGANISM: Artificial Sequence
<220> FEATURE:
<223> OTHER INFORMATION: Primer sequence

<400> SEQUENCE: 21
ctcgagtgtt gatctcttag cttc                                              24

<210> SEQ ID NO 22
<211> LENGTH: 10
<212> TYPE: PRT
<213> ORGANISM: Artificial Sequence
<220> FEATURE:
<223> OTHER INFORMATION: Linker sequence

<400> SEQUENCE: 22

Gly Gly Gly Gly Ser Gly Gly Gly Gly Ser
1               5                   10

<210> SEQ ID NO 23
<211> LENGTH: 24
<212> TYPE: DNA
<213> ORGANISM: Artificial Sequence
<220> FEATURE:
<223> OTHER INFORMATION: Primer sequence

<400> SEQUENCE: 23
gacacgctcg aggaattcgg tacc                                              24

<210> SEQ ID NO 24
<211> LENGTH: 24
<212> TYPE: DNA
<213> ORGANISM: Artificial Sequence
<220> FEATURE:
<223> OTHER INFORMATION: Primer sequence

<400> SEQUENCE: 24
```

-continued gatggtgatg actgcagatc agaa                                    24

<210> SEQ ID NO 25
<211> LENGTH: 30
<212> TYPE: DNA
<213> ORGANISM: Artificial Sequence
<220> FEATURE:
<223> OTHER INFORMATION: Primer sequence

<400> SEQUENCE: 25
cgattaatct gagtttttct gatctgcagt                              30

<210> SEQ ID NO 26
<211> LENGTH: 23
<212> TYPE: DNA
<213> ORGANISM: Artificial Sequence
<220> FEATURE:
<223> OTHER INFORMATION: Primer sequence

<400> SEQUENCE: 26
cgatcaccgt tccggccaat gtc                                     23

<210> SEQ ID NO 27
<211> LENGTH: 23
<212> TYPE: DNA
<213> ORGANISM: Artificial Sequence
<220> FEATURE:
<223> OTHER INFORMATION: Primer sequence

<400> SEQUENCE: 27
gacacgtgac ttctcgtctc ctt                                     23

<210> SEQ ID NO 28
<211> LENGTH: 24
<212> TYPE: DNA
<213> ORGANISM: Artificial Sequence
<220> FEATURE:
<223> OTHER INFORMATION: Primer sequence

<400> SEQUENCE: 28
gatggtgatg actgcagatc agaa                                    24

<210> SEQ ID NO 29
<211> LENGTH: 628
<212> TYPE: DNA
<213> ORGANISM: Trifolium repens

<400> SEQUENCE: 29
caccatggca caacctcaag ttcaagtcca ctcaacaaca acacaccgtc aagaaactgc    60
tacctaccca tcaacccaaa acattcgtaa agatgtttac gaaaatgtta actatcccgg   120
ccaacgcggt cgttataacg accgctataa tgatagtggt cgttatgatg gtggtattgc   180 ctccttttg tcagagagaa gtcctccagc ctctcaaatc ctcgctaccg ttggaggatt    240
tttcataggt ggtactctat ttttattagc tagcatttca tttatcgcca gtcttattgg   300
attggcgata atgacaccac tttttatcct ttttagcccg gttttagtcc ctgctgccct   360
cactataggg ctagcagtgg ctggaatatt gacagcagat gcttgcgggt tgacggggct   420
tatgtcgttg tcgtggaccg tgaaatatgt tagggattta caagcagtag tgcccgaaca   480
aatggattcg atgaagggac gtgtcgcgga tgtcgcgagt tatgttggac aaaagactaa   540
ggatgttgga caaaaacta aagaggttgg acaagacata caacaaaag cacatgaagc    600 taagagatca acagtcgacc tcgagtga                                     628

<210> SEQ ID NO 30
<211> LENGTH: 633
<212> TYPE: DNA
<213> ORGANISM: Trifolium repens

<400> SEQUENCE: 30

| | | | | | |
|---|---|---|---|---|---|
| tctagaggta | ctatggcaca | acctcaagtt | caagtccact | caacaacaac | acaccgtcaa | 60 |
| gaaactgcta | cctacccatc | aacccaaaac | attcgtaaag | atgtttacga | aaatgttaac | 120 |
| tatcccggcc | aacgcggtcg | ttataacgac | cgctataatg | atagtggtcg | ttatgatggt | 180 |
| ggtattgcct | cctttttgtc | agagagaagt | cctccagcct | ctcaaatcct | cgctaccgtt | 240 |
| ggaggatttt | tcataggtgg | tactctattt | ttattagcta | gcatttcatt | tatcgccagt | 300 |
| cttattggat | tggcgataat | gacaccactt | tttatccttt | ttagcccggt | tttagtccct | 360 |
| gctgccctca | ctatagggct | agcagtggct | ggaatattga | cagcagatgc | ttgcgggttg | 420 |
| acggggctta | tgtcgttgtc | gtggaccgtg | aaatatgtta | gggatttaca | agcagtagtg | 480 |
| cccgaacaaa | tggattcgat | gaagggacgt | gtcgcggatg | tcgcgagtta | tgttggacaa | 540 |
| aagactaagg | atgttggaca | aaaaactaaa | gaggttggac | aagacataca | aacaaaagca | 600 |
| catgaagcta | agagatcaac | aggtactact | agt | | | 633 |

<210> SEQ ID NO 31
<211> LENGTH: 613
<212> TYPE: DNA
<213> ORGANISM: Trifolium repens

<400> SEQUENCE: 31

| | | | | | |
|---|---|---|---|---|---|
| cccggggtac | tatggcacaa | cctcaagttc | aagtccactc | aacaacaaca | caccgtcaag | 60 |
| aaactgctac | ctacccatca | acccaaaaca | ttcgtaaaga | tgtttacgaa | aatgttaact | 120 |
| atcccggcca | acgcggtcgt | tataacgacc | gctataatga | tagtggtcgt | tatgatggtg | 180 |
| gtattgcctc | cttttgtca | gagagaagtc | ctccagcctc | tcaaatcctc | gctaccgttg | 240 |
| gaggattttt | cataggtggt | actctatttt | tattagctag | catttcattt | atcgccagtc | 300 |
| ttattggatt | ggcgataatg | acaccacttt | ttatccttt | tagcccggtt | ttagtccctg | 360 |
| ctgccctcac | tatagggcta | gcagtggctg | gaatattgac | agcagatgct | tgcgggttga | 420 |
| cggggcttat | gtcgttgtcg | tggaccgtga | aatatgttag | ggatttacaa | gcagtagtgc | 480 |
| ccgaacaaat | ggattcgatg | aagggacgtg | tcgcggatgt | cgcgagttat | gttggacaaa | 540 |
| agactaagga | tgttggacaa | aaaactaaag | aggttggaca | agacatacaa | acaaaagcac | 600 |
| aggtactctg | cag | | | | | 613 |

<210> SEQ ID NO 32
<211> LENGTH: 633
<212> TYPE: DNA
<213> ORGANISM: Trifolium repens

<400> SEQUENCE: 32

| | | | | | |
|---|---|---|---|---|---|
| aagcttggta | ctatggcaca | acctcaagtt | caagtccact | caacaacaac | acaccgtcaa | 60 |
| gaaactgcta | cctacccatc | aacccaaaac | attcgtaaag | atgtttacga | aaatgttaac | 120 |
| tatcccggcc | aacgcggtcg | ttataacgac | cgctataatg | atagtggtcg | ttatgatggt | 180 |
| ggtattgcct | cctttttgtc | agagagaagt | cctccagcct | ctcaaatcct | cgctaccgtt | 240 |
| ggaggatttt | tcataggtgg | tactctattt | ttattagcta | gcatttcatt | tatcgccagt | 300 |
| cttattggat | tggcgataat | gacaccactt | tttatccttt | ttagcccggt | tttagtccct | 360 |

```
gctgccctca ctatagggct agcagtggct ggaatattga cagcagatgc ttgcgggttg      420
acggggctta tgtcgttgtc gtggaccgtg aaatatgtta gggatttaca agcagtagtg      480
cccgaacaaa tggattcgat gaagggacgt gtcgcggatg tcgcgagtta tgttggacaa      540
aagactaagg atgttggaca aaaaactaaa gaggttggac aagacataca aacaaaagca      600
catgaagcta agagatcaac aggtactatc gat                                   633

<210> SEQ ID NO 33
<211> LENGTH: 630
<212> TYPE: DNA
<213> ORGANISM: Trifolium repens

<400> SEQUENCE: 33
gtcgacggta cttctatggc acaacctcaa gttcaagtcc actcaacaac aacacaccgt       60
caagaaactg ctacctaccc atcaacccaa acattcgta aagatgttta cgaaaatgtt      120
aactatcccg gccaacgcgg tcgttataac gaccgctata atgatagtgg tcgttatgat      180
ggtggtattg cctccttttt gtcagagaga agtcctccag cctctcaaat cctcgctacc      240
gttggaggat ttttcatagg tggtactcta tttttattag ctagcatttc atttatcgcc      300
agtcttattg gattggcgat aatgacacca ctttttatcc ttttagcccc ggttttagtc      360
cctgctgccc tcactatagg gctagcagtg gctggaatat tgacagcaga tgcttgcggg      420
ttgacggggc ttatgtcgtt gtcgtggacc gtgaaatatg ttagggattt acaagcagta      480
gtgcccgaac aaatggattc gatgaaggga cgtgtcgcgg atgtcgcgag ttatgttgga      540
caaaagacta aggatgttgg acaaaaaact aaagaggttg acaagacat acaaacaaaa      600 gcacatgaag ctaagagatc aacactcgag                                      630

<210> SEQ ID NO 34
<211> LENGTH: 709
<212> TYPE: DNA
<213> ORGANISM: Trifolium repens

<400> SEQUENCE: 34
caccatggca caacctcaag ttcaagtcca ctcaacaaca acacaccgtc aagaaactgc       60
tacctaccca tcaacccaaa acattcgtaa agatgtttac gaaaatgtta actatcccgg      120
ccaacgcggt cgttataacg accgctataa tgatagtggt cgttatgatg gtggtattgc      180 ctccttttg tcagagagaa gtcctccagc ctctcaaatc ctcgctaccg ttggaggatt      240
tttcataggt ggtactctat ttttattagc tagcatttca tttatcgcca gtcttattgg      300
attggcgata atgacaccac tttttatcct ttttagcccg gttttagtcc ctgctgccct      360
cactataggg ctagcagtgg ctggaatatt gacagcagat gcttgcgggt tgacggggct      420
tatgtcgttg tcgtggaccg tgaaatatgt tagggattta caagcagtag tgcccgaaca      480
aatggattcg atgaagggac gtgtcgcgga tgtcgcgagt tatgttggac aaaagactaa      540
ggatgttgga caaaaaacta aagaggttgg acaagacata caaacaaaag cacatgaagc      600
taagagatca acagagctcc accgcggtgg cggccgctct agaactagtg gatccccgg      660 gctgcaggaa ttcgatatca agcttatcga taccgtcgac ctcgagtga                 709

<210> SEQ ID NO 35
<211> LENGTH: 1336
<212> TYPE: DNA
<213> ORGANISM: Trifolium repens

<400> SEQUENCE: 35
```

```
caccatggca caacctcaag ttcaagtcca ctcaacaaca acacaccgtc aagaaactgc    60
tacctaccca tcaacccaaa acattcgtaa agatgtttac gaaaatgtta actatcccgg   120
ccaacgcggt cgttataacg accgctataa tgatagtggt cgttatgatg gtggtattgc   180
ctccttttg tcagagagaa gtcctccagc ctctcaaatc ctcgctaccg ttggaggatt   240
tttcataggt ggtactctat ttttattagc tagcatttca tttatcgcca gtcttattgg   300
attggcgata atgacaccac ttttatcct tttagcccg gttttagtcc ctgctgccct    360
cactataggg ctagcagtgg ctggaatatt gacagcagat gcttgcgggt tgacggggct   420
tatgtcgttg tcgtggaccg tgaaatatgt tagggattta caagcagtag tgcccgaaca   480
aatggattcg atgaagggac gtgtcgcgga tgtcgcgagt tatgttggac aaaagactaa   540
ggatgttgga caaaaaacta aagaggttgg acaagacata caaacaaaag cacatgaagc   600
taagagatca acagagctcc accgcggtgg cggccgctct agaggtacta tggcacaacc   660
tcaagttcaa gtccactcaa caacaacaca ccgtcaagaa actgctacct acccatcaac   720
ccaaaacatt cgtaaagatg tttacgaaaa tgttaactat cccggccaac gcggtcgtta   780
taacgaccgc tataatgata gtggtcgtta tgatggtggt attgcctcct ttttgtcaga   840
gagaagtcct ccagcctctc aaatcctcgc taccgttgga ggattttca taggtggtac   900
tctattttta ttagctagca tttcatttat cgccagtctt attggattgg cgataatgac   960
accactttt atccttttta gcccggtttt agtccctgct gccctcacta tagggctagc  1020
agtggctgga atattgacag cagatgcttg cgggttgacg gggcttatgt cgttgtcgtg  1080
gaccgtgaaa tatgttaggg atttacaagc agtagtgccc gaacaaatgg attcgatgaa  1140
gggacgtgtc gcggatgtcg cgagttatgt tggacaaaag actaaggatg ttggacaaaa  1200
aactaaagag gttggacaag acatacaaac aaaagcacat gaagctaaga gatcaacagg  1260
tactactaga actagtggat cccccgggct gcaggaattc gatatcaagc ttatcgatac  1320
cgtcgacctc gagtga                                                 1336

<210> SEQ ID NO 36
<211> LENGTH: 1958
<212> TYPE: DNA
<213> ORGANISM: Trifolium repens

<400> SEQUENCE: 36
caccatggca caacctcaag ttcaagtcca ctcaacaaca acacaccgtc aagaaactgc    60
tacctaccca tcaacccaaa acattcgtaa agatgtttac ggaaaatgtt aactatcccg   120
gccaacgcgg tcgttataac gaccgctata atgatagtgg tcgttatgat ggtggtattg   180
cctccttttt gtcagagaga agtcctccag cctctcaaat cctcgctacc gttggaggat   240
ttttcatagg tggtactcta ttttattag ctagcatttc atttatcgcc agtcttattg   300
gattggcgat aatgacacca cttttatcc tttagccc ggtttagtc cctgctgccc     360
tcactatagg gctagcagtg gctggaatat tgacagcaga tgcttgcggg ttgacggggc   420
ttatgtcgtt gtcgtggacc gtgaaatatg ttagggattt acaagcagta gtgcccgaac   480
aaatggattc gatgaaggga cgtgtcgcgg atgtcgcgag ttatgttgga caaaagacta   540
aggatgttgg acaaaaaact aaagaggttg gacaagacat acaaacaaaa gcacatgaag   600
ctaagagatc aacagagctc caccgcggtg gcggccgctc tagaggtact atggcacaac   660
ctcaagttca gtccactca acaacaacac accgtcaaga aactgctacc tacccatcaa   720
cccaaaacat tcgtaaagat gtttacgaaa atgttaacta tcccggccaa cgcggtcgtt   780
```

```
ataacgaccg ctataatgat agtggtcgtt atgatggtgg tattgcctcc ttttttgtcag    840 agagaagtcc tccagcctct caaatcctcg ctaccgttgg aggattttc  ataggtggta    900 ctctattttt attagctagc atttcattta tcgccagtct tattggattg gcgataatga    960
caccactttt tatccttttt agcccggttt tagtccctgc tgccctcact atagggctag   1020
cagtggctgg aatattgaca gcagatgctt gcgggttgac ggggcttatg tcgttgtcgt   1080
ggaccgtgaa atatgttagg gatttacaag cagtagtgcc cgaacaaatg gattcgatga   1140
agggacgtgt cgcggatgtc gcgagttatg ttggacaaaa gactaaggat gttggacaaa   1200
aaactaaaga ggttggacaa gacatacaaa caaaagcaca tgaagctaag agatcaacag   1260
gtactactag aactagtgga tcccccgggg gtactatggc acaacctcaa gttcaagtcc   1320
actcaacaac aacacaccgt caagaaactg ctacctaccc atcaacccaa acattcgta    1380 aagatgttta cgaaaatgtt aactatcccg gccaacgcgg tcgttataac gaccgctata   1440
atgatagtgg tcgttatgat ggtggtattg cctccttttt gtcagagaga agtcctccag   1500
cctctcaaat cctcgctacc gttggaggat ttttcatagg tggtactcta tttttattag   1560
ctagcatttc atttatcgcc agtcttattg gattggcgat aatgacacca ctttttatcc   1620
tttttagccc ggttttagtc cctgctgccc tcactatagg gctagcagtg gctggaatat   1680
tgacagcaga tgcttgcggg ttgacggggc ttatgtcgtt gtcgtggacc gtgaaatatg   1740
ttagggattt acaagcagta gtgcccgaac aaatggattc gatgaaggga cgtgtcgcgg   1800
atgtcgcgag ttatgttgga caaaagacta aggatgttgg acaaaaaact aaagaggttg   1860
gacaagacat acaaacaaaa gcacatgaag ctaagagatc aacaggtact ctgcaggaat   1920
tcgatatcaa gcttatcgat accgtcgacc tcgagtga                           1958

<210> SEQ ID NO 37
<211> LENGTH: 500
<212> TYPE: DNA
<213> ORGANISM: Trifolium repens

<400> SEQUENCE: 37
caacaaayaa cwcaccgtca agaaactgct acctacccat caacccawwa cattcgtaaa     60
gatgtttacg aaaatgttaa ctatcccggc caacgcggtc gttataacga ccgctataat   120
gatagtggtc gttatgatgg tggtattgcc tccttttttgt cagagagaag tcctccagcc   180
accgttggag gattttcat aggtggtact ctatttttat tagctagcat ttcatttatc   240
gccagtctta ttggattggc gataatgaca ccactttttta tctcaaatcc tcgcttcctt   300
tttagcccgg ttttagtccc tgctgccctc actatagggc tagcagtggc tggaatattg   360
acagcagatg cttgcgggtt gacggggctt atgtcgttgt cgtggaccgt gaaatatgtt   420
agggatttac aagcagtagt gcccgaacaa atggattcga tgaagggacg tgtcgcggat   480
gtcgcgagtt atgttggaca                                               500

<210> SEQ ID NO 38
<211> LENGTH: 662
<212> TYPE: DNA
<213> ORGANISM: Trifolium repens

<400> SEQUENCE: 38
gatatcaagc ttggtactaw tggcacaacc tcaagttcaa gtccactcaa caacaacaca     60
ccgtcaagaa aactgctacc tacccatcaa cccaaaacat tcgtaaagat gtttacgaaa   120
aatgtttaac tatcccggcc aacgcggtcg ttataacgac cgctataatg atagtggtcg   180
```

| | |
|---|---|
| tttatgatgg tggtattgcc tcctttttgt cagagagaag tcctccagcc tctcaaatcc | 240 |
| tcgctaccgt tggaggattt ttcataggtg gtactctatt tttattagct agcatttcat | 300 |
| ttatcgccag tcttattgga ttggcgataa tgacaccact tttatccttt tttagcccgg | 360 |
| twttagtccc tgctgccctc actatagggc tagcagtggc tggaatattg acagcagatg | 420 |
| cttgcgggtt gacggggctt atgtcgttgt cgtggaccgt gaaatatgtt agggatttac | 480 |
| aagcagtagt gcccgaacaa atggattcga tgaagggacg tgtcgcggat gtcgcgagtt | 540 |
| atgttggaca aaagactaag gatgttggac aaaaaactaa agaggttgga caagacatac | 600 |
| aaacaaaagc acatgaagct aagagatcaa caggtactat cgataccgtc gacctcgagt | 660 |
| ga | 662 |

<210> SEQ ID NO 39
<211> LENGTH: 794
<212> TYPE: DNA
<213> ORGANISM: Trifolium repens

<400> SEQUENCE: 39

| | |
|---|---|
| atacaaacaa aagcacatga agctaagaga tcaacaggta ctctgcagga attcgatatc | 60 |
| aagcttggta ctatggcaca acctcaagtt caagtccact caacaacaac acaccgtcaa | 120 |
| gaaactgcta cctacccatc aacccaaaac attcgtaaag atgtttacga aaatgttaac | 180 |
| tatcccggcc aacgcggtcg ttataacgac cgctataatg atagtggtcg ttatgatggt | 240 |
| ggtattgcct cctttttgtc agagagaagt cctccagcct ctcaaatcct cgctaccgtt | 300 |
| ggaggatttt tcataggtgg tactctattt ttattagcta gcatttcatt tatcgccagt | 360 |
| cttattggat tggcgataat gacaccactt tttatccttt ttagcccggt tttagtccct | 420 |
| gctgccctca ctatagggct agcagtggct ggaatattga cagcagatgc ttgcgggttg | 480 |
| acggggctta tgtcgttgtc gtggaccgtg aaatatgtta gggatttaca agcagtagtg | 540 |
| cccgaacaaa tggattcgat gaagggacgt gtcgcggatg tcgcgagtta tgttggacaa | 600 |
| aagactaagg atgttggaca aaaaactaaa gaggttggac aagacataca aacaaaagca | 660 |
| catgaagcta agagatcaac aggtactatc gataccgtcg acctcgagtg aaagggtggg | 720 |
| cgcgccgacc cagcttttctt gtacaaagtt ggcattataa gaaagcattg cttatcaatt | 780 |
| tgttgcaacg aaca | 794 |

<210> SEQ ID NO 40
<211> LENGTH: 609
<212> TYPE: DNA
<213> ORGANISM: Trifolium repens

<400> SEQUENCE: 40

| | |
|---|---|
| atggcacaac tcaagttca agtccactca acaacaacac accgtcaaga aactgctacc | 60 |
| tacccatcaa cccaaaacat tcgtaaagat gtttacgaaa atgttaacta tcccggccaa | 120 |
| cgcggtcgtt ataacgaccg ctataatgat agtggtcgtt atgatggtgg tattgcctcc | 180 |
| tttttgtcag agagaagtcc tccagcctct caaatcctcg ctaccgttgg aggattttttc | 240 |
| ataggtggta ctctattttt attagctagc atttcattta tcgccagtct tattggattg | 300 |
| gcgataatga caccactttt tatccttttt agcccggttt tagtccctgc tgccctcact | 360 |
| atagggctag cagtggctgg aatattgaca gcagatgctt gcgggttgac ggggcttatg | 420 |
| tcgttgtcgt ggaccgtgaa atatgttagg gatttacaag cagtagtgcc cgaacaaatg | 480 |
| gattcgatga agggacgtgt cgcggatgtc gcgagttatg ttggacaaaa gactaaggat | 540 |

```
gttggacaaa aaactaaaga ggttggacaa gacatacaaa caaaagcaca tgaagctaag    600
agatcaaca                                                            609

<210> SEQ ID NO 41
<211> LENGTH: 609
<212> TYPE: DNA
<213> ORGANISM: Trifolium repens

<400> SEQUENCE: 41
atggcacaac ctcaagttca agtccactca acaacaacac accgtcaaga aactgctacc     60
tacccatcaa cccaaaacat tcgtaaagat gtttacgaaa atgttaacta tcccggccaa    120
cgcggtcgtt ataacgaccg ctataatgat agtggtcgtt atgatggtgg tattgcctcc    180
tttttgtcag agagaagtcc tccagcctct caaatcctcg ctaccgttgg aggattttc     240 ataggtggta ctctattttt attagctagc atttcattta tcgccagtct tattggattg    300
gcgataatga caccactttt tatcctttt agcccggttt tagtccctgc tgccctcact     360
atagggctag cagtggctgg aatattgaca gcagatgctt gcgggttgac ggggcttatg    420
tcgttgtcgt ggaccgtgaa atatgttagg gatttacaag cagtagtgcc cgaacaaatg    480
gattcgatga agggacgtgt cgcggatgtc gcgagttatg ttggacaaaa gactaaggat    540
gttggacaaa aaactaaaga ggttggacaa gacatacaaa caaaagcaca tgaagctaag    600
agatcaaca                                                            609

<210> SEQ ID NO 42
<211> LENGTH: 869
<212> TYPE: DNA
<213> ORGANISM: Trifolium repens

<400> SEQUENCE: 42
agatcaacag gtactatcga taccgtcgac ctcgacggta cttctatggc acaacctcaa     60
gttcaagtcc actcaacaac aacacaccgt caagaaactg ctacctaccc atcaacccaa    120 acattcgta aagatgttta cgaaaatgtt aactatcccg ccaacgcgg tcgttataac    180 daccgctata atgatagtgg tcgttatgat ggtggtattg cctccttttt gtcagagaga    240
agtcctccag cctctcaaat cctcgctacc gttggaggat ttttcatagg tggtactcta    300
tttttattag ctagcatttc atttatcgcc agtcttattg gattggcgat aatgacacca    360 cttttatcc tttttagccc ggttttagtc cctgctgccc tcactatagg gctagcagtg    420
gctggaatat tgacagcaga tgcttgcggg ttgacggggc ttatgtcgtt gtcgtggacc    480
gtgaaatatg ttagggattt acaagcagta gtgcccgaac aaatggattc gatgaaggga    540
cgtgtcgcgg atgtcgcgag ttatgttgga caaaagacta aggatgttgg acaaaaaact    600
aaagaggttg gacaagacat acaaacaaaa gcacatgaag ctaagagatc aacactcgag    660
tgaaagggtg ggcgcgccga cccagctttc ttgtacaaag ttggcattat aagaaagcat    720
tgcttatcaa tttgttgcaa cgaacaggtc actatcagtc aaaataaaat cattatttgc    780
catccagctg atatccccta tagtgagtcg tattacatgg tcatagctgt ttcctggcag    840
ctctggcccg tgtctcaaaa tctctgatg                                      869

<210> SEQ ID NO 43
<211> LENGTH: 818
<212> TYPE: DNA
<213> ORGANISM: Trifolium repens

<400> SEQUENCE: 43
```

```
gacatacaaa caaaagcaca tgaagctaag agatcaacag gtactatcga taccgtcgac    60
ctcgacggta cttctatggc acaacctcaa gttcaagtcc actcaacaac aacacaccgt   120
caagaaactg ctacctaccc atcaacccaa aacattcgta aagatgttta cgaaaatgtt   180
aactatcccg gccaacgcgg tcgttataac gaccgctata atgatagtgg tcgttatgat   240
ggtggtattg cctccttttt gtcagagaga agtcctccag cctctcaaat cctcgctacc   300
gttggaggat ttttcatagg tggtactcta ttttattag ctagcatttc atttatcgcc    360
agtcttattg gattggcgat aatgacacca cttttatcc ttttagcccc ggttttagtc    420
cctgctgccc tcactatagg gctagcagtg gctggaatat tgacagcaga tgcttgcggg   480
ttgacggggc ttatgtcgtt gtcgtggacc gtgaaatatg ttagggattt acaagcagta   540
gtgcccgaac aaatggattc gatgaaggga cgtgtcgcgg atgtcgcgag ttatgttgga   600
caaaagacta aggatgttgg acaaaaaact aaagaggttg acaagacat acaaacaaaa    660 gcacatgaag ctaagagatc aacactcgag tgaaagggtg ggcgcgccga cccagcttc    720 ttgtacaaag ttgscattat aagaaagcat tgcttatcaa tttgtkgcaa cgaacaggtc   780
actatcagtc aaaataaaat ckattattg ctcgattg                            818

<210> SEQ ID NO 44
<211> LENGTH: 304
<212> TYPE: DNA
<213> ORGANISM: Arabidopsis thaliana

<400> SEQUENCE: 44
gtaaatttct gtgttcctta ttctctcaaa atcttcgatt ttgttttcgt tcgatcccaa    60
tttcgtatat gttctttggt ttagattctg ttaatcttag atcgaagacg attttctggg   120
tttgatcgtt agatatcatc ttaattctcg attagggttt catagatatc atccgatttg   180
ttcaaataat ttgagttttg tcgaataatt actcttcgat ttgtgatttc tatctagatc   240
tggtgttagt ttctagtttg tgcgatcgaa tttgtcgatt aatctgagtt tttctgatta   300
acag                                                                304

<210> SEQ ID NO 45
<211> LENGTH: 304
<212> TYPE: DNA
<213> ORGANISM: Arabidopsis thaliana

<400> SEQUENCE: 45
gtaaatttct gtgttcctta ttctctcaaa atcttcgatt ttgttttcgt tcgatcccaa    60
tttcgtatat gttctttggt ttagattctg ttaatcttag atcgaagacg attttctggg   120
tttgatcgtt agatatcatc ttaattctcg attagggttt catagatatc atccgatttg   180
ttcaaataat ttgagttttg tcgaataatt actcttcgat ttgtgatttc tatctagatc   240
tggtgttagt ttctagtttg tgcgatcgaa tttgtcgatt aatctgagtt tttctgatct   300
gcag                                                                304

<210> SEQ ID NO 46
<211> LENGTH: 301
<212> TYPE: DNA
<213> ORGANISM: Arabidopsis thaliana

<400> SEQUENCE: 46
gtaaatttct gtgttcctta ttctctcaaa atcttcgatt ttgttttcgt tcgatcccaa    60
tttcgtatat gttctttggt ttagattctg ttaatcttag atcgaagacg attttctggg   120
```

```
tttgatcgtt agatatcatc ttaattctcg attagggttt catagatatc atccgatttg      180
ttcaaataat ttgagttttg tcgaataatt actcttcgat ttgtgatttc tatctagatc      240
tggtgttagt ttctagtttg tgcgatcgaa tttgtcgatt aatctgagtt tttctgatca      300
g                                                                      301
```

<210> SEQ ID NO 47
<211> LENGTH: 870
<212> TYPE: PRT
<213> ORGANISM: Sesamum indicum

<400> SEQUENCE: 47

```
Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
                20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
                100                 105                 110

Leu Glu Ser Ala Lys Thr Lys Leu Ala Ser Lys Ala Arg Glu Met Lys
            115                 120                 125

Asp Arg Ala Glu Gln Phe Ser Gln Pro Val Ala Gly Ser Gln Thr
    130                 135                 140

Ser Met Ala Glu His Tyr Gly Gln Gln Gln Thr Arg Ala Pro His
145                 150                 155                 160

Leu Gln Leu Gln Pro Arg Ala Gln Arg Val Val Lys Ala Ala Thr Ala
                165                 170                 175

Val Thr Ala Gly Gly Ser Leu Leu Val Leu Ser Gly Leu Thr Leu Ala
            180                 185                 190

Gly Thr Val Ile Ala Leu Thr Ile Ala Thr Pro Leu Leu Val Ile Phe
    195                 200                 205

Ser Pro Val Leu Val Pro Ala Val Ile Thr Ile Phe Leu Leu Gly Ala
210                 215                 220

Gly Phe Leu Ala Ser Gly Gly Phe Gly Val Ala Ala Leu Ser Val Leu
225                 230                 235                 240

Ser Trp Ile Tyr Arg Tyr Leu Thr Gly Lys His Pro Pro Gly Ala Asp
                245                 250                 255

Gln Leu Glu Ser Ala Lys Thr Lys Leu Ala Ser Lys Ala Arg Glu Met
            260                 265                 270

Lys Asp Arg Ala Glu Gln Phe Ser Gln Pro Val Ala Gly Ser Gln
    275                 280                 285

Thr Ser Met Ala Glu His Tyr Gly Gln Gln Gln Thr Arg Ala Pro
290                 295                 300

His Leu Gln Leu Gln Pro Arg Ala Gln Arg Val Val Lys Ala Ala Thr
305                 310                 315                 320

Ala Val Thr Ala Gly Gly Ser Leu Leu Val Leu Ser Gly Leu Thr Leu
                325                 330                 335
```

-continued

```
Ala Gly Thr Val Ile Ala Leu Thr Ile Ala Thr Pro Leu Val Ile
            340                 345                 350

Phe Ser Pro Val Leu Val Pro Ala Val Ile Thr Ile Phe Leu Leu Gly
            355                 360                 365

Ala Gly Phe Leu Ala Ser Gly Gly Phe Gly Val Ala Ala Leu Ser Val
370                 375                 380

Leu Ser Trp Ile Tyr Arg Tyr Leu Thr Gly Lys His Pro Pro Gly Ala
385                 390                 395                 400

Asp Gln Leu Glu Ser Ala Lys Thr Lys Leu Ala Ser Lys Ala Arg Glu
                405                 410                 415

Met Lys Asp Arg Ala Glu Gln Phe Ser Gln Pro Val Ala Gly Ser
            420                 425                 430

Gln Thr Ser Met Ala Glu His Tyr Gly Gln Gln Gln Thr Arg Ala
            435                 440                 445

Pro His Leu Gln Leu Gln Pro Arg Ala Gln Arg Val Val Lys Ala Ala
    450                 455                 460

Thr Ala Val Thr Ala Gly Gly Ser Leu Leu Val Leu Ser Gly Leu Thr
465                 470                 475                 480

Leu Ala Gly Thr Val Ile Ala Leu Thr Ile Ala Thr Pro Leu Leu Val
                485                 490                 495

Ile Phe Ser Pro Val Leu Val Pro Ala Val Ile Thr Ile Phe Leu Leu
            500                 505                 510

Gly Ala Gly Phe Leu Ala Ser Gly Gly Phe Gly Val Ala Ala Leu Ser
            515                 520                 525

Val Leu Ser Trp Ile Tyr Arg Tyr Leu Thr Gly Lys His Pro Pro Gly
    530                 535                 540

Ala Asp Gln Leu Glu Ser Ala Lys Thr Lys Leu Ala Ser Lys Ala Arg
545                 550                 555                 560

Glu Met Lys Asp Arg Ala Glu Gln Phe Ser Gln Pro Val Ala Gly
                565                 570                 575

Ser Gln Thr Ser Met Ala Glu His Tyr Gly Gln Gln Gln Thr Arg
            580                 585                 590

Ala Pro His Leu Gln Leu Gln Pro Arg Ala Gln Arg Val Val Lys Ala
            595                 600                 605

Ala Thr Ala Val Thr Ala Gly Gly Ser Leu Leu Val Leu Ser Gly Leu
    610                 615                 620

Thr Leu Ala Gly Thr Val Ile Ala Leu Thr Ile Ala Thr Pro Leu Leu
625                 630                 635                 640

Val Ile Phe Ser Pro Val Leu Val Pro Ala Val Ile Thr Ile Phe Leu
                645                 650                 655

Leu Gly Ala Gly Phe Leu Ala Ser Gly Gly Phe Gly Val Ala Ala Leu
            660                 665                 670

Ser Val Leu Ser Trp Ile Tyr Arg Tyr Leu Thr Gly Lys His Pro Pro
            675                 680                 685

Gly Ala Asp Gln Leu Glu Ser Ala Lys Thr Lys Leu Ala Ser Lys Ala
    690                 695                 700

Arg Glu Met Lys Asp Arg Ala Glu Gln Phe Ser Gln Pro Val Ala
705                 710                 715                 720

Gly Ser Gln Thr Ser Met Ala Glu His Tyr Gly Gln Gln Gln Thr
                725                 730                 735

Arg Ala Pro His Leu Gln Leu Gln Pro Arg Ala Gln Arg Val Val Lys
            740                 745                 750

Ala Ala Thr Ala Val Thr Ala Gly Gly Ser Leu Leu Val Leu Ser Gly
            755                 760                 765
```

```
Leu Thr Leu Ala Gly Thr Val Ile Ala Leu Thr Ile Ala Thr Pro Leu
        770                 775                 780

Leu Val Ile Phe Ser Pro Val Leu Val Pro Ala Val Ile Thr Ile Phe
785                 790                 795                 800

Leu Leu Gly Ala Gly Phe Leu Ala Ser Gly Gly Phe Gly Val Ala Ala
                805                 810                 815

Leu Ser Val Leu Ser Trp Ile Tyr Arg Tyr Leu Thr Gly Lys His Pro
            820                 825                 830

Pro Gly Ala Asp Gln Leu Glu Ser Ala Lys Thr Lys Leu Ala Ser Lys
            835                 840                 845

Ala Arg Glu Met Lys Asp Arg Ala Glu Gln Phe Ser Gln Pro Val
        850                 855                 860

Ala Gly Ser Gln Thr Ser
865                 870

<210> SEQ ID NO 48
<211> LENGTH: 839
<212> TYPE: PRT
<213> ORGANISM: Sesamum indicum

<400> SEQUENCE: 48

Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
                20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Pro Val Ala Gly Ser Gln Thr
130                 135                 140

Ser Ile Asp Pro Ser Ser Trp Leu Glu Met Ala Glu His Tyr Gly Gln
145                 150                 155                 160

Gln Gln Gln Thr Arg Ala Pro His Leu Gln Leu Gln Pro Arg Ala Gln
                165                 170                 175

Arg Val Val Lys Ala Ala Thr Ala Val Thr Ala Gly Gly Ser Leu Leu
            180                 185                 190

Val Leu Ser Gly Leu Thr Leu Ala Gly Thr Val Ile Ala Leu Thr Ile
        195                 200                 205

Ala Thr Pro Leu Leu Val Ile Phe Ser Pro Val Leu Val Pro Ala Val
    210                 215                 220

Ile Thr Ile Phe Leu Leu Gly Ala Gly Phe Leu Ala Ser Gly Gly Phe
225                 230                 235                 240

Gly Val Ala Ala Leu Ser Val Leu Ser Trp Ile Tyr Arg Tyr Leu Thr
                245                 250                 255

Gly Lys His Pro Pro Gly Ala Asp Gln Leu Glu Ser Ala Lys Thr Lys
            260                 265                 270
```

-continued

Leu Ala Ser Lys Ala Arg Glu Met Lys Asp Arg Ala Glu Gln Phe Ser
            275                 280                 285
Gln Gln Pro Val Ala Gly Ser Gln Thr Ser His Met Phe Lys Trp Pro
            290                 295                 300
Ser Ala Met Ala Glu His Tyr Gly Gln Gln Gln Thr Arg Ala Pro
305                 310                 315                 320
His Leu Gln Leu Gln Pro Arg Ala Gln Arg Val Val Lys Ala Ala Thr
                325                 330                 335
Ala Val Thr Ala Gly Gly Ser Leu Leu Val Leu Ser Gly Leu Thr Leu
                340                 345                 350
Ala Gly Thr Val Ile Ala Leu Thr Ile Ala Thr Pro Leu Leu Val Ile
                355                 360                 365
Phe Ser Pro Val Leu Val Pro Ser Ser Ser Glu Leu Pro Trp Val Asp
            370                 375                 380
Met Ala Glu His Tyr Gly Gln Gln Gln Gln Thr Arg Ala Pro His Leu
385                 390                 395                 400
Gln Leu Gln Pro Arg Ala Gln Arg Val Val Lys Ala Ala Thr Ala Val
                405                 410                 415
Thr Ala Gly Gly Ser Leu Leu Val Leu Ser Gly Leu Thr Leu Ala Gly
                420                 425                 430
Thr Val Ile Ala Leu Thr Ile Ala Thr Pro Leu Leu Val Ile Phe Ser
                435                 440                 445
Pro Val Leu Val Pro Ala Val Ile Thr Ile Phe Leu Leu Gly Ala Gly
            450                 455                 460
Phe Leu Ala Ser Gly Gly Phe Gly Val Ala Ala Leu Ser Val Leu Ser
465                 470                 475                 480
Trp Ile Tyr Arg Tyr Leu Thr Gly Lys His Pro Pro Gly Ala Asp Gln
                485                 490                 495
Leu Glu Ser Ala Lys Thr Lys Leu Ala Ser Lys Ala Arg Glu Met Lys
                500                 505                 510
Asp Arg Ala Glu Gln Phe Ser Gln Gln Pro Val Ala Gly Ser Gln Thr
                515                 520                 525
Ser His Met Glu Phe Lys Leu Ser Thr Met Ala Glu His Tyr Gly Gln
                530                 535                 540
Gln Gln Gln Thr Arg Ala Pro His Leu Gln Leu Gln Pro Arg Ala Gln
545                 550                 555                 560
Arg Val Val Lys Ala Ala Thr Ala Val Thr Ala Gly Gly Ser Leu Leu
                565                 570                 575
Val Leu Ser Gly Leu Thr Leu Ala Gly Thr Val Ile Ala Leu Thr Ile
                580                 585                 590
Ala Thr Pro Leu Leu Val Ile Phe Ser Pro Val Leu Val Pro Ala Val
                595                 600                 605
Ile Thr Ile Phe Leu Leu Gly Ala Gly Phe Leu Ala Ser Gly Gly Phe
                610                 615                 620
Gly Val Ala Ala Leu Ser Val Leu Ser Trp Ile Tyr Arg Tyr Leu Thr
625                 630                 635                 640
Gly Lys His Pro Pro Gly Ala Asp Gln Leu Glu Ser Ala Lys Thr Lys
                645                 650                 655
Leu Ala Ser Lys Ala Arg Glu Met Lys Asp Arg Ala Glu Gln Phe Ser
                660                 665                 670
Gln Gln Pro Val Ala Gly Ser Gln Thr Ser Ile Asp Gln Gln Val Asn
                675                 680                 685
Val His Met Ala Glu His Tyr Gly Gln Gln Gln Gln Thr Arg Ala Pro

```
                690                 695                 700
His Leu Gln Leu Gln Pro Arg Ala Gln Arg Val Val Lys Ala Ala Thr
705                 710                 715                 720

Ala Val Thr Ala Gly Gly Ser Leu Leu Val Leu Ser Gly Leu Thr Leu
                725                 730                 735

Ala Gly Thr Val Ile Ala Leu Thr Ile Ala Thr Pro Leu Leu Val Ile
                740                 745                 750

Phe Ser Pro Val Leu Val Pro Ala Val Ile Thr Ile Phe Leu Leu Gly
                755                 760                 765

Ala Gly Phe Leu Ala Ser Gly Gly Phe Gly Val Ala Ala Leu Ser Val
                770                 775                 780

Leu Ser Trp Ile Tyr Arg Tyr Leu Thr Gly Lys His Pro Pro Gly Ala
785                 790                 795                 800

Asp Gln Leu Glu Ser Ala Lys Thr Lys Leu Ala Ser Lys Ala Arg Glu
                805                 810                 815

Met Lys Asp Arg Ala Glu Gln Phe Ser Gln Gln Pro Val Ala Gly Ser
                820                 825                 830

Gln Thr Ser Pro Trp Leu Glu
                835

<210> SEQ ID NO 49
<211> LENGTH: 869
<212> TYPE: PRT
<213> ORGANISM: Sesamum indicum

<400> SEQUENCE: 49

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
                20                  25                  30

Thr Ala Gly Gly Ser Leu Leu Val Leu Ser Gly Leu Thr Leu Ala Gly
                35                  40                  45

Thr Val Ile Ala Leu Thr Ile Ala Thr Pro Leu Leu Val Ile Phe Ser
        50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
                100                 105                 110

Leu Glu Ser Ala Lys Thr Lys Leu Ala Ser Lys Ala Arg Glu Met Lys
                115                 120                 125

Asp Arg Ala Glu Gln Phe Ser Gln Gln Pro Val Ala Gly Ser Gln Thr
                130                 135                 140

Ser Met Ala Glu His Tyr Gly Gln Gln Gln Thr Arg Ala Pro His
145                 150                 155                 160

Leu Gln Leu Gln Pro Arg Ala Gln Arg Val Val Lys Ala Ala Thr Ala
                165                 170                 175

Val Thr Ala Gly Gly Ser Leu Leu Val Leu Ser Gly Leu Thr Leu Ala
                180                 185                 190

Gly Thr Val Ile Ala Leu Thr Ile Ala Thr Pro Leu Leu Val Ile Phe
                195                 200                 205

Ser Pro Val Leu Val Pro Ala Val Ile Thr Ile Phe Leu Leu Gly Ala
        210                 215                 220

Gly Phe Leu Ala Ser Gly Gly Phe Gly Val Ala Ala Leu Ser Val Leu
```

-continued

```
                225                 230                 235                 240
Ser Trp Ile Tyr Arg Tyr Leu Thr Gly Lys His Pro Gly Ala Asp
                245                 250                 255
Gln Leu Glu Ser Ala Lys Thr Lys Leu Ala Ser Lys Ala Arg Glu Met
                260                 265                 270
Lys Asp Arg Ala Glu Gln Phe Ser Gln Gln Pro Val Ala Gly Ser Gln
                275                 280                 285
Thr Ser Met Ala Glu His Tyr Gly Gln Gln Gln Thr Arg Ala Pro
                290                 295                 300
His Leu Gln Leu Gln Pro Arg Ala Gln Arg Val Val Lys Ala Ala Thr
305                 310                 315                 320
Ala Val Thr Ala Gly Gly Ser Leu Leu Val Leu Ser Gly Leu Thr Leu
                325                 330                 335
Ala Gly Thr Val Ile Ala Leu Thr Ile Ala Thr Pro Leu Leu Val Ile
                340                 345                 350
Phe Ser Pro Val Leu Val Pro Ala Val Ile Thr Ile Phe Leu Leu Gly
                355                 360                 365
Ala Gly Phe Leu Ala Ser Gly Gly Phe Gly Val Ala Ala Leu Ser Val
                370                 375                 380
Leu Ser Trp Ile Tyr Arg Tyr Leu Thr Gly Lys His Pro Pro Gly Ala
385                 390                 395                 400
Asp Gln Leu Glu Ser Ala Lys Thr Lys Leu Ala Ser Lys Ala Arg Glu
                405                 410                 415
Met Lys Asp Arg Ala Glu Gln Phe Ser Gln Gln Pro Val Ala Gly Ser
                420                 425                 430
Gln Thr Ser Met Ala Glu His Tyr Gly Gln Gln Gln Thr Arg Ala
                435                 440                 445
Pro His Leu Gln Leu Gln Pro Arg Ala Gln Arg Val Val Lys Ala Ala
                450                 455                 460
Thr Ala Val Thr Ala Gly Gly Ser Leu Leu Val Leu Ser Gly Leu Thr
465                 470                 475                 480
Leu Ala Gly Thr Val Ile Ala Leu Thr Ile Ala Thr Pro Leu Leu Val
                485                 490                 495
Ile Phe Ser Pro Val Leu Val Pro Ala Val Ile Thr Ile Phe Leu Leu
                500                 505                 510
Gly Ala Gly Phe Leu Ala Ser Gly Gly Phe Gly Val Ala Ala Leu Ser
                515                 520                 525
Val Leu Ser Trp Ile Tyr Arg Tyr Leu Thr Gly Lys His Pro Pro Gly
                530                 535                 540
Ala Asp Gln Leu Glu Ser Ala Lys Thr Lys Leu Ala Ser Lys Ala Arg
545                 550                 555                 560
Glu Met Lys Asp Arg Ala Glu Gln Phe Ser Gln Gln Pro Val Ala Gly
                565                 570                 575
Ser Gln Thr Ser Met Ala Glu His Tyr Gly Gln Gln Gln Thr Arg
                580                 585                 590
Ala Pro His Leu Gln Leu Gln Pro Arg Ala Gln Arg Val Val Lys Ala
                595                 600                 605
Ala Thr Ala Val Thr Ala Gly Gly Ser Leu Leu Val Leu Ser Gly Leu
                610                 615                 620
Thr Leu Ala Gly Thr Val Ile Ala Leu Thr Ile Ala Thr Pro Leu Leu
625                 630                 635                 640
Val Ile Phe Ser Pro Val Leu Val Pro Ala Val Ile Thr Ile Phe Leu
                645                 650                 655
```

```
Leu Gly Ala Gly Phe Leu Ala Ser Gly Gly Phe Gly Val Ala Ala Leu
            660                 665                 670

Ser Val Leu Ser Trp Ile Tyr Arg Tyr Leu Thr Gly Lys His Pro Pro
        675                 680                 685

Gly Ala Asp Gln Leu Glu Ser Ala Lys Thr Lys Leu Ala Ser Lys Ala
    690                 695                 700

Arg Glu Met Lys Asp Arg Ala Glu Gln Phe Ser Gln Gln Pro Val Ala
705                 710                 715                 720

Gly Ser Gln Thr Met Ala Glu His Tyr Gly Gln Gln Gln Thr Arg
            725                 730                 735

Ala Pro His Leu Gln Leu Gln Pro Arg Ala Gln Arg Val Val Lys Ala
                740                 745                 750

Ala Thr Ala Val Thr Ala Gly Gly Ser Leu Leu Val Leu Ser Gly Leu
            755                 760                 765

Thr Leu Ala Gly Thr Val Ile Ala Leu Thr Ile Ala Thr Pro Leu Leu
    770                 775                 780

Val Ile Phe Ser Pro Val Leu Val Pro Ala Val Ile Thr Ile Phe Leu
785                 790                 795                 800

Leu Gly Ala Gly Phe Leu Ala Ser Gly Gly Phe Gly Val Ala Ala Leu
            805                 810                 815

Ser Val Leu Ser Trp Ile Tyr Arg Tyr Leu Thr Gly Lys His Pro Pro
        820                 825                 830

Gly Ala Asp Gln Leu Glu Ser Ala Lys Thr Lys Leu Ala Ser Lys Ala
    835                 840                 845

Arg Glu Met Lys Asp Arg Ala Glu Gln Phe Ser Gln Gln Pro Val Ala
    850                 855                 860

Gly Ser Gln Thr Ser
865

<210> SEQ ID NO 50
<211> LENGTH: 3289
<212> TYPE: DNA
<213> ORGANISM: Artificial Sequence
<220> FEATURE:
<223> OTHER INFORMATION: Synthetic sequence

<400> SEQUENCE: 50
aataatgatt ttattttgac tgatagtgac ctgttcgttg caacaaattg atgagcaatg      60
cttttttata atgccaactt tgtacaaaaa agcaggctcc gcggccgctt gctccgttaa     120
aaaaaaccat ggcagagcac tacgggcagc agcaacaaac acgtgccccc cacttgcaac     180
tgcaaccgcg tgctcagcgt gttgtaaagg cagcgaccgc ggttactgcc ggaggtagcc     240
tgttggtgtt atccgggttg accctggctg gaacggtcat tgcgctgaca atcgccacac     300
ctctcctggt gatcttctcg cctgtactgg tccctgcagg taaatttctg tgttccttat     360
tctctcaaaa tcttcgattt tgttttcgtt cgatcccaat ttcgtatatg ttctttggtt     420
tagattctgt taatcttaga tcgaagacga ttttctgggt ttgatcgtta gatatcatct     480
taattctcga ttagggtttc atagatatca tccgatttgt tcaaataatt tgagttttgt     540
cgaataatta ctcttcgatt tgtgatttct atctagatct ggtgttagtt tctagtttgt     600
gcgatcgaat ttgtcgatta atctgagttt ttctgatctg cagtcatcac catcttcctg     660
ttgggagcgg ttttctggc aagcggggga tttggtgttg ccgctctgtc tgtgctgtcc     720
tggatctacc gttacctgac ggggaaacat ccaccggag cggatcagtt ggagtcggcc     780
aagacaaagt tggcgagcaa ggcccgtgaa atgaaggacc gtgccgagca gttcagtcag     840
```

-continued

```
caaccggtag cagggtctca gaccagcatc gatccatcct cctggctcga gatggcggaa    900
cactacgggc aacaacagca gactcgtgct ccccacctgc aattacaacc ccgtgcccaa    960
cgtgttgtga aagcggcaac agcagtaacg gcaggggaa gtttgctggt cttatcgggg   1020
ttgaccttag cgggaaccgt gattgccctg acaattgcga ctccgctgct ggttatcttc   1080
agccccgtat tggttccggc cgtgatcacg attttttgc tggggcagg attttagcc     1140
agcggaggat ttggggtcgc agcgttgtct gtgctgagtt ggatctatcg ttatttgacc   1200
gggaagcacc cacctggagc agaccagctg gagagcgcga aaacgaagct ggcatcgaag   1260
gcgcgtgaaa tgaaggatcg tgctgaacaa ttctcccagc agcctgttgc cggttctcag   1320
accagccata tgtttaaatg ccaagcgct atggccgagc attatgggca gcaacagcaa    1380
acccgtgccc cgcatctgca attgcaacct cgtgcccagc gtgtcgttaa ggcggctact   1440
gcggtaacag cgggagggag cttactggta ttaagcgggc tgacattggc cggaacggtg   1500
atcgccttaa caatcgcgac acccttgctg gtcatcttca gtccggttct ggtgcccgcg   1560
gtgattacga ttttcctgct gggagccggt ttcttagcat cggggggttt tggggtagca   1620
gccttgagtg tcctgtcgtg gatctatcgt tacttaactg gaaaacaccc ggccaggagct  1680
gaccagttgg agtctgcaaa aactaagctg gcgtccaaag cccgtgaaat gaaggatcgt   1740
gctgagcagt ttagccagca gccagttgcg ggaagtcaga cctcttcatc tgagctccca   1800
tgggtcgaca tggcggagca ttacggtcaa cagcaacaga cccgtgctcc gcacttacaa   1860
ttgcaaccac gtgctcaacg tgtcgtaaaa gccgccacgg cagttactgc gggggatca    1920
ttgctggtgt taagtgggtt gacactggcg gggacagtta ttgcactgac gatcgcgacc   1980
cccttgttag tgatcttctc ccccgttctg gttccggcgg tcattacaat ctttctgttg   2040
ggtgccggat tttagcctc tggggatttt ggagtagctg ccctgtcagt gttgagctgg   2100
atctaccgtt acttaacagg gaagcaccct cccggggcag atcagttgga aagcgccaag   2160
accaagctgg caagtaaagc gcgtgaaatg aaggaccgtg ccgaacaatt ttcgcagcaa   2220
ccggttgcgg gatcacagac ctctagtact ccatcctcct ggcatatgat ggccgagcac   2280
tatggacaac agcagcagac gcgtgccct catctgcaac tgcaacccc tgctcaacgt    2340
gtcgttaagg ctgcgacagc agtaaccgct gggggttctc tgttagtgtt gtcagggctg   2400
actttggcgg gacgtaat tgcgttgacc attgccaccc cgctgttagt gattttcagc    2460
ccggtactgg tgccagcagt tatcacgatc ttcttgctgg gtgccggatt cttggcaagt   2520
ggaggttttg gagttgcggc gctgtcagtt ttatcctgga tctatcgtta tctgacagga   2580
aaacatcccc caggtgccga tcagctggag agtgccaaga caaaactggc gtctaaggca   2640
cgtgaaatga aggatcgtgc cgaacagttt tctcaacagc ccgtagcggg gtcacagacc   2700
tcgatcgatc agcaggttaa cgtgcacatg ccgaacatt acggacagca acaacagacg   2760
cgtgctccac acctgcaatt gcaaccgcgt gctcaacgtg ttgtcaaagc ggcgaccgcc   2820
gtaacagcag gaggatcact gttagtgctg tcgggtttaa ccttggccgg gaccgtcatt   2880
gcattgacta ttgcgacgcc cttactgtga atcttttctc cggtgctggt tcccgccgtt   2940
attaccatct tcttgttagg ggcaggattc ctggcatcag ggggattcgg agttgcggcg   3000
ttgagtgtct taagttggat ctaccgttat ctgactggaa agcacccgcc tggggccgat   3060
caactggagt cagccaaaac gaaattggcg tcaaaagcgc gtgaaatgaa ggaccgtgct   3120
gagcagtttt ctcagcagcc tgtggcagga tcccagacat caccatggct cgagtaatga   3180
agcggccgca cccagctttc ttgtacaaag ttggcattat aagaaagcat tgcttatcaa   3240
```
tttgttgcaa cgaacaggtc actatcagtc aaaataaaat cattatttg          3289

<210> SEQ ID NO 51
<211> LENGTH: 914
<212> TYPE: PRT
<213> ORGANISM: Artificial Sequence
<220> FEATURE:
<223> OTHER INFORMATION: Synthetic sequence

<400> SEQUENCE: 51

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Pro Val Ala Gly Ser Gln Thr
    130                 135                 140

Ser Ile Asp Pro Ser Ser Trp Leu Glu Met Ala Glu His Tyr Gly Gln
145                 150                 155                 160

Gln Gln Gln Thr Arg Ala Pro His Leu Gln Leu Gln Pro Arg Ala Gln
                165                 170                 175

Arg Val Val Lys Ala Ala Thr Ala Val Thr Ala Gly Gly Ser Leu Leu
            180                 185                 190

Val Leu Ser Gly Leu Thr Leu Ala Gly Thr Val Ile Ala Leu Thr Ile
        195                 200                 205

Ala Thr Pro Leu Leu Val Ile Phe Ser Pro Val Leu Val Pro Ala Val
    210                 215                 220

Ile Thr Ile Phe Leu Leu Gly Ala Gly Phe Leu Ala Ser Gly Gly Phe
225                 230                 235                 240

Gly Val Ala Ala Leu Ser Val Leu Ser Trp Ile Tyr Arg Tyr Leu Thr
                245                 250                 255

Gly Lys His Pro Pro Gly Ala Asp Gln Leu Glu Ser Ala Lys Thr Lys
            260                 265                 270

Leu Ala Ser Lys Ala Arg Glu Met Lys Asp Arg Ala Glu Gln Phe Ser
        275                 280                 285

Gln Gln Pro Val Ala Gly Ser Gln Thr Ser His Met Phe Lys Trp Pro
    290                 295                 300

Ser Ala Met Ala Glu His Tyr Gly Gln Gln Gln Thr Arg Ala Pro
305                 310                 315                 320

His Leu Gln Leu Gln Pro Arg Ala Gln Arg Val Val Lys Ala Ala Thr
                325                 330                 335

Ala Val Thr Ala Gly Gly Ser Leu Leu Val Leu Ser Gly Leu Thr Leu
            340                 345                 350

Ala Gly Thr Val Ile Ala Leu Thr Ile Ala Thr Pro Leu Leu Val Ile
        355                 360                 365

```
Phe Ser Pro Val Leu Val Pro Ala Val Ile Thr Ile Phe Leu Leu Gly
    370                 375                 380
Ala Gly Phe Leu Ala Ser Gly Gly Phe Gly Val Ala Ala Leu Ser Val
385                 390                 395                 400
Leu Ser Trp Ile Tyr Arg Tyr Leu Thr Gly Lys His Pro Pro Gly Ala
                405                 410                 415
Asp Gln Leu Glu Ser Ala Lys Thr Lys Leu Ala Ser Lys Ala Arg Glu
                420                 425                 430
Met Lys Asp Arg Ala Glu Gln Phe Ser Gln Gln Pro Val Ala Gly Ser
            435                 440                 445
Gln Thr Ser Ser Ser Glu Leu Pro Trp Val Asp Met Ala Glu His Tyr
        450                 455                 460
Gly Gln Gln Gln Gln Thr Arg Ala Pro His Leu Gln Leu Gln Pro Arg
465                 470                 475                 480
Ala Gln Arg Val Val Lys Ala Ala Thr Ala Val Thr Ala Gly Gly Ser
                485                 490                 495
Leu Leu Val Leu Ser Gly Leu Thr Leu Ala Gly Thr Val Ile Ala Leu
                500                 505                 510
Thr Ile Ala Thr Pro Leu Leu Val Ile Phe Ser Pro Val Leu Val Pro
            515                 520                 525
Ala Val Ile Thr Ile Phe Leu Leu Gly Ala Gly Phe Leu Ala Ser Gly
        530                 535                 540
Gly Phe Gly Val Ala Ala Leu Ser Val Leu Ser Trp Ile Tyr Arg Tyr
545                 550                 555                 560
Leu Thr Gly Lys His Pro Pro Gly Ala Asp Gln Leu Glu Ser Ala Lys
                565                 570                 575
Thr Lys Leu Ala Ser Lys Ala Arg Glu Met Lys Asp Arg Ala Glu Gln
                580                 585                 590
Phe Ser Gln Gln Pro Val Ala Gly Ser Gln Thr Ser Ser Thr Pro Ser
            595                 600                 605
Ser Trp His Met Met Ala Glu His Tyr Gly Gln Gln Gln Gln Thr Arg
        610                 615                 620
Ala Pro His Leu Gln Leu Gln Pro Arg Ala Gln Arg Val Val Lys Ala
625                 630                 635                 640
Ala Thr Ala Val Thr Ala Gly Gly Ser Leu Leu Val Leu Ser Gly Leu
                645                 650                 655
Thr Leu Ala Gly Thr Val Ile Ala Leu Thr Ile Ala Thr Pro Leu Leu
                660                 665                 670
Val Ile Phe Ser Pro Val Leu Val Pro Ala Val Ile Thr Ile Phe Leu
            675                 680                 685
Leu Gly Ala Gly Phe Leu Ala Ser Gly Gly Phe Gly Val Ala Ala Leu
        690                 695                 700
Ser Val Leu Ser Trp Ile Tyr Arg Tyr Leu Thr Gly Lys His Pro Pro
705                 710                 715                 720
Gly Ala Asp Gln Leu Glu Ser Ala Lys Thr Lys Leu Ala Ser Lys Ala
                725                 730                 735
Arg Glu Met Lys Asp Arg Ala Glu Gln Phe Ser Gln Pro Val Ala
                740                 745                 750
Gly Ser Gln Thr Ser Ile Asp Gln Gln Val Asn Val His Met Ala Glu
            755                 760                 765
His Tyr Gly Gln Gln Gln Gln Thr Arg Ala Pro His Leu Gln Leu Gln
        770                 775                 780
Pro Arg Ala Gln Arg Val Val Lys Ala Ala Thr Ala Val Thr Ala Gly
```

```
                        785                 790                 795                 800
Gly Ser Leu Leu Val Leu Ser Gly Leu Thr Leu Ala Gly Thr Val Ile
                    805                 810                 815
Ala Leu Thr Ile Ala Thr Pro Leu Leu Val Ile Phe Ser Pro Val Leu
                820                 825                 830
Val Pro Ala Val Ile Thr Ile Phe Leu Leu Gly Ala Gly Phe Leu Ala
            835                 840                 845
Ser Gly Gly Phe Gly Val Ala Ala Leu Ser Val Leu Ser Trp Ile Tyr
        850                 855                 860
Arg Tyr Leu Thr Gly Lys His Pro Pro Gly Ala Asp Gln Leu Glu Ser
865                 870                 875                 880
Ala Lys Thr Lys Leu Ala Ser Lys Ala Arg Glu Met Lys Asp Arg Ala
                885                 890                 895
Glu Gln Phe Ser Gln Gln Pro Val Ala Gly Ser Gln Thr Ser Pro Trp
                900                 905                 910
Leu Glu
```

<210> SEQ ID NO 52
<211> LENGTH: 3291
<212> TYPE: DNA
<213> ORGANISM: Artificial Sequence
<220> FEATURE:
<223> OTHER INFORMATION: Synthetic sequence

<400> SEQUENCE: 52

```
caaataatga ttttattttg actgatagtg acctgttcgt tgcaacaaat tgatgagcaa      60
tgctttttta taatgccaac tttgtacaaa aaagcaggct ccgcggccgc ttgctccgtt     120
aaaaaaaacc atggcagagc actacgggca gcagcaacaa acacgtgccc ccacttgca     180
actgcaaccg cgtgctcagc gtgttgtaaa ggcagcgacc gcggttactg ccggaggtag     240
cctgttggtg ttatccgggt tgaccctggc tggaacggtc attgcgctga caatcgccac     300
acctctcctg gtgatcttct cgcctgtact ggtccctgca ggtaaatttc tgtgttcctt     360
attctctcaa aatcttcgat tttgttttcg ttcgatccca atttcgtata tgttctttgg     420
tttagattct gttaatctta gatcgaagac gattttctgg gtttgatcgt tagatatcat     480
cttaattctc gattagggtt tcatagatat catccgattt gttcaaataa tttgagtttt     540
gtcgaataat tactcttcga tttgtgattt ctatctagat ctggtgttag tttctagttt     600
gtgcgatcga atttgtcgat taatctgagt ttttctgatc tgcagtcatc accatcttcc     660
tgttgggagc gggttttctg gcaagcgggg gatttggtgt tgccgctctg tctgtgctgt     720
cctggatcta ccgttacctg acggggaaac atccacccgg agcggatcag ttggagtcgg     780
ccaagacaaa gttggcgagc aaggcccgtg aaatgaagga ccgtgccgag cagttcagtc     840
agcaaccggt agcagggtct cagaccagca tcgatccatc ctcctggctc gagatggcgg     900
aacactacgg gcaacaacag cagactcgtg ctccccacct gcaattacaa cccgtgccc     960
aacgtgttgt gaaagcggca acagcagtaa cggcaggggg aagtttgctg gtcttatcgg    1020
ggttgacctt agcgggaacc gtgattgccc tgacaattgc gactccgctg ctggttatct    1080
tcagccccgt attggttccg gccgtgatca cgatttttt gctgggggca ggattttta g    1140
ccagcggagg atttggggtc gcagcgttgt ctgtgctgag ttggatctat cgttatttga    1200
ccgggaagca cccacctgga gcagaccagc tggagagcgc gaaaacgaag ctggcatcga    1260
aggcgcgtga aatgaaggat cgtgctgaac aattctccca gcagcctgtt gccggttctc    1320
agaccagcca tatgtttaaa tggccaagcg ctatggccga gcattatggg cagcaacagc    1380
```

| | |
|---|---|
| aaacccgtgc cccgcatctg caattgcaac ctcgtgccca gcgtgtcgtt aaggcggcta | 1440 |
| ctgcggtaac agcgggaggg agcttactgg tattaagcgg gctgacattg gccggaacgg | 1500 |
| tgatcgcctt aacaatcgcg acacccttgc tggtcatctt cagtccggtt ctggtgcccg | 1560 |
| cggtgattac gattttcctg ctgggagccg gtttcttagc atcgggggt tttggggtag | 1620 |
| cagccttgag tgtcctgtcg tggatctatc gttacttaac tggaaaacac ccgccaggag | 1680 |
| ctgaccagtt ggagtctgca aaaactaagc tggcgtccaa agcccgtgaa atgaaggatc | 1740 |
| gtgctgagca gtttagccag cagccagttg cgggaagtca gacctcttca tctgagctcc | 1800 |
| catgggtcga catggcggag cattacggtc aacagcaaca gacccgtgct ccgcacttac | 1860 |
| aattgcaacc acgtgctcaa cgtgtcgtaa aagccgccac ggcagttact gcggggggat | 1920 |
| cattgctggt gttaagtggg ttgacactgg cggggacagt tattgcactg acgatcgcga | 1980 |
| ccccttgtt agtgatcttc tcccccgttc tggttccggc ggtcattaca atctttctgt | 2040 |
| tgggtgccgg attttagcc tctggggat ttggagtagc tgccctgtca gtgttgagct | 2100 |
| ggatctaccg ttacttaaca gggaagcacc ctcccggggc agatcagttg gaaagcgcca | 2160 |
| agaccaagct ggcaagtaaa gcgcgtgaaa tgaaggaccg tgccgaacaa ttttcgcagc | 2220 |
| aaccggttgc gggatcacag acctctagta ctccatcctc ctggcatatg atggccgagc | 2280 |
| actatggaca acagcagcag acgcgtgccc ctcatctgca actgcaaccc cgtgctcaac | 2340 |
| gtgtcgttaa ggctgcgaca gcagtaaccg ctgggggttc tctgttagtg ttgtcagggc | 2400 |
| tgactttggc ggggacggta attgcgttga ccattgccac cccgctgtta gtgattttca | 2460 |
| gcccggtact ggtgccagca gttatcacga tcttcttgct gggtgccgga ttcttggcaa | 2520 |
| gtggaggttt tggagttgcg gcgctgtcag ttttatcctg gatctatcgt tatctgacag | 2580 |
| gaaaacatcc cccaggtgcc gatcagctgg agagtgccaa gacaaaactg gcgtctaagg | 2640 |
| cacgtgaaat gaaggatcgt gccgaacagt tttctcaaca gcccgtagcg gggtcacaga | 2700 |
| cctcgatcga tcagcaggtt aacgtgcaca tggccgaaca ttacggacag caacaacaga | 2760 |
| cgcgtgctcc acacctgcaa ttgcaaccgc gtgctcaacg tgttgtcaaa gcggcgaccg | 2820 |
| ccgtaacagc aggaggatca ctgttagtgc tgtcgggttt aaccttggcc gggaccgtca | 2880 |
| ttgcattgac tattgcgacg cccttactgg tgatcttttc tccggtgctg gttcccgccg | 2940 |
| ttattaccat cttcttgtta ggggcaggat tcctggcatc aggggattc ggagttgcgg | 3000 |
| cgttgagtgt cttaagttgg atctaccgtt atctgactgg aaagcacccg cctggggccg | 3060 |
| atcaactgga gtcagccaaa acgaaattgg cgtcaaaagc gcgtgaaatg aaggaccgtg | 3120 |
| ctgagcagtt ttctcagcag cctgtggcag gatcccagac atcaccatgg ctcgagtaat | 3180 |
| gaagcggccg cacccagctt tcttgtacaa agttggcatt ataagaaagc attgcttatc | 3240 |
| aatttgttgc aacgaacagg tcactatcag tcaaaataaa atcattattt g | 3291 |

<210> SEQ ID NO 53
<211> LENGTH: 1350
<212> TYPE: DNA
<213> ORGANISM: Artificial Sequence
<220> FEATURE:
<223> OTHER INFORMATION: Synthetic sequence

<400> SEQUENCE: 53

| | |
|---|---|
| ttgctccgtt aaaaaaaacc atggctgagc attatggtca acaacagcag accagggcgc | 60 |
| ctcacctgca gctgcagccg cgcgcccagc gggtagtgaa ggcggccacc gccgtgacag | 120 |
| ccggcggctc gcttctcgtc ctctctggcc tcactttagc cggaactgtt attgcgctca | 180 |

```
ccatcgccac tccgctgctt gtgatcttta gccccgttct ggtgccggcg gtcataacca    240 tttcttgct gggtgcgggt tttctggcat ccggaggctt cggcgtggcg gcgctgagtg    300
tgctgtcgtg gatttacaga tatctgacag ggaaacaccc gccggggggcg gatcagctgg    360 aatcggcaaa gacgaagctg gcgagcaagg cgcgagagat gaaggatagg gcagagcagt    420
tctcgcagca gcctgttgga ggcggtggat ccggaggcgg tggtagtatg gctgagcatt    480
atggtcaaca acagcagacc agggcgcctc acctgcagct gcagccgcgc gcccagcggg    540
tagtgaaggc ggccaccgcc gtgacagccg gcggctcgct tctcgtcctc tctggcctca    600
ctttagccgg aactgttatt gcgctcacca tcgccactcc gctgcttgtg atctttagcc    660
ccgttctggt gccggcggtc ataaccattt tcttgctggg tgcgggtttt ctggcatccg    720
gaggcttcgg cgtggcggcg ctgagtgtgc tgtcgtggat tacagatat ctgacaggga    780 aacacccgcc gggggcggat cagctggaat cggcaaagac gaagctggcg agcaaggcgc    840
gagagatgaa ggatagggca gagcagttct cgcagcagcc tgttggggc ggtggatccg    900 gtggagggg atccatggct gagcattatg gtcaacaaca gcagaccagg gcgcctcacc    960
tgcagctgca gccgcgcgcc cagcgggtag tgaaggcggc caccgccgtg acagccggcg   1020
gctcgcttct cgtcctctct ggcctcactt tagccggaac tgttattgcg ctcaccatcg   1080
ccactccgct gcttgtgatc tttagccccg ttctggtgcc ggcggtcata accattttct   1140
tgctgggtgc gggttttctg gcatccggag gcttcggcgt ggcggcgctg agtgtgctgt   1200
cgtggattta cagatatctg acagggaaac acccgccggg ggcggatcag ctggaatcgg   1260
caaagacgaa gctggcgagc aaggcgcgag atgaagga tagggcagag cagttctcgc   1320
agcagcctgt tccatggctc gagtaatgaa                                   1350
```

<210> SEQ ID NO 54
<211> LENGTH: 2878
<212> TYPE: DNA
<213> ORGANISM: Artificial Sequence
<220> FEATURE:
<223> OTHER INFORMATION: Synthetic sequence

<400> SEQUENCE: 54

```
gaaggagata tacatatgaa agaaaccgct gctgctaaat tcgaacgcca gcacatggac     60
agcccagatc tgggtacccct ggtgccacgc ggttccatgg ctgagcatta tggtcaacaa    120
cagcagacca gggcgcctca cctgcagctg cagccgcgcg cccagcgggt agtgaaggcg    180
gccaccgccg tgacagccgg cggctcgctt ctcgtcctct ctggcctcac tttagccgga    240
actgttattg cgctcaccat cgccactccg ctgcttgtga tctttagccc cgttctggtg    300
ccggcggtca taaccatttt cttgctgggt gcgggttttc tggcatccgg aggcttcggc    360
gtggcggcgc tgagtgtgct gtcgtggatt tacagatatc tgacaggaa cacccgccg    420 ggggcggatc agctggaatc ggcaaagacg aagctggcga gcaaggcgcg agagatgaag    480
gatagggcag agcagttctc gcagcagcct gttccatggc tgatatcgga tccgaattcg    540
agctccgtcg acaagcttgc ggccgcactc gagatggcgg aacactacgg caacaacag    600 cagactcgtg ctccccacct gcaattacaa cccgtgccc aacgtgttgt gaaagcggca    660
acagcagtaa cggcagggg aagtttgctg gtcttatcgg ggttgacctt agcgggaacc    720
gtgattgccc tgacaattgc gactccgctg ctggttatct tcagccccgt attggttccg    780
gccgtgatca cgattttttt gctggggca ggattttag ccagcggagg attgggtc    840 gcagcgttgt ctgtgctgag ttggatctat cgttatttga ccgggaagca cccacctgga    900
```

```
gcagaccagc tggagagcgc gaaaacgaag ctggcatcga aggcgcgtga aatgaaggat     960
cgtgctgaac aattctccca gcagcctgtt gccggttctc agaccagcca tatgtttaaa    1020
tggccaagcg ctatggccga gcattatggg cagcaacagc aaacccgtgc ccgcatctg     1080
caattgcaac ctcgtgccca gcgtgtcgtt aaggcggcta ctgcggtaac agcgggaggg    1140
agcttactgg tattaagcgg gctgacattg gccggaacgg tgatcgcctt aacaatcgcg    1200
acacccttgc tggtcatctt cagtccggtt ctggtgcccg cggtgattac gattttcctg    1260
ctgggagccg gtttcttagc atcgggggt tttggggtag cagccttgag tgtcctgtcg    1320
tggatctatc gttacttaac tggaaaacac ccgccaggag ctgaccagtt ggagtctgca    1380
aaaactaagc tggcgtccaa agcccgtgaa atgaaggatc gtgctgagca gtttagccag    1440
cagccagttg cgggaagtca gacctcttca tctgagctcc catgggtcga catggcggag    1500
cattacggtc aacagcaaca gacccgtgct ccgcacttac aattgcaacc acgtgctcaa    1560
cgtgtcgtaa aagccgccac ggcagttact gcggggggat cattgctggt gttaagtggg    1620
ttgacactgg cggggacagt tattgcactg acgatcgcga cccccttgtt agtgatcttc    1680
tcccccgttc tggttccggc ggtcattaca atctttctgt gggtgccgg attttttagcc    1740
tctggggat ttggagtagc tgccctgtca gtgttgagct ggatctaccg ttacttaaca    1800
gggaagcacc ctcccggggc agatcagttg gaaagcgcca agaccaagct ggcaagtaaa    1860
gcgcgtgaaa tgaaggaccg tgccgaacaa ttttcgcagc aaccggttgc gggatcacag    1920
acctctagta ctccatcctc ctggcatatg atggccgagc actatggaca cagcagcag    1980
acgcgtgccc ctcatctgca actgcaaccc cgtgctcaac gtgtcgttaa ggctgcgaca    2040
gcagtaaccg ctgggggttc tctgttagtg ttgtcagggc tgactttggc ggggacggta    2100
attgcgttga ccattgccac cccgctgtta gtgattttca gcccggtact ggtgccagca    2160
gttatcacga tcttcttgct gggtgccgga ttccttggcaa gtggaggttt tggagttgcg    2220
gcgctgtcag ttttatcctg gatctatcgt tatctgacag gaaaacatcc cccaggtgcc    2280
gatcagctgg agagtgccaa gacaaaactg gcgtctaagg cacgtgaaat gaaggatcgt    2340
gccgaacagt tttctcaaca gcccgtagcg gggtcacaga cctcgatcga tcagcaggtt    2400
aacgtgcaca tggccgaaca ttacggacag caacaacaga cgcgtgctcc acacctgcaa    2460
ttgcaaccgc gtgctcaacg tgttgtcaaa gcggcgaccg ccgtaacagc aggaggatca    2520
ctgttagtgc tgtcgggttt aaccttggcc gggaccgtca ttgcattgac tattgcgacg    2580
cccttactgg tgatctttc tccggtgctg gttcccgccg ttattaccat cttcttgtta    2640
ggggcaggat tcctggcatc agggggattc ggagttgcgg cgttgagtgt cttaagttgg    2700
atctaccgtt atctgactgg aaagcacccg cctggggccg atcaactgga gtcagccaaa    2760
acgaaattgg cgtcaaaagc gcgtgaaatg aaggaccgtg ctgagcagtt ttctcagcag    2820
cctgtggcag gatcccagac atcaccatgg ctcgagcacc accaccacca ccactgag     2878
```

<210> SEQ ID NO 55
<211> LENGTH: 1068
<212> TYPE: DNA
<213> ORGANISM: Artificial Sequence
<220> FEATURE:
<223> OTHER INFORMATION: Synthetic sequence

<400> SEQUENCE: 55

```
gaaggagata tacatatgaa agaaaccgct gctgctaaat cgaacgcca gcacatggac     60
agcccagatc tgggtaccct ggtgccacgc ggttccatgg ctgagcatta tggtcaacaa   120
```

```
cagcagacca gggcgcctca cctgcagctg cagccgcgcg cccagcgggt agtgaaggcg      180
gccaccgccg tgacagccgg cggctcgctt ctcgtcctct ctggcctcac tttagccgga      240
actgttattg cgctcaccat cgccactccg ctgcttgtga tctttagccc cgttctggtg      300
ccggcggtca taaccatttt cttgctgggt gcgggttttc tggcatccgg aggcttcggc      360
gtggcggcgc tgagtgtgct gtcgtggatt tacagatatc tgacagggaa acacccgccg      420
ggggcggatc agctggaatc ggcaaagacg aagctggcga gcaaggcgcg agagatgaag      480
gatagggcag agcagttctc gcagcagcct gttggaggcg gtggatccgg aggcggtggt      540
agtatggctg agcattatgg tcaacaacag cagaccaggg cgcctcacct gcagctgcag      600
ccgcgcgccc agcgggtagt gaaggcggcc accgccgtga cagccggcgg ctcgcttctc      660
gtcctctctg gcctcacttt agccggaact gttattgcgc tcaccatcgc cactccgctg      720
cttgtgatct ttagccccgt tctggtgccg gcggtcataa ccattttctt gctgggtgcg      780
ggttttctgg catccggagg cttcggcgtg gcggcgctga gtgtgctgtc gtggatttac      840
agatatctga cagggaaaca cccgccgggg gcggatcagc tggaatcggc aaagacgaag      900
ctggcgagca aggcgcgaga gatgaaggat agggcagagc agttctcgca gcagcctgtt      960
gggggcggtg gatccggtgg aggggatccc atggcgatat cggatccgaa ttcgagctcc     1020
gtcgacaagc ttgcggccgc actcgagcac caccaccacc accactga                  1068

<210> SEQ ID NO 56
<211> LENGTH: 1929
<212> TYPE: DNA
<213> ORGANISM: Artificial Sequence
<220> FEATURE:
<223> OTHER INFORMATION: Synthetic sequence

<400> SEQUENCE: 56
gaaggagata tacatatgaa agaaaccgct gctgctaaat cgaacgccag cacatggac       60 agcccagatc tgggtacccct ggtgccacgc ggttccatgg ctgagcatta tggtcaacaa     120
cagcagacca gggcgcctca cctgcagctg cagccgcgcg cccagcgggt agtgaaggcg     180
gccaccgccg tgacagccgg cggctcgctt ctcgtcctct ctggcctcac tttagccgga     240
actgttattg cgctcaccat cgccactccg ctgcttgtga tctttagccc cgttctggtg     300
ccggcggtca taaccatttt cttgctgggt gcgggttttc tggcatccgg aggcttcggc     360
gtggcggcgc tgagtgtgct gtcgtggatt tacagatatc tgacagggaa acacccgccg     420
ggggcggatc agctggaatc ggcaaagacg aagctggcga gcaaggcgcg agagatgaag     480
gatagggcag agcagttctc gcagcagcct gttccatggc gatatcggat ccgaattcga     540
gctccgtcga caagcttgcg gccgcttgct ccgttaaaaa aaaccatggc tgagcattat     600
ggtcaacaac agcagaccag ggcgcctcac ctgcagctgc agccgcgcgc ccagcgggta     660
gtgaaggcgg ccaccgccgt gacagccggc ggctcgcttc tcgtcctctc tggcctcact     720
ttagccggaa ctgttattgc gctcaccatc gccactccgc tgcttgtgat ctttagcccc     780
gttctggtgc cggcggtcat aaccattttc ttgctgggtg cgggttttct ggcatccgga     840
ggcttcggcg tggcggcgct gagtgtgctg tcgtggattt acagatatct gacagggaaa     900
cacccgccgg gggcggatca gctggaatcg gcaaagacga agctggcgag caaggcgcga     960
gagatgaagg atagggcaga gcagttctcg cagcagcctg ttggaggcgg tggatccgga    1020
ggcggtggta gtatggctga gcattatggt caacaacagc agaccagggc gcctcacctg    1080
cagctgcagc cgcgcgccca gcgggtagtg aaggcggcca ccgccgtgac agccggcggc    1140
```

| | |
|---|---|
| tcgcttctcg tcctctctgg cctcacttta gccggaactg ttattgcgct caccatcgcc | 1200 |
| actccgctgc ttgtgatctt tagccccgtt ctggtgccgg cggtcataac catttcttg | 1260 |
| ctgggtgcgg gttttctggc atccggaggc ttcggcgtgg cggcgctgag tgtgctgtcg | 1320 |
| tggatttaca gatatctgac agggaaacac ccgccggggg cggatcagct ggaatcggca | 1380 |
| aagacgaagc tggcgagcaa ggcgcgagag atgaaggata gggcagagca gttctcgcag | 1440 |
| cagcctgttg ggggcggtgg atccggtgga ggggatcca tggctgagca ttatggtcaa | 1500 |
| caacagcaga ccagggcgcc tcacctgcag ctgcagccgc gcgcccagcg ggtagtgaag | 1560 |
| gcggccaccg ccgtgacagc cggcggctcg cttctcgtcc tctctggcct cactttagcc | 1620 |
| ggaactgtta ttgcgctcac catcgccact ccgctgcttg tgatctttag ccccgttctg | 1680 |
| gtgccggcgg tcataaccat tttcttgctg ggtgcgggtt ttctggcatc cggaggcttc | 1740 |
| ggcgtggcgg cgctgagtgt gctgtcgtgg atttacagat atctgacagg gaaacacccg | 1800 |
| ccgggggcgg atcagctgga atcggcaaag acgaagctgg cgagcaaggc gcgagagatg | 1860 |
| aaggataggg cagagcagtt ctcgcagcag cctgttccat ggctcgagca ccaccaccac | 1920 |
| caccactga | 1929 |

<210> SEQ ID NO 57
<211> LENGTH: 2403
<212> TYPE: DNA
<213> ORGANISM: Artificial Sequence
<220> FEATURE:
<223> OTHER INFORMATION: Synthetic sequence

<400> SEQUENCE: 57

| | |
|---|---|
| gaaggagata tacatatgaa agaaaccgct gctgctaaat cgaacgcca gcacatggac | 60 |
| agcccagatc tgggtaccct ggtgccacgc ggttccatgg ctgagcatta tggtcaacaa | 120 |
| cagcagacca gggcgcctca cctgcagctg cagccgcgcg cccagcgggt agtgaaggcg | 180 |
| gccaccgccg tgacagccgg cggctcgctt ctcgtcctct ctggcctcac tttagccgga | 240 |
| actgttattg cgctcaccat cgccactccg ctgcttgtga tctttagccc cgttctggtg | 300 |
| ccggcggtca taaccatttt cttgctgggt gcgggttttc tggcatccgg aggcttcggc | 360 |
| gtggcggcgc tgagtgtgct gtcgtggatt tacagatatc tgacagggaa acacccgccg | 420 |
| ggggcggatc agctggaatc ggcaaagacg aagctggcga gcaaggcgcg agagatgaag | 480 |
| gatagggcag agcagttctc gcagcagcct gttggaggcg gtggatccgg aggcggtggt | 540 |
| agtatggctg agcattatgg tcaacaacag cagaccaggg cgcctcacct gcagctgcag | 600 |
| ccgcgcgccc agcgggtagt gaaggcggcc accgccgtga cagccggcgg ctcgcttctc | 660 |
| gtcctctctg gcctcacttt agccggaact gttattgcgc tcaccatcgc cactccgctg | 720 |
| cttgtgatct ttagccccgt tctggtgccg gcggtcataa ccattttctt gctgggtgcg | 780 |
| ggttttctgg catccggagg cttcggcgtg gcggcgctga gtgtgctgtc gtggatttac | 840 |
| agatatctga cagggaaaca cccgccgggg gcggatcagc tggaatcggc aaagacgaag | 900 |
| ctggcgagca aggcgcgaga gatgaaggat agggcagagc agttctcgca gcagcctgtt | 960 |
| gggggcggtg gatccggtgg agggggatcc atgggatatc ggatccgaat tcgagctccg | 1020 |
| tcgacaagct tgcggccgct tgctccgtta aaaaaaacca tggctgagca ttatggtcaa | 1080 |
| caacagcaga ccagggcgcc tcacctgcag ctgcagccgc gcgcccagcg ggtagtgaag | 1140 |
| gcggccaccg ccgtgacagc cggcggctcg cttctcgtcc tctctggcct cactttagcc | 1200 |
| ggaactgtta ttgcgctcac catcgccact ccgctgcttg tgatctttag ccccgttctg | 1260 |

```
gtgccggcgg tcataaccat tttcttgctg ggtgcgggtt ttctggcatc cggaggcttc  1320
ggcgtggcgg cgctgagtgt gctgtcgtgg atttacagat atctgacagg gaaacacccg  1380
ccggggggcg atcagctgga atcggcaaag acgaagctgg cgagcaaggc gcagagatg   1440 aaggataggg cagagcagtt ctcgcagcag cctgttggag gcggtggatc cggaggcggt  1500
ggtagtatgg ctgagcatta tggtcaacaa cagcagacca gggcgcctca cctgcagctg  1560
cagccgcgcg cccagcgggt agtgaaggcg gccaccgccg tgacagccgg cggctcgctt  1620
ctcgtcctct ctggcctcac tttagccgga actgttattg cgctcaccat cgccactccg  1680
ctgcttgtga tctttagccc cgttctggtg ccggcggtca taaccatttt cttgctgggt  1740
gcgggttttc tggcatccgg aggcttcggc gtggcggcgc tgagtgtgct gtcgtggatt  1800
tacagatatc tgacagggaa acaccegccg ggggcggatc agctggaatc ggcaaagacg  1860
aagctggcga gcaaggcgcg agagatgaag gatagggcag agcagttctc gcagcagcct  1920 gttggggcg gtggatccgg tggaggggga tccatggctg agcattatgg tcaacaacag  1980
cagaccaggg cgcctcacct gcagctgcag ccgcgcgccc agcgggtagt gaaggcggcc  2040
accgccgtga cagccggcgg ctcgcttctc gtcctctctg gcctcacttt agccggaact  2100
gttattgcgc tcaccatcgc cactccgctg cttgtgatct ttagccccgt tctggtgccg  2160
gcggtcataa ccatttcttt gctgggtgcg gttttctgg catccggagg cttcggcgtg  2220
gcggcgctga gtgtgctgtc gtggatttac agatatctga cagggaaaca cccgccgggg  2280
gcggatcagc tggaatcggc aaagacgaag ctggcgagca aggcgcgaga gatgaaggat  2340
agggcagagc agttctcgca gcagcctgtt ccatggctcg agcaccacca ccaccaccac  2400
tga                                                                2403
```

<210> SEQ ID NO 58
<211> LENGTH: 953
<212> TYPE: PRT
<213> ORGANISM: Artificial Sequence
<220> FEATURE:
<223> OTHER INFORMATION: Synthetic sequence

<400> SEQUENCE: 58

```
Met Lys Glu Thr Ala Ala Lys Phe Glu Arg Gln His Met Asp Ser
1               5                   10                  15

Pro Asp Leu Gly Thr Leu Val Pro Arg Gly Ser Met Ala Glu His Tyr
            20                  25                  30

Gly Gln Gln Gln Gln Thr Arg Ala Pro His Leu Gln Leu Gln Pro Arg
        35                  40                  45

Ala Gln Arg Val Val Lys Ala Ala Thr Ala Val Thr Ala Gly Gly Ser
    50                  55                  60

Leu Leu Val Leu Ser Gly Leu Thr Leu Ala Gly Thr Val Ile Ala Leu
65                  70                  75                  80

Thr Ile Ala Thr Pro Leu Leu Val Ile Phe Ser Pro Val Leu Val Pro
                85                  90                  95

Ala Val Ile Thr Ile Phe Leu Leu Gly Ala Gly Phe Leu Ala Ser Gly
            100                 105                 110

Gly Phe Gly Val Ala Ala Leu Ser Val Leu Ser Trp Ile Tyr Arg Tyr
        115                 120                 125

Leu Thr Gly Lys His Pro Pro Gly Ala Asp Gln Leu Glu Ser Ala Lys
    130                 135                 140

Thr Lys Leu Ala Ser Lys Ala Arg Glu Met Lys Asp Arg Ala Glu Gln
145                 150                 155                 160
```

```
Phe Ser Gln Gln Pro Val Pro Trp Leu Ile Ser Asp Pro Asn Ser Ser
                165                 170                 175

Ser Val Asp Lys Leu Ala Ala Leu Glu Met Ala Glu His Tyr Gly
            180                 185                 190

Gln Gln Gln Gln Thr Arg Ala Pro His Leu Gln Leu Gln Pro Arg Ala
                195                 200                 205

Gln Arg Val Val Lys Ala Ala Thr Ala Val Thr Ala Gly Gly Ser Leu
    210                 215                 220

Leu Val Leu Ser Gly Leu Thr Leu Ala Gly Thr Val Ile Ala Leu Thr
225                 230                 235                 240

Ile Ala Thr Pro Leu Leu Val Ile Phe Ser Pro Val Leu Val Pro Ala
                245                 250                 255

Val Ile Thr Ile Phe Leu Leu Gly Ala Gly Phe Leu Ala Ser Gly Gly
                260                 265                 270

Phe Gly Val Ala Ala Leu Ser Val Leu Ser Trp Ile Tyr Arg Tyr Leu
            275                 280                 285

Thr Gly Lys His Pro Pro Gly Ala Asp Gln Leu Glu Ser Ala Lys Thr
            290                 295                 300

Lys Leu Ala Ser Lys Ala Arg Glu Met Lys Asp Arg Ala Glu Gln Phe
305                 310                 315                 320

Ser Gln Gln Pro Val Ala Gly Ser Gln Thr Ser His Met Phe Lys Trp
                325                 330                 335

Pro Ser Ala Met Ala Glu His Tyr Gly Gln Gln Gln Gln Thr Arg Ala
                340                 345                 350

Pro His Leu Gln Leu Gln Pro Arg Ala Gln Arg Val Val Lys Ala Ala
            355                 360                 365

Thr Ala Val Thr Ala Gly Gly Ser Leu Leu Val Leu Ser Gly Leu Thr
            370                 375                 380

Leu Ala Gly Thr Val Ile Ala Leu Thr Ile Ala Thr Pro Leu Leu Val
385                 390                 395                 400

Ile Phe Ser Pro Val Leu Val Pro Ala Val Ile Thr Ile Phe Leu Leu
                405                 410                 415

Gly Ala Gly Phe Leu Ala Ser Gly Gly Phe Gly Val Ala Ala Leu Ser
                420                 425                 430

Val Leu Ser Trp Ile Tyr Arg Tyr Leu Thr Gly Lys His Pro Pro Gly
            435                 440                 445

Ala Asp Gln Leu Glu Ser Ala Lys Thr Lys Leu Ala Ser Lys Ala Arg
    450                 455                 460

Glu Met Lys Asp Arg Ala Glu Gln Phe Ser Gln Gln Pro Val Ala Gly
465                 470                 475                 480

Ser Gln Thr Ser Ser Glu Leu Pro Trp Val Asp Met Ala Glu His
                485                 490                 495

Tyr Gly Gln Gln Gln Gln Thr Arg Ala Pro His Leu Gln Leu Gln Pro
            500                 505                 510

Arg Ala Gln Arg Val Val Lys Ala Ala Thr Ala Val Thr Ala Gly Gly
            515                 520                 525

Ser Leu Leu Val Leu Ser Gly Leu Thr Leu Ala Gly Thr Val Ile Ala
            530                 535                 540

Leu Thr Ile Ala Thr Pro Leu Leu Val Ile Phe Ser Pro Val Leu Val
545                 550                 555                 560

Pro Ala Val Ile Thr Ile Phe Leu Leu Gly Ala Gly Phe Leu Ala Ser
                565                 570                 575

Gly Gly Phe Gly Val Ala Ala Leu Ser Val Leu Ser Trp Ile Tyr Arg
```

```
                        580                 585                 590
Tyr Leu Thr Gly Lys His Pro Pro Gly Ala Asp Gln Leu Glu Ser Ala
            595                 600                 605
Lys Thr Lys Leu Ala Ser Lys Ala Arg Glu Met Lys Asp Arg Ala Glu
        610                 615                 620
Gln Phe Ser Gln Gln Pro Val Ala Gly Ser Gln Thr Ser Ser Thr Pro
625                 630                 635                 640
Ser Ser Trp His Met Met Ala Glu His Tyr Gly Gln Gln Gln Gln Thr
                645                 650                 655
Arg Ala Pro His Leu Gln Leu Gln Pro Arg Ala Gln Arg Val Val Lys
            660                 665                 670
Ala Ala Thr Ala Val Thr Ala Gly Gly Ser Leu Leu Val Leu Ser Gly
        675                 680                 685
Leu Thr Leu Ala Gly Thr Val Ile Ala Leu Thr Ile Ala Thr Pro Leu
    690                 695                 700
Leu Val Ile Phe Ser Pro Val Leu Val Pro Ala Val Ile Thr Ile Phe
705                 710                 715                 720
Leu Leu Gly Ala Gly Phe Leu Ala Ser Gly Gly Phe Gly Val Ala Ala
                725                 730                 735
Leu Ser Val Leu Ser Trp Ile Tyr Arg Tyr Leu Thr Gly Lys His Pro
            740                 745                 750
Pro Gly Ala Asp Gln Leu Glu Ser Ala Lys Thr Lys Leu Ala Ser Lys
        755                 760                 765
Ala Arg Glu Met Lys Asp Arg Ala Glu Gln Phe Ser Gln Gln Pro Val
    770                 775                 780
Ala Gly Ser Gln Thr Ser Ile Asp Gln Gln Val Asn Val His Met Ala
785                 790                 795                 800
Glu His Tyr Gly Gln Gln Gln Thr Arg Ala Pro His Leu Gln Leu
                805                 810                 815
Gln Pro Arg Ala Gln Arg Val Val Lys Ala Ala Thr Ala Val Thr Ala
            820                 825                 830
Gly Gly Ser Leu Leu Val Leu Ser Gly Leu Thr Leu Ala Gly Thr Val
        835                 840                 845
Ile Ala Leu Thr Ile Ala Thr Pro Leu Leu Val Ile Phe Ser Pro Val
    850                 855                 860
Leu Val Pro Ala Val Ile Thr Ile Phe Leu Leu Gly Ala Gly Phe Leu
865                 870                 875                 880
Ala Ser Gly Gly Phe Gly Val Ala Ala Leu Ser Val Leu Ser Trp Ile
                885                 890                 895
Tyr Arg Tyr Leu Thr Gly Lys His Pro Pro Gly Ala Asp Gln Leu Glu
            900                 905                 910
Ser Ala Lys Thr Lys Leu Ala Ser Lys Ala Arg Glu Met Lys Asp Arg
        915                 920                 925
Ala Glu Gln Phe Ser Gln Gln Pro Val Ala Gly Ser Gln Thr Ser Pro
    930                 935                 940
Trp Leu Glu His His His His His His
945                 950

<210> SEQ ID NO 59
<211> LENGTH: 350
<212> TYPE: PRT
<213> ORGANISM: Artificial Sequence
<220> FEATURE:
<223> OTHER INFORMATION: Synthetic sequence

<400> SEQUENCE: 59
```

```
Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Glu His Tyr
            20                  25                  30

Gly Gln Gln Gln Thr Arg Ala Pro His Leu Gln Leu Gln Pro Arg
        35                  40                  45

Ala Gln Arg Val Val Lys Ala Thr Ala Val Thr Ala Gly Gly Ser
    50                  55                  60

Leu Leu Val Leu Ser Gly Leu Thr Leu Ala Gly Thr Val Ile Ala Leu
65                  70                  75                  80

Thr Ile Ala Thr Pro Leu Val Ile Phe Ser Pro Val Leu Val Pro
                85                  90                  95

Ala Val Ile Thr Ile Phe Leu Leu Gly Ala Gly Phe Leu Ala Ser Gly
            100                 105                 110

Gly Phe Gly Val Ala Ala Leu Ser Val Leu Ser Trp Ile Tyr Arg Tyr
        115                 120                 125

Leu Thr Gly Lys His Pro Pro Gly Ala Asp Gln Leu Glu Ser Ala Lys
    130                 135                 140

Thr Lys Leu Ala Ser Lys Ala Arg Glu Met Lys Asp Arg Ala Glu Gln
145                 150                 155                 160

Phe Ser Gln Gln Pro Val Gly Gly Gly Ser Gly Gly Gly Ser
                165                 170                 175

Met Ala Glu His Tyr Gly Gln Gln Gln Thr Arg Ala Pro His Leu
            180                 185                 190

Gln Leu Gln Pro Arg Ala Gln Arg Val Val Lys Ala Ala Thr Ala Val
    195                 200                 205

Thr Ala Gly Gly Ser Leu Leu Val Leu Ser Gly Leu Thr Leu Ala Gly
    210                 215                 220

Thr Val Ile Ala Leu Thr Ile Ala Thr Pro Leu Val Ile Phe Ser
225                 230                 235                 240

Pro Val Leu Val Pro Ala Val Ile Thr Ile Phe Leu Leu Gly Ala Gly
                245                 250                 255

Phe Leu Ala Ser Gly Gly Phe Gly Val Ala Ala Leu Ser Val Leu Ser
            260                 265                 270

Trp Ile Tyr Arg Tyr Leu Thr Gly Lys His Pro Pro Gly Ala Asp Gln
    275                 280                 285

Leu Glu Ser Ala Lys Thr Lys Leu Ala Ser Lys Ala Arg Glu Met Lys
    290                 295                 300

Asp Arg Ala Glu Gln Phe Ser Gln Gln Pro Val Gly Gly Gly Ser
305                 310                 315                 320

Gly Gly Gly Gly Ser Met Ala Ile Ser Asp Pro Asn Ser Ser Val
            325                 330                 335

Asp Lys Leu Ala Ala Ala Leu Glu His His His His His His
            340                 345                 350

<210> SEQ ID NO 60
<211> LENGTH: 637
<212> TYPE: PRT
<213> ORGANISM: Artificial Sequence
<220> FEATURE:
<223> OTHER INFORMATION: Synthetic sequence

<400> SEQUENCE: 60

Met Lys Glu Thr Ala Ala Ala Lys Phe Glu Arg Gln His Met Asp Ser
1               5                   10                  15
```

```
Pro Asp Leu Gly Thr Leu Val Pro Arg Gly Ser Met Ala Glu His Tyr
         20                  25                  30
Gly Gln Gln Gln Thr Arg Ala Pro His Leu Gln Leu Gln Pro Arg
     35                  40                  45
Ala Gln Arg Val Val Lys Ala Thr Ala Val Thr Ala Gly Gly Ser
 50                  55                  60
Leu Leu Val Leu Ser Gly Leu Thr Leu Ala Gly Thr Val Ile Ala Leu
 65                  70                  75                  80
Thr Ile Ala Thr Pro Leu Leu Val Ile Phe Ser Pro Val Leu Val Pro
                 85                  90                  95
Ala Val Ile Thr Ile Phe Leu Leu Gly Ala Gly Phe Leu Ala Ser Gly
                100                 105                 110
Gly Phe Gly Val Ala Ala Leu Ser Val Leu Ser Trp Ile Tyr Arg Tyr
             115                 120                 125
Leu Thr Gly Lys His Pro Pro Gly Ala Asp Gln Leu Glu Ser Ala Lys
         130                 135                 140
Thr Lys Leu Ala Ser Lys Ala Arg Glu Met Lys Asp Arg Ala Glu Gln
145                 150                 155                 160
Phe Ser Gln Gln Pro Val Pro Trp Arg Tyr Arg Ile Arg Ile Arg Ala
                165                 170                 175
Pro Ser Thr Ser Leu Arg Pro Leu Ala Pro Leu Lys Lys Thr Met Ala
                180                 185                 190
Glu His Tyr Gly Gln Gln Gln Thr Arg Ala Pro His Leu Gln Leu
            195                 200                 205
Gln Pro Arg Ala Gln Arg Val Val Lys Ala Ala Thr Ala Val Thr Ala
    210                 215                 220
Gly Gly Ser Leu Leu Val Leu Ser Gly Leu Thr Leu Ala Gly Thr Val
225                 230                 235                 240
Ile Ala Leu Thr Ile Ala Thr Pro Leu Leu Val Ile Phe Ser Pro Val
                245                 250                 255
Leu Val Pro Ala Val Ile Thr Ile Phe Leu Leu Gly Ala Gly Phe Leu
                260                 265                 270
Ala Ser Gly Gly Phe Gly Val Ala Ala Leu Ser Val Leu Ser Trp Ile
            275                 280                 285
Tyr Arg Tyr Leu Thr Gly Lys His Pro Pro Gly Ala Asp Gln Leu Glu
    290                 295                 300
Ser Ala Lys Thr Lys Leu Ala Ser Lys Ala Arg Glu Met Lys Asp Arg
305                 310                 315                 320
Ala Glu Gln Phe Ser Gln Pro Val Gly Gly Gly Ser Gly
                325                 330                 335
Gly Gly Ser Met Ala Glu His Tyr Gly Gln Gln Gln Thr Arg Ala
            340                 345                 350
Pro His Leu Gln Leu Gln Pro Arg Ala Gln Arg Val Val Lys Ala Ala
        355                 360                 365
Thr Ala Val Thr Ala Gly Gly Ser Leu Leu Val Leu Ser Gly Leu Thr
    370                 375                 380
Leu Ala Gly Thr Val Ile Ala Leu Thr Ile Ala Thr Pro Leu Leu Val
385                 390                 395                 400
Ile Phe Ser Pro Val Leu Val Pro Ala Val Ile Thr Ile Phe Leu Leu
                405                 410                 415
Gly Ala Gly Phe Leu Ala Ser Gly Gly Phe Gly Val Ala Ala Leu Ser
                420                 425                 430
Val Leu Ser Trp Ile Tyr Arg Tyr Leu Thr Gly Lys His Pro Pro Gly
            435                 440                 445
```

```
Ala Asp Gln Leu Glu Ser Ala Lys Thr Lys Leu Ala Ser Lys Ala Arg
    450                 455                 460

Glu Met Lys Asp Arg Ala Glu Gln Phe Ser Gln Gln Pro Val Gly Gly
465                 470                 475                 480

Gly Gly Ser Gly Gly Gly Ser Met Ala Glu His Tyr Gly Gln Gln
                485                 490                 495

Gln Gln Thr Arg Ala Pro His Leu Gln Leu Gln Pro Arg Ala Gln Arg
            500                 505                 510

Val Val Lys Ala Ala Thr Ala Val Thr Ala Gly Gly Ser Leu Leu Val
        515                 520                 525

Leu Ser Gly Leu Thr Leu Ala Gly Thr Val Ile Ala Leu Thr Ile Ala
    530                 535                 540

Thr Pro Leu Leu Val Ile Phe Ser Pro Val Leu Val Pro Ala Val Ile
545                 550                 555                 560

Thr Ile Phe Leu Leu Gly Ala Gly Phe Leu Ala Ser Gly Gly Phe Gly
                565                 570                 575

Val Ala Ala Leu Ser Val Leu Ser Trp Ile Tyr Arg Tyr Leu Thr Gly
            580                 585                 590

Lys His Pro Pro Gly Ala Asp Gln Leu Glu Ser Ala Lys Thr Lys Leu
        595                 600                 605

Ala Ser Lys Ala Arg Glu Met Lys Asp Arg Ala Glu Gln Phe Ser Gln
    610                 615                 620

Gln Pro Val Pro Trp Leu Glu His His His His His His
625                 630                 635

<210> SEQ ID NO 61
<211> LENGTH: 795
<212> TYPE: PRT
<213> ORGANISM: Artificial Sequence
<220> FEATURE:
<223> OTHER INFORMATION: Synthetic sequence

<400> SEQUENCE: 61

Met Lys Glu Thr Ala Ala Ala Lys Phe Glu Arg Gln His Met Asp Ser
1               5                   10                  15

Pro Asp Leu Gly Thr Leu Val Pro Arg Gly Ser Met Ala Glu His Tyr
            20                  25                  30

Gly Gln Gln Gln Gln Thr Arg Ala Pro His Leu Gln Leu Gln Pro Arg
        35                  40                  45

Ala Gln Arg Val Val Lys Ala Ala Thr Ala Val Thr Ala Gly Gly Ser
    50                  55                  60

Leu Leu Val Leu Ser Gly Leu Thr Leu Ala Gly Thr Val Ile Ala Leu
65                  70                  75                  80

Thr Ile Ala Thr Pro Leu Leu Val Ile Phe Ser Pro Val Leu Val Pro
                85                  90                  95

Ala Val Ile Thr Ile Phe Leu Leu Gly Ala Gly Phe Leu Ala Ser Gly
            100                 105                 110

Gly Phe Gly Val Ala Ala Leu Ser Val Leu Ser Trp Ile Tyr Arg Tyr
        115                 120                 125

Leu Thr Gly Lys His Pro Pro Gly Ala Asp Gln Leu Glu Ser Ala Lys
    130                 135                 140

Thr Lys Leu Ala Ser Lys Ala Arg Glu Met Lys Asp Arg Ala Glu Gln
145                 150                 155                 160

Phe Ser Gln Gln Pro Val Gly Gly Gly Ser Gly Gly Gly Ser
                165                 170                 175
```

```
Met Ala Glu His Tyr Gly Gln Gln Gln Thr Arg Ala Pro His Leu
            180                 185                 190

Gln Leu Gln Pro Arg Ala Gln Arg Val Val Lys Ala Ala Thr Ala Val
        195                 200                 205

Thr Ala Gly Gly Ser Leu Leu Val Leu Ser Gly Leu Thr Leu Ala Gly
    210                 215                 220

Thr Val Ile Ala Leu Thr Ile Ala Thr Pro Leu Leu Val Ile Phe Ser
225                 230                 235                 240

Pro Val Leu Val Pro Ala Val Ile Thr Ile Phe Leu Leu Gly Ala Gly
                245                 250                 255

Phe Leu Ala Ser Gly Gly Phe Gly Val Ala Ala Leu Ser Val Leu Ser
                260                 265                 270

Trp Ile Tyr Arg Tyr Leu Thr Gly Lys His Pro Pro Gly Ala Asp Gln
            275                 280                 285

Leu Glu Ser Ala Lys Thr Lys Leu Ala Ser Lys Ala Arg Glu Met Lys
        290                 295                 300

Asp Arg Ala Glu Gln Phe Ser Gln Gln Pro Val Gly Gly Gly Gly Ser
305                 310                 315                 320

Gly Gly Gly Gly Ser Met Gly Tyr Arg Ile Arg Ile Arg Ala Pro Ser
                325                 330                 335

Thr Ser Leu Arg Pro Leu Ala Pro Leu Lys Lys Thr Met Ala Glu His
            340                 345                 350

Tyr Gly Gln Gln Gln Thr Arg Ala Pro His Leu Gln Leu Gln Pro
        355                 360                 365

Arg Ala Gln Arg Val Val Lys Ala Ala Thr Ala Val Thr Ala Gly Gly
    370                 375                 380

Ser Leu Leu Val Leu Ser Gly Leu Thr Leu Ala Gly Thr Val Ile Ala
385                 390                 395                 400

Leu Thr Ile Ala Thr Pro Leu Leu Val Ile Phe Ser Pro Val Leu Val
                405                 410                 415

Pro Ala Val Ile Thr Ile Phe Leu Leu Gly Ala Gly Phe Leu Ala Ser
            420                 425                 430

Gly Gly Phe Gly Val Ala Ala Leu Ser Val Leu Ser Trp Ile Tyr Arg
        435                 440                 445

Tyr Leu Thr Gly Lys His Pro Pro Gly Ala Asp Gln Leu Glu Ser Ala
    450                 455                 460

Lys Thr Lys Leu Ala Ser Lys Ala Arg Glu Met Lys Asp Arg Ala Glu
465                 470                 475                 480

Gln Phe Ser Gln Gln Pro Val Gly Gly Gly Ser Gly Gly Gly Gly
                485                 490                 495

Ser Met Ala Glu His Tyr Gly Gln Gln Gln Thr Arg Ala Pro His
        500                 505                 510

Leu Gln Leu Gln Pro Arg Ala Gln Arg Val Val Lys Ala Ala Thr Ala
    515                 520                 525

Val Thr Ala Gly Gly Ser Leu Leu Val Leu Ser Gly Leu Thr Leu Ala
    530                 535                 540

Gly Thr Val Ile Ala Leu Thr Ile Ala Thr Pro Leu Leu Val Ile Phe
545                 550                 555                 560

Ser Pro Val Leu Val Pro Ala Val Ile Thr Ile Phe Leu Leu Gly Ala
                565                 570                 575

Gly Phe Leu Ala Ser Gly Gly Phe Gly Val Ala Ala Leu Ser Val Leu
            580                 585                 590

Ser Trp Ile Tyr Arg Tyr Leu Thr Gly Lys His Pro Pro Gly Ala Asp
        595                 600                 605
```

```
Gln Leu Glu Ser Ala Lys Thr Lys Leu Ala Ser Lys Ala Arg Glu Met
    610                 615                 620

Lys Asp Arg Ala Glu Gln Phe Ser Gln Gln Pro Val Gly Gly Gly Gly
625                 630                 635                 640

Ser Gly Gly Gly Gly Ser Met Ala Glu His Tyr Gly Gln Gln Gln Gln
                645                 650                 655

Thr Arg Ala Pro His Leu Gln Leu Gln Pro Arg Ala Gln Arg Val Val
            660                 665                 670

Lys Ala Ala Thr Ala Val Thr Ala Gly Gly Ser Leu Leu Val Leu Ser
        675                 680                 685

Gly Leu Thr Leu Ala Gly Thr Val Ile Ala Leu Thr Ile Ala Thr Pro
    690                 695                 700

Leu Leu Val Ile Phe Ser Pro Val Leu Val Pro Ala Val Ile Thr Ile
705                 710                 715                 720

Phe Leu Leu Gly Ala Gly Phe Leu Ala Ser Gly Gly Phe Gly Val Ala
                725                 730                 735

Ala Leu Ser Val Leu Ser Trp Ile Tyr Arg Tyr Leu Thr Gly Lys His
            740                 745                 750

Pro Pro Gly Ala Asp Gln Leu Glu Ser Ala Lys Thr Lys Leu Ala Ser
        755                 760                 765

Lys Ala Arg Glu Met Lys Asp Arg Ala Glu Gln Phe Ser Gln Gln Pro
    770                 775                 780

Val Pro Trp Leu Glu His His His His His
785                 790                 795

<210> SEQ ID NO 62
<211> LENGTH: 441
<212> TYPE: PRT
<213> ORGANISM: Artificial Sequence
<220> FEATURE:
<223> OTHER INFORMATION: Synthetic sequence

<400> SEQUENCE: 62

Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Pro Val Gly Gly Gly Gly Ser
    130                 135                 140

Gly Gly Gly Gly Ser Met Ala Glu His Tyr Gly Gln Gln Gln Gln Thr
145                 150                 155                 160

Arg Ala Pro His Leu Gln Leu Gln Pro Arg Ala Gln Arg Val Val Lys
                165                 170                 175
```

```
Ala Ala Thr Ala Val Thr Ala Gly Gly Ser Leu Leu Val Leu Ser Gly
            180                 185                 190

Leu Thr Leu Ala Gly Thr Val Ile Ala Leu Thr Ile Ala Thr Pro Leu
        195                 200                 205

Leu Val Ile Phe Ser Pro Val Leu Val Pro Ala Val Ile Thr Ile Phe
    210                 215                 220

Leu Leu Gly Ala Gly Phe Leu Ala Ser Gly Gly Phe Gly Val Ala Ala
225                 230                 235                 240

Leu Ser Val Leu Ser Trp Ile Tyr Arg Tyr Leu Thr Gly Lys His Pro
            245                 250                 255

Pro Gly Ala Asp Gln Leu Glu Ser Ala Lys Thr Lys Leu Ala Ser Lys
        260                 265                 270

Ala Arg Glu Met Lys Asp Arg Ala Glu Gln Phe Ser Gln Gln Pro Val
    275                 280                 285

Gly Gly Gly Gly Ser Gly Gly Gly Ser Met Ala Glu His Tyr Gly
290                 295                 300

Gln Gln Gln Gln Thr Arg Ala Pro His Leu Gln Leu Gln Pro Arg Ala
305                 310                 315                 320

Gln Arg Val Val Lys Ala Ala Thr Ala Val Thr Ala Gly Gly Ser Leu
            325                 330                 335

Leu Val Leu Ser Gly Leu Thr Leu Ala Gly Thr Val Ile Ala Leu Thr
        340                 345                 350

Ile Ala Thr Pro Leu Leu Val Ile Phe Ser Pro Val Leu Val Pro Ala
    355                 360                 365

Val Ile Thr Ile Phe Leu Leu Gly Ala Gly Phe Leu Ala Ser Gly Gly
    370                 375                 380

Phe Gly Val Ala Ala Leu Ser Val Leu Ser Trp Ile Tyr Arg Tyr Leu
385                 390                 395                 400

Thr Gly Lys His Pro Pro Gly Ala Asp Gln Leu Glu Ser Ala Lys Thr
            405                 410                 415

Lys Leu Ala Ser Lys Ala Arg Glu Met Lys Asp Arg Ala Glu Gln Phe
        420                 425                 430

Ser Gln Gln Pro Val Pro Trp Leu Glu
            435                 440

<210> SEQ ID NO 63
<211> LENGTH: 149
<212> TYPE: PRT
<213> ORGANISM: Artificial Sequence
<220> FEATURE:
<223> OTHER INFORMATION: Synthetic sequence

<400> SEQUENCE: 63

Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
```

```
            100                 105                 110
Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Pro Trp Leu Glu His
        130                 135                 140

His His His His His
145

<210> SEQ ID NO 64
<211> LENGTH: 2227
<212> TYPE: DNA
<213> ORGANISM: Artificial Sequence
<220> FEATURE:
<223> OTHER INFORMATION: Synthetic sequence

<400> SEQUENCE: 64
```

| | | | | | |
|---|---|---|---|---|---|
| tcgacgaatt | aattccaatc | ccacaaaaat | ctgagcttaa | cagcacagtt | gctcctctca | 60 |
| gagcagaatc | gggtattcaa | caccctcata | tcaactacta | cgttgtgtat | aacggtccac | 120 |
| atgccggtat | atacgatgac | tggggttgta | caaaggcggc | aacaaacggc | gttcccggag | 180 |
| ttgcacacaa | gaaatttgcc | actattacag | aggcaagagc | agcagctgac | gcgtacacaa | 240 |
| caagtcagca | aacagacagg | ttgaacttca | tccccaaagg | agaagctcaa | ctcaagccca | 300 |
| agagctttgc | taaggcccta | caagcccac | aaagcaaaa | agcccactgg | ctcacgctag | 360 |
| gaaccaaaag | gcccagcagt | gatccagccc | caaagagat | ctcctttgcc | ccggagatta | 420 |
| caatggacga | tttcctctat | ctttacgatc | taggaaggaa | gttcgaaggt | gaaggtgacg | 480 |
| acactatgtt | caccactgat | aatgagaagg | ttagcctctt | caatttcaga | agaatgctg | 540 |
| acccacagat | ggttagagag | gcctacgcag | caggtctcat | caagacgatc | tacccgagta | 600 |
| acaatctcca | ggagatcaaa | taccttccca | agaaggttaa | agatgcagtc | aaaagattca | 660 |
| ggactaattg | catcaagaac | acagagaaag | acatatttct | caagatcaga | agtactattc | 720 |
| cagtatggac | gattcaaggc | ttgcttcata | accaaggca | agtaatagag | attggagtct | 780 |
| ctaaaaaggt | agttcctact | gaatctaagg | ccatgcatgg | agtctaagat | tcaaatcgag | 840 |
| gatctaacag | aactcgccgt | gaagactggc | gaacagttca | tacagagtct | tttacgactc | 900 |
| aatgacaaga | gaaaatcttc | gtcaacatg | gtggagcacg | acactctggt | ctactccaaa | 960 |
| aatgtcaaag | atacagtctc | agaagaccaa | agggctattg | agacttttca | acaaaggata | 1020 |
| atttcgggaa | acctcctcgg | attccattgc | ccagctatct | gtcacttcat | cgaaaggaca | 1080 |
| gtagaaaagg | aaggtggctc | ctacaaatgc | catcattgcg | ataaaggaaa | ggctatcatt | 1140 |
| caagatctct | ctgccgacag | tggtcccaaa | gatggacccc | cacccacgag | gagcatcgtg | 1200 |
| gaaaaagaag | acgttccaac | cacgtcttca | agcaagtgg | attgatgtga | catctccact | 1260 |
| gacgtaaggg | atgacgcaca | atcccactat | ccttcgcaag | acccttcctc | tatataagga | 1320 |
| agttcatttc | atttggagag | gacacgctcg | aggaattcgg | taccccatca | caagtttgta | 1380 |
| caaaaaagca | ggctccgcgg | ccgcttgctc | cgttaaaaaa | aaccatggca | gagcactacg | 1440 |
| ggcagcagca | acaaacacgt | gcccccccact | tgcaactgca | accgcgtgct | cagcgtgttg | 1500 |
| taaaggcagc | gaccgcggtt | actgccggag | gtagcctgtt | ggtgttatcc | gggttgacccc | 1560 |
| tggctggaac | ggtcattgcg | ctgacaatcg | ccacacctct | cctggtgatc | ttctcgcctg | 1620 |
| tactggtccc | tgcaggtaaa | tttctgtgtt | ccttattctc | tcaaaatctt | cgattttgtt | 1680 |
| ttcgttcgat | cccaatttcg | tatatgttct | ttggtttaga | ttctgttaat | cttagatcga | 1740 |
| agacgatttt | ctgggtttga | tcgttagata | tcatcttaat | tctcgattag | ggtttcatag | 1800 |

```
atatcatccg atttgttcaa ataatttgag ttttgtcgaa taattactct tcgatttgtg   1860
atttctatct agatctggtg ttagtttcta gtttgtgcga tcgaatttgt cgattaatct   1920
gagtttttct gatctgcagt catcaccatc ttcctgttgg gagcgggttt tctggcaagc   1980
gggggatttg gtgttgccgc tctgtctgtg ctgtcctgga tctaccgtta cctgacgggg   2040
aaacatccac ccggagcgga tcagttggag tcggccaaga caaagttggc gagcaaggcc   2100
cgtgaaatga aggaccgtgc cgagcagttc agtcagcaac cggtagcagg gtctcagacc   2160
agcatcgatc catcctcctg gctcgagtaa tgaagcggcc gcacccagct ttcttgtaca   2220
aagtggt                                                            2227
```

<210> SEQ ID NO 65
<211> LENGTH: 3133
<212> TYPE: DNA
<213> ORGANISM: Artificial Sequence
<220> FEATURE:
<223> OTHER INFORMATION: Synthetic sequence

<400> SEQUENCE: 65

```
tcgacgaatt aattccaatc ccacaaaaat ctgagcttaa cagcacagtt gctcctctca     60
gagcagaatc gggtattcaa caccctcata tcaactacta cgttgtgtat aacggtccac    120
atgccggtat atacgatgac tggggttgta caaaggcggc aacaaacggc gttcccggag    180
ttgcacacaa gaaatttgcc actattacag aggcaagagc agcagctgac gcgtacacaa    240
caagtcagca acagacagg ttgaacttca tccccaaagg agaagctcaa ctcaagccca     300
agagctttgc taaggcccta caagcccac aaagcaaaa agcccactgg ctcacgctag      360
gaaccaaaag gcccagcagt gatccagccc aaaagagat ctcctttgcc ccggagatta     420
caatggacga tttcctctat ctttacgatc taggaaggaa gttcgaaggt gaaggtgacg    480
acactatgtt caccactgat aatgagaagg ttagcctctt caatttcaga aagaatgctg    540
acccacagat ggttagagag gcctacgcag caggtctcat caagacgatc tacccgagta    600
acaatctcca ggagatcaaa taccttccca gaaggttaa agatgcagtc aaaagattca    660
ggactaattg catcaagaac acagagaaag acatatttct caagatcaga agtactattc    720
cagtatggac gattcaaggc ttgcttcata accaaggca agtaatagag attggagtct    780
ctaaaaaggt agttcctact gaatctaagg ccatgcatgg agtctaagat tcaaatcgag    840
gatctaacag aactcgccgt gaagactggc gaacagttca tacagagtct tttacgactc    900
aatgacaaga gaaaatctt cgtcaacatg gtggagcacg acactctggt ctactccaaa    960
aatgtcaaag atacagtctc agaagaccaa agggctattg agacttttca acaaggata   1020 atttcgggaa acctcctcgg attccattgc ccagctatct gtcacttcat cgaaggaca   1080 gtagaaaagg aaggtggctc ctacaaatgc catcattgcg ataaaggaaa ggctatcatt   1140
caagatctct ctgccgacag tggtcccaaa gatggacccc acccacgag gagcatcgtg   1200 gaaaaagaag acgttccaac cacgtcttca aagcaagtgg attgatgtga catctccact   1260
gacgtaaggg atgacgcaca atcccactat ccttcgcaag accttcctc tatataagga   1320 agttcatttc atttggagag gacacgctcg aggaattcgg tacccatca caagtttgta   1380 caaaaaagca ggctccgcgg ccgcttgctc cgttaaaaaa aaccatggca gagcactacg   1440
ggcagcagca acaaacacgt gccccccact tgcaactgca accgcgtgct cagcgtgttg   1500
taaaggcagc gaccgcggtt actgccggag gtagcctgtt ggtgttatcc gggttgaccc   1560
tggctggaac ggtcattgcg ctgacaatcg ccacacctct cctggtgatc ttctcgcctg   1620
```

| | |
|---|---|
| tactggtccc tgcaggtaaa tttctgtgtt ccttattctc tcaaaatctt cgattttgtt | 1680 |
| ttcgttcgat cccaatttcg tatatgttct ttggtttaga ttctgttaat cttagatcga | 1740 |
| agacgatttt ctgggtttga tcgttagata tcatcttaat tctcgattag ggtttcatag | 1800 |
| atatcatccg atttgttcaa ataatttgag ttttgtcgaa taattactct tcgatttgtg | 1860 |
| atttctatct agatctggtg ttagtttcta gtttgtgcga tcgaatttgt cgattaatct | 1920 |
| gagttttctt gatctgcagt catcaccatc ttcctgttgg gagcgggttt tctggcaagc | 1980 |
| gggggatttg tgttgccgc tctgtctgtg ctgtcctgga tctaccgtta cctgacgggg | 2040 |
| aaacatccac ccggagcgga tcagttggag tcggccaaga caaagttggc gagcaaggcc | 2100 |
| cgtgaaatga aggaccgtgc cgagcagttc agtcagcaac cggtagcagg gtctcagacc | 2160 |
| agcatcgatc catcctcctg gcatatgatg gccgagcact atggacaaca gcagcagacg | 2220 |
| cgtgcccctc atctgcaact gcaaccccgt gctcaacgtg tcgttaaggc tgcgacagca | 2280 |
| gtaaccgctg ggggttctct gttagtgttg tcagggctga cttggcggg acggtaatt | 2340 |
| gcgttgacca ttgccacccc gctgttagtg attttcagcc cggtactggt gccagcagtt | 2400 |
| atcacgatct tcttgctggg tgccggattc ttggcaagtg gaggttttgg agttgcggcg | 2460 |
| ctgtcagttt tatcctggat ctatcgttat ctgacaggaa acatcccc aggtgccgat | 2520 |
| cagctggaga gtgccaagac aaaactggcg tctaaggcac gtgaaatgaa ggatcgtgcc | 2580 |
| gaacagtttt ctcaacagcc cgtagcgggg tcacagacct cgatcgatca gcaggttaac | 2640 |
| gtgcacatgg ccgaacatta cggacagcaa aacagacgc gtgctccaca cctgcaattg | 2700 |
| caaccgcgtg ctcaacgtgt tgtcaaagcg gcgaccgccg taacagcagg aggatcactg | 2760 |
| ttagtgctgt cgggtttaac cttggccggg accgtcattg cattgactat tgcgacgccc | 2820 |
| ttactggtga tcttttctcc ggtgctggtt cccgccgtta ttaccatctt cttgttaggg | 2880 |
| gcaggattcc tggcatcagg gggattcgga gttgcggcgt tgagtgtctt aagttggatc | 2940 |
| taccgttatc tgactggaaa gcacccgcct ggggccgatc aactggagtc agccaaaacg | 3000 |
| aaattggcgt caaaagcgcg tgaaatgaag gaccgtgctg agcagttttc tcagcagcct | 3060 |
| gtggcaggat cccagacatc accatggctc gagtaatgaa gcggccgcac ccagctttct | 3120 |
| tgtacaaagt ggt | 3133 |

<210> SEQ ID NO 66
<211> LENGTH: 3610
<212> TYPE: DNA
<213> ORGANISM: Artificial Sequence
<220> FEATURE:
<223> OTHER INFORMATION: Synthetic sequence

<400> SEQUENCE: 66

| | |
|---|---|
| tcgacgaatt aattccaatc ccacaaaaat ctgagcttaa cagcacagtt gctcctctca | 60 |
| gagcagaatc gggtattcaa caccctcata tcaactacta cgttgtgtat aacggtccac | 120 |
| atgccggtat atacgatgac tggggttgta caaaggcggc aacaaacggc gttcccggag | 180 |
| ttgcacacaa gaaatttgcc actattacag aggcaagagc agcagctgac gcgtacacaa | 240 |
| caagtcagca aacagacagg ttgaacttca tccccaaagg agaagctcaa ctcaagccca | 300 |
| agagctttgc taaggcccta acaagcccac caaagcaaaa agcccactgg ctcacgctag | 360 |
| gaaccaaaag gcccagcagt gatccagccc caaagagat ctcctttgcc ccggagatta | 420 |
| caatggacga tttcctctat ctttacgatc taggaaggaa gttcgaaggt gaaggtgacg | 480 |
| acactatgtt caccactgat aatgagaagg ttagcctctt caatttcaga aagaatgctg | 540 |

```
acccacagat ggttagagag gcctacgcag caggtctcat caagacgatc tacccgagta      600
acaatctcca ggagatcaaa taccttccca agaaggttaa agatgcagtc aaaagattca      660
ggactaattg catcaagaac acagagaaag acatatttct caagatcaga agtactattc      720
cagtatggac gattcaaggc ttgcttcata aaccaaggca agtaatagag attggagtct      780
ctaaaaaggt agttcctact gaatctaagg ccatgcatgg agtctaagat tcaaatcgag      840
gatctaacag aactcgccgt gaagactggc gaacagttca tacagagtct tttacgactc      900
aatgacaaga agaaaatctt cgtcaacatg gtggagcacg acactctggt ctactccaaa      960
aatgtcaaag atacagtctc agaagaccaa agggctattg agacttttca acaaaggata     1020
atttcgggaa acctcctcgg attccattgc ccagctatct gtcacttcat cgaaaggaca     1080
gtagaaaagg aaggtggctc ctacaaatgc catcattgcg ataaaggaaa ggctatcatt     1140
caagatctct ctgccgacag tggtcccaaa gatggacccc cacccacgag gagcatcgtg     1200 gaaaagaag acgttccaac cacgtcttca agcaagtgg attgatgtga catctccact     1260
gacgtaaggg atgacgcaca atcccactat ccttcgcaag acccttcctc tatataagga     1320
agttcatttc atttggagag gacacgctcg aggaattcgg tacccatca caagtttgta     1380 caaaaagca ggctccgcgg ccgcttgctc cgttaaaaaa aaccatggca gagcactacg     1440
ggcagcagca acaaacacgt gccccccact tgcaactgca accgcgtgct cagcgtgttg     1500
taaaggcagc gaccgcggtt actgccggag gtagcctgtt ggtgttatcc gggttgaccc     1560
tggctggaac ggtcattgcg ctgacaatcg ccacacctct cctggtgatc ttctcgcctg     1620
tactggtccc tgcaggtaaa tttctgtgtt ccttattctc tcaaaatctt cgattttgtt     1680
ttcgttcgat cccaatttcg tatatgtcct ttggtttaga ttctgttaat cttagatcga     1740
agacgatttt ctgggtttga tcgttagata tcatcttaat tctcgattag ggtttcatag     1800
atatcatccg atttgttcaa ataatttgag ttttgtcgaa taattactct tcgatttgtg     1860
atttctatct agatctggtg ttagtttcta gtttgtgcga tcgaatttgt cgattaatct     1920 gagttttct gatctgcagt catcaccatc ttcctgttgg gagcgggttt tctggcaagc     1980
gggggatttg gtgttgccgc tctgtctgtg ctgtcctgga tctaccgtta cctgacgggg     2040
aaacatccac ccggagcgga tcagttggag tcggccaaga caaagttggc gagcaaggcc     2100
cgtgaaatga aggaccgtgc cgagcagttc agtcagcaac cggtagcagg gtctcagacc     2160
agcatcgatc catcctcctg gctcgagatg gcggaacact acgggcaaca acagcagact     2220
cgtgctcccc acctgcaatt acaaccccgt gcccaacgtg ttgtgaaagc ggcaacagca     2280
gtaacggcag ggggaagttt gctggtctta tcggggttga ccttagcggg aaccgtgatt     2340
gccctgacaa ttgcgactcc gctgctggtt atcttcagcc ccgtattggt tccggccgtg     2400
atcacgattt ttttgctggg ggcaggattt ttagccagcg gaggatttgg ggtcgcagcg     2460
ttgtctgtgc tgagttggat ctatcgttat ttgaccggga agcacccacc tggagcagac     2520
cagctggaga gcgcgaaaac gaagctggca tcgaaggcgc gtgaaatgaa ggatcgtgct     2580
gaacaattct cccagcagcc tgttgccggt tctcagacca gccatatgat ggccgagcac     2640
tatggacaac agcagcagac gcgtgcccct catctgcaac tgcaaccccg tgctcaacgt     2700
gtcgttaagg ctgcgacagc agtaaccgct ggggttctc tgttagtgtt gtcagggctg     2760
actttggcgg ggacggtaat tgcgttgacc attgccaccc cgctgttagt gattttcagc     2820
ccggtactgg tgccagcagt tatcacgatc ttccttgctgg gtgccggatt cttgcaagt     2880 ggaggttttg gagttgcggc gctgtcagtt ttatcctgga tctatcgtta tctgacagga     2940
```

```
aaacatcccc caggtgccga tcagctggag agtgccaaga caaaactggc gtctaaggca   3000
cgtgaaatga aggatcgtgc cgaacagttt tctcaacagc ccgtagcggg gtcacagacc   3060
tcgatcgatc agcaggttaa cgtgcacatg gccgaacatt acggacagca acaacagacg   3120
cgtgctccac acctgcaatt gcaaccgcgt gctcaacgtg ttgtcaaagc ggcgaccgcc   3180
gtaacagcag gaggatcact gttagtgctg tcgggtttaa ccttggccgg gaccgtcatt   3240
gcattgacta ttgcgacgcc cttactgtg atctttctc cggtgctggt tcccgccgtt    3300
attaccatct tcttgttagg ggcaggattc ctggcatcag ggggattcgg agttgcggcg   3360
ttgagtgtct taagttggat ctaccgttat ctgactggaa agcacccgcc tggggccgat   3420
caactggagt cagccaaaac gaaattggcg tcaaaagcgc gtgaaatgaa ggaccgtgct   3480
gagcagtttt ctcagcagcc tgtggcagga tcccagacat caccatggct cgagtaatga   3540
agcggccgca cccagctttc ttgtacaaag tggtgatggg ttcgaaatcg ataagcttgg   3600
atcctctaga                                                         3610

<210> SEQ ID NO 67
<211> LENGTH: 4510
<212> TYPE: DNA
<213> ORGANISM: Artificial Sequence
<220> FEATURE:
<223> OTHER INFORMATION: Synthetic sequence

<400> SEQUENCE: 67
tcgacgaatt aattccaatc ccacaaaaat ctgagcttaa cagcacagtt gctcctctca     60
gagcagaatc gggtattcaa caccctcata tcaactacta cgttgtgtat aacggtccac    120
atgccggtat atacgatgac tggggttgta caaaggcggc aacaaacggc gttcccggag    180
ttgcacacaa gaaatttgcc actattacag aggcaagagc agcagctgac gcgtacacaa    240
caagtcagca aacagacagg ttgaacttca tccccaaagg agaagctcaa ctcaagccca    300
agagctttgc taaggcccta acaagcccac caaagcaaaa agcccactgg ctcacgctag    360
gaaccaaaag gcccagcagt gatccagccc caaaagagat ctcctttgcc ccggagatta    420
caatggacga tttcctctat ctttacgatc taggaaggaa gttcgaaggt gaaggtgacg    480
acactatgtt caccactgat aatgagaagg ttagcctctt caatttcaga agaatgctg     540 acccacagat ggttagagag gcctacgcag caggtctcat caagacgatc tacccgagta    600
acaatctcca ggagatcaaa taccttccca gaaggttaa agatgcagtc aaaagattca    660
ggactaattg catcaagaac acagagaaag acatatttct caagatcaga agtactattc    720
cagtatggac gattcaaggc ttgcttcata accaaggca agtaatagag attggagtct    780
ctaaaaaggt agttcctact gaatctaagg ccatgcatgg agtctaagat tcaaatcgag    840
gatctaacag aactcgccgt gaagactggc gaacagttca tacagagtct tttacgactc    900
aatgacaaga agaaaatctt cgtcaacatg gtggagcacg acactctggt ctactccaaa    960
aatgtcaaag atacagtctc agaagaccaa agggctattg agactttttca acaaaggata   1020 atttcgggaa acctcctcgg attccattgc ccagctatct gtcacttcat cgaaaggaca   1080
gtagaaaagg aaggtggctc ctacaaatgc catcattgcg ataaaggaaa ggctatcatt   1140
caagatctct ctgccgacag tggtcccaaa gatggacccc cacccacgag gagcatcgtg   1200
gaaaaagaag acgttccaac cacgtcttca aagcaagtgg attgatgtga catctccact   1260
gacgtaaggg atgacgcaca atcccactat ccttcgcaag accttcctc tatataagga    1320 agttcatttc atttggagag gacacgctcg aggaattcgg tacccccatca caagtttgta  1380
```

```
caaaaaagca ggctccgcgg ccgcttgctc cgttaaaaaa aaccatggca gagcactacg   1440
ggcagcagca acaaacacgt gccccccact tgcaactgca accgcgtgct cagcgtgttg   1500
taaaggcagc gaccgcggtt actgccggag gtagcctgtt ggtgttatcc gggttgaccc   1560
tggctggaac ggtcattgcg ctgacaatcg ccacacctct cctggtgatc ttctcgcctg   1620
tactggtccc tgcaggtaaa tttctgtgtt ccttattctc tcaaaatctt cgattttgtt   1680
ttcgttcgat cccaatttcg tatatgttct ttggtttaga ttctgttaat cttagatcga   1740
agacgatttt ctgggtttga tcgttagata tcatcttaat tctcgattag ggtttcatag   1800
atatcatccg atttgttcaa ataatttgag ttttgtcgaa taattactct tcgatttgtg   1860
atttctatct agatctggtg ttagtttcta gtttgtgcga tcgaatttgt cgattaatct   1920 gagttttttct gatctgcagt catcaccatc ttcctgttgg gagcgggttt tctggcaagc   1980
gggggatttg tgttgccgc tctgtctgtg ctgtcctgga tctaccgtta cctgacgggg   2040
aaacatccac ccggagcgga tcagttggag tcggccaaga caaagttggc gagcaaggcc   2100
cgtgaaatga aggaccgtgc cgagcagttc agtcagcaac cggtagcagg gtctcagacc   2160
agcatcgatc catcctcctg gctcgagatg gcggaacact acgggcaaca acagcagact   2220
cgtgctcccc acctgcaatt acaaccccgt gcccaacgtg ttgtgaaagc ggcaacagca   2280
gtaacggcag ggggaagttt gctggtctta tcggggttga ccttagcggg aaccgtgatt   2340
gccctgacaa ttgcgactcc gctgctggtt atcttcagcc ccgtattggt tccggccgtg   2400
atcacgattt ttttgctggg ggcaggattt ttagccagcg gaggatttgg ggtcgcagcg   2460
ttgtctgtgc tgagttggat ctatcgttat ttgaccggga agcacccacc tggagcagac   2520
cagctggaga gcgcgaaaac gaagctggca tcgaaggcgc gtgaaatgaa ggatcgtgct   2580
gaacaattct cccagcagcc tgttgccggt tctcagacca gccatatgtt taaatggcca   2640
agcgctatgg ccgagcatta tgggcagcaa cagcaaaccc gtgccccgca tctgcaattg   2700
caacctcgtg cccagcgtgt cgttaaggcg gctactgcgg taacagcggg agggagctta   2760
ctggtattaa gcgggctgac attggccgga acggtgatcg ccttaacaat cgcgacaccc   2820
ttgctggtca tcttcagtcc ggttctggtg cccgcggtga ttacgatttt cctgctggga   2880
gccggtttct tagcatcggg ggggttttggg gtagcagcct tgagtgtcct gtcgtggatc   2940
tatcgttact taactggaaa acacccgcca ggagctgacc agttggagtc tgcaaaaact   3000
aagctggcgt ccaaagcccg tgaaatgaag gatcgtgctg agcagtttag ccagcagcca   3060
gttgcgggaa gtcagacctc ttcatctgag ctcccatggg tcgacatggc ggagcattac   3120
ggtcaacagc aacagacccg tgctccgcac ttacaattgc aaccacgtgc tcaacgtgtc   3180
gtaaaagccg ccacggcagt tactgcgggg ggatcattgc tggtgttaag tgggttgaca   3240
ctggcgggga cagttattgc actgacgatc gcgaccccct tgttagtgat cttctccccc   3300
gttctggttc cggcggtcat tacaatcttt ctgttgggtg ccggattttt agcctctggg   3360
ggatttggag tagctgccct gtcagtgttg agctggatct accgttactt aacagggaag   3420
caccctcccg gggcagatca gttggaaagc gccaagacca agctggcaag taaagcgcgt   3480
gaaatgaagg accgtgccga acaatttcg cagcaaccgg ttgcgggatc acagacctct   3540
agtactccat cctcctggca tatgatggcc gagcactatg gacaacagca gcagacgcgt   3600
gcccctcatc tgcaactgca accccgtgct caacgtgtcg ttaaggctgc gacagcagta   3660
accgctgggg gttctctgtt agtgttgtca gggctgactt tggcggggac ggtaattgcg   3720
ttgaccattg ccaccccgct gttagtgatt ttcagcccgg tactggtgcc agcagttatc   3780
```

```
acgatcttct tgctgggtgc cggattcttg gcaagtggag gttttggagt tgcggcgctg   3840
tcagttttat cctggatcta tcgttatctg acaggaaaac atcccccagg tgccgatcag   3900
ctggagagtg ccaagacaaa actggcgtct aaggcacgtg aaatgaagga tcgtgccgaa   3960
cagttttctc aacagcccgt agcggggtca cagacctcga tcgatcagca ggttaacgtg   4020
cacatggccg aacattacgg acagcaacaa cagacgcgtg ctccacacct gcaattgcaa   4080
ccgcgtgctc aacgtgttgt caaagcggcg accgccgtaa cagcaggagg atcactgtta   4140
gtgctgtcgg gtttaacctt ggccgggacc gtcattgcat tgactattgc gacgccctta   4200
ctggtgatct tttctccggt gctggttccc gccgttatta ccatcttctt gttaggggca   4260
ggattcctgg catcaggggg attcggagtt gcggcgttga gtgtcttaag ttggatctac   4320
cgttatctga ctggaaagca cccgcctggg gccgatcaac tggagtcagc caaaacgaaa   4380
ttggcgtcaa aagcgcgtga aatgaaggac cgtgctgagc agttttctca gcagcctgtg   4440
gcaggatccc agacatcacc atggctcgag taatgaagcg gccgcaccca gctttcttgt   4500
acaaagtggt                                                          4510

<210> SEQ ID NO 68
<211> LENGTH: 1706
<212> TYPE: DNA
<213> ORGANISM: Artificial Sequence
<220> FEATURE:
<223> OTHER INFORMATION: Synthetic sequence

<400> SEQUENCE: 68
gcaggaactc tctggtaagc tagctccact ccccagaaac aaccggcgcc aaattgcgcg     60
aattgctgac ctgaagacgg aacatcatcg tcgggtcctt gggcgattgc ggcggaagat    120
gggtcagctt gggcttgagg acgagacccg aatccgagtc tgttgaaaag gttgttcatt    180
ggggatttgt atacggagat tggtcgtcga gaggtttgag ggaaaggaca aatgggtttg    240
gctctggaga aagagagtgc ggctttagag agagaattga gaggtttaga gagagatgcg    300
gcggcgatga gcggaggaga gacgacgagg acctgcatta tcaaagcagt gacgtggtga    360
aatttggaac ttttaagagg cagatagatt tattatttgt atccattttc ttcattgttc    420
tagaatgtcg cggaacaaat tttaaaacta atcctaaatt ttttctaatt ttgttgccaa    480
tagtggatat gtgggccgta tagaaggaat ctattgaagg cccaaaccca tactgacgag    540
cccaaaggtt cgttttgcgt tttatgtttc ggttcgatgc caacgccaca ttctgagcta    600
ggcaaaaaac aaacgtgtct ttgaatagac tcctctcgtt aacacatgca gcggctgcat    660
ggtgacgcca ttaacacgtg gcctacaatt gcatgatgtc tccattgaca cgtgacttct    720
cgtctccttt cttaatatat ctaacaaaca ctcctacctc ttccaaaata tatacacatc    780
tttttgatca atctctcatt caaaatctca ttctctctag taaacaagaa caaaaaggt    840 accccatcac aagtttgtac aaaaaagcag gctccgcggc cgcttgctcc gttaaaaaaa    900
accatggcag agcactacgg gcagcagcaa caaacacgtg ccccccactt gcaactgcaa    960
ccgcgtgctc agcgtgttgt aaaggcagcg accgcggtta ctgccggagg tagcctgttg   1020
gtgttatccg ggttgaccct ggctggaacg gtcattgcgc tgacaatcgc acacctctc    1080 ctggtgatct tctcgcctgt actggtccct gcaggtaaat ttctgtgttc cttattctct   1140
caaaatcttc gattttgttt tcgttcgatc ccaatttcgt atatgttctt ggtttagat    1200 tctgttaatc ttagatcgaa gacgattttc tgggtttgat cgttagatat catcttaatt   1260
ctcgattagg gtttcataga tatcatccga tttgttcaaa taatttgagt tttgtcgaat   1320
```

| aattactctt cgatttgtga tttctatcta gatctggtgt tagtttctag tttgtgcgat | 1380 |
| cgaatttgtc gattaatctg agtttttctg atctgcagtc atcaccatct tcctgttggg | 1440 |
| agcgggtttt ctggcaagcg ggggatttgg tgttgccgct ctgtctgtgc tgtcctggat | 1500 |
| ctaccgttac ctgacgggga acatccacc cggagcggat cagttggagt cggccaagac | 1560 |
| aaagttggcg agcaaggccc gtgaaatgaa ggaccgtgcc gagcagttca gtcagcaacc | 1620 |
| ggtagcaggg tctcagacca gcatcgatcc atcctcctgg ctcgagtaat gaagcggccg | 1680 |
| cacccagctt tcttgtacaa agtggt | 1706 |

<210> SEQ ID NO 69
<211> LENGTH: 2612
<212> TYPE: DNA
<213> ORGANISM: Artificial Sequence
<220> FEATURE:
<223> OTHER INFORMATION: Synthetic sequence

<400> SEQUENCE: 69

| gcaggaactc tctggtaagc tagctccact ccccagaaac aaccggcgcc aaattgcgcg | 60 |
| aattgctgac ctgaagacgg aacatcatcg tcgggtcctt gggcgattgc ggcggaagat | 120 |
| gggtcagctt gggcttgagg acgagacccg aatccgagtc tgttgaaaag gttgttcatt | 180 |
| ggggatttgt atacggagat tggtcgtcga gaggtttgag ggaaaggaca aatgggtttg | 240 |
| gctctggaga aagagagtgc ggctttagag agagaattga gaggtttaga gagagatgcg | 300 |
| gcggcgatga gcggaggaga gacgacgagg acctgcatta tcaaagcagt gacgtggtga | 360 |
| aatttggaac ttttaagagg cagatagatt tattatttgt atccattttc ttcattgttc | 420 |
| tagaatgtcg cggaacaaat tttaaaacta atcctaaat tttctaatt ttgttgccaa | 480 |
| tagtggatat gtgggccgta tagaaggaat ctattgaagg cccaaaccca tactgacgag | 540 |
| cccaaaggtt cgttttgcgt tttatgtttc ggttcgatgc caacgccaca ttctgagcta | 600 |
| ggcaaaaaac aaacgtgtct ttgaatagac tcctctcgtt aacacatgca gcggctgcat | 660 |
| ggtgacgcca ttaacacgtg cctacaatt gcatgatgtc tccattgaca cgtgacttct | 720 |
| cgtctccttt cttaatatat ctaacaaaca ctcctacctc ttccaaaata tatacacatc | 780 |
| ttttttgatca atctctcatt caaaatctca ttctctctag taaacaagaa caaaaaggt | 840 |
| accccatcac aagtttgtac aaaaaagcag gctccgcggc cgcttgctcc gttaaaaaaa | 900 |
| accatggcag agcactacgg gcagcagcaa caaacacgtg ccccccactt gcaactgcaa | 960 |
| ccgcgtgctc agcgtgttgt aaaggcagcg accgcggtta ctgccggagg tagcctgttg | 1020 |
| gtgttatccg ggttgaccct ggctggaacg gtcattgcgc tgacaatcgc cacacctctc | 1080 |
| ctggtgatct tctcgcctgt actggtccct gcaggtaaat ttctgtgttc cttattctct | 1140 |
| caaaatcttc gattttgttt tcgttcgatc ccaatttcgt atatgttctt tggtttagat | 1200 |
| tctgttaatc ttagatcgaa gacgattttc tgggtttgat cgttagatat catcttaatt | 1260 |
| ctcgattagg gtttcataga tatcatccga tttgttcaaa taatttgagt tttgtcgaat | 1320 |
| aattactctt cgatttgtga tttctatcta gatctggtgt tagtttctag tttgtgcgat | 1380 |
| cgaatttgtc gattaatctg agtttttctg atctgcagtc atcaccatct tcctgttggg | 1440 |
| agcgggtttt ctggcaagcg ggggatttgg tgttgccgct ctgtctgtgc tgtcctggat | 1500 |
| ctaccgttac ctgacgggga acatccacc cggagcggat cagttggagt cggccaagac | 1560 |
| aaagttggcg agcaaggccc gtgaaatgaa ggaccgtgcc gagcagttca gtcagcaacc | 1620 |
| ggtagcaggg tctcagacca gcatcgatcc atcctcctgg catatgatgg ccgagcacta | 1680 |

-continued

| | |
|---|---|
| tggacaacag cagcagacgc gtgcccctca tctgcaactg caaccccgtg ctcaacgtgt | 1740 |
| cgttaaggct gcgacagcag taaccgctgg gggttctctg ttagtgttgt cagggctgac | 1800 |
| tttggcgggg acgtaattg cgttgaccat tgccacccg ctgttagtga ttttcagccc | 1860 |
| ggtactggtg ccagcagtta tcacgatctt cttgctgggt gccggattct tggcaagtgg | 1920 |
| aggttttgga gttgcggcgc tgtcagtttt atcctggatc tatcgttatc tgacaggaaa | 1980 |
| acatccccca ggtgccgatc agctggagag tgccaagaca aaactggcgt ctaaggcacg | 2040 |
| tgaaatgaag gatcgtgccg aacagttttc tcaacagccc gtagcggggt cacagacctc | 2100 |
| gatcgatcag caggttaacg tgcacatggc cgaacattac ggacagcaac aacagacgcg | 2160 |
| tgctccacac ctgcaattgc aaccgcgtgc tcaacgtgtt gtcaaagcgg cgaccgccgt | 2220 |
| aacagcagga ggatcactgt tagtgctgtc gggtttaacc ttggccggga ccgtcattgc | 2280 |
| attgactatt gcgacgccct tactggtgat cttttctccg gtgctggttc ccgccgttat | 2340 |
| taccatcttc ttgttagggg caggattcct ggcatcaggg ggattcggag ttgcggcgtt | 2400 |
| gagtgtctta agttggatct accgttatct gactggaaag caccccgcctg ggccgatca | 2460 |
| actggagtca gccaaaacga aattggcgtc aaaagcgcgt gaaatgaagg accgtgctga | 2520 |
| gcagttttct cagcagcctg tgcaggatc ccagacatca ccatggctcg agtaatgaag | 2580 |
| cggccgcacc cagctttctt gtacaaagtg gt | 2612 |

<210> SEQ ID NO 70
<211> LENGTH: 3089
<212> TYPE: DNA
<213> ORGANISM: Artificial Sequence
<220> FEATURE:
<223> OTHER INFORMATION: Synthetic sequence

<400> SEQUENCE: 70

| | |
|---|---|
| gcaggaactc tctggtaagc tagctccact ccccagaaac aaccggcgcc aaattgcgcg | 60 |
| aattgctgac ctgaagacgg aacatcatcg tcgggtcctt gggcgattgc ggcggaagat | 120 |
| gggtcagctt gggcttgagg acgagacccg aatccgagtc tgttgaaaag gttgttcatt | 180 |
| ggggatttgt atacggagat tggtcgtcga gaggtttgag ggaaaggaca aatgggtttg | 240 |
| gctctggaga aagagagtgc ggcttttaga agagaattga gaggtttaga gagagatgcg | 300 |
| gcggcgatga gcggaggaga gacgacgagg acctgcatta tcaaagcagt gacgtggtga | 360 |
| aatttggaac ttttaagagg cagatagatt tattatttgt atccattttc ttcattgttc | 420 |
| tagaatgtcg cggaacaaat tttaaaacta atcctaaat ttttctaatt ttgttgccaa | 480 |
| tagtggatat gtgggccgta tagaaggaat ctattgaagg cccaaaccca tactgacgag | 540 |
| cccaaaggtt cgttttgcgt tttatgtttc ggttcgatgc caacgccaca ttctgagcta | 600 |
| ggcaaaaaac aaacgtgtct ttgaatagac tcctctcgtt aacacatgca gcggctgcat | 660 |
| ggtgacgcca ttaacacgtg gcctacaatt gcatgatgtc tccattgaca cgtgacttct | 720 |
| cgtctccttt cttaatatat ctaacaaaca ctcctacctc ttccaaaata tatacacatc | 780 |
| ttttttgatca atctctcatt caaatctca ttctctctag taaacaagaa caaaaaaggt | 840 |
| accccatcac aagtttgtac aaaaaagcag gctccgcggc gcttgctcc gttaaaaaaa | 900 |
| accatggcag agcactacgg gcagcagcaa caaaacacgtg ccccccactt gcaactgcaa | 960 |
| ccgcgtgctc agcgtgttgt aaaggcagcg accgcggtta ctgccggagg tagcctgttg | 1020 |
| gtgttatccg ggttgaccct ggctggaacg gtcattgcgc tgacaatcgc cacacctctc | 1080 |
| ctggtgatct tctcgcctgt actggtccct gcaggtaaat ttctgtgttc cttattctct | 1140 |

```
caaaatcttc gattttgttt tcgttcgatc ccaatttcgt atatgttctt tggtttagat    1200
tctgttaatc ttagatcgaa gacgattttc tgggtttgat cgttagatat catcttaatt    1260
ctcgattagg gtttcataga tatcatccga tttgttcaaa taatttgagt tttgtcgaat    1320
aattactctt cgatttgtga tttctatcta gatctggtgt tagtttctag tttgtgcgat    1380
cgaatttgtc gattaatctg agtttttctg atctgcagtc atcaccatct tcctgttggg    1440
agcgggtttt ctggcaagcg ggggatttgg tgttgccgct ctgtctgtgc tgtcctggat    1500
ctaccgttac ctgacgggga aacatccacc cggagcggat cagttggagt cggccaagac    1560
aaagttggcg agcaaggccc gtgaaatgaa ggaccgtgcc gagcagttca gtcagcaacc    1620
ggtagcaggg tctcagacca gcatcgatcc atcctcctgg ctcgagatgg cggaacacta    1680
cgggcaacaa cagcagactc gtgctcccca cctgcaatta caaccccgtg cccaacgtgt    1740
tgtgaaagcg gcaacagcag taacggcagg gggaagtttg ctggtcttat cggggttgac    1800
cttagcggga accgtgattg ccctgacaat tgcgactccg ctgctggtta tcttcagccc    1860
cgtattggtt ccggccgtga tcacgatttt tttgctgggg gcaggatttt tagccagcgg    1920
aggatttggg gtcgcagcgt tgtctgtgct gagttggatc tatcgttatt tgaccgggaa    1980
gcacccacct ggagcagacc agctggagag cgcgaaaacg aagctggcat cgaaggcgcg    2040
tgaaatgaag gatcgtgctg aacaattctc ccagcagcct gttgccggtt tcagaccag    2100 ccatatgatg gccgagcact atggacaaca gcagcagacg cgtgcccctc atctgcaact    2160 gcaacccgt gctcaacgtg tcgttaaggc tgcgacagca gtaaccgctg ggggttctct    2220
gttagtgttg tcagggctga ctttggcggg gacggtaatt gcgttgacca ttgccacccc    2280
gctgttagta attttcagcc cggtactggt gccagcagtt atcacgatct tcttgctggg    2340
tgccggattc ttggcaagtg gaggttttgg agttgcggcg ctgtcagttt tatcctggat    2400
ctatcgttat ctgacaggaa aacatccccc aggtgccgat cagctggaga gtgccaagac    2460
aaaactggcg tctaaggcac gtgaaatgaa ggatcgtgcc gaacagtttt ctcaacagcc    2520
cgtagcgggg tcacagacct cgatcgatca gcaggttaac gtgcacatgg ccgaacatta    2580
cggacagcaa caacagacgc gtgctccaca cctgcaattg caaccgcgtg ctcaacgtgt    2640
tgtcaaagcg gcgaccgccg taacagcagg aggatcactg ttagtgctgt cgggtttaac    2700
cttggccggg accgtcattg cattgactat tgcgacgccc ttactggtga tcttttctcc    2760
ggtgctggtt cccgccgtta ttaccatctt cttgttaggg gcaggattcc tggcatcagg    2820
gggattcgga gttgcggcgt tgagtgtctt aagttggatc taccgttatc tgactggaaa    2880
gcacccgcct ggggccgatc aactggagtc agccaaaacg aaattggcgt caaaagcgcg    2940
tgaaatgaag gaccgtgctg agcagttttc tcagcagcct gtggcaggat cccagacatc    3000
accatggctc gagtaatgaa gcggccgcac ccagctttct tgtacaaagt ggtgatgggt    3060
tcgaaatcga taagcttgga tcctctaga                                      3089
```

<210> SEQ ID NO 71
<211> LENGTH: 3989
<212> TYPE: DNA
<213> ORGANISM: Artificial Sequence
<220> FEATURE:
<223> OTHER INFORMATION: Synthetic sequence

<400> SEQUENCE: 71

```
gcaggaactc tctggtaagc tagctccact ccccagaaac aaccggcgcc aaattgcgcg      60
aattgctgac ctgaagacgg aacatcatcg tcgggtcctt gggcgattgc ggcggaagat     120
```

```
gggtcagctt gggcttgagg acgagacccg aatccgagtc tgttgaaaag gttgttcatt      180
ggggatttgt atacggagat tggtcgtcga gaggtttgag ggaaaggaca aatgggtttg      240
gctctggaga aagagagtgc ggctttagag agagaattga gaggtttaga gagagatgcg      300
gcggcgatga gcggaggaga gacgacgagg acctgcatta tcaaagcagt gacgtggtga      360
aatttggaac ttttaagagg cagatagatt tattatttgt atccattttc ttcattgttc      420
tagaatgtcg cggaacaaat tttaaaacta aatcctaaat ttttctaatt ttgttgccaa      480
tagtggatat gtgggccgta tagaaggaat ctattgaagg cccaaaccca tactgacgag      540
cccaaaggtt cgttttgcgt tttatgtttc ggttcgatgc caacgccaca ttctgagcta      600
ggcaaaaaac aaacgtgtct ttgaatagac tcctctcgtt aacacatgca gcggctgcat      660
ggtgacgcca ttaacacgtg gcctacaatt gcatgatgtc tccattgaca cgtgacttct      720
cgtctccttt cttaatatat ctaacaaaca ctcctacctc ttccaaaata tatacacatc      780
tttttgatca atctctcatt caaaatctca ttctctctag taaacaagaa caaaaaaggt      840
accccatcac aagtttgtac aaaaaagcag gctccgcggc cgcttgctcc gttaaaaaaa      900
accatggcag agcactacgg gcagcagcaa caaacacgtg cccccacttt gcaactgcaa      960
ccgcgtgctc agcgtgttgt aaaggcagcg accgcggtta ctgccggagg tagcctgttg     1020
gtgttatccg ggttgaccct ggctggaacg gtcattgcgc tgacaatcgc cacacctctc     1080
ctggtgatct tctcgcctgt actggtccct gcaggtaaat ttctgtgttc cttattctct     1140
caaaatcttc gattttgttt tcgttcgatc ccaatttcgt atatgttctt tggtttagat     1200
tctgttaatc ttagatcgaa gacgattttc tgggtttgat cgttagatat catcttaatt     1260
ctcgattagg gttcatagaa tatcatccga tttgttcaaa taatttgagt tttgtcgaat     1320
aattactctt cgatttgtga tttctatcta gatctggtgt tagtttctag tttgtgcgat     1380
cgaatttgtc gattaatctg agttttttctg atctgcagtc atcaccatct tcctgttggg     1440
agcgggtttt ctggcaagcg ggggatttgg tgttgccgct ctgtctgtgc tgtcctggat     1500
ctaccgttac ctgacgggga aacatccacc cggagcggat cagttggagt cggccaagac     1560
aaagttggcg agcaaggccc gtgaaatgaa ggaccgtgcc gagcagttca gtcagcaacc     1620
ggtagcaggg tctcagacca gcatcgatcc atcctcctgg ctcgagatgg cggaacacta     1680
cgggcaacaa cagcagactc gtgctcccca cctgcaatta caacccgtg cccaacgtgt      1740 tgtgaaagcg gcaacagcag taacggcagg gggaagtttg ctggtcttat cggggttgac     1800
cttagcggga accgtgattg ccctgacaat tgcgactccg ctgctggtta tcttcagccc     1860
cgtattggtt ccggccgtga tcacgatttt tttgctgggg gcaggatttt tagccagcgg     1920
aggatttggg gtcgcagcgt tgtctgtgct gagttggatc tatcgttatt tgaccgggaa     1980
gcacccacct ggagcagacc agctggagag cgcgaaaacg aagctggcat cgaaggcgcg     2040
tgaaatgaag gatcgtgctg aacaattctc ccagcagcct gttgccggtt ctcagaccag     2100
ccatatgttt aaatggccaa gcgctatggc cgagcattat gggcagcaac agcaaacccg     2160
tgccccgcat ctgcaattgc aacctcgtgc ccagcgtgtc gttaaggcgg ctactgcggt     2220
aacagcggga gggagcttac tggtattaag cgggctgaca ttggccggaa cggtgatcgc     2280
cttaacaatc gcgacaccct tgctggtcat cttcagtccg gttctggtgc ccgcggtgat     2340
tacgattttc ctgctgggag ccggtttctt agcatcgggg ggttttgggg tagcagcctt     2400
gagtgtcctg tcgtggatct atcgttactt aactggaaaa cacccgccag gagctgacca     2460
gttggagtct gcaaaaacta agctggcgtc caaagcccgt gaaatgaagg atcgtgctga     2520
```

```
gcagtttagc cagcagccag ttgcgggaag tcagacctct tcatctgagc tcccatgggt    2580
cgacatggcg gagcattacg gtcaacagca acagaccgt gctccgcact tacaattgca    2640
accacgtgct caacgtgtcg taaaagccgc cacggcagtt actgcggggg gatcattgct    2700
ggtgttaagt gggttgacac tggcggggac agttattgca ctgacgatcg cgacccccct    2760
gttagtgatc ttctccccg ttctggttcc ggcggtcatt acaatctttc tgttgggtgc    2820 cggatttta gcctctgggg gatttggagt agctgccctg tcagtgttga gctggatcta    2880
ccgttactta acagggaagc accctcccgg ggcagatcag ttggaaagcg ccaagaccaa    2940
gctggcaagt aaagcgcgtg aaatgaagga ccgtgccgaa caattttcgc agcaaccggt    3000
tgcgggatca cagacctcta gtactccatc ctcctggcat atgatggccg agcactatgg    3060
acaacagcag cagacgcgtg cccctcatct gcaactgcaa ccccgtgctc aacgtgtcgt    3120
taaggctgcg acagcagtaa ccgctggggg ttctctgtta gtgttgtcag ggctgacttt    3180 ggcgggacg gtaattgcgt tgaccattgc caccccgctg ttagtgattt tcagcccggt    3240
actggtgcca gcagttatca cgatcttctt gctgggtgcc ggattcttgg caagtggagg    3300
ttttggagtt gcggcgctgt cagttttatc ctggatctat cgttatctga caggaaaaca    3360
tcccccaggt gccgatcagc tggagagtgc caagacaaaa ctggcgtcta aggcacgtga    3420
aatgaaggat cgtgccgaac agttttctca acagcccgta gcggggtcac agacctcgat    3480
cgatcagcag gttaacgtgc acatggccga acattacgga cagcaacaac agacgcgtgc    3540
tccacacctg caattgcaac cgcgtgctca acgtgttgtc aaagcggcga ccgccgtaac    3600
agcaggagga tcactgttag tgctgtcggg tttaaccttg gccgggaccg tcattgcatt    3660
gactattgcg acgcccttac tggtgatctt ttctccggtg ctggttcccg ccgttattac    3720
catcttcttg ttaggggcag gattcctggc atcaggggga ttcggagttg cggcgttgag    3780
tgtcttaagt tggatctacc gttatctgac tggaaagcac ccgcctgggg ccgatcaact    3840
ggagtcagcc aaaacgaaat tggcgtcaaa agcgcgtgaa atgaaggacc gtgctgagca    3900
gttttctcag cagcctgtgg caggatccca gacatcacca tggctcgagt aatgaagcgg    3960
ccgcacccag ctttcttgta caaagtggt                                     3989
```

<210> SEQ ID NO 72
<211> LENGTH: 2787
<212> TYPE: DNA
<213> ORGANISM: Artificial Sequence
<220> FEATURE:
<223> OTHER INFORMATION: Synthetic sequence

<400> SEQUENCE: 72

```
tcgacgaatt aattccaatc ccacaaaaat ctgagcttaa cagcacagtt gctcctctca      60
gagcagaatc gggtattcaa caccctcata tcaactacta cgttgtgtat aacggtccac     120
atgccggtat atacgatgac tggggttgta caaaggcggc aacaaacggc gttcccggag     180
ttgcacacaa gaaatttgcc actattacag aggcaagagc agcagctgac gcgtacacaa     240
caagtcagca aacagacagg ttgaacttca tccccaaagg agaagctcaa ctcaagccca     300
agagctttgc taaggcccta acaagcccac caaagcaaaa agcccactgg ctcacgctag     360
gaaccaaaag gcccagcagt gatccagccc aaaagagat ctcctttgcc ccggagatta      420
caatggacga tttcctctat ctttacgatc taggaaggaa gttcgaaggt gaaggtgacg     480
acactatgtt caccactgat aatgagaagg ttagcctctt caatttcaga aagaatgctg     540
acccacagat ggttagagag gcctacgcag caggtctcat caagacgatc tacccgagta     600
```

```
acaatctcca ggagatcaaa taccttccca agaaggttaa agatgcagtc aaaagattca    660
ggactaattg catcaagaac acagagaaag acatatttct caagatcaga agtactattc    720
cagtatggac gattcaaggc ttgcttcata aaccaaggca agtaatagag attggagtct    780
ctaaaaaggt agttcctact gaatctaagg ccatgcatgg agtctaagat tcaaatcgag    840
gatctaacag aactcgccgt gaagactggc gaacagttca tacagagtct tttacgactc    900
aatgacaaga agaaaatctt cgtcaacatg gtggagcacg acactctggt ctactccaaa    960
aatgtcaaag atacagtctc agaagaccaa agggctattg agacttttca acaaaggata   1020
atttcgggaa acctcctcgg attccattgc ccagctatct gtcacttcat cgaaaggaca   1080
gtagaaaagg aaggtggctc ctacaaatgc catcattgcg ataaaggaaa ggctatcatt   1140
caagatctct ctgccgacag tggtcccaaa gatggacccc cacccacgag gagcatcgtg   1200
gaaaaagaag acgttccaac cacgtcttca aagcaagtgg attgatgtga catctccact   1260
gacgtaaggg atgacgcaca atcccactat ccttcgcaag acccttcctc tatataagga   1320
agttcatttc atttggagag gacacgctcg aggaattcgg tacccatca caagtttgta    1380 caaaaaagca ggctccgcgg ccgcttgctc cgttaaaaaa aaccatggct gagcattatg   1440
gtcaacaaca gcagaccagg gcgcctcacc tgcagctgca gccgcgcgcc cagcgggtag   1500
tgaaggcggc caccgccgtg acagccgcg gctcgcttct cgtcctctct ggcctcactt   1560
tagccggaac tgttattgcg ctcaccatcg ccactccgct gcttgtgatc tttagccccg   1620
ttctggtgcc ggcggtcata accatttttct tgctgggtgc gggttttctg gcatccggag   1680
gcttcggcgt ggcggcgctg agtgtgctgt cgtggattta cagatatctg acagggaaac   1740
acccgccggg ggcggatcag ctggaatcgg caaagacgaa gctggcgagc aaggcgcgag   1800
agatgaagga tagggcagag cagttctcgc agcagcctgt tggaggcggt ggatccggag   1860
gcggtggtag tatggctgag cattatggtc aacaacagca gaccagggcg cctcacctgc   1920
agctgcagcc gcgcgcccag cgggtagtga aggcggccac cgccgtgaca gccggcggct   1980
cgcttctcgt cctctctggc ctcactttag ccggaactgt tattgcgctc accatcgcca   2040
ctccgctgct tgtgatcttt agccccgttc tggtgccggc ggtcataacc attttcttgc   2100
tgggtgcggg ttttctggca tccggaggct cggcgtggc ggcgctgagt gtgctgtcgt   2160
ggatttacag atatctgaca gggaaacacc cgccgggggc ggatcagctg gaatcggcaa   2220
agacgaagct ggcgagcaag gcgcgagaga tgaaggatag gcagagcag ttctcgcagc   2280 agcctgttgg gggcggtgga tccggtggag ggggatccat ggctgagcat tatggtcaac   2340
aacagcagac cagggcgcct cacctgcagc tgcagccgcg cgcccagcgg gtagtgaagg   2400
cggccaccgc cgtgacagcc ggcggctcgc ttctcgtcct ctctggcctc actttagccg   2460
gaactgttat tgcgctcacc atcgccactc cgctgcttgt gatctttagc ccgttctgg   2520 tgccggcggt cataaccatt ttcttgctgg gtgcgggttt tctggcatcc ggaggcttcg   2580
gcgtggcggc gctgagtgtg ctgtcgtgga tttacagata tctgacaggg aaacacccgc   2640 cggggcgga tcagctggaa tcggcaaaga cgaagctggc gagcaaggcg cgagagatga   2700
aggatagggc agagcagttc tcgcagcagc ctgttccatg gctcgagtaa tgaagcggcc   2760
gcacccagct ttcttgtaca aagtggt                                       2787
```

<210> SEQ ID NO 73
<211> LENGTH: 2263
<212> TYPE: DNA
<213> ORGANISM: Artificial Sequence
<220> FEATURE:
<223> OTHER INFORMATION: Synthetic sequence

<400> SEQUENCE: 73

| | | | | | |
|---|---|---|---|---|---|
| gcaggaactc | tctggtaagc | tagctccact | ccccagaaac | aaccggcgcc | aaattgcgcg | 60 |
| aattgctgac | ctgaagacgg | aacatcatcg | tcgggtcctt | gggcgattgc | ggcggaagat | 120 |
| gggtcagctt | gggcttgagg | acgagacccg | aatccgagtc | tgttgaaaag | gttgttcatt | 180 |
| ggggatttgt | atacggagat | tggtcgtcga | gaggtttgag | ggaaaggaca | aatgggtttg | 240 |
| gctctggaga | aagagagtgc | ggctttagag | agagaattga | gaggtttaga | gagagatgcg | 300 |
| gcggcgatga | gcggaggaga | gacgacgagg | acctgcatta | tcaaagcagt | gacgtggtga | 360 |
| aatttggaac | ttttaagagg | cagatagatt | tattatttgt | atccatttc | ttcattgttc | 420 |
| tagaatgtcg | cggaacaaat | tttaaaacta | aatcctaaat | ttttctaatt | ttgttgccaa | 480 |
| tagtggatat | gtgggccgta | tagaaggaat | ctattgaagg | cccaaaccca | tactgacgag | 540 |
| cccaaaggtt | cgttttgcgt | tttatgtttc | ggttcgatgc | caacgccaca | ttctgagcta | 600 |
| ggcaaaaaac | aaacgtgtct | ttgaatagac | tcctctcgtt | aacacatgca | gcggctgcat | 660 |
| ggtgacgcca | ttaacacgtg | gcctacaatt | gcatgatgtc | tccattgaca | cgtgacttct | 720 |
| cgtctccttt | cttaatatat | ctaacaaaca | ctcctacctc | ttccaaaata | tatacacatc | 780 |
| tttttgatca | atctctcatt | caaaatctca | ttctctctag | taaacaagaa | caaaaaggt | 840 |
| accccatcac | aagtttgtac | aaaaaagcag | gctccgcggc | cgcttgctcc | gttaaaaaaa | 900 |
| accatggctg | agcattatgg | tcaacaacag | cagaccaggg | cgcctcacct | gcagctgcag | 960 |
| ccgcgcgccc | agcgggtagt | gaaggcggcc | accgccgtga | cagccggcgg | ctcgcttctc | 1020 |
| gtcctctctg | gcctcacttt | agccggaact | gttattgcgc | tcaccatcgc | cactccgctg | 1080 |
| cttgtgatct | ttagccccgt | tctggtgccg | gcggtcataa | ccatttctt | gctgggtgcg | 1140 |
| ggttttctgg | catccggagg | cttcggcgtg | gcggcgctga | gtgtgctgtc | gtggatttac | 1200 |
| agatatctga | caggaaaaca | cccgccgggg | gcggatcagc | tggaatcggc | aaagacgaag | 1260 |
| ctggcgagca | aggcgcgaga | gatgaaggat | agggcagagc | agttctcgca | gcagcctgtt | 1320 |
| ggaggcggtg | gatccggagg | cggtggtagt | atggctgagc | attatggtca | acaacagcag | 1380 |
| accagggcgc | ctcacctgca | gctgcagccg | cgcgcccagc | gggtagtgaa | ggcggccacc | 1440 |
| gccgtgacag | ccggcggctc | gcttctcgtc | ctctctggcc | tcactttagc | cggaactgtt | 1500 |
| attgcgctca | ccatcgccac | tccgctgctt | gtgatcttta | gccccgttct | ggtgccggcg | 1560 |
| gtcataacca | ttttcttgct | gggtgcgggt | tttctggcat | ccggaggctt | cggcgtggcg | 1620 |
| gcgctgagtg | tgctgtcgtg | gatttacaga | tatctgacag | gaaacaccc | gccggggcg | 1680 |
| gatcagctgg | aatcggcaaa | gacgaagctg | gcgagcaagg | cgcgagagat | gaaggatagg | 1740 |
| gcagagcagt | tctcgcagca | gcctgttggg | ggcggtggat | ccggtggagg | gggatccatg | 1800 |
| gctgagcatt | atggtcaaca | acagcagacc | agggcgcctc | acctgcagct | gcagccgcgc | 1860 |
| gcccagcggg | tagtgaaggc | ggccaccgcc | gtgacagccg | gcggctcgct | tctcgtcctc | 1920 |
| tctggcctca | ctttagccgg | aactgttatt | gcgctcacca | tcgccactcc | gctgcttgtg | 1980 |
| atctttagcc | ccgttctggt | gccggcggtc | ataaccattt | tcttgctggg | tgcgggtttt | 2040 |
| ctggcatccg | gaggcttcgg | cgtggcggcg | ctgagtgtgt | tgtcgtggat | ttacagatat | 2100 |
| ctgacaggga | aacacccgcc | ggggcggat | cagctggaat | cggcaaagac | gaagctggcg | 2160 |
| agcaaggcgc | gagagatgaa | ggatagggca | gagcagttct | cgcagcagcc | tgttccatgg | 2220 |
| ctcgagtaat | gaagcggccg | cacccagctt | tcttgtacaa | agt | | 2263 |

<210> SEQ ID NO 74
<211> LENGTH: 153
<212> TYPE: PRT
<213> ORGANISM: Artificial Sequence
<220> FEATURE:
<223> OTHER INFORMATION: Synthetic sequence

<400> SEQUENCE: 74

```
Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser Ile Asp Pro Ser Ser Trp Leu Glu
145                 150
```

<210> SEQ ID NO 75
<211> LENGTH: 455
<212> TYPE: PRT
<213> ORGANISM: Artificial Sequence
<220> FEATURE:
<223> OTHER INFORMATION: Synthetic sequence

<400> SEQUENCE: 75

```
Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser Ile Asp Pro Ser Ser Trp His Met Met Ala Glu His Tyr Gly Gln
145                 150                 155                 160
```

```
Gln Gln Gln Thr Arg Ala Pro His Leu Gln Leu Gln Pro Arg Ala Gln
                165                 170                 175

Arg Val Val Lys Ala Ala Thr Ala Val Thr Ala Gly Gly Ser Leu Leu
            180                 185                 190

Val Leu Ser Gly Leu Thr Leu Ala Gly Thr Val Ile Ala Leu Thr Ile
        195                 200                 205

Ala Thr Pro Leu Leu Val Ile Phe Ser Pro Val Leu Val Pro Ala Val
    210                 215                 220

Ile Thr Ile Phe Leu Leu Gly Ala Gly Phe Leu Ala Ser Gly Gly Phe
225                 230                 235                 240

Gly Val Ala Ala Leu Ser Val Leu Ser Trp Ile Tyr Arg Tyr Leu Thr
                245                 250                 255

Gly Lys His Pro Pro Gly Ala Asp Gln Leu Glu Ser Ala Lys Thr Lys
            260                 265                 270

Leu Ala Ser Lys Ala Arg Glu Met Lys Asp Arg Ala Glu Gln Phe Ser
        275                 280                 285

Gln Gln Pro Val Ala Gly Ser Gln Thr Ser Ile Asp Gln Gln Val Asn
    290                 295                 300

Val His Met Ala Glu His Tyr Gly Gln Gln Gln Thr Arg Ala Pro
305                 310                 315                 320

His Leu Gln Leu Gln Pro Arg Ala Gln Arg Val Val Lys Ala Ala Thr
                325                 330                 335

Ala Val Thr Ala Gly Gly Ser Leu Leu Val Leu Ser Gly Leu Thr Leu
            340                 345                 350

Ala Gly Thr Val Ile Ala Leu Thr Ile Ala Thr Pro Leu Leu Val Ile
        355                 360                 365

Phe Ser Pro Val Leu Val Pro Ala Val Ile Thr Ile Phe Leu Leu Gly
    370                 375                 380

Ala Gly Phe Leu Ala Ser Gly Gly Phe Gly Val Ala Ala Leu Ser Val
385                 390                 395                 400

Leu Ser Trp Ile Tyr Arg Tyr Leu Thr Gly Lys His Pro Pro Gly Ala
                405                 410                 415

Asp Gln Leu Glu Ser Ala Lys Thr Lys Leu Ala Ser Lys Ala Arg Glu
            420                 425                 430

Met Lys Asp Arg Ala Glu Gln Phe Ser Gln Gln Pro Val Ala Gly Ser
        435                 440                 445

Gln Thr Ser Pro Trp Leu Glu
    450                 455

<210> SEQ ID NO 76
<211> LENGTH: 602
<212> TYPE: PRT
<213> ORGANISM: Artificial Sequence
<220> FEATURE:
<223> OTHER INFORMATION: Synthetic sequence

<400> SEQUENCE: 76

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60
```

-continued

```
Pro Val Leu Val Pro Ala Val Ile Thr Ile Phe Leu Leu Gly Ala Gly
 65                  70                  75                  80

Phe Leu Ala Ser Gly Gly Phe Gly Val Ala Leu Ser Val Leu Ser
             85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
130                 135                 140

Ser Ile Asp Pro Ser Ser Trp Leu Glu Met Ala Glu His Tyr Gly Gln
145                 150                 155                 160

Gln Gln Gln Thr Arg Ala Pro His Leu Gln Leu Gln Pro Arg Ala Gln
                165                 170                 175

Arg Val Val Lys Ala Ala Thr Ala Val Thr Ala Gly Gly Ser Leu Leu
            180                 185                 190

Val Leu Ser Gly Leu Thr Leu Ala Gly Thr Val Ile Ala Leu Thr Ile
        195                 200                 205

Ala Thr Pro Leu Leu Val Ile Phe Ser Pro Val Leu Val Pro Ala Val
210                 215                 220

Ile Thr Ile Phe Leu Leu Gly Ala Gly Phe Leu Ala Ser Gly Gly Phe
225                 230                 235                 240

Gly Val Ala Ala Leu Ser Val Leu Ser Trp Ile Tyr Arg Tyr Leu Thr
                245                 250                 255

Gly Lys His Pro Pro Gly Ala Asp Gln Leu Glu Ser Ala Lys Thr Lys
            260                 265                 270

Leu Ala Ser Lys Ala Arg Glu Met Lys Asp Arg Ala Glu Gln Phe Ser
        275                 280                 285

Gln Gln Pro Val Ala Gly Ser Gln Thr Ser His Met Met Ala Glu His
290                 295                 300

Tyr Gly Gln Gln Gln Thr Arg Ala Pro His Leu Gln Leu Gln Pro
305                 310                 315                 320

Arg Ala Gln Arg Val Val Lys Ala Ala Thr Ala Val Thr Ala Gly Gly
                325                 330                 335

Ser Leu Leu Val Leu Ser Gly Leu Thr Leu Ala Gly Thr Val Ile Ala
            340                 345                 350

Leu Thr Ile Ala Thr Pro Leu Leu Val Ile Phe Ser Pro Val Leu Val
        355                 360                 365

Pro Ala Val Ile Thr Ile Phe Leu Leu Gly Ala Gly Phe Leu Ala Ser
370                 375                 380

Gly Gly Phe Gly Val Ala Ala Leu Ser Val Leu Ser Trp Ile Tyr Arg
385                 390                 395                 400

Tyr Leu Thr Gly Lys His Pro Pro Gly Ala Asp Gln Leu Glu Ser Ala
                405                 410                 415

Lys Thr Lys Leu Ala Ser Lys Ala Arg Glu Met Lys Asp Arg Ala Glu
            420                 425                 430

Gln Phe Ser Gln Gln Pro Val Ala Gly Ser Gln Thr Ser Ile Asp Gln
        435                 440                 445

Gln Val Asn Val His Met Ala Glu His Tyr Gly Gln Gln Gln Gln Thr
450                 455                 460

Arg Ala Pro His Leu Gln Leu Gln Pro Arg Ala Gln Arg Val Val Lys
465                 470                 475                 480

Ala Ala Thr Ala Val Thr Ala Gly Gly Ser Leu Leu Val Leu Ser Gly
                485                 490                 495
```

```
Leu Thr Leu Ala Gly Thr Val Ile Ala Leu Thr Ile Ala Thr Pro Leu
                500                 505                 510

Leu Val Ile Phe Ser Pro Val Leu Pro Ala Val Ile Thr Ile Phe
            515                 520                 525

Leu Leu Gly Ala Gly Phe Leu Ala Ser Gly Gly Phe Gly Val Ala Ala
        530                 535                 540

Leu Ser Val Leu Ser Trp Ile Tyr Arg Tyr Leu Thr Gly Lys His Pro
545                 550                 555                 560

Pro Gly Ala Asp Gln Leu Glu Ser Ala Lys Thr Lys Leu Ala Ser Lys
                565                 570                 575

Ala Arg Glu Met Lys Asp Arg Ala Glu Gln Phe Ser Gln Gln Pro Val
                580                 585                 590

Ala Gly Ser Gln Thr Ser Pro Trp Leu Glu
            595                 600

<210> SEQ ID NO 77
<211> LENGTH: 914
<212> TYPE: PRT
<213> ORGANISM: Artificial Sequence
<220> FEATURE:
<223> OTHER INFORMATION: Synthetic sequence

<400> SEQUENCE: 77

Met Ala Glu His Tyr Gly Gln Gln Gln Thr Arg Ala Pro His Leu
1               5                   10                  15

Gln Leu Gln Pro Arg Ala Gln Arg Val Val Lys Ala Thr Ala Val
                20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
                100                 105                 110

Leu Glu Ser Ala Lys Thr Lys Leu Ala Ser Lys Ala Arg Glu Met Lys
            115                 120                 125

Asp Arg Ala Glu Gln Phe Ser Gln Gln Pro Val Ala Gly Ser Gln Thr
130                 135                 140

Ser Ile Asp Pro Ser Ser Trp Leu Glu Met Ala Glu His Tyr Gly Gln
145                 150                 155                 160

Gln Gln Gln Thr Arg Ala Pro His Leu Gln Leu Gln Pro Arg Ala Gln
                165                 170                 175

Arg Val Val Lys Ala Ala Thr Ala Val Thr Ala Gly Gly Ser Leu Leu
                180                 185                 190

Val Leu Ser Gly Leu Thr Leu Ala Gly Thr Val Ile Ala Leu Thr Ile
            195                 200                 205

Ala Thr Pro Leu Leu Val Ile Phe Ser Pro Val Leu Val Pro Ala Val
        210                 215                 220

Ile Thr Ile Phe Leu Leu Gly Ala Gly Phe Leu Ala Ser Gly Gly Phe
225                 230                 235                 240

Gly Val Ala Ala Leu Ser Val Leu Ser Trp Ile Tyr Arg Tyr Leu Thr
                245                 250                 255
```

```
Gly Lys His Pro Pro Gly Ala Asp Gln Leu Glu Ser Ala Lys Thr Lys
            260                 265                 270

Leu Ala Ser Lys Ala Arg Glu Met Lys Asp Arg Ala Glu Gln Phe Ser
        275                 280                 285

Gln Gln Pro Val Ala Gly Ser Gln Thr Ser His Met Phe Lys Trp Pro
    290                 295                 300

Ser Ala Met Ala Glu His Tyr Gly Gln Gln Gln Thr Arg Ala Pro
305                 310                 315                 320

His Leu Gln Leu Gln Pro Arg Ala Gln Arg Val Val Lys Ala Ala Thr
                325                 330                 335

Ala Val Thr Ala Gly Gly Ser Leu Leu Val Leu Ser Gly Leu Thr Leu
            340                 345                 350

Ala Gly Thr Val Ile Ala Leu Thr Ile Ala Thr Pro Leu Leu Val Ile
        355                 360                 365

Phe Ser Pro Val Leu Val Pro Ala Val Ile Thr Ile Phe Leu Leu Gly
    370                 375                 380

Ala Gly Phe Leu Ala Ser Gly Gly Phe Gly Val Ala Ala Leu Ser Val
385                 390                 395                 400

Leu Ser Trp Ile Tyr Arg Tyr Leu Thr Gly Lys His Pro Pro Gly Ala
                405                 410                 415

Asp Gln Leu Glu Ser Ala Lys Thr Lys Leu Ala Ser Lys Ala Arg Glu
            420                 425                 430

Met Lys Asp Arg Ala Glu Gln Phe Ser Gln Gln Pro Val Ala Gly Ser
        435                 440                 445

Gln Thr Ser Ser Ser Glu Leu Pro Trp Val Asp Met Ala Glu His Tyr
    450                 455                 460

Gly Gln Gln Gln Gln Thr Arg Ala Pro His Leu Gln Leu Gln Pro Arg
465                 470                 475                 480

Ala Gln Arg Val Val Lys Ala Ala Thr Ala Val Thr Ala Gly Gly Ser
                485                 490                 495

Leu Leu Val Leu Ser Gly Leu Thr Leu Ala Gly Thr Val Ile Ala Leu
            500                 505                 510

Thr Ile Ala Thr Pro Leu Leu Val Ile Phe Ser Pro Val Leu Val Pro
        515                 520                 525

Ala Val Ile Thr Ile Phe Leu Leu Gly Ala Gly Phe Leu Ala Ser Gly
    530                 535                 540

Gly Phe Gly Val Ala Ala Leu Ser Val Leu Ser Trp Ile Tyr Arg Tyr
545                 550                 555                 560

Leu Thr Gly Lys His Pro Pro Gly Ala Asp Gln Leu Glu Ser Ala Lys
                565                 570                 575

Thr Lys Leu Ala Ser Lys Ala Arg Glu Met Lys Asp Arg Ala Glu Gln
            580                 585                 590

Phe Ser Gln Gln Pro Val Ala Gly Ser Gln Thr Ser Ser Thr Pro Ser
        595                 600                 605

Ser Trp His Met Met Ala Glu His Tyr Gly Gln Gln Gln Gln Thr Arg
    610                 615                 620

Ala Pro His Leu Gln Leu Gln Pro Arg Ala Gln Arg Val Val Lys Ala
625                 630                 635                 640

Ala Thr Ala Val Thr Ala Gly Gly Ser Leu Leu Val Leu Ser Gly Leu
                645                 650                 655

Thr Leu Ala Gly Thr Val Ile Ala Leu Thr Ile Ala Thr Pro Leu Leu
            660                 665                 670

Val Ile Phe Ser Pro Val Leu Val Pro Ala Val Ile Thr Ile Phe Leu
        675                 680                 685
```

```
Leu Gly Ala Gly Phe Leu Ala Ser Gly Gly Phe Gly Val Ala Ala Leu
            690                 695                 700

Ser Val Leu Ser Trp Ile Tyr Arg Tyr Leu Thr Gly Lys His Pro Pro
705                 710                 715                 720

Gly Ala Asp Gln Leu Glu Ser Ala Lys Thr Lys Leu Ala Ser Lys Ala
            725                 730                 735

Arg Glu Met Lys Asp Arg Ala Glu Gln Phe Ser Gln Gln Pro Val Ala
            740                 745                 750

Gly Ser Gln Thr Ser Ile Asp Gln Gln Val Asn Val His Met Ala Glu
            755                 760                 765

His Tyr Gly Gln Gln Gln Gln Thr Arg Ala Pro His Leu Gln Leu Gln
            770                 775                 780

Pro Arg Ala Gln Arg Val Val Lys Ala Ala Thr Ala Val Thr Ala Gly
785                 790                 795                 800

Gly Ser Leu Leu Val Leu Ser Gly Leu Thr Leu Ala Gly Thr Val Ile
            805                 810                 815

Ala Leu Thr Ile Ala Thr Pro Leu Leu Val Ile Phe Ser Pro Val Leu
            820                 825                 830

Val Pro Ala Val Ile Thr Ile Phe Leu Leu Gly Ala Gly Phe Leu Ala
835                 840                 845

Ser Gly Gly Phe Gly Val Ala Ala Leu Ser Val Leu Ser Trp Ile Tyr
850                 855                 860

Arg Tyr Leu Thr Gly Lys His Pro Pro Gly Ala Asp Gln Leu Glu Ser
865                 870                 875                 880

Ala Lys Thr Lys Leu Ala Ser Lys Ala Arg Glu Met Lys Asp Arg Ala
            885                 890                 895

Glu Gln Phe Ser Gln Gln Pro Val Ala Gly Ser Gln Thr Ser Pro Trp
            900                 905                 910

Leu Glu

<210> SEQ ID NO 78
<211> LENGTH: 153
<212> TYPE: PRT
<213> ORGANISM: Artificial Sequence
<220> FEATURE:
<223> OTHER INFORMATION: Synthetic sequence

<400> SEQUENCE: 78

Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
```

```
                130                 135                 140
Ser Ile Asp Pro Ser Ser Trp Leu Glu
145                 150
```

<210> SEQ ID NO 79
<211> LENGTH: 455
<212> TYPE: PRT
<213> ORGANISM: Artificial Sequence
<220> FEATURE:
<223> OTHER INFORMATION: Synthetic sequence

<400> SEQUENCE: 79

```
Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser Ile Asp Pro Ser Ser Trp His Met Met Ala Glu His Tyr Gly Gln
145                 150                 155                 160

Gln Gln Gln Thr Arg Ala Pro His Leu Gln Leu Gln Pro Arg Ala Gln
                165                 170                 175

Arg Val Val Lys Ala Ala Thr Ala Val Thr Ala Gly Gly Ser Leu Leu
            180                 185                 190

Val Leu Ser Gly Leu Thr Leu Ala Gly Thr Val Ile Ala Leu Thr Ile
        195                 200                 205

Ala Thr Pro Leu Leu Val Ile Phe Ser Pro Val Leu Val Pro Ala Val
    210                 215                 220

Ile Thr Ile Phe Leu Leu Gly Ala Gly Phe Leu Ala Ser Gly Gly Phe
225                 230                 235                 240

Gly Val Ala Ala Leu Ser Val Leu Ser Trp Ile Tyr Arg Tyr Leu Thr
                245                 250                 255

Gly Lys His Pro Pro Gly Ala Asp Gln Leu Glu Ser Ala Lys Thr Lys
            260                 265                 270

Leu Ala Ser Lys Ala Arg Glu Met Lys Asp Arg Ala Glu Gln Phe Ser
        275                 280                 285

Gln Gln Pro Val Ala Gly Ser Gln Thr Ser Ile Asp Gln Gln Val Asn
    290                 295                 300

Val His Met Ala Glu His Tyr Gly Gln Gln Gln Thr Arg Ala Pro
305                 310                 315                 320

His Leu Gln Leu Gln Pro Arg Ala Gln Arg Val Val Lys Ala Ala Thr
                325                 330                 335

Ala Val Thr Ala Gly Gly Ser Leu Leu Val Leu Ser Gly Leu Thr Leu
            340                 345                 350
```

```
Ala Gly Thr Val Ile Ala Leu Thr Ile Ala Thr Pro Leu Leu Val Ile
        355                 360                 365

Phe Ser Pro Val Leu Val Pro Ala Val Ile Thr Ile Phe Leu Leu Gly
    370                 375                 380

Ala Gly Phe Leu Ala Ser Gly Gly Phe Gly Val Ala Ala Leu Ser Val
385                 390                 395                 400

Leu Ser Trp Ile Tyr Arg Tyr Leu Thr Gly Lys His Pro Pro Gly Ala
            405                 410                 415

Asp Gln Leu Glu Ser Ala Lys Thr Lys Leu Ala Ser Lys Ala Arg Glu
        420                 425                 430

Met Lys Asp Arg Ala Glu Gln Phe Ser Gln Gln Pro Val Ala Gly Ser
            435                 440                 445

Gln Thr Ser Pro Trp Leu Glu
        450                 455

<210> SEQ ID NO 80
<211> LENGTH: 602
<212> TYPE: PRT
<213> ORGANISM: Artificial Sequence
<220> FEATURE:
<223> OTHER INFORMATION: Synthetic sequence

<400> SEQUENCE: 80

Met Ala Glu His Tyr Gly Gln Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
        35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Ala Gly Ser Gln Thr
    130                 135                 140

Ser Ile Asp Pro Ser Ser Trp Leu Glu Met Ala Glu His Tyr Gly Gln
145                 150                 155                 160

Gln Gln Gln Thr Arg Ala Pro His Leu Gln Leu Gln Pro Arg Ala Gln
                165                 170                 175

Arg Val Val Lys Ala Ala Thr Ala Val Thr Ala Gly Gly Ser Leu Leu
            180                 185                 190

Val Leu Ser Gly Leu Thr Leu Ala Gly Thr Val Ile Ala Leu Thr Ile
        195                 200                 205

Ala Thr Pro Leu Leu Val Ile Phe Ser Pro Val Leu Val Pro Ala Val
    210                 215                 220

Ile Thr Ile Phe Leu Leu Gly Ala Gly Phe Leu Ala Ser Gly Gly Phe
225                 230                 235                 240

Gly Val Ala Ala Leu Ser Val Leu Ser Trp Ile Tyr Arg Tyr Leu Thr
                245                 250                 255
```

Gly Lys His Pro Pro Gly Ala Asp Gln Leu Glu Ser Ala Lys Thr Lys
            260                 265                 270

Leu Ala Ser Lys Ala Arg Glu Met Lys Asp Arg Ala Glu Gln Phe Ser
            275                 280                 285

Gln Gln Pro Val Ala Gly Ser Gln Thr Ser His Met Met Ala Glu His
        290                 295                 300

Tyr Gly Gln Gln Gln Thr Arg Ala Pro His Leu Gln Leu Gln Pro
305                 310                 315                 320

Arg Ala Gln Arg Val Val Lys Ala Ala Thr Ala Val Thr Ala Gly Gly
                325                 330                 335

Ser Leu Leu Val Leu Ser Gly Leu Thr Leu Ala Gly Thr Val Ile Ala
            340                 345                 350

Leu Thr Ile Ala Thr Pro Leu Leu Val Ile Phe Ser Pro Val Leu Val
            355                 360                 365

Pro Ala Val Ile Thr Ile Phe Leu Leu Gly Ala Gly Phe Leu Ala Ser
        370                 375                 380

Gly Gly Phe Gly Val Ala Ala Leu Ser Val Leu Ser Trp Ile Tyr Arg
385                 390                 395                 400

Tyr Leu Thr Gly Lys His Pro Pro Gly Ala Asp Gln Leu Glu Ser Ala
            405                 410                 415

Lys Thr Lys Leu Ala Ser Lys Ala Arg Glu Met Lys Asp Arg Ala Glu
            420                 425                 430

Gln Phe Ser Gln Gln Pro Val Ala Gly Ser Gln Thr Ser Ile Asp Gln
        435                 440                 445

Gln Val Asn Val His Met Ala Glu His Tyr Gly Gln Gln Gln Gln Thr
    450                 455                 460

Arg Ala Pro His Leu Gln Leu Gln Pro Arg Ala Gln Arg Val Val Lys
465                 470                 475                 480

Ala Ala Thr Ala Val Thr Ala Gly Gly Ser Leu Leu Val Leu Ser Gly
                485                 490                 495

Leu Thr Leu Ala Gly Thr Val Ile Ala Leu Thr Ile Ala Thr Pro Leu
            500                 505                 510

Leu Val Ile Phe Ser Pro Val Leu Val Pro Ala Val Ile Thr Ile Phe
            515                 520                 525

Leu Leu Gly Ala Gly Phe Leu Ala Ser Gly Gly Phe Gly Val Ala Ala
        530                 535                 540

Leu Ser Val Leu Ser Trp Ile Tyr Arg Tyr Leu Thr Gly Lys His Pro
545                 550                 555                 560

Pro Gly Ala Asp Gln Leu Glu Ser Ala Lys Thr Lys Leu Ala Ser Lys
                565                 570                 575

Ala Arg Glu Met Lys Asp Arg Ala Glu Gln Phe Ser Gln Gln Pro Val
            580                 585                 590

Ala Gly Ser Gln Thr Ser Pro Trp Leu Glu
        595                 600

<210> SEQ ID NO 81
<211> LENGTH: 914
<212> TYPE: PRT
<213> ORGANISM: Artificial Sequence
<220> FEATURE:
<223> OTHER INFORMATION: Synthetic sequence

<400> SEQUENCE: 81

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val

```
                    20                  25                  30
Thr Ala Gly Gly Ser Leu Leu Val Leu Ser Gly Leu Thr Leu Ala Gly
                35                  40                  45
Thr Val Ile Ala Leu Thr Ile Ala Thr Pro Leu Leu Val Ile Phe Ser
        50                  55                  60
Pro Val Leu Val Pro Ala Val Ile Thr Ile Phe Leu Leu Gly Ala Gly
65                  70                  75                  80
Phe Leu Ala Ser Gly Gly Phe Gly Val Ala Ala Leu Ser Val Leu Ser
                85                  90                  95
Trp Ile Tyr Arg Tyr Leu Thr Gly Lys His Pro Pro Gly Ala Asp Gln
                100                 105                 110
Leu Glu Ser Ala Lys Thr Lys Leu Ala Ser Lys Ala Arg Glu Met Lys
                115                 120                 125
Asp Arg Ala Glu Gln Phe Ser Gln Gln Pro Val Ala Gly Ser Gln Thr
                130                 135                 140
Ser Ile Asp Pro Ser Ser Trp Leu Glu Met Ala Glu His Tyr Gly Gln
145                 150                 155                 160
Gln Gln Gln Thr Arg Ala Pro His Leu Gln Leu Gln Pro Arg Ala Gln
                165                 170                 175
Arg Val Val Lys Ala Ala Thr Ala Val Thr Ala Gly Gly Ser Leu Leu
                180                 185                 190
Val Leu Ser Gly Leu Thr Leu Ala Gly Thr Val Ile Ala Leu Thr Ile
                195                 200                 205
Ala Thr Pro Leu Leu Val Ile Phe Ser Pro Val Leu Val Pro Ala Val
                210                 215                 220
Ile Thr Ile Phe Leu Leu Gly Ala Gly Phe Leu Ala Ser Gly Gly Phe
225                 230                 235                 240
Gly Val Ala Ala Leu Ser Val Leu Ser Trp Ile Tyr Arg Tyr Leu Thr
                245                 250                 255
Gly Lys His Pro Pro Gly Ala Asp Gln Leu Glu Ser Ala Lys Thr Lys
                260                 265                 270
Leu Ala Ser Lys Ala Arg Glu Met Lys Asp Arg Ala Glu Gln Phe Ser
                275                 280                 285
Gln Gln Pro Val Ala Gly Ser Gln Thr Ser His Met Phe Lys Trp Pro
                290                 295                 300
Ser Ala Met Ala Glu His Tyr Gly Gln Gln Gln Gln Thr Arg Ala Pro
305                 310                 315                 320
His Leu Gln Leu Gln Pro Arg Ala Gln Arg Val Val Lys Ala Ala Thr
                325                 330                 335
Ala Val Thr Ala Gly Gly Ser Leu Leu Val Leu Ser Gly Leu Thr Leu
                340                 345                 350
Ala Gly Thr Val Ile Ala Leu Thr Ile Ala Thr Pro Leu Leu Val Ile
                355                 360                 365
Phe Ser Pro Val Leu Val Pro Ala Val Ile Thr Ile Phe Leu Leu Gly
                370                 375                 380
Ala Gly Phe Leu Ala Ser Gly Gly Phe Gly Val Ala Ala Leu Ser Val
385                 390                 395                 400
Leu Ser Trp Ile Tyr Arg Tyr Leu Thr Gly Lys His Pro Pro Gly Ala
                405                 410                 415
Asp Gln Leu Glu Ser Ala Lys Thr Lys Leu Ala Ser Lys Ala Arg Glu
                420                 425                 430
Met Lys Asp Arg Ala Glu Gln Phe Ser Gln Gln Pro Val Ala Gly Ser
                435                 440                 445
```

```
Gln Thr Ser Ser Ser Glu Leu Pro Trp Val Asp Met Ala Glu His Tyr
    450                 455                 460

Gly Gln Gln Gln Gln Thr Arg Ala Pro His Leu Gln Leu Gln Pro Arg
465                 470                 475                 480

Ala Gln Arg Val Val Lys Ala Ala Thr Ala Val Thr Ala Gly Gly Ser
                485                 490                 495

Leu Leu Val Leu Ser Gly Leu Thr Leu Ala Gly Thr Val Ile Ala Leu
            500                 505                 510

Thr Ile Ala Thr Pro Leu Leu Val Ile Phe Ser Pro Val Leu Val Pro
        515                 520                 525

Ala Val Ile Thr Ile Phe Leu Leu Gly Ala Gly Phe Leu Ala Ser Gly
    530                 535                 540

Gly Phe Gly Val Ala Ala Leu Ser Val Leu Ser Trp Ile Tyr Arg Tyr
545                 550                 555                 560

Leu Thr Gly Lys His Pro Pro Gly Ala Asp Gln Leu Glu Ser Ala Lys
                565                 570                 575

Thr Lys Leu Ala Ser Lys Ala Arg Glu Met Lys Asp Arg Ala Glu Gln
            580                 585                 590

Phe Ser Gln Gln Pro Val Ala Gly Ser Gln Thr Ser Ser Thr Pro Ser
            595                 600                 605

Ser Trp His Met Met Ala Glu His Tyr Gly Gln Gln Gln Gln Thr Arg
        610                 615                 620

Ala Pro His Leu Gln Leu Gln Pro Arg Ala Gln Arg Val Val Lys Ala
625                 630                 635                 640

Ala Thr Ala Val Thr Ala Gly Gly Ser Leu Leu Val Leu Ser Gly Leu
                645                 650                 655

Thr Leu Ala Gly Thr Val Ile Ala Leu Thr Ile Ala Thr Pro Leu Leu
            660                 665                 670

Val Ile Phe Ser Pro Val Leu Val Pro Ala Val Ile Thr Ile Phe Leu
        675                 680                 685

Leu Gly Ala Gly Phe Leu Ala Ser Gly Gly Phe Gly Val Ala Ala Leu
    690                 695                 700

Ser Val Leu Ser Trp Ile Tyr Arg Tyr Leu Thr Gly Lys His Pro Pro
705                 710                 715                 720

Gly Ala Asp Gln Leu Glu Ser Ala Lys Thr Lys Leu Ala Ser Lys Ala
                725                 730                 735

Arg Glu Met Lys Asp Arg Ala Glu Gln Phe Ser Gln Gln Pro Val Ala
            740                 745                 750

Gly Ser Gln Thr Ser Ile Asp Gln Val Asn Val His Met Ala Glu
            755                 760                 765

His Tyr Gly Gln Gln Gln Gln Thr Arg Ala Pro His Leu Gln Leu Gln
    770                 775                 780

Pro Arg Ala Gln Arg Val Val Lys Ala Ala Thr Ala Val Thr Ala Gly
785                 790                 795                 800

Gly Ser Leu Leu Val Leu Ser Gly Leu Thr Leu Ala Gly Thr Val Ile
                805                 810                 815

Ala Leu Thr Ile Ala Thr Pro Leu Leu Val Ile Phe Ser Pro Val Leu
            820                 825                 830

Val Pro Ala Val Ile Thr Ile Phe Leu Leu Gly Ala Gly Phe Leu Ala
        835                 840                 845

Ser Gly Gly Phe Gly Val Ala Ala Leu Ser Val Leu Ser Trp Ile Tyr
    850                 855                 860

Arg Tyr Leu Thr Gly Lys His Pro Pro Gly Ala Asp Gln Leu Glu Ser
865                 870                 875                 880
```

```
Ala Lys Thr Lys Leu Ala Ser Lys Ala Arg Glu Met Lys Asp Arg Ala
            885                 890                 895

Glu Gln Phe Ser Gln Gln Pro Val Ala Gly Ser Gln Thr Ser Pro Trp
            900                 905                 910

Leu Glu

<210> SEQ ID NO 82
<211> LENGTH: 441
<212> TYPE: PRT
<213> ORGANISM: Artificial Sequence
<220> FEATURE:
<223> OTHER INFORMATION: Synthetic sequence

<400> SEQUENCE: 82

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
            20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
    50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
            115                 120                 125

Asp Arg Ala Glu Gln Phe Ser Gln Gln Pro Val Gly Gly Gly Ser
130                 135                 140

Gly Gly Gly Gly Ser Met Ala Glu His Tyr Gly Gln Gln Gln Thr
145                 150                 155                 160

Arg Ala Pro His Leu Gln Leu Gln Pro Arg Ala Gln Arg Val Val Lys
            165                 170                 175

Ala Ala Thr Ala Val Thr Ala Gly Gly Ser Leu Leu Val Leu Ser Gly
            180                 185                 190

Leu Thr Leu Ala Gly Thr Val Ile Ala Leu Thr Ile Ala Thr Pro Leu
            195                 200                 205

Leu Val Ile Phe Ser Pro Val Leu Val Pro Ala Val Ile Thr Ile Phe
            210                 215                 220

Leu Leu Gly Ala Gly Phe Leu Ala Ser Gly Gly Phe Gly Val Ala Ala
225                 230                 235                 240

Leu Ser Val Leu Ser Trp Ile Tyr Arg Tyr Leu Thr Gly Lys His Pro
            245                 250                 255

Pro Gly Ala Asp Gln Leu Glu Ser Ala Lys Thr Lys Leu Ala Ser Lys
            260                 265                 270

Ala Arg Glu Met Lys Asp Arg Ala Glu Gln Phe Ser Gln Gln Pro Val
            275                 280                 285

Gly Gly Gly Gly Ser Gly Gly Gly Ser Met Ala Glu His Tyr Gly
            290                 295                 300

Gln Gln Gln Thr Arg Ala Pro His Leu Gln Leu Gln Pro Arg Ala
305                 310                 315                 320

Gln Arg Val Val Lys Ala Ala Thr Ala Val Thr Ala Gly Gly Ser Leu
```

```
                          325                 330                 335
Leu Val Leu Ser Gly Leu Thr Leu Ala Gly Thr Val Ile Ala Leu Thr
                340                 345                 350

Ile Ala Thr Pro Leu Leu Val Ile Phe Ser Pro Val Leu Val Pro Ala
            355                 360                 365

Val Ile Thr Ile Phe Leu Leu Gly Ala Gly Phe Leu Ala Ser Gly Gly
        370                 375                 380

Phe Gly Val Ala Ala Leu Ser Val Leu Ser Trp Ile Tyr Arg Tyr Leu
385                 390                 395                 400

Thr Gly Lys His Pro Pro Gly Ala Asp Gln Leu Glu Ser Ala Lys Thr
                405                 410                 415

Lys Leu Ala Ser Lys Ala Arg Glu Met Lys Asp Arg Ala Glu Gln Phe
            420                 425                 430

Ser Gln Gln Pro Val Pro Trp Leu Glu
                435                 440

<210> SEQ ID NO 83
<211> LENGTH: 441
<212> TYPE: PRT
<213> ORGANISM: Artificial Sequence
<220> FEATURE:
<223> OTHER INFORMATION: Synthetic sequence

<400> SEQUENCE: 83

Met Ala Glu His Tyr Gly Gln Gln Gln Thr Arg Ala Pro His Leu
1               5                   10                  15

Gln Leu Gln Pro Arg Ala Gln Arg Val Val Lys Ala Ala Thr Ala Val
                20                  25                  30

Thr Ala Gly Gly Ser Leu Leu Val Leu Ser Gly Leu Thr Leu Ala Gly
            35                  40                  45

Thr Val Ile Ala Leu Thr Ile Ala Thr Pro Leu Leu Val Ile Phe Ser
        50                  55                  60

Pro Val Leu Val Pro Ala Val Ile Thr Ile Phe Leu Leu Gly Ala Gly
65                  70                  75                  80

Phe Leu Ala Ser Gly Gly Phe Gly Val Ala Ala Leu Ser Val Leu Ser
                85                  90                  95

Trp Ile Tyr Arg Tyr Leu Thr Gly Lys His Pro Pro Gly Ala Asp Gln
            100                 105                 110

Leu Glu Ser Ala Lys Thr Lys Leu Ala Ser Lys Ala Arg Glu Met Lys
        115                 120                 125

Asp Arg Ala Glu Gln Phe Ser Gln Gln Pro Val Gly Gly Gly Gly Ser
130                 135                 140

Gly Gly Gly Gly Ser Met Ala Glu His Tyr Gly Gln Gln Gln Thr
145                 150                 155                 160

Arg Ala Pro His Leu Gln Leu Gln Pro Arg Ala Gln Arg Val Val Lys
                165                 170                 175

Ala Ala Thr Ala Val Thr Ala Gly Gly Ser Leu Leu Val Leu Ser Gly
            180                 185                 190

Leu Thr Leu Ala Gly Thr Val Ile Ala Leu Thr Ile Ala Thr Pro Leu
        195                 200                 205

Leu Val Ile Phe Ser Pro Val Leu Val Pro Ala Val Ile Thr Ile Phe
210                 215                 220

Leu Leu Gly Ala Gly Phe Leu Ala Ser Gly Gly Phe Gly Val Ala Ala
225                 230                 235                 240

Leu Ser Val Leu Ser Trp Ile Tyr Arg Tyr Leu Thr Gly Lys His Pro
                245                 250                 255
```

-continued

```
Pro Gly Ala Asp Gln Leu Glu Ser Ala Lys Thr Lys Leu Ala Ser Lys
            260                 265                 270

Ala Arg Glu Met Lys Asp Arg Ala Glu Gln Phe Ser Gln Gln Pro Val
            275                 280                 285

Gly Gly Gly Gly Ser Gly Gly Gly Ser Met Ala Glu His Tyr Gly
        290                 295                 300

Gln Gln Gln Gln Thr Arg Ala Pro His Leu Gln Leu Gln Pro Arg Ala
305                 310                 315                 320

Gln Arg Val Val Lys Ala Ala Thr Ala Val Thr Ala Gly Gly Ser Leu
                325                 330                 335

Leu Val Leu Ser Gly Leu Thr Leu Ala Gly Thr Val Ile Ala Leu Thr
            340                 345                 350

Ile Ala Thr Pro Leu Leu Val Ile Phe Ser Pro Val Leu Val Pro Ala
            355                 360                 365

Val Ile Thr Ile Phe Leu Leu Gly Ala Gly Phe Leu Ala Ser Gly Gly
        370                 375                 380

Phe Gly Val Ala Ala Leu Ser Val Leu Ser Trp Ile Tyr Arg Tyr Leu
385                 390                 395                 400

Thr Gly Lys His Pro Pro Gly Ala Asp Gln Leu Glu Ser Ala Lys Thr
                405                 410                 415

Lys Leu Ala Ser Lys Ala Arg Glu Met Lys Asp Arg Ala Glu Gln Phe
            420                 425                 430

Ser Gln Gln Pro Val Pro Trp Leu Glu
        435                 440

<210> SEQ ID NO 84
<211> LENGTH: 500
<212> TYPE: DNA
<213> ORGANISM: Trifolium repens

<400> SEQUENCE: 84
caacaaayaa cwcaccgtca agaaactgct acctacccat caacccawwa cattcgtaaa      60
gatgtttacg aaaatgttaa ctatcccggc caacgcggtc gttataacga ccgctataat     120
gatagtggtc gttatgatgg tggtattgcc tcctttttgt cagagagaag tcctccagcc     180
tctcaaatcc tcgctaccgt tggaggattt ttcataggtg gtactctatt tttattagct     240
agcatttcat ttatcgccag tcttattgga ttggcgataa tgacaccact ttttatcctt     300
tttagcccgg ttttagtccc tgctgccctc actataggc tagcagtggc tggaatattg     360
acagcagatg cttgcgggtt gacggggctt atgtcgttgt cgtggaccgt gaaatatgtt     420
agggatttac aagcagtagt gcccgaacaa atggattcga tgaagggacg tgtcgcggat     480
gtcgcgagtt atgttggaca                                                 500
```

POLYOLEOSINS

The present invention relates to constructs including one or more nucleic acids encoding two or more oleosin repeat units, and methods of use thereof. The present invention also relates to recombinant polypeptides including two or more oleosin repeat units, and methods of use thereof.

Triacylglycerol

Most plants synthesise and store significant amounts of triacylglycerol (TAG) only in developing embryos and pollen cells where it is subsequently utilised to provide catabolizable energy during germination and pollen tube growth. Dicotyledonous plants can accumulate up to approximately 60% of their seed weight as TAG. Ordinarily, this level is considerably lower in the monocotyledonous seeds where the main form of energy storage is carbohydrates (e.g., starch).

The only committed step in TAG biosynthesis is the last one, i.e., the addition of a third fatty acid to an existing diacylglycerol, thus generating TAG. In plants this step is performed by one of three enzymes including: acyl CoA: diacylglycerol acyltransferase (DGAT1); an unrelated acyl CoA: diacylglycerol acyl transferase (DGAT2); and phospholipid: diacylglycerol acyltransferase (PDAT) (Bouvier-Nave et al., 2000; Dahlqvist et al., 2000; Lardizabal et al., 2001; Zou et al., 1999).

Oleosin

Oleosins are specific plant proteins usually found only in seeds and pollen. Their function is to stop oil bodies coalescing during seed and pollen dehiscence. In nature, TAG produced in seeds and pollen form micelles encapsulated by a spherical phospholipid monolayer and one or several species of oleosin proteins. Oil bodies in fruit tissues (such as olives and avocados) do not contain oleosins.

Figure 2:
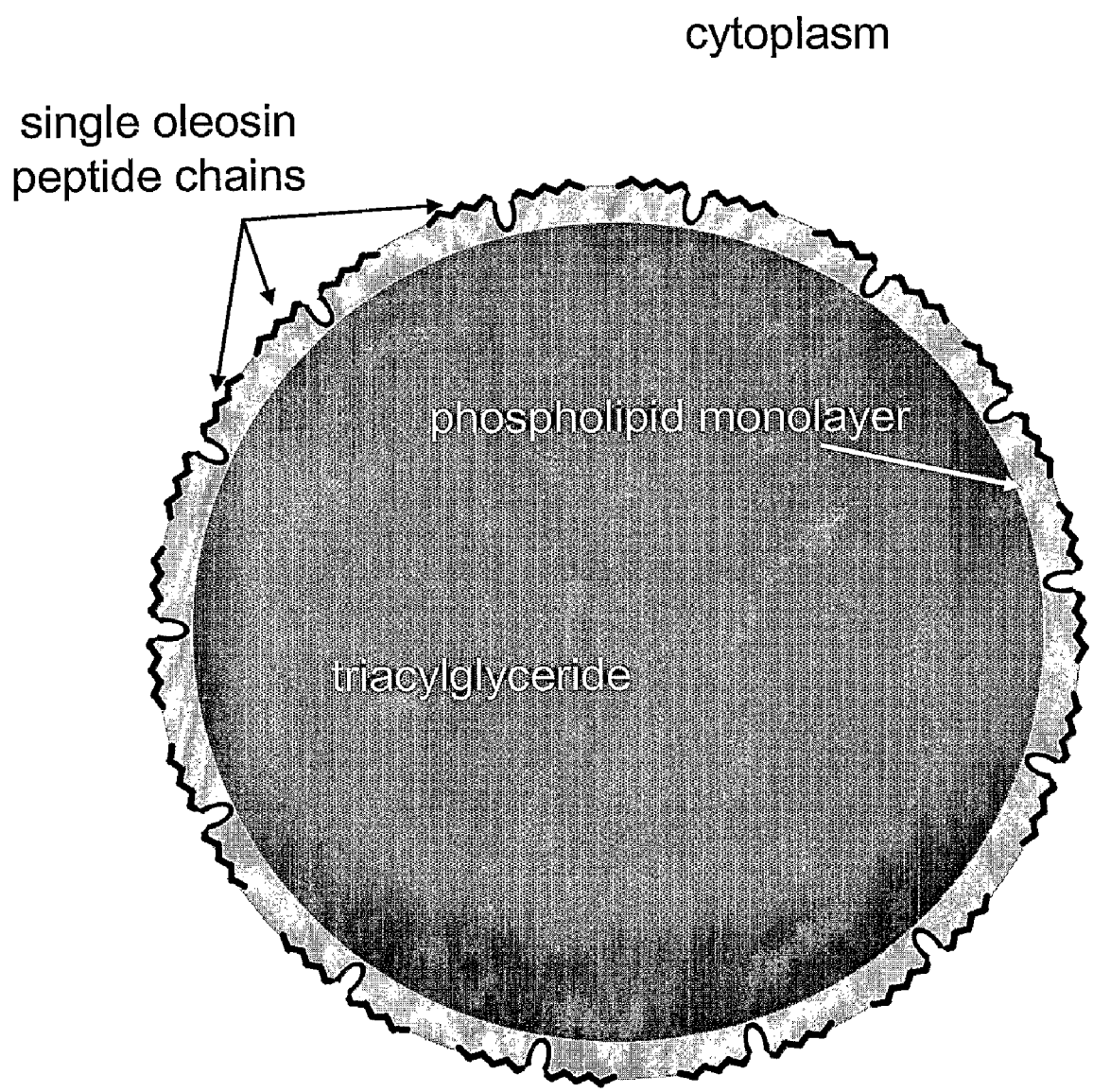

The physiochemical properties of the major oleosins is relatively conserved between plants and is characterised by the following:
- 15-25 kDa protein corresponding to approximately 140-230 amino acid residues.
- The protein sequence can be divided almost equally along its length into 4 parts that correspond to a N-terminal hydrophilic region; two centre hydrophobic regions (joined by a proline knot or knob) and a C-terminal hydrophilic region.
- The topology of oleosin is attributed to its physiochemical properties, which includes a folded hydrophobic core flanked by hydrophilic domains (FIG. 1). This arrangement confers an amphipathic nature to oleosin resulting in the hydrophobic domain being embedded in the phospholipid monolayer (Tzen et al., 1992) while the flanking hydrophilic domains are exposed to the aqueous environment of the cytoplasm (FIG. 2).

Oil Bodies

An oil body that is produced in seed or pollen consists of a droplet of TAG surrounded by a monolayer of phospholipid where the hydrophobic acyl moieties of the phospholipids interact with the encapsulated TAG and the hydrophilic head groups face the cytoplasm. Oil bodies are naturally produced in the seeds and pollen of many plants. Oil bodies can also be generated artificially by combining oleosins, triacylglycerides and phospholipids (Peng et al., 2004).

The outside of the oil body is coated with oleosins which are orientated with their central hydrophobic amino acid domains protruding through the phospholipid monolayer and into the TAG core of the oil body (FIGS. 2-6).

The size of the oil body may be regulated by oleosin imparting a defined curvature; the curvature is dependent on the oleosin::oil ratio as well as the type of oleosin and oil.

Biohydrogenation

It has been demonstrated that the lipid profile of ruminant animal feed in turn influences the lipid profile of meat and dairy products (Demeyer and Doreau, 1999). Different plants have different lipid profiles; by selectively feeding animals only plants with the desired lipid profile it is possible to positively influence the lipid profile of downstream meat and dairy products. In ruminants the final lipid make up of the meat and milk is not only influenced by the dietary lipids but is also heavily influenced by biohydrogenation. Biohydrogenation is the hydrogenation of non-reduced compounds (such as unsaturated fats) by the biota present in the rumen.

Emulsions

Emulsions are produced when one or more liquids that are immiscible (usually due to different polarities and thus different hydrophobicities) in another liquid are uniformly suspended within that liquid, for example when oil droplets are dispersed uniformly in water or water droplets dispersed uniformly in oil. Generation of a relatively stable emulsion requires the use of an emulsifier, which lowers the interfacial tension between the liquids. The stability of an emulsion is generally a measure of what conditions and for how long the uniform dispersion persists. Emulsifiers are commonly used in the food and cosmetic industry; as such the emulsifiers need to have high emulsion stability as well as be safe for consumption and topical application.

It is an object of the present invention to overcome, or at least alleviate, one or more of the difficulties or deficiencies associated with the prior art.

In one aspect the present invention provides a construct including one or more nucleic acids encoding two or more oleosin repeat units. For expression in vegetative plant tissue preferably the construct further includes a nucleic acid encoding a diacylglycerol acryltransferase.

The term "oleosin" as used herein includes any functionally active plant oleosin, including functionally active fragments and variants thereof (e.g., L-oleosin, H-oleosin, steroleosin and caoleosin).

In a preferred embodiment, the oleosin repeat unit may be from white clover or sesame seed, or may be a synthetic or recombinant version of an oleosin repeat unit from white clover or sesame seed.

While Applicants have exemplified the invention using white clover and sesame seed oleosins, the invention is not limited thereto and any functionally active plant oleosin sequence may be used in the constructs of the present invention. The oleosin sequence may be naturally occurring, recombinant or synthetic.

By "repeat units" is meant multiple copies of nucleotide sequences encoding oleosin within a single polynucleotide, or multiple copies of amino acid sequences encoding oleosin within a single polypeptide, which may or may not contain intervening nucleotide or amino acid sequences. The repeat units may be tandem repeats. The repeat units may be homo- or hetero-repeats (homo or heteromeric).

The oleosin repeat units may be linked either directly, for example by direct fusion of the repeats, or by using linking sequences.

In a preferred embodiment of this aspect of the invention linker sequences may be included between the oleosin repeats to facilitate rotation of the oleosin hydrophilic domains relative to each other to form the correct topology. Such linker sequences also facilitate recombinatorial subcloning of sequences encoding desired peptides in between the oleosin repeats, and also facilitate chemical or enzymatic cleavage, for example to destroy the multimeric oleosin chain and/or release the desired peptide from the multimeric oleosin chain.

Thus, the construct may further include nucleotide sequences encoding linking sequences between two or more of the oleosin repeat units. The linking sequences may be short sequences, for example sequences that allow flexibility between the repeat units (act as a flexible hinge) or induce a directional change (act as a directional induction hinge) between the repeats, enable degradation between the oleosin repeat units, for example by peptidases, unrelated peptide sequences that may have bioactive properties, or sites for enzymatic cleavage and or subsequent fusion.

More particularly, the linking nucleotide sequence(s) between the oleosin repeat units may encode the native N- and C-termini of the respective repeats, sequences that code for comparatively short peptides that allow flexibility between the repeats, comparatively short peptides with amino acid residues that induce a directional change in the chain (for example proline), sequences that enable the future targeted cloning of additional sequences between the repeats, sequences that encode for specific targeted peptidase degradation, sequences that encode for bioactive peptides, and/or sequences encoding sites for specific enzymatic cleavage and subsequent fusion, e.g., modified self splicing intein and polymerisation cyclisation (Williams et al., 2005).

The multiple oleosin nucleotide sequences may code for the same oleosin peptide sequence or code for different oleosin peptide sequences. The multiple oleosin nucleotide sequences may code for the same oleosin peptide sequence but use alternate codons in the nucleotide sequence where applicable. This enables the construct to also be used in prokaryotic expression systems that are not non-recombinant minus (rec⁻). It also enables the use of oleosins that contain different affinities for the oil body.

In a particularly preferred embodiment of the present invention, the nucleic acid encoding an oleosin repeat unit includes a nucleotide sequence selected from the group consisting of sequences shown in FIGS. 13, 15, 17, 19, 21, 23, 25, 27, 31, 34, 70, 72-77 and 97-106 hereto, and functionally active fragments and variants thereof.

The construct of the present invention includes one or more nucleic acids encoding two or more oleosin repeats, preferably between two or three and twenty oleosin repeats, more preferably between two or three and ten oleosin repeats, most preferably between two or three and five or six oleosin repeats.

The diacylglycerol acyltransferase may be of any suitable type, including functionally active fragments and variants thereof. In a preferred form, the diacylglycerol acyltransferase is selected from the group consisting of DGAT1, DGAT2 and PDAT.

Nucleic acids according to the invention may be full-length genes or part thereof, and are also referred to as "nucleic acid fragments" and "nucleotide sequences" in this specification.

The nucleic acid may be of any suitable type and includes DNA (such as cDNA or genomic DNA) and RNA (such as mRNA) that is single- or double-stranded, optionally containing synthetic, non-natural or altered nucleotide bases, and combinations thereof.

By "functionally active" in respect of a nucleotide sequence is meant that the fragment or variant (such as an analogue, derivative or mutant) is capable of modifying lipids in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the oleosin repeat sequences exemplified herein, more preferably at least approximately 90% identity, most preferably at least approximately 95% identity. Such functionally active variants and fragments include, for example, those having nucleic acid changes that result in conservative amino acid substitutions of one or more residues in the corresponding amino acid sequence. For example, the nucleic acid sequence may be modified to enhance expression without altering the amino acid sequence. Preferably the fragment has a size of at least 30 nucleotides, more preferably at least 45 nucleotides, most preferably at least 60 nucleotides.

By "functionally active" in the context of a polypeptide is meant that the fragment or variant has one or more of the biological properties of oleosin polypeptides. Additions, deletions, substitutions and derivatizations of one or more of the amino acids are contemplated so long as the modifications do not result in loss of functional activity of the fragment or variant. Preferably the functionally active fragment or variant has at least approximately 60% identity to the relevant part of the oleosin polypeptides exemplified herein, more preferably at least approximately 80% identity, most preferably at least approximately 90% identity. Such functionally active variants and fragments include, for example, those having conservative amino acid substitutions of one or more residues in the corresponding amino acid sequence. Preferably the fragment has a size of at least 10 amino acids, more preferably at least 15 amino acids, most preferably at least 20 amino acids.

By "operatively linked" is meant that a regulatory element is capable of causing expression of said nucleic acid in a cell and/or a terminator is capable of terminating expression of said nucleic acid in a cell. Preferably, said regulatory element is upstream of said nucleic acid and said terminator is downstream of said nucleic acid.

By "an effective amount" is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the relevant disclosure of which is incorporated herein by reference.

It will also be understood that the term "comprises" (or its grammatical variants) as used in this specification is equivalent to the term "includes" and should not be taken as excluding the presence of other elements or features.

The construct of the present invention may be a vector. In a preferred embodiment of this aspect of the invention, the vector may include at least one regulatory element, such as a promoter, operatively linked to the nucleic acid. The vector may also include an operatively linked terminator.

The vector may be of any suitable type and may be viral or non-viral. The vector may be an expression vector. Such vectors include chromosomal, non-chromosomal and synthetic nucleic acid sequences, eg. derivatives of plant viruses; bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, or integrative or viable in the relevant cell.

The regulatory element and terminator may be of any suitable type and may be endogenous to the target cell or may be exogenous, provided that they are functional in the target cell.

Preferably one of the regulatory elements is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the cell to be transformed. Particularly suitable constitutive promoters for use in plants include the Cauliflower Mosaic Virus 35S (CaMV 35S) promoter, the maize Ubiquitin promoter, and the rice Actin promoter. In a preferred embodiment the promoter may be chosen to enable the expression of oleosin in the desired organ, tissue and stage of development.

A variety of terminators which may be employed in the vectors of the present invention are also well known to those skilled in the art. The terminator may be from the same gene as the promoter sequence or a different gene. Particularly suitable terminators for use in plants are polyadenylation signals, such as the CaMV 35S polyA and other terminators from the nopaline synthase (nos) and the octopine synthase (ocs) genes.

The vector, in addition to the regulatory element, the nucleic acid and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes (such as the neomycin phosphotransferase (npt2) gene, the hygromycin phosphotransferase (hph) gene, the phosphinothricin acetyltransferase (bar or pat) gene), and reporter genes (such as green fluorescence protein (GFP), beta-glucuronidase (GUS) gene (gusA)). The vector may also contain a ribosome binding site for translation initiation. The vector may also include appropriate sequences for facilitating correct transcription, amplifying expression, increasing mRNA stability, enhancing protein translation or facilitating accurate translation.

As an alternative to use of a selectable marker gene to provide a phenotypic trait for selection of transformed host cells, the presence of the construct or vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the construct or vector are operatively linked; so as to result in expression of said nucleic acid. Techniques for operatively linking the components of the construct or vector of the present invention are well known to those skilled in the art. Such techniques include the use of linkers, such as synthetic linkers, for example including one or more restriction enzyme sites.

The constructs and vectors of the present invention may be incorporated into a variety of plants, including monocotyledons (such as grasses from the genera *Lolium, Festuca, Paspalum, Pennisetum, Panicum* and other forage and turf-grasses, corn, rice, sugarcane, oat, wheat and barley) dicotyledons (such as *arabidopsis*, tobacco, soybean, canola, cotton, potato, chickpea, medics, white clover, red clover, subterranean clover, alfalfa, eucalyptus, poplar, hybrid aspen, and gymnosperms (pine tree)). In a preferred embodiment, the constructs and vectors are used to transform commercial crops that are fed directly to animals.

The constructs and vectors of the present invention may also be incorporated into other eukaryotic expression systems, including yeast, insect and mammalian cells. Thus, repeat oleosins, such as multimeric tandem repeat oleosins, (either homo or hetero repeats) may be generated by recombinant protein expression in eukaryotic expression systems and subsequently purified as functional recombinant oil bodies having the additional properties afforded by the presence of repeat oleosins.

The constructs and vectors of the present invention may also be incorporated into prokaryotic expression systems. Thus, repeat oleosins, such as multimeric tandem repeat oleosins, (either homo or hetero repeats) may be generated by recombinant protein expression in bacteria such as *Escherichia coli* and subsequently purified and recombined with for example, phospholipids and triacyl glyceride to generate functional recombinant oil bodies with the additional properties afforded by the presence of repeat oleosins.

The constructs and vectors of the present invention may be constructed by any suitable method, including:

Amplification and subsequent cloning of oleosin sequences, for example using PCR with primers designed to publicly available oleosin sequences. For plant based expression clones these may include oleosins amplified from genomic DNA that may also contain introns depending on the clone. For prokaryotic and non-plant eukaryotic expression systems the source of the template for PCR preferably comes from cDNA which will not contain plant introns.

Restriction digestion and ligation of oleosin clones that contain suitable inframe restriction sites at both N and C termini. Restriction sites may be added by techniques such as PCR or ligation of sticky ends.

Engineering different restriction sites (that correspond to a cloning polylinker sequence) onto the ends of individual oleosin clones, then building up the multimer by a series of digestions and ligations by firstly ligating the polylinker to the 3' end of the first oleosin clone.

Chemically synthesising the complete construct.

A combination of the above.

Techniques for incorporating the constructs and vectors of the present invention into cells (for example by transduction, transfection or transformation) are well known to those skilled in the art. For plant cells, techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of cell to be transformed.

Cells incorporating the constructs and vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a construct or vector of the present invention.

The plant cell, plant, plant seed or other plant part may be from any suitable species, including monocotyledons, dicotyledons and gymnosperms. In a preferred embodiment the plant cell, plant, plant seed or other plant part is from a commercial plant that is normally fed directly to animals.

The present invention also provides a plant, plant seed or other plant part derived from a plant cell of the present invention and including a construct or vector of the present invention. The present invention also provides a plant, plant seed or other plant part derived from a plant of the present invention and including a construct or vector of the present invention.

The present invention also provides a eukaryotic cell, such as a yeast, insect or mammalian cell, including, eg. transformed with, a construct or vector of the present invention.

The present invention also provides a prokaryotic cell, eg. a bacteria such E. coli, including, eg. transformed with, a construct or vector of the present invention.

The present invention also provides a method of producing repeat oleosins in a plant, said method including introducing into said plant a construct or vector of the present invention. By "repeat oleosin" is meant a recombinant polypeptide including two or more oleosin repeat units.

The present invention also provides a method of producing repeat oleosins in a eukaryotic cell, said method including introducing into said eukaryotic cell a construct or vector of the present invention. The method may include the further step of partially or substantially purifying said repeat oleosin from said cell. In a preferred form the repeat oleosin may be partially or substantially purified by the generation of oil bodies. The oil bodies may be produced within the cell, e.g. plant seed.

The present invention also provides a method of producing repeat oleosins in a prokaryotic cell, said method including introducing into said prokaryotic cell a construct or vector of the present invention. The method may include the further steps of partially or substantially purifying said repeat oleosin from said cell. In a preferred form the repeat oleosin may be partially or substantially purified by the generation of oil bodies. The oil bodies may be produced artificially using recombinant oleosin repeats from other expression systems such as $E.\ coli$.

The oleosin protein repeats may be purified using affinity chromatography, such as a fused Histidine tag and $Ni^{2+}$ resin purification.

The present invention also provides a partially or substantially purified and/or recombinant polypeptide including two or more oleosin repeat units.

The polypeptide may be produced by expression of a construct or vector according to the present invention.

The present invention also provides a lipid encapsulated by a polypeptide according to the present invention.

The oleosin repeat units may be of any suitable type, including functionally active fragments and variants thereof. For example, the oleosin repeat units may be selected from the group consisting of L-oleosin, H-oleosin, steroleosin and caoleosin and functionally active fragments and variants thereof. The oleosin repeats may be tandem repeats. The oleosin repeats may be multimeric tandem repeats. The oleosin repeats may be homo- or hetero-repeats.

In a preferred embodiment, the oleosin repeat unit may be from white clover or sesame seed, or may be a synthetic or recombinant version of an oleosin repeat unit from white clover or sesame seed. However, the invention is not limited thereto and the polypeptide of the present invention may include any functionally active plant oleosin sequence.

The oleosin repeat units may be linked either directly or by linking sequences. Thus, the polypeptide may further include linking sequences between two or more of the oleosin repeat units. The linking sequences may allow flexibility, induce a directional change or enable degradation between the oleosin repeat units.

In a particularly preferred embodiment of the present invention, the oleosin repeat unit includes an amino acid sequence selected from the group consisting of the sequences shown in FIGS. 69, 70, 78-83 and 107-116 hereto, and functionally active fragments and variants thereof.

In another particularly preferred embodiment of the present invention, the oleosin repeat unit is encoded by a nucleotide sequence selected from the group consisting of sequences shown in FIGS. 13, 15, 17, 19, 21, 23, 25, 27, 31, 34, 70, 72-77 and 97-106 hereto, and functionally active fragments and variants thereof.

The recombinant polypeptide of the present invention includes two or more oleosin repeats, preferably between two or three and twenty oleosin repeats, more preferably between two or three and ten oleosin repeats, most preferably between two or three and five or six oleosin repeats.

Applicants have found that that repeat oleosins, such as recombinant multimeric tandem repeat oleosins, (either homo or hetero repeats) may be expressed in the seeds of plants which would mean that the extract would contain a mixture of native oleosins along with the repeat oleosins. If a single species of oleosin multiples are required the repeat oleosins may be expressed in plants in which native oleosin expression has been suppressed, e.g., by mutagenesis, gene silencing or natural selection.

In addition, the repeat oleosins may be coexpressed with a diacylglyerol acyltransferase such as DGAT1 or DGAT2 or PDAT, in plant vegetative organs allowing the generation of emulsion complexes containing substantially only the desired species of oleosin (since oleosins are not normally expressed in the vegetative portions of plants). Thus, co-expression of DGAT1, DGAT2 or PDAT with polyoleosin in the vegetative portions of plants produces oil bodies encapsulated by the polyoleosin.

Furthermore, the repeat oleosins may be expressed and purified from bacteria, such as $E.\ coli$, since oleosins are not naturally present in $E.\ coli$. Expression of repeat oleosins in some bacteria may require modification of the nucleotide sequence to avoid recombination events occurring in rec⁻ strains.

Applicants have found that use of a series of oleosin repeats generates a recombinant protein with exploitable properties. Linking oleosin units to give homo or hetero multimeric repeats reduces the number of N-termini available for the initiation amino peptidase degradation in the rumen and/or stomach as well as altering the physiochemical characteristics (e.g., the hydrophobic interactions) of the protein and thus broadening the range of emulsification properties. In particular, this has a number of exploitable benefits, including:

Generating a simple method for producing foodstuffs such as meat and milk with health promoting lipid profiles by reducing the degree of biohydrogenation.

Allowing for the delivery of fused bioactive peptides to be ingested and delivered intact to the site of absorption.

Providing a rapid mechanism to alter the emulsion properties of reconstituted feeds, pharmaceuticals, beauty products etc.

Allowing for the delivery of lipid soluble active compounds to be delivered and released in a controlled fashion by topical application.

Allowing for the delivery of lipid soluble bioactive compounds to be ingested and delivered intact to the site of absorption.

Applicants have found that by the use of repeat oleosins, such as recombinant multimeric tandem repeat oleosins (either homo or hetero repeats) the stability of an oil body may be regulated. The incorporation of amino acid residues between the oleosin repeats may be desirable to allow sufficient flex between the repeats, to influence the curvature of the oil body, to control the direction of the repeats relative to each other, to incorporate bioactive peptides, to provide sites for directed proteolytic degradation, or to provide sites for specific enzymatic cleavage and subsequent fusion, e.g., modified self splicing intein and polymerisation cyclisation (Williams et al., 2005).

Thus, the present invention also provides a mechanism for the delivery of bioactive peptides that may be fused between the repeats or at the end of the repeats.

The present invention also provides a mechanism for allowing free rotation between the repeats or for directing the orientation of the repeats relative to each other by incorporating linking sequences between the repeats.

The size of the suspended particles contributes to the stability of the suspension and the amount of material that may be suspended and this allows the emulsification properties to be tailored for the application. By altering the number of oleosin repeats in a peptide sequence (preferably using recombinant technologies) oleosins with different emulsification properties may be generated. These may confer enhanced stabilities in terms of, for example, temperature stability, pH stability and/or altered particle size. In turn this broadens the number of compounds that may be emulsified, as well as expanding the applications of the emulsifications, for example, by extending their stability and the amount of compounds that may be emulsified.

In a further aspect the present invention provides a method of manipulating lipids in a plant, said method including introducing into said plant a construct including one or more nucleic acids encoding two or more oleosin repeat units.

Manipulation of lipids includes, but is not limited to, alteration of emulsification properties, including stability of suspension and amount of material that may be suspended, alteration of physiochemical properties, including hydrophobic interactions, and altering the degree of biohydrogenation.

In a preferred embodiment, the present invention provides a method of altering stability of an oil body in a plant, said method including modifying an oleosin in said plant to include two or more oleosin repeat units. This may in turn alter the ratio of oleosin to oil in said oil body.

Reduction of Biohydrogenation

In ruminants, biohydrogenation is the hydrogenation of non-reduced compounds (such as unsaturated fats) with hydrogen from rumen biota. Applicants have engineered oleosin to generate oil bodies containing unsaturated fats in the TAG (surrounded by a phospholipid monolayer) encapsulated by the oleosin repeats of the present invention. This may be less susceptible to the process of biohydrogenation in the rumen before it passes into the intestine for absorption. While applicants do not wish to be restricted by theory, it is thought that a chain of oleosin units would have fewer N-termini per unit of oleosin available for amino peptidase degradation (the main form of protein degradation in the rumen). In turn this would reduce the degree of oleosin degradation and therefore reduce the loss of oil body integrity and subsequently reduce the degree of biohydrogenation of the unsaturated fats in the TAG. In turn this would lead to an increase in the level of unsaturated fats reaching the site of adsorption in the intestine. In turn this would lead to a change in the fatty acid profile of foodstuffs such as milk and meat products from the animal eating such a product.

Thus, the present invention provides a method of altering biohydrogenation of a lipid, said method including encapsulating said lipid in a recombinant polypeptide including two or more oleosin repeat units.

The present invention also provides a method of protecting unsaturated lipids from biohydrogenation, said method including incorporating said unsaturated lipids into an oil body including a recombinant polypeptide including two or more oleosin repeat units.

Delivery of Fused Bioactive Peptides Orally and Topically

Applicants have engineered restriction sites between the oleosin repeats to enable insertion of a frame coding sequence (such as those encoding bioactive peptides that would normally be susceptible to degradation in the intestines). While applicants do not wish to be restricted by theory it is thought that a chain of oleosin units would have enhanced stability in the digestive acid conditions of the stomach as well as fewer N-termini per unit of oleosin available for amino peptidase degradation (the main form of protein degradation in the rumen). Thus a peptide inserted between multimeric oleosin tandem repeats is afforded a degree of protection from degradation by digestive acidic conditions and aminopeptidases. In turn this would reduce the degree of active peptide degradation in the stomach and rumen. In turn this would lead to higher levels of active peptides reaching the site of adsorption in the intestine. In turn this would lead to an increased absorption of bioactive peptides by the organism. The degree of protection may be altered by the position of the bioactive peptide in the oleosin chain, the nature of the oleosins in the chain, and/or the amino acid sequences joining the oleosins and bioactive peptides.

Thus, the present invention provides a method of delivering a bioactive peptide, to animals including humans, said method including inserting said peptide at the N- or C-terminus of a series of two or more oleosin repeat units or between two or more oleosin repeat units to produce a recombinant polypeptide and administering said recombinant polypeptide to said animal.

Preferably, the bioactive peptides are delivered orally or topically. The bioactive peptides may be delivered to the intestine. The bioactive peptides may be delivered by timed release, eg. sustained release or delayed release.

The present invention also provides a partially or substantially purified or recombinant polypeptide including two or more oleosin repeat units and further including one or more bioactive peptides.

The bioactive peptide may be inserted at the N- or C-terminus of a series of two or more oleosin repeat units or between two or more oleosin repeat units.

The recombinant polypeptide may be produced by expression of a construct or vector according to the present invention.

Thus, the present invention also provides a construct including one or more nucleic acids encoding two or more oleosin repeat units and further including one or more nucleic acids encoding bioactive peptides.

Delivery of Encapsulated Bioactive Peptides and Other Compounds Orally and Topically Polyoleosin provides a mechanism for the development and delivery of compounds such as therapeutic and prophylactic drugs, including drugs for internal parasites in humans and animals and bioactive peptides; and organisms such as health promoting bacteria (e.g., *lactobacillus*) by encapsulation of the compound or organism within the oil body. In particular, it provides a mechanism for delivering bioactive peptides through the rumen and into the digestive system, substantially without loss of bioactivity. This issue currently represents a major hurdle for the development of bioactives for internal parasites in rumens. Polyoleosins thus facilitate development of bioactive drug development and delivery.

In addition, polyoleosin has a similar application in the delivery of encapsulated bioactives in cosmetics, eg. creams and may be applied epidermally, for example to wounds or skin problems. Polyolesin may also have applications for controlled release in dermal applications.

Thus, the present invention also provides a method of delivering compounds and/or organisms to animals including humans, said method including encapsulation said compound or organism in an oil body including two or more oleosin repeat units and administering said oil body to said animal.

Preferably the compound is a therapeutic or prophylactic drug or a bioactive peptide or protein.

Preferably the organism is a bacterium, more preferably a health promoting bacterium such as *lactobacillus*.

Preferably the compound or organism is delivered orally or topically. The compound or organism may be delivered to the intestine. The compound or organism may be delivered by timed release eg. sustained release or delayed release.

Emulsification and Encapsulation of Bioactives

Repeat oleosins, such as recombinant multimeric tandem repeat oleosins (either homo or hetero repeats), may be used to tailor emulsion complexes and to encapsulate bioactive compounds that may exist in the emulsion. By the use of repeat oleosins, the stability of an oil body may be tailored by oleosin. The size of the suspended particles contributes both to the stability of the suspension and the amount of material that may be suspended. By altering the number of oleosin repeats in a peptide sequence (preferably using recombinant technologies) oleosins with different emulsification properties are generated. These confer enhanced stabilities in terms of, for example, temperature and pH stability and altered particle size. In turn this broadens the number of compounds that may be emulsified as well as expanding the applications of the emulsifications.

Polyoleosin allows the manufacturer to tailor the emulsification properties by altering the number of oleosin repeats. The majority of processed foods utilise emulsifiers of some form or another. In addition, polyoleosins may be utilised in the cosmetics industry. The oil based encapsulation mechanism provides an ideal delivery mechanism for any compound, notably bioactives for dermal application.

Accordingly, in a further aspect the present invention provides a method of altering the emulsification properties of an oleosin, said method including recombinantly producing the oleosin with two or more oleosin repeat units.

Altering the emulsification properties of the oleosin may include altering temperature and/or pH stability and/or size of oil bodies including the oleosin.

The present invention also provides a recombinant oleosin with altered emulsification properties, said oleosin including two or more oleosin repeat units.

The recombinant polypeptide may be produced by expression of a construct or vector according to the present invention.

Thus, in the polypeptides of the present invention tandem oleosins may be fused directly or by small linking (eg. hinge) sequences. The polypeptides may contain fused bioactive peptides either at the terminal ends of the repeats or located between the repeats.

Such polyoleosins may be used to deliver encapsulated products/compounds/proteins that do not have to be fused to the oleosin peptides but rather are generated during the process of creating oil bodies or AOBs.

Polyoleosins may also be used to deliver bioactive peptides either encapsulated within oil bodies, AOBs or fused to the ends of oleosin repeats or fused between the repeats.

Polyoleosins used for emulsification or delivery or protection of compounds may be tailored by changing the number of oleosin tandem repeats rather than simply being the fusion of a peptide of insert fused between two oleosin repeats.

The present invention will now be more fully described with reference to the accompanying Examples and drawings. It should be understood, however, that the description following is illustrative only and should not be taken in any way as a restriction on the generality of the invention described above.

IN THE FIGURES

FIG. 1. Kyte and Doolittle hydrophobic plot (window=17) of a typical oleosin sequence.

FIG. 2. Oil body showing topology of oleosin single peptide chains.

Figure 3:
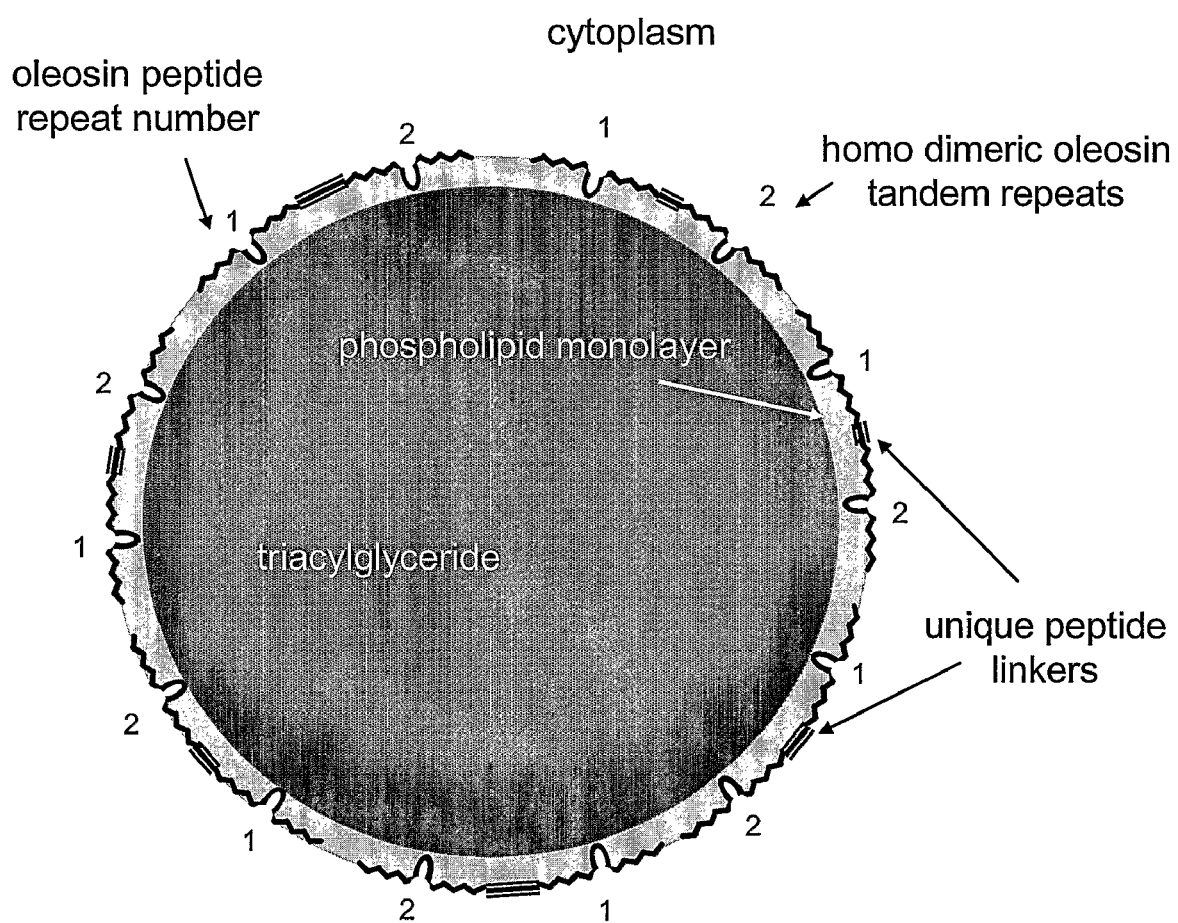

FIG. 3. Oil body showing topology of dimeric oleosin repeat peptide chains joined by unique peptide linkers.

Figure 4:
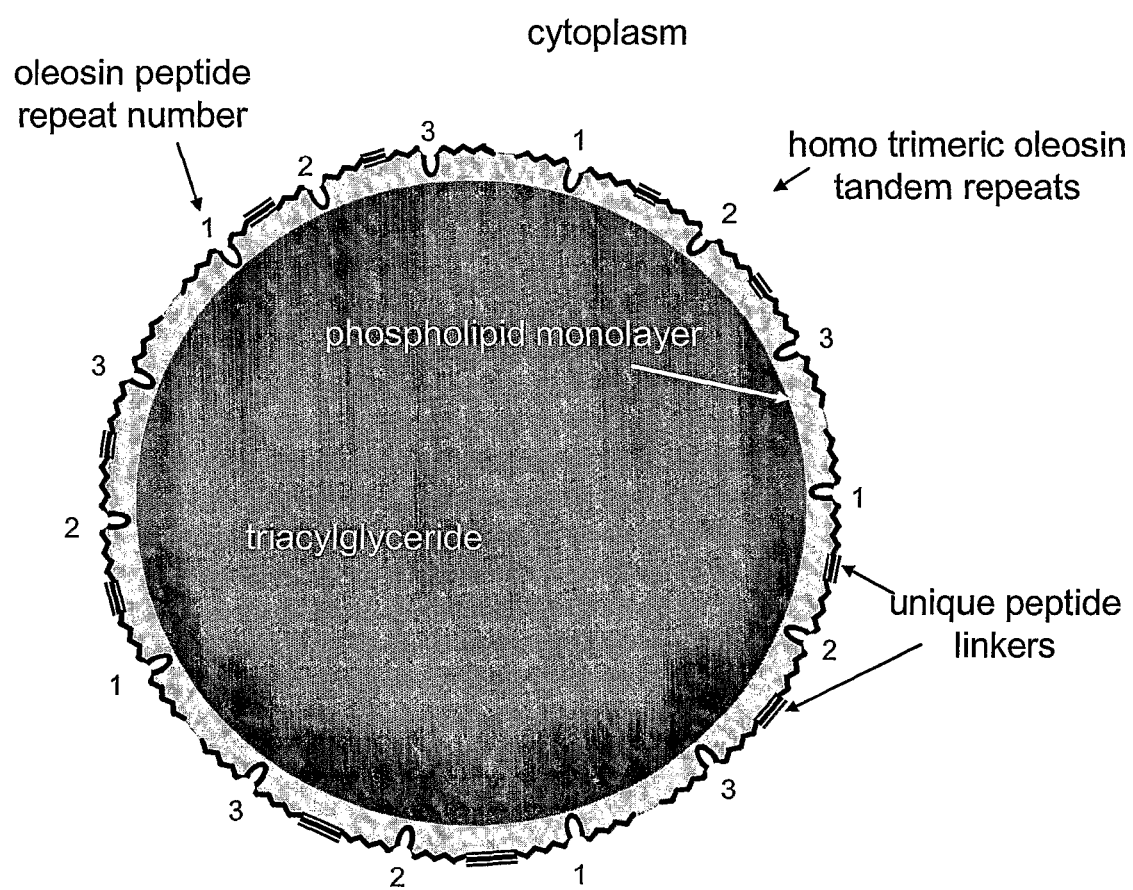

FIG. 4. Oil body showing topology of trimeric oleosin repeat peptide chains joined by unique peptide linkers.

Figure 5:
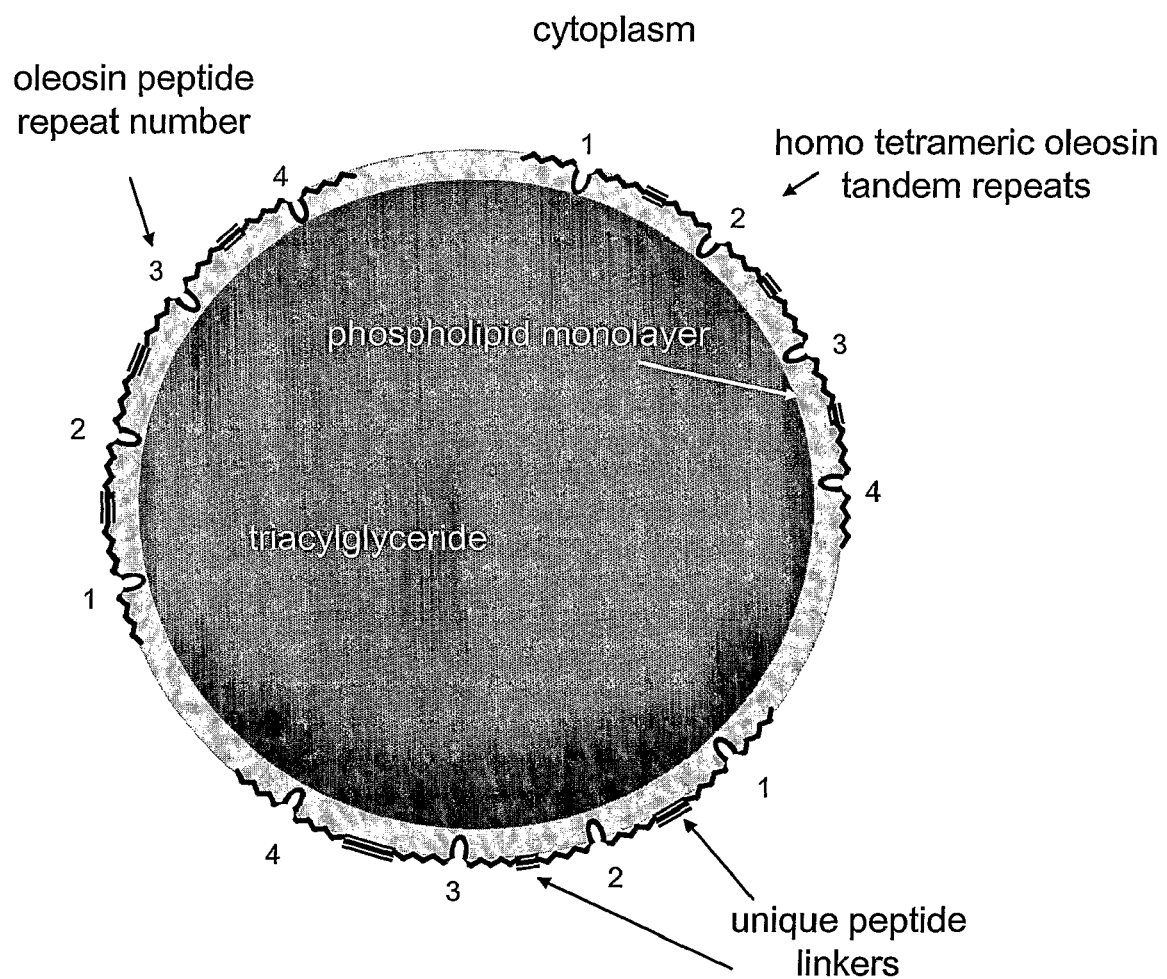

FIG. 5. Oil body showing topology of tetrameric oleosin repeat peptide chains joined by unique peptide linkers.

Figure 6:
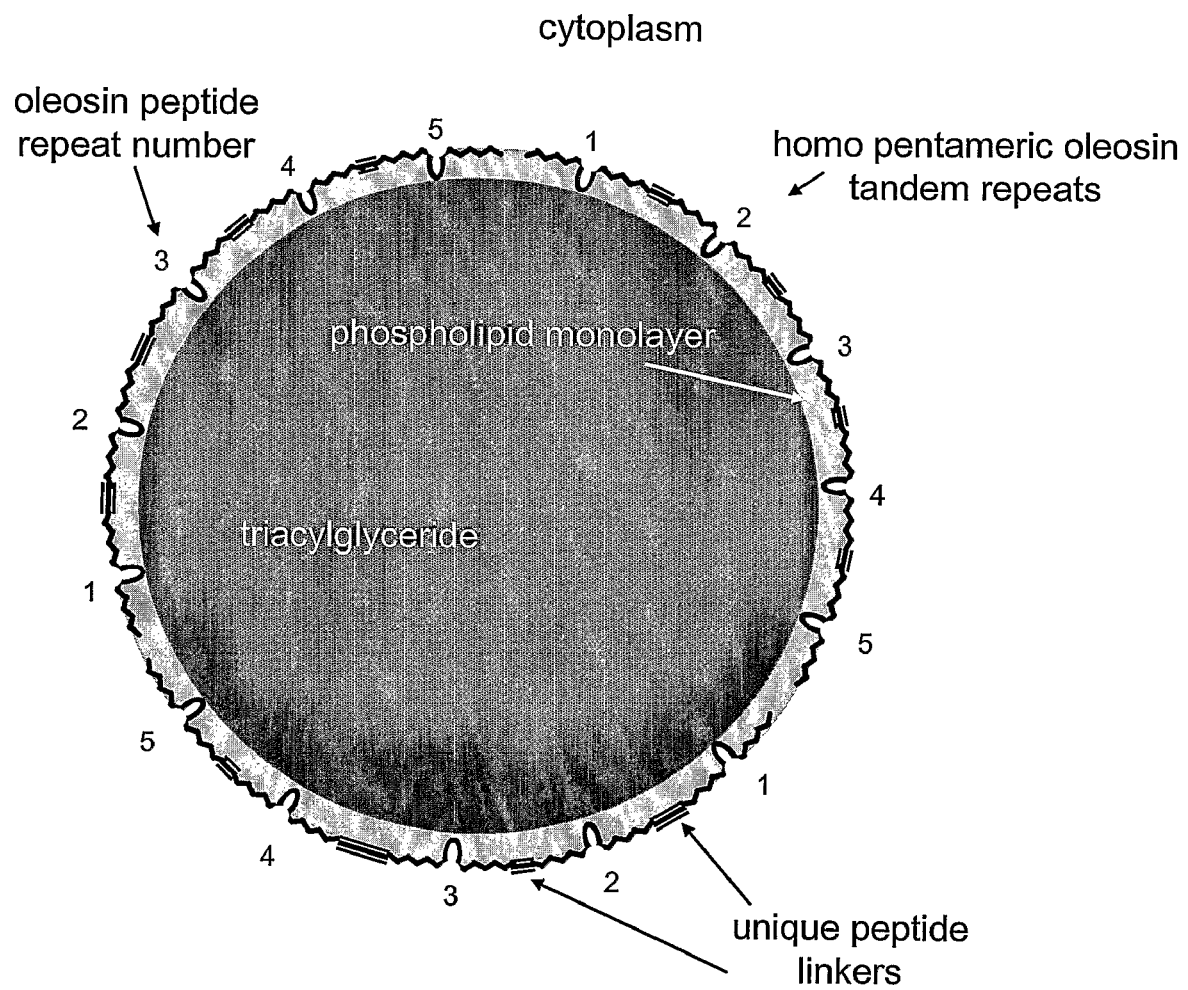

FIG. 6. Oil body showing topology of pentameric oleosin repeat peptide chains joined by unique peptide linkers.

Figure 7:
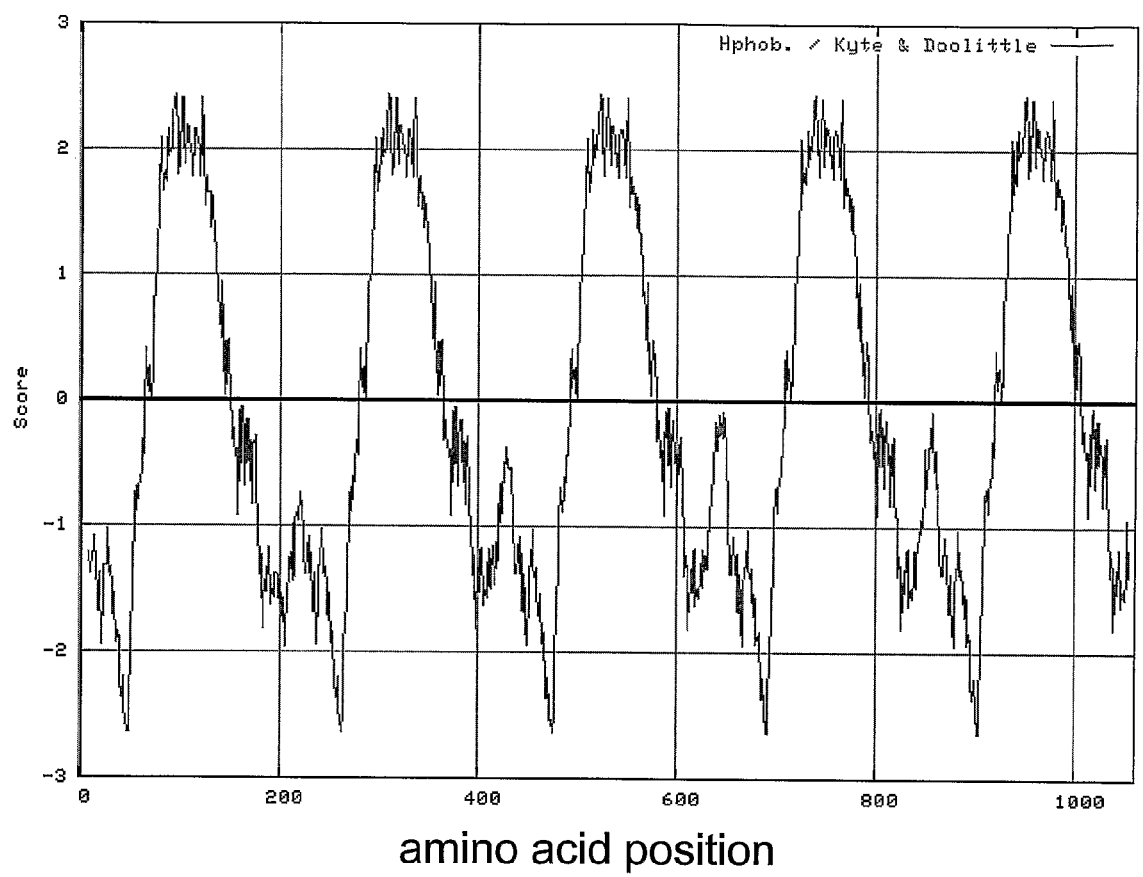

FIG. 7. Typical Kyte and Doolittle hydrophobicity plot (window=17) of homo or hetero pentameric oleosin tandem repeat containing unique inter oleosin peptide liners.

FIG. 8. pBLUESCRIPT II SK MCS sequence and translated amino acid sequence. With the exception of EcoRV all other restriction sites are not present in either the white clover oleosin clone or the Gateway PCR entry vector pENTR/D • and XXX=codon not part of a restriction site.

FIG. 9. Standard layout of primers and PCR products to generate white clover polyoleosin constructs.

Figure 10:
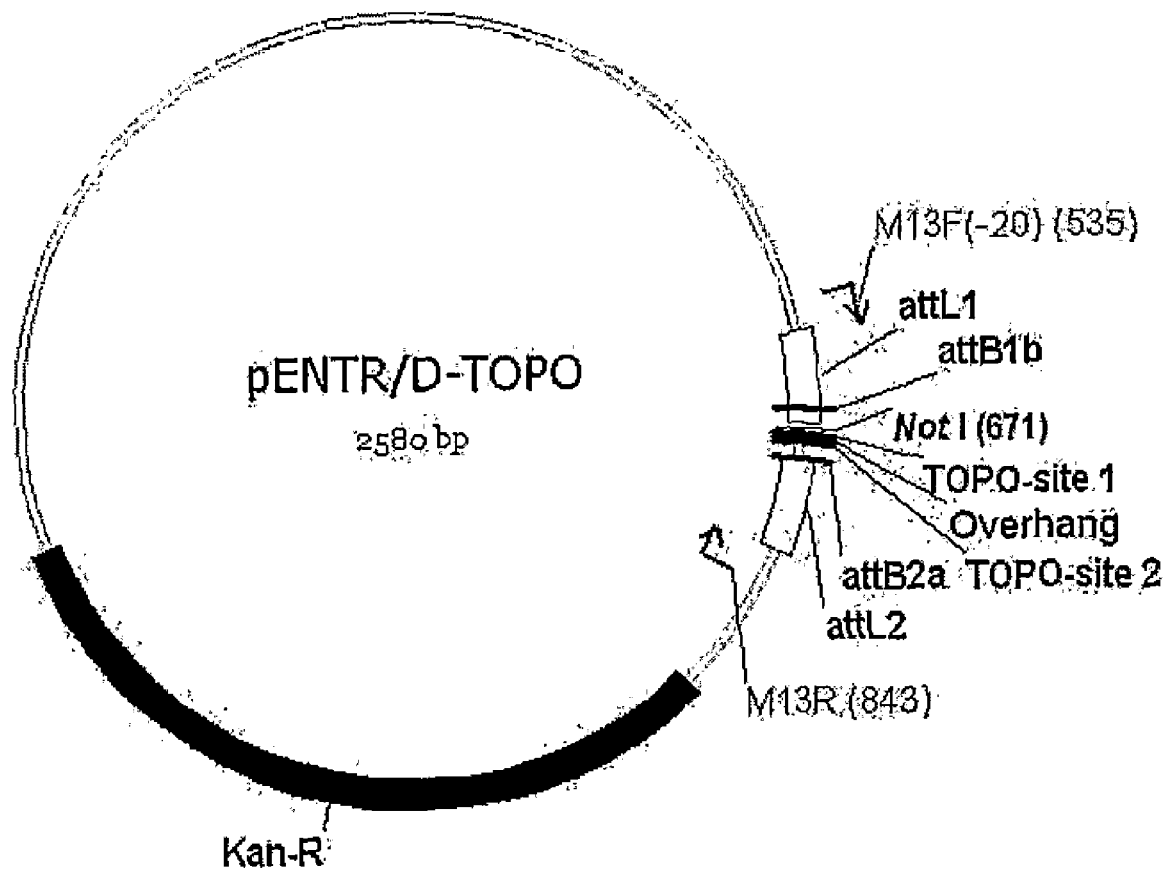

FIG. 10. Map of pENTR/D-TOPO.

Figure 11:
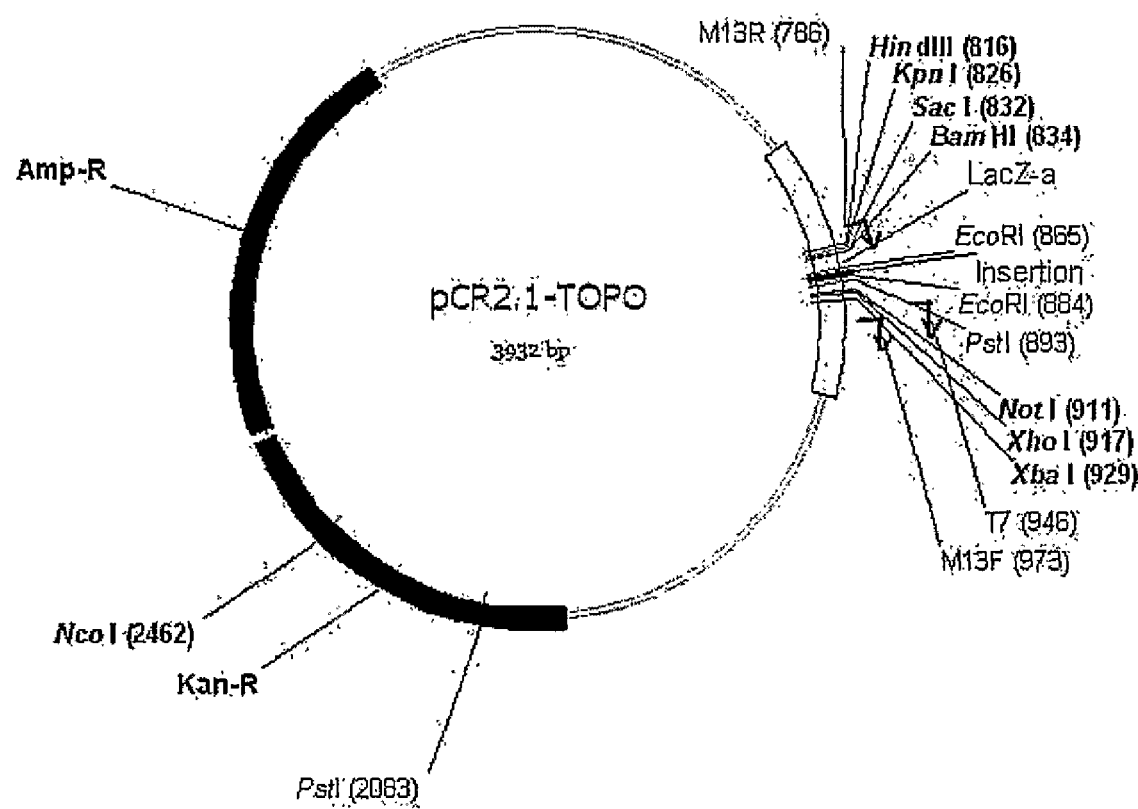

FIG. 11. Map of pCR2.1-TOPO.

Figure 12:
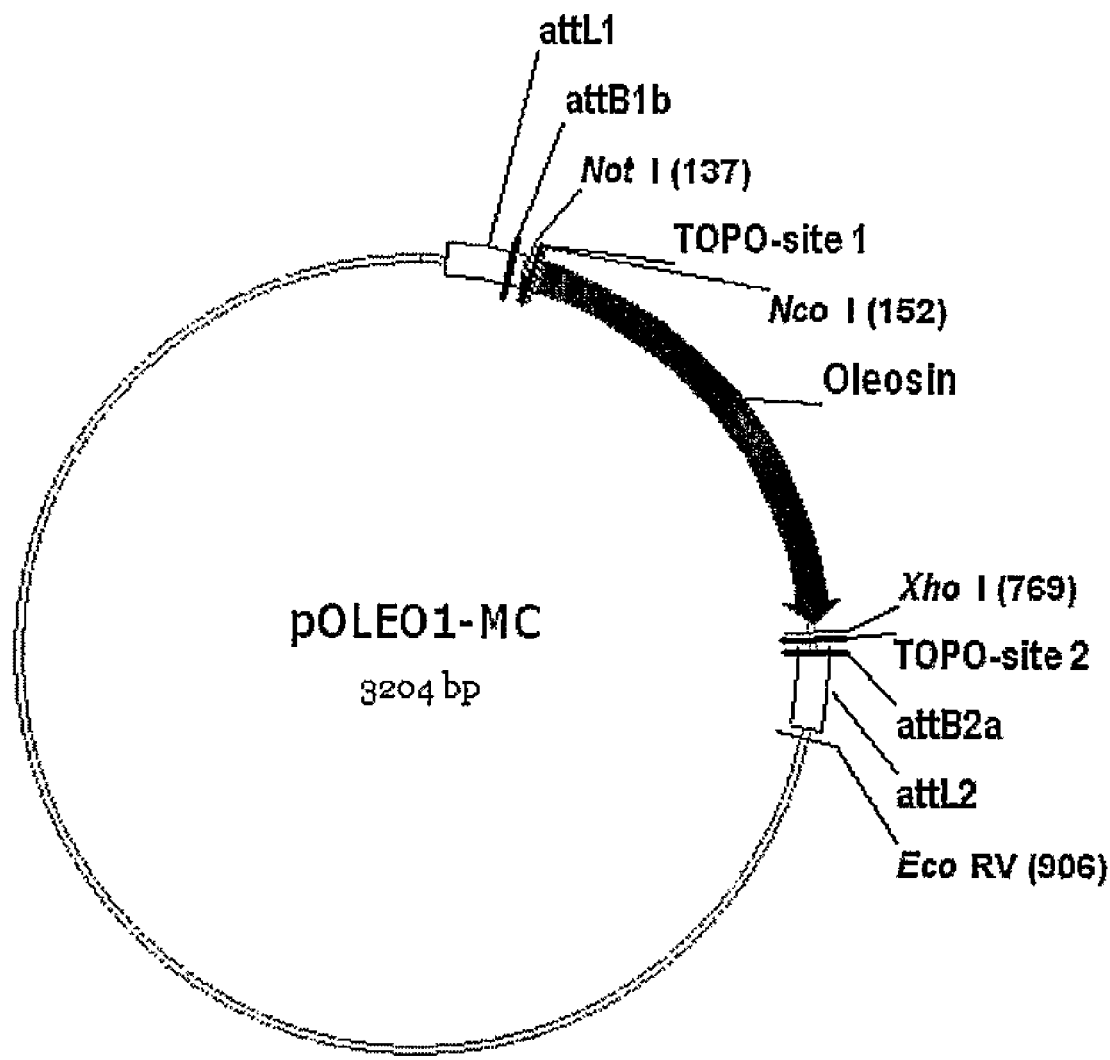

FIG. 12. Map of pOLE01-MC.

FIG. 13. Sequence of the oleosin coding region in pOLE01-MC (Seq ID No. 29). CACC=GATEWAY™ adapter, XXXX=oleosin sequence, XXXXXX=restriction enzyme site—included in primer, TGA=stop codon.

Figure 14:
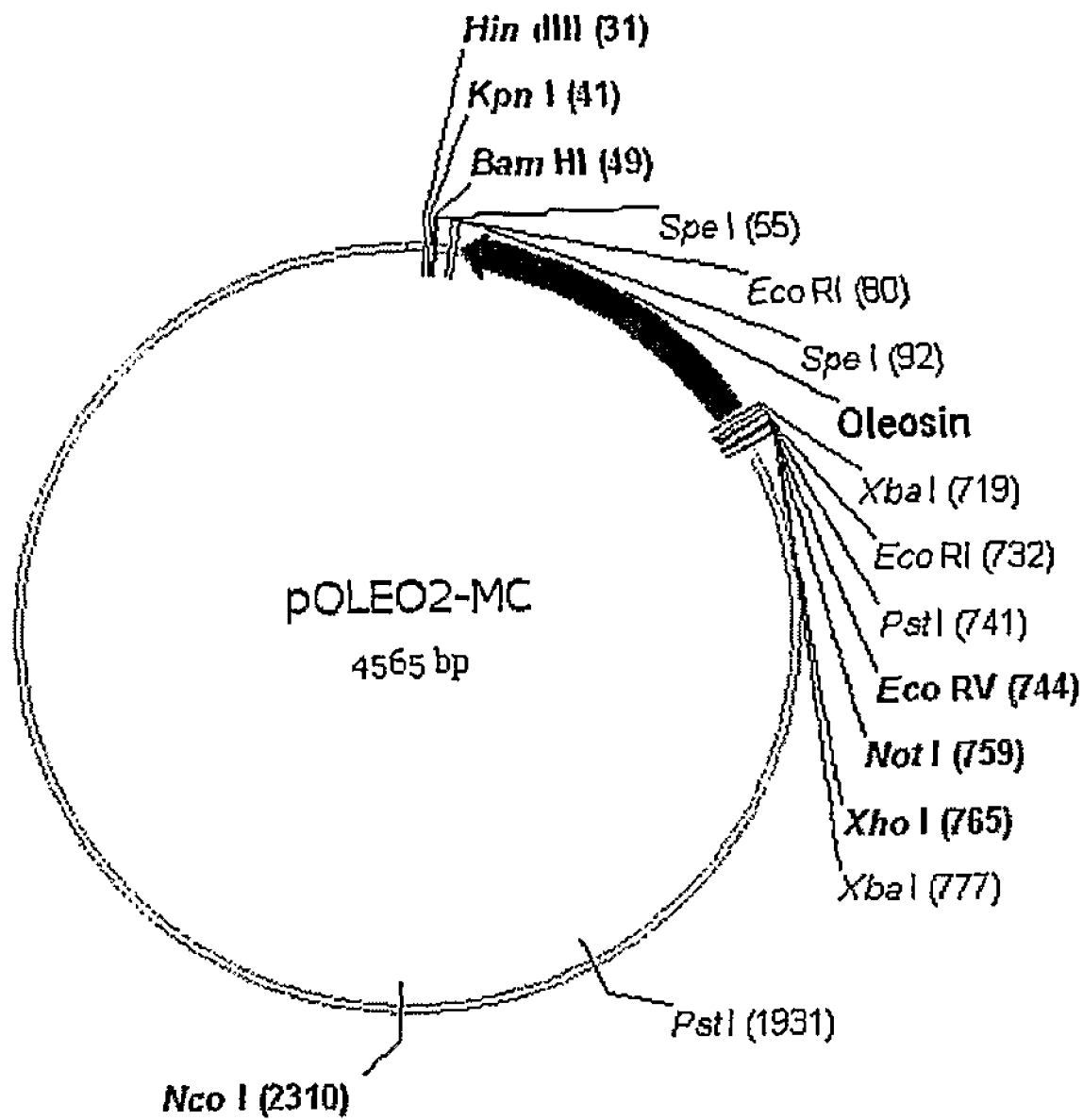

FIG. 14. Map of pOLE02-MC.

FIG. 15. Sequence of the oleosin coding region in pOLE02-MC (Seq ID No. 30). XXXX=oleosin sequence, XXXXXX=restriction enzyme site—included in primer, XXXXXX=codons for extra amino acids—included in primer.

Figure 16:
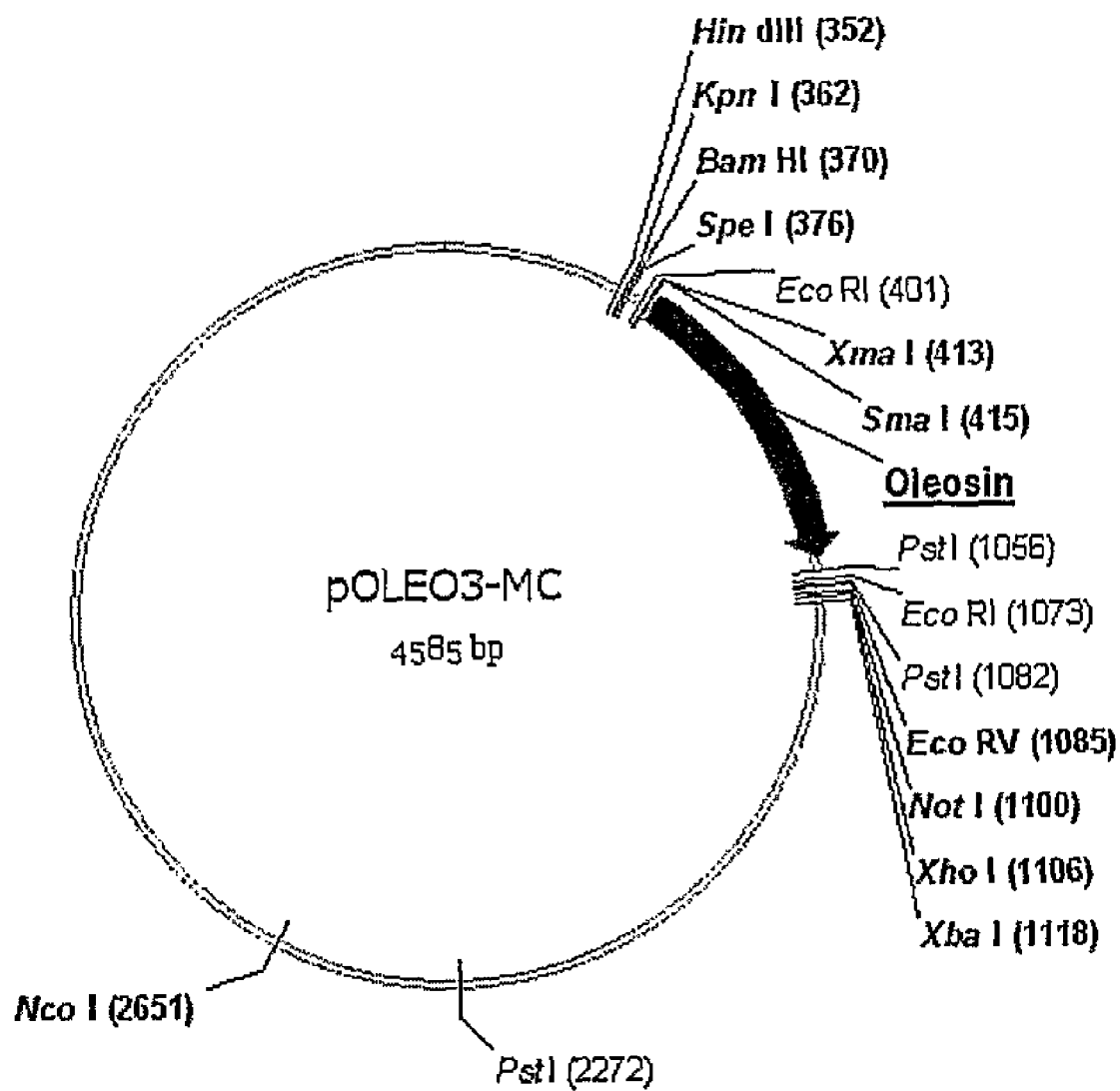

FIG. 16. Map of pOLE03-MC.

FIG. 17. Sequence of the oleosin coding region in pOLE03-MC (Seq ID No. 31). XXXX=oleosin sequence, XXXXXX=restriction enzyme site—included in primer, XXXXXX=codons for extra amino acids—included in primer.

Figure 18:
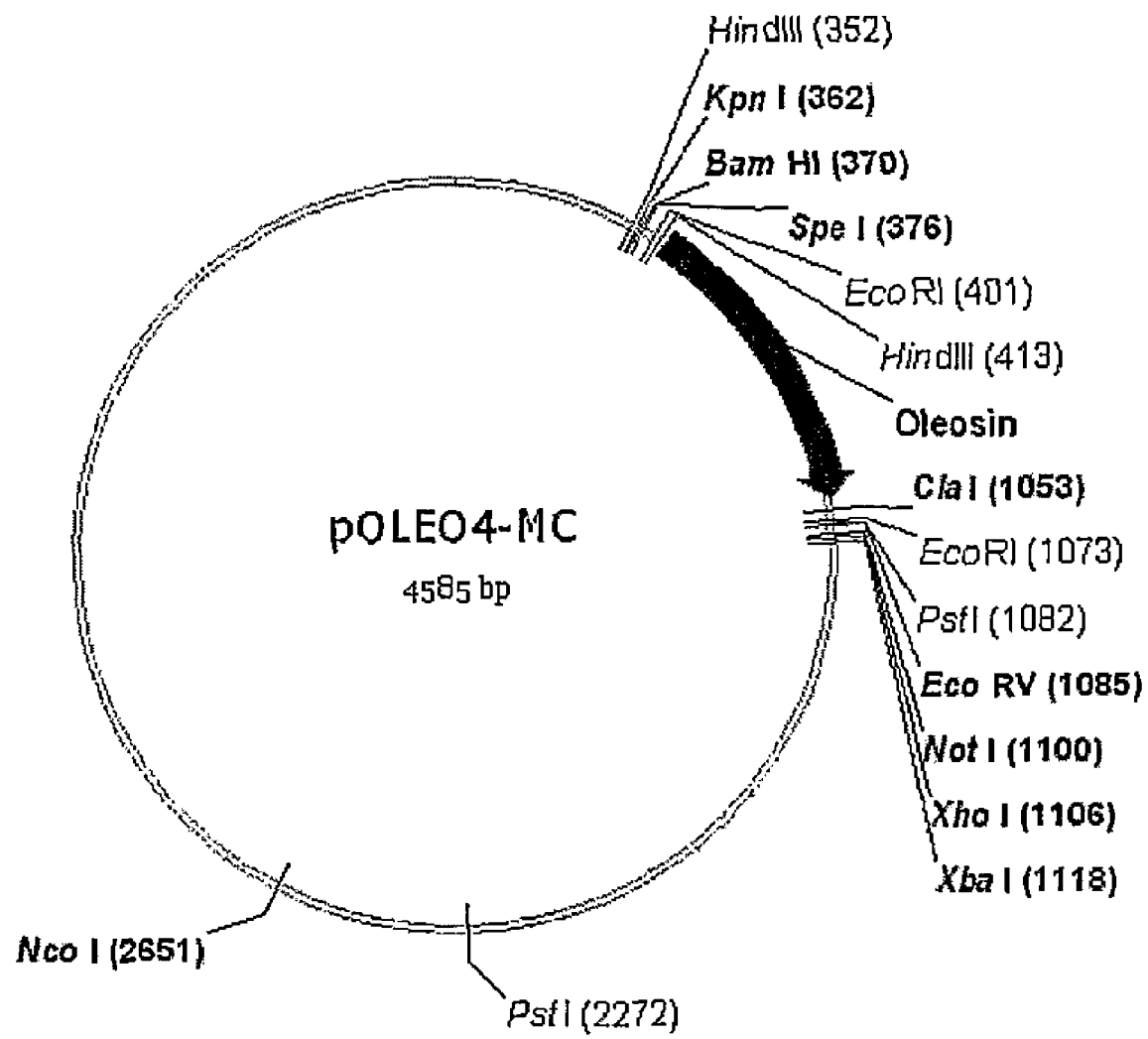

FIG. 18. Map of pOLE04-MC.

FIG. 19. Sequence of the oleosin coding region in pOLE04-MC (Seq ID No. 32). XXXX=oleosin sequence, XXXXXX=restriction enzyme site—included in primer, XXXXXX=codons for extra amino acids—included in primer.

Figure 20:
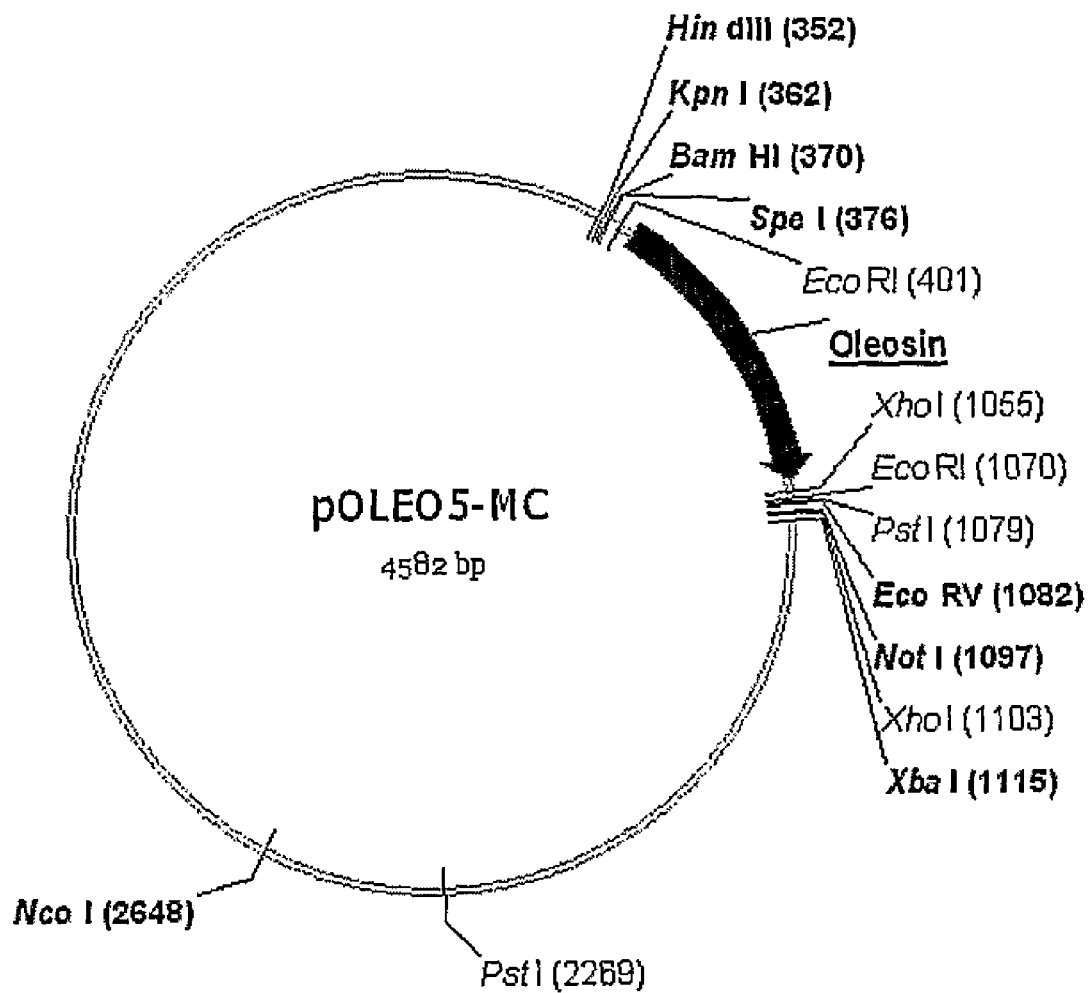

FIG. 20. Map of pOLE05-MC.

FIG. 21. Sequence of the oleosin coding region in pOLE05-MC (Seq ID No. 33). XXXX=oleosin sequence, XXXXXX=restriction enzyme site—included in primer, XXXXXX=codons for extra amino acids—included in primer.

Figure 22:
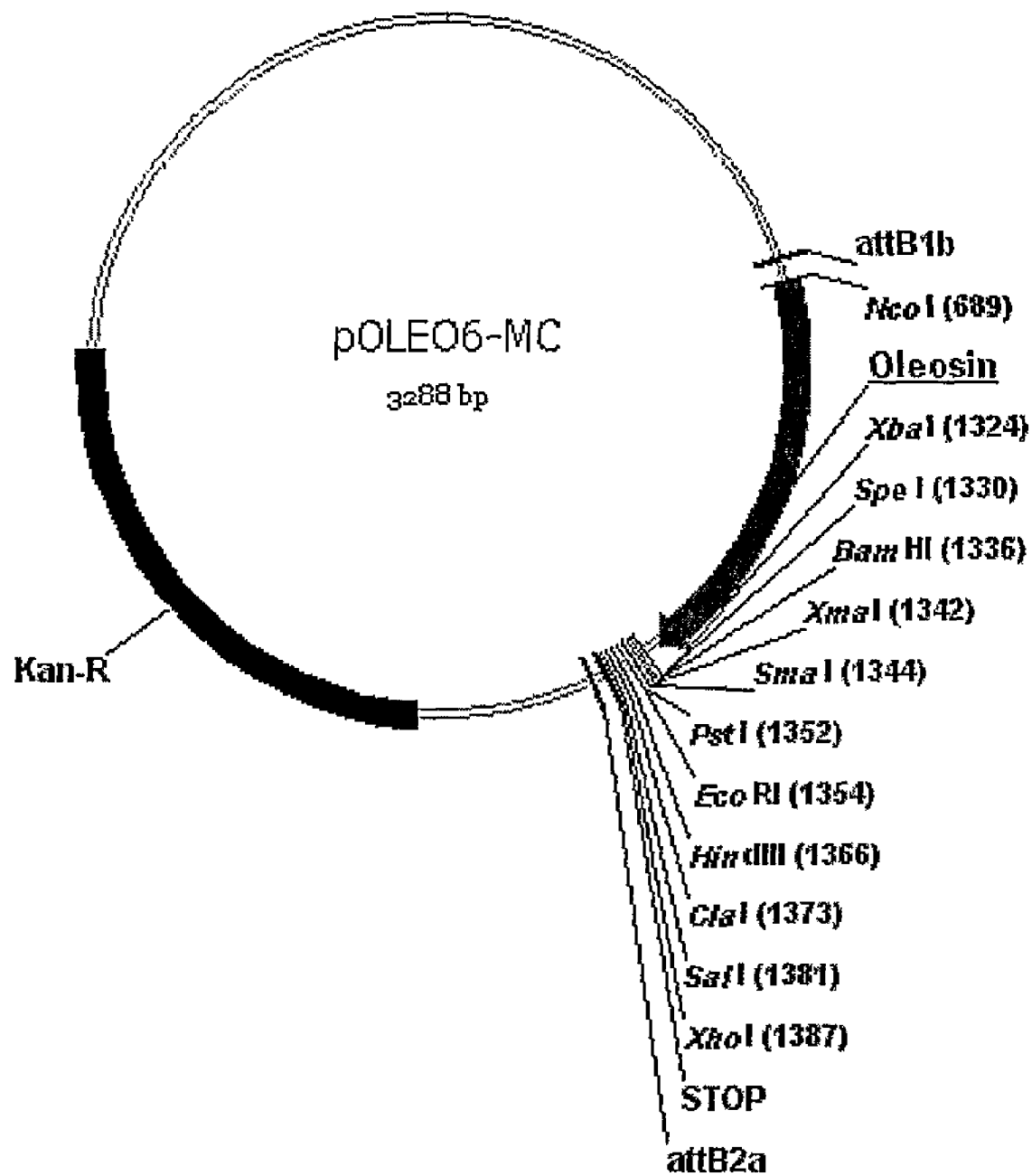

FIG. 22. Map of pOLE06-MC.

FIG. 23. Sequence of the oleosin coding region in pOLE06-MC (Seq ID No. 34). XXXX=GATEWAY™ adapter sequence, XXXX=oleosin sequence, XXXXXX=base pairs encoding for additional amino acids—included in primer, XXXX=polylinker sequence,

 = stop condon.

Figure 24:
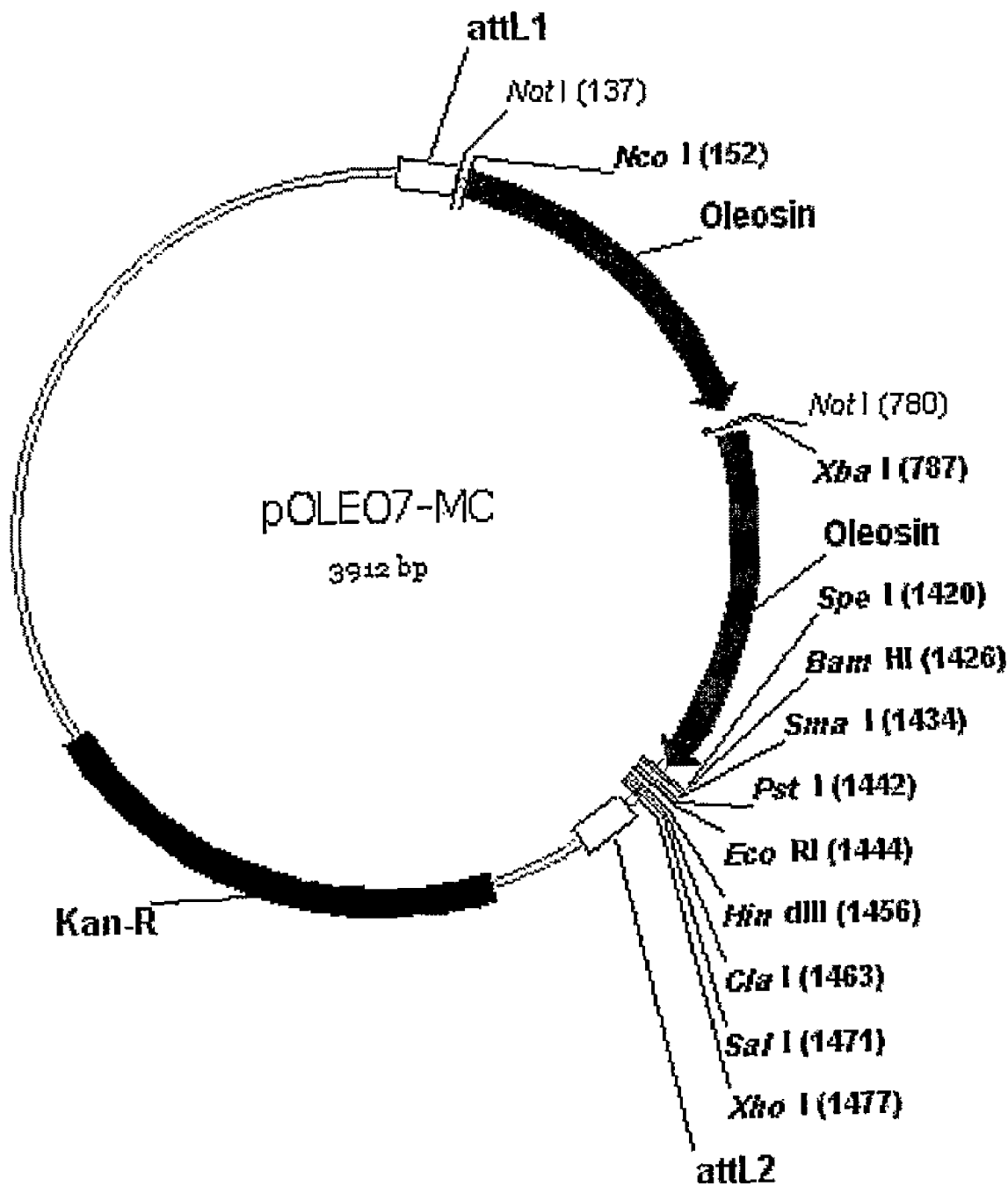

FIG. 24. Map of pOLE07-MC.

FIG. 25. Sequence of the oleosin coding region in pOLE07-MC (Seq ID No. 35). XXXX=GATEWAY™ adapter sequence, XXXX=oleosin sequence, XXXXXX=base pairs encoding for additional amino acids—included in primer, XXXX=polylinker sequence,

 = stop condon.

Figure 26:
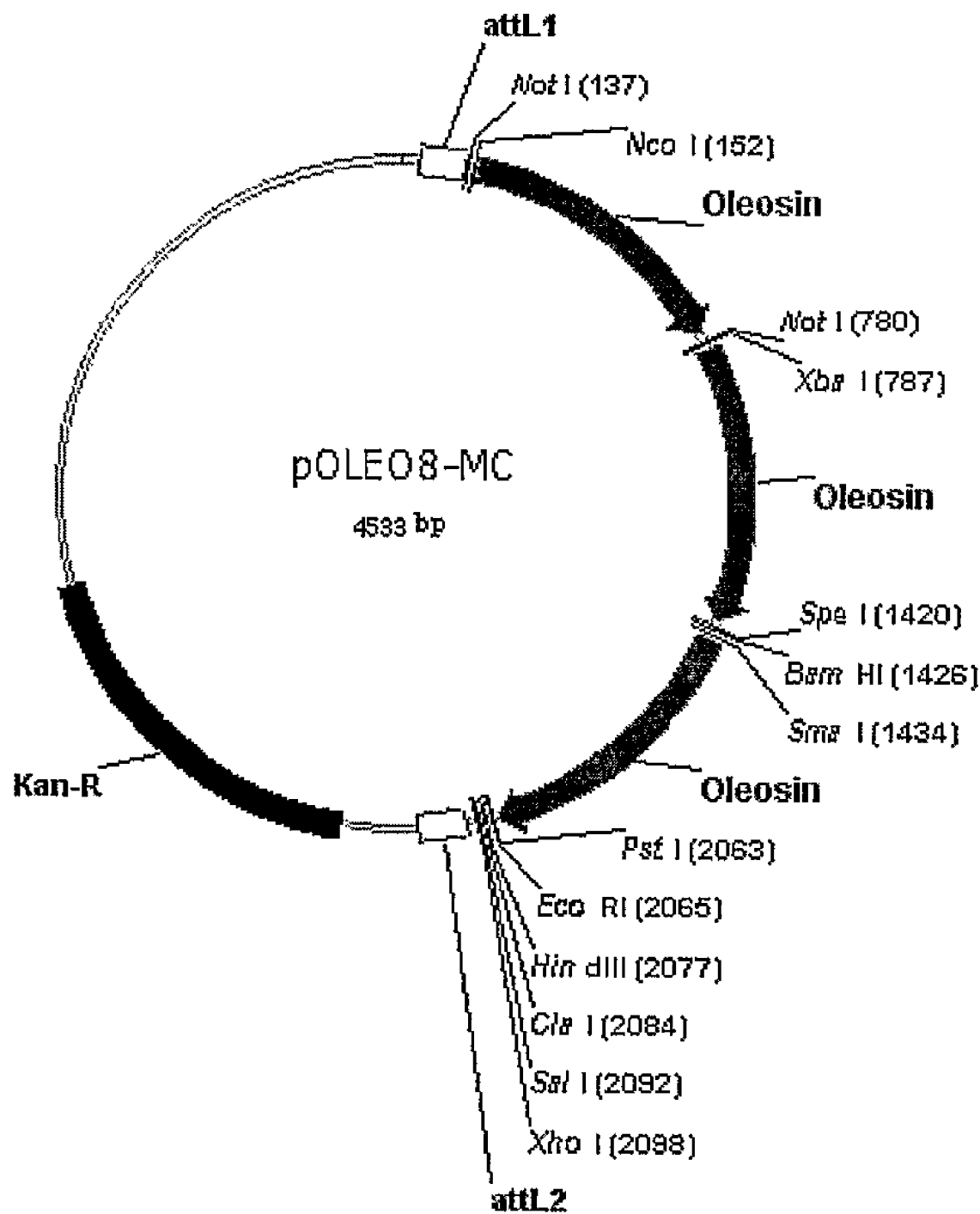

FIG. 26. Map of pOLE08-MC.

FIG. 27. Sequence of the oleosin coding region in pOLE08-MC (Seq ID No. 36). XXXX=GATEWAY™ adapter sequence, XXXX=oleosin sequence, XXXXXX=base pairs encoding for additional amino acids—included in primer, XXXX=polylinker sequence,

 = stop condon.

Figure 28:
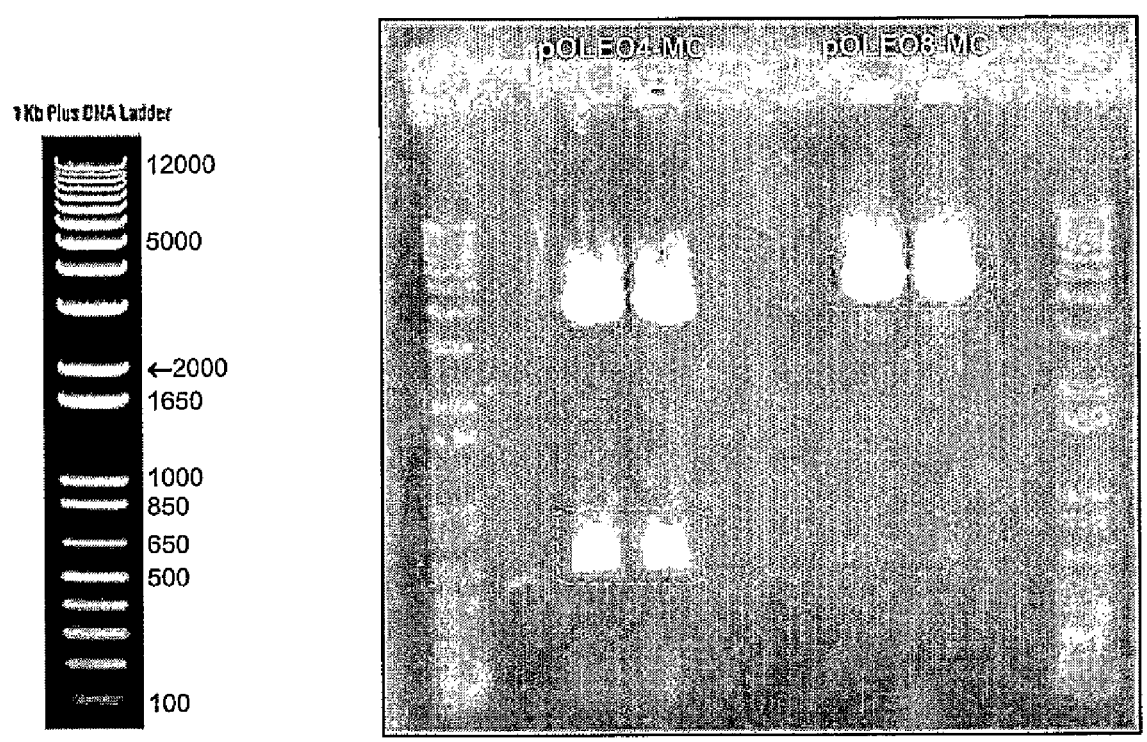

FIG. 28. Agarose gel of HindIII/ClaI digested pOLE04-MC and pOLE08-MC. Dotted boxes outline the regions excised for extraction from gel.

Figure 29:
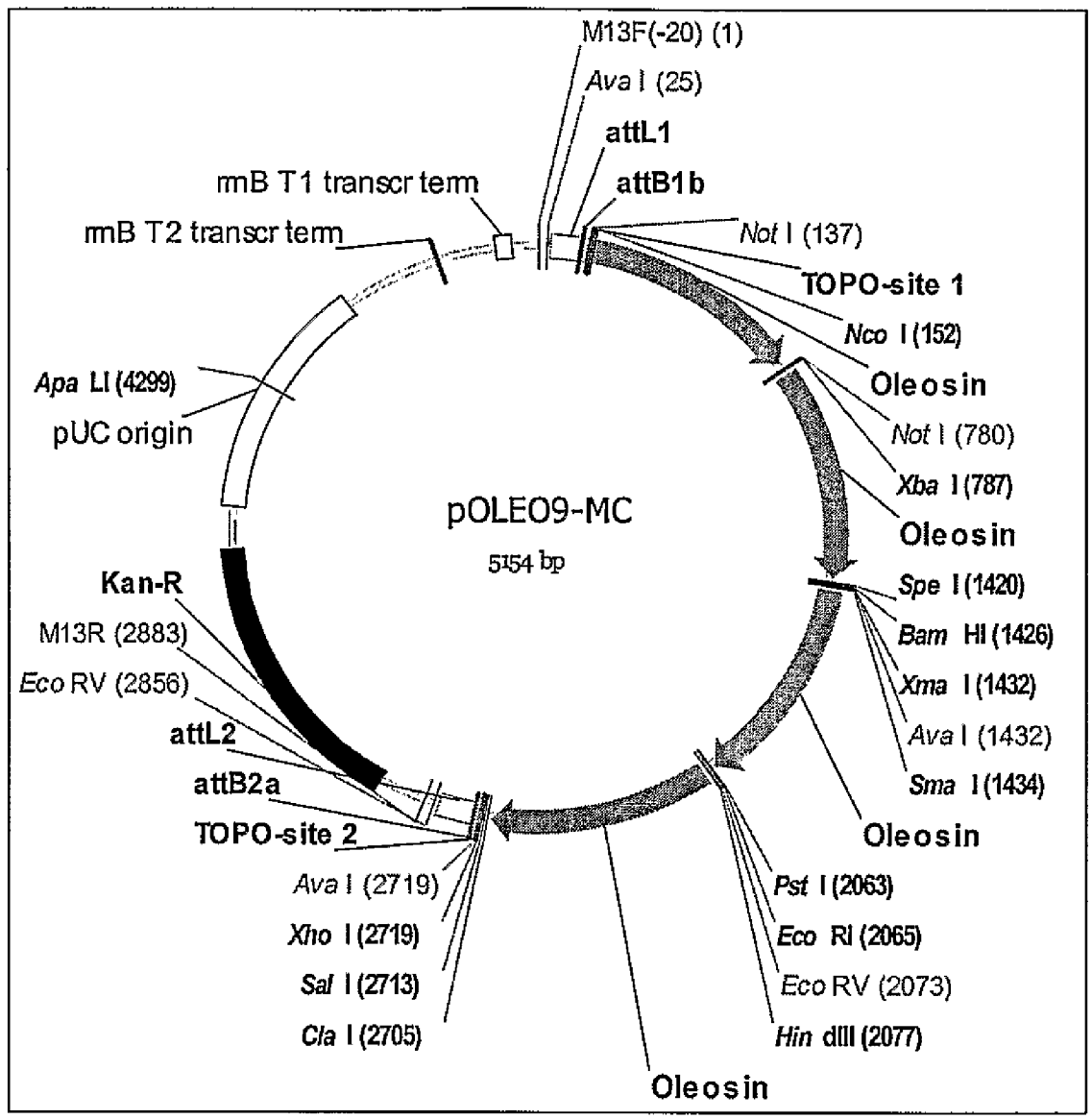

FIG. 29. Map of pOLE09-MC.

Figure 30:
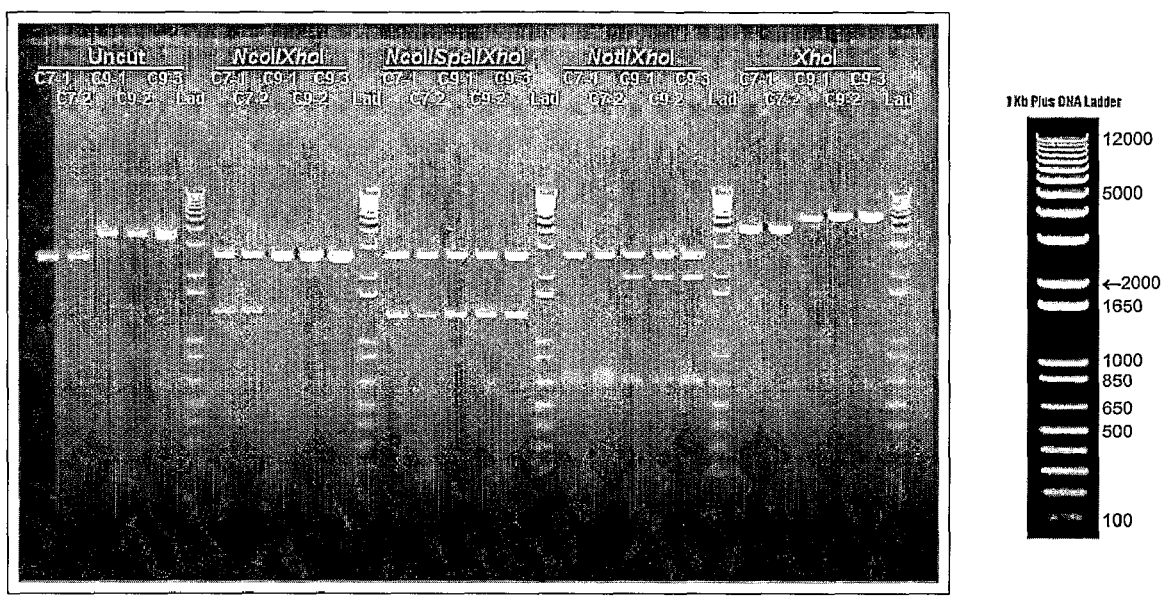

FIG. 30. Agarose gel results from checking pOLE09-MC.
Expected Sizes:
Clone 7
  NcoI/XhoI—2.6 kb and 1.3 kb
  NcoI/SpeI/XhoI—2.6 kb, 1.3 kb & 57 bp
  NotI/XhoI—2.6 kb, 697 bp, & 643 bp
  XhoI—3.9 kb
Clone 9
  NcoI/XhoI—two bands at ~2.6 kb clones C9.1-C9.3 correct
  NcoI/SpeI/XhoI—2.6 kb & two bands at ~1.3 kb clones C9.1-C9.3 correct
  NotI/XhoI—2.6 kb, 1.9 kb & 643 bp clones C9.1-C9.3 correct
  XhoI—5.2 kb clones C9.1-C9.3 correct Clones 9.1-9.3 all showed the correct/expected sizes for pOLE09-MC.

The region in the pOLE09-MC cassette containing the newly inserted oleosin was then sequenced.

Figure 31:
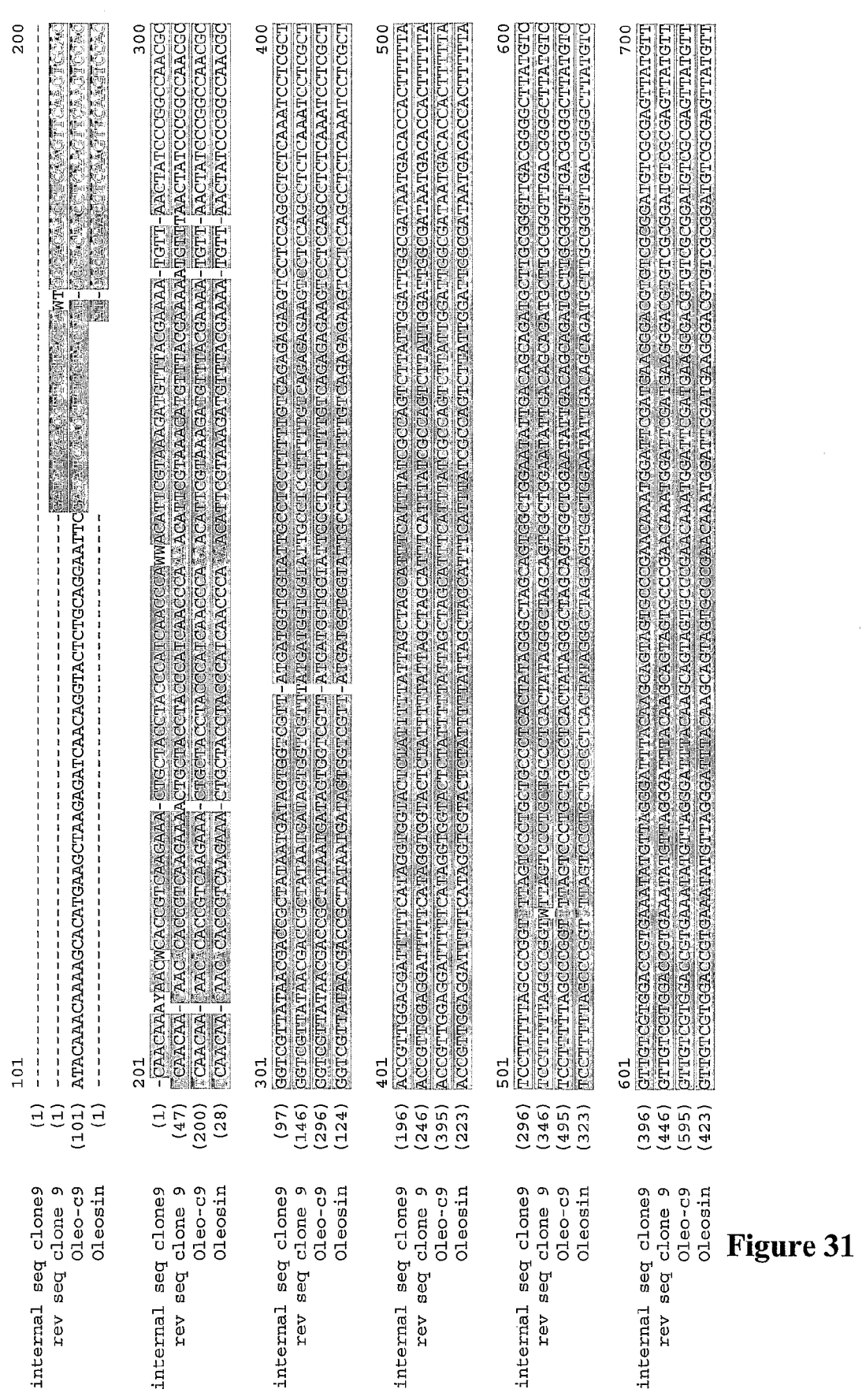
Figure 31:
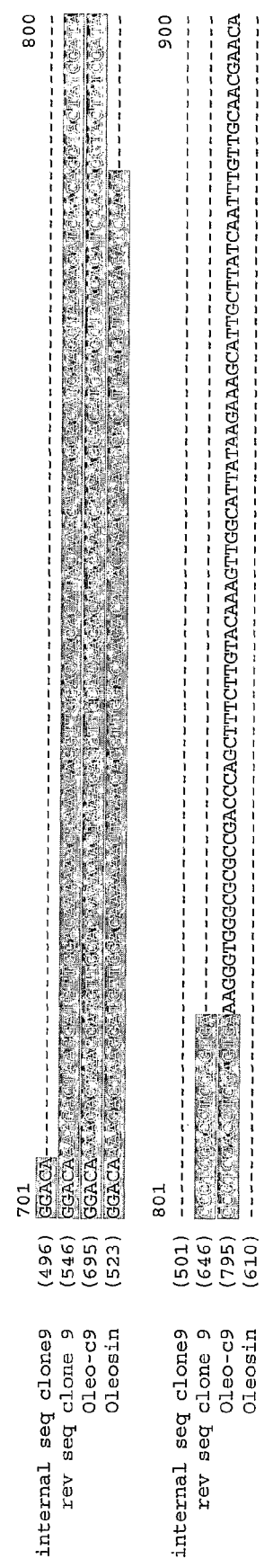

FIG. 31. Sequence of pOLE09-MC, confirming the addition of the oleosin from pOLE04-MC into pOLE08-MC. Sequence was obtained by sequencing across the last oleosin in pOLE09-MC into the original pOLE08-MC vector. All mismatches were checked back to the original electropherogram to confirm errors were due to software misreads. (Seq ID Nos. 84 and 38-40)

Figure 32:
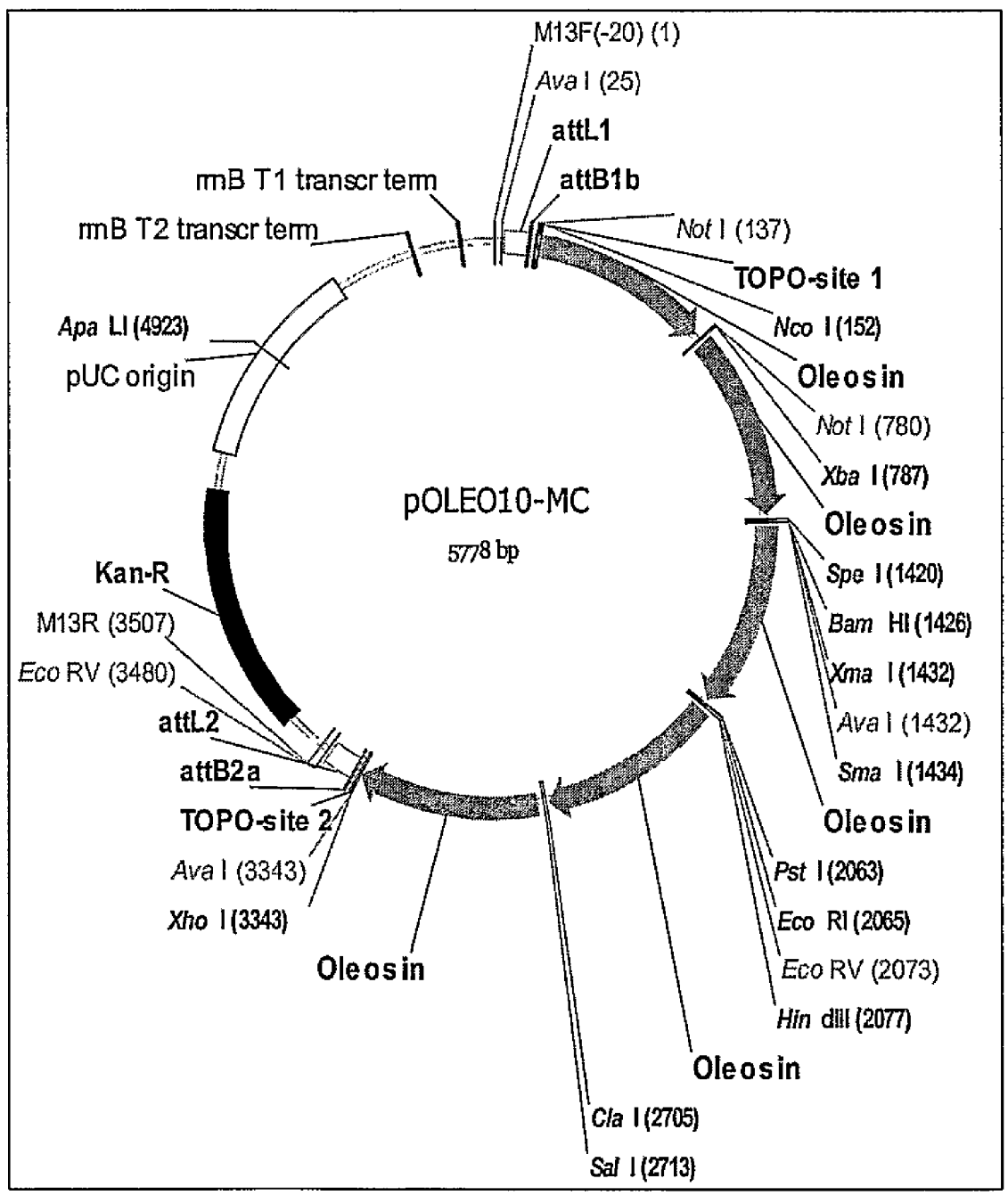

FIG. 32. Map of pOLE10-MC.

Figure 33:
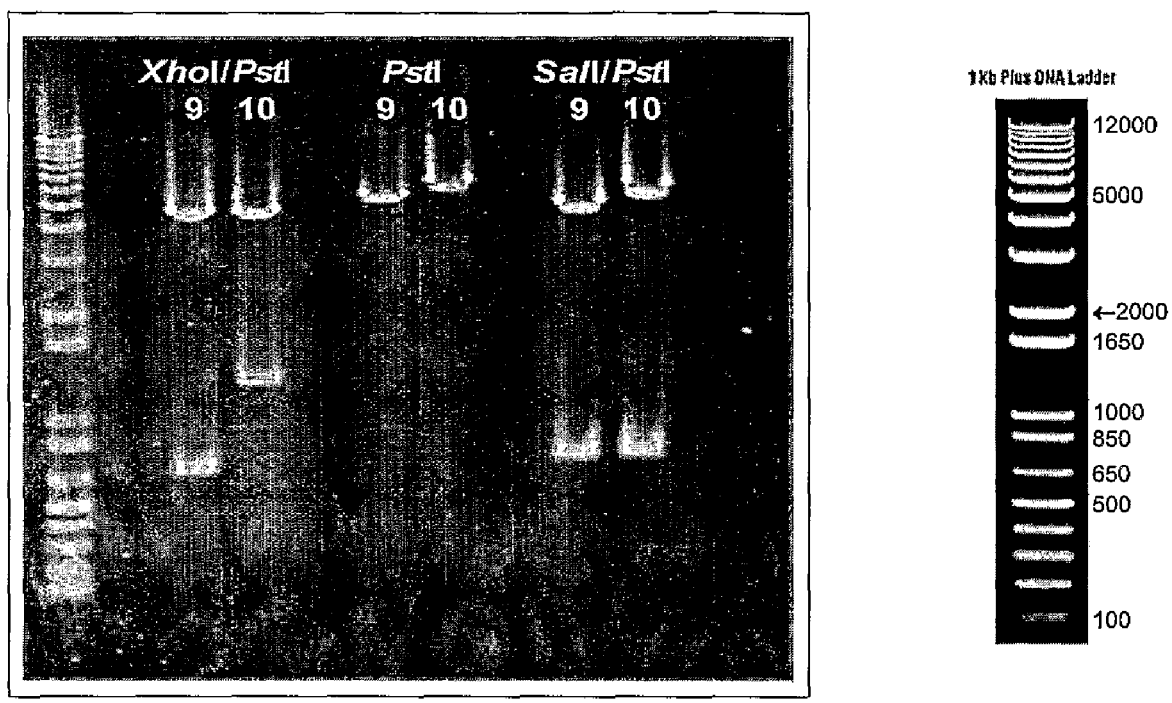

FIG. 33. Agarose gel analysis of a restriction enzyme digested pOLE10-MC clone, compared to pOLE09-MC.
Expected Sizes:

| Clone 9 | | |
| --- | --- | --- |
| XhoI/PstI | ~4.5 kb and 650 bp | correct |
| PstI | ~5.1 kb | correct |
| SalI/PstI | ~4.5 kb and 650 bp | correct |

Expected Sizes:

| Clone 10 | | |
| --- | --- | --- |
| XhoI/PstI | ~4.5 kb and 1.2 kb | correct |
| PstI | ~5.7 kb | correct |
| SalI/PstI | ~5.1 kb and 650 bp | correct |

Both pOLE09-MC and pOLE10-MC clones were found to be correct when analysed by restriction digests.

The region in the pOLE10-MC cassette containing the newly inserted oleosin was then sequenced using the M13-Reverese primer (five clones sequenced and found to match the predicted sequence.

Figure 34:
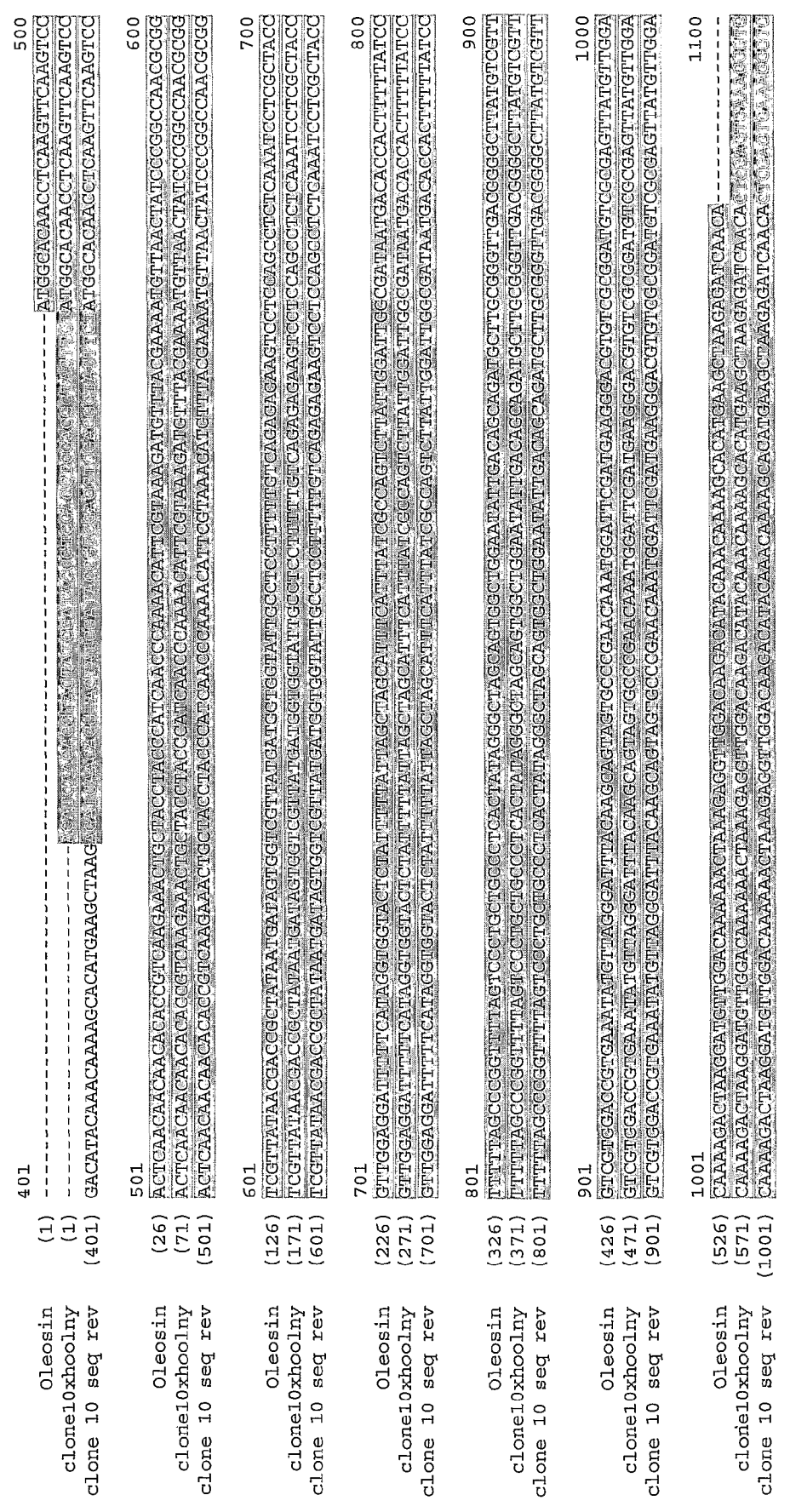
Figure 34:
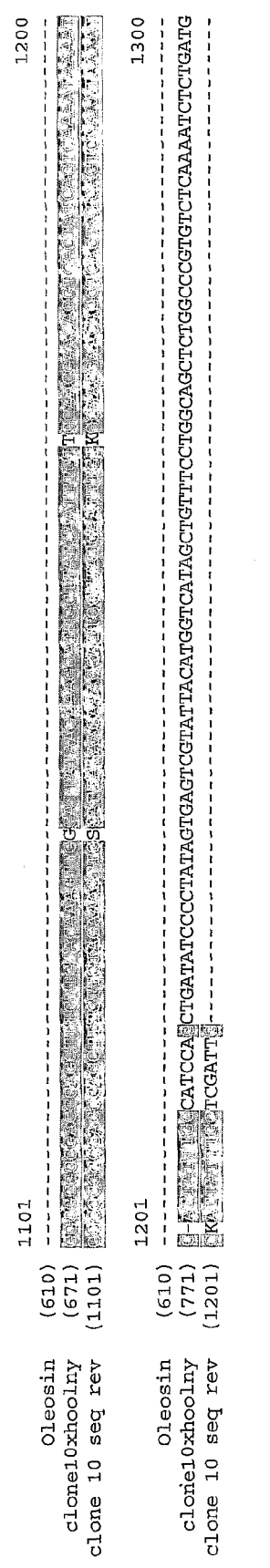

FIG. 34. Sequence of pOLE10-MC, confirming the addition of the oleosin from pOLE05-MC, into pOLE09-MC. Sequence was obtained via sequencing into the fifth pOLE10-MC and back across into pOLE09-MC. (Seq ID Nos. 41-43)

Figure 35:
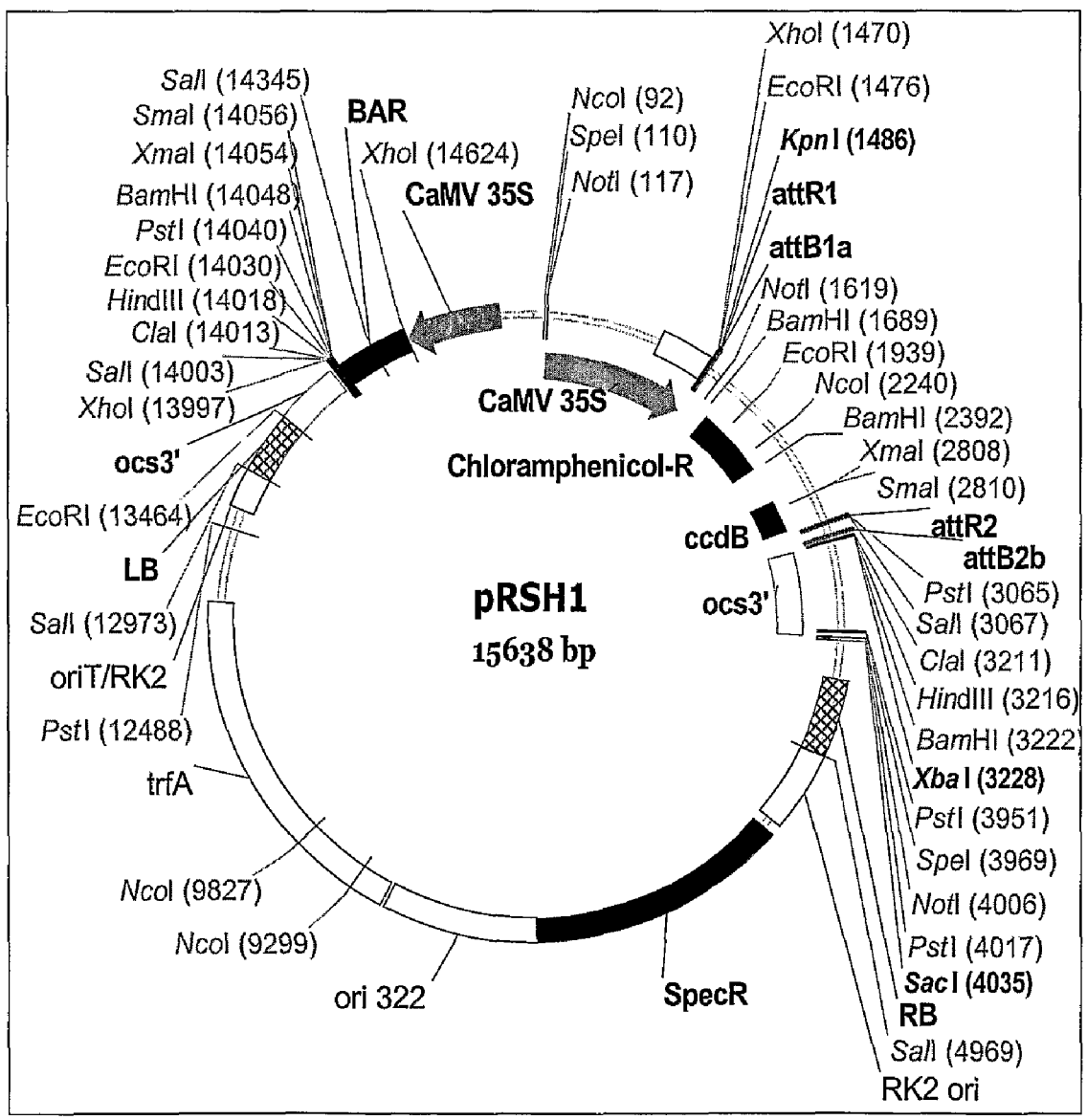

FIG. 35. Map of pRSh1.

Figure 36:
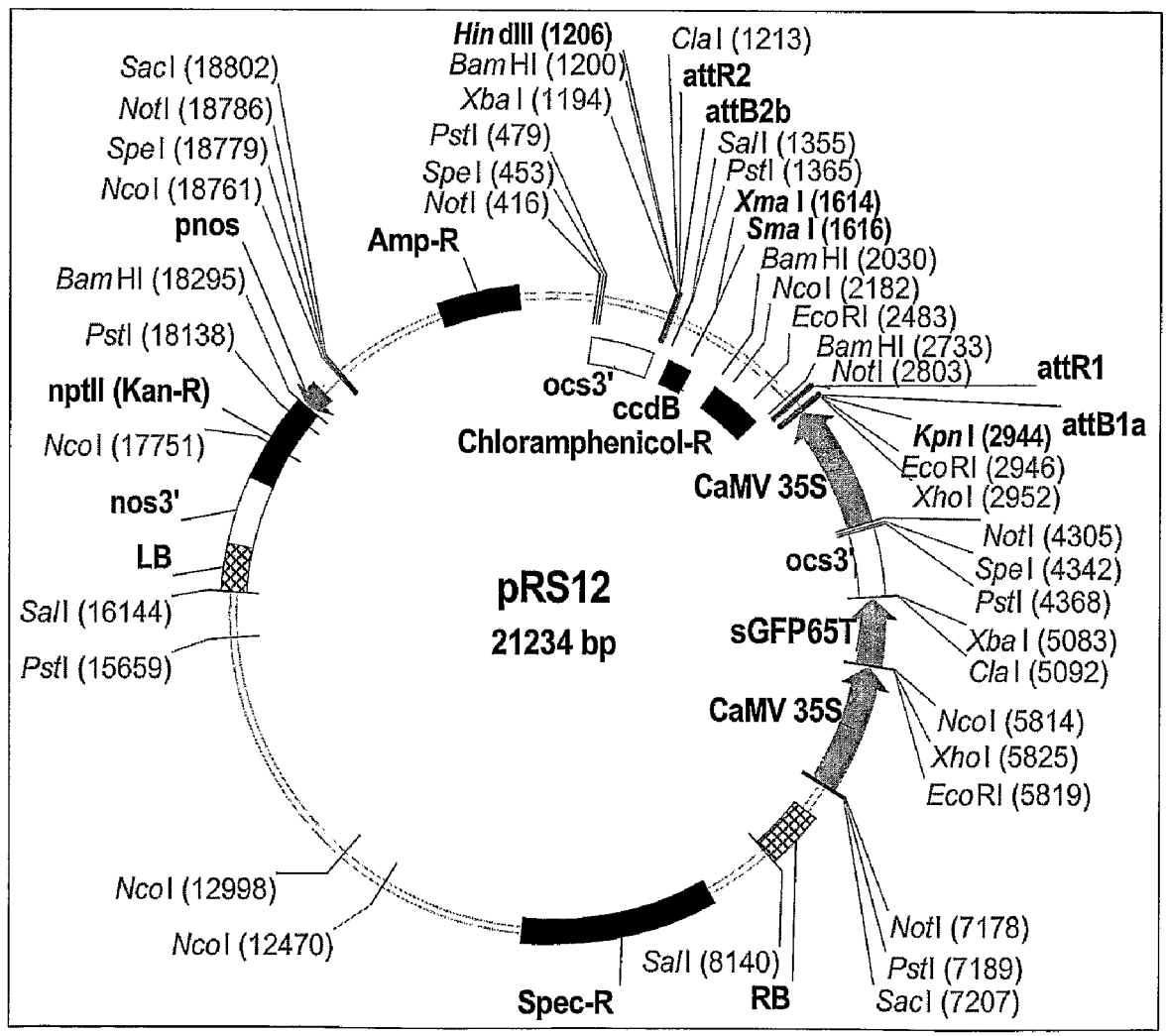

FIG. 36. Map of pRS12.

Figure 37:
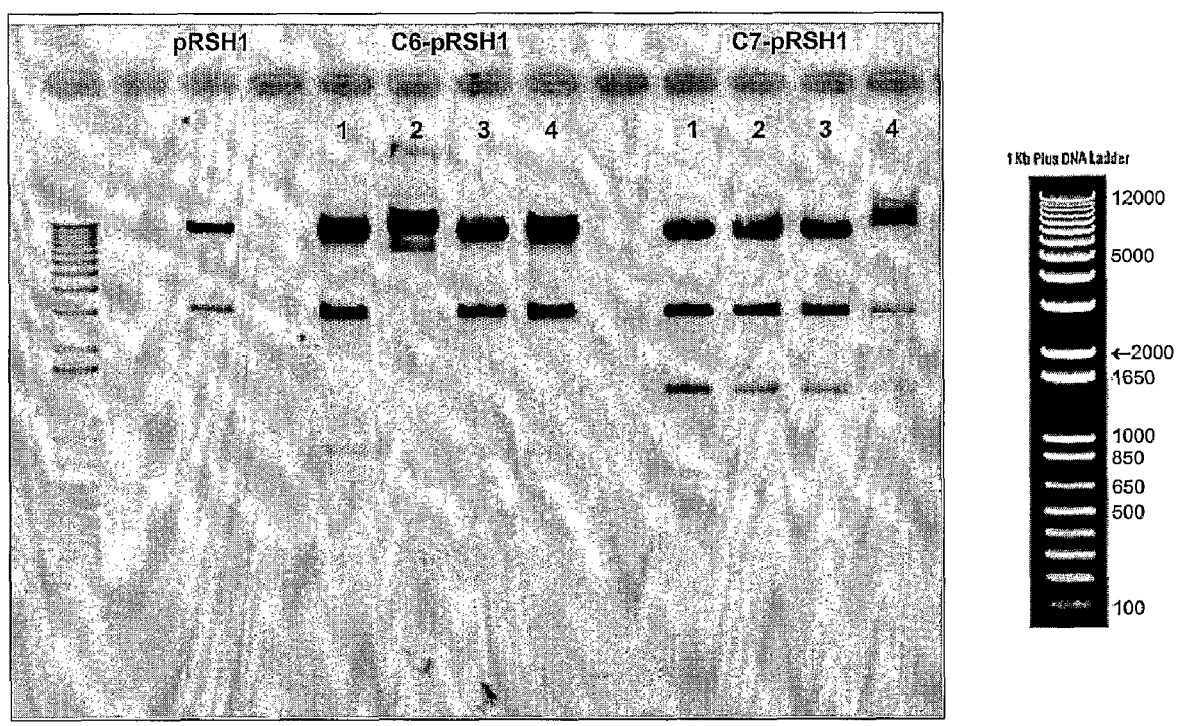

FIG. 37. EcoRI digest of C6 and C7 clones in pRSH1.
Expected Sizes:

| | | |
| --- | --- | --- |
| Clone 6-pRSH1 | 10,349 bp, 3084 bp, 725 bp and 566 bp | clones 1, 3, & 4 correct |
| Clone 7-pRSH1 | 10,349 bp, 3084 bp, 1352 bp and 566 bp | clones 1, 2, & 3 correct |
| pRSH1 | 11,525 bp, 3084 bp, 566 bp and 463 bp. | |

Figure 38:
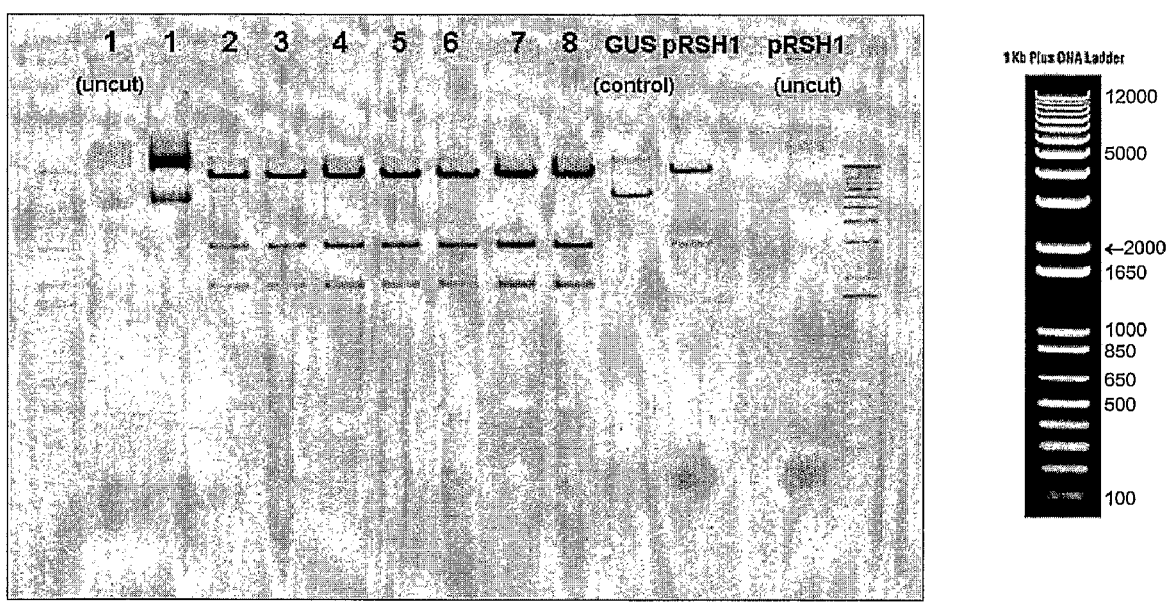

FIG. 38. EcoRI digest of C8 clones in pRSH1.
Expected Sizes:

| | | |
| --- | --- | --- |
| Clone 8-pRSH1 | 10,349 bp, 3084 bp, 1973 bp and 566 bp | clones 2-8 correct |
| pRSH1 | 11,525 bp, 3084 bp, 566 bp and 463 bp. | |

Figure 39:
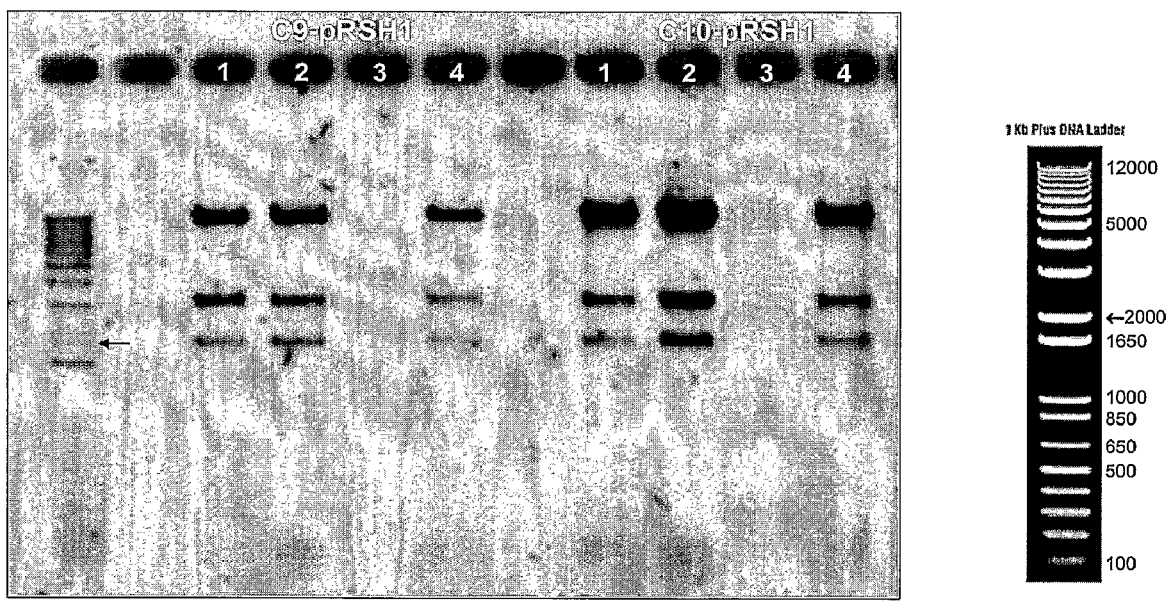

FIG. 39. EcoRI digest of C9 and C10 clones in pRSH1.
Expected Sizes:

| | | |
| --- | --- | --- |
| Clone 9-pRSH1 | 10,970 bp, 3084 bp, 1973 bp and 566 bp | clones 1, 2, & 4 correct |
| Clone 10-pRSH1 | 11,594 bp, 3084 bp, 1973 bp and 566 bp | clones 1, 2, & 4 correct. |

Figure 40:
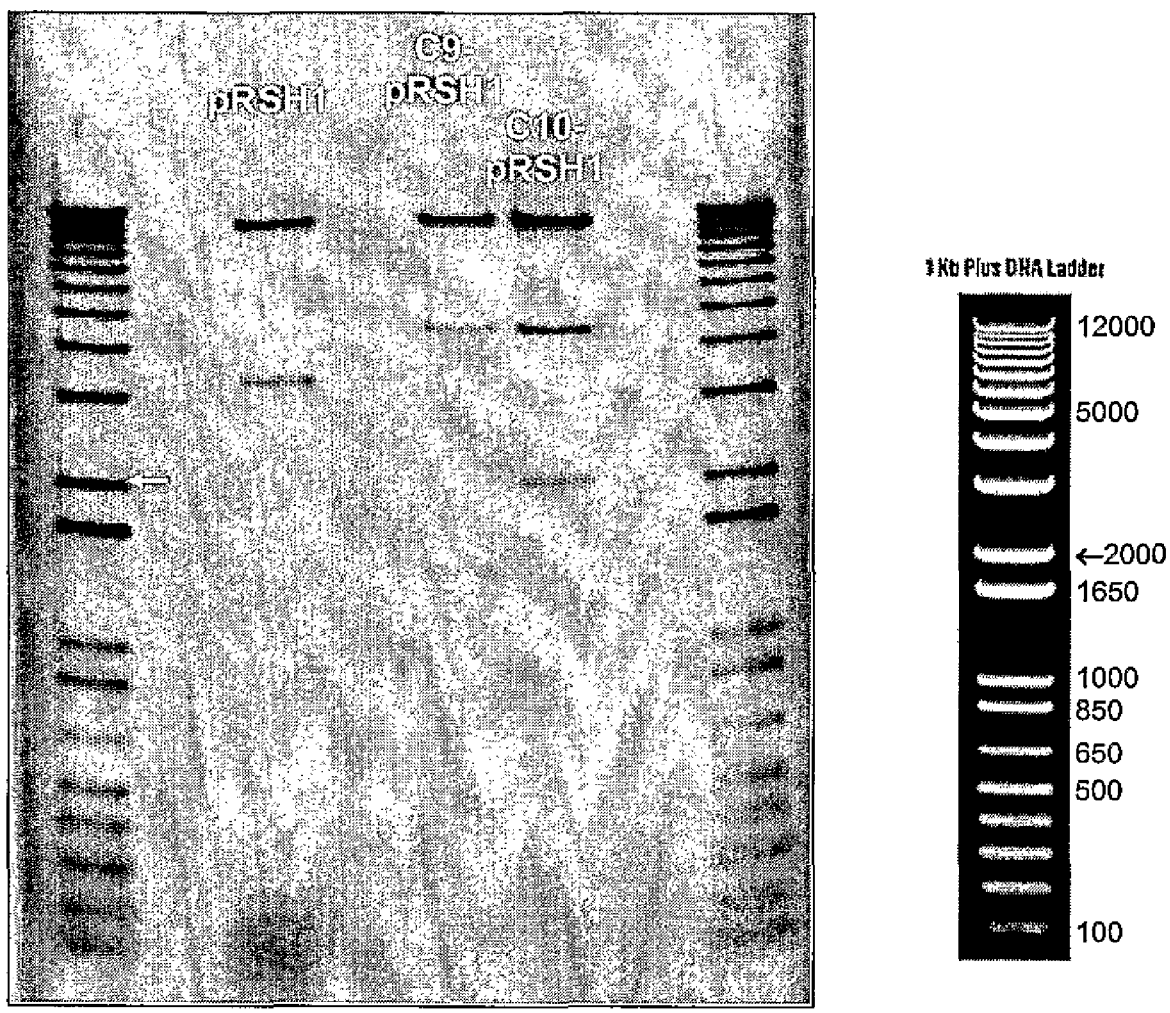

FIG. 40. BamHI digest of C9 and C10 clones in pRSH1.

Expected Sizes:

| Clone 9-pRSH1 | 10826 bp, 4400 bp and 1367 bp | clone correct |
| Clone 10-pRSH1 | 10826 bp, 4400 bp and 1991 bp | clone correct |
| pRSH1 | 10826 bp, 3279 bp, 830 bp and 703 bp. | |

Figure 41:
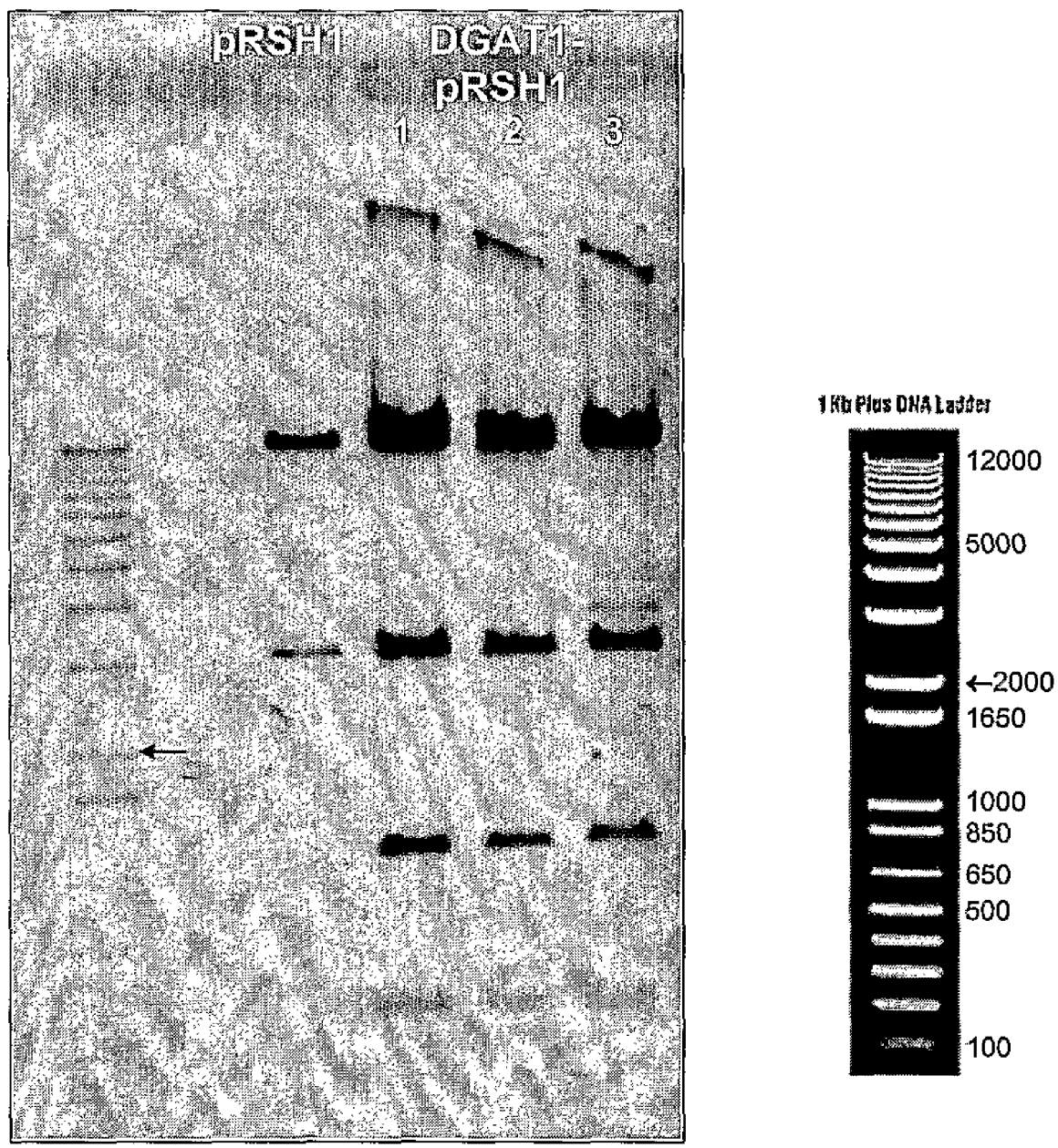

FIG. 41. EcoRI digest of DGAT1 clones in pRSH1.

Expected Sizes:

| DGAT1-pRSH1 | 10700 bp, 3084 bp, 1232 bp and 566 bp | clones 1-3 correct |
| pRSH1 | 11525 bp, 3084 bp, 566 bp and 463 bp. | |

Figure 42:
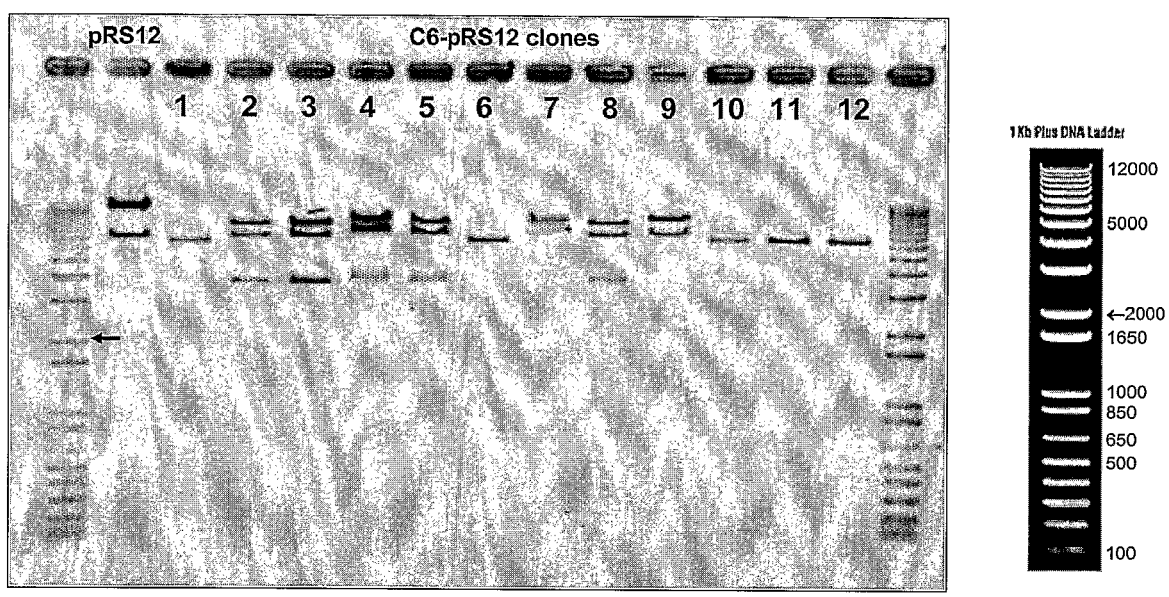

FIG. 42. EcoRV digest of C6 clones in pRS12.

Expected Sizes:

| C6-pRS12 | 9131 bp, 7424 bp and 3762 bp | clones 2, 3, 5, & 8 correct |
| pRS12 | 13810 bp and 7424 bp. | |

Figure 43:
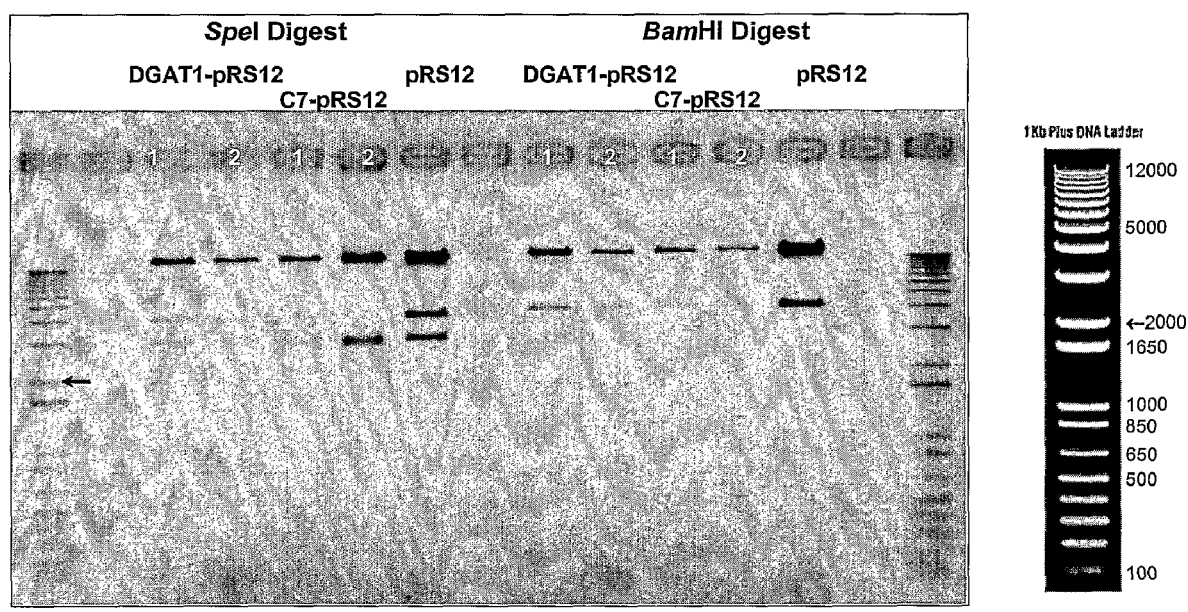

FIG. 43. Restriction digest of DGAT1 and C7 clones in pRS12.

Expected Sizes:

| DGAT1-pRS12 | SpeI | 14437 bp, 3833 bp and 2908 bp | clones 1 & 2 correct |
| C7-pRS12 | SpeI | 14437 bp, 2908 bp, 2724 bp and 878 bp | clones 1 & 2 correct |
| pRS12 | SpeI | 14437 bp, 3889 bp and 2908 bp | |
| DGAT1-pRS12 | BamHI | 17039 bp and 4139 bp | clones 1 & 2 correct |
| C7-pRS12 | BamHI | 16683 bp, 4139 bp and 125 bp | clones 1 & 2 correct |
| pRS12 | BamHI | 15562 bp, 4139 bp, 830 bp and 703 bp. | |

Figure 44:
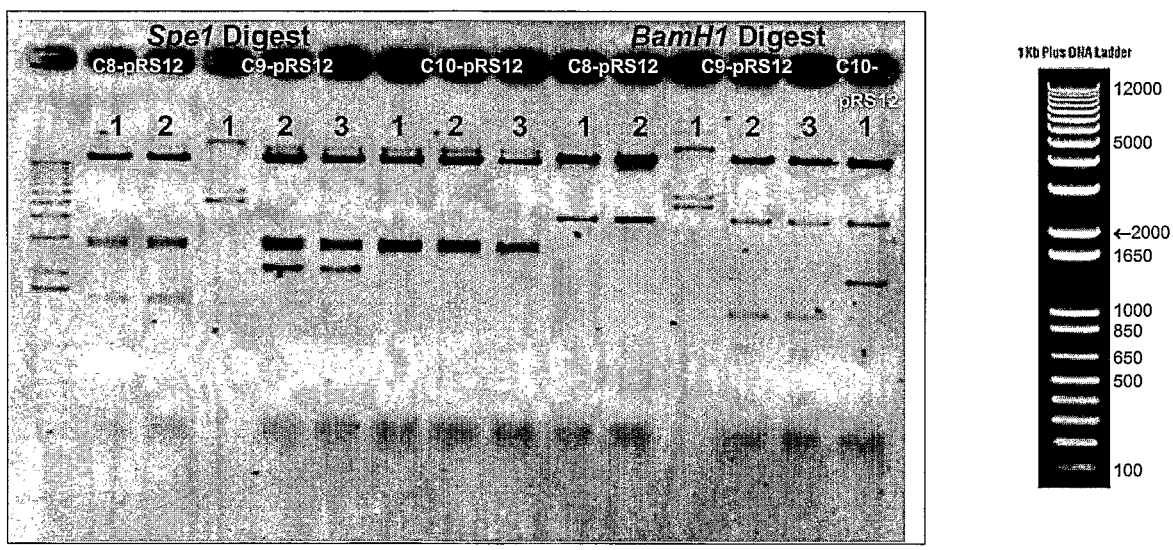

FIG. 44. Restriction digest of C8, C9 and C10 clones in pRS12.

Expected Sizes:

| C8-pRS12 | SpeI | 14437 bp, 2908 bp, 2724 bp and 1499 bp | clones 1 & 2 correct |
| C9-pRS12 | SpeI | 14437 bp, 2908 bp, 2724 bp and 2120 bp | clones 2 & 3 correct |
| C10-pRS12 | SpeI | 14437 bp, 2908 bp, 2744 bp and 2724 bp | clones 1-3 correct |
| pRS12 | SpeI | 14437 bp, 3889 bp and 2908 bp | |
| C8-pRS12 | BamHI | 16683 bp, 4139 bp and 746 bp | clones 1 & 2 correct |
| C9-pRS12 | BamHI | 16683 bp, 4139 bp and 1367 bp | clones 2 & 3 correct |
| C10-pRS12 | BamHI | 16683 bp, 4139 bp and 1991 bp | clone 1 . . . correct |
| pRS12 | BamHI | 15562 bp, 4139 bp, 830 bp and 703 bp. | |

Figure 45:
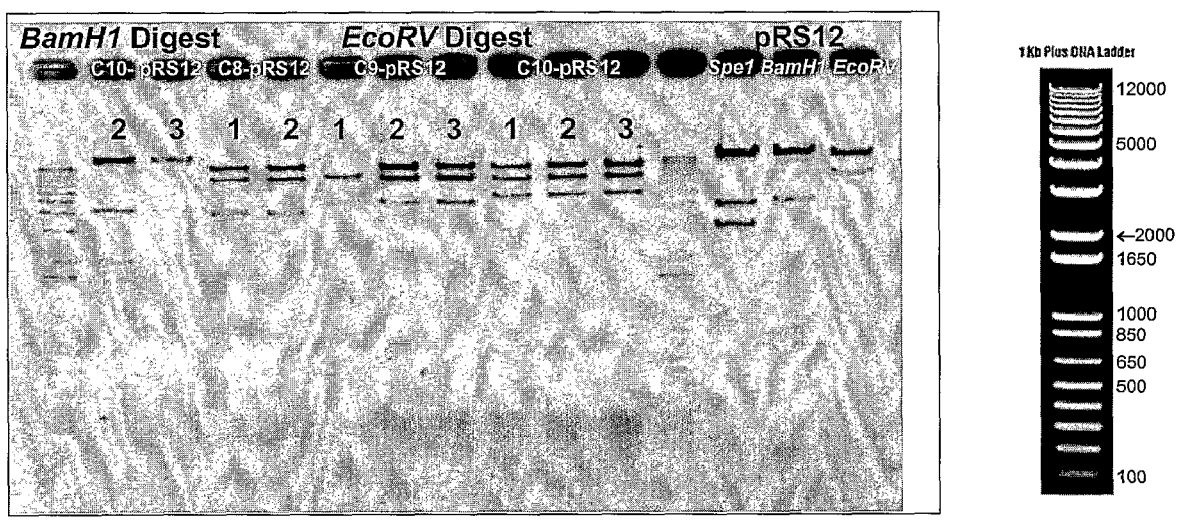

FIG. 45. Restriction digest of C8, C9 and C10 clones in pRS12.

Expected Sizes:

| C10-pRS12 | BamHI | 16683 bp, 4139 bp and 1991 bp | clones . . . 2 & 3 correct |
| C8-pRS12 | EcoRV | 10382 bp, 7424 bp and 3762 bp | clones 1 & 2 correct |
| C9-pRS12 | EcoRV | 10382 bp, 7424 bp and 4383 bp | clones 2 & 3 correct |
| C10-pRS12 | EcoRV | 10382 bp, 7424 bp and 5007 bp | clones 1-3 correct |
| pRS12 | SpeI | 14437 bp, 3889 bp and 2908 bp | |
| pRS12 | BamHI | 15562 bp, 4139 bp, 830 bp and 703 bp | |
| pRS12 | EcoRV | 13810 bp and 7424 bp. | |

Figure 46:
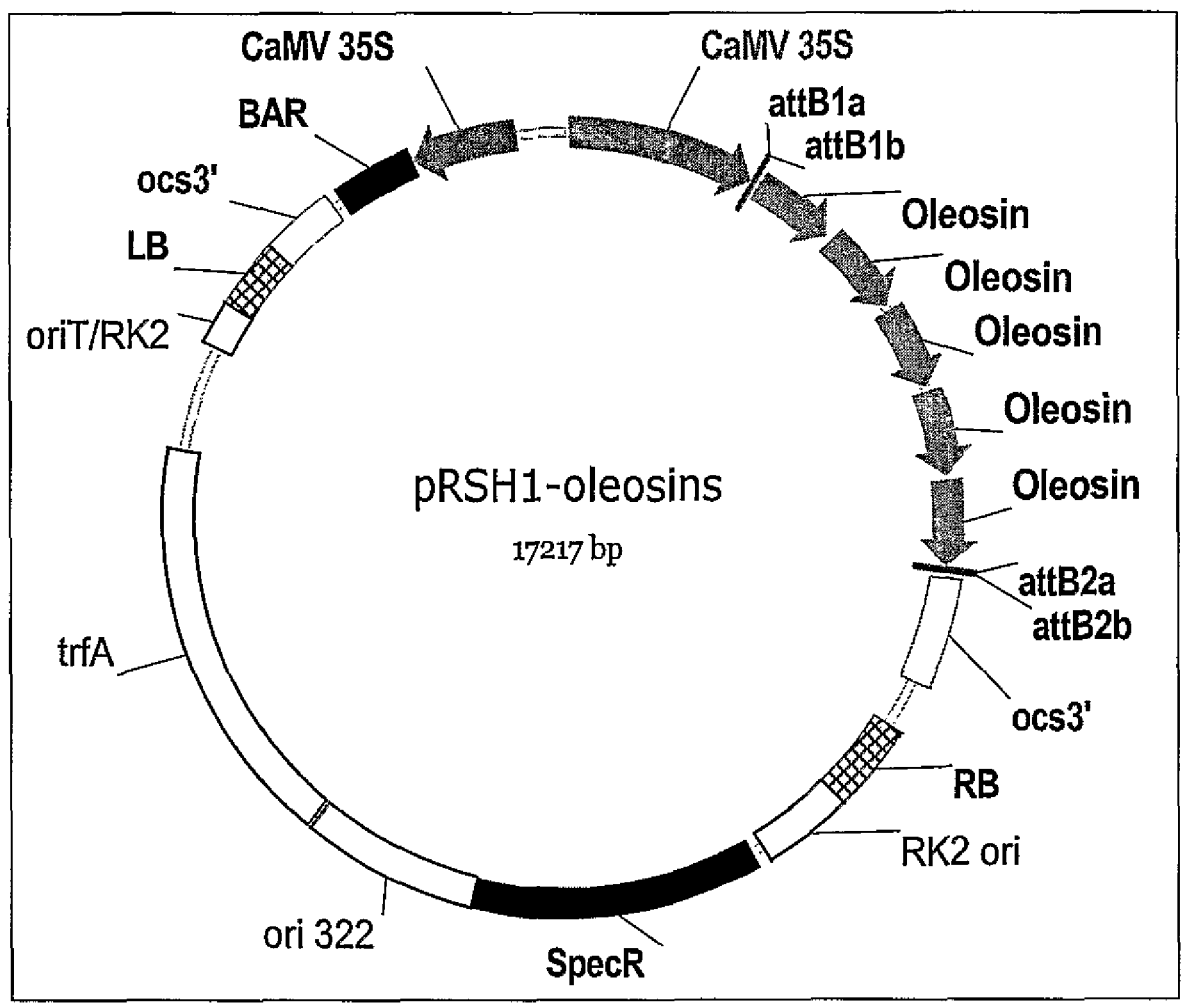

FIG. 46. A representative diagram of the pRSh1 binary vector containing oleosin multimers.

Figure 47:
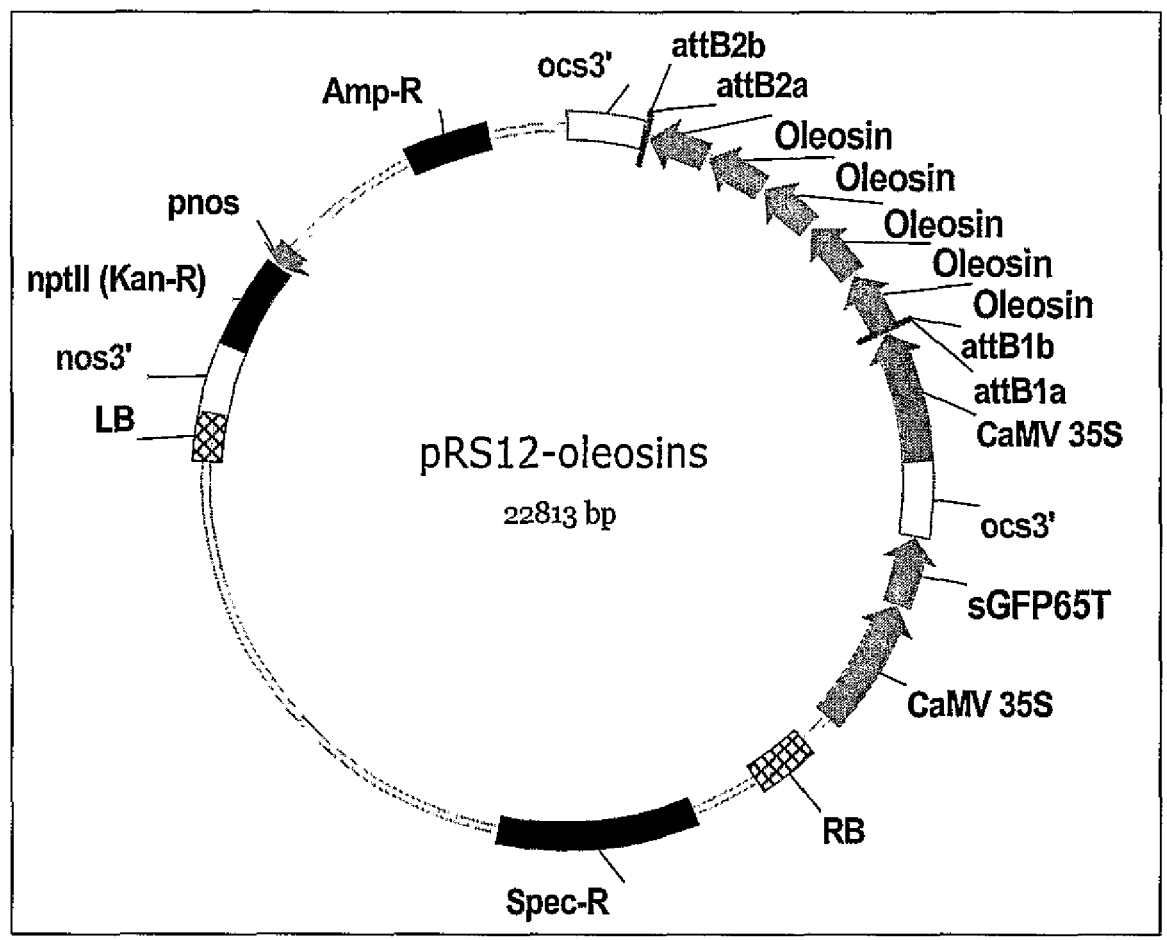

FIG. 47. A representative diagram of the pRS12 binary vector containing oleosin multimers.

Figure 48:
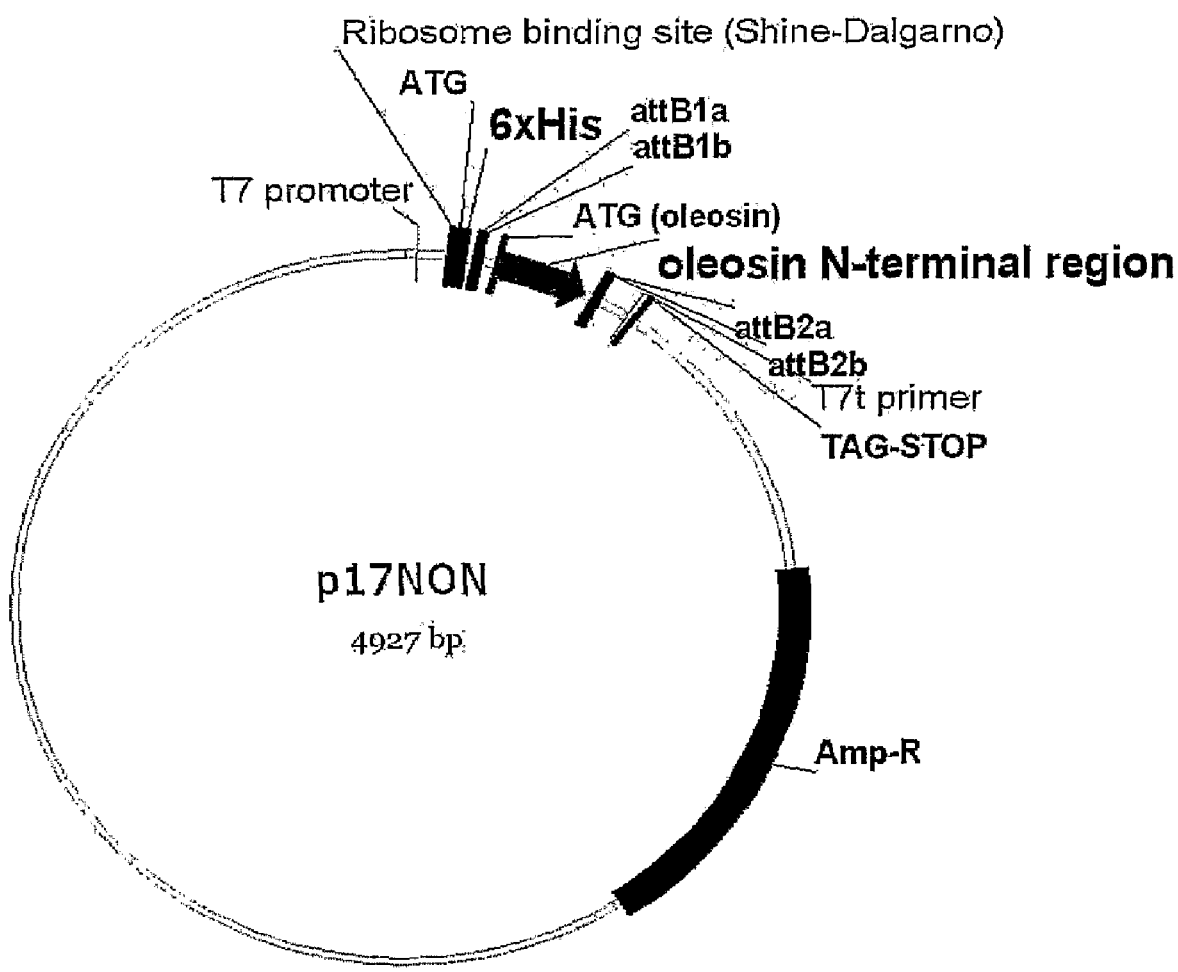

FIG. 48. Plasmid map for the expression vector p17NON (N terminal oleosin, in pDEST17).

Figure 49:
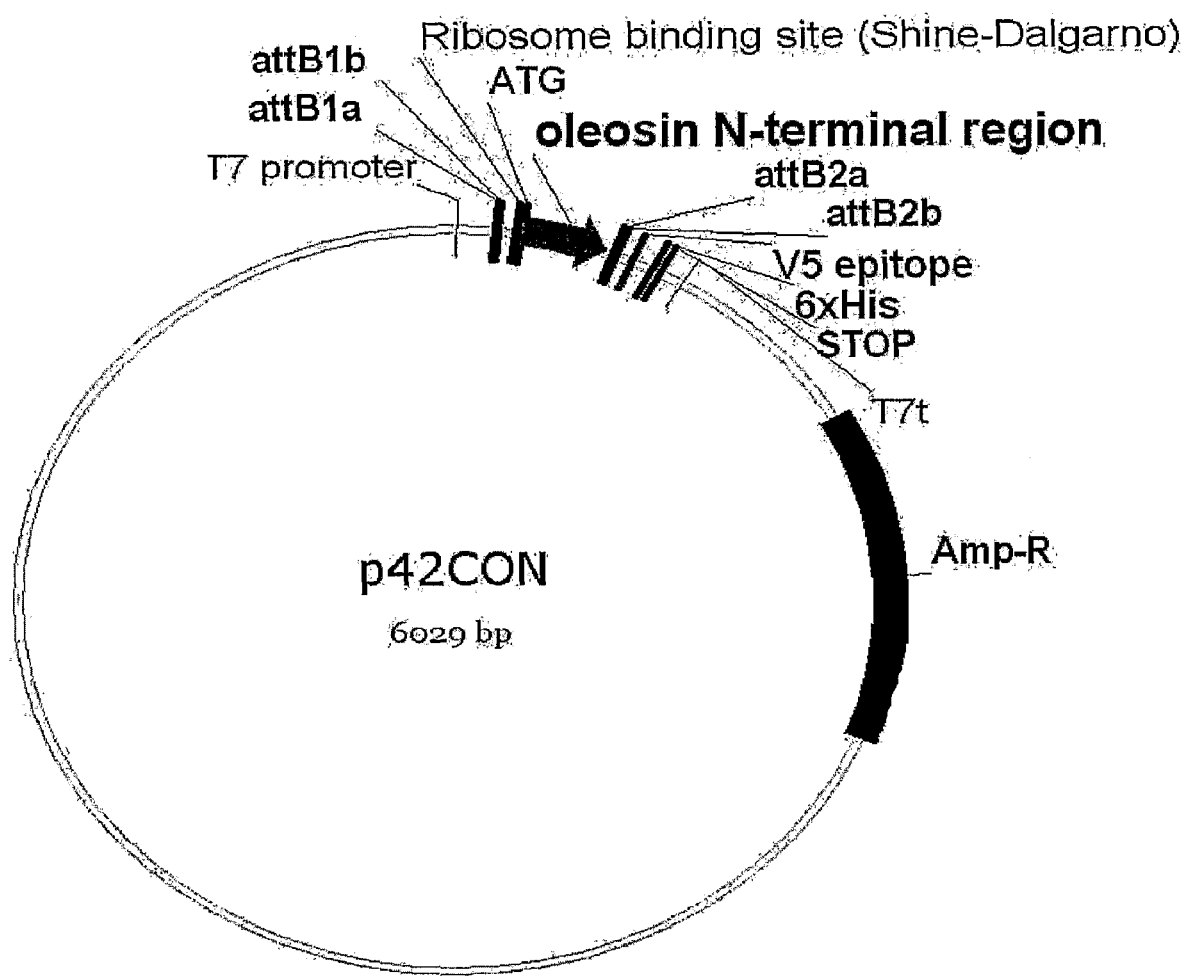

FIG. 49. Plasmid maps for the expression vectors p42CON (N terminal oleosin in pET DEST42).

Figure 50:
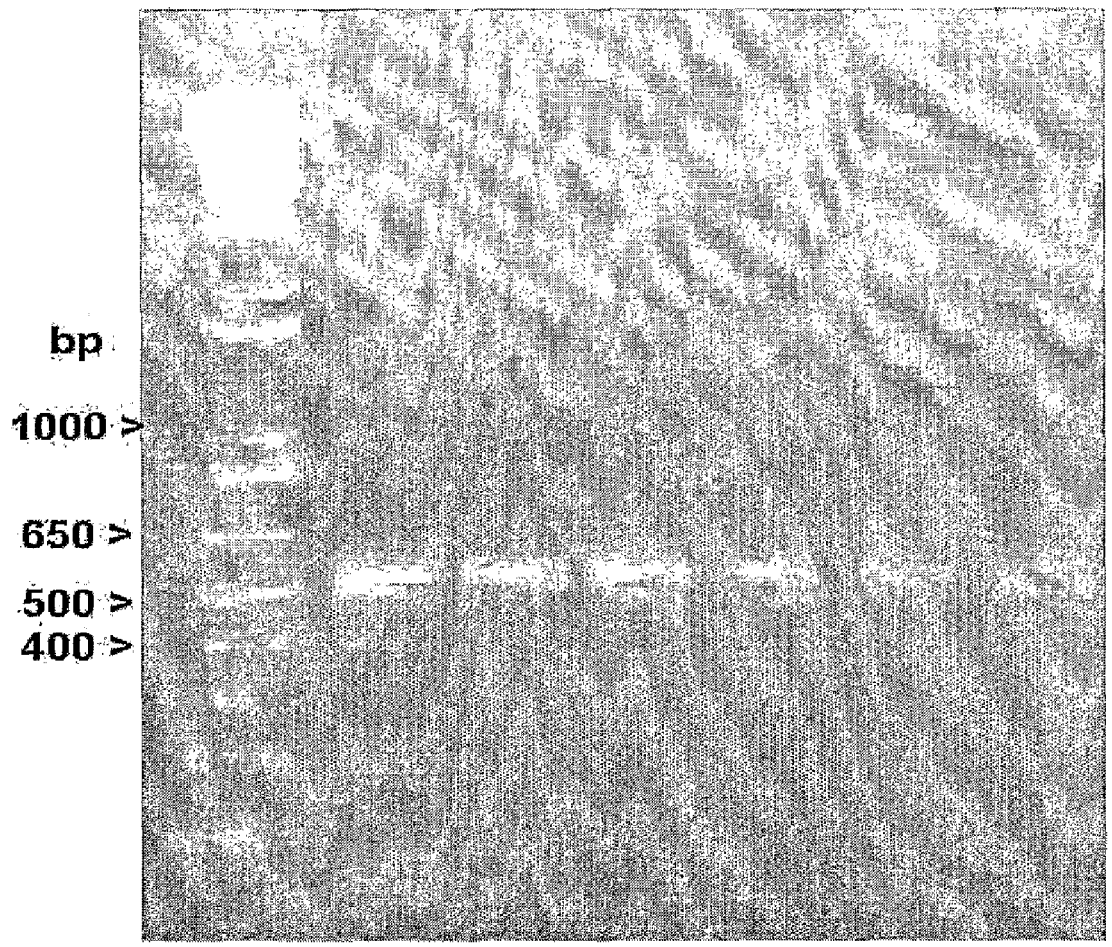

FIG. 50. Characterisation of p17NON by PCR analysis.

Expected Sizes: NT –505 bp

All plasmids appear to contain an insert of the expected size

Figure 51:
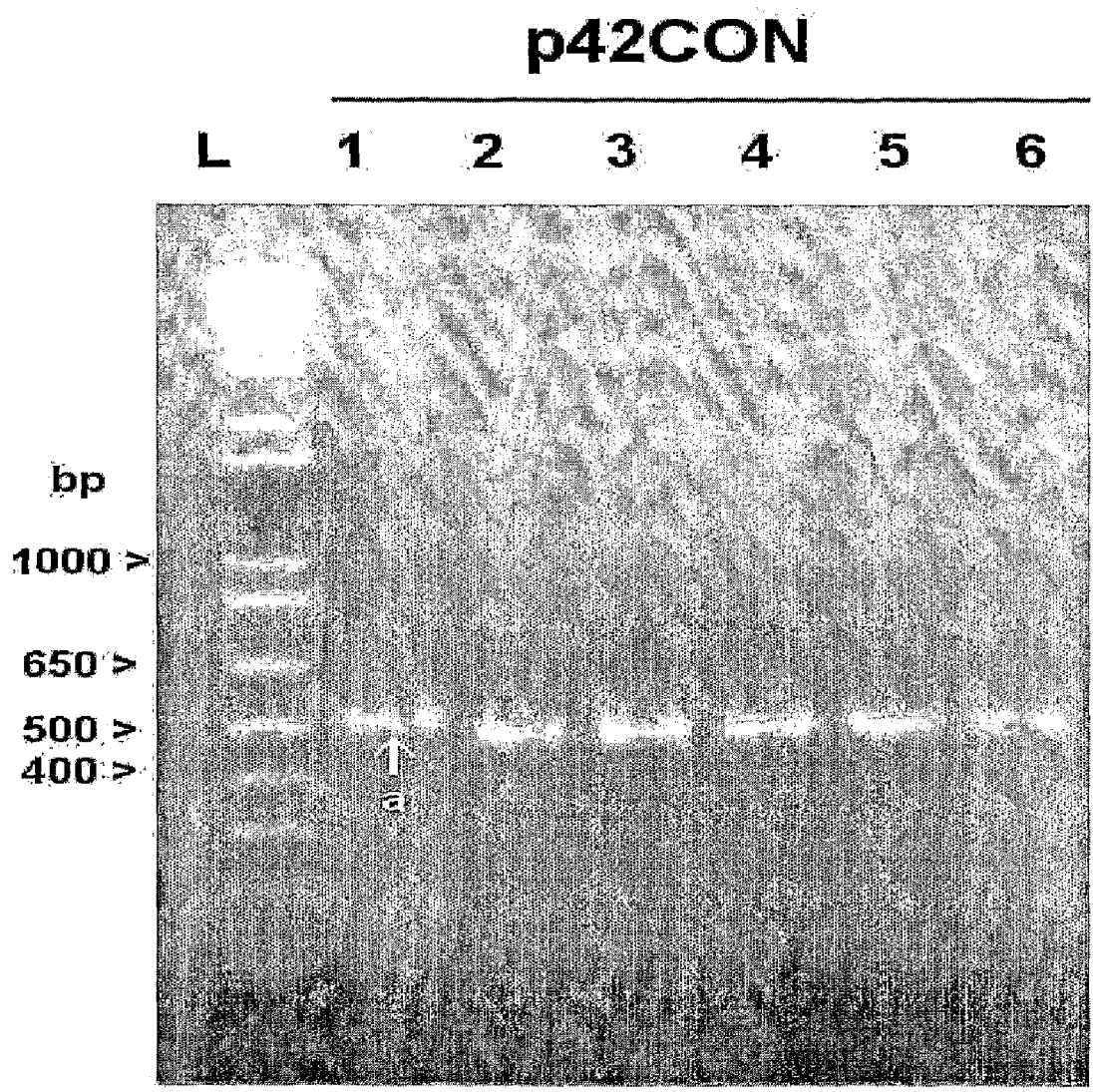

This amplification confirms the presence of the N terminal oleosin gene in the pDEST17 plasmid→p17NON FIG. 51. Characterisation of p42CON by PCR analysis.

Expected Sizes: NT –561 bp

NT#1 appears to contain a slightly larger insert.

All others appear to contain an insert of the expected size

Figure 52:
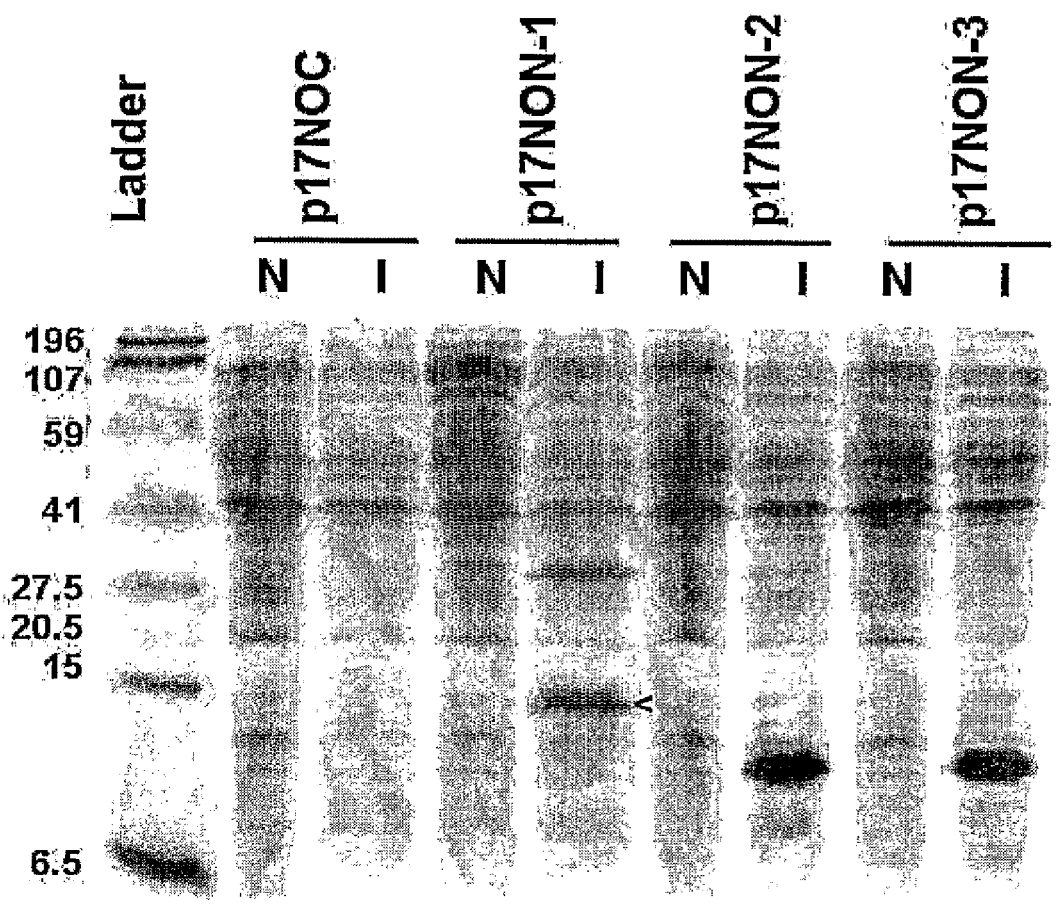

This amplification confirms the presence of the N-terminal oleosin gene in the pET DEST42 plasmid→p42CON FIG. 52. Expression analysis by SDS PAGE of 6HON. N=Non-induced I=Induced <=putative expressed 6HON expected size 6HON=14.7 kD.

Figure 53:
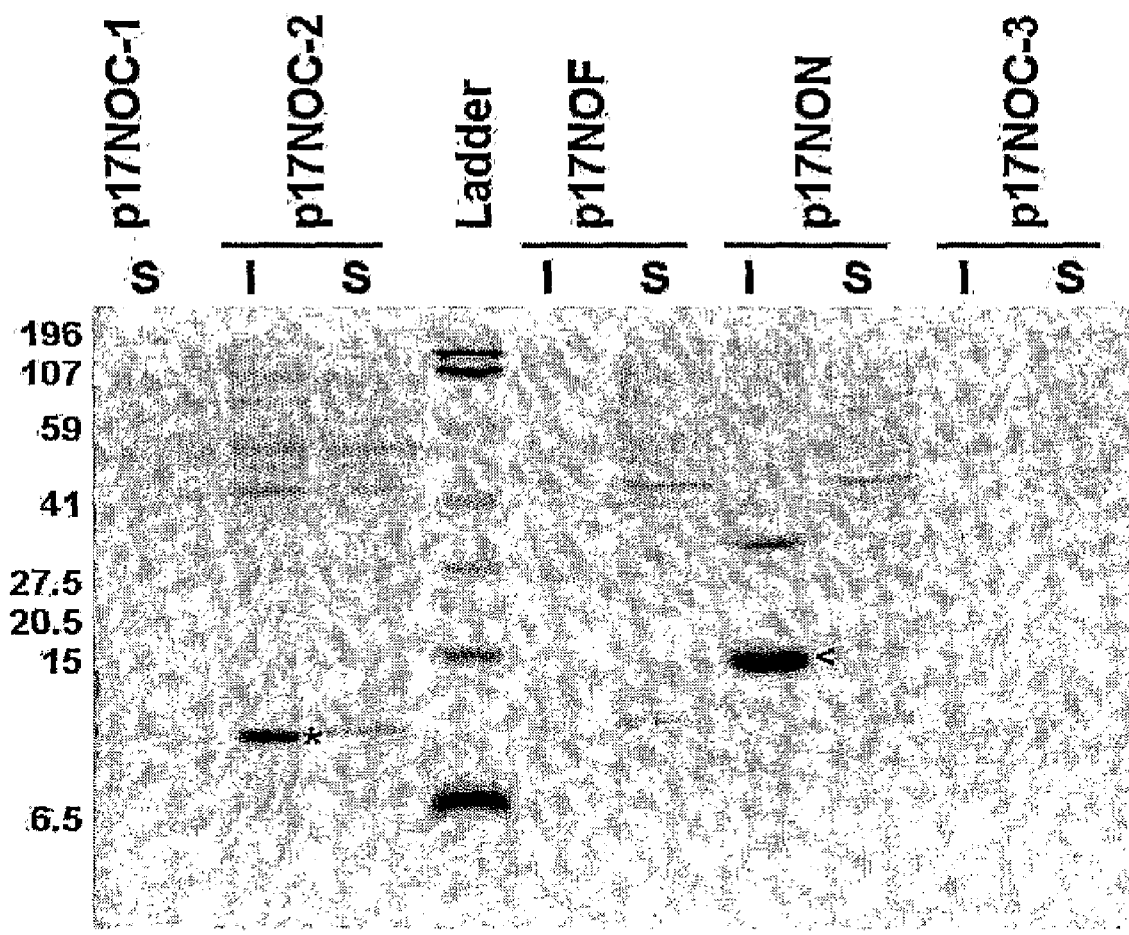

FIG. 53. Inclusion body analysis by SDS PAGE of the 6HONpeptide. N=Non induced, I=Induced, <=putative expressed 6HON, expected size 6HON=14.7 kD

*=putative expressed 6HOC expected size 6HOC=12.8 kD

Figure 54:
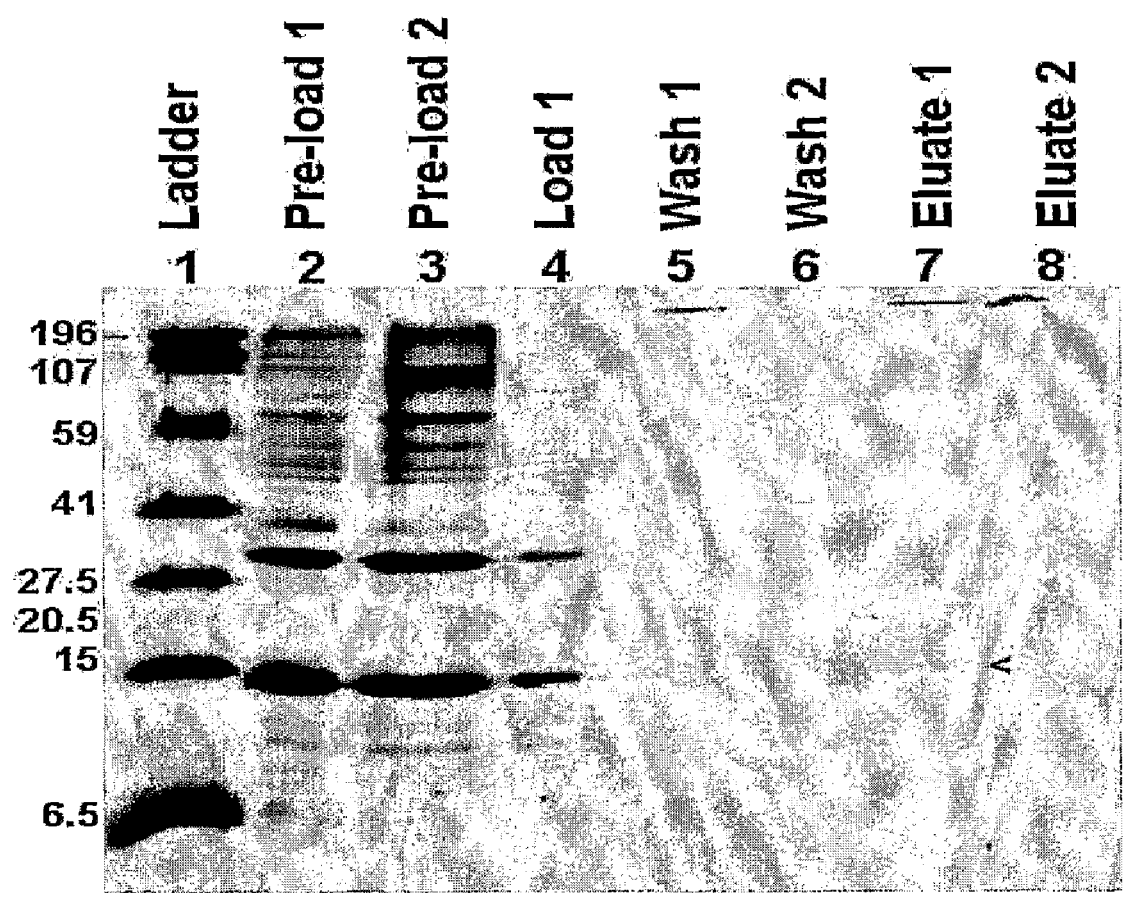

FIG. 54. Trial scale Nickel column purification analysis by SDS PAGE of 6HON. <=putative expressed 6HON expected size 6HON=14.7 kD.

Samples loaded as equivalent volumes.

Figure 55:
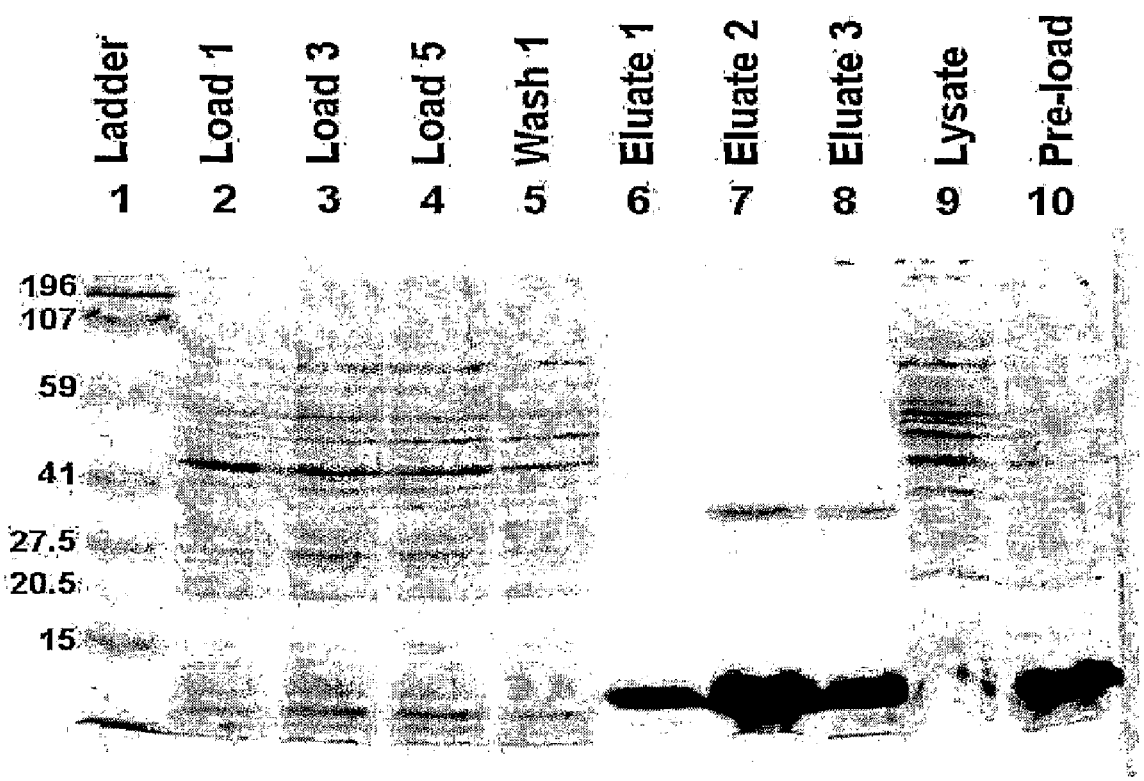

FIG. 55. Large scale Nickel purification analysis by SDS PAGE of 6HON. Expected size of 6HON=14.7 kD.

Figure 56:
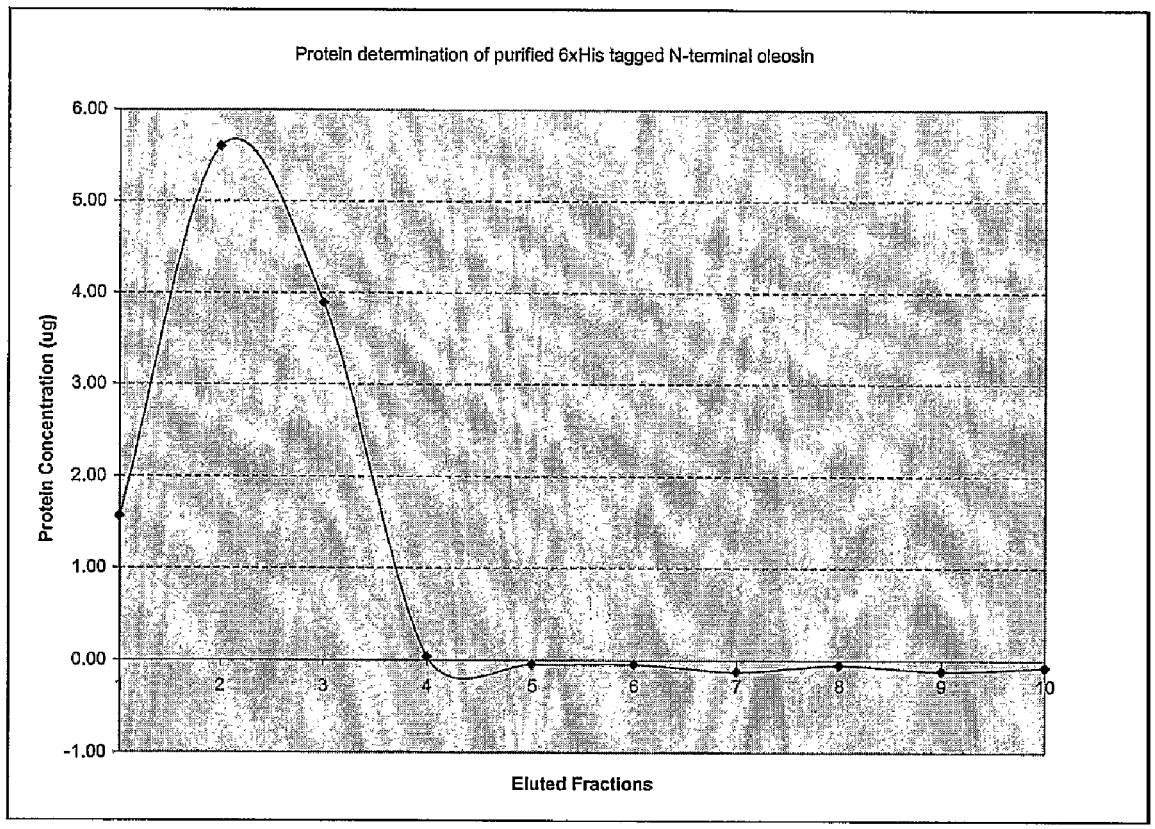

FIG. 56. Concentration of 6HON. Volume of each eluted fraction was approximately 1 mL.

Figure 57:
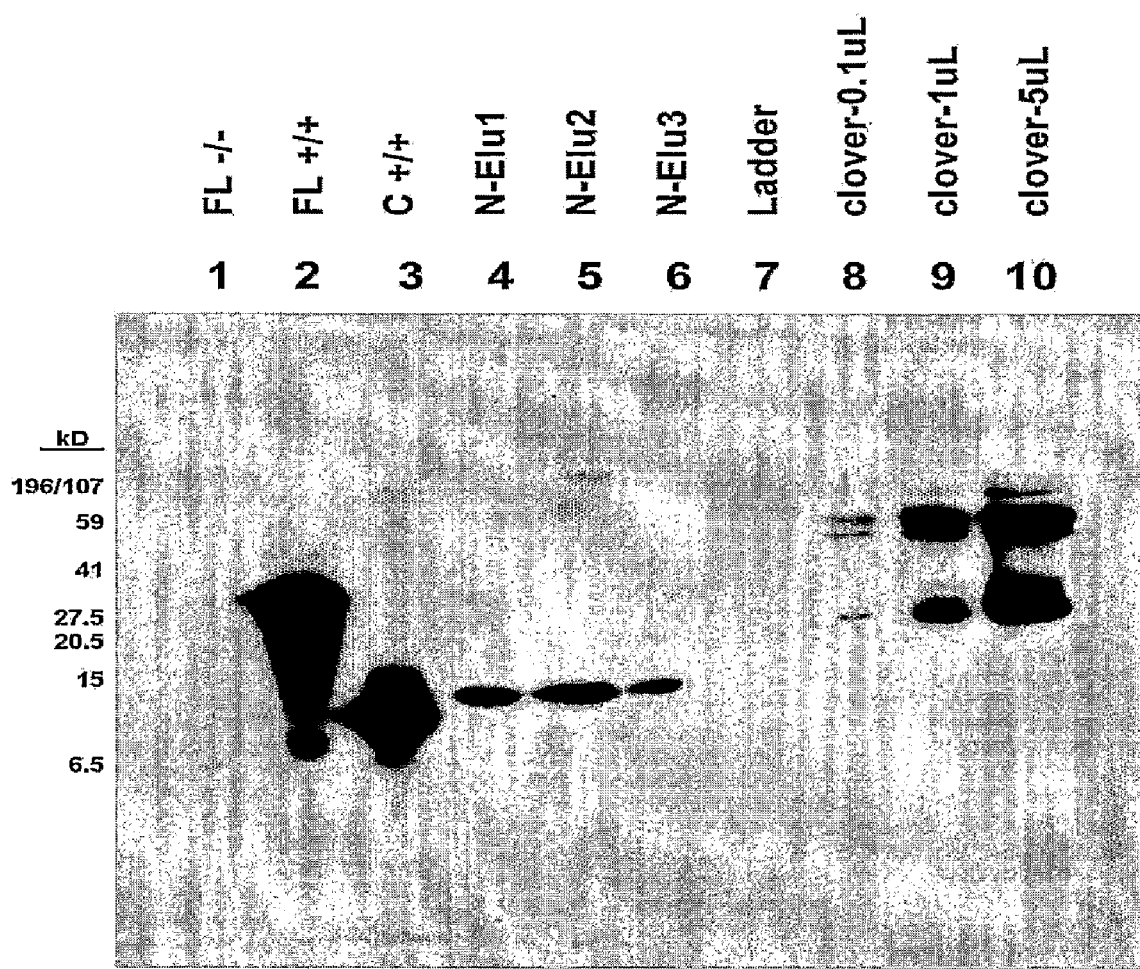

FIG. 57. SDS-PAGE/immunoblot screened against anti oleosin N terminal antibody. Run on 18% SDS PAGE gel, 90 min 150V. 1° and 2° antibody diluted in 20 mL PBS. 1° antibody=1:2000 (10 μL). 2° antibody=1:5000 (4 μL) anti rabbit Ig, Horseradish Peroxidase linked whole antibody from donkey.

Lanes 4, 5, and 6 contained 1.8, 6.9, and 4.7 ng purified 6HON, respectively. Antibody appears to bind to 17OF (Lane 2), 17OC (Lane 3) and a number of peptides present in the extract from clover seed. Reason for binding to 17OC unclear, but may be due to similarities in 6×His tag and neighbouring regions.

Figure 58:
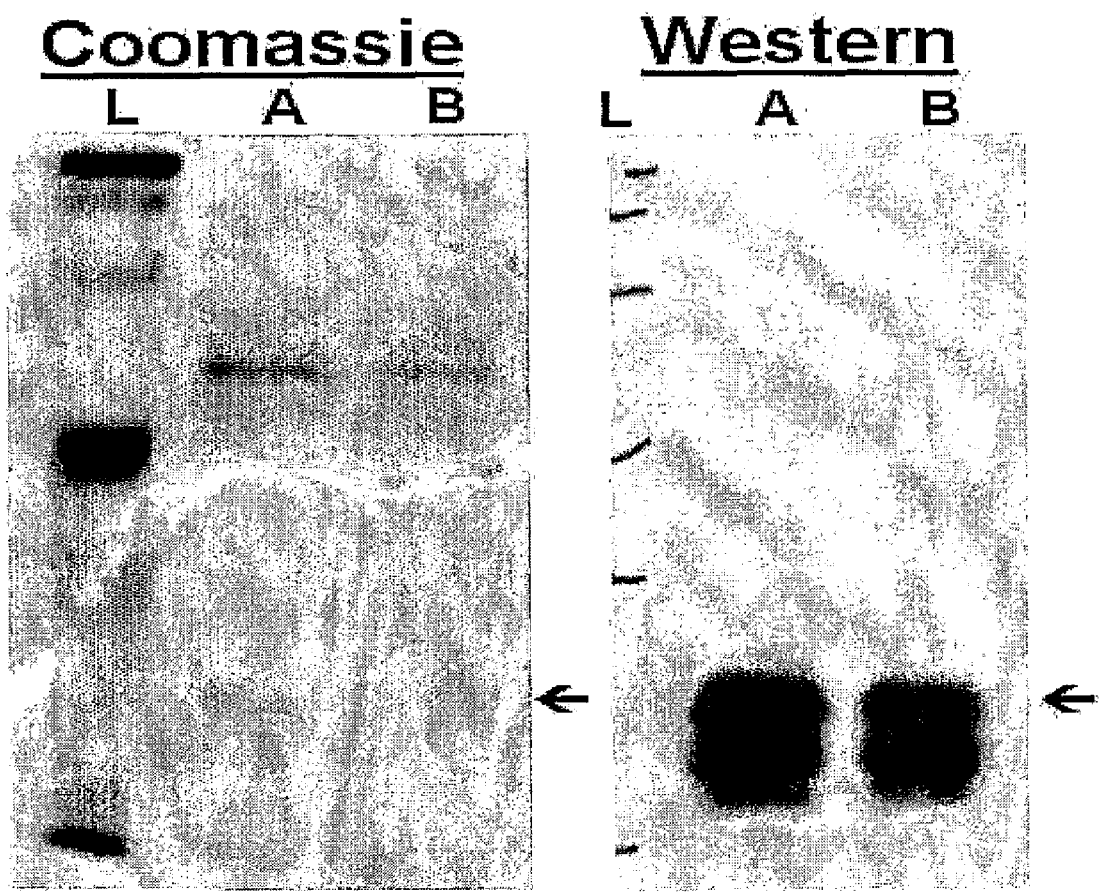

FIG. 58. Coomassie and subsequent immunoblot analysis of oil bodies extracted from clover seed. Arrow indicates expected size of clover seed oleosin (20 kDa).

L=Ladder; A & B=duplicate oil body extracts from clover seed.

Figure 59:
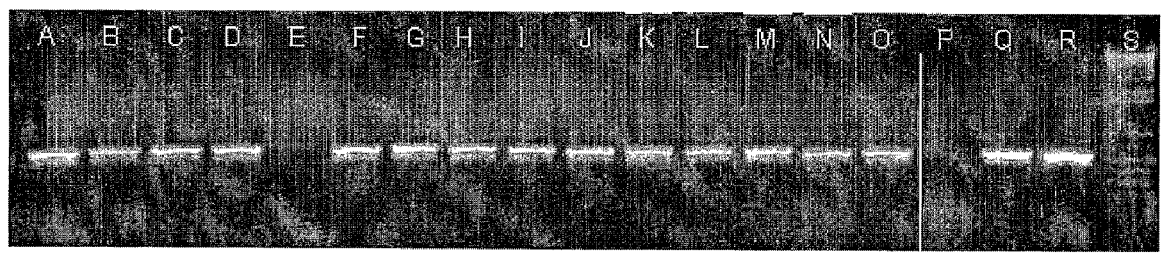

FIG. 59. PCR analysis of *Agrobacterium* colonies transformed with oleosin clone plasmids.

Lane A=AgR6; B=AgR 7; C=AgR 8;

D=AgR9; E & F=AgR10; G, H, I=AgR 7;

J, K, L=AgR 8; M, N, O=AgR 9; P=untransformed LBA4404; Q and R=AgR 7 plasmid DNA; S=1 Kb plus ladder FIG. 60. Effect of Basta on regeneration from hypocotyl (top) and cotyledon explants (bottom).

Figure 61:
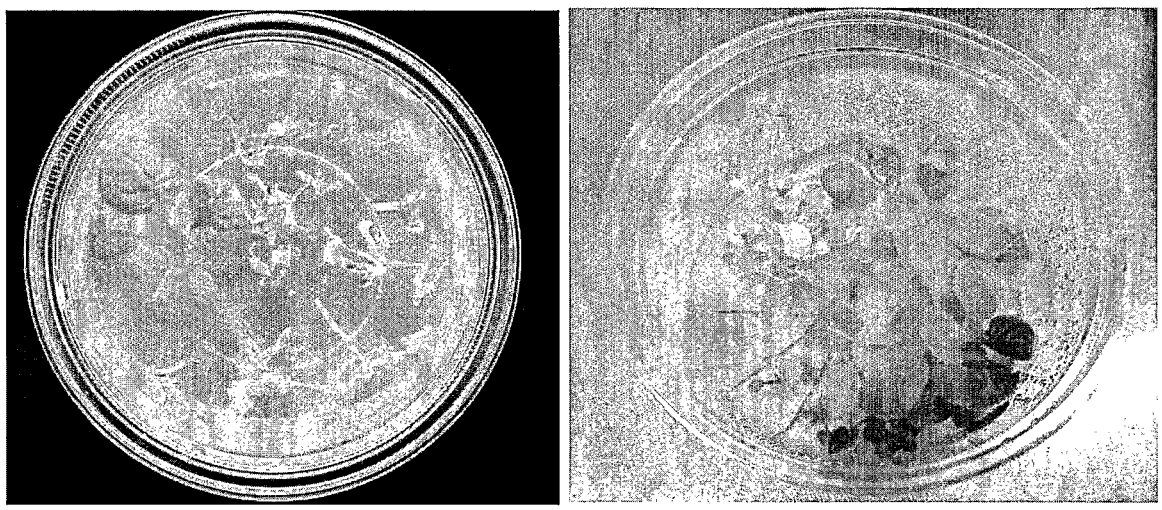

FIG. 61. Growth of Basta resistant and sensitive shoots from DGAT co cultivated explants on 5 mg/L Basta.

Figure 62:
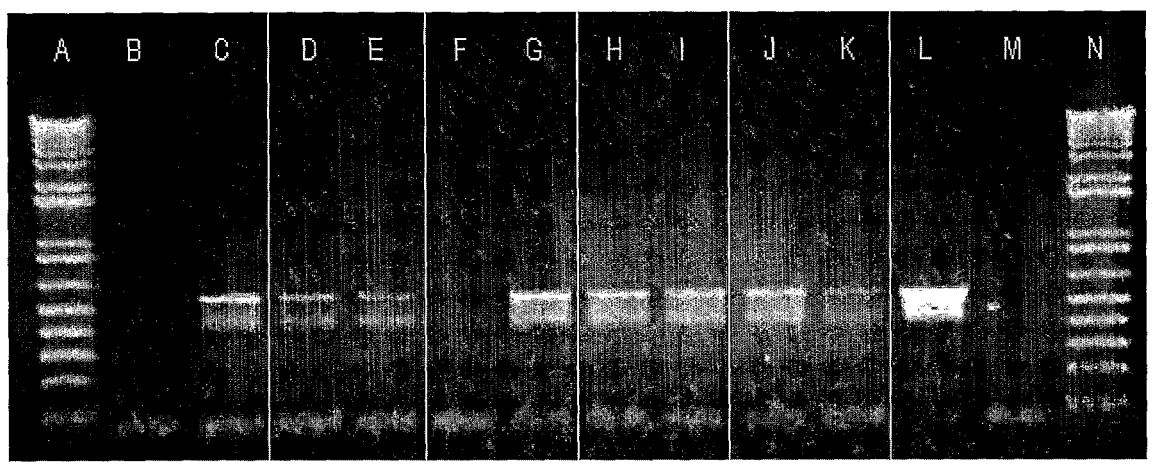

FIG. 62. PCR for the bar gene on putative transgenic shoots.

Figure 63:
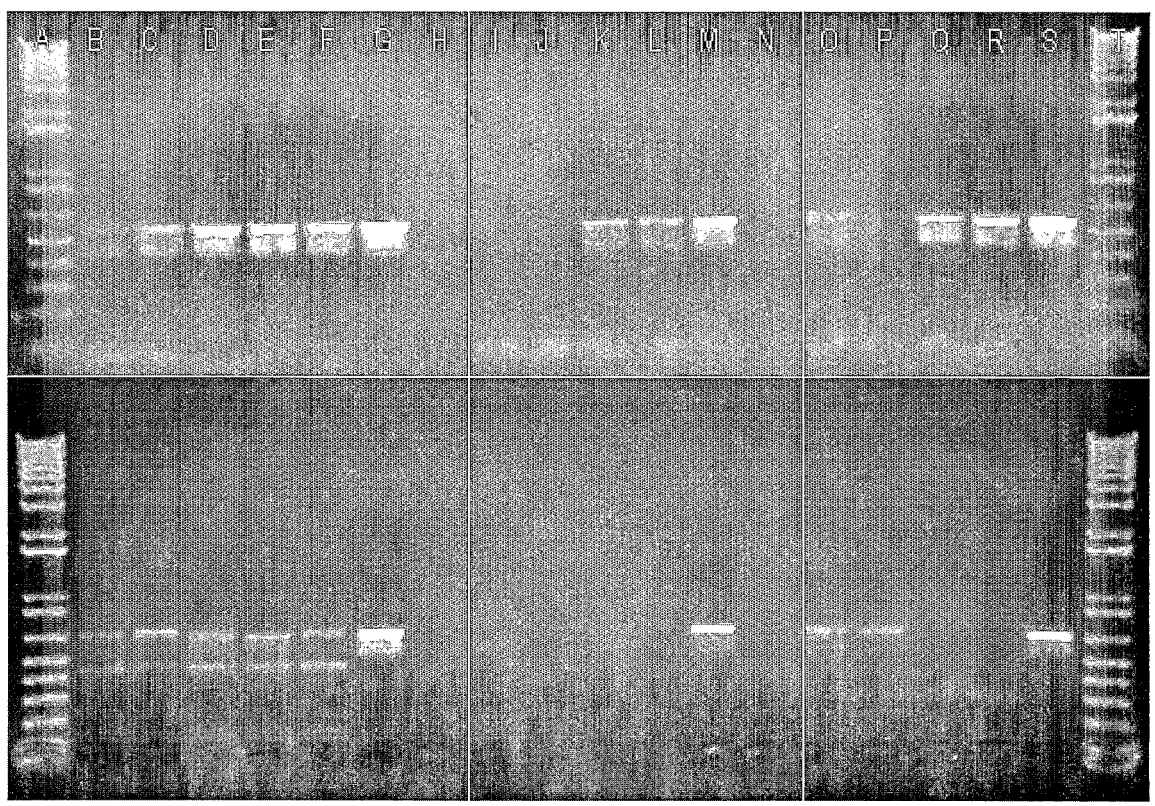

Lanes A and N 1 Kb plus ladder; lanes B and C DNA from AgR 6 shoots; lanes D and E DNA from AgR 7 shoots; lanes F and G DNA from AgR 8 shoots; lanes H and I DNA from AgR 9 shoots; lanes J and K DNA from AgR 10 shoots; lane L AgR 7 plasmid DNA; lane M blank FIG. 63. PCR for the Bar and oleosin gene.

Top panel =PCR for bar gene, Bottom panel =PCR with the same DNA using oleosin clone specific primers

| Lanes | A = 1 kb plus ladder; | B F = pRSH1 C6 plants; |
|---|---|---|
| | G = pRSH1 C6 plasmid; | H = blank; |
| | I L = pRSH1 C7 plants; | M = pRSH1 C7 plasmid; |
| | N = blank; | OR = pRSH1 C8 plants; |
| | S = pRSH1 C6 plasmid; | T = 1 kb plus ladder |

Figure 64:

FIG. 64. RT PCR for oleosin from pRSH1 C6 transgenic shoots.

Lanes A and N=1 Kb plus ladder;
B F=reverse transcriptase treated RNA from pRSH1 C6 plants;
G K RNASE treated RNA from pRSH1 C6 plants;
L=pRSH1 C6 plasmid DNA;
M blank FIG. 65. Northern blot analysis of 5 µg total RNA from *Lotus japonicus* hairy roots transformed with 1, 2, 3, 4 or 5 oleosin repeats.

Probed with 25 ng random primed 5 µCi 32P labelled oleosin cDNA.

Positive controls: +=4 pg; +=20 pg (arrows in ladder lane); oleosin gene (PCR product).

Line in single oleosin lanes indicates main transcript size detected (approximately 1.4 Kb);

Line in tandem oleosin construct lanes indicates main transcript size detected (approximately 2 Kb);

Line in trimeric oleosin construct lanes indicates main transcript size detected (approximately 2.7 Kb);

Line in tetrameric oleosin construct lanes indicates main transcript size detected (approximately 3.4 Kb);

Line in pentameric construct lanes indicates main transcript size detected (approximately 4 Kb);

Small black arrows indicate oleosin hybridising transcripts of aberrant size.

Figure 66:
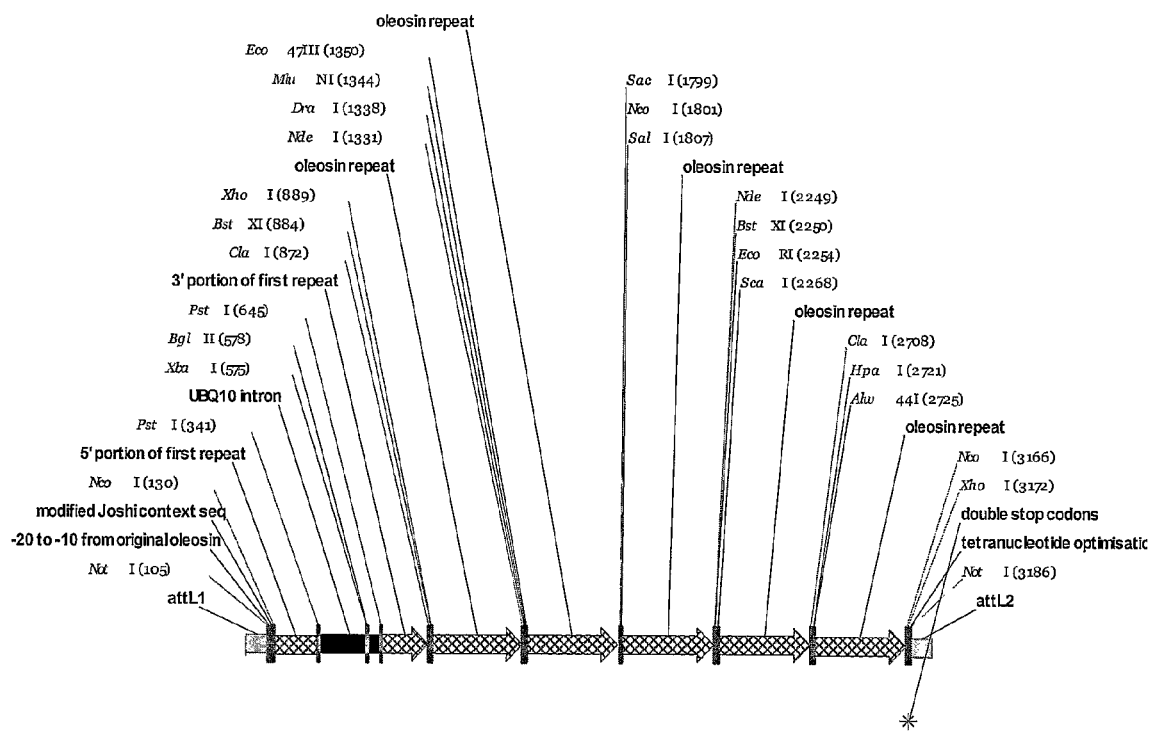

FIG. 66. Schematic diagram of the synthetic sesame seed polyoleosin construct. The sequence was generated using optimised codons selected for expression and elevated GC content, randomised between the repeats with elevated mRNA stability, cryptic splice sites removed, UBQ10 intron, Kozak, tetranucleotide stop codon and restriction sites added.

Figure 67:
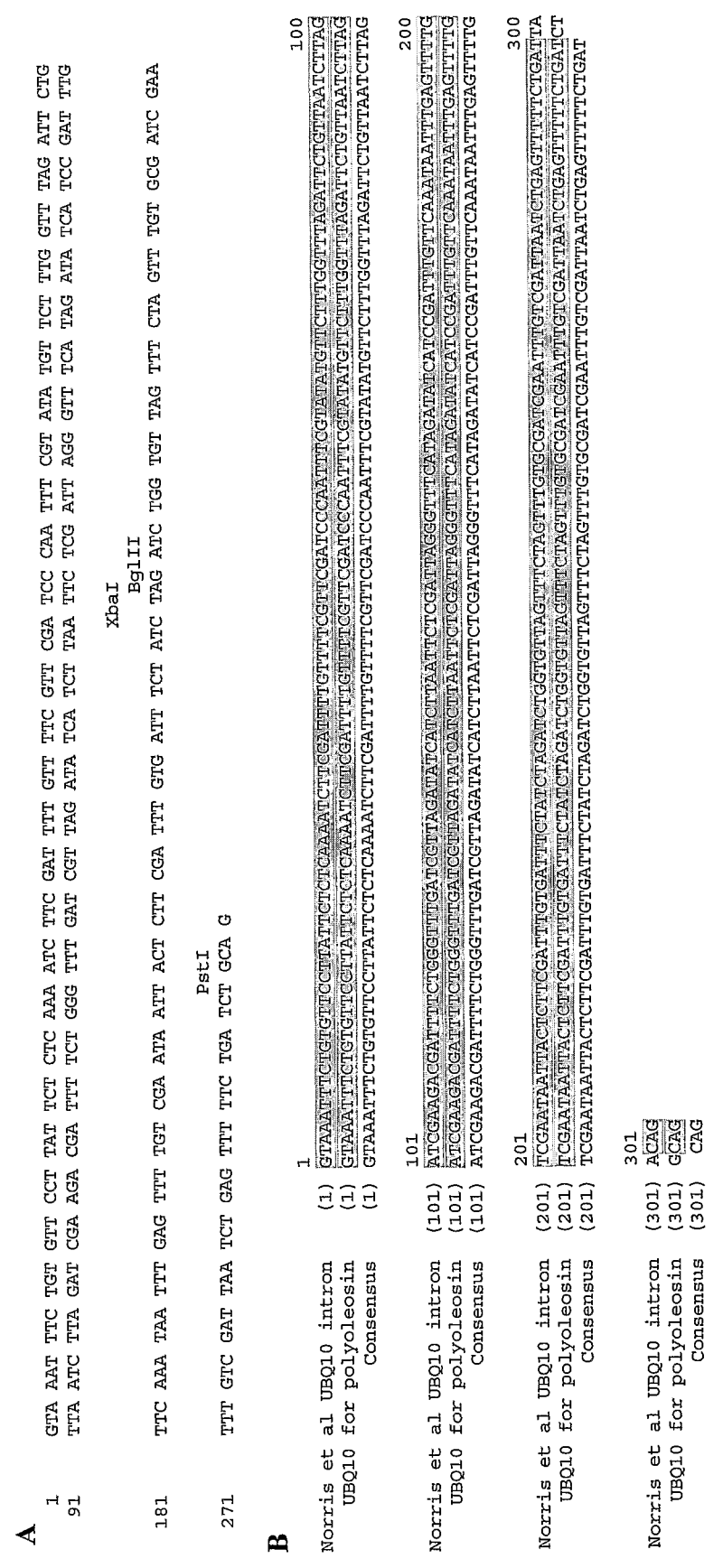

FIG. 67. *Arabidopsis thaliana* UBQ10 intron modifications.

A. Modified *Arabidopsis thaliana* UBQ10 intron (3' splice site modified to be PstI as per Rose and Beliakoff, 2000) (Seq ID No. 44).

B. Comparison of the modified UBQ10 intron (Seq ID No. 44) with the original sequence from Norris et al., (1993) (Seq ID No. 45). Consensus=Seq ID No. 46.

Figure 68:
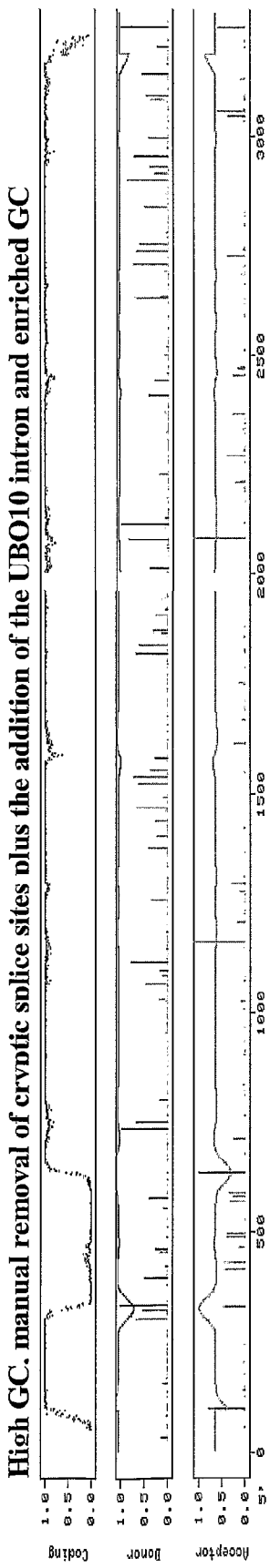

FIG. 68. NetGene2 graphical output prediction of splicing of the synthetic sesame seed polyoleosin construct. The GC content had been elevated, cryptic splice sites had been manually removed, and the *Arabidopsis thaliana* UBQ10 intron had been added.

FIG. 69. Alignment of the translated sequences of 6 tandem repeats of the original sesame seed oleosin (without linkers) (Seq ID No. 47) with the 6 tandem repeats containing random assignment of the appropriate degenerate codons, GC optimised and modified linkers (with the intron removed) (Seq ID No. 48). Consensus=Seq ID No. 49.

The alignment shows the oleosin peptide sequences of each repeat are identical, also there is no change between the randomised codons sequences with and without intron.

FIG. 70. Nucleic acid (Seq ID No. 50) and amino acid (Seq ID No. 51) Sequence and feature map of the synthetic sesame seed hexameric polyoleosin with randomised optimal degenerate codons, enriched GC content, enhanced mRNA stability, engineered restriction sites (also optimised for codon usage) and modified UBQ10 intron.

Key: attL sites (bold); engineered restriction sites and linkers (italics); oleosin repeats (grey box, white letters); double stop codon to ensure no read through due to amber codon (bold, underline); tetra-nucleotide stop codon (black box, white letter); UBQ10 intron (grey box, black letters); −20 to −11 from original cDNA (underline); −10 to −1 modified Joshi et al (1997) consensus sequence (bold, italics, underline).

Figure 71:
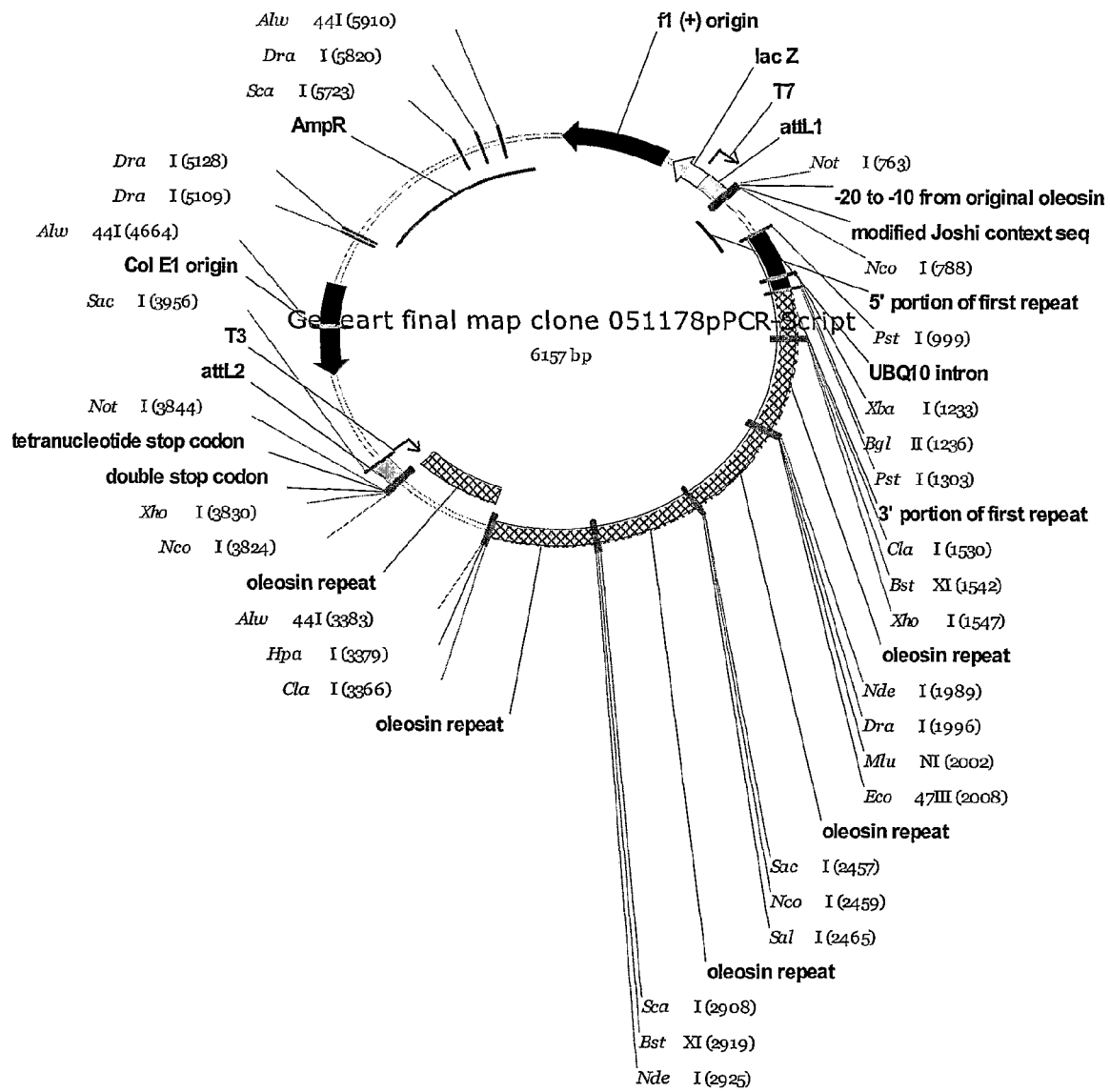

FIG. 71. Vector map of the synthetic sesame seed polyoleosin construct in PCR Script.

FIG. 72. Nucleotide sequence of clone synthesised by GENEART AG containing 6 tandem Sesame seed oleosin repeats with randomised degerate codons (Seq ID No. 52).

FIG. 73. Feature map of the nucleotide sequence of the identical triple oleosin repeats synthesised by GENEART AG (Seq ID No. 53).

FIG. 74. Feature map of nucleotide sequence of pET29+Ole6-6×His (Seq ID No. 54).

FIG. 75. Feature map of nucleotide sequence of pET29+Ole2-6×His (Seq ID No. 55).

FIG. 76. Feature map of nucleotide sequence of pET29+Ole4-6×His (Seq ID No. 56).

FIG. 77. Feature map of nucleotide sequence of pET29+Ole5-6×His (Seq ID No. 57).

FIG. 78. Peptide sequence of: pET29+Ole6-6×His (Seq ID No. 58).

FIG. 79. Peptide sequence of: pET29+Ole2-6×His (Seq ID No. 59).

FIG. 80. Peptide sequence of: pET29+Ole4-6×His (Seq ID No. 60).

FIG. 81. Peptide sequence of: pET29+Ole5-6×His (Seq ID No. 61).

FIG. 82. Peptide sequence of: pUCOle3+(Seq ID No. 62).

FIG. 83. Peptide sequence of: p29Ole (Seq ID No. 63).

Figure 84A:
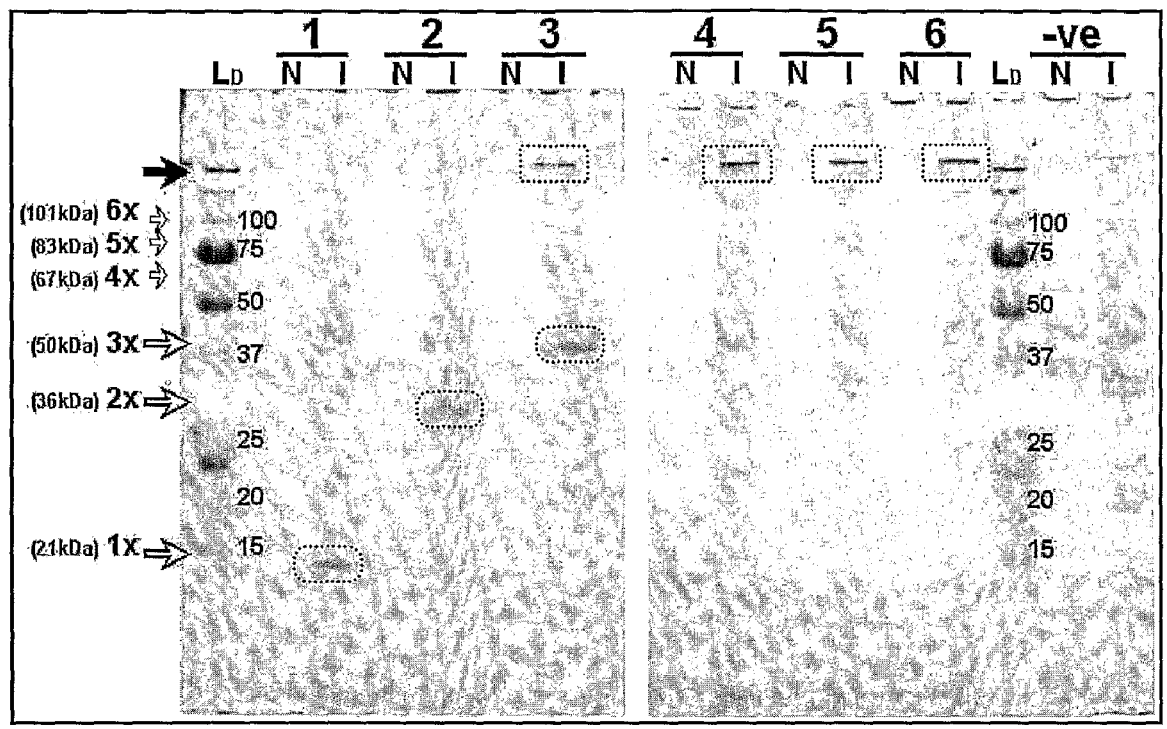
Figure 84B:
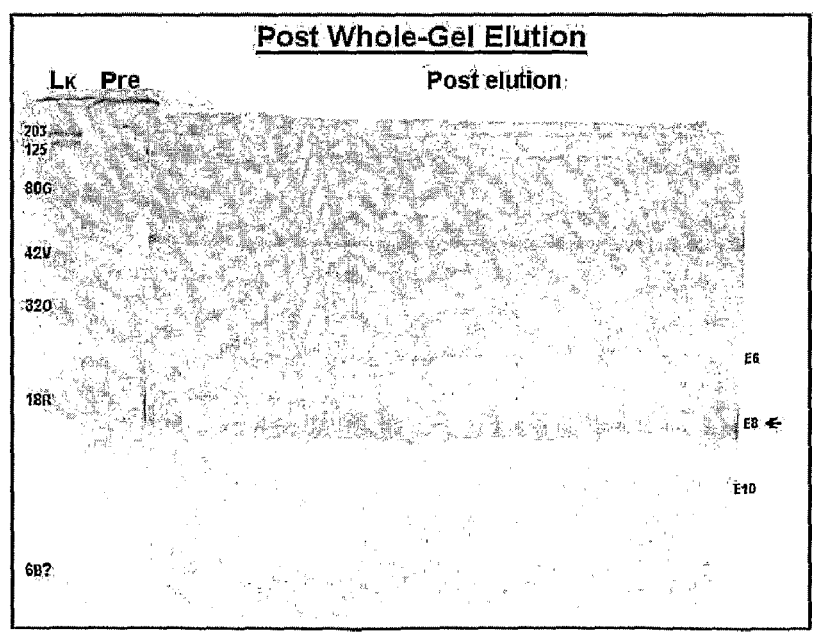

FIG. 84. Whole gel elution results from prokaryotic expression and purification of sesame seed oleosin.

A. Preliminary analysis of 1×–6×AOBs by SDS-PAGE separation.

Small arrows indicate expected sizes of 4×, 5× and 6× oleosin (rectangular boxes). Large arrows indicate bands of putative polyoleosin protein corresponding to 1×, 2, and 3× oleosins (oval boxes). Expected molecular weights are shown in brackets.

B. Coomassie stained SDS-PAGE gel after whole gel elution (39C_sesame_oleosin_AOBs.doc).

$L_K$=BioRad Kaleidoscope Standards (cat#161-0324) Pre=Coomassie stained slice of acrylamide gel prior to elution ←=expected size of oleosin.

Figure 85:
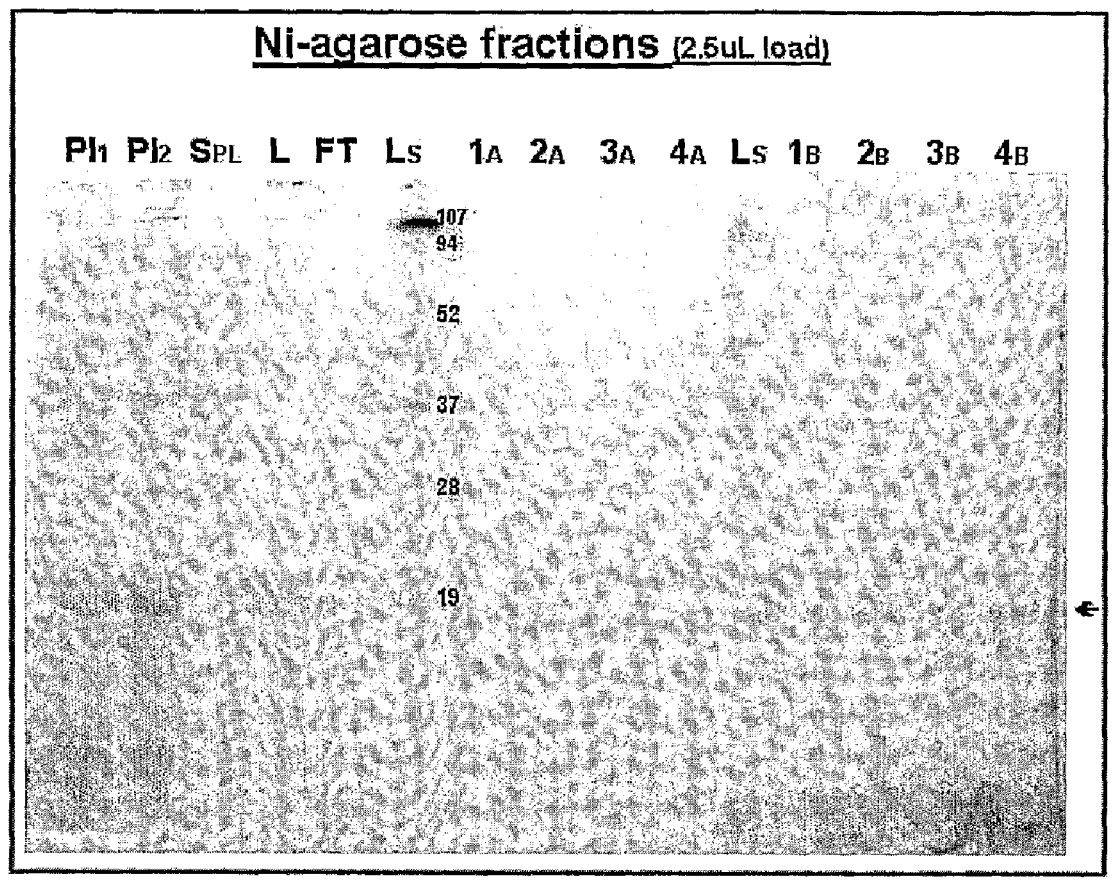

FIG. 85. SDS-PAGE analysis of fractions from Ni-affinity purification of prokaryotically expressed denatured sesame seed oleosin (48C_sesame_oleosin_His_pur.doc).
PI=Post Induction SPL=Supernatant, Post Lysis
L=Lysate FT=Flow Through
$L_S$=BioRad Prestained SDS-PAGE Standards, Low Range (cat#161-0305)
$\#_A$ & $\#_B$=Fraction number from either column A or B.
←=expected size of oleosin.

Figure 86:
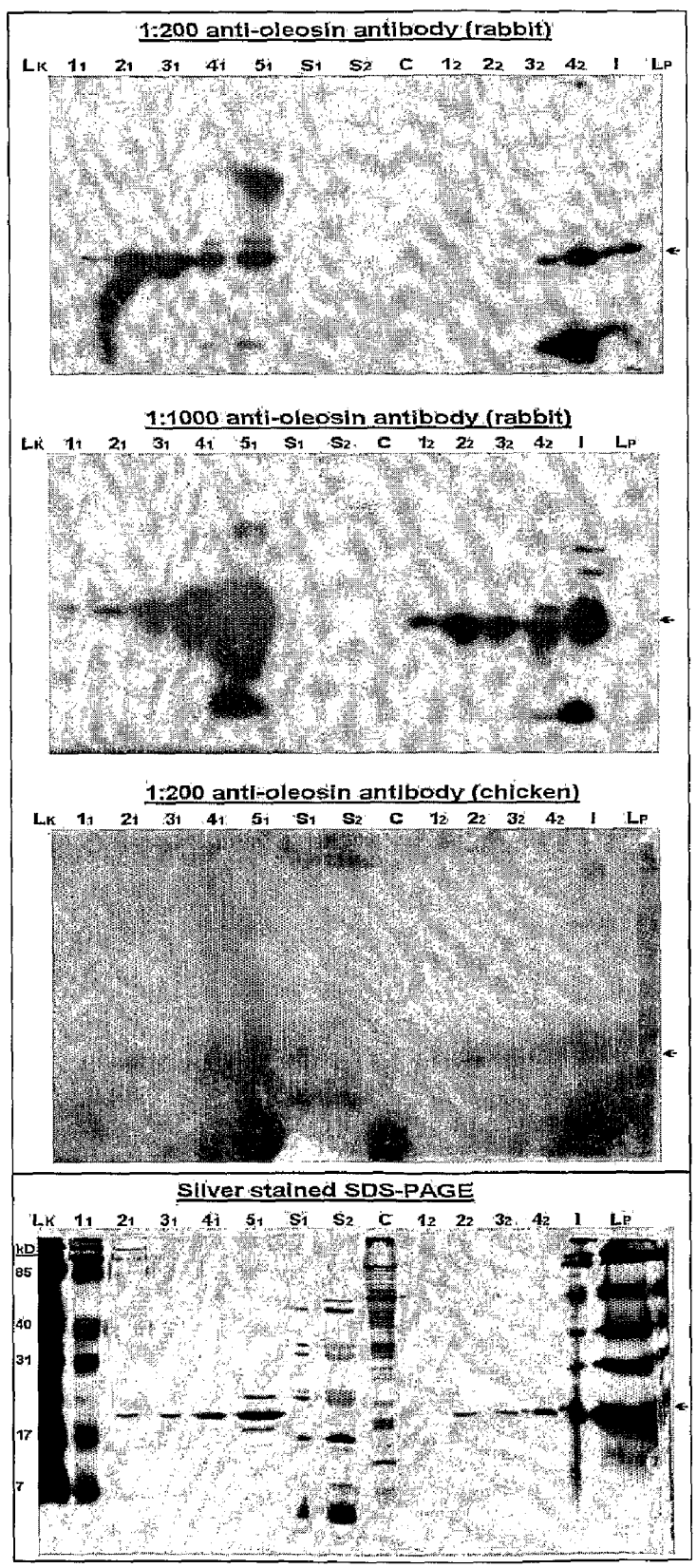

FIG. 86. Analysis of rabbit anti-sesame seed oleosin antiserum by immunoblot and silver staining. Analysis of antibody titre and specificity.
LK=BioRad Kaleidoscope Standards (cat#161 0324)
11=3 ng of 1 A 21=13 ng 1 A 31=27 ng 1 A 41=132 ng 1 A 51=663 ng 1 A
S1 & S2=sesame seed extract C=clover seed extract
12=3 ng of 1B 22=14 ng 1B 32=29 ng 1B 42=143 ng 1B
I=crude post-induction sample LP=BioRad Precision Plus Standard (cat#161 0363).
☐=expected size of oleosin. Overflow of the standards can be seen in lanes 11 and I.

The rabbit raised antibodies show a high affinity for the affinity purified recombinant oleosin, detecting down to at least 3 ng. The antibodies also show high specificity, with no cross-reactivity against soluble seed proteins and low cross-reactivity to bacterial proteins (lane 1).

Figure 87:
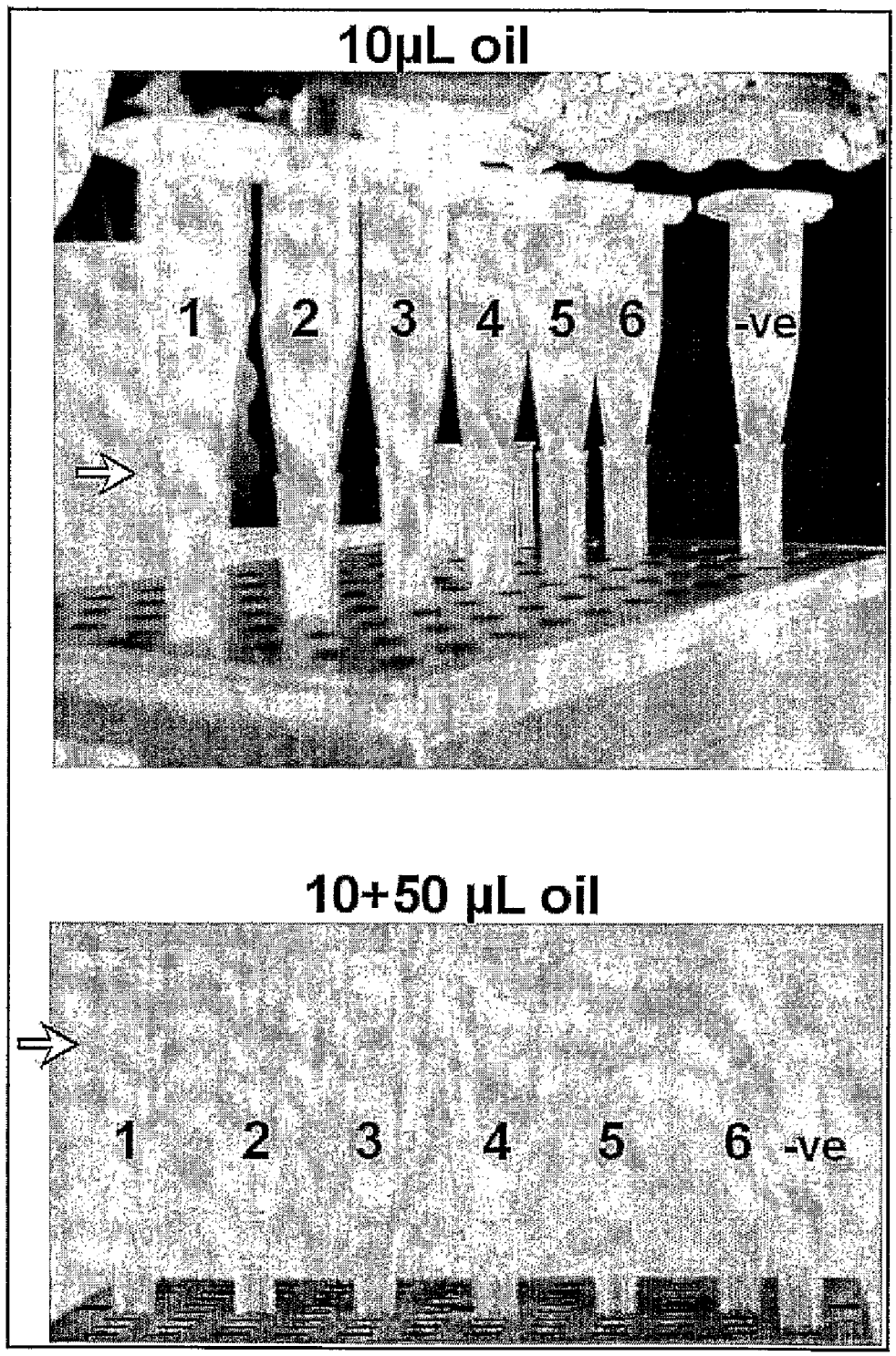

FIG. 87. Visualisation of emulsification layer containing artificial oil bodies (AOBs) after first (top) and second (bottom) rounds of sonication.

Figure 88:
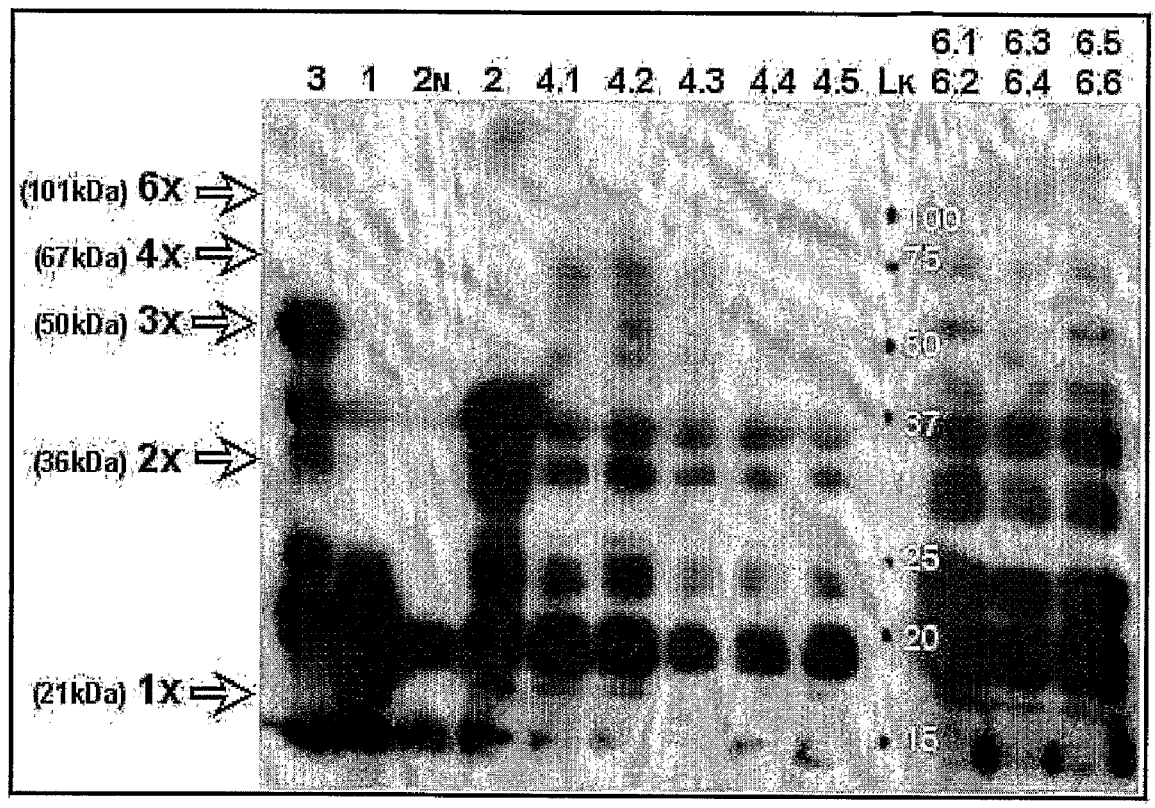

FIG. 88. SDS-PAGE/immunoblot analysis of AOB 1×, 2×, 3×, 4× and 6× oleosin.

For analysis of the 6× polyoleosin two samples were loaded per lane. $_N$=non-induced negative control.

Figure 89:
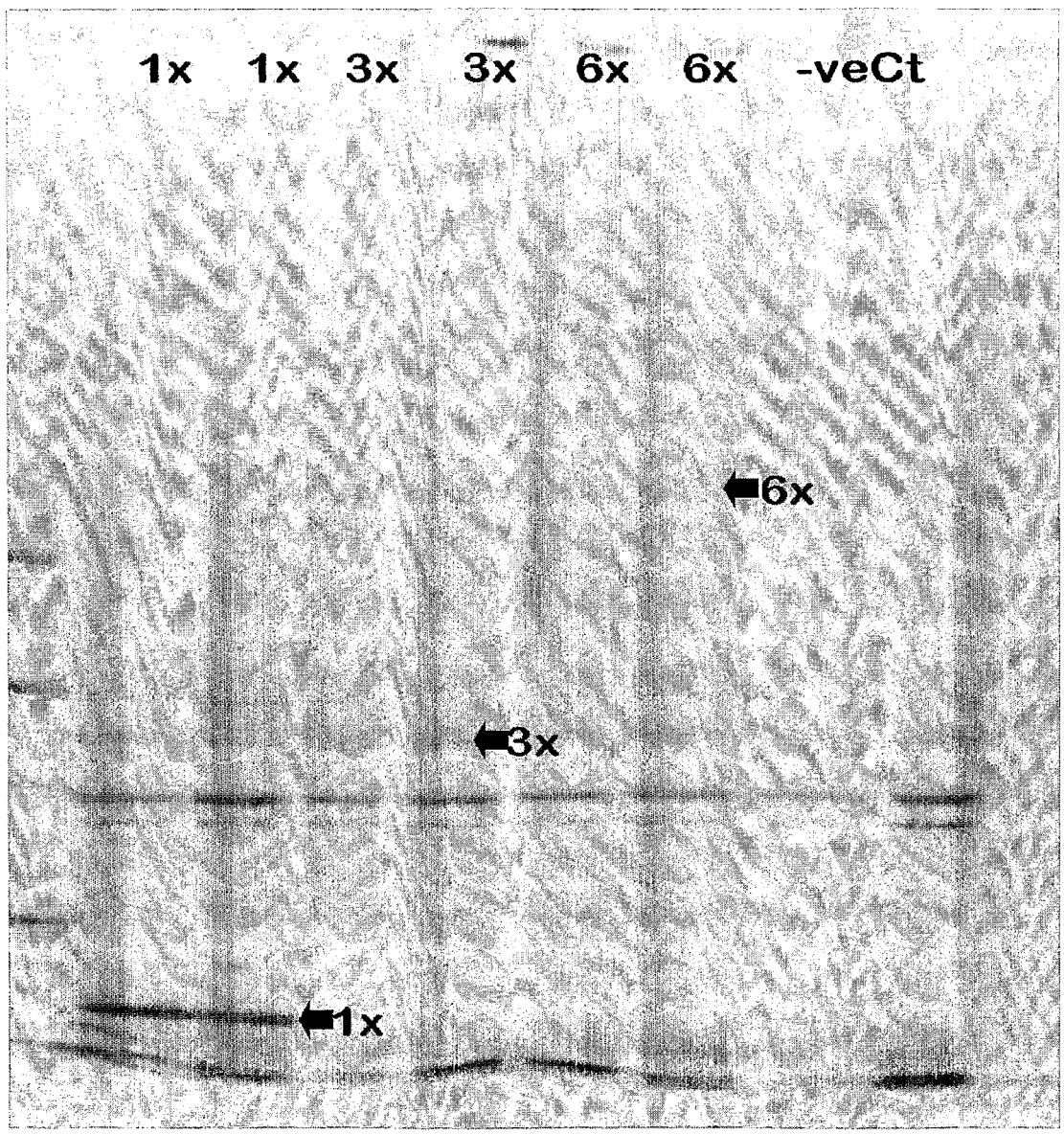

FIG. 89. Analysis of AOBs containing 1×-6× Sesame seed polyoleosin proteins by SDS/urea-Gradient PAGE/SafeStain.

Figure 90:
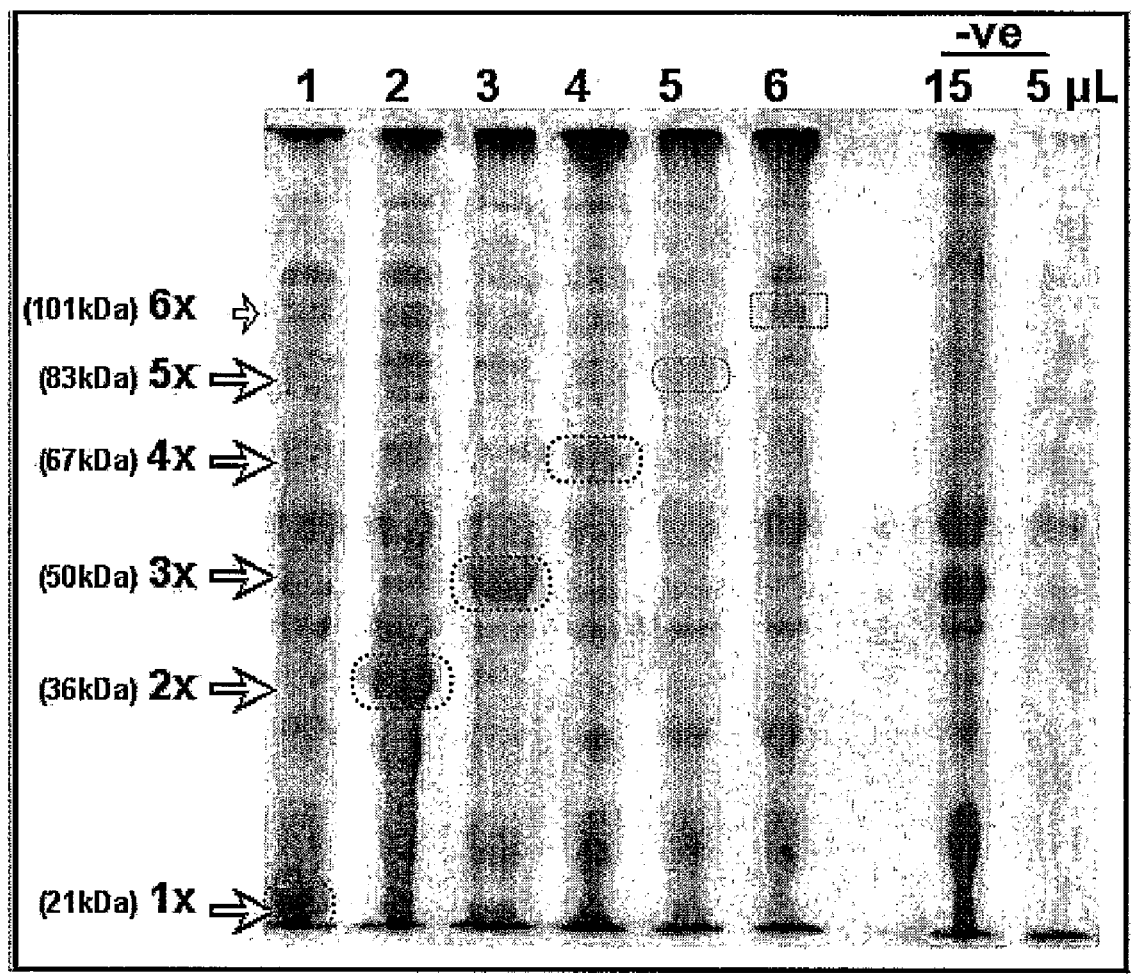

FIG. 90. SDS, urea-PAGE/immunoblot of AOB Analysis of 1×-6× AOBs by SDS/urea-PAGE/SafeStain.

Small arrow indicates expected position of 6× oleosin (rectangular box). Large arrows indicate bands of putative polyoleosin protein corresponding to 1×, 2, 3×, 4×, and 5× oleosins (oval boxes). Expected molecular weights are shown in brackets.

Figure 91:
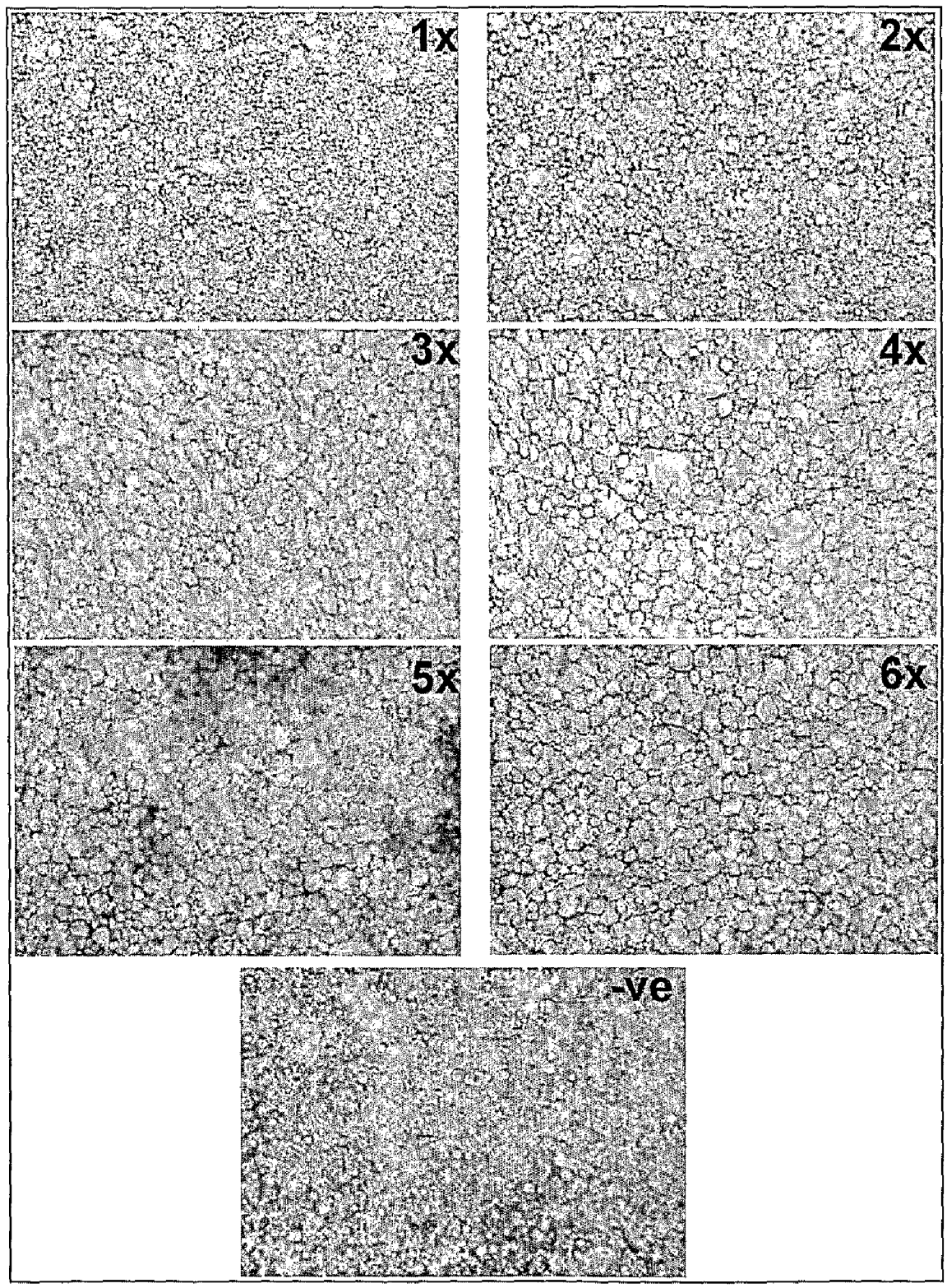

FIG. 91. Microscopic analysis of AOB containing a different number of oleosin repeats. Size of AOBs when prepared with polyoleosins containing increasing numbers of repeating oleosin units.

Figure 92:
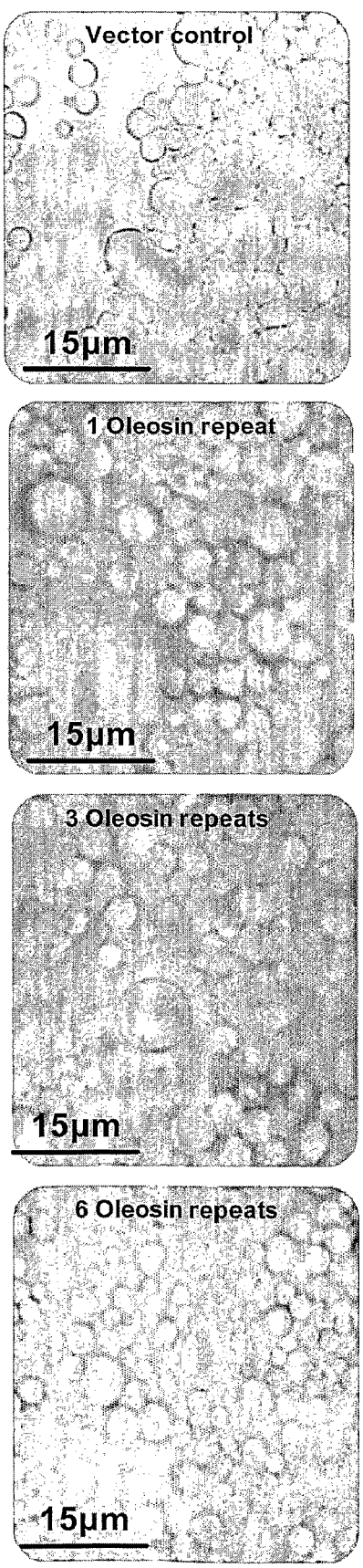

FIG. 92. Effect of polyoleosin on the stability over time of AOB containing a different number of oleosin repeats after 7 days at 4° C. AOBs were prepared with different polyoleosins containing increasing numbers of repeating oleosin units. Vector control AOBs were prepared using inclusion bodies from E. coli containing a vector control.

Figure 93:
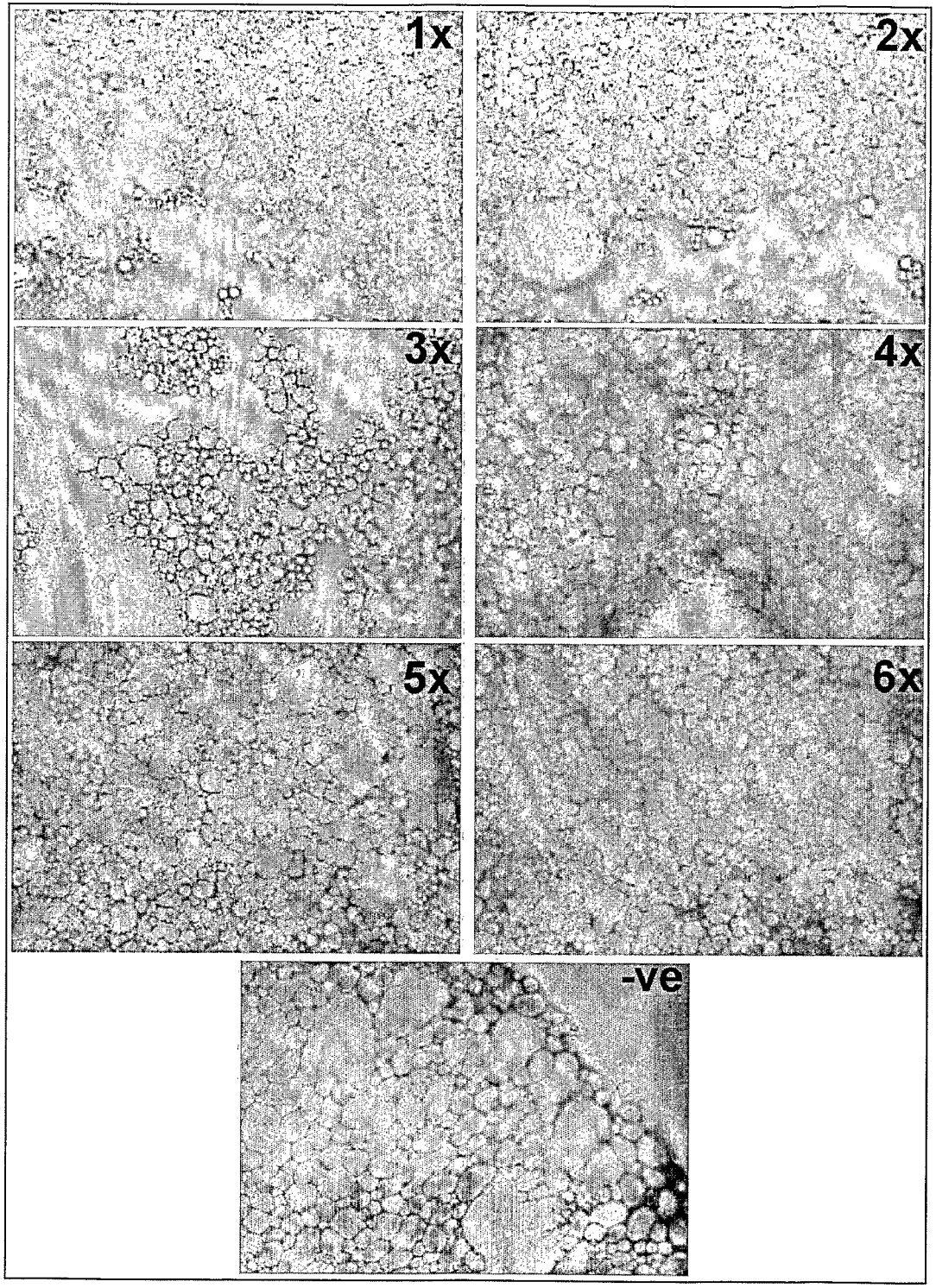

FIG. 93. Microscopic analysis of size of AOB containing a different number of oleosin repeats after heat treatment at 90° C. for 15 min.

Figure 94:
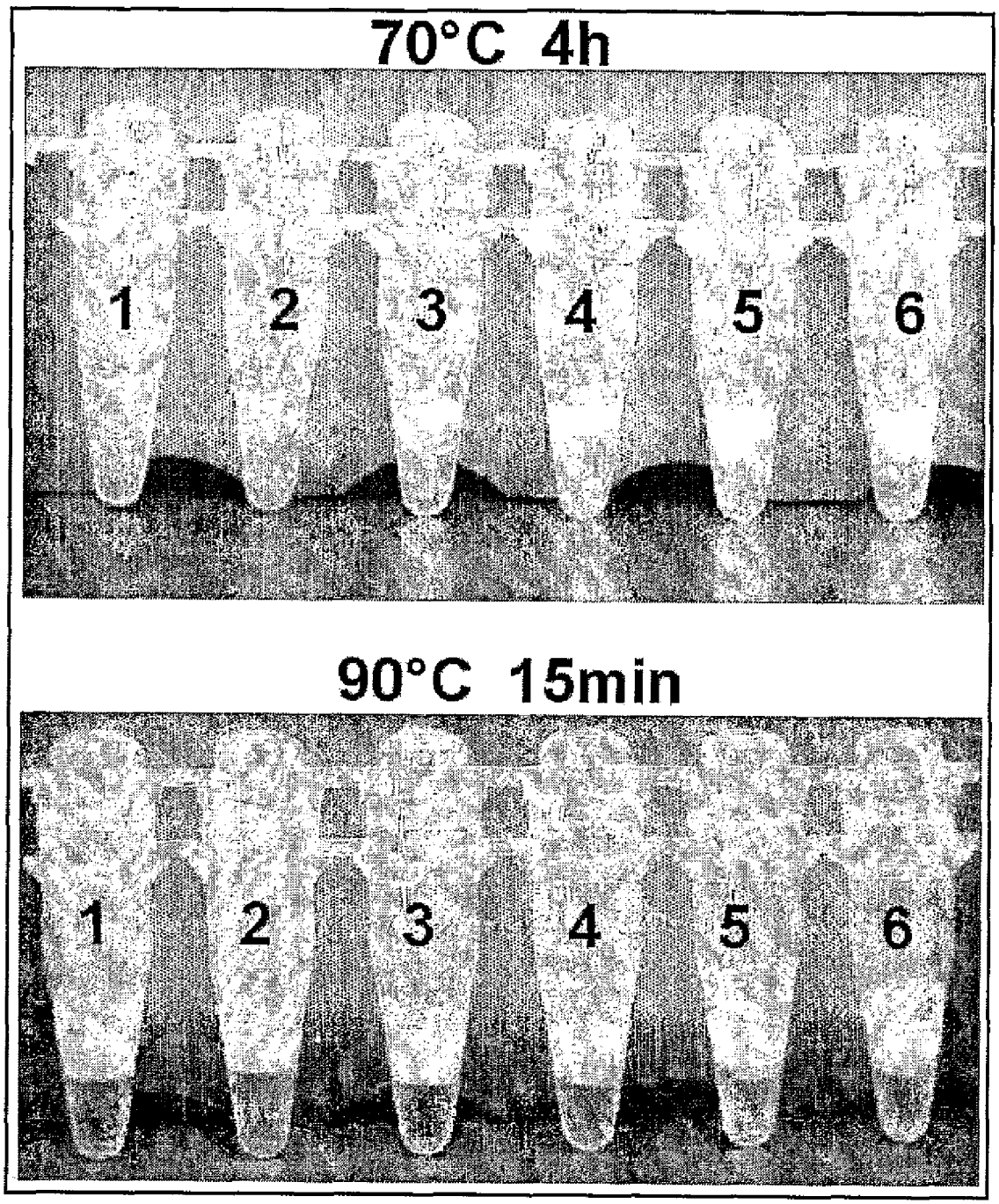

FIG. 94. Heat stability of emulsification layers (containing AOB) in relation to the number of repeat oleosin units.

Figure 95:
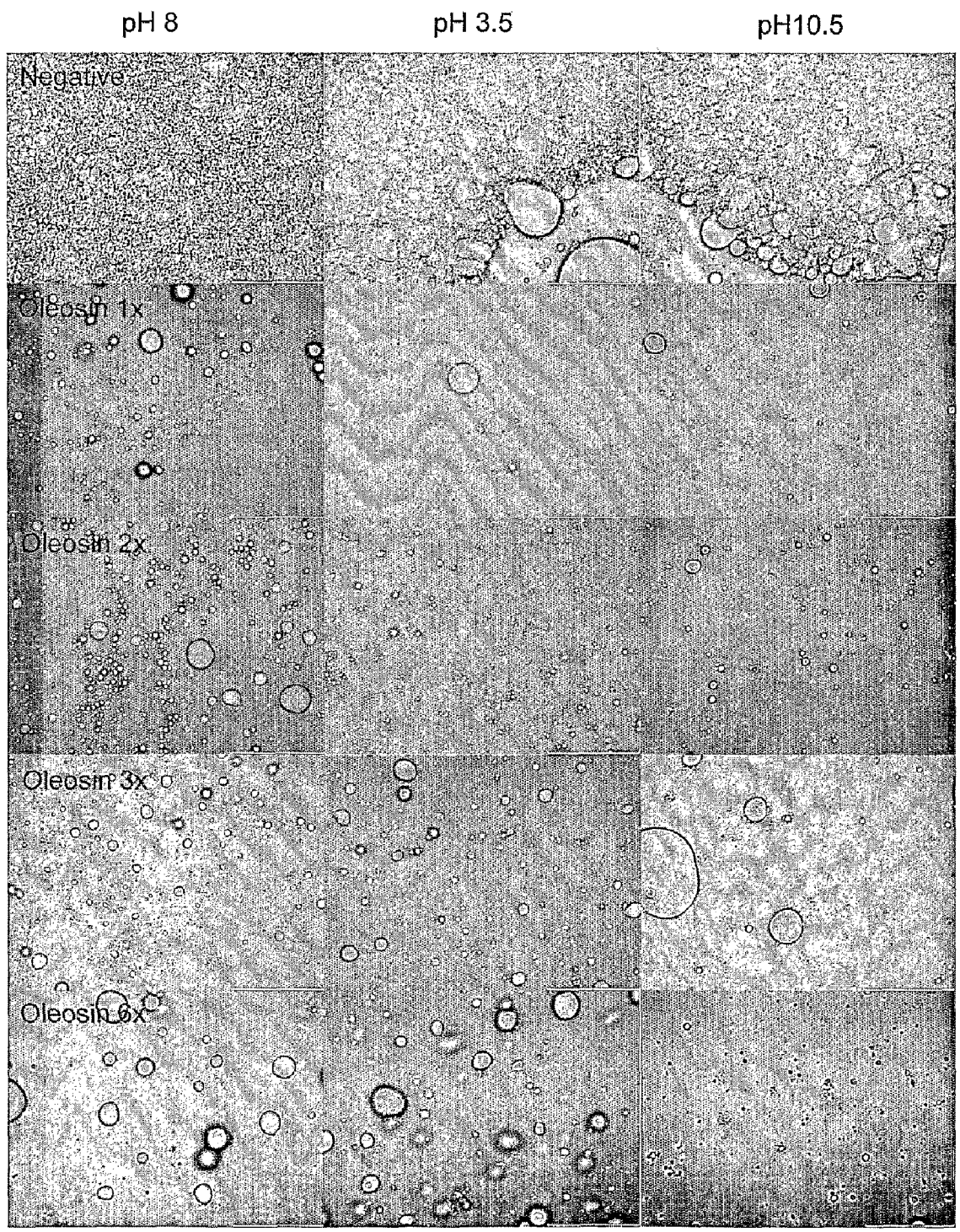

FIG. 95. Microscopic analysis of AOB containing a different number of oleosin repeats after incubation in different pH buffers.

Figure 96:
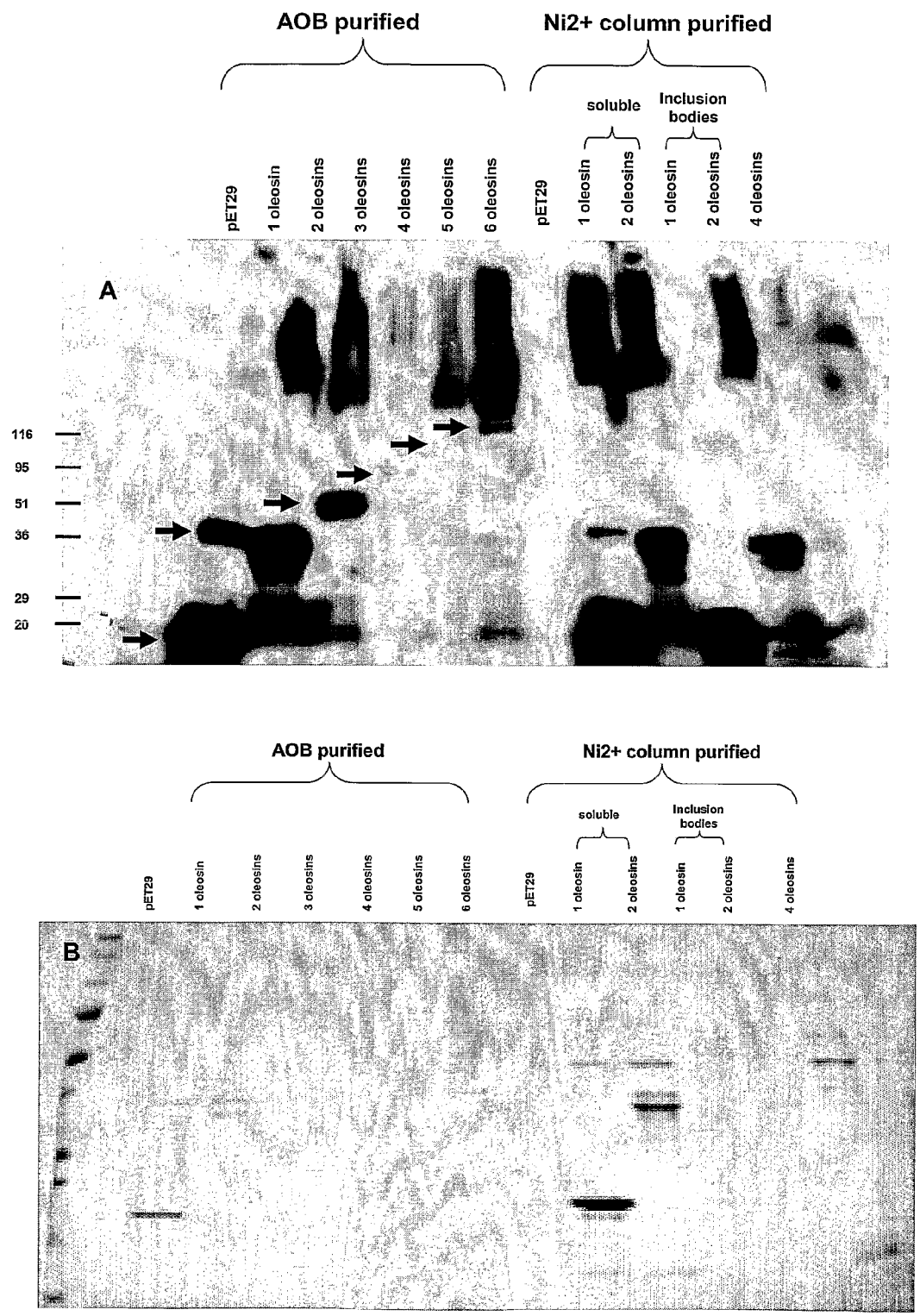

FIG. 96. SDS-PAGE/immunoblot (A) and Coomassie (B) analysis of prokaryotically produced recombinant polyoleosin purified by Artificial Oil Body or $Ni^{2+}$ affinity column.

FIG. 97. Feature map of nucleotide sequence of attB flanking regions, single oleosin clone and UBQ10 in pRSh1-PSP1 (CaMV35S driving 1 oleosin tandem repeats with the UBQ10 intron in the first repeat) (Seq ID No. 64).

FIG. 98. Feature map of nucleotide sequence of attB flanking regions, single oleosin clone and UBQ10 in pRSh1-PSP3 (CaMV35S driving 3 oleosin tandem repeats with the UBQ10 intron in the first repeat) (Seq ID No. 65).

FIG. 99. Feature map of nucleotide sequence of attB flanking regions, single oleosin clone and UBQ10 in pRSh1-PSP4 (CaMV35S driving 4 oleosin tandem repeats with the UBQ10 intron in the first repeat) (Seq ID No. 66).

FIG. 100. Feature map of nucleotide sequence of attB flanking regions, single oleosin clone and UBQ10 in pRSh1-PSP6 (CaMV35S driving 6 oleosin tandem repeats with the UBQ10 intron in the first repeat) (Seq ID No. 67).

FIG. 101. Feature map of nucleotide sequence of attB flanking regions, single oleosin clone and UBQ10 in pRSh3-PSP1 (*Arabidopsis* oleosin seed promoter driving 1 oleosin repeat with the UBQ10 intron in the first repeat) (Seq ID No. 68).

FIG. 102. Feature map of nucleotide sequence of attB flanking regions, single oleosin clone and UBQ10 in pRSh3-PSP3 (*Arabidopsis* oleosin seed promoter driving 3 oleosin tandem repeats with the UBQ10 intron in the first repeat) (Seq ID No. 69).

FIG. 103. Feature map of nucleotide sequence of attB flanking regions, single oleosin clone and UBQ10 in pRSh3-PSP4 (*Arabidopsis* oleosin seed promoter driving 4 oleosin tandem repeats with the UBQ10 intron in the first repeat) (Seq ID No. 70).

FIG. 104. Feature map of nucleotide sequence of attB flanking regions, single oleosin clone and UBQ10 in pRSh3-PSP6 (*Arabidopsis* oleosin seed promoter driving 6 oleosin tandem repeats with the UBQ10 intron in the first repeat) (Seq ID No. 71).

FIG. 105. Feature map of nucleotide sequence of attB flanking regions, identical oleosin clones in pRSh1-Ole3+ (CaMV35s promoter driving 3 identical oleosin tandem repeats; no intron) (Seq ID No. 72).

FIG. 106. Feature map of nucleotide sequence of attB flanking regions, identical oleosin clones in pRSh1-Ole3+ (*Arabidopsis* oleosin seed promoter driving 3 identical oleosin tandem repeats; no intron) (Seq ID No. 73).

FIG. 107. Peptide sequence of: pRSh1-PSP1 (CaMV35S driving 1 oleosin tandem repeats with the UBQ10 intron in the first repeat) (Seq ID No. 74).

FIG. 108. Peptide sequence of: pRSh1-PSP3 (CaMV35S driving 3 oleosin tandem repeats with the UBQ10 intron in the first repeat) (Seq ID No. 75).

FIG. 109. Peptide sequence of: pRSh1-PSP4 (CaMV35S driving 4 oleosin tandem repeats with the UBQ10 intron in the first repeat) (Seq ID No. 76).

FIG. 110. Peptide sequence of: pRSh1-PSP6 (CaMV35S driving 6 oleosin tandem repeats with the UBQ10 intron in the first repeat) (Seq ID No. 77).

FIG. 111. Peptide sequence of: pRSh3-PSP1 (*Arabidopsis* oleosin seed promoter driving 1 oleosin repeat with the UBQ10 intron in the first repeat) (Seq ID No. 78).

FIG. 112. Peptide sequence of: pRSh3-PSP3 (*Arabidopsis* oleosin seed promoter driving 3 oleosin tandem repeats with the UBQ10 intron in the first repeat) (Seq ID No. 79).

FIG. 113. Peptide sequence of: pRSh3-PSP4 (*Arabidopsis* oleosin seed promoter driving 4 oleosin tandem repeats with the UBQ10 intron in the first repeat) (Seq ID No. 80).

FIG. 114. Peptide sequence of: pRSh3-PSP6 (*Arabidopsis* oleosin seed promoter driving 6 oleosin tandem repeats with the UBQ10 intron in the first repeat) (Seq ID No. 81).

FIG. 115. Peptide sequence of: pRSh1-Ole3+ (CaMV35s promoter driving 3 identical oleosin tandem repeats; no intron) (Seq ID No. 82).

FIG. 116. Peptide sequence of: pRSh3-Ole3+ (*Arabidopsis* oleosin seed promoter driving 3 identical oleosin tandem repeats; no intron) (Seq ID No. 83).

Figure 117:
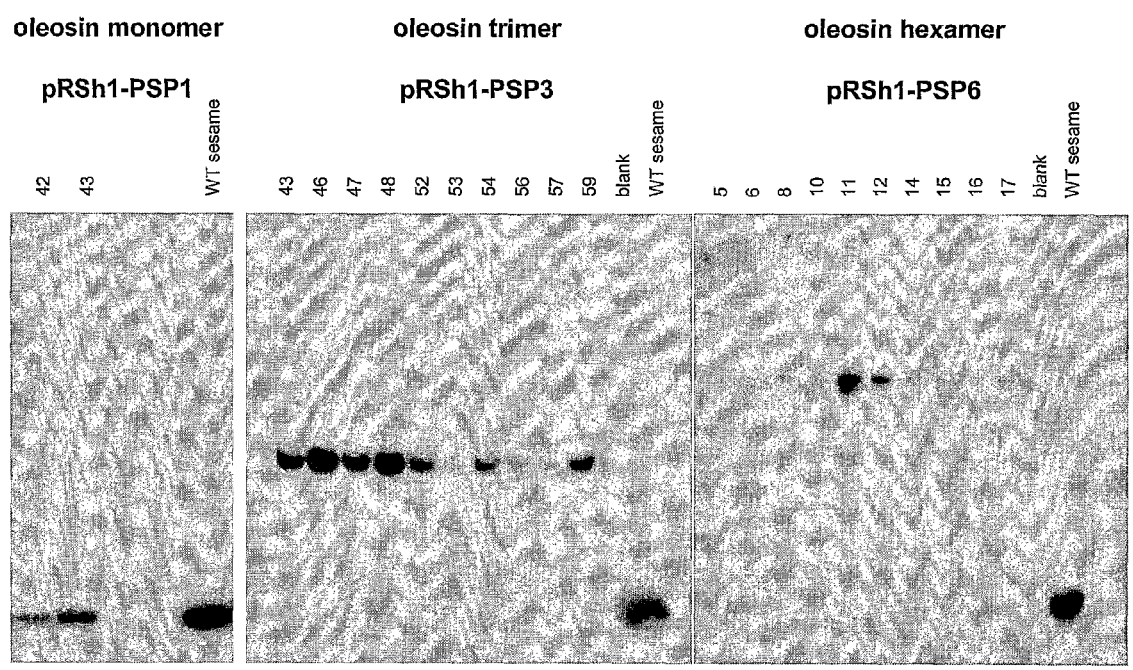

FIG. 117. SDS-PAGE/immunoblot showing production of Sesame seed polyoleosin in *Arabidopsis thaliana* seeds. Analysis of oil bodies from transgenic *Arabidopsis thaliana* seeds over expressing varying tandem repeats of the sesame seed oleosin.

Figure 118:
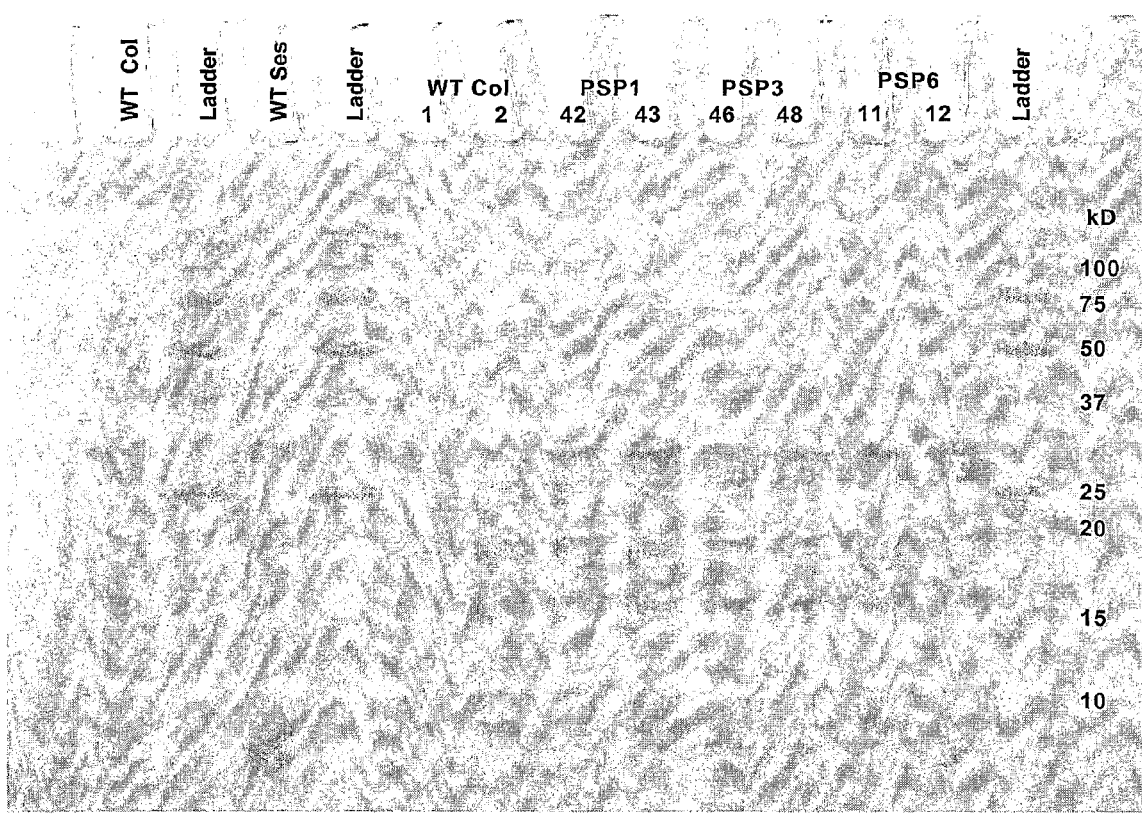

FIG. 118. SDS-PAGE/Coomassie showing crude protein extracts from *Arabidopsis thaliana* wild type seeds and transgenic seeds expressing Sesame seed polyoleosin.

Figure 119:
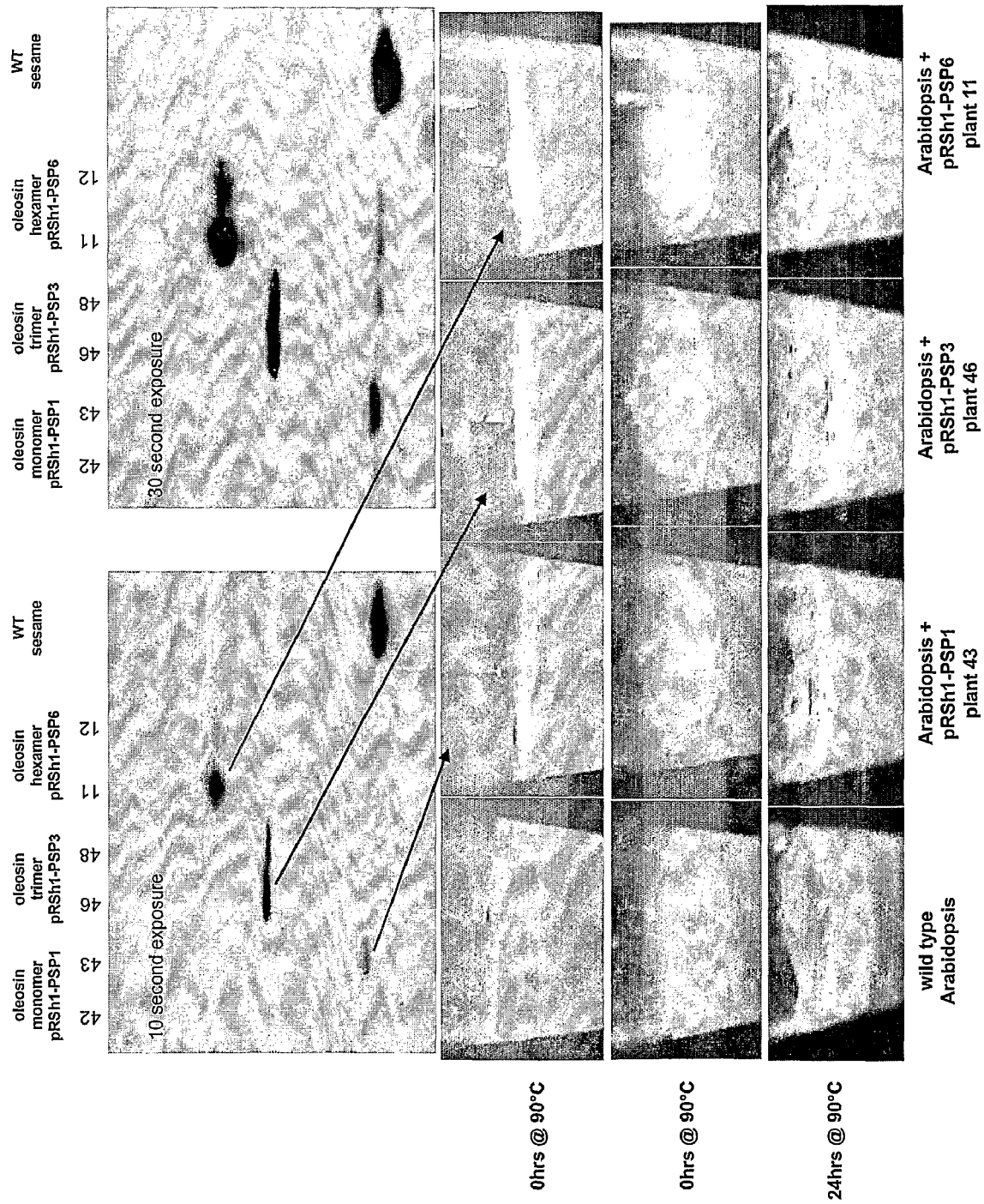

FIG. 119. Picture of relative recombinant protein levels in *Arabidopsis* oil bodies and effects of different Sesame seed polyoleosin lengths on emulsification thicknesses after heating. SDS-PAGE/immunoblot analysis and emulsification stability analysis of oil bodies from transgenic *Arabidopsis thaliana* over expressing varying tandem repeats of the sesame seed oleosin and the increase in heat stability of the emulsification layers extracted from these transformants. The reduction in oleosin repeat numbers correlates with a decrease in the emulsification layer remaining after 24 hr at 90° C., where the thickest emulsification can be seen from plants expressing the hexameric polyoleosin construct.

Figure 120:
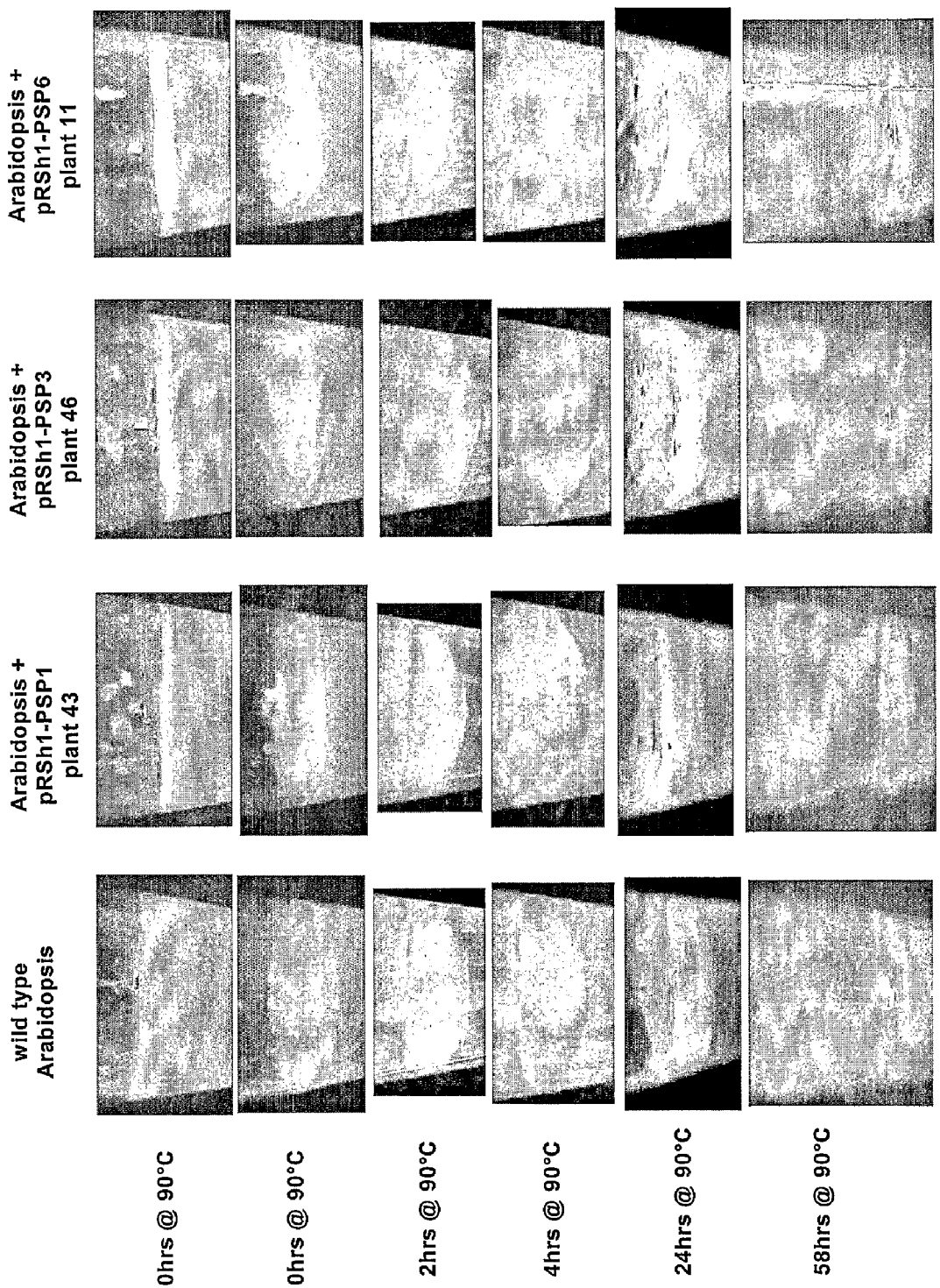

FIG. 120. Picture of heating effect on emulsification thicknesses of transgenic *Arabidopsis* oil bodies expressing different polyoleosins. Heat stability analysis of the emulsification layers from transformants expressing 1, 3 or 6 oleosin repeats. The reduction in oleosin repeat numbers correlates with a decrease in the emulsification layer remaining after 24 hr at 90° C., where the thickest emulsification can be seen from plants expressing the hexameric polyoleosin construct. At 0 hrs through to 24 hrs at 90° C. the higher the number of oleosin repeats correlates with a thicker emulsification layer. After 58 hrs at 90° C. the oil bodies from the wild type *arabidopsis* has been reduced to a very thin layer with a small ring of emulsion deposited on the tube above the remaining aqueous phase. In comparison, the ring of emulsion remaining in the transformant samples is much greater.

EXAMPLES

Example 1

White Clover Polyoleosin Construction

We have generated a dimeric, trimeric, tetrameric and a pentameric homo white clover oleosin tandem repeat construct and placed these into plant binary vectors for plant transformation. The following is a description of the methods used to generate the constructs. It should be noted that the oleosin sequence used is for example only. Any oleosin sequence or combinations of oleosins, steroleosins and caoleosins and oleosin linking sequences could be used.

Overview of Experimental Approach to Generation of White Clover Oleosin Repeats

Five oleosin clones (Pole01-MC to pOLE05-MC), containing suitable restriction sites, were prepared for the subsequent generation of constructs containing oleosin repeats. In this description clones pOLE01-MC to pOLE05-MC were used to prepare monomer, dimer, trimer, tetramer and pentamer oleosin repeat constructs, pOLE06-MC to pOLE10-MC respectively. The pBLUESCRIPT polylinker (FIG. 8) was used in the preparation of pOLE01-MC to provide the multiple restriction sites required to build the oleosin repeat constructs.

Standard Method of Generating Restriction Enzyme/White Clover Oleosin Cassette

PCR products were produced using a proof-reading polymerase to amplify the existing oleosin open reading frame (609 bases) of an oleosin clone containing no SacI, XbaI, SpeI, BamHI, SmaI, PstI, EcoRI, HindIII Bsp1061, SalI or XhoI sites. For each cassette unique primers were designed to amplify the oleosin sequence and add specific flanking restriction sites (FIG. 9). Additional base pairs coding for specific amino acids were also included between the restriction site and oleosin priming sequence. In the polyoleosin peptide these amino acids could be expected to act as spacer arms enabling the individual oleosins to be separated from each other, reducing the chances of any misfolding occurring.

The oleosin PCR product to generate pOLE01-MC was then TOPO cloned into the pENTR/D-TOPO vector with the primary purpose of maintaining the flanked oleosin sequence. The oleosin PCR product to generate pOLE02, 03, 04, 05-MC was then TOPO cloned into the pCR2.1-TOPO vector with the primary purpose of maintaining the flanked oleosin sequence. Maps of the vectors used for cloning, pENTR/D-TOPO and pCR2.1-TOPO are shown in FIGS. 10 and 11, respectively.

The new construct was transformed into competent *E. coli* cells and plated out for single colonies. Individual colonies were cultured and the purified plasmid from these cultures was analysed by digestion with a range of suitable restriction enzymes. If no suitable colonies were identified then this process was repeated. Those colonies/plasmid preps that produced predicted patterns by restriction enzyme digestion were then sequenced across the cassette containing the oleosin insert and the resulting data compared against the predicted sequence for the construct/plasmid.

The construction of constructs pOLE01-MC to pOLE05-MC is summarised below, based on the method outlined above. Each cassette was fully sequenced after construction, with all sequences being confirmed as correct.

We have generated polyclonal antibodies to a number of white clover oleosin fragments, the generation and characterisation of these antisera is summarised below.

pOLE01-MC

```
(1) Primer design
Forward primer  CACCXXXXXXXXXXXXXXXXXXX          (Seq ID No. 1)
Reverse primer  TCACTCGAGGAGCTCXXXXXXXXXXXXXXXXX  (Seq ID No. 2)
```

In the forward primer XXXX represents an oleosin specific primer that has a 5' end beginning with the first ATG site in the open reading frame.

In the reverse primer XXXX represents an oleosin specific primer that has a 5' end complementary to the sequence for last codon in the open reading frame.

(2) Outline of PCR Product

CACC■■■■■■SacI/XhoI/

cloned into pENTR/D-TOPO to generate pOLE01-MC
■■■■■■ Oleosin ORF sequence
CACC pENTR/D-TOPO adapter sequence
SacI/XhoI Engineered restriction sites, each site adds 6 base pairs

Stop Codon

A map of pOLE01-MC is shown in FIG. 12. The sequence of pOLE01-MC is shown in FIG. 13.

pOLE02-MC (3) Primer design (Seq ID No. 3)
Forward primer    TCTAGAGGTACTXXXXXXXXXXXXXXXXXX (Seq ID No. 4)
Reverse primer    ACTAGTAGTACCXXXXXXXXXXXXXXXXXX In the forward primer XXXX represents an oleosin specific primer that has a 5' end beginning with the first ATG site in the open reading frame.

In the reverse primer XXXX represents an oleosin specific primer that has a 5' end complementary to the sequence for last codon in the open reading frame.

Outline of PCR Product

XbaI/GGTACT■■■■■■GGTACT/SpeI cloned into pCR2.1-TOPO to generate pOLE02-MC
■■■■■■ Oleosin ORF sequence
GGTACT Extra bases to code for glycine and threonine.

A map of pOLE02-MC is shown in FIG. 14. The sequence of pOLE02-MC is shown in FIG. 15.

pOLE03-MC

Primer design (Seq ID No. 5)
Forward primer    CCCGGGGGTACTXXXXXXXXXXXXXXXXXX (Seq ID No. 6)
Reverse primer    CTGCAGAGTACCXXXXXXXXXXXXXXXXXX In the forward primer XXXX represents an oleosin specific primer that has a 5' end beginning with the first ATG site in the open reading frame.

In the reverse primer XXXX represents an oleosin specific primer that has a 5' end complementary to the sequence for last codon in the open reading frame.

Outline of PCR Product

SmaI/GGTACT■■■■■■GGTACT/PstI cloned into PCR2.1-TOPO to generate pOLE03-MC
■■■■■■ Oleosin ORF sequence
GGTACT Extra bases to code for glycine and threonine A map of pOLE03-MC is shown in FIG. 16. The sequence of pOLE03-MC is shown in FIG. 17.

pOLE04-MC (4) Primer design (Seq ID No. 7)
Forward primer    AAGCTTGGTACTXXXXXXXXXXXXXXXXXX (Seq ID No. 8)
Reverse primer    ATCGATAGTACCXXXXXXXXXXXXXXXXXX In the forward primer XXXX represents an oleosin specific primer that has a 5' end beginning with the first ATG site in the open reading frame.

In the reverse primer XXXX represents an oleosin specific primer that has a 5' end complementary to the sequence for last codon in the open reading frame.

Outline of PCR Product

HindIII/GGTACT■■■■■■GGTACT/Bsp1061 cloned into pCR2.1-TOPO to generate pOLE04-MC
■■■■■■ Oleosin ORF sequence
GGTACT Extra bases to code for glycine and threonine A map of pOLE04-MC is shown in FIG. 18. The sequence of pOLE04-MC is shown in FIG. 19.

pOLE05-MC (5) Primer design (Seq ID No. 9)
Forward primer    GTCGACGGTACTTCTXXXXXXXXXXXXXXXXXX (Seq ID No. 10)
Reverse primer    CTCGAGXXXXXXXXXXXXXXXXXX In the forward primer XXXX represents an oleosin specific primer that has a 5' end beginning with the first ATG site in the open reading frame.

In the reverse primer XXXX represents an oleosin specific primer that has a 5' end complementary to the sequence for last codon in the open reading frame.

Outline of PCR Product

SalI/GGTACTTCT■■■■■■XhoI cloned into pCR2.1-TOPO to generate pOLE05-MC
■■■■■■ Oleosin ORF sequence
GGTACTTCT Extra bases to code for glycine, threonine and serine A map of pOLE05-MC is shown in FIG. 20. The sequence of pOLE05-MC is shown in FIG. 21.

pOLE06-MC pOLE01-MC and pBLUESCRIPT were digested using SacI and XhoI. The pBLUESCRIPT fragment was ligated into the open pOLE01-MC vector to form pOLE06-MC (FIG. 22). The sequence of pOLE06-MC is shown in FIG. 23.

CACC■SacI/••••••/XbaI/SpeI/BamHI/SmaI/PstI/EcoRI/EcoRV/HindIII/Bsp106/•/SalI/XhoI/

CACC pENTR/D-TOPO adapter sequence
■ Oleosin ORF sequence
SacI to XhoI Restriction sites within pBLUESCRIPT
• amino acids encoded within the MCS but not corresponding to a restriction site

Stop Codon

Confirmation of the addition of the polylinker was carried out via digestion with SacI, XhoI, XbaI, BamHI, SmaI, PstI, EcoRI, HindIII and SalI. The pOLE06-MC cassette was then sequenced.

pOLE07-MC pOLE06-MC was digested using XbaI and pOLE02-MC was digested with XbaI and SpeI, the resulting fragments were ligated together to form pOLE07-MC (FIG. 24). The sequence of pOLE07-MC is shown in FIG. 25.
CACC■SacI/••••••/XbaI/••/■/••/SpeI/BamHI/SmaI/PstI/EcoRI/EcoRV/HindIII/Bsp106I/•/SalI/XhoI/

CACC pENTR/D-TOPO adapter sequence
■ Oleosin ORF sequences
SpeI to XhoI Restriction sites within pBLUESCRIPT
• amino acids encoded within the MCS but not corresponding to a restriction site

Stop Codon

Confirmation of the generation of pOLE07-MC was carried via XbaI/EcoRI, PstI, and HindIII/PstI digests. In order to gain a complete sequence of the clone, an LR reaction was performed to transfer the pOLE07-MC cassette into pET-DEST42. The pOLE07-MC cassette was then sequenced.

pOLE08-MC pOLE07-MC and pOLE03-MC were digested using SmaI and PstI, then the required fragments were ligated together to form pOLE08-MC (FIG. 26). The sequence of pOLE08-MC is shown in FIG. 27.
CACC■SacI/••••••/XbaI/••/■/••/SpeI/BamHI/SmaI/••/■/••/PstI/EcoRI/EcoRV/HindIII/Bsp106I/•/SalI/XhoI/

CACC pENTR/D-TOPO adapter sequence
■ Oleosin ORF sequences
PstI to XhoI Restriction sites within pBLUESCRIPT
• amino acids encoded within the MCS but not corresponding to a restriction site

Stop Codon

Confirmation of the generation of pOLE08-MC was carried out via PstI/NcoI, NotI/XhoI and BamHI digests. In order to gain a complete sequence of the clone, the pOLE08-MC oleosin cassette was transferred into pET-DEST42 by an LR reaction. The cassette was then sequenced and the sequence of the polylinker, and the pOLE03-MC oleosin fragment ligated into pOLE07-MC.

pOLE09-MC pOLE08-MC containing the oleosin trimer, was digested using HindIII and ClaI (ClaI is an isoschizomer of Bsp106I), and pOLE04-MC was digested with HindIII and ClaI (Table 1), the resulting fragments were gel purified (FIG. 28). The digests were purified from the agarose gel using the QIAGEN QIAquick Gel Extraction Kit. The HindIII/ClaI digested oleosin isolated from pOLE04-MC was then cloned into the HindIII/ClaI linearised pOLE08-MC vector (table 2) to generate pOLE09-MC (FIG. 29).
CACC■SacI/••••••/XbaI/••/■/••/SpeI/BamHI/SmaI/••/■/••/PstI/EcoRI/EcoRV/HindIII/••/■/••ClaI/•/SalI/XhoI/

CACC pENTR/D-TOPO adapter sequence
■ Oleosin ORF sequences
ClaI to XhoI Restriction sites within pBLUESCRIPT
• amino acids encoded within the MCS but not corresponding to a restriction site

Stop Codon

TABLE 1

Table describing the components used in the restriction enzyme digest to produce the linearised pOLE08-MC vector and the oleosin insert/fragment from pOLE04-MC

| 4 | 8 | | |
|---|---|---|---|
| 10 | | μL | pOLE04-MC |
| | 10 | μL | pOLE08-MC |
| 1 | 1 | μL | HindIII (Roche) |
| 1 | 1 | μL | ClaI (Roche) |
| 2 | 2 | μL | Buffer B (Roche) |
| 6 | 6 | μL | sH$_2$O |
| 20 | 20 | μL | Total volume |
| After 2.5 h at 37° C. added | | | |
| 1 | 1 | μL | Phosphatase (Roche, CAP, 20 U/uL) |

Incubated for a further 30 min at 37° C.

TABLE 2

Table describing the components used in the ligation of the linearised pOLE08-MC vector and the oleosin insert/fragment from pOLE04-MC to produce pOLE09-MC.

| Ct8 | Ct4 | 1:1 | 1:3 | 1:6 | | |
|---|---|---|---|---|---|---|
| 3.5 | | 3.5 | 3.5 | 3.5 | μL | pOLE08-MC HindIII/ClaI linearised vector |
| | 8 | 2 | 6 | 12 | μL | Oleosin HindIII/ClaI fragment from |
| 4 | 4 | 4 | 4 | 4 | μL | Ligase buffer |
| 1 | 1 | 1 | 1 | 1 | μL | T4 DNA Ligase (Roche) |
| 11.5 | 7 | 9.5 | 5.5 | | μL | sH$_2$0 |
| 20 | 20 | 20 | 20 | 20.5 | μL | Total volume |

Incubated at 11° C. overnight.

5 μL of each of the above ligation reactions were then transformed into *E. coli* DH5α to allow screening for correct pOLE09-MC plasmids.

Confirmation of the generation of pOLE09-MC was carried via agarose gel/ethidium bromide analysis of the NcoI/XhoI, NcoI/SpeI/XhoI, XhoI, and NotI/XhoI digests (FIG. 30).

In order to gain a complete sequence of the clone, the pOLE09-MC oleosin cassette was transferred into pET-DEST42 by an LR reaction. The cassette was then sequenced (FIG. 31).

pOLE10-MC

Due to poor restriction enzyme digestion efficiency when digesting the oleosin tetramer pOLE09-MC with SalI, pOLE09-M was digested using only XhoI (Table 3). SalI generated ends that are compatible with XhoI generated ends and thereby the SalI/XhoI generated fragment was ligated into the XhoI linearised vector. pOLE05-MC was digested with SalI and XhoI and the resulting oleosin fragment was ligated with pOLE09-MC (table 3) to form pOLE10-MC (FIG. 32).

CACC■SacI/•••••/XbaI/••/■/••/SpeI/BamHI/SmaI/••/■/••PstI/EcoRI/EcoRV/HindIII/••/■/••ClaI/•/SalI/••/■XhoI/

CACC pENTR/D-TOPO adapter sequence
■ Oleosin ORF sequences
ClaI to XhoI Restriction sites within pBLUESCRIPT
• amino acids encoded within the MCS but not corresponding to a restriction site

Stop Codon

TABLE 3

Table describing the components used in the restriction enzyme digest to produce the linearised oleosin tetramer pOLE09-MC vector and the oleosin insert/fragment from pOLE05-MC.

| 5 x3 | 9 x2 | | |
|---|---|---|---|
| 6 | | µL | pOLE05-MC (midipreped DNA) |
| | 6 | µL | pOLE09-MC (midipreped DNA) |
| 1 | 2 | µL | XhoI (Roche) |
| 1 | x | µL | SalI (Roche) |
| 2 | 2 | µL | Buffer H (Roche) |
| 10 | 10 | µL | sH$_2$O |
| 20 | 20 | µL | Total volume |

TABLE 3-continued

After 2.5 h at 37° C. added

| — | 1 | µL | Phosphatase (Roche, CAP, 20 U/uL) |

Incubated for a further 30 min at 37° C.

The digests were purified from the agarose gel using the QIAGEN QIAquick Gel Extraction Kit. The XhoI/SalI digested oleosin isolated from pOLE05-MC was then cloned into the XhoI linearised pOLE09-MC vector (Table 4) to generate pOLE10-MC.

TABLE 4

Table describing the components used in the ligation of the linearised pOLE09-MC vector and the oleosin insert/fragment from pOLE05-MC to produce pOLE10-MC.

| Ct9 | Ct5 | 1:3 | 1:9 | | |
|---|---|---|---|---|---|
| 3 | 6 | 3 | 3 | µL | pOLE09-MC XhoI/SalI linearised vector |
| | | 3 | 9 | µL | Oleosin XhoI/SalI fragment from pOLE05-MC |
| 1 | 1 | 1 | 1 | µL | Ligase buffer |
| 4 | 4 | 4 | 4 | µL | T4 DNA Ligase (Roche) |
| 12 | 9 | 9 | 3 | µL | sH$_2$O |
| 20 | 20 | 20 | 20.5 | µL | Total volume |

Incubated at 11° C. overnight.

5 µL of each of the above ligation reactions were then transformed into E. coli DH5α to allow screening for correct pOLE10-MC plasmids. Confirmation of the generation of pOLE10-MC was carried via PstI/XhoI, PstI and SalI/PstI restriction enzyme digests. One clone was selected for detailed agarose/ethidium bromide gel analysis, and compared to pOLE09-MC digested with the same enzymes (FIG. 33).

In order to gain a complete sequence of the clone, the pOLE10-MC oleosin cassette was transferred into pET-DEST42 by an LR reaction. The cassette was then sequenced (FIG. 34).

Generation of Binary Constructs

Clones pOLE06-MC through to pOLE10-MC were generated as GATEWAY™ entry vectors. The following is a description of subsequent LR reactions performed to transfer the oleosin constructs into two plant binary vectors, pRSh1 (Table 5 and FIG. 35) and pRS12 (Table 5 and FIG. 36).

TABLE 5

Table describing the components between the left and right borders of two plant binary vectors used to transform the multimeric oleosin repeats into plants.

| Construct Name | Plasmid Type | Cassette Design | Bacterial Selectable Marker | Plant Selectable Marker |
|---|---|---|---|---|
| pRSh1 | Plant binary | CaMV35s::attR1::GW::attR2::OCS3' | Spectinomycin$^r$ | BASTA$^r$ |
| pRS12 | Plant binary | CaMV35s::attR1::GW::attR2::OCS3' | Spectinomycin$^r$ | Kanamycin$^r$ & GFP expression |

Key:
attR1 GATEWAY ™ recombination site
attR2 GATEWAY ™ recombination site
CaMV35s Cauliflower mosaic virus promoter sequence
GFP Jelly Fish Green Fluoresence Protein sequence
GW GATEWAY ™ destination cassette
OCS3' Octapine Synthase Terminator sequence Overview of Experimental Approaches Used to Clone White Clover Oleosin Repeats and DGAT1 into pRSH1.
Linerasing the Entry Clones When cloning into pRSH1, linearising the entry clone seemed to make the reaction more efficient. 2 μg of each of the six constructs were digested in 20 μL volumes with the enzyme Alw44I (Roche) which cuts once in the back bone of PENTRD™. Digests were cleaned up using the QIAGEN QIAquick PCR Purification Kit.™.

LR reactions were set up between pRSH1 with pOLE06-MC to pOLE10-MC as well as with DGAT1 as per Table 6.

TABLE 6

LR reactions for cloning oleosin repeats and DGAT1 into pRSH1.

| Component | Rxn 1 C6 | Rxn 2 C7 | Rxn 3 C8 | Rxn 4 C9 | Rxn 5 C10 | Rxn 6 DGAT1 |
|---|---|---|---|---|---|---|
| Linear entry clone | 5.55 | 5.55 | 5.55 | 5.55 | 5.55 | 5.55 |
| pRSH1 (1.5 μg/μL) | 0.2 | 0.2 | 0.2 | 0.2 | 0.2 | 0.2 |
| LR Clonase ™ (μL) | 2 | 2 | 2 | 2 | 2 | 2 |
| LR Rxn mix ™ (μL) | 2 | 2 | 2 | 2 | 2 | 2 |
| Topoisomerase (μL) | 0.25 | 0.25 | 0.25 | 0.25 | 0.25 | 0.25 |
| H$_2$O (μL) | — | — | — | — | — | — |
| Total (μL): | 10 | 10 | 10 | 10 | 10 | 10 |

C6 = pOLE06-MC etc.

The LR reactions were incubated overnight at 25° C., and were then transformed into *E. coli* DH5α. Four colonies were picked for each of the constructs C6-pRSH1, C7-pRSH1, C9-pRSH1 & C10-pRSH1, eight colonies were picked for C8-pRSH1 and three colonies for DGAT1-pRSH1.
Restriction Enzyme Digests to Screen Colonies Plasmid DNA was extracted from clones, and purified plasmid was analysed by restriction digest using the following protocol:

| μL | Component |
|---|---|
| 2 | Plasmid DNA (construct in pRSH1) |
| 1 | EcoRI (Roche) |
| 2 | Buffer H (Roche) |
| 15 | sH$_2$O |
| 20 | Total volume |

Incubated at 37° C. for 2 hours.
Digests were analysed by agarose/ethidium bromide gel electrophoresis and are shown in FIGS. 37-39.

Due to difficulties distinguishing between the two constructs C9-pRSH1 and C10-pRSH1 with the EcoRI digest clone1 of C9-pRSH1 and clone2 of C10-pRSH1 were digested with BamHI to determine if both constructs were correct. Digests were analysed by agarose/ethidum bromide gel electrophoresis and are shown in FIGS. 40-41.
Overview of Experimental Approaches Used to Clone White Clover Oleosin Repeats and DGAT1 into pRS12.
Linearising the Binary Plasmid When cloning into pRS12, linearising the binary plasmid rather than the entry clone seemed to make the reaction more efficient. 2 μg of pRS12 was digested in a 20 μL reaction volume with the enzyme SmaI (Roche), which makes a single cut between the GATEWAY™ att recombination sites in pRS12. The digest was cleaned up using phenol:chloroform:isoamyl alcohol (25:24:1 v/v) and then chloroform. 100% recovery of DNA was assumed from this cleanup method.

LR reactions were set up between pRS12 with pOLE06-MC to pOLE10-MC as well as with DGAT1 as per Table 7.

TABLE 7

For LR cloning oleosin repeats and DGAT1 into pRS12.

| Component | Rxn 1 C6 | Rxn 2 C7 | Rxn 3 C8 | Rxn 4 C9 | Rxn 5 C10 | Rxn 6 DGAT1 |
|---|---|---|---|---|---|---|
| Linear entry clone | 1 | 1 | 1 | 1 | 1 | 1 |
| pRS12 (2 μg/μL) | 0.2 | 0.2 | 0.2 | 0.2 | 0.2 | 0.2 |
| LR Clonase ™ (μL) | 2 | 2 | 2 | 2 | 2 | 2 |
| LR Rxn mix ™ (μL) | 2 | 2 | 2 | 2 | 2 | 2 |
| Topoisomerase | 0.25 | 0.25 | 0.25 | 0.25 | 0.25 | 0.25 |
| H$_2$O (μL) | 5.3 | 5.3 | 5.3 | 5.3 | 5.3 | 5.3 |
| Total (μL): | 10 | 10 | 10 | 10 | 10 | 10 |

C6 = pOLE06-MC etc.

The LR reactions were incubated overnight at 25° C., and were then transformed into *E. coli* DH5α. Twelve colonies were picked for analysis from the C6-pRS12 construct, two colonies from C7-pRS12, two from C8-pRS12, three from C9-pRS12, three from C10-pRS12, and two from DGAT1-pRS12.
Restriction Enzyme Digests to Screen Colonies Plasmid DNA was extracted from clones, and purified plasmid was analysed by restriction digest using the following protocol:

| μL | Component |
|---|---|
| 2 | Plasmid DNA (construct in pRS12) |
| 1 | Restriction enzyme (Roche) |
| 2 | Buffer (Roche) |
| 15 | sH$_2$O |
| 20 | Total volume |

Incubated at 37° C. for 2 hours.
Digests were analysed by agarose/ethidium bromide gel electrophoresis and are shown in FIGS. 42-45.
Representative maps of a pRSH1 binary vector containing white clover oleosin multimers is shown in FIG. 46.
Representative maps of a pRS12 binary vector containing white clover oleosin multimers is shown in FIG. 47.
Generation of Polyclonal Antibodies to White Clover Oleosin
Cloning of N-Terminal Region of White Clover Oleosin Into the pDEST17 and pET-DEST42 Expression Vectors The N-terminal region of oleosin was cloned into the pENTR-D vector, to produce the construct pEON. The N-terminal region of oleosin was transferred into the pDEST17 and pET-DEST42 vectors (Invitrogen) by the LR reaction to produce the constructs p17NON (FIG. 48) and p42CON (FIG. 49), which were then transformed into *E. coli* DH5α. p17NON was designed to express the N-terminal oleosin peptide with an N-terminal 6×His tag (6HON). The p42CON was designed to express the N-terminal oleosin peptides with a C-terminal 6×His tag (ON6H).

Plasmid DNA purified from the putative constructs was analysed by PCR using T7 and T7t primers (as marked on the maps in FIG. 48 and FIG. 49), to determine if the terminal regions were present (FIG. 50 and FIG. 51).

Plasmid DNA from lines p42CON-2 and p17NON-1 were transformed into *E. coli* strains BL21 and BL21-AI for protein expression.

(b) Sequence Analysis of Putative p17NON and p42CON

The p17NON and p42CON plasmid lines were sequenced from the 5' and 3' ends using T7 and T7t primers, respectively. The sequences obtained showed that the N-terminal regions of oleosin had been cloned in frame into both the pDEST17 and pET-DEST42 vectors.

Expression of Tagged Peptides

Example of Standard Culture and Induction Protocol 10 mL LB Amp100 broths were inoculated with expression construct in *E. coli* BL21-AI and incubated overnight at 37° C. 220 rpm. The next day duplicate 10 mL LB Amp100 broths were inoculated with 500 μL of the overnight cultures (to give $OD_{600}$=0.05-0.1). All cultures were incubated for approximately three hours at 37° C. 220 rpm, until $OD_{600}$=0.5-0.7 was reached. One set of the duplicate cultures was induced by the addition of 20% Arabinose to a final concentration of 0.2% and IPTG (isopropyl β-D-thiogalactopyranoside) to a final concentration of 1 mM. The second set of duplicate cultures was used as the non-induced negative controls, and therefore nothing was added to these cultures. All cultures were then incubated overnight at 37° C. 220 rpm. 1 mL aliquots were removed from each culture and prepared for SDS-PAGE analysis (Table 8).

TABLE 8

Standard prokaryotic induction protocol.

| | |
|---|---|
| 1° broth | 10 mL LB Amp100 broths |
| 1° inoculation | Colony picked from plate by toothpick |
| 1° incubation conditions | Overnight at 37° C. 220 rpm |
| 2° broth | 10 mL LB Amp100 broths (in duplicate) |
| 2° inoculation | 500 μL of the overnight cultures (to give OD600 = 0.05-0.1) |
| 2° incubation conditions | Approximately three hours at 37° C. 220 rpm, until OD600 = 0.5-0.7 |
| Induction | +ve - 20% Arabinose to a final concentration of 0.2% and IPTG (isopropyl β-D-thiogalactopyranoside) to a final concentration of 1 mM −ve - nothing added to non-induced negative control cultures |
| Induction incubation conditions | Overnight at 37° C. 220 rpm |
| Additional preparation | This may include harvesting and lysing cells |
| Analysis | 1 mL aliquots were removed from each culture and prepared for SDS-PAGE analysis |

Purification of Tagged White Clover Oleosin Peptides

HIS-Select Nickel Affinity Gel (Sigma) was used to purify the oleosin 6xHIS tagged proteins under denaturing conditions (Table 9 shows the buffers used).

Denaturing Buffers

TABLE 9

Buffers used to purify tagged white clover oleosin.

| | | | | Final vol. (mL) | | |
|---|---|---|---|---|---|---|
| | | Stock (M) | Final conc (M) | 100 EQUIL'N BUFFER | 100 WASH BUFFER | 100 ELUTION BUFFER |
| PO | mL | 0.25 | 0.1 | 40 | 40 | 40 |
| Urea | g | | 6 | 36 g | 36 g | 36 g |
| (Mr = 60.06) | | | | | | |
| NaCl | mL | 5 | 0.3 | 6 | 6 | 6 |
| Imidazole | mL | 2 | 0.005 | 0.25 | | |
| Imidazole | mL | 2 | 0.02 | | 1 | |
| Imidazole | mL | 2 | 0.25 | | | 12.5 |
| pH | | 5M HCl | | 8.0 | 8.0 | 8.0 |

Example of Standard Large Scale Purification Protocol 1.5 mL of HIS-Select Nickel Affinity Gel was transferred to a chromatography column. The affinity gel was washed with two volumes of deionized water and then equilibrated with three volumes of equilibration buffer. The clarified crude extract was loaded onto the column at a flow rate of 2 to 10 column volumes/hour. After the extract was loaded, the column was washed with wash buffer at a flow rate of about 10 to 20 column volumes/hour. The 6xHis tagged protein was eluted from the column using 3 to 10 column volumes of elution buffer at a flow rate of 2 to 10 column volumes/hour. Fractions were collected continuously and assayed for the target protein using Bradford's protein assay.

N-Terminal Fragment of White Clover Oleosin

Induction of p17NON and the Expression of 6HON (Oleosin N-Terminal with N-6xHis tag)

TABLE 10

Large scale induction protocol.

| | |
|---|---|
| 1° broth | 10 mL LB Amp100 broths |
| 1° inoculation | p17NON in *E. coli* BL21-Al, colony picked from plate by toothpick |
| 1° incubation conditions | Overnight at 37° C. 220 rpm |
| 2° broth | 10 mL LB Amp100 broths |
| 2° inoculation | 500 µL of the overnight cultures (to give OD600 = 0.05-0.1) |
| 2° incubation conditions | Approximately three hours at 37° C. 220 rpm, until OD600 = 0.5-0.7 |
| Induction | 20% Arabinose to a final concentration of 0.2% and IPTG (isopropyl β-D-thiogalactopyranoside) to a final concentration of 1 mM |
| Induction incubation conditions | Overnight at 37° C. 220 rpm |
| Analysis | 1 mL aliquots were removed from each culture and prepared for SDS-PAGE analysis (FIG. 52) |

Inclusion Body Preparation of 6HON For Purification

TABLE 11

Inclusion body preparation for *E. coli* expressed white clover oleosin.

| | |
|---|---|
| 1° broth | 5 mL LB Amp100 broths |
| 1° inoculation | p17NON in *E. coli* BL21-AI |
| 1° incubation conditions | Overnight at 37° C. 220 rpm |
| 2° broth | 50 mL LB Amp100 broths |
| 2° inoculation | 3.5 mL of the overnight cultures (to give OD600 = 0.05-0.1) |
| 2° incubation conditions | Approximately three hours at 37° C. 220 rpm, until OD600 = 0.5-0.7 |
| Induction | 20% Arabinose to a final concentration of 0.2% and IPTG (isopropyl β-D-thiogalactopyranoside) to a final concentration of 1 mM |
| Induction incubation conditions | Overnight at 37° C. 220 rpm |
| Additional preparation | The induced cells were collected by centrifugation and resuspended in 1/10 culture volume of buffer (50 mM Tris-HCl pH 8.0, 2 mM EDTA). Lysozyme was added to a concentration of 100 µg/mL, 1/10 volume of 1% Triton X-100 was then added, mixed gently and incubated at 30° C. for 15 minutes. DNA was sheared by sonication and the insoluble protein fraction was separated from the soluble fraction by centrifugation. |
| Analysis | 1 mL aliquots were removed from each culture and prepared for SDS-PAGE analysis (FIG. 53) |

Nickel Affinity Chromatography to Purify 6HON

HIS-Select Nickel Affinity Gel (Sigma) was used to purify the 6HON under denaturing conditions (as described above).

A trial scale purification of 6HON was carried out using a 2 mL sample from the insoluble protein fraction (as described above). The isolated 6HON was visualised using SDS-PAGE (FIG. 54).

Large Scale Purification of 6HON

TABLE 12

Large scale preparation for prokaryotically produced white clover oleosin for antibody generation.

| | |
|---|---|
| 1° broth | 5 mL LB Amp100 broths |
| 1° inoculation | p17NON in *E. coli* BL21-AI |
| 1° incubation conditions | Overnight at 37° C. 220 rpm |
| 2° broth | 500 mL LB Amp100 broths |
| 2° inoculation | 50 mL of the overnight cultures (to give OD600 = 0.05-0.1) |
| 2° incubation conditions | Approximately three hours at 37° C. 220 rpm, until OD600 = 0.5-0.7 |
| Induction | 20% Arabinose to a final concentration of 0.2% and IPTG (isopropyl β-D-thiogalactopyranoside) to a final concentration of 1 mM |
| Induction incubation conditions | Overnight at 37° C. 220 rpm |

TABLE 12-continued

Large scale preparation for prokaryotically produced white clover oleosin for antibody generation.

| | |
|---|---|
| Additional preparation | The induced cells were collected by centrifugation and resuspended in 1/10 culture volume of buffer (50 mM Tris-HCl pH 8.0, 2 mM EDTA). Lysozyme was added to a concentration of 100 µg/mL, 1/10 volume of 1% Triton X-100 was then added, mixed gently and incubated at 30° C. for 15 minutes. DNA was sheared by sonication and the insoluble protein fraction was separated from the soluble fraction by centrifugation. |
| Analysis | 1 mL aliquots were removed from each culture and prepared for SDS-PAGE analysis |

HIS-Select Nickel Affinity Gel was used to purify 6HON under denaturing conditions (as described above). A large scale purification of 6HON was carried out using the 500 mL sample (induced as described above). The purified 6HON was visualised using SDS-PAGE (FIG. 55) and the concentration of the eluted protein was estimated using a Bradford's protein assay, and found to be approximately 0.72, 2.74 and 1.89 mg/mL, for Elutions 1, 2 and 3 respectively (FIG. 56).

Generation of Rabbit Anti-White Clover Oleosin Antisera
Immunisation of Rabbit

66 µL of Elution 2 (see Large scale purification of 6HON, above), containing 250 µg purified protein, was mixed with 433 µL PBS. This was passed to the Massey University Small Animals Unit for immunisation of a rabbit (male, ID#124, Massey University Animal Ethics Committee (MUAEC) approval number 04/28). 25 days after the primary immunisation the first boost was administered (66 µL of Elution 2, containing 250 µg purified protein, mixed with 433 µL PBS), and the second boost was given 46 days after the primary immunisation (128 µL of Elution 1, containing 250 µg purified protein, mixed with 372 µL PBS).

Preparation of Rabbit Anti-White Clover Oleosin Antisera 53 days after the primary immunisation approximately 3 mL of blood was taken from the rabbit and placed at 4° C. for approximately 16 h. To separate the serum the blood was centrifuged at 1500×g 20 min 4° C. The serum (1.5 mL) was transferred to a fresh tube and stabilised with 0.25% Phenol in PBS and 0.01% Methiolate.

Assaying Titre and Specificity of Rabbit Anti-White Clover Oleosin Antisera by SDS-PAGE Immunoblot Analysis The samples outlined in Table 13 were analysed by SDS-PAGE immunoblot analysis using the anti oleosin N terminal antibody (FIG. 57).

TABLE 13

Samples used to determine titre and specificity of polyclonal rabbit anti-white clover oleosin antisera.

| Lane | ID | Load | Oleosin | Induced | Expressed |
|---|---|---|---|---|---|
| 1 | FLA-BL21_AI, E. coli | 1 µL | 6HOF | − | − |
| 2 | FLA-BL21_AI, E. coli | 1 µL | 6HOF | + | + |
| 3 | 17C-2-BL21_AI, E. coli | 1 µL | 6HOC | + | + |
| 4 | Elu1, 1:200, pure | 1 µL | 6HON, 1.8 ng | + | + |
| 5 | Elu2, 1:200, pure | 1 µL | 6HON, 6.9 ng | + | + |
| 6 | Elu3, 1:200, pure | 1 µL | 6HON, 4.7 ng | + | + |
| 8 | clover seed extract | 0.1 µL | 1.6 µg total protein | | |
| 9 | clover seed extract | 1 µL | 16 µg total protein | | |
| 10 | clover seed extract | 5 µL | 80 µg total protein | | |

Using Rabbit Anti-White Clover Oleosin Antisera to Detect Oleosin in Clover Seed Oil Bodies We checked to see if the antibodies were capable of detecting full-length oleosin. Early analysis of the antibodies on crude clover seed protein extracts had shown that the antibodies were able to be used to detect a protein of the expected size when clover seed oil body extracts were analysed by Immunoblot analysis (FIG. 58).

Results from the immunoblot showed that the anti-oleosin N-terminal antibodies could be used to specifically detect a ~20 kDa protein—the expected size of the clover oleosin protein.

Overview of Experimental Approaches Used to Transform Plants with White Clover Polyoleosin Clones.

Transformation of Brassica oleracea with White Clover Polyoleosin and DGAT1 Constructs A total of 12 constructs were transformed into Brassica oleracea (Table 14. These were all transferred into Agrobacterium tumefaciens strain LBA4404 via the freeze-thaw method described in Christey and Braun (2004). Colonies were selected on LB medium containing 100 ml/l streptomycin and 100 ml/l spectinomycin. PCR analysis for the BAR gene was used to confirm plasmid presence in Agrobacterium colonies.

TABLE 14

Summary of constructs placed into Brassica oleracea.

| Construct | C&F code | Genes | Marker |
|---|---|---|---|
| pRSH1-C6 | AgR 6 | 35S-oleosin monomer | 35S-BAR |
| pRSH1-C7 | AgR 7 | 35S-oleosin dimer | 35S-BAR |

TABLE 14-continued

Summary of constructs placed into Brassica oleracea.

| Construct | C&F code | Genes | Marker |
|---|---|---|---|
| pRSH1-C8 | AgR 8 | 35S-oleosin trimer | 35S-BAR |
| pRSH1-C9 | AgR 9 | 35S-oleosin tetramer | 35S-BAR |
| pRSH1-C10 | AgR 10 | 35S-oleosin pentamer | 35S-BAR |
| pRSH1-At DGAT | DGAT | 35S-Arab. DGAT | 35S-BAR |
| pRSh4 | | Arab. oleosin seed promoter + GUSi | 35S-BAR |
| pRSh6 | | oleosin seed prom. + oleosin monomer | 35S-BAR |
| pRSh7 | | oleosin seed prom. + oleosin dimer | 35S-BAR |
| pRSh8 | | oleosin seed prom. + oleosin trimer | 35S-BAR |
| pRSh9 | | oleosin seed prom. + oleosin tetramer | 35S-BAR |
| pRSh10 | | oleosin seed prom. + oleosin pentamer | 35S-BAR |

Plant Material and Transformation

For these experiments a rapid cycling (RC) *B. oleracea* line, DH1012, selected for high regeneration and transformation ability by Sparrow et al. (2004) was used. Seeds were germinated in vitro as described in Christey et al. (1997). Hypocotyl and cotyledonary petiole explants from 4-5 day-old seedlings were co-cultivated briefly with a culture of *Agrobacterium* grown overnight in LB medium containing antibiotics prior to 1:10 dilution in antibiotic-free minimal medium (7.6 mM $(NH_4)_2SO_4$, 1.7 mM sodium citrate, 78.7 mM $K_2HPO_4$, 0.33M $KH_2PO_4$, 1 mM $MgSO_4$, 0.2% sucrose) with growth for a further 4 hrs. Explants were cultured on Murashige-Skoog (MS; Murashige and Skoog, 1962) based medium with B5 vitamins and 2.5 mg/L BA. After 3 days co-cultivation, explants were transferred to the same medium with 300 mg/L Timentin (SmithKline Beecham) and subsequently placed on selection medium with 2.5 mg/L Basta. Green shoots were transferred to hormone-free Linsmaier-Skoog based medium (LS; Linsmaier and Skoog, 1965) containing 5 mg/L Basta and solidified with 10 gm/L Danisco Standard Agar. Explants were cultured in tall Petri dishes (9 cm diameter, 2 cm tall) sealed with Micropore (3M) surgical tape. Shoots were cultured in clear plastic tubs (98 mm, 250 ml, Vertex). All culture manipulations were conducted at 25° C. with a 16 h/day photoperiod, provided by Cool White fluorescent lights (20 $\mu E/m^2/s$).

Determination of Selective Levels of Basta

Hypocotyl and cotyledon explants from 4 day-old seedlings were cultured on LSN medium containing 2.5 mg/L BAP and 300 mg/L Timentin and 5 different levels of Basta (0, 2.5, 5, 10 and 25 mg/L) to determine the appropriate level to use for selection in co-cultivation experiments.

To determine the selective level of Basta for maintenance of in vitro shoots, small healthy apical cuttings were transferred to tall pots of hormone-free LSn containing either 2.5 or 5 mg/L Basta.

Conformation of *Brassica oleracea* Transformation by PCR

DNA was isolated from leaves of in vitro shoots using the rapid method described in Christey and Braun (2004). PCR was conducted to test for the presence of the bar gene using the primers baran (5'-tcagatctcggtgacgggcagg-3') (Seq ID No. 11) and barse (5'-atgagccaagaacgacgcccgg-3') (Seq ID No. 12) to produce a 551 bp product. PCR conditions were: 94° C. for 30 sec, 65° C. for 30 sec and 72° C. for 30 sec over 40 cycles.

PCR was conducted on Bar positive samples to check for the presence of the oleosin clones using the primers outlined in Table 15. PCR conditions were: 94° C. for 30 s, 45° C. for 30 s and 68° C. for 30 s for 30 cycles. A 650 bp product was expected.

TABLE 15

Primers used for oleosin PCR.

| Primer name | Sequence | Sequence IDs |
|---|---|---|
| AgR 6 forward | CACCATGGCACAACCT CAAGTT | SEQUENCE ID NO. 13 |
| AgR 7 forward | GCTCCACCGCG | SEQUENCE ID NO. 14 |
| AgR 6/7 reverse | TCCACTAGTTCTAG | SEQUENCE ID NO. 15 |
| AgR 8 forward | CTAGAACTAGTGGAT | SEQUENCE ID NO. 16 |
| AgR 8 reverse | TCCTGCAGAGTAC | SEQUENCE ID NO. 17 |
| AgR 9 forward | GTACTCTGCAGGA | SEQUENCE ID NO. 18 |
| AgR 9 reverse | ATACGATAGTAC | SEQUENCE ID NO. 19 |
| AgR 10 forward | CTATCGATACCGTCG | SEQUENCE ID NO. 20 |
| AgR 10 reverse | CTCGAGTGTTGATCTC TTAGCTTC | SEQUENCE ID NO. 21 |

Conformation of White Clover Polyoleosin Construct Gene Expression in *Brassica oleracea* Transformants by RT-PCR RNA was isolated from plants using the Concert™ small scale isolation reagent (Invitrogen). DNA was digested using Turbo DNase (Ambion). For RT-PCR the primers described in Table 15 were used to amplify the transcribed region. Reactions were performed on RNA samples using the Superscript™ III (Invitrogen) Reverse Transcriptase, with the RT step performed at 50° C. followed by PCR.

*Agrobacterium* Transformation

PCR for the Bar gene was used to confirm the presence of the oleosin-containing plasmids in *Agrobacterium* colonies (FIG. 59). Two BAR positive colonies from each transformation event were selected for storage at −80° C. in glyercols and used in subsequent explant co-cultivation experiments.

Determination of Selective Levels of Basta

Figure 60:
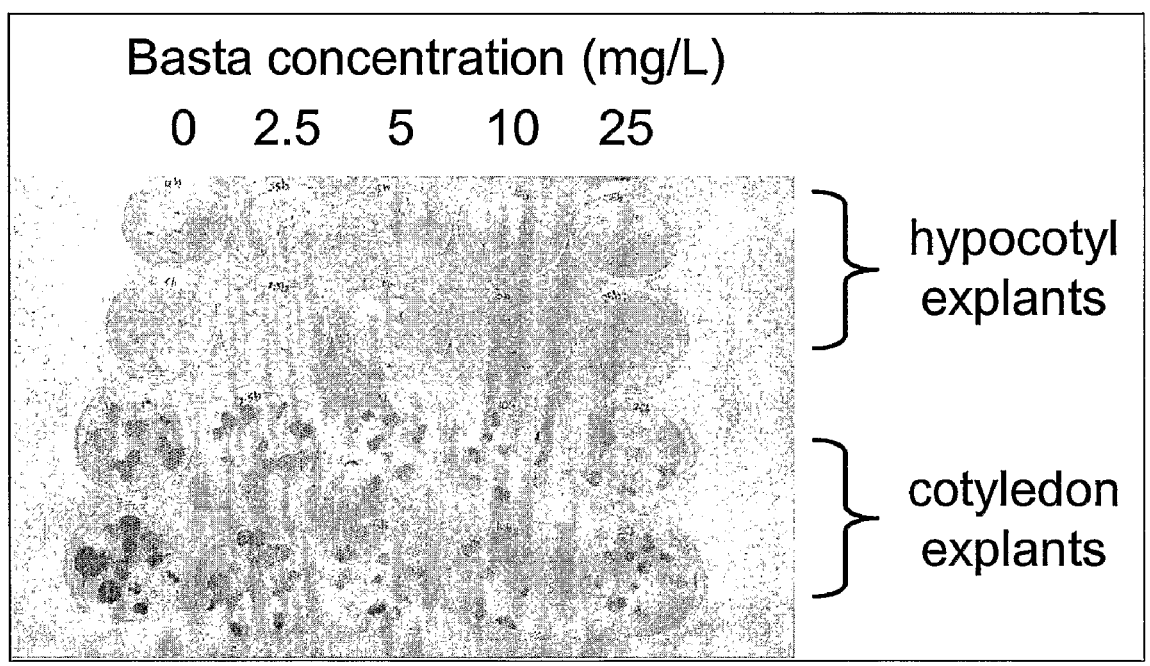

The results of the explant selection experiment confirmed that use of 2.5 mg/L Basta was suitable for use as the selection level for subsequent co-cultivation experiments. After 2-4 weeks on this level rare shoot regeneration was noted (FIG. 60). In contrast, in vitro shoot cuttings showed some development on 2.5 mg/L Basta with root development apparent on some. In contrast, after 4-5 weeks on 5 mg/L Basta cuttings turned brown with no root development. This level was used in subsequent experiments for growth of putative transgenic shoots.

Selection of Transgenic Shoots

At least 150 explants were co-cultivated with each construct (Table 16). Three to four weeks after co-cultivation rare small green shoots were apparent. Putative Basta resistant shoots were excised and transferred to hormone-free media containing 5 mg/L Basta. In vitro shoot and root growth on Basta-containing medium confirmed plants were transgenic. Transgenic plants were healthy with good shoot and root development and normal phenotype. In contrast, Basta sensitive cuttings showed little development (FIG. 61). Transgenic shoots were obtained mainly from hypocotyl explants with only rare transgenic shoots obtained from cotyledon explants. While the overall transformation rate was only 1.2%, there was a lot of variation between both experiments and explants, with some combinations producing over 5% transformation in some experiments.

TABLE 16

Summary of PCR positive shoots.

| Construct | No. explants cocultivated | | No. PCR +ve for BAR | | Total |
|---|---|---|---|---|---|
| | cotyledon | hypocotyl | cotyledon | hypocotyl | |
| pRSH1-C6 | 70 | 90 | 0 | 6 | 6 |
| pRSH1-C7 | 170 | 110 | 1 | 3 | 4 |
| pRSH1-C8 | 390 | 190 | 2 | 2 | 4 |
| pRSH1-C9 | 390 | 190 | 0 | 4 | 4 |
| pRSH1-C10 | 250 | 120 | 3 | 7 | 10 |
| At DGAT | 416 | 195 | 0 | 8 | 8 |
| pRSh4 | 200 | 120 | 2 | 2 | 4 |
| pRSh6 | 100 | 50 | 0 | 0 | 0 |
| pRSh7 | 110 | 30 | 0 | 1 | 1 |
| pRSh8 | 110 | 50 | 1 | 2 | 3 |
| pRSh9 | 110 | 50 | 0 | 0 | 0 |
| pRSh10 | 110 | 50 | 1 | 0 | 1 |
| Total | 2426 | 1245 | 10 | 35 | 45 |

Conformation of Transformation by PCR

Shoots growing on 5 mg/L Basta that were still green and showing good root development after at least two subcultures had DNA extracted and PCR performed for the bar gene. Over 250 shoots were analysed with 45 confirmed as having the bar gene (20%) (Table 10). PCR analysis confirmed the presence of the Bar gene in all plants that had shown good growth on selective levels of Basta in vitro. PCR for the Bar gene produced a 551 bp fragment (FIG. 62). PCR analysis of Bar positive shoots for the oleosin gene indicated that not all plants contain the oleosin gene as well (FIG. 63).

Transgenic shoots were obtained for 10 of the 12 constructs in Table 14. Most constructs had at least 4 independent transgenic shoots but no transgenic shoots were obtained for pRSh6 and pRSh9. Negative shoots were retained on 5 mg/L Basta in case they were false negatives and re-tested if they remained green with roots. Generally PCR negative shoots showed Basta sensitivity symptoms in subsequent subculture rounds suggesting negative PCR results were genuine. For all transgenic lines 1-2 pots of clonal cuttings remain in vitro. All lines appeared healthy with good root and shoot development and normal phenotype.

Conformation of Expression by RT-PCR

RT-PCR analysis confirmed expression of the oleosin construct in 4 out of 5 lines tested (FIG. 64).

Transformation of *Lotus japonicus* with *Agrobacterium rhizogenes*

Northern Analysis of RNA Extracted from Hairy Roots

Figure 65:
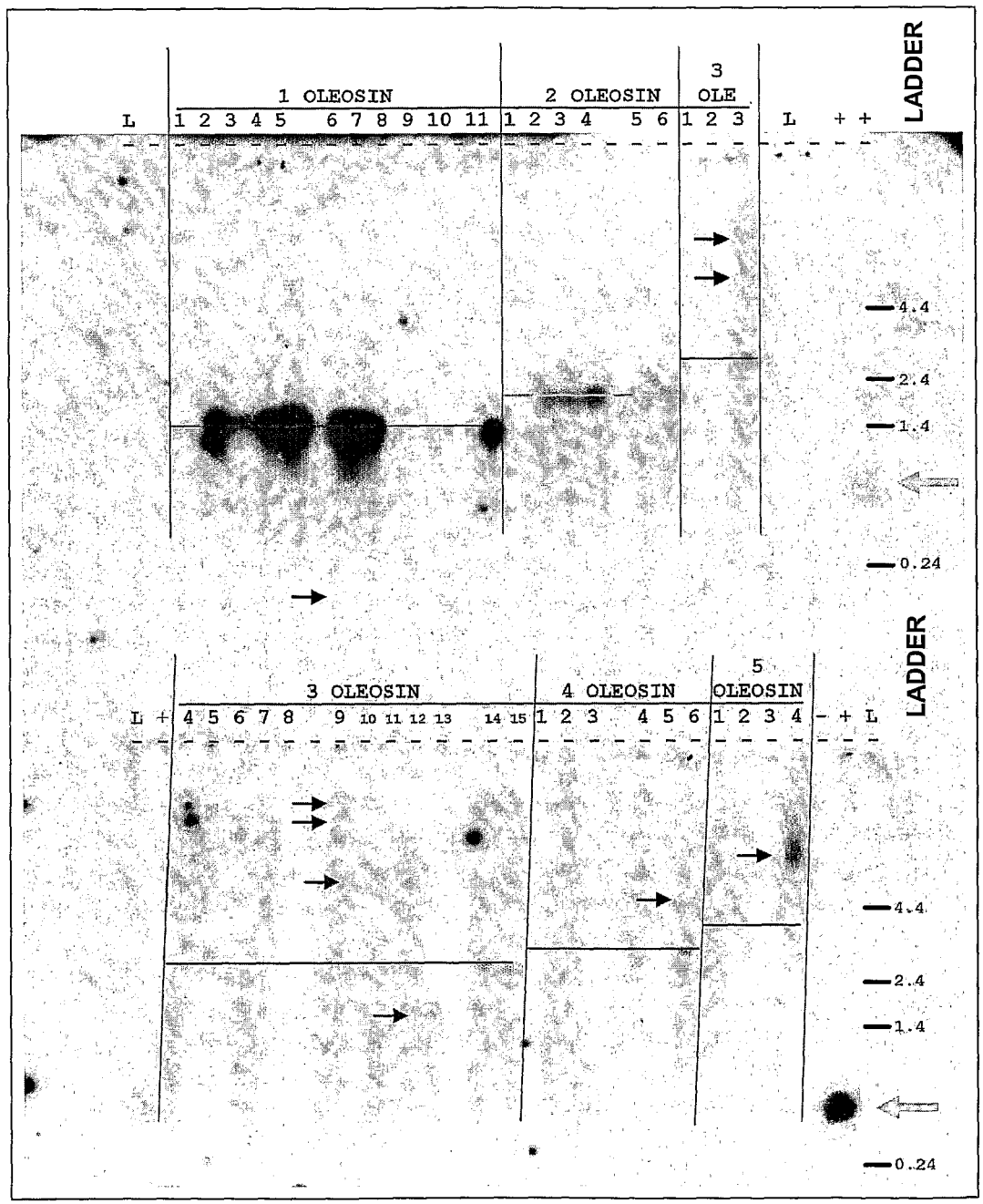

Northern blot analysis was performed on transformed *Lotus japonicus* hairy roots (see below) to confirm the expression of the polyoleosin constructs. The blot was probed with $^{32}$P labeled, random primed, white clover oleosin cDNA (FIG. 65). The Northern blot analysis shows that the constructs are transcribed. In each case it appears that transcription has finished close to the 3' end of the OCS terminator where a single oleosin transcript and the terminator are roughly 1.5 kb in length. It is clear that the transcript from the single oleosin is highly expressed in the majority of the single oleosin transformants. Each additional oleosin repeat resulted in the increase in the transcript size by the appropriate amount (~650b). As such that the sizes are as follows 1.4 kb, 2 kb, 2.7 kb, 3.4 kb and 4 kb for the oleosin monomer, dimer, trimer, tetramer and pentamer, respectively. The level of transcript accumulated appears to be inversely proportional to the number of oleosin repeats. Furthermore, the transformants containing either the oleosin monomer or dimer did not have any transcripts of unexpected size hybridising to the oleosin probe, whereas the transformants containing the oleosin trimer, tetramer or pentamer had a number of additional hybridising bands. In the majority of cases the bands were considerably larger than the expected size, frequently >4.4 kb, and in only one case did the hybridising band appear to be smaller than the predicted transcript. Since the extra bands only appear in lines transformed with the trimeric or larger oleosin repeats, we have assumed that these bands represent aberrantly processed oleosin RNA, and in many cases the processing appears to have failed to terminate transcription.

Transformation of *Lotus japonicus* with *Agrobacterium rhizogenes* (A4T)

Protocol

Day 1

Scarify lotus seeds using p220 wet/dry sand paper

Sterilise seeds by rotating for 20 min in 10 mL sterilisation soln:
  7 mL 100% ethanol
  1 mL 30% $H_2O_2$
  2 mL $H_2O$ Wash 3 times in sterile $H_2O$ Place seeds on 1% water agar plates Wrap plates in tinfoil (dark) and germinate at 25° C. for 2 days Streak TY agar plate with *Agrobacterium rhizogenes* (A4T) glycerol stock and grow overnight @ 28° C.

Day 2

Inoculate 50 mL YEB culture broth with colony from A4T plate and grow overnight @ 28° C. shaking (220 rpm)

Day 3

Make *Agrobacterium* competent cells and transform with binary plasmid containing gene of interest, plate on TY agar plates and grow for 2 days at 28° C. (refer: Transformation of *Agrobacterium*)

Transfer germinated seeds to ½ B5 media, approx 10 across each plate, roots pointing down.

Tape plates together, grow vertically on lab bench.

Day 5

Pick colonies from *Agrobacterium* plates into 10 mL TY-spectomycin broths and grow at 28° C. shaking (220 rpm) for 2 days.

Day 6

Perform PCR on *Agrobacterium* broths to check for desired gene.

Day 7

Inoculate *Lotus japonicus* plants by dipping a sterile scalpel into the *Agrobacterium* broth and cutting off the root. After inoculation tape plates together, wrap in tinfoil and leave overnight on lab bench Day 8

Unwrap plates and grow for 2 days vertically on lab bench

Day 9

Transfer plants to MS (CRO) media containing the antibiotic cephotaximine, 10 across a plate. Grow vertically on lab bench.

Roots can be viewed (for GFP) under a Microscope 10-20 days later.

Media
½ B5 Media (No Sucrose)

| | |
|---|---|
| 0.0425 g | $NaH_2PO_4 \cdot 2H_2O$ |
| 0.625 g | $KNO_3$ |
| 0.0335 g | $(NH_4)_2SO_4$ |
| 0.0625 g | $MgSO_4 \cdot 2H_2O$ |
| 0.01 g | Ferric EDTA |
| 0.025 g | Myo-Inositol |
| 0.25 mL | Stock A |
| 0.25 mL | Stock B |
| 0.25 mL | Stock C |
| 0.25 mL | Stock D |

Adjust pH to 5.5 with 0.2M KOH or 0.2M $HC_{1-6}$
6 g Agar
Make up to 500 mL with sterile H20

MS(CRO) Media

| | |
|---|---|
| 50 mL | MS Macro Stock |
| 5 mL | MS Macro Stock |
| 5 mL | MS Fe (EDTA) Stock |
| 1 mL | B5B Vitamins stock |
| 30 g | Sucrose |
| 100 mg | Myo-Inositol |
| 8 g | Phytagel agar | pH to 5.7 with NaOH
Final volume = 1000 mL

MS Macro Stock

| | |
|---|---|
| 33 g | $NH_4NO_3$ |
| 38 g | $KNO_3$ |
| 8.8 g | $CaCl_2 \cdot 2H_2O$ |
| 3.4 g | $KH_2PO_4$ |
| 7.4 g | $MgSO_4 \cdot 7H_2O$ |

Final volume = 1000 mL

MS Fe (EDTA) Stock

| | |
|---|---|
| 4 g | Ferric EDTA (Fe Na Ethylene diaminetetra acetic) |

Final volume = 500 mL

MS Micro Stock

| | |
|---|---|
| 1.24 g | $H_3BO_3$ |
| 4.46 g | $MnSO_4 \cdot 4H_2O$ |
| 1.72 g | $ZnSO_4 \cdot 7H_2O$ |
| 0.166 g | KI |
| 0.05 g | $Na_2MoO_4 \cdot 2H_2O$ |
| 0.005 g | $CuSO_4 \cdot 5H_2O$ |
| 0.005 g | $CoCl_2 \cdot 6H_2O$ |

Final volume = 1000 mL

B5 Vitamin Stock

| | |
|---|---|
| 0.1 g | Nicotinic Acid |
| 1.0 g | Thiamine HCl |
| 0.1 g | Pyridoxine HCl |

Final volume = 100 mL

| | |
|---|---|
| 1 mL | aliquots into eppendorfs |

Store at −20° C.

Notes
Transformation of *Lotus*:
This protocol includes the transformation of *Agrobacterium* which sometimes is just being grown from glycerols. Also is written as for GFP—if for PPT resistant plants then on day 9 (or just when roots are visible) we transfer to selective plates. Usually 4 plants (roots only) per plate. Once selection has taken place (either GFP or PPT) individual roots are transferred to individual plates. Supposedly we transfer all or some of the tissue to a new plate each month. Once we are growing root portions only the plates are kept horizontal, sealed and in darkness, usually in the 25 C room.

Transformation of *Agrobacterium rhizogenes* (A4T)
1. Streak a TY agar plate with *Agrobacterium rhizogenes* (A4T) glycerol stock and grow 28° C. overnight.
2. Inoculate 50 mL of YEB broth with a colony from *Agrobacterium* plate and grow at 28° C., shaking (220 rpm) until $OD_{600}$ is approx 0.5 (16 h)
3. Centrifuge cells for 15 min @ 400 rpm, discard supernatant and resuspend in 10 mL of 0.15M $NaC_{1-4}$
4. Centrifuge cells for 10 min @ 4000 rpm, discard supernatant, and resuspend in 1 mL of ice-cold 20 mM $CaCl_2$
5. Aliquot 200 μL of cells into an eppendorf tube, add 5 μg of DNA and incubate on ice for 30 min.
6. With what is left of the 1 mL aliquot 186 μL of cells and 14 μL of DMSO into eppendorf tubes and freeze in liquid $N_2$ then store at −70° C.
7. After incubation on ice for 30 mins freeze the DNA/cells in liquid $N_2$ for 1 min.
8. Thaw in a 37° C. waterbath
9. Repeat steps 7 & 8
10. Add 1 mL of YEB broth and incubate cells for 4 h @ 28° C. with gentle shaking
11. Plate cells on TY agar containing spectomycin and grow for 2 days @ 28° C.
12. Pick colonies from the *Agrobacterium* plates into 10 mL TY broths containing spectomycin and grow for 2 days @ 28° C., shaking at 220 rpm.

*Agrobacterium* transformed with a binary vector are prepared for infiltration by plating or spreading a bacterial lawn on the appropriate plate with appropriate antibiotics (although Rifampicin is not normally included). The *Agrobacterium* should be grown at 28° C. for 2-3 days.

Clover Seed Oilbody Purification
Buffers for Oilbody Extraction
Buffer A

| | |
|---|---|
| 4 mL | 500 mM NaPhosphate Buffer, pH 7.5 |
| 41.1 g | sucrose |

Final volume = 200 mL (with $dH_2O$)

Buffer D

| | |
|---|---|
| 1 mL | 500 mM NaPhosphate Buffer, pH 7.5 |
| 17.1 g | sucrose |
| 23.4 g | NaCl |

Final volume = 200 mL (with $dH_2O$)

Detergent Washing Solution

| | |
|---|---|
| 0.4 mL | 10% Tween 20 (0.1%) |
| 20 mL | Floating Buffer (½× Buffer D) |

Final volume = 40 mL (with dH$_2$O)

Procedure
1. Weigh 2 g of clover seed.
2. Homogenate the seed in ~20 mL of Buffer A with sand in a mortar and pestle.
3. Transfer to two 15 mL Falcon tubes and centrifuge 3200×g 10 min RT.
4. Transfer upper aqueous phase and any floating material to two 15 mL Falcon tubes and add 1 mL Buffer D.
5. Resuspend the oil bodies thoroughly by sonication Power-1 Duty Cycle-100% 5×30 sec.
6. Centrifuge 10,000 rpm 10 min RT.
7. Transfer upper/floating oil-body layer at the top with a bended spatula to 2 mL microfuge tubes containing 1.5 mL of Detergent Washing Solution.
8. Resuspend the oil bodies thoroughly by sonication Power-1 Duty Cycle-100% 5×30 sec.
9. Centrifuge 10,000 rpm 10 min RT.
10. Transfer upper/floating oil-body layer at the top with a bended spatula to 2 mL microfuge tubes containing 1.5 mL of Buffer A.
11. Resuspend the oil bodies thoroughly by sonication Power-1 Duty Cycle-100% 5×30 sec.
12. Centrifuge 10,000 rpm 10 min RT.
13. Transfer upper/floating oil-body layer at the top with a bended spatula to 2 mL microfuge tubes containing 500 μL of Buffer A.
14. Resuspend the oil bodies thoroughly by vortexing and prepare samples for SDS-PAGE analysis.

RNA Isolation from Plants Using the QIAGEN RNeasy Kit

RNA was isolated from *Agrobacterium tumefaciens* infected *N. benthamiana* leaves and *Agrobacterium rhizogenes* infected *L. japonicus* roots using the RNeasy Plant Mini Kit (QIAGEN, Hilden, Germany). Approximately 0.1 g of tissue was removed from the plant, placed into a 1.5 mL microcentrifuge tube, frozen in liquid nitrogen and ground to a fine powder using a stainless steel rod. 450 μL RLT Buffer (guanidinium isothiocyanate) and 4.5 μL β-mercaptoethanol were added and the mixture vortexed vigorously until the sample thawed then for a further 30 sec. The lysate was transferred onto a QIAshredder spin column (lilac), fitted in a 2 mL collection tube (supplied) using a 1 mL pipette with the end of the tip cut off to prevent blockages. The mixture was spun in microfuge for 2 min at 13000 rpm. The filtrate was transferred to a 1.5 mL centrifuge tube taking care not to disturb the debris in collection tube. 225 μL Absolute Ethanol (0.5 vols.) was added and mixed immediately by pipetting. The filtrate/ethanol mix, and any precipitate, was decanted onto the RNeasy mini spin column (pink) which had been fitted in a 2 mL collection tube (supplied). The mixture was spun in a microfuge for 15 sec at 13000 rpm. The filtrate was then discarded, but the column and collection tube were retained for the next step. To column was washed by loading on 700 μL RW1 Buffer then spun in a microfuge for 15 sec at 13000 rpm. The filtrate was discarded, and 500 μL RPE Buffer was loaded onto the column, which was then spun in a microfuge for 15 sec at 13000 rpm. Again, the filtrate was discarded and another 500 μL RPE Buffer was loaded onto the column and spun for 15 sec at 13000 rpm. The filtrate was discarded, and the column was spun for an additional min at 13000 rpm to thoroughly dry the column. Next the column was carefully removed from the collection tube, avoiding the carry-over of ethanol/wash buffer. The RNeasy column was then placed into a fresh 1.5 mL collection tube (supplied) and 30 μL RNase-free H$_2$O was added onto the column. The column was spun in a microfuge for 60 sec at 13000 rpm to elute the RNA. The RNA was stored at −20° C. until required.

RT-PCR cDNA synthesis.

Expand Reverse Transcriptase, Roche, cat#1785826, supplied with 5× Buffer and DTT.

| | |
|---|---|
| 8.5-9.5 μL | Total RNA (1 μg recommended) |
| either 2 μL | 10 μM gene specific reverse primer |
| or 1 μL | Oligo(dT)$_{12-18}$ @ 100 pmoles/μL |

Total volume 10.5 μL (with RNase-free sterile H$_2$O)

Denatured RNA and primer for 10 min at 65° C.
Immediately cooled on ice.
Added respective reagents separately to each tube in the following order (no cocktail):

| | |
|---|---|
| 4 μL | 5 × Expand reverse transcriptase buffer (first-strand) (1×) |
| 2 μL | 100 mM DTT (10 mM) |
| 2 μL | 10 mM dNTP Mix (dATP + dCTP + dGTP + dTTP, Roche cat#1581295; 1 mM) |
| 0.5 μL | RNase Inhibitor (Roche, cat#799017, 40 U/μL; 20U) |
| 1 μL | Expand Reverse Transcriptase (Roche cat#11 785 834 001; 50 U/μL; 50U) |

Total volume 20 μL (with RNase-free sterile H$_2$O)

Mixed and pulse spun.
Incubated at 43° C. for 45-60 min.
Quenched on ice.
Used immediately.

First Round PCR Reaction.

| | |
|---|---|
| 5 μL | cDNA |
| 1 μL | 10 mM dNTP Mix (dATP + dCTP + dGTP + dTTP, Roche cat#1581295; 200 μM) |
| 0.3 μL | 25 μM Forward primer (150 nM) |
| 0.3 μL | 25 μM Reverse primer (150 nM) |
| 5 μL | 10× PCR reaction buffer with MgCl$_2$ (Roche cat#1 647 679; 1×) |
| 1 μL | Taq DNA Polymerase (Roche cat#1 647 679; 1 U/μL; 1U) |

Total volume 50 μL (with sH$_2$O)

First Round PCR Amplification.

| | | |
|---|---|---|
| 95° C. | 2:00 | 1 cycle |
| 95° C. | 0:30 | |
| 58° C. | 0:30 | 30 cycles |
| 72° C. | 2:30 | |
| 72° C. | 7:00 | 1 cycle |

Northern Analysis of RNA 4 pg pMC6 (Clone 6) used as template.
Amplified using pMC1 (Clone 1) forward and reverse primers and standard Taq reaction.
Extracted bands purified using QIAGEN Gel Purification kit.
Product quantified to 55 ng/μL.

Formaldehyde Gels
***All water should be sourced fresh from the still.

10× MOPS/EDTA Buffer
(A) 52.3 g MOPS (Free Acid, Mr=209, 500 mM)
  Adjust pH to 7.0 with 10N NaOH.
  Final vol 250 mL.
(B) 1.86 g EDTA (Na salt, Mr=372, 10 mM, or 1 mL 500 mM EDTA in 500 mL)
  Adjust pH to 7.5 with 10 N NaOH.
  Final vol 250 mL
  Add 250 mL MOPS to 250 mL EDTA to obtain correct final concentrations.
  Store in the dark at room temperature.
  The buffer may yellow with age or autoclaving but this will not affect buffering capacity.

Buffer A
  300 µL 10×MOPS/EDTA Buffer
Final vol 1 mL.

Formaldehyde/Formamide

| 89 µL  | AR Formaldehyde (37-40%) |
| 250 µL | Formamide (TOXIC. Fumehood and Gloves) |

Gel Loading Buffer

| 400 mg | Sucrose |
| 320 µL | Buffer A |

Mix to dissolve then add

| 5 mg | Xylene cyanol |
| 5 mg | Bromophenol blue |

Mix to dissolve. Add

| 178 µL | AR Formaldehyde (37-40%) (TOXIC. Fumehood and Gloves) |
| 500 µL | Formamide (TOXIC. Fumehood and Gloves) |

Store in 100 µL aliquots at −20° C.

Running Buffer (=1×MOPS/EDTA)

| 225 mL | 10× MOPS/EDTA Buffer |

Total vol = 2.25 L

Sample Preparation

| 30 µg | RNA (as a dry pellet) |
| 5.5 µL | Buffer A |

Resuspend RNA. Add

| 12 µL | Formamide/Formaldehyde (TOXIC. Fumehood and Gloves) |

Heat to 70° C. (heating block) for 10 min then quench on ice.
  Add 4.5 µL Gel Loading Buffer Load onto submerged gel.

Pouring Formaldehyde Gel
Prepare gel tray by wiping out with ethanol and taping both ends with a double layer of masking tape.

| 250 | 200 | 125 | mL | Final vol. |
| 2.5 | 2.0 | 1.25 | g | Agarose |
| 25 | 20 | 12.5 | mL | 10x MOPS/EDTA Buffer |
| 180 | 144 | 90 | mL | H$_2$O |

For today's work 2 gels 150 × 100 mm prepared with 30-tooth combs in each.

Mix in a 500 mL flask and dissolve in microwave. Stir while cooling.
All of following steps should be done in the fumehood:

| Add 45 mL | 36 mL | 22.5 mL | AR Formaldehyde (37-40%) |

Mix and pour into prepared gel tray, with comb in place.
Allow to set for 30-45 min.
Cover with Running Buffer, load and run initially at 50V for 15 min to get samples into gel, then turn voltage down to 12V and run overnight.

Northern Blot
20×SSC

| 175.3 g | AR NaCl (=3M) |
| 88.2 g | AR Sodium citrate (=0.3M) |

Adjust pH to 7.0

Total Volume 1 L
This Northern Blot method uses the flow of buffer DOWN through a gel then a nylon membrane to transfer denatured RNA from the gel onto the membrane. Based on the design of the Schleicher & Schuell TurboBlotter.

1. Two 3 cm stacks of interfolded paper hand towels (Hygenex Royale, 245×270 mm, cat#2170360) were placed side-by-side in a plastic tray
2. Two sheet of 3 mM paper, cut to 220×160 mm were placed on top, followed by one sheet pre-wetted in 10×SSC.
3. The nylon membrane (Hybond-XL (Amersham; cat no: RPN303S) was cut to 220×160 mm, pre-wetted with dH$_2$O, rinsed for 1 min in 10×SSC, and finally placed onto the stack.
4. The gel was removed from the gel plate and washed for 20 min in 10×SSC.
5. The washed gel was then placed onto the membrane ensuring that no bubbles were trapped between the gel and the membrane. Note care was taken to ensure that the gel was positioned correctly as transfer may be initiated as soon as the gel comes into contact with the membrane.
6. Three sheets of pre-wetted 3 mM paper, cut to 230×170 mm, were layered onto the stack. Again ensuring that no bubbles were trapped between the layers.
7. Finally the pre-wetted 3 mM wick, cut to ~800×180 mm, was placed across the stack, with each end folded over and submerged in 100 mL 20×SSC, which was in containers at the side of the blot/stack.

NOTE
1. The wick was kept flat at all times (i.e. the containers were long enough so that the wick did not have to be crammed in).
2. The sides of the containers were only 1-2 cm high so that the capillary action could easily draw the 20×SSC up and out of the reservoirs.

Next Day
1. The blot was carefully taken apart down to the gel. A soft leaded pencil was pushed through the wells, and used to mark the position of each well on the membrane.
2. The RNA crosslinked to the membrane using a
3. The membrane was then placed between two sheets of dry 3 mM paper and allowed to dry.
4. Finally the membrane was wrapped in Gladwrap and stored at 4° C. overnight.

Labelling the Probes
RadPrime DNA Labeling System (Invitrogen, Cat. No.: 18428-011)

1. Denature 25 ng DNA dissolved in 19 μL of sterile distilled water or TE in a microcentrifuge tube by heating for 5 min in a boiling water bath; then immediately cool on ice
2. Perform the following additions on ice:

| | | |
|---|---|---|
| 1 | μL | 500 μM dATP |
| 1 | μL | 500 μM dGTP |
| 1 | μL | 500 μM dTTP |
| 20 | μL | 2.5X Random Primers Solution |
| 5 | μL | [α-32P]dCTP (3000 Ci/mmol. 10 mCi/mL, approximately 50 μCi) |
| To | 49 μL | with dH$_2$O |

3. Pulse spin
4. Mix briefly, add
   1   μL   Klenow Fragment
5. Mix gently but thoroughly
6. Pulse spin
7. Incubate at 37° C. for 10 min
8. Add    5    μL    Stop Buffer Purifying the Probe.
ProbeQuant G-50 Micro Columns, Amersham Biosciences, cat#27-5335-01.
1. Loosen the lid of the column and snap off the seal at the bottom.
2. Place the column into a 1.5 mL microcentrifuge tube.
3. Spin at 735×g for 1 min to remove the liquid.
4. Place the column into a fresh 1.5 mL microcentrifuge tube.
5. Layer the labelled probe onto the column.
6. Spin at 735×g for 2 min (unincorporated nucleotides, dyes, and salts will remain on the column).
7. The purified labelled probe will collect in the microfuge tube.
8. Denature the labelled DNA by heating to 95-100° C. for 5 min and snap-cool on ice.
9. Pulse spin.
10. Immediately add into Pre/Hybridisation Solution in tubes (do not place directly onto blot).

Probing Blots
20×SSC

| | |
|---|---|
| 175.3 g | AR NaCl (=3M) |
| 88.2 g | AR Sodium citrate (=0.3M) |

Adjust pH to 7.0
Total volume 1 L

Pre/Hybridisation Solution.
(from: Church G M & Gilbert W. 1984, *Genomic Sequencing, Proc. Natl. Acad. Sci. USA*).

| | |
|---|---|
| 12.5 mL | 1M NaHPO$_4$ Buffer pH 7.2 (250 mM) |
| 20 mL | H$_2$O |
| 100 μL | 0.5 M EDTA (1 mM) |
| 17.5 mL | 20% SDS (7%) |
| 0.5 g | BSA (1%) |

Final volume ~50 mL.

Pre-wet blots in 2×SSC before placing in hybridisation oven tubes.
Pre-hybridise in 45 mL Pre/Hybridisation Solution at 65° C. for 2 h.
Add denatured probe (see above) to the Pre/Hybridisation Solution and hybridise at 65° C. overnight.

Washing Blots
2× Wash Buffer

| | |
|---|---|
| 50 mL | 20 × SSC (2 × SSC) |
| 2.5 mL | 20% SDS (0.1% SDS) |

Final volume = 500 mL.

1× Wash Buffer.

| | |
|---|---|
| 25 mL | 20 × SSC (1 × SSC) |
| 2.5 mL | 20% SDS (0.1% SDS) |

Final volume = 500 mL.

0.2× Wash Buffer.

| | |
|---|---|
| 5 mL | 20 × SSC (0.2 × SSC) |
| 2.5 mL | 20% SDS (0.1% SDS) |

Final volume = 500 mL.

0.1× Wash Buffer.

| | |
|---|---|
| 2.5 mL | 20 × SSC (0.1 × SSC) |
| 2.5 mL | 20% SDS (0.1% SDS) |

Final volume = 500 mL.

Wash Filters
2× Wash Buffer 2×15 min at 65° C. (~200 mL per hybridisation tube).
1× Wash Buffer 2×15 min at 65° C. (~200 mL per hybridisation tube).
0.2× Wash Buffer 2×15 min at 65° C. (~200 mL per hybridisation tube).
0.1× Wash Buffer 2×5 min at 65° C. (~200 mL per hybridisation tube).

Seal membranes in thin plastic bag, check counts using Geiger counter, and expose to X-ray film with intensifying screen at −70° C., overnight (if ~20 counts per second) or longer depending on signal intensity after washing.
Blots were exposed for 3 days.

Example 2

Synthetic Sesame Seed Polyoleosin Construction

Background
We designed a synthetic sesame seed oleosin with tandem repeats for expression in both *E. coli* as well as plants (e.g., *Arabidopsis* and *Lotus*). It should be noted that the oleosin sequence used is for example only. Any oleosin sequence or combinations of oleosins, steroleosins and caoleosins and oleosin linking sequences could be used. The original sesame seed oleosin nucleotide sequence and translated peptide sequence are from a sesame seed oleosin, GenBank clone AF091840 (Tai et al., 2002). The codons were optimised for both E. coli and Arabidopsis expression. Each repeat used randomised degenerate codons to code for the specific amino acid sequence thus ensuring that the repeats will not be rearranged by non rec⁻ bacteria such as Agrobacterium tumefaciens or Agrobacterium rhizogenes. The construct was designed so that it can be relatively simply subcloned from the original backbone (pUC57) into both pET29a and various plant binary vectors. In order to allow simple restriction digestion and re-ligation to reduce the number of repeats as well as to enable us to paste in future peptides between the repeats we engineered restriction sites between them.

The design allows various numbers of tandem repeats to be easily transferred into pET29a and to perform simple digestions on the original clone to remove different numbers of inserts then transfer to binary vectors. This included a NcoI site on each end of the sesame oleosin to place it into pET29a which gives the peptide an N-terminal S*Tag and thrombin cleavage site and a C-terminal His.Tag. For transfer to plant binary vectors we designed an attL1 site to the 5' end and an attL2 site to the 3' end, these are compatible for with our GATEWAY plant binary constructs built in house.

Unique restriction sites (Eco47 µl, DraI, MluNI, SacI, SalI, EcoRI, HindIII, ScaI, HpaI, Alw44I) were also engineered between the repeats to allow future additions of peptides between the repeats. A single oleosin repeat can be generated by XhoI digestion and re-ligation. Similarly, constructs for a dimeric, trimeric and tetrameric oleosin repeats can be generated by digestion and re-ligation with ClaI, BstXI and NdeI respectively. These can then be transferred to chosen binary vectors via the LR reaction. If the intron is not required then this can be removed after transfer to the binary. NotI sites flanked the ORF of the complete clone to allow sub-cloning into pART binary vectors if necessary.

We have mainly concentrated on constructs using cauliflower mosaic virus 35S promoter (CaMV35S), a well-characterized over-expression promoter. It is expected that polyoleosin expression will only be seen in the seeds of transformed plants where triglyceride will be present (de Boer and Somerville, 2001). We have also created a binary vector containing the Arabidopsis oleosin promoter; this can also be utilised for discreet polyoleosin expression in the seed.

In addition we created several alternative trimeric oleosin-repeat constructs, In E. coli, we have had success expressing a trimer of direct repeats of the sesame oleosin that was successfully expressed by Dr. Bocky Chi-Chung Peng (Peng et al., 2004). We created two binary vectors (CaMV35S and Oleosin promoters) containing this direct repeat trimer. These constructs have been transformed into Arabidopsis.

Codon Analysis

We compared the codon usage by both E. coli and Arabidopsis (Table 17). From this we were able to identify codons that were not suitable for use in this construct; these included the following:

| | |
|---|---|
| Arg | AGG |
| Arg | AGA |
| Arg | CGG |
| Arg | CGA |
| Arg | CGC |
| Ile | ATA |
| Leu | CTA |
| stop | TAG |

These codons were removed from the codon Table, the remaining codons were placed in a spread sheet which randomised the possibilities still available for each amino acid. Thus, while the codon usage was randomised the peptide sequence for the sesame seed oleosin was conserved. The randomisation was repeated 6 times, one for each oleosin repeat. An alignment of these sequences showed that the homology dropped to approximately 75% between each repeat and the drop in homology was generally distributed evenly across the whole sequence.

TABLE 17

Comparison of E. coli and A. thaliana codon usage.

| Amino Acid | Codon | E. coli frequency | A. thaliana frequency |
|---|---|---|---|
| Gly | GGG | 0.16 | 0.15 |
| Gly | GGA | 0.12 | 0.37 |
| Gly | GGT | 0.34 | 0.34 |
| Gly | GGC | 0.38 | 0.14 |
| Glu | GAG | 0.32 | 0.48 |
| Glu | GAA | 0.68 | 0.52 |
| Asp | GAT | 0.63 | 0.68 |
| Asp | GAC | 0.37 | 0.32 |
| Val | GTG | 0.36 | 0.26 |
| Val | GTA | 0.16 | 0.15 |
| Val | GTT | 0.26 | 0.41 |
| Val | GTC | 0.22 | 0.19 |
| Ala | GCG | 0.34 | 0.14 |
| Ala | GCA | 0.22 | 0.27 |
| Ala | GCT | 0.17 | 0.44 |
| Ala | GCC | 0.27 | 0.16 |
| Arg | AGG | 0.03 | 0.20 |
| Arg | AGA | 0.05 | 0.35 |
| Ser | AGT | 0.16 | 0.16 |
| Ser | AGC | 0.27 | 0.13 |
| Lys | AAG | 0.24 | 0.52 |
| Lys | AAA | 0.76 | 0.48 |
| Asn | AAT | 0.47 | 0.52 |
| Asn | AAC | 0.53 | 0.48 |
| Met | ATG | 1.00 | 1.00 |
| Ile | ATA | 0.09 | 0.24 |
| Ile | ATT | 0.50 | 0.41 |
| Ile | ATC | 0.41 | 0.35 |
| Thr | ACG | 0.27 | 0.15 |
| Thr | ACA | 0.15 | 0.30 |
| Thr | ACT | 0.17 | 0.34 |
| Thr | ACC | 0.41 | 0.20 |
| Trp | TGG | 1.00 | 1.00 |
| End | TGA | 0.32 | 0.43 |
| Cys | TGT | 0.44 | 0.60 |
| Cys | TGC | 0.56 | 0.40 |
| End | TAG | 0.08 | 0.20 |
| End | TAA | 0.60 | 0.36 |
| Tyr | TAT | 0.58 | 0.52 |
| Tyr | TAC | 0.42 | 0.48 |
| Leu | TTG | 0.13 | 0.22 |
| Leu | TTA | 0.13 | 0.14 |
| Phe | TTT | 0.58 | 0.51 |
| Phe | TTC | 0.42 | 0.49 |

TABLE 17-continued

Comparison of *E. coli* and *A. thaliana* codon usage.

| | | | |
|---|---|---|---|
| Ser | TCG | 0.15 | 0.10 |
| Ser | TCA | 0.13 | 0.20 |
| Ser | TCT | 0.15 | 0.28 |
| Ser | TCC | 0.15 | 0.13 |
| Arg | CGG | 0.11 | 0.09 |
| Arg | CCA | 0.07 | 0.12 |
| Arg | CGT | 0.36 | 0.17 |
| Arg | CGC | 0.37 | 0.07 |
| Gln | CAG | 0.66 | 0.44 |
| Gln | CAA | 0.34 | 0.56 |
| His | CAT | 0.58 | 0.61 |
| His | CAC | 0.42 | 0.39 |
| Leu | CTG | 0.48 | 0.11 |
| Leu | CTA | 0.04 | 0.11 |
| Leu | CTT | 0.11 | 0.26 |
| Leu | CTC | 0.10 | 0.17 |
| Pro | CCG | 0.50 | 0.18 |
| Pro | CCA | 0.20 | 0.33 |
| Pro | CCT | 0.17 | 0.38 |
| Pro | CCC | 0.13 | 0.11 |

Each number represents the proportion that codon is used to code for the respective amino acid. Codons in grey were not used in the polyoleosin construct since they coded for the respective amino acid less than 10% of the time in either organism. Codons in bold and underlined were removed to raise the GC content and to remove cryptic splice sites and mRNA degradation signals (ATTTA).

Selection and Location of Restriction Sites Between Oleosin Repeats

Restriction sites were inserted as linkers between the repeats. The sites were chosen to allow the subcloning of different combinations of oleosin repeats; they also allowed for the generation of 8 amino acid linkers between each repeat to allow for free rotation etc. Linkers with undesirable codons were not used.

The multiple cloning sites of both pUC57 and pET29a allowed the design of a sub-cloning strategy using multiple placements of the following restriction sites within the polyoleosin construct.

| Bst XI | Cla I | Pst I | Nco I | Nde I | Not I | Xho I |
|---|---|---|---|---|---|---|

The randomised oleosin repeats were checked for these sites and alternative codons were then used to eliminate the sites when discovered.

Unique Restriction Sites

We also engineered unique Eco47 III, Dra I, Mlu NI, Sac I, Sal I, Sca I, Hpa I, Alw44I sites between different repeats. These have been included to allow future additions of peptides between the repeats.

Not I Sites

Not I sites flank the ORF of the complete clone. This is to allow sub-cloning into pART binary vectors if necessary.

A schematic diagram of the construct is shown in FIG. 66.

Optimisation for: Improving Translation Efficiency; Increasing RNA Stability; Correct Splicing.

Tetranucleotide Stop Codon.

Brown et al., (1990) reported that there was an increasing number of reports where the tri-nucleotide stop codons do not signal the termination of protein synthesis; they found that the signals UAA(A/G) and UGA(A/G) are the preferred stop codons in eukaryotes. Hence we have added an A to the 3' end of the second stop codon (TGA) in our construct.

mRNA Degradation Signal

Beelman and Parker (1995) reported the degradation signal ATTTA (AUUUA) can destabilize transcripts in plants as well as animals. The proposed construct ORF originally had 7 ATTTA sites. These were predominantly caused by the sequence coding for isoleucine followed by a tyrosine residue. The ATTTA sites were removed by changing the relevant isoleucine codons to ATC. Re-analysis of the splice sites after the removal of the ATTTA sites showed that fewer regions were predicted to be introns (partially determined by the GC content).

pOly T

The original proposed construct ORF would have had 27 TTTT sites and 12 TTTTT sites.

To reduce the number of these regions the phenylalanine codon TTT was removed and replaced by TTC; in one case the site was eliminated by moving the engineered DraI site to the 5' end of the Mlu NI site. Combined these changes reduced the number of TTTT sites to 14 and the number of TTTTT sites to 1.

Plant Intron Insertion

The insertion of a recognised plant intron into an expression construct frequently results in a significantly enhanced expression of the construct in planta; this is termed Intron Mediated Enhancement (Rose 2004 and references therein). The sequence and position of the intron is important in terms of expression enhancement with the highest gains obtained by placing the *Arabidopsis thaliana* ubiquitin10 (UBQ10) intron within the first 250 bases or so of the 5' end of the transcript (Rose, 2002; 2004 and references therein). Rose and Beliakoff (2000) found that utilising a PstI site was a useful way to insert introns. This was achieved by engineering a PstI site to the 5' end of the intron and by modifying the existing 3' end of the intron to contain a PstI site, from this they were able to add or delete functional introns wherever a PstI site existed in the gene or cDNA.

Vector NTI identified approximately 4 PstI sites within the proposed polyoleosin construct with the closest to the 5' end occurring approximately 500 bases downstream. All these sites were eliminated using various combinations of degenerate codons and a new PstI site was engineered at position 300 using the degenerate codons. This places the intron in the first oleosin repeat and therefore enables the generation of all truncated versions with the intron (see Sub-Cloning Strategy below). Using the UBQ10 intron sequence (Norris et al., 1993) we engineered the 3' end to include a PstI site; the comparison with the original sequence is shown in FIG. 67.

The new polyoleosin construct (containing the intron) was then analysed by NetGene2 (Hebsgaard et al., 1996; Brunak et al., 1991, web site address www.cbs.dtu.dk/services/NetGene2/ to confirm that the engineered intron would be predicted to be spliced correctly. This analysis revealed that not only would the UBQ10 be spliced out correctly but there were also high confidence cryptic donor and acceptor sites that would likely result in aberrant splicing. The putative cryptic splice sites were either eliminated wherever possible or reduced in confidence by using alternative redundant codons. The analysis was repeated and showed that the only high confidence donor and acceptor sites remaining were flanking the engineered UBQ10 intron (NetGene 2 results of both the polyoleosin prior to cryptic splice site removal and polyoleosin with intron and cryptic splice sites removed are shown below); it was predicted that the splicing would remove only the intron and would leave the construct in frame. The analysis showed that a number of regions did not appear to be coding regions and as such may be susceptible to some aberrant splicing. To further reduce the possibility of cryptic splicing we then modified the GC content of the construct (see GC content below).

GC Content

Oleosins with optimised and randomised codons; no ATTTA sites or TTT were still found to have relatively low GC content compared to the original sequence. To increase the GC content the additional codons were removed: ATT, AAT, TTA, CTT; this raised the GC content to close to the original content (Table 18).

The repeats were linked using the previously engineered linking regions. These sequences were modified to remove all but the first Pst I sites in the first oleosin repeat and the removal of an Xho site in the second oleosin repeat. In our construct the ORF has no ATTTA or TTTT sites. Furthermore, when the sequence was re-analysed by NetGene2 the only predicted intron splice site in the ORF was the UBQ10 intron engineered into the PstI site and the % identity of the repeats increased from an average of 74.8% identical to 79.1% identical.

NetGene2 was used to predict the splicing of the proposed construct. The results indicated that the RNA should only be spliced at the acceptor and donor sites of the UBQ10 intron (Table 19 and FIG. 68).

Conformation of Sequence

The coding sequence of the complete ORF (after splicing) was then checked against a heptameric repeat of the original oleosin translated sequence and found to be identical over the oleosin coding regions (FIG. 69).

The sequence and feature map of the proposed construct is shown in FIG. 70 and the vector map is shown in FIG. 71.

Sub-Cloning Strategy.

Plant Intron Removal

The intron is designed to be removed by Pst I digestion, fragment removal and re-ligation. However, due to the presence of a Pst I site in the multiple cloning site of pUC57 it would be necessary to perform a partial digestion to remove this fragment. It would be preferable to attempt this at least once in order to generate full length clones with and without the intron in the initial cloning vector. Alternatively the full length clones can be transferred to expression vectors prior to Pst I digestion as detailed above.

Transfer to E. coli Expression Vector pET29a and Generation of Different Number of Repeats.

Transfer the complete clone via partial NcoI digestion then re-ligation into pET29a. The intron can then be removed by Pst I digestion and re-ligation. Full Nco I digestion of the original clone then transfer to pET29a will also yield two trimeric oleosin clones, one will contain the intron. All NcoI digests going into pET29a will have to also be checked for orientation, as this step is not directional. Following intron removal in pET29a a single oleosin repeat can be generated by Xho I digestion and re-ligation. Similarly, constructs for a dimeric, trimeric and tetrameric oleosin repeats can be generated by digestion and re-ligation with Cla I, Bst Xl and Nde I respectively.

Transfer to pRS Series of GATEWAY Adapted Binary Vectors and Generation of Different Number of Repeats.

A single oleosin repeat can be generated by Xho I digestion and religation. Similarly, constructs for a dimeric, trimeric and tetrameric oleosin repeats can be generated by digestion and re-ligation with Cla I, Bst Xl and Nde I respectively. These can then be transferred to chosen binary vectors via the LR reaction. If the intron is not required then this can be removed after transfer to the binary vector or by partial digestion in pUC57.

TABLE 18

Comparison of GC content of each synthetic oleosin repeat and the original oleosin sequence.

| Construct Design | Original Oleosin | Oleosin Repeat Number | | | | | |
|---|---|---|---|---|---|---|---|
| | | 1 | 2 | 3 | 4 | 5 | 6 |
| Oleosins with initial selection of optimised and randomised codons; no ATTTA sites or TTT codons | 60.9% | 54% | 54% | 53% | 57% | 56.8% | 53.8% |
| Oleosins with initial selection of optimised and randomised codons; no ATTTA sites or TTT codons and additionally no ATT, AAT, TTA or CTT codons | 60.9% | 58.7% | 59.1% | 59.8% | 60.5% | 59.5% | 57.7% |

TABLE 19

NetGene2 tabulated output prediction of splicing in polyoleosin after manual removal of cryptic splice sites plus the addition of the UBQ10 intron and enriched GC content. The predicted cryptic splice site at position 97 was ignored since this is in the attL1 site and is not part of the transcribed region.
With Intron, optimised codons, enriched GC content, RNA stability modifications

| Donor splice sites, direct strand | | | | |
|---|---|---|---|---|
| pos 5'->3' | phase | strand | confidence | 5' exon intron 3' |
| 332 | 2 | + | 1.00 | GTACCTGCAG GTAAATTTCT H |

TABLE 19-continued

NetGene2 tabulated output prediction of splicing in polyoleosin after manual removal of cryptic splice sites plus the addition of the UBQ10 intron and enriched GC content. The predicted cryptic splice site at position 97 was ignored since this is in the attL1 site and is not part of the transcribed region.
With Intron, optimised codons, enriched GC content, RNA stability modifications

| Acceptor splice sites, direct strand | | | | |
|---|---|---|---|---|
| pos 5'->3' | phase | strand | confidence | 5' intron exon 3' |
| 97 | 1 | + | 0.90 | AAAAAAGCAG^GCTCCGCGGC |
| 635 | 1 | + | 1.00 | TGATCTGCAG^TCATCACAAT H |

| Branch points, direct strand | | | | |
|---|---|---|---|---|
| acceptor pos 5'->3' | branch pos 5'->3' | strand | score | 5' A 3' |
| 97 | 52 | + | −2.41 | CAACAAATTGATAAGCAATG |
| 635 | 617 | + | −3.71 | GATTAATCTGAGTTTTTCTG |

Prokaryotic Expression Constructs.

Three sesame seed oleosin direct repeat constructs were used to generate the prokaryotic expression constructs (FIGS. 66, 72 and 73). One clone provided by Dr Bocky Peng (Graduate Institute of Biotechnology, National Chung Hsing University, Taichung, Taiwan 40227) contained a single oleosin clone using the cDNA nucleotide sequence obtained from the sesame seed oleosin clone as reported by Peng et al., (2004). A second clone generated synthetically by GENEART AG contained 3 identical tandem repeats of the cDNA nucleotide sequence obtained from the sesame seed oleosin clone (FIG. 73); each repeats was linked with a nucleotide sequence encoding glycine-glycine-glycine-glycine-serine-glycine-glycine-glycine-glycine-serine (GGGGSGGGGS) (Seq ID No. 22). The third clone was the synthetic sesame seed oleosin hexameric repeat generated by GENEART AG (FIG. 66). Combinations of the GENEART AG synthesised clones including the prokaryotic specific constructs and the plant optimised construct were used to generate prokaryotic expression vectors in the Novagen pET29 backbone containing between 1 to 6 repeats of the oleosin transcript (FIGS. 74-83).

The first new synthetic oleosin clone was designed around the sesame seed oleosin minus the six C terminal amino acids but a different C terminal linker to the 6×His tag. Successful expression of this clone in the pET29a vector would indicate that a specific C terminal linker amino acid sequence is not essential for successful expression. The design of the linker also allows for many different oleosin sequences/repeats to be cloned into the 3' region of the clone, including components of the existing synthetic oleosin sequence with altered codons.

In the synthetic sesame seed oleosin identical triplicate nucleotide repeat clone (FIGS. 73 and 83), the linker sequence between each unit in the repeat has a repetitive amino acid motif of GGGGSGGGGS, which is designed to allow free movement of each unit in relation to the other units. The C terminal sequence is also be the same as C terminal sequence from the protein expressed by p29Ole, i.e., the single sesame seed oleosin construct. A summary of the constructs and their design is listed in Table 20.

TABLE 20

Constructs in the pET29 (Novagen) backbone for sesame seed polyoleosin expression in E. coli.

| Construct name | Purpose | Number of sesame seed oleosin repeats | Source of repeats |
|---|---|---|---|
| p29Ole | prokaryotic expression | 1 | original cDNA (FIG. 83) |
| p29Ole2-6xHis | prokaryotic expression | 2 | triplet identical repeats from GENEART AG clone (FIG. 73) |
| p29PS3a | prokaryotic expression | 3 | first 3 randomised codon repeats from GENEART AG (FIG. 70) |
| p29PS3b | prokaryotic expression | 3 | second 3 random repeats from GENEART AG (FIG. 70) |
| p29Ole3+ | prokaryotic expression | 3 | Triplet identical repeats from GENEART AG (FIG. 73) |
| p29Ole4-6xHis | prokaryotic expression | 4 | Original cDNA and triplicate identical repeats from GENEART AG (FIG. 73) |
| p29Ole5-6xHis | prokaryotic expression | 5 | Triplicate identical repeats from GENEART AG (FIG. 73) |

TABLE 20-continued

Constructs in the pET29 (Novagen) backbone for sesame seed polyoleosin expression in E. coli.

| Construct name | Purpose | Number of sesame seed oleosin repeats | Source of repeats |
|---|---|---|---|
| p29Ole6-6xHis | prokaryotic expression | 6 | randomised codon repeats from GENEART AG (FIG. 70) |

Generation of Polyclonal Antibodies to Sesame Seed Oleosin
Culture and Induction of Expression System A 50 mL LB broth, supplemented with 50 µg/L kanamycin (Kan50), was inoculated with a loop of pET29 (containing the nucleotide sequence encoding a single sesame seed oleosin with a C-terminal His tag) culture from a plate and incubated 37° C. 200 rpm overnight (16 h). The following day 6 mL aliquots of the overnight culture were used to inoculate 2×125 mL LB Kan50 broths in 1 L conical flasks (initial OD600=0.16). The cultures were incubated 37° C. 200 rpm for ~2 h ($OD_{600}$=0.6) and IPTG was added to a final concentration of 0.24 mg/mL (1 mM). The induced cultures were returned to incubate at 37° C. 200 rpm for a further 4 h. The cultures were transferred to 250 mL centrifuge pots and spun at 4000×g 4° C. for 10 min (5000 rpm, Sorvall, SS34 rotor).

The supernatant was discarded and the remaining cells were lysed by adding 10 mL of B PER® Reagent (Novagen) to the pellet and vortexing/pipetting up and down until the cell suspension was homogeneous. The lysed culture was then incubated with gentle mixing for 20 min. Soluble proteins were separated from insoluble proteins by centrifugation at 12,000×g 4° C. for 25 min (13,400 rpm, microfuge). The supernatant was discarded (i.e. retained insoluble proteins in pellet). To increase the purity of the inclusion bodies, 5 mL B PER® Reagent+200 µg/mL lysozyme was added to the pellet, which was then vortexed/pipetted up and down to resuspend. The mixture was then incubated at RT for 5 min, then spun at 12,000×g 4° C. for 25 min (13,400 rpm, microfuge). The supernatant was discarded (i.e. retained insoluble proteins in pellet, pellet very diffuse) and pellet/dissolved inclusion bodies was resuspended in 4 mL Binding Buffer (100 mM $NaPO_4$, pH8.0, 500 mM NaCl, 6M urea and 10 mM imidazole). To remove debris the mixture was spun at 12,000×g 4° C. for 15 min (13,400 rpm, microfuge).

Ni-Agarose Purification and Concentration of His-Tagged Recombinant Protein 2 mL aliquots of Invitrogen Ni agarose slurry was placed into two empty columns (A and B) and spun in a hand-operated centrifuge to remove storage buffer. To equilibrate the columns 3×4 mL Binding Buffer was passed through the columns, spinning in the hand-operated centrifuge between each equilibration. The lysate was added to the column and the Ni agarose was gently resuspended into the lysate. The columns were incubated at RT for 10 min with gentle end-over-end mixing then spun in a hand-operated centrifuge to remove post bind filtrate. To remove non-bound proteins the columns were washed 3×4 mL Wash Buffer (100 mM $NaPO_4$, pH8.0, 500 mM NaCl, 6M urea and 50 mM imidazole), spinning in a hand-operated centrifuge between each wash. Note that the Wash Buffer previously contained 25 mM imidazole the higher concentration (50 mM) was found to increase the purity of the His-tagged target protein in the eluted fractions. Finally, fractions were eluted in the following sequential volumes of Elution Buffer (100 mM $NaPO_4$, pH8.0, 500 mM NaCl, 6M urea and 250 mM imidazole), with spinning in a hand-operated centrifuge between each fraction: 1 mL (fraction 1), 2 mL (fraction 2), 1 mL (fraction 3), 1 mL overnight (fraction 4).

200 µL of fraction 3A and 3B was removed and put aside, fractions 1A, 2A, and the remainder of fraction 3A were pooled as were fractions 1B, 2B, and the remainder of fraction 3B giving approximately 2.5 mL each. Each pool was placed into a spin concentrator with a 10 kD molecular weight cut off. The concentrators were spun 3181×g 4° C. for 60 min. The concentrate was transferred to a fresh tube and the membrane washed with 2×100 uL of the respective retained Fraction 3, the washes were then added to the concentrate.

Whole Gel Elution/Purification of Target Protein

Whole gel elution was performed using the Bio Rad Mini Whole Gel Eluter as per manufacturers instructions. A denaturing elution buffer was used (250 mM Tris, 125 mM boric acid, 0.1% SDS, check final pH=8.7) and the gel was eluted at 85 mA (constant) for 25 min.

The whole gel elution technique was used to increase the purity of a sample of $Ni^{2+}$ agarose purified recombinant sesame oleosin. Table 21 outlines the loss of recombinant protein that occurred at each stage of the purification process.

TABLE 21

Protein losses during the whole gel elution procedure.

| Following . . . | Total Protein (µg) | Volume (µL) | Remaining (%) |
|---|---|---|---|
| Ni-agarose column | 4106 | 830 | 100 |
| Concentration | 978 | 60 | 24 |
| Whole gel elution | 272 | 3000 | 7 |
| Concentration | 83 | 70 | 2 |

Following the whole gel elution the gel (FIG. 84) and cellophane (not shown) were Coomassie stained to try to identify where the loss had occurred.

An intense band of the same molecular weight as the oleosin could be seen both in the gel and on the cellophane. This indicated that the region of the gel containing the oleosin had not been completely over one of the slots in the whole gel eluter, and only an estimated 40% of the target protein was actually eluted from the gel. The presence of oleosin on the cellophane membrane suggested that the oleosin was either precipitating out at high concentrations or the oleosin was binding to the cellophane, which is possible given the hydropathic clusters within the protein.

Ni Agarose Chromatography Affinity Purification

Following the failure of the whole gel elution another culture was prepared and passed through two Ni2+ agarose affinity columns (A and B) and washed at a high stringency (50 mM imidazole). Eluted fractions were analysed by Coomassie stained SDS PAGE (FIG. 85) and the protein concentration of fractions 1A and 1B was measured using the Bradford's Assay (Table 22).

TABLE 22

Protein concentration of selected fractions from Ni$^{2+}$ agarose purification.

| Sample | Read 1 | Read 2 | Average | ug | uL in rxn | ug/uL | Final vol. (uL) | Final amt. (ug) |
|---|---|---|---|---|---|---|---|---|
| 1A | 0.584 | 0.583 | 0.584 | 2.65 | 1 | 2.65 | 400 | 1060 |
| 1B | 0.608 | 0.605 | 0.608 | 2.86 | 1 | 2.86 | 400 | 1146 |

Raising Antibodies in Rabbits

The first injection was prepared by mixing equal amount of Freunds Complete Adjuvant and the solution containing 265 µg of the target protein, to a maximum final volume of 0.5 mL. The injection was then administered into multiple sites across the back of the neck and shoulder area of the rabbit. Booster shots containing 77 µg of the target protein were delivered 3 4 weeks after the primary. Then 10-14 days later a test bleed of ~3 mL was removed for preliminary analysis.

Bleeds were normally stored overnight at 4° C. The following day this was spun at 1500×g 4° C. for 5 min. Clear serum was removed from the top of the clot and initially stored as 200 µL aliquots at 20° C. After thawing, phenol and methiolate was added to the serum (to a final concentration of 0.25% and 0.01% respectively)

Analysis of Rabbit Anti-Sesame Seed Oleosin Antiserum

Four SDS PAGE gels were prepared and loaded identically with samples containing varying amounts of affinity purified oleosin (first fractions from columns A and B). The gels were run out and three were used for immunoblot analysis and one was silver stained.

Serum from the test sample was prepared as described above for the rabbit anti-white clover oleosin antisera and used at 1:200 and 1:1000 dilutions (in TBS-Tween) to screen two of the immunoblots. The remaining immunoblot was screened with a 1:200 dilution (in TBS-Tween) of a chicken anti oleosin antibody raised by Professor Jason Tzen (Graduate Institute of Biotechnology, National Chung Hsing University, Taichung, Taiwan 40227). Results from the immunoblot analysis and silver staining are shown in FIG. 86.

Expression and Analysis of 1×-6× Polyoleosin in *E. coli*

Preparation of *E. coli* Expression Lines

100 µL competent *E. coli* Rosetta cells were transformed with 2.5 µL plasmid DNA. Samples were then incubated on ice for 20 min; heat shocked 42° C. 1 min; cooled rapidly on ice 2 min; and incubated with the addition of 900 µL LB broth at 37° C. 60 min 1400 rpm (Thermomixer). Pelleted cells were spread on LB Kan50 plates and incubated at 37° C. overnight.

Preparation of Artificial Oil Bodies (AOBs)

The primary methods for investigating the properties of the putative triple sesame polyoleosin protein was to compare with the single sesame recombinant protein in terms of:
  AOB size
  AOB stability over time and at various temperatures and pH values
  Stability of AOBs in the rumen Day 1

10 mL LB Kan50 broth toothpick inoculated with original colony from p29Ole3+(8b) and p29Ole, then incubated at 37° C. overnight.

Day 2

5 mL overnight culture inoculated into a 100 mL LB Kan50 broth (500 mL flask). Incubated 37° C. 150 min. Induced with 400 µL 250 mM IPTG, incubated 37° C. 3 h.

Each culture was transferred to 2×50 mL Falcon tubes and cells pelleted by centrifugation 10 min 4° C. 3200×g. Pellet resuspended in 4 mL B Per Reagent (Pierce) and incubated to lyse (RT 20 min, gentle end-over-end mixing).

Insoluble protein pelleted by centrifugation 20 min 4° C. 3200×g. Supernatant discarded and pellets resuspended in 2 mL Oilbody Buffer (total vol.; 50 mM NaPO$_4$ pH8.0, 50 mM NaCl) and stored at −20° C.

Day 3

Samples removed from −20° C. and thawed. 2×500 µL each prep mixed with 4.5 mL Oilbody Buffer and either 200 µL(A) or 500 µL(B) of purified sesame oil (remaining 1 mL of each prep returned to −20° C.).

Samples were then sonicated (Sonics & Materials Vibra~Cell VC600, 600 W, 20 kHz; ⅛" tapered micro-tip probe) on ice at Power 4, 80% pulse, 1×90 sec (probe heated up at this setting); followed by Power 4, 50% pulse, 2×180 sec. After incubation on ice for 90 min the samples were again sonicated on ice at Power 4, 50% pulse, 2×180 sec.

To concentrate the AOBs the samples were spun 10 min 4° C. 3200×g and the lower phase decanted off from under upper oilbody phase. Oilbodies were then mixed in 5 mL Oilbody Buffer and completely resuspended by sonication at Power 4, 50% pulse, 1×180 sec. The AOBs were then stored at 4° C. until required for subsequent analysis.

Alternatively, pellets from 20 mL induced cultures of 1×6× polyoleosin lines were resuspended in 1 mL Oilbody Buffer and sonicated (Sonics & Materials Vibra~Cell VC600, 600 W, 20 kHz; ⅛" tapered micro tip probe) off/on ice at:

| Pulse | Time | Power |
|---|---|---|
| 100 | 20 | 3 |
| 100 | 20 | 3 |
| 100 | 20 | 3 |
| 100 | 20 | 3 |

The mixture was then spun in a microfuge 4° C. 10 min 14,000×g (14,500 rpm), the supernatant discarded and 1 mL Oilbody Buffer added to the pellets. 10 µL Purified Sesame Oil added to 240606 samples and 50 µL Purified Sesame Oil added to 210606 samples. Sonicated:

| Pulse | Time | Power |
|---|---|---|
| 100 | 20 | 3 |
| 100 | 20 | 3 |
| 100 | 20 | 3 |
| 100 | 10 | 5 |

Spun in a microfuge 4° C. 15 min 14,000×g (14,500 rpm). None of the samples had formed AOBs. Supernatant discarded and 1 mL Oilbody Buffer added to pellets. 50 µL Purified Sesame Oil added to all 240606 and 210606 samples, including those that had already formed AOBs (white layer). Sonicated:

| Pulse | Time | Power |
|---|---|---|
| 100 | 15 | 5 |
| 100 | 15 | 5 |
| 100 | 15 | 5 |
| 100 | 15 | 5 |

Spun in a microfuge 4° C. 15 min 14,000×g (14,500 rpm). The supernatant was transferred to a fresh 1.5 mL tube, and the supernatant and AOBs were stored at 4° C. overnight.

It can be seen by the formation of two layers that (AOB layer=upper), all samples form AOBs including the negative controls (FIG. 87), which consist of induced *E. coli* Rosetta strain containing the pET22 vector. However, the AOBs formed using non-oleosin *E. coli* proteins are unstable and rapidly breakdown and coalesce (FIG. 92).

Alternative methods to prepare artificial oil bodies can also be used including varying the oil/buffer/protein emulsion via different proportions or different oils and buffers. It is also possible to vary the ultrasonic energy required or to dispense with the requirement for ultrasonication via use of other disruptive methods such as vortexing and the use of organic solvents to purify the polyoleosin prior to use.

Analysis of the Purity of Polyoleosins from AOBs

750 µL Oilbody Buffer added to AOBs, then sonicated:

| Pulse | Time | Power |
|-------|------|-------|
| 100   | 15   | 5     |

30 µL of each sample was mixed with an equal volume of SDS GLB [@ 2×SDS], and the remaining AOBs were stored at 4° C. Protein denatured in boiling water bath for 5 min. Samples loaded onto 12% SDS PAGE [@ 2×SDS] gel at 15 µL per lane for the supernatant (S) and 2.5 µL per lane for the AOBs (A). Run at 150V 75 min. After electrophoresis gels were transferred to PVDF membrane for subsequent immunoblot analysis with rabbit anti-oleosin antibodies (FIG. 88). Alternatively samples were loaded onto a 4-15% gradient SDS-PAGE (with no stacking gel) and after electrophoresis gels were stained with SafeStain (Invitrogen) (FIG. 89). Earlier attempts to analyse artificial oil bodies from bacteria by SDS-PAGE showed that varying portions of the 3×, 4×, 5× and 6× samples do not run into the gel, and stop at the stacking/separating gel interface. As it was possible that the polyoleosin proteins with higher numbers of repeats were forming high molecular weight aggregates. This problem is partially alleviated by using SDS/urea denaturing PAGE (Table 23) and visualised using SafeStain (FIG. 90).

TABLE 23

Recipe for SDS/urea denaturing PAGE.

| SDS/urea Separating Gel | SDS/urea Stacking Gel |
|---|---|
| 2.5 mL 4× Tris-SDS Separating Buffer | 5 mL 2× Tris-SDS Stacking Buffer |
| 3 mL 40% Acrylamide | 1.25 mL 40% Acrylamide |
| 4.8 g Urea (Mr = 60, 8M final conc.) | 4.8 g Urea (Mr = 60, 8M final conc.) |
| Made to 10 mL with H$_2$O | Made to 10 mL with H$_2$O |
| pH adjusted to 8.8 with conc. HCl | pH adjusted to 6.8 with 1M HCl |
| 10 µL TEMED | 10 µL TEMED |
| 100 µL 10% APS | Washed top of polymerised separating gel with 200 µL aliquots. |
| | 100 µL 10% APS |

* Rinsed wells immediately before loading samples *

AOB Properties

5 µL aliquots of AOBs were placed on a microscope slide and observed at 1000× magnification (FIG. 91). When observed under the microscope the 1× oleosin AOBs appeared to be the smallest, and as the number of oleosin repeats increased the average size of the AOBs increased; up to the 3× polyoleosin, when AOB size appeared to remain similar for the 3×, 4×, 5× and 6× polyoleosin.

It is likely that significantly more single oleosin was used to make AOB than any of the multimeric tandem repeat proteins. This would explain the comparatively small size of the 1× oleosin AOB size.

AOB Stability Over Time

A 50 µL aliquot of AOBs was transferred to a 250 µL PCR tube and incubated at 4° C. for 168 h. 5 µL aliquots of the AOBs were then placed on a microscope slide and observed at 1000× (FIG. 92). AOB generated from vector control protein extracts showed almost complete coalescence of the oil. After 168 h the size of the AOB in the samples containing recombinant oleosins was inversley related to the number of oleosin repeats. In other words the AOB containing single chain oleosin units were on average larger than those containing 3 linked oleosin units that in turn were on average larger than those containing 6 linked oleosin units (FIG. 92). Thus the long-term stability of the emulsification can be tailored by altering the number of oleosin repeats used to generate the AOB.

AOB Heat Stability

A 50 µL aliquot of AOBs was transferred to a 250 µL PCR tube and incubated either at 70° C. for 4 h, or at 90° C. for 15 min in a PCR machine. To clearly define the amount of intact AOBs remaining, the tubes were spun 10 min 4° C. 3200×g (4000 rpm, Eppendorf 5810R centrifuge, A 4 62 swing out rotor). 5 µL aliquots of the AOBs were then placed on a microscope slide and observed at 1000× (FIG. 93).

Although there did not appear to be much difference in the size of the different AOBs after heat treatment, a large proportion of the AOBs formed with the 1× and 2× polyoleosins had coalesced (FIG. 93) to form large pools of oil. Those AOBs that were observed from samples formed with the 3× polyoleosin were of relatively the same size as before the heat treatment, but had formed a very thick emulsion. Some coalescence was observed in the 4× and 5× AOBs, but no large pools of oil were observed (FIG. 93). With the 6× polyoleosin there was no change in the size of the AOBs, nor was there any evidence of coalescence (FIG. 93). Thus the heat stability of the emulsification can be tailored by altering the number of oleosin repeats used to generate the AOB.

In addition, thickness of the emulsion layer remaining after heat treatment was correlated with an increase in oleosin repeat number (FIG. 94). Thus the stability of the emulsification at elevated temperatures can be tailored by altering the number of oleosin repeats used to generate the AOB.

Stability of AOB with Different Polyoleosins at pH 3.5, 8.0 and 10.5

A large number of proteins have been found experimentally to have different optimum pH of maximal stability where pH influences the folding and the net charge of the proteins. We tested for stability of AOBs generated with different polyoleosins at pH 3.5, 8.0 and 10.5.

Buffers: 50 mM Sodium Phosphate pH 8,100 mM NaC$_{1-50}$
50 mM Glycine-HCl pH 3.5
50 mm Glycine-NaOH pH 10.5

AOBs were generated using 1, 2, 3 or 6 polyoleosins; the negative control consisted of AOBs generated using inclusion bodies generated from E. coli containing an empty expression vector. Each preparation was sonicated to evenly suspend them in buffer containing 50 mM sodium phosphate pH 8, 100 mM NaCl. A 25 μl suspension of each polyoleosin-oil body was aliquot into microtubes containing 75 μL of the buffers at different pH. The tubes were incubated at room temperature (~22° C.) with every 5 minutes interval of 15 seconds vigorously shaking (~1,400 rpm) using a Thermomixer. After approximately 4 hours, samples were taken (~4 μL) and dropped on glass slice for microscoping at 1000× magnification.

After 4 hours at room temperature the negative control AOBs were beginning to coalesce at both pH3.5 and 10.5; while no coalescence of the negative control was seen at pH8 the AOBs were no longer spherical (FIG. 95). The AOBs containing 1 oleosin repeat appeared to be unstable at both pH3.5 and 10.5 but were stable at pH8.0. In comparison, AOBs containing 2 or more oleosin repeats were relatively stable at both pH 8.0 and 3.5. At pH 10.5 the AOBs containing 2 or more oleosin repeats were still visible but appeared to be smaller than those in lower pH buffers (FIG. 95). Some precipitation/aggregation of the emulsification was noted in the preparations containing 2 or more oleosin repeats at pH 10.5. Comparison of Purification of Oleosin by AOB Generation Versus Affinity Purification Prokaryotically produced polyoleosins were purified by either AOB generation or $Ni^{2+}$ affinity column. These samples were analysed by both SDS-PAGE/immunoblot or Coomassie stain or SafeStain (FIG. 96). This demonstrates that both methods can be used for polyoleosin purification.

Transformation of Arabidopsis thaliana with Polyoleosin Constructs Under the Control of the CaMV35s Construct or the Arabidopsis Oleosin Seed Promoter.

A range of plant binary vectors containing from 1 to 6 oleosin repeats were created using the synthetic sequences generated by GENEART AG (FIGS. 66, 70, 71 & 72) and two plant binary vectors containing either the CaMV35s promoter or the Arabidopsis oleosin seed promoter (Table 24 and FIGS. 97-116).

TABLE 24

Summary of constructs generated for expression of polyoleosin in plants.

| Construct name | Plant promoter | Terminator | Oleosin cassette | UBQ10 intron in first repeat | Selectable marker |
|---|---|---|---|---|---|
| pRSh1-PSP1 | CaMV35s | ocs3' | 1 oleosin, randomised degenerarte codons | yes | Spectinomycin & Basta |
| pRSh1-PSP3 | CaMV35s | ocs3' | 3 oleosins, randomised degenerate codons | yes | Spectinomycin & Basta |
| pRSh1-PSP4 | CaMV35s | ocs3' | 4 oleosins, randomised degenerate codons | yes | Spectinomycin & Basta |
| pRSh1-PSP6 | CaMV35s | ocs3' | 6 oleosins, randomised degenerate codons | yes | Spectinomycin & Basta |
| pRSh3-PSP1 | Oleosin seed | ocs3' | 1 oleosin, randomised degenerate codons | yes | Spectinomycin & Basta |
| pRSh3-PSP3 | Oleosin seed | ocs3' | 3 oleosins, randomised degenerate codons | yes | Spectinomycin & Basta |
| pRSh3-PSP4 | Oleosin seed | ocs3' | 4 oleosins, randomised degenerate codons | yes | Spectinomycin & Basta |
| pRSh3-PSP6 | Oleosin seed | ocs3' | 6 oleosins, randomised degenerate codons | yes | Spectinomycin & Basta |
| pRSh1-Ole3+ | CaMV35s | ocs3' | 3 oleosins, identical nucleotides codons | no | Spectinomycin & Basta |

Analysis of Agrobacterium Plasmid Preps

Agrobacterium tumefaciens (strain GV3101) was transformed using the freeze thaw method. 5 μg of plasmid was added to 250 μL of competent GV3101 cells and incubated on ice for 30 min. The cells were then frozen in liquid nitrogen for 1 min and thawed in a 37° C. water bath for 1 min. This process was repeated once then 1 mL LB broth was added to the cell mix. Following incubation at 28° C. for 4-6 h, the cells were pelleted, resuspended in 100 μL LB and plated (20 μL and 50 μL) onto LB Spec.

Transformed colonies were visualised on LB spec plates after approximately 48 h and single colonies were re streaked on LB spec to ensure the use of single colonies. From these new plates, single colonies were selected and plasmid preps obtained by using 8-10 mL of overnight culture in a modified QIAGEN Mini Prep protocol. Quantification of the preps was by NanoDrop spectrophotometer, and as yields were typically low, the presence of the construct in *Agrobacterium* was detected by PCR.

Primers pRSh1-PSP4:

```
                                       (Seq ID No. 23)
35S(3'end)Fwd  5' GAC ACG CTC GAG GAA TTC GGT ACC (Seq ID No. 24)
UBQ10IntRev    5' GAT GGT GAT GAC TGC AGA TCA GAA
```

Product size=609 bp pRSh1-PSP6:

```
UBQ10IntFwd
                                       (Seq ID No. 25)
5' CGA TTA ATC TGA GTT TTT CTG ATC TGC AGT CA

PolySes3R
                                       (Seq ID No. 26)
5' CGA TCA CCG TTC CGG CCA ATG TC
```

Product size=889 bp

The pRSh1-PSP4 primers could be used on any of the 35S promoter polyoleosin constructs.

Cycle

94° C./2 min (94° C./30 seq; 63° C./30 sec; 72° C./1 min)×30

72° C./7 min

Primers pRSh3-PSP4 and pRSh3-PSP6:

```
                                       (Seq ID No. 27)
OlePro     5' GAC ACG TGA CTT CTC GTC TCC TT (Seq ID No. 28)
UBQ10IntRev  5' GAT GGT GAT GAC TGC AGA TCA GAA
```

Product size=722 bp

In theory, these primers will detect any of the plant polyoleosin constructs containing the oleosin promoter. The constructs were thoroughly checked by restriction digestion and sequencing when purified from *E. coli*. The positive controls were the respective pRSh3-PSP4 and pRSh3-PSP6 plasmid preps from *E. coli*.

Cycle

94° C./2 min (94° C./30 sec; 63° C./30 sec; 72° C./45 sec)×30

72° C./7 min

Transformation of *Arabidopsis thaliana* var *Columbia* with Polyoleosin Binary Constructs Flow Chart of Project-Polyoleosin Expression in Plants pPCR-PSP6 (GeneArt)
Restriction digestion with appropriate enzyme
↓

-continued pPCR-PSP1, pPCR-PSP3 or pPCR-PSP6
LR reaction with binary vectors containing either the CaMV35S or the *Arabidopsis-oleosin* promoter
↓

Plant expression constructs containing 1x, 3x or 6x oleosin
Transformation of *Agrobacterium*
↓

Spectinomycin-resistant Agrobacterium containing plant expression construct
Transformation of *Arabidopsis*
↓

T₁ seed
Germination and selection with Basta
↓

Basta-resistant T₁ plants
Selfing of T1 plants
↓

Germination of T₂ seed
Analyses of T2 seeds for polyoleosin

Columbia plants were transformed using the floral dip method. The efficiency of this process can vary depending on a number of variables, including the construct itself, the health and floral development stage of the plant and the strain of *Agrobacterium*. For some constructs, two variations on the floral dip method were employed in order to try and optimise infiltration effectiveness.

One method involved dipping the entire plant or pot of plants (Full-dip) into *Agrobacterium* culture suspended in a solution of 5% (w/v) sucrose and 10 mM magnesium chloride, pH 5.7. Prior to dipping, Silwet L77 (a silicone polyether copolymer) was added to the culture solution to aid infiltration. Plants could be dipped up to three times, at a frequency of no more than once per week. We now have some idea of the efficiency of our full dip method using the polyoleosin constructs, which looks to be about 0.05 0.1%. This indicates that 1 g of T1 seed (approx 50,000 seed) should yield 25 herbicide resistant plants. One batch of 200 dipped plants should yield between 2 g and 5 g of seed.

The alternative method involved dropping *Agrobacterium* culture, suspended in the floral dip solution described above, onto individual flowers using a sterile transfer pipette (Floral drop). The rationale here was to avoid the entire plant being covered in *Agrobacterium*, thus aiding plant recovery. Florets were infiltrated as often as every second day and up to four times in total.

The seed collected from these transformation events represent T1 seed, which were germinated and sprayed with Basta herbicide in order to select transformed T1 plants. The total number of plants subjected to either of these methods with the different constructs is summarised in Table 25.

TABLE 25

Summary of *Arabidopsis* transformations completed with the polyoleosin monomeric, trimeric, tetrameric and hexameric polyoleosin constructs.

| Batch Number | Construct | Promoter | Terminator | Resistance | Approx number of plants treated | Method of transformation |
|---|---|---|---|---|---|---|
| GH 22083 | pRSh1-PSP1 | CaMV 35S | ocs3' | Spec/Basta | 200 | Full-dip |
| GH 22242 | pRSh1-PSP1 | CaMV 35S | ocs3' | Spec/Basta | 60 | Floral drop |
| GH 22243 | | | | | | |
| GH 22082 | pRSh1-PSP3 | CaMV 35S | ocs3' | Spec/Basta | 200 | Full-dip |
| GH 22244 | pRSh1-PSP3 | CaMV 35S | ocs3' | Spec/Basta | 60 | Floral drop |
| GH 22188 | | | | | | |
| GH 22446 | pRSh1-PSP4 | CaMV 35S | ocs3' | Spec/Basta | 200 | Full dip |
| GH 22017 | pRSh1-PSP6 | CaMV 35S | ocs3' | Spec/Basta | 300 | Full dip |
| GH 22150 | | | | | | |
| GH 22171-2 | pRSh1-PSP6 | CaMV 35S | ocs3' | Spec/Basta | 60 | Floral drop |
| GH 22209-10 | | | | | | |
| GH 22447 | pRSh3-PSP4 | *Arabidopsis oleosin* | ocs3' | Spec/Basta | 200 | Full dip |
| GH 22286 | pRSh3-PSP6 | *Arabidopsis oleosin* | ocs3' | Spec/Basta | 300 | Full dip |
| GH 22430 | | | | | | |
| GH 22196 | pRSh3-PSP6 | *Arabidopsis oleosin* | ocs3' | Spec/Basta | 60 | Floral drop |
| GH 22646 | pRSh1-Ole3+ | CaMV 35S | ocs3' | Spec/Basta | 200 | Full dip |
| GH 22485 | pRSh3-Ole3+ | *Arabidopsis oleosin* | ocs3' | Spec/Basta | 200 | Full dip |

PCR Testing of Herbicide Resistant T1 Plants

T1 seed from batch GH 22017 (Table 25) was collected and 1 g of seed germinated. Spraying with Basta herbicide resulted in approximately 20 herbicide resistant plants. These plants were also tested by PCR on genomic DNA. Genomic DNA was extracted from the rosette leaves of selected plants once they were of a suitable size. Extraction was carried out using the QIAGEN DNeasy mini kit protocol and 100 ng genomic DNA was used as PCR template. Two primer pairs were used to detect different areas of the polyoleosin insertion, thus giving information as to whether any gross rearrangements occurred during integration of the construct into the plant genome.

Plants Transformed with Tandem Repeats of Identical Nucleotide Sesame Seed Oleosin Transcripts.

The concern with using a construct containing repeating units of exactly the same sequence, as is the case with the Ole3+ constructs, is that non rec⁻ bacteria such as *Agrobacterium* may utilise their natural recombination mechanism to rearrange the sequence each time a new generation of bacteria is grown. Most laboratory strains of *E. coli* have the rec mutation to prevent this phenomenon. The PCR results go some way towards investigating this possibility, by using 2 sets of primers at each end of the repeating unit structure in the constructs. This suggests the constructs are intact after one round of sub-culturing. An additional check is to digest the plasmid preps from *Agrobacterium* with restriction enzymes and check the banding pattern obtained. The plasmid prep yield from *Agrobacterium* is typically too low to be able to perform digests, so the prep of clone #1 from each construct was used to transform *E. coli* TOP10 cells by heatshock. Plasmid preps were prepared by overnight culture of three single colonies and extraction using the Qiagen miniprep kit. The preps were analysed by three restriction enzymes the correct banding pattern is observed for all the clones tested. This result indicates that the Ole3+ constructs are intact in the *Agrobacterium* with no rearrangement. In the white clover constructs (discussed above), aberrent RNA species were only found to be expressed in *Lotus japonicus* roots when the number of identical white clover oleosin repeats was greater than 3. This could be due to rearrangements occurring in the *Agrobacterium* prior to plant transformation or during the process of stable integration into the plant geneome.

An additional check of integrity is to sequence through the repeating units of the *E. coli* preps from TOP10 cells transformed with plasmid obtained from *Agrobacterium*. We have sequenced through 90% of the repeating units and for the sequence completed, the construct sequence matches with the expected database sequence.

The possibility of rearrangement is potentially greater as the *Agrobacterium* integrates its T-DNA into the plant genome. We have no control over this event, so can only check for rearrangement events in the genomic DNA of herbicide resistant plants once they have been identified.

Analysis of *Arabidopis thaliana* Seeds Expressing Sesame Seed Oleosin.

Protein Expression

The herbicide resistant *Arabidopsis* seeds (T1) from the floral dip and full dip plants (T0) were allowed to self and set seed (T2). Seeds were collected from plants as the sliques matured (i.e., turned brown and became dry). Seeds were separated from the sliques and all seeds from 1 plant were pooled. Given the method of transformation the T2 seeds consist of segregating populations. It could be expected that for a single insertion event the T2 seed will demonstrate a 3:1 segregation pattern for a dominant trait (as would be expected for protein expression under the CaMV35s promoter). This would consist of 25% homozygous, 50% hemizygous and 25% wild type (untransformed).

Immunoblot Analysis of *Arabidopsis thaliana* Oil Bodies Containing Sesame Seed Oleosin.

T2 seeds from approximately 10 individual transformation events for each construct were analysed for protein expression. Seed lots for analysis were chosen based on the total amount of seed collected per plant.

Weigh out 25 mg of seed collected from 1 plant; combine with approximately 100 mg of dried, clean sand and 500 µL buffer A (600 mM Sucrose in 10 mM Sodium Phosphate buffer, pH 7.5).

Grind to a paste using mortar and pestle.

Recover maximum volume using pipette.

Rinse mortar and pestel 2× with 500 µL buffer A.

Combine extract and rinse in eppendorf tube, spin at 13 k rpm for 5 minutes.

Quickly recover the majority of the aqueous layer (bottom layer) using a piptette and transfer to a fresh tube.

Recover overlying oil layer by piptette after tilting the tube horizontally; transfer to a fresh tube.

To both fractions (aqueous and oil layer) add buffer A to a final volume of 500 µL; mix by pipetting.

Mix with equal volumes of loading buffer, vortex, boil for 5 minutes and analyse by SDS-PAGE/immunoblot using rabbit anti-sesame seed oleosin antiserum as the primary antibody (FIG. 117).

The rabbit anti-sesame seed oleosin antiserum showed no binding with extracts from wild type plants. Immunoreactive protein of the expected size was detected in the plants transformed with the polyoleosin constructs including the monomeric, trimeric and tetrameric constructs (dimeric and tetrameric transformants were not included) (FIG. 117). The SDS-PAGE/immunoblot analysis demonstrates that the constructs can be expressed and translated and that the protein is of the expected molecular weight, it accumulates in the seed and is targeted to the oil bodies in the correct manner. The T2 seed populations screened here contained segregating populations, hence it could be reasonably anticipated that even higher levels of expression would exist in homozygous plants as well perhaps in transgenic plants yet to be analysed. The presences of the immunoreactive band at the molecular weight of the monomeric sesame seed oleosin in all extracts from plants transformed with the polyoleosin trimer and polyoleosin hexamer suggests that either some protein cleavage is occurring or that some of the transcript is only translated as far as the first oleosin repeat before being terminated. The ratio of monomer to either trimer or hexamer is relatively low indicating that the level of accumulation of the monomer is also low.

SDS-PAGE/Coomassie analysis of the crude protein extracts from seeds of the same samples shows that the level of recombinant protein in the hemizygous transgenic plants is too low to be detected by Coomassie stain in the background of native proteins (FIG. 118).

Properties of Sesame Seed Polyoleosin Expressed in *Arabidopsis thaliana* Seeds.

Heat Stability

Oil bodies from two wild type, pRSh1-PSP1, pRSh1-PSP3 and pRSh1-PSP6 *Arabidopsis* transformants were compared for heat stability. 25 mg of seed from each plant was ground separately in a mortar and pestle containing xxµL oil body extraction buffer (10 mM Sodium Phosphate buffer containing 600 mM sucrose)). This was transferred to a microfuge tube, the mortar and pestle was rinsed a further two times with 500 µL of oil body extraction buffer, combined with the original extract and the volumes were made up to 500 µL with oil body extraction buffer. The tubes were spun at 13 k rpm for 10 minutes and photographed (FIG. 119). Each sample showed a thin layer (containing the oil bodies) floating on the surface of extraction buffer. 400 µL of the oil body extraction buffer was removed using a protein gel loading tip attached to an eppendorf. Small aliquots of oil body extraction buffer were used to resuspend the oil layer and removed to a new 2 ml eppendorf tube. The oil body layers were made up to the same final volume (approximately 500 µL with oil body extraction buffer and resuspended fully by pipetting. 50 µL of the suspension was loaded into PCR tubes and capped; 50 µL was stored at 4° C. The PCR tubes were heated at 90° C. for 2, 4, 24 and 58 hrs. At each time point the tubes were removed from the heating block, spun for 10 minutes at 13 k rpm to separate the suspensions and photographed (FIG. 120). The reduction in oleosin repeat numbers correlates with a decrease in the emulsification layer remaining after 24 hr at 90° C., where the thickest emulsification can be seen from plants expressing the hexameric polyoleosin construct. The reduction in oleosin repeat numbers correlates with a decrease in the emulsification layer remaining after 24 hr at 90° C., where the thickest emulsification can be seen from plants expressing the hexameric polyoleosin construct. At 0 hrs through to 24 hrs at 90° C. the higher the number of oleosin repeats correlates with a thicker emulsification layer. After 58 hrs at 90° C. the oil bodies from the wild type *arabidopsis* has been reduced to a very thin layer with a small ring of emulsion deposited on the tube above the remaining aqueous phase. In comparison, the ring of emulsion remaining in the transformant samples is much greater (FIG. 120). Thus the stability of the emulsification derived from seed extracts at elevated temperatures can be tailored by altering the number of oleosin repeats used to transform the plant.

REFERENCES

Beelman C A and Parker R. (1995). Degradation of mRNA ineukaryotes. Cell, 81(2) 179-183.

Bouvier-Nave P, Benveniste P, Oelkers P, Sturley S L, Schaller H. (2000) Expression in yeast and tobacco of plant cDNAs encoding acyl CoA:diacylglycerol acyltransferase. *Eur. J. Biochem.* 267, 85-96.

Brown C M, Stockwell P A, Trotman C N, Tate W P. (1990). Sequence analysis suggests that tetra-nucleotides signal the termination of protein synthesis in eukaryotes. Nucleic Acids Research. 18(21): 6339-6349.

Brunak, S., Engelbrecht, J., and Knudsen, S. (1991). Prediction of Human mRNA Donor and Acceptor Sites from the DNA Sequence, Journal of Molecular Biology, 220, 49-65)

Christey, M. C. and Braun R. H. 2004. Production of Hairy Root Cultures and Transgenic Plants by *Agrobacterium rhizogenes*-mediated Transformation p. 47-60. In: L. Pena (ed.), Methods in Molecular Biology, Vol. 286: Transgenic Plants. Humana Press Inc., Totowa, N.J.

Christey, M. C., Sinclair, B. K., Braun, R. H. and Wyke, L. 1997. Regeneration of transgenic vegetable brassicas (*Brassica oleracea* and *B. campestrisl*) via Ri-mediated transformation. Plant Cell Reports 16: 587-593.

Dahlqvist A, Stahl U, Lenman M, Banas A, Lee M, Sandager L, Ronne H, Stymne S. (2000) Phospholipid:diacylglycerol acyltransferase: an enzyme that catalyzes the acyl-CoA-independent formation of triacylglycerol in yeast and plants. Proc Natl Acad Sci USA. 97, 6487-6492.

de Boer G-J and Somerville C. (2001). The many changing colours of fatty acid biosynthesis. Proc. Nat. Plant Lipid Cooperative Supplement. Stanford Sierra Summer Camp, Fallen Leaf Lake, Calif.)

Demeyer, D., Doreau, M. 1999. Targets and procedures for altering ruminant meat and milk lipids. Proceedings of the Nutrition Society 58:593-607.

Hebsgaard, S M. Korning, P. G. Tolstrup, N. Engelbrecht, J. Rouze, P. Brunak. S. (1996): Splice site prediction in *Arabidopsis thaliana* DNA by combining local and global sequence information, Nucleic Acids Research, 24(17) 3439-3452.

Lardizabal K D, Mai J T, Wagner N W, Wyrick A, Voelker T, Hawkins D J. (2001) DGAT2 Is a new diacylglycerol acyltransferase gene family. J.B.C. 276, 38862-38869.

Linsmaier, E. M. and Skoog, F. 1965. Organic growth factor requirements of tobacco tissue cultures. Physiol. Plant. 18:100-127.

Murashige, T. and Skoog, F. 1962. A revised medium for rapid growth and bioassay with tobacco tissue cultures. Physiol. Plant. 15: 473-497.

Norris S R, Meyer S E and Callis J (1993). The intron of *Arabidopsis thaliana* polyubiquitin genes is conserved in location and is a quantitative determinant of chimeric gene expression. Plant Molecular Biology, 21, 895-906

Peng C-C, Chen J C F, Shyu D J H, Chen M-J, Tzen J T C. (2004) A system for purification of recombinant proteins in *Escherichia coli* via artificial oil bodies constituted with their oleosin-fused polypeptides. *J. Biotech.* 111, 51-57

Rose A B (2002). Requirements for intron-mediated enhancement of gene expression in *Arabidopsis*. RNA, 8, 1444-1453

Rose A B (2004). The effect of intron location on intron-mediated enhancement of gene expression in *Arabidopsis*. The Plant Journal, 40, 744-751

Rose A B and Beliakoff J A (2000). Intron-mediated enhancement of gene expression independent of unique intron sequences and splicing. Plant Physiology, 122, 535-542

Sparrow, P. A. C., Dale, P. J. and Irwin, J. A. 2004. The use of phenotypic markers to identify *Brassica oleracea* genotypes for routine high throughput *Agrobacterium*-mediated transformation. Plant Cell Reports 23: 64-70.

Tai, S S K, Chen, M C M, Peng, C C, Tzen J T C. (2002). Gene family of oleosin isoforms and their structural stabilization in sesame seed oil bodies. Biosci. Biotechnol. Biochem. 66(10): 2146-2153.

Tzen J T, Lie G C, Huang A H. (1992). Characterization of the charged components and their topology on the surface of plant seed oil bodies. J Biol. Chem. 267(22):15626-34.

Williams N K, Liepinsh E, Watt S J, Prosselkov P, Matthews J M, Attard P, Beck J L, Dixon N E, Otting G. (2005). Stabilization of native protein fold by intein-mediated covalent cyclization. J. Mol. Biol., 346(4):1095-1108.

Zou J, Wei Y, Jako C, Kumar A, Selvaraj G, Taylor D C. (1999) The *Arabidopsis thaliana* TAG1 mutant has a mutation in a diacylglycerol acyltransferase gene. *Plant J.* 19, 645-653.

Reference to any prior art in the specification is not, and should not be taken as, an acknowledgement or any form of suggestion that this prior art forms part of the common general knowledge in Australia or any other jurisdiction.

Finally, it is to be understood that various alterations, modifications and/or additions may be made without departing from the spirit of the present invention as outlined herein.

The invention claimed is:

1. A construct comprising nucleic acid sequences encoding three or more oleosin repeat units.

2. A construct according to claim 1 wherein the oleosin repeat units are tandem repeats.

3. A construct according to claim 1 further comprising a nucleotide sequence encoding a linking sequences disposed between nucleic acids sequences encoding two of the oleosin repeat units.

4. A construct according to claim 3 wherein said linking sequences are selected to enable degradation, allow flexibility and/or induce a directional change between the oleosin repeat units.

5. A construct according to claim 3 wherein the linking sequences comprise a site for enzymatic cleavage or subsequent fusion.

6. A construct according to claim 1 further comprising one or more nucleic acid sequences encoding bioactive peptides.

7. A construct according to claim 1 wherein the construct comprises nucleic acids encoding between three and ten oleosin repeat units.

8. A construct according to claim 1 wherein the nucleic acid sequences encoding oleosin repeat units are from white clover or sesame seed or are a recombinant or synthetic version thereof.

9. A construct according to claim 8 wherein the construct is modified to enhance expression of said nucleic acids.

10. A construct according to claim 1 wherein the nucleic acid sequences encoding oleosin repeat units comprise a nucleotide sequence selected from the group consisting of Seq ID Nos. 29-43, 50, 52-57, 64-73 and 84, and functionally active fragments and variants thereof.

11. A construct according to claim 1 further comprising a nucleic acid sequence encoding a diacylglycerol acyltransferase or a functionally active fragment or variant thereof.

12. A method of producing repeat oleosins in a cell, said method comprising introducing into said cell a construct according to claim 1, and expressing the construct.

13. A method according to claim 12, wherein the cell is a plant cell and is part of a plant.

14. A method according to claim 12, wherein the cell is a prokaryotic cell.

15. An eukaryotic or prokaryotic cell comprising a construct comprising nucleic acid sequences encoding three or more oleosin repeat units.

16. A cell in accordance with claim 15, wherein the cell is a plant cell, and the plant cell is isolated or part of a plant, plant seed or other plant part.

17. A partially or substantially purified and/or recombinant polypeptide comprising three or more oleosin repeat units.

18. A polypeptide according to claim 17 produced by expression of a construct comprising nucleic acid sequences encoding three or more oleosin repeat units.

19. A polypeptide according to claim 17 wherein the oleosin repeat units are tandem repeats.

20. A polypeptide according to claim 17 further comprising linking sequences between two or more of the oleosin repeat units.

21. A polypeptide according to claim 17 further comprising one or more bioactive peptides.

22. A polypeptide according to claim 21 wherein said bioactive peptide is inserted at the N or C terminus of said oleosin repeat units or between two or more oleosin repeat units.

23. A polypeptide according to claim 17 comprising between three and ten oleosin repeat units.

24. A polypeptide according to claim 17 wherein the oleosin repeat units are from white clover or sesame seed or are a synthetic or recombinant version thereof.

25. A polypeptide according to claim 17 including an amino acid sequence selected from the group consisting of Seq ID Nos.: 47, 48, 51, 58-63 and 74-83, and functionally active fragments and variants thereof.

26. An oil body comprising lipid encapsulated by a polypeptide according to claim 17.

27. A polypeptide according to claim 17, wherein the polypeptide is a recombinant oleosin having altered emulsification properties compared to a polypeptide with a single oleosin unit.

28. A method for modifying lipid metabolism or storage in a cell or organism, comprising introducing into said cell or organism a construct according to claim 1 and expressing the construct.

29. A method according to claim 28 wherein the cell or organism is a plant, thereby altering emulsification properties, physiochemical properties or degree of biohydrogenation of said lipids.

30. A method according to claim 28, wherein the cell or organism is a plant, thereby altering stability of an oil body in a plant.

31. A method of altering biohydrogenation of a lipid, said method comprising encapsulating said lipid in a recombinant polypeptide comprising three or more oleosin repeat units.

32. A method according to claim 31, wherein the lipid is an unsaturated lipid and said unsaturated lipid incorporated into an oil body comprising the recombinant polypeptide.

33. A method of delivering a bioactive peptide, to animals including humans, said method comprising inserting said peptide at the N- or C-terminus of a series of three or more oleosin repeat units or between two or more oleosin repeat units in a series of three or more oleosin repeat units to produce a recombinant polypeptide and administering said recombinant polypeptide to said animal.

34. A method of delivering compounds and/or organisms to animals including humans, said method comprising encapsulating said compound or organism in an oil body including three or more oleosin repeat units and administering said oil body to said animal.

35. A method of altering the emulsification properties of an oleosin, said method comprising recombinantly producing an oleosin having three or more oleosin repeat units.

* * * * *